US012377140B2

(12) United States Patent
Besin et al.

(10) Patent No.: US 12,377,140 B2
(45) Date of Patent: Aug. 5, 2025

(54) MULTIVALENT PNEUMOCOCCAL VACCINES

(71) Applicant: Affinivax, Inc., Cambridge, MA (US)

(72) Inventors: Gilles R. Besin, Brookline, MA (US); Teresa J. Broering, Brookline, MA (US); Heidi Burke, Saugus, MA (US); Yingjie Lu, West Roxbury, MA (US); Richard Malley, Beverly, MA (US); Janet E. McCombs, New Orleans, LA (US); Velupillai Puvanesarajah, Chapel Hill, NC (US); Shite Sebastian, Shrewsbury, MA (US); Onkar Sharma, Chestnut Hill, MA (US); Taylor C. Stevenson, Cambridge, MA (US); Gang Yao, Belmont, MA (US); Fan Zhang, West Roxbury, MA (US)

(73) Assignee: Affinivax, Inc., Cambridge, MA (US)

( * ) Notice: Subject to any disclaimer, the term of this patent is extended or adjusted under 35 U.S.C. 154(b) by 0 days.

(21) Appl. No.: 18/734,015

(22) Filed: Jun. 5, 2024

(65) Prior Publication Data

US 2024/0398924 A1 Dec. 5, 2024

Related U.S. Application Data

(63) Continuation of application No. 17/942,089, filed on Sep. 9, 2022, now Pat. No. 12,036,276.

(60) Provisional application No. 63/353,014, filed on Jun. 16, 2022, provisional application No. 63/242,487, filed on Sep. 9, 2021.

(51) Int. Cl.
*A61K 39/09* (2006.01)
*A61K 39/00* (2006.01)

(52) U.S. Cl.
CPC .. *A61K 39/092* (2013.01); *A61K 2039/55505* (2013.01); *A61K 2039/62* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 5,858,677 A | 1/1999 | Forsgren | |
| 6,287,568 B1 | 9/2001 | Wang et al. | |
| 7,217,791 B2 | 5/2007 | Chen et al. | |
| 7,585,669 B2 | 9/2009 | Chen et al. | |
| 7,588,920 B2 | 9/2009 | Doucette-Stamm et al. | |
| 9,499,593 B2 | 11/2016 | Malley et al. | |
| 10,017,548 B2 | 7/2018 | Malley et al. | |
| 10,766,932 B2 | 9/2020 | Malley et al. | |
| 11,013,793 B2 | 5/2021 | Malley et al. | |
| 2002/0032323 A1 | 3/2002 | Kunsch et al. | |
| 2005/0002948 A1 | 1/2005 | Ryall | |
| 2005/0226899 A1 | 10/2005 | Castiglioni et al. | |
| 2006/0228380 A1 | 10/2006 | Hausdorff et al. | |
| 2006/0251675 A1 | 11/2006 | Hagen | |
| 2006/0257421 A1 | 11/2006 | Ochs et al. | |
| 2007/0082005 A1 | 4/2007 | Doucette-Stamm et al. | |
| 2007/0128183 A1 | 6/2007 | Meinke et al. | |
| 2007/0184443 A1 | 8/2007 | Covacci | |
| 2008/0032340 A1 | 2/2008 | Ghosh et al. | |
| 2008/0112964 A1 | 5/2008 | Kirkham et al. | |
| 2008/0160045 A1 | 7/2008 | Contorni et al. | |
| 2009/0054251 A1 | 2/2009 | O'Connor et al. | |
| 2009/0068288 A1 | 3/2009 | Kruger | |
| 2009/0148894 A1 | 6/2009 | Broedel et al. | |
| 2009/0148897 A1 | 6/2009 | Dai | |
| 2009/0285846 A1 | 11/2009 | Tweten | |
| 2010/0003266 A1 | 1/2010 | Simon | |
| 2010/0020945 A1 | 1/2010 | Li et al. | |
| 2010/0022401 A1 | 1/2010 | Nordlund et al. | |
| 2010/0166802 A1 | 7/2010 | Caplan et al. | |
| 2010/0209450 A1 | 8/2010 | Biemans et al. | |
| 2010/0330112 A1 | 12/2010 | Long et al. | |
| 2011/0020386 A1 | 1/2011 | Gierahn et al. | |
| 2011/0027265 A1 | 2/2011 | Bubeck-Wardenburg et al. | |
| 2011/0065660 A1 | 3/2011 | Baron et al. | |
| 2011/0159040 A1 | 6/2011 | Malley et al. | |
| 2011/0293664 A1 | 12/2011 | Cohane et al. | |
| 2012/0135025 A1 | 5/2012 | Flechtner et al. | |
| 2012/0189649 A1 | 7/2012 | Gierahn et al. | |
| 2012/0251577 A1 | 10/2012 | Malley et al. | |
| 2013/0115230 A1 | 5/2013 | Simon | |
| 2013/0121958 A1 | 5/2013 | Leclerc et al. | |
| 2014/0154286 A1 | 6/2014 | Malley et al. | |
| 2014/0154287 A1 | 6/2014 | Malley et al. | |
| 2015/0374811 A1 | 12/2015 | Malley et al. | |
| 2016/0090404 A1 | 3/2016 | Malley et al. | |
| 2017/0021006 A1 | 1/2017 | Watson et al. | |
| 2018/0312552 A1 | 11/2018 | Tweten | |

(Continued)

FOREIGN PATENT DOCUMENTS

| | | |
|---|---|---|
| CN | 101797381 A | 8/2010 |
| CN | 101951948 A | 1/2011 |

(Continued)

OTHER PUBLICATIONS

"Centers for Disease Control and Prevention." "Preventing pneumococcal disease among infants and young children." "Morbidity and Mortality Weekly Report. 49: 1-55 (2000)".

(Continued)

*Primary Examiner* — Oluwatosin A Ogunbiyi

(74) *Attorney, Agent, or Firm* — Cynthia Lan Martin; Nicole Ginanni

(57) ABSTRACT

Technologies for the prevention and/or treatment of pneumococcal infections.

21 Claims, 58 Drawing Sheets

Specification includes a Sequence Listing.

(56) References Cited

U.S. PATENT DOCUMENTS

2019/0119335 A1 4/2019 Malley et al.
2020/0087361 A1 3/2020 Malley et al.
2020/0222522 A1 7/2020 Malley et al.
2020/0407404 A1 12/2020 Malley et al.
2021/0332090 A1 10/2021 Malley et al.
2023/0091255 A1 3/2023 Besin et al.

FOREIGN PATENT DOCUMENTS

EP 0497524 A2 8/1992
EP 1838345 A2 10/2007
EP 3849587 A1 7/2021
JP H11-502820 A 3/1999
JP 2001-505415 A 4/2001
JP 2001/510031 A 7/2001
JP 2002/504080 A 2/2002
JP 2002-504096 A 2/2002
JP 2002-521058 A 7/2002
JP 2003/515341 A 5/2003
JP 2007-504237 A 3/2007
JP 2007/525157 A 9/2007
JP 2008-509682 A 4/2008
JP 2010-517532 A 5/2010
JP 2014/514363 A 6/2014
JP 2014-517835 A 7/2014
JP 6366501 B2 8/2018
JP 6666389 B2 3/2020
KR 20080090411 A 10/2008
RU 2164943 C2 4/2001
RU 2006117425 A 12/2007
RU 2378008 C2 1/2010
RU 2407749 C2 12/2010
WO WO-90/11087 A1 10/1990
WO WO-1995021195 A1 8/1995
WO WO-1996/029094 A1 9/1996
WO WO-1998/018930 A2 5/1998
WO WO-98/47530 A2 10/1998
WO WO-99/03884 A2 1/1999
WO WO-00/06737 A2 2/2000
WO WO-2000/006738 A2 2/2000
WO WO-01/40472 A2 6/2001
WO WO-02/077021 A2 10/2002
WO WO-2003/044185 A2 5/2003
WO WO-2003/094960 A2 11/2003
WO WO-2004/092209 A2 10/2004
WO WO-2005/037190 A2 4/2005
WO WO-2005/039501 A2 5/2005
WO WO-05/76696 A2 8/2005
WO WO-05/108580 A1 11/2005
WO WO-2006/017929 A1 2/2006
WO WO-2006/067632 A2 6/2006
WO WO-2006/084467 A1 8/2006
WO WO-2007/026249 A2 3/2007
WO WO-2007/067681 A2 6/2007
WO WO-2007/081583 A2 7/2007
WO WO-2007/150020 A1 12/2007
WO WO-2008/094986 A2 8/2008
WO WO-2008/119358 A2 10/2008
WO WO-2008/152448 A2 12/2008
WO WO-2009/016515 A2 2/2009
WO WO-2009/021548 A1 2/2009
WO WO-2009/029831 A1 3/2009
WO WO-2009/143413 A1 11/2009
WO WO-2010/053559 A1 5/2010
WO WO-2010/071986 A1 7/2010
WO WO-2010/081875 A1 7/2010
WO WO-2011/008548 A1 1/2011
WO WO-11/112906 A2 9/2011
WO WO-2011/137354 A2 11/2011
WO WO-2012/155007 A1 11/2012
WO WO-2012/155053 A1 11/2012
WO WO-2014/018904 A1 1/2014
WO WO-2014/92378 A1 6/2014
WO WO-2014/124228 A1 8/2014
WO WO-2017/013548 A1 1/2017
WO WO-2018/156465 A1 8/2018
WO WO-2018/183475 A1 10/2018
WO WO-2019/152921 A1 8/2019
WO WO-2019/167008 A1 9/2019
WO WO-2020/056127 A1 3/2020
WO WO-2020/056202 A1 3/2020
WO WO-22/178015 A1 8/2022
WO WO-2023/039223 A1 3/2023

OTHER PUBLICATIONS

Ahmad, A. et al., Sequential release of antigens from chloroform-treated *Staphylococcus epidermidis*: application towards a possible vaccine, J. Appl. Bacteriol., 69(5):676-685 (1990).

Anttila, M. et al., Avidity of IgG for *Streptococcus pneumoniae* type 6B and 23F polysaccharides in infants primed with pneumococcal conjugates and boosted with polysaccharide or conjugate vaccines, J. Infect. Dis., 177(6):1614-1621 (1998).

Avci, F.Y. et al, A mechanism for glycoconjugate vaccine activation of the adaptive immune system and its implications or vaccine design, Nat. Med., 17(12): 1602-1609 (2011).

Basset, A. et al., Antiboby-independent, CD4+ T-Cell-Dependent protection against pneumococcal colonization elicited by intranasal immunization with purified pneumococcal proteins, Infection and Immunity, 75(11):5460-5464 (2007).

Beghetto, E. et al., Discovery of novel *Streptococcus pneumoniae* antigens by screening a whole-genome lambda-display library, FEMS Microbial Lett., 262(1):14-21 (2006).

Berry, A. M. et al, Comparative virulence of *Streptococcus pneumoniae* strains with insertion-duplication, point, and deletion mutations in the pneumolysin gene, Infection and Immunity, 67(2):981-985 (1999).

Berry, M. A. et al., Effect of Defined Point Mutations in Pneumolysin Gene on the Virulence of *Streptococcus pneumonia*, Infection and Immunity, 63(5):1969-1974 (1995).

Boslego et al., "Gonorrhea Vaccines" Vaccine and Immunotherapy Ch. 17 211 (1991).

Bowie, J. U. et al., Deciphering the message in protein sequences: tolerance to amino acid substitutions, Science, 257(4948):1306-1310 (1990).

Caierao, J. et al., Characteristics of serogroup 20 S.pneumoniae isolates from Brazil, BMC Infectious Diseases, 16:418 (2016).

Centers for Disease Control and Prevention. "Prevention of pneumococcal disease among infants and children—use of 13-valent pneumococcal conjugate vaccine and 23-valent pneumococcal polysaccharide vaccine." Morbidity and Mortality Weekly Report. 59: 1-24 (2010).

Chase, H. C., Perinatal and infant mortality in the United States and six West European countries, Am J Public Health Nations Health. 57(10):1735-48 (1967).

Chichili, G.R. et al., Phase 1/2 study of a novel 24-valent pneumococcal vaccine in healthy adults aged 18 to 64 years and in older adults aged 65 to 85 years, Vaccine, 40(31):4190-4198, (2022).

Colino, J. et al, Noncovalent association of protein and capsular polysaccharide on bacteria-sized latex beads as a model for polysaccharide-specific humoral immunity to intact Gram-positive extracellular bacteria, J. Immunol., 191(6): 3254-3263 (2013).

Colino, J. et al, Parameters Underlying Distinct T Cell-Dependent Polysaccharide-Specific IgG Responses to an Intact Gram-Positive Bacterium versus a Soluble Conjugate Vaccine, The Journal of Immunology, 1552-1559 (2009).

Concepcion, N. F. and Frasch, C. E.,. Pneumococcal type 22f polysaccharide absorption improves the specificity of a pneumococcal-polysaccharide enzyme-linked immunosorbent assay, Clin Diagn Lab Immunol. 8(2):266-72 (2001).

Cortajarena, A.L., et al, A receptor-binding region in *Escherichia coli* alpha-haemolysin, J. Biol. Chem., 278(21):19159-63 (2003).

Dagan, R. et al., Glycoconjugate vaccines and immune interference: A review, Vaccine, 28(34): 5513-5523 (2010).

Daniels, C. C. et al., The Proline-Rich Region of Pneumococcal Surface Proteins A and C Contains Surface-Accessible Epitopesn Common to All Pneumococci and Elicits Antibody-Mediated Protection against Sepsis, Infection and Immunity, 78(5):2163-2172 (2010).

(56) References Cited

OTHER PUBLICATIONS

Database, UniProt KB/TrEMBL, B3Q265_RHIE6, retrieved Jan. 3, 2021.
Database, UniProt KB/TrEMBL, F2AA21_RHIET, retrieved Jan. 4, 2021.
Database, UniProt KB/TrEMBL, Q8KKW2_RHIEC, retrieved Jan. 4, 2021.
Douce, G. et al., Genetically detoxified mutants of heat-labile toxin from *Escherichia coli* are able to act as oral adjuvants, Infect Immun., 67(9):4400-4406 (1999).
Douce, G. et al., Mutants of *Escherichia coli* heat-labile toxin lacking ADP-ribosyltransferase activity act as non-toxic, mucosal adjuvants, PNAS 92:1644-1648 (1995).
Elgert, K. D., Immunology Understanding the Immune System, John Wiley & Sons, Inc. Hoboken, New Jersey, p. 111 (2009).
Ellis, New Technologies for making vaccines, Vaccine Ch. 29, 568-574 (1988).
Evans, J. T. et al., Enhancement of antigen-specific immunity via the TLR4 ligands MPL adjuvant and Ribi.529, Expert Rev Vaccines, 2(2):219-229 (2003).
Fauvart, M. et al, Genome Sequence of Rhizobium etli CNPAF512, a Nitrogen-Fixing Symbiont Isolated from Bean Root Nodules in Brazil, Journal of Bacteriology, 193(12): 3158-3159 (2011).
Ferreira, D. M. et al., DNA vaccines based on genetically detoxified derivatives of pneumolysin fail to protect mice against challenge with *Streptococcus pneumonia*, FEMS Immunology Med. Microbial 46: 291-297 (2006).
Frey, S. E. et al., A Phase I, dose-escalation trial in adult of three recombinant attenuated *Salmonella Typhi* vaccine vectors producing *Streptococcus pneumoniae* surface protein antigen PspA, Vaccine 31(42):4874-80 (2013).
Gaj, T. et al., The AviD-tag, a NeutrAvidin/avidin specific peptide affinity tag for the immobilization and purification of recombinant proteins, Protein Expr. Purif., 56(1):54-61 (2007).
Geno K. A. et al., Pneumococcal Capsules and their types: past, present, and future, Clin Microbiol Rev 28(3):871-899 (2015).
Giuliani, M. M. et al., Mucosal adjuvanticity and immunogenicity of LTR72, a novel mutant of *Escherichia coli* heat-labile enterotoxin with partial knockout of ADP-ribosyltransferase activity, J. Exp. Med., 187(7):1123-1132 (1998).
González, V. et al, The mosaic structure of the symbiotic plasmid of Rhizobium etli CFN42 and its relation to other symbiotic genome compartments, Genome Biol., 4(6): R36 (2003).
Greenspan, N. S. and Cera, E. D., Defining epitopes: It's not easy as it seems, Nature Biotechnology, 17:936-937 (1999).
Gruber, M.F. et al., Pratt D, Haase M. Licensing of pneumococcal conjugate vaccines for children and adults: Regulatory perspective from the European Medicines Agency and the U.S. Food and Drug Administration, Pneumococcal Vaccines: The Impact of Conjugate Vaccine, 183-96 (2008).
Grun, C. H. et al, One-step biotinylation procedure for carbohydrates to study carbohydrate-protein interactions, Anal. Biochem., 354(1):54-63 (2006).
Helppolainen, S. H. et al, Bradavidin II from Bradyrhizobium japonicum: a new avidin-like biotin-binding protein, Biochim. Biophys. Acta., 1784(7-8):1002-10 (2008).
Helppolainen, S.H. et al., Rhizavidin from Rhizobium etli: the first natural dimer in the avidin protein family, Biochem J., 405(3): 397-405 (2007).
Hermanson, G. T., Bioconjugate Techniques, Elsevier Science, ProQuest Ebook Central, http://ebookcentral.proquest.com/lib.uspto-ebooks/detail.action?docID=307203, created from uspto-ebooks on Sep. 6, 2017, 570-592 (1996).
Holliger, P. et al., "Diabodies": small bivalent and bi specific antibody fragments, Proc. Natl. Acad, Sci, USA, 90:6444-6448 (1993).
Hsu, T-L. et al, Profiling Carbohydrate-Receptor Interaction with Recombinant Innate Immunity Receptor-Fc Fusion Proteins, J. Biol. Chem., 284(50): 34479-34489 (2009).
Huang, H. et al, Robust stimulation of humoral and cellular immune responses following vaccination with antigen-loaded beta-glucan particles, MBio, 1(3):e00164-10 (2010).
Hytonen, V.P. et al., Efficient production of active chicken avidin using a bacterial signal peptide in *Escherichia coli*, Biochem J., 384(Pt 2): 385-90 (2004).
Insel, R. et al., Response to oligosaccharide-protein conjugate vaccine against Hemophilus influenzae b in two patients with IgG2 deficiency unresponsive to capsular polysaccharide vaccine, N. Engl J. Med., 315:8, p. 499-503 (1986).
International Search Report for PCT/2019/050907 (Multivalent Pneumococcal Vaccines, filed Sep. 12, 2019), issued by ISA/US, 5 pages (mailed Feb. 2, 2020).
International Search Report for PCT/US11/28052 (Novel Immunogens and Methods for Discovery and Screening Thereof, filed Mar. 11, 2011) issued by ISA/KR, 6 pages (Dec. 27, 2011).
International Search Report for PCT/US19/50800, 4 pages (mailed Dec. 31, 2019).
International Search Report for PCT/US2012/037412 (Multiple Antigen Presenting Immunogenic Composition, and Methods and Uses Thereof, filed May 11, 2012), issued by ISA/FIPS, 3 pages (Aug. 23, 2012).
International Search Report for PCT/US2012/037541 (Modified Biotin-Binding Protein, Fusion Proteins Thereof and Applications, filed May 11, 2012), issued by ISA/FIPS, 4 pages (Aug. 30, 2012).
International Search Report for PCT/US2014/015254 (Protein Antigens That Provide Protection Against Pneumococcal Colonization and/or Disease, filed Feb. 7, 2014), issued by ISA/US, 4 pages (May 5, 2014).
International Search Report for PCT/US2018/24810 (A Multiple Antigen Presenting System (MAPS)-Based *Staphylococcus aureus* Vaccine, Immunogenic Composition, and Uses Thereof, filed Mar. 28, 2018), issued by ISA/US, 6 pages (mailed Aug. 31, 2018).
International Search Report for PCT/US22/43156, 6 pages (mailed Dec. 7, 2022).
International Search Report for PCT2019050907, 5 pages (mailed Feb. 2, 2020).
Ishizaka, S.T. and Hawkins, L.D., E6020: a synthetic Toll-like receptor 4 agonist as a vaccine adjuvant, Expert Rev. Vaccines, 6(5):773-784 (2007).
Izard, J. W. and Kendall, D. A., Signal peptides: exquisitely designed transport promoters, Mol. Microbiol. 13(5):765-73 (1994).
Jin, Z. et al., Conjugates of group A and W135 capsular polysaccharides of neisseria meningitidis bound to recombinant *Staphylococcus aureus* enterotoxin C1: preparation, physicochemical characterization, and immunological properties in mice, Infect Immun, 73(12):7887-7893 (2005).
Kauffmann, F. et al., Proposal for a change in the nomenclature of *Diplococcus pneumoniae* and a comparison of the Danish and American type designations, Intl Bulletin of Bacterial Nomenclature and Taxonomy 10(1):31-40 (1960).
Kehoe, M. et al., Cloning, Expression, and Mapping of the *Staphylococcus aureus* a-Hemolysin Determinant in *Escherichia coli* K-12, 41(3):1105-1111 (1985).
Kim, K. H. et al., Efficiency of a Pneumococcal Opsonophagocytic Killing Assay Improved by Multiplexing and by Coloring Colonies, Clin. Diagn. Lab. Immunol., 10(4):616-621 (2003).
Kojima, K. et al., Quantitation of IgG subclass antibodies to pneumococcal capsular polysaccharides by ELISA, using Pneumovax-specific antibodies as a reference, Tohoku J. Exp. Med., 161(3):209-215 (1990).
Koskela, M. and Leinonen, M., Comparison of ELISA and RIA for measurement of pneumococcal antibodies before and after vaccination with 14-valent pneumococcal capsular polysaccharide vaccine, J. Clin. Pathol., 34(1):93-98 (1981).
Laine, C. et al., Age-specific immunoglobulin G (IgG) and IgA to pneumococcal protein antigens in a population in coastal Kenya, Infection and Immunity, 72(6):3331-3335 (2004).
Lees, A. et al, Enhanced immunogenicity of protein-dextran conjugates: I. Rapid stimulation of enhanced antibody responses to poorly immunogenic molecules, Vaccine, 12(13): 1160-1166 (1994).

(56) References Cited

OTHER PUBLICATIONS

Ling, E. et al., Glycolytic enzymes associated with the cell surface of *Streptococcus pneumoniae* are antigenic in humans and elicit protective immune responses in the mouse, Clin. Exp. Immunol., 138:290-298 (2004).
Lu, Y. J. et al., A Bivalent Vaccine to Protect against *Streptococcus pneumoniae* and *Salmonella typhi*, Vaccine, 30(23):3405-3412 (2012).
Lu, Y. J. et al., Protection against Pneumococcal Colonization and Fatal Pneumonia by a Trivalent Conjugate of a Fusion Protein with the Cell Wall Polysaccharide, Infection and Immunity, 77(5):2076-2083 (2009).
Lu, Y. J.. et al., Interleukin-17A Mediates Acquired Immunity to Pneumococcal Colonization, PLoS Pathogens, 4(9):1-11 (2008).
Lu, Y-J. et al., Options for Inactivation, Adjuvant, and Route of Topical Administration of a Killed, Unencapsulated Pneumococcal Whole-Cell Vaccine, Clinical and Vaccine Immunology, 17(6): 1005-1012 (2010).
Malley, R. et al., Antibody and cell-mediated immunity to *Streptococcus pneumoniae*: implications for vaccine development, Journal of Molecular Medicine, 88(2):135-142 (2010).
Malley, R. et al., CD4+ T Cells Mediate Antibody-Independent Acquired Immunity to Pneumococcal Colonization, PNAS, 102(13):4848-4853 (2005).
Malley, R. et al., Intranasal Immunization with Killed Unencapsulated Whole Cells Prevents Colonization and Invasive Disease by Capsulated Pneumococci, Infection and Immunity, 69(8):4870-4873 (2001).
Malley, R. et al., Multiserotype Protection of Mice Against Pneumococcal Colonization of the Nasopharynx and Middle 3 Ear by Killed Nonencapsulated Cells Given Intranasally with a Nontoxic Adjuvanl, Infection and Immunity, 72 (7):4290-4292 (2004).
Martinez, J. E. et al., A flow cytometric opsonophagocytic assay for measurement of functional antibodies elicited after vaccination with the 23-valent pneumococcal polysaccharide vaccine, Clin. Diagn. Lab Immunol., 6(4):581-586 (1999).
Menzies, B. E. and Kernodle, D. S., Site-Directed Mutagenesis of the Alpha-Toxin Gene of *Staphylococcus aureus*: Role of Histidines in Toxin Activity in Vitro and in a Murine Model, Infection and Immunity, 62(5):1843-1847 (1994).
Moffitt, K. and Malley, R., Rationale and prospects for novel pneumococcal vaccines, Human Vaccines and Immunotherapeutics, 12:2 383-392 (2016).
Moffitt, K. L. et al., Identification of Protective Pneumococcal Thl 7 Antigens from the Soluble Fraction of a Killed Whole Cell Vaccine, PLoS ONE 7(8):e43445 (2012).
Moffitt, K. L. et al., TH17-Based vaccine design for prevention of *Streptococcus pneumoniae* colonization, Cell Host and Microbe, 9:158-165 (2011).
Munro, C. S. et al., Assessment of biological activity of immunoglobulin preparations by using opsonized micro-organisms to stimulate neutrophil chemiluminescence, Clin. Exp. Immunol., 61(1):183-188 (1985).
Myers, E W. and Miller, W., Optimal alignments in linear space, CABIOS, 4:11-17 (1989).
Nabors, G. S. et al., Immunization of healthy adults with a single recombinant pneumococcal surface protein A (PspA) variant stimulates broadly cross-reactive antibodies to heterologous PspA molecules, Vaccine 18(17):1743-54 (2000).
Nordlund, H. R. et al., Tetravalent single-chain avidin: from subunits to protein domains via circularly permuted avidins, Biochem. J., 392(Pt 3): 485-491 (2005).
Nuorti, J. P. and Whitney, C. G., Prevention of pneumococcal disease among infants and children—use of 13-valent pneumococcal conjugate vaccine and 23-valent pneumococcal polysaccharide vaccine, Morbidity and Mortality Weekly Report, 59:1-24 (2010).
Ojo-Amaize, E. A. et al., A rapid and sensitive chemiluminescence assay for evaluation of functional opsonic activity of Haemophilus influenzae type b-specific antibodies, Clin. Diagn. Lab. Immunol., 2(3):286-290 (1995).
Oloo, E. O. et al., Structure-guided antigen engineering yields pneumolysin mutants suitable for vaccination against pneumococcal disease, J. Biol. Chem. 286(14):12133-40 (2011).
O'Reilly, M. et al., Inactivation of the alpha-haemolysin gene of *Staphylococcus aureus* 8325-4 by site-directed mutagenesis and studies on the expression of its haemolysins, Microbial Pathogenesis, 1:125-138 (1986).
Paton, P C. et al., Purification and immunogenicity of genetically obtained pneumolysin toxoids and their conjugation to *Streptococcus pneumoniae* type 19F polysaccharide, Infect. Lmmun., 59(7):2297-2304 (1991).
Pneumovax® 23 (prescribing information). Whitehouse Station, NJ: Merck & Co.; May 2015.
Poljak, R. J., Production and structure of diabodies, Structure. 2(12):1121-1123 (1994).
Pollabauer, E. M. et al., The influence of carrier protein on the immunogenicity of simultaneously administered conjugate vaccines in infants, Vaccine, 27(11): 1674-1679 (2009).
Portnoi, M. et al., The vaccine potential of *Streptococcus pneumoniae* surface lectin- and non-lectin proteins, Vaccine, 24:1868-1873 (2006).
Prevnar 13® (prescribing information). New York, NY: Pfizer; Aug. 2017.
Richter, S. S. et al., Changes in pneumococcal serotypes and antimicrobial resistance after introduction of the 13 valent conjugate vaccine in the United States, Antimicrob Agents Chemother., 58:6484-6489 (2014).
Romero-Steiner, S. et al., Avidity determinations for Haemophilus influenzae Type b anti-polyribosylribitol phosphate antibodies, Clin. Diagn. Lab. Immunol., 12(9):1029-1035 (2005).
Romero-Steiner, S. et al., Standardization of an opsonophagocytic assay for the measurement of functional antibody activity against *Streptococcus pneumoniae* using differentiated HL-60 cells, Clin. Diagn. Lab. Immunol., 4(4):415-422 (1997).
Rosenberg, I.M., Protein Analysis and Purification, Springer Science + Business Media New York, 153-182 (1996).
Saeland, E. et al., Pneumococcal pneumonia and bacteremia model in mice for the analysis of protective antibodies, Microb. Pathog., 29(2):81-91 (2000).
Sanabria-Valentin, Dissertation, Department of Basic Medical Sciences, NYU, p. 8-9 describing the general structure of LPS (2008).
Sano, T. et al, Methods in Enzymology, Elsevier, 326: 305-307 (2000).
Saunders, F. K. et al., Pneumolysin, the thiol-activated toxin of *Streptococcus pneumoniae*, does not require a thiol group for in vitro activity, Infect. Immun. 57(8):2547-2552 (1989).
Scott, D. et al., Immunogenicity of biotinylated hapten-avidin complexes, Mol. Immunol., 21(11):1055-1060 (1984).
Sen, G. et al., In vivo humoral immune responses to isolated Pneumococcal polysaccharides are dependent on the presence of associated TLR ligands, The Journal of Immunology, 175(5):3084-3091 (2005).
Singh, M. and Indresh S., Advances in vaccine adjuvants for infectious diseases, Current HIV research 1(3):309-320 (2003).
Skolnick, J. and Fetrow, J. S., From genes to protein structure and function: novel applications of computational approaches in the genomic era, Trends in Biotechnology, 18:34-39 (2000).
Stack, A. M. et al., Minimum protective serum concentrations of pneumococcal anti-capsular antibodies in infant rats, J. Infect. Dis., 177(4):986-990 (1998).
Stevenson, T. et al, Synergistic protective effect of antibodies against polysaccharide type 3 and pneumococcal proteins in a highly virulent type 3 invasive disease model in mice Immunization with SPP2 Protects Against Type 3 Pneumococcal Sepsis Immunization with SPP2 and CPS3 Protect Synergistically Against High Dose (2022). <URL:https://affinivax.com/wp-content/uploads/2022/06/ISPPD_Final-Poster-Abstract_20Jun2022.pdf> [retrieved on Nov. 28, 2022].
Takakura, Y. et al, Tamavidin, a versatile affinity tag for protein purification and immobilization, J. Biotechnol., 145(4): 317-322 (2010).

(56) References Cited

OTHER PUBLICATIONS

Thermo Scientific Avidin-Biotin Technical Handbook, 2009, p. 16-17. Found on the Internet on May 5, 2016 at: https://www.thermofisher.com/content/dam/LifeTech/Images/integration/1601675_AvBi_HB_INTL.pdf.
Trzcinski, K. et al., Antibodies to Conserved Pneumococcal Antigens Correlate with, but Are Not Required for, 5 Protection Against Pneumococcal Colonization Induced by Prior Exposure in a Mouse Model, Infection and Immunity, 73(10):7043-7046 (2005).
Vickerman, M. M. et al., Genome-wide transcriptional changes in *Streptococcus gordonii* in response to competence signaling peptide, Journal of Bacteriology, 189(21):7799-7807 (2007).
Walker, B. and Bayley, H. et al., Key Residues for Membrane Binding, Oligomerization, and Pore Forming Activity of Staphylococcal a-Hemolysin Identified by Cysteine Scanning Mutagenesis and Targeted Chemical Modification*, The Journal of Biological Chemistry, 270(39):23065-23071 (1995).
Wardenburg, J. and Schneewind, O., Vaccine protection against *Staphylococcus aureus* pneumonia, J. Exp. Med., 205(2): 287-94 (2008).
Williams et al., Innate Imprinting by the Modified Heat-Labile Toxin of *Escherichia coli* (LTK63) Provides Generic Protection against Lung Infectious Disease, The Journal of Immunology, 173: 7435-7443 (2004).
Wizeman et al., Use of a while Genome Approach to Identify Vaccine Molecules Affording Protection against *Streptococcus pneumoniae* Infection, Infection and Immunity, 69(3):1593-1598 (2001).
Written Opinion for PCT/US11/28052 (Novel Immunogens and Methods for Discovery and Screening Thereof, filed Mar. 11, 2011) issued by ISA/KR, 6 pages (Dec. 27, 2011).
Written Opinion for PCT/US19/50800, 8 pages (mailed Dec. 31, 2019).
Written Opinion for PCT/US2012/037412 (Multiple Antigen Presenting Immunogenic Composition, and Methods and Uses Thereof, filed May 11, 2012), issued by ISA/FIPS, 4 pages (Aug. 23, 2012).
Written Opinion for PCT/US2012/037541 (Modified Biotin-Binding Protein, Fusion Proteins Thereof and Applications, filed May 11, 2012), issued by ISA/FIPS, 3 pages (Aug. 30, 2012).
Written Opinion for PCT/US2014/015254 (Protein Antigens That Provide Protection Against Pneumococcal Colonization and/or Disease, filed Feb. 7, 2014), issued by ISA/US, 5 pages (May 5, 2014).
Written Opinion for PCT/US2018/24810 (A Multiple Antigen Presenting System (MAPS)-Based *Staphylococcus aureus* Vaccine, Immunogenic Composition, and Uses Thereof, filed Mar. 28, 2018), issued by ISA/US, 9 pages (mailed Aug. 31, 2018).
Written Opinion for PCT/US22/43156, 7 pages (mailed Dec. 7, 2022).
Written Opinion for PCT2019050907, 6 pages (mailed Feb. 2, 2020).
Wu, W. et al., Th17-stimulating protein vaccines confer protection against Pseudomonas aeruginosa pneumonia, Am. J. Respir. Grit. Care Med., 186(5):420-427 (2012).
Zhang, F. et al, Design and evaluation of multiple antigen presenting system (MAPS)-based pneumococcal vaccine to prevent invasive disease and carriage, poster presented at the 10th International Symposium on Pneumococci and Pneumococcal Diseases (ISPPD-10), Glasgow, Scotland, Jun. 26-30, 2016.
Zhang, F. et al., Carrier Proteins Facilitate the Generation of Antipolysaccharide Immunit via Multi le Mechanisms, nBio, 1-13 (2022).
Zhang, F. et al., Multiple antigen-presenting system (MAPS) to induce comprehensive B- and T-cell immunity, Proc. Natl. Acad. Sci., 110(33):13564-13569 (2013).
Zhang, F. et al., Protection against *Staphylococcus aureus* Colonization and Infection by B- and T-Cell-Mediated Mechanisms, mBio, 9(5):e01949-18 (2018).

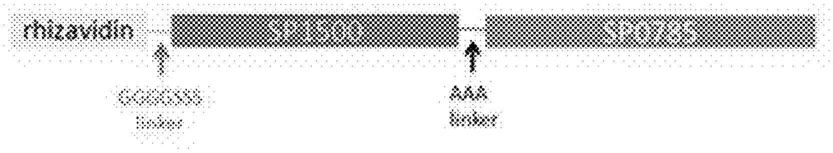

Rhizavidin
- Amino acids 45-179 of the biotin-binding protein rhizavidin (no signal peptide); 17 kDa
- No cross-reactivity in human serum samples obtained from subjects exposed to avidin

SP1500 (Amino Acid ABC Transporter, amino acid-binding protein (no signal peptide), conserved across *S. pneumonia* strains)
- Amino acids 27-278 of 278 amino acid parent (no signal peptide); 28 kDa
- No human homology

SP0785 (an efflux transporter protein conserved across *S. pneumonia* strains)
- Amino acids 33-399 of 399 amino acid parent (no signal peptide); 38 kDa
- No human homology

Linkers
- "GGGGSSS": "SSS" is from the Sac I site on PET21/24b plasmid. "GGGG" was added to create a flexible linker with minimal steric hindrance
- "AAA", the Not I site on PET21/24b plasmid.

| TYPE | STRUCTURE | ADDITIONAL INFORMATION |
| --- | --- | --- |
| 1 | 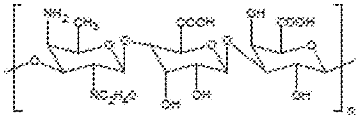<br>[→$^3$AAT*p*$^1$→$^4$D-Gal*p*A$^1$→$^3$D-Gal*p*A$^1$→]$_n$ | MW ($H^+$): 538.165 ($C_{20}H_{30}N_2O_{15}$)<br>MW ($Na^+$): 583.136 ($C_{20}H_{28}N_2O_{15}Na_2$)<br>MW ($Na^+$, OAc): 625.147 ($C_{22}H_{31}N_2O_{16}Na_2$)<br>Monosaccharides: 1 AAT, 2 D-GalA<br>AAT: 2-acetamido-4-amino-2,4,6-tridexoy- D-galactopyranose<br>Structure: Linear<br>Net Charge: -1<br>O-Acetate: 1 |
| 2 | 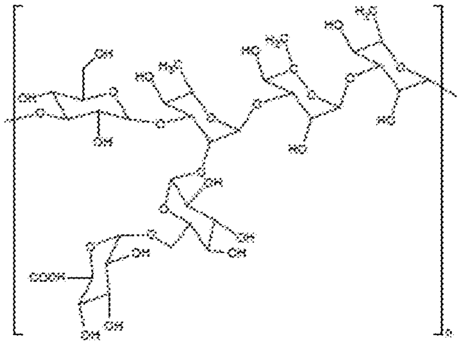<br>[→$^4$D-Glc*p*$^1$→$^3$L-Rha*p*$^1$→$^3$L-Rha*p*$^1$→$^3$L-Rha*p*$^1$→]$_n$<br>D-Glc*p*A$^1$→$^6$D-Glc*p*$^1$ $J^2$ | MW ($H^+$): 938.829 ($C_{36}H_{58}O_{28}$)<br>MW ($Na^+$): 960.811 ($C_{36}H_{57}O_{28}Na_1$)<br>Monosaccharides: 2 D-Glc, 3 L-Rha, 1 D-GlcA<br>Structure: Branched<br>Net Charge: -1 |
| 3 | 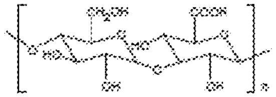<br>[→$^4$D-Glc*p*$^1$→$^3$D-Glc*p*A$^1$→]$_n$ | MW ($H^+$): 338.085 ($C_{12}H_{18}O_{11}$)<br>MW ($Na^+$): 360.067 ($C_{12}H_{17}O_{11}Na_1$)<br>Monosaccharides: 1 D-Glc, 1 D-GlcA<br>Structure: Linear<br>Net Charge: -1 |

*Figure continued on next page*

FIG. 9 cont'd

| TYPE | STRUCTURE | ADDITIONAL INFORMATION |
| --- | --- | --- |
| 4 | 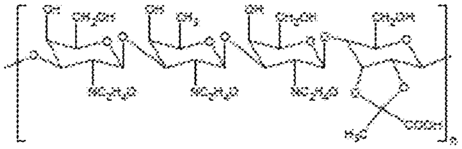<br>[→$^{3}$D-ManpNac$^{1}$→$^{3}$L-FucpNac$^{1}$→$^{3}$D-GalpNac$^{1}$→$^{4}$D-Galp$^{1}$→]<br>$^{3}$[ Pyr ]$^{2}$ | MW ($H^+$): 825.302 ($C_{33}H_{51}N_3O_{21}$)<br>MW ($Na^+$): 847.283 ($C_{33}H_{50}N_3O_{21}Na_1$)<br>Monosaccharides: 1 D-Gal, 1 D-GalNac, 1 D-ManNac, 1 L-FucNac<br>Structure: Linear<br>Net Charge: -1<br>Pyruvate: 1 |
| 5 | 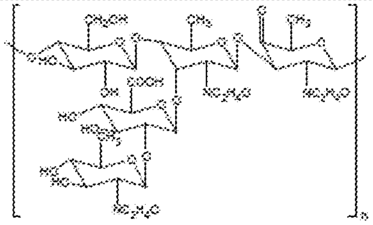<br>[→$^{4}$D-Glcp$^{1}$→$^{4}$L-FucpNAc$^{1}$→$^{3}$D-Sugp$^{1}$→]$_n$<br>L-PnepNAc$^{1}$→$^{2}$D-GlcpA$^{1}$]$^{3}$ | MW ($H^+$): 897.323 ($C_{36}H_{55}N_3O_{23}$)<br>MW ($Na^+$): 919.305 ($C_{36}H_{54}N_3O_{23}Na_1$)<br>Monosaccharides: 1 D-Glc, 1 L-FucNac, 1 D-GlcA, 1 D-Sug, 1 L-PneNAc<br>D-Sug: 2-acetamido-2,6,-dideoxy-D- xylohexos-4-ulose<br>L-PneNac: 2-acetamido-2,6,-dideoxy-L-talose (pneumosamine)<br>Structure: Branched<br>Net Charge: -1 |
| 6A | 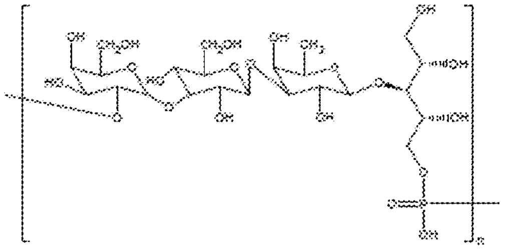<br>[→$^{2}$D-Galp$^{1}$→$^{3}$D-Glcp$^{1}$→$^{3}$L-Rhap$^{1}$→$^{4}$D-Ribitol$^{5}$→$PO_4$→]$_n$ | MW ($H^+$): 683.525 ($C_{23}H_{40}O_{21}P_1$)<br>MW ($Na^+$): 704.507 ($C_{23}H_{39}O_{21}P_1Na_1$)<br>Monosaccharides: 1 D-Glc, 1 D-Gal, 1 L-Rha, 1 Ribitol<br>Structure: Linear<br>Net Charge: -1<br>Phosphorous: 1 in polysaccharide backbone |

*Figure continued on next page*

FIG. 9 cont'd

| TYPE | STRUCTURE | ADDITIONAL INFORMATION |
| --- | --- | --- |
| 6B | 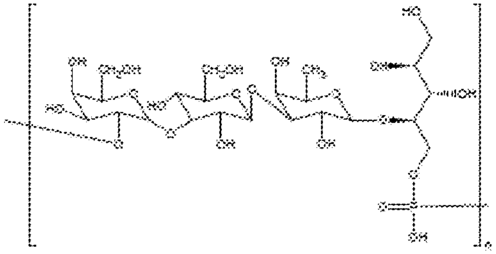<br>[→³D-Gal*p*¹→³D-Glc*p*¹→³L-Rha*p*¹→⁴D-Ribitol⁵→PO₄→]ₙ | MW (H⁺): 684.188 ($C_{23}H_{41}O_{21}P_1$)<br>MW (Na⁺): 706.170 ($C_{23}H_{40}O_{21}P_1Na_1$)<br>Monosaccharides: 1 D-Glc, 1 D-Gal, 1 L-Rha, 1 Ribitol<br>Structure: Linear<br>Net Charge: -1<br>Phosphorus: 1 in polysaccharide backbone |
| 7F | 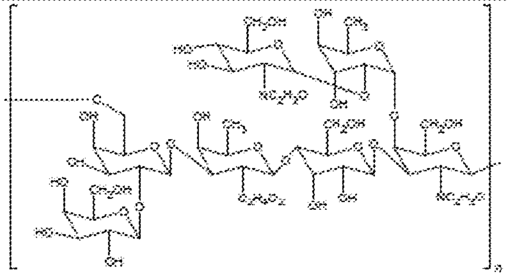<br>[→⁶D-Gal*p*¹→³L-Rha*p*¹→⁴D-Glc*p*¹→³D-Gal*p*NAc¹→]ₙ<br>D-Gal*p*¹ ↑² AcO ↑³ D-Glc*p*NAc¹→²L-Rha*p*¹ ↑⁴ | MW (H⁺): 1226.444 ($C_{48}H_{77}N_2O_{34}$)<br>Monosaccharides: 1 D-Glc, 2 D-Gal, 2 L-Rha, 1 D-GlcNac, 1 D-GalNac<br>Structure: Branched<br>Net Charge: 0<br>O-Acetate: 1 |
| 8 | 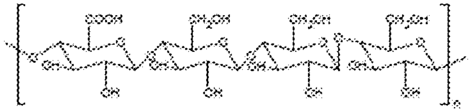<br>[→⁴D-Glc*p*A¹→⁴D-Glc*p*¹→⁴DGlc*p*¹→⁴D-Gal*p*¹→]ₙ | MW (H⁺): 662.546 ($C_{24}H_{38}O_{21}$)<br>MW (Na⁺): 684.528 ($C_{24}H_{37}O_{21}Na_1$)<br>Monosaccharides: 2 D-Glc, 1 D-Gal, 1 D-GlcA<br>Structure: Linear<br>Net Charge: -1 |

*Figure continued on next page*

FIG. 9 cont'd

| TYPE | STRUCTURE | ADDITIONAL INFORMATION |
|---|---|---|
| 9N | 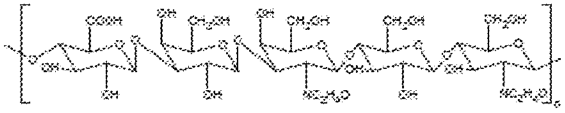<br>$[\rightarrow{}^{4}$D-GlcpA$^{1}\rightarrow{}^{3}$D-Galp$^{1}\rightarrow{}^{4}$D-ManpNAc$^{1}\rightarrow{}^{4}$D-Glcp$^{1}\rightarrow{}^{4}$D-GlcpNAc$^{1}\rightarrow]_{n}$ | MW ($H^+$): 906.296 ($C_{34}H_{54}N_2O_{26}$)<br>MW ($Na^+$): 928.278 ($C_{34}H_{53}N_2O_{26}Na_1$)<br>Monosaccharides: 1 D-Glc, 1 D-Gal, 1 D-GlcNac, 1 D-ManNac, 1 D-GlcA<br>Structure: Linear<br>Net Charge: -1 |
| 9V | 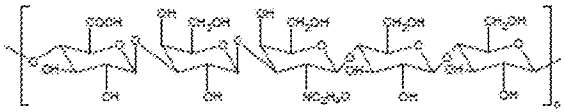<br>$[\rightarrow{}^{4}$D-GlcpA$^{1}\rightarrow{}^{3}$D-Galp$^{1}\rightarrow{}^{3}$D-ManpNAc$^{1}\rightarrow{}^{4}$D-Glcp$^{1}\rightarrow{}^{4}$D-Glcp$^{1}\rightarrow]_{n}$ | MW ($H^+$): 865.270 ($C_{32}H_{51}NO_{26}$)<br>MW ($Na^+$): 887.252 ($C_{32}H_{50}NO_{26}Na_1$)<br>MW ($Na^+$, OAc): 971.273 ($C_{36}H_{54}NO_{28}Na_1$)<br>Monosaccharides: 2 D-Glc, 1 D-Gal, 1 D-ManNac, 1 D-GlcA<br>Structure: Linear<br>Net Charge: -1<br>O-Acetate: 2 |
| 10A | 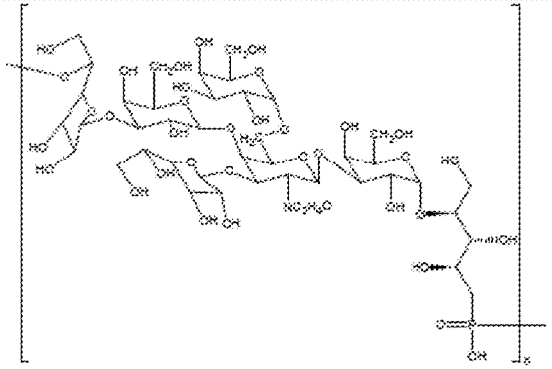<br>D-Galp$^{1}\downarrow^{6}$<br>$[\rightarrow{}^{3}$D-Galf$^{1}\rightarrow{}^{3}$D-Galp$^{1}\rightarrow{}^{4}$D-GalpNAc$^{1}\rightarrow{}^{3}$D-Galp$^{1}\rightarrow{}^{5}$D-Ribitol$^{5}\rightarrow$PO$_{4}\rightarrow]_{n}$<br>D-Galf$^{1}\uparrow^{2}$ | MW ($H^+$): 1242.076 ($C_{45}H_{80}NO_{36}P_1$)<br>MW ($Na^+$): 1264.057 ($C_{45}H_{79}NO_{36}P_1Na_1$)<br>Monosaccharides: 5 D-Gal, 1 D-GalNac, 1 Ribitol<br>Structure: Branched<br>Net Charge: -1<br>Phosphorous: 1 in polysaccharide backbone |

Figure continued on next page

FIG. 9 cont'd

| TYPE | STRUCTURE | ADDITIONAL INFORMATION |
|---|---|---|
| 11A | 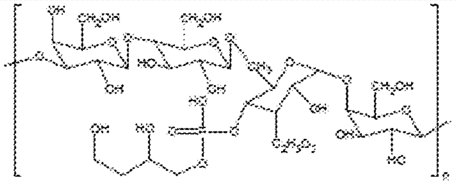<br>[→$^{3}$D-Gal$p^{1}$→$^{4}$D-Glc$p^{1}$→$^{6}$D-Glc$p^{1}$→$^{4}$D-Gal$p^{1}$→]$_n$<br>Glycerol$^{1}$→ PO$_4$ J$^{4}$ | MW ($H^+$): 859.692 ($C_{30}H_{52}O_{26}P_1$)<br>MW ($Na^+$): 881.674 ($C_{30}H_{51}O_{26}P_1Na_1$)<br>MW ($Na^+$, OAc): 923.711 ($C_{32}H_{53}O_{27}P_1Na_1$)<br>Monosaccharides: 2 D-Glc, 2 D-Gal, 1 Glycerol<br>Structure: Linear<br>Net Charge: -1<br>Phosphorous: 1 in polysaccharide sidechain<br>O-Acetate: 1 |
| 12F | 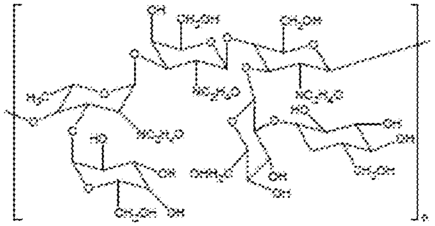<br>[→$^{4}$L-Fuc$p$NAc$^{1}$→$^{3}$D-Gal$p$NAc$^{1}$→$^{4}$D-Man$p$NAcA$^{1}$→]<br>D-Gal$p^{1}$ J$^{3}$ D-Glc$p^{1}$→$^{2}$D-Glc$p^{1}$ J$^{3}$ | MW ($H^+$): 1080.000 ($C_{42}H_{68}N_2O_{30}$)<br>Monosaccharides: 2 D-Glc, 1 D-Gal, 1 D-GalNac, 1 L- FucNac, 1 D-ManNacA<br>Structure: Branched<br>Net Charge: -1 |
| 14 | 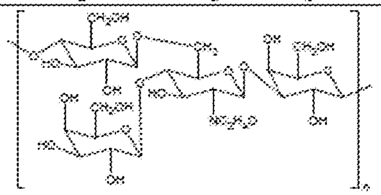<br>[→$^{4}$D-Glc$p^{1}$→$^{6}$D-Glc$p$NAc$^{1}$→$^{3}$D-Gal$p^{1}$→]$_n$<br>D-Gal$p^{1}$ J$^{4}$ | MW ($H^+$): 689.238 ($C_{26}H_{43}NO_{20}$)<br>Monosaccharides: 1 D-Glc, 2 D-Gal, 1 D-GlcNac<br>Structure: Branched<br>Net Charge: 0 |

*Figure continued on next page*

FIG. 9 cont'd

| TYPE | STRUCTURE | ADDITIONAL INFORMATION |
| --- | --- | --- |
| 15B | 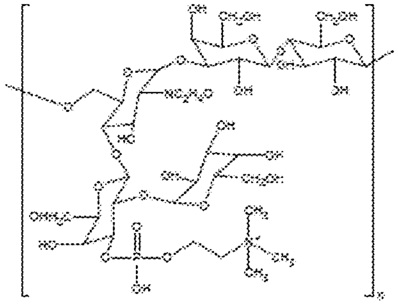<br>[→$^4$D-GlcpNAc$^1$→$^3$D-Galp$^1$→$^4$D-Glcp$^1$→]n<br>$^4$↑$^1$D-Galp$^2$←$^1$D-Galp<br>$^3$↑[PO$_4$→CH$_2$CHN(CH$_3$)$_3$]$_{0.2}$ | MW (H$^+$): 851.755 ($C_{32}H_{53}NO_{25}$)<br>MW (H$^+$, OAc): 893.792 ($C_{34}H_{55}NO_{26}$)<br>MW (Na$^+$, OAc, PC): 1059.927 ($C_{39}H_{65}N_2O_{29}P_1$)<br>Monosaccharides: 1 D-Glc, 3 D-Gal, 1 D-GlcNac<br>Structure: Branched<br>Net Charge: -1<br>Phosphorous: 1 in polysaccharide sidechain<br>O-Acetate: 1<br>Pyruvate: 1<br>Note: Published structure indicates 0.2 mol of phosphocholine per mol of repeat unit. Nuclear magnetic resonance analysis at Merck suggests that phosphocholine is not present. |
| 17F | 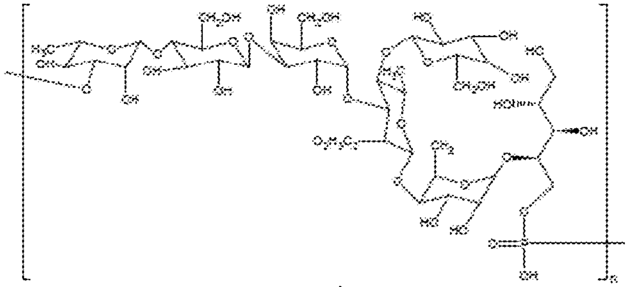<br>OAc↓$^3$<br>[→$^3$L-Rhap$^1$→$^4$D-Glcp$^1$→$^3$D-Galp$^1$→$^3$L-Rhap$^1$→$^4$L-Rhap$^1$→$^2$D-Arabinitol$^1$→PO$_4$→]$_n$<br>D-Galp$^1$↓$^4$ | MW (H$^+$): 1179.985 ($C_{43}H_{72}O_{35}P_1$)<br>MW (Na$^+$): 1201.966 ($C_{43}H_{71}O_{35}P_1Na_1$)<br>Monosaccharides: 1 D-Glc, 2 D-Gal, 3 L-Rha, 1 Arabinitol<br>Structure: Branched<br>Net Charge: -1<br>Phosphorous: 1 in polysaccharide backbone<br>O-Acetate: 1<br>Pyruvate: 1 |

Figure continued on next page

FIG. 9 cont'd

| TYPE | STRUCTURE | ADDITIONAL INFORMATION |
|---|---|---|
| 18C | 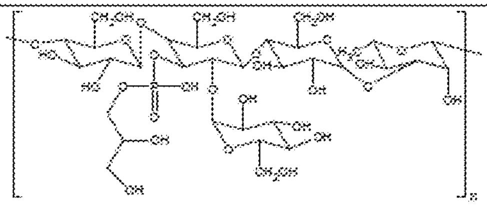<br>D-Glc$p^{1}\downarrow^{2}$<br>[$\rightarrow^{4}$D-Glc$p^{1}\rightarrow^{6}$D-Gal$p^{1}\rightarrow^{4}$D-Glc$p^{1}\rightarrow^{3}$L-Rha$p^{1}\rightarrow$]$_n$<br>Glycerol$^{1}\rightarrow$PO$_4$]$^{3}$ | MW ($H^+$): 948.272 ($C_{33}H_{57}O_{29}P_1$)<br>MW ($Na^+$): 970.254 ($C_{33}H_{56}O_{29}P_1Na_1$)<br>MW ($Na^+$, OAc): 1012.265 ($C_{35}H_{58}O_{30}P_1Na_1$)<br>Monosaccharides: 3 D-Glc, 1 D-Gal, 1 L-Rha, 1 Glycerol<br>Structure: Branched<br>Net Charge: -1<br>Phosphorous: 1 in polysaccharide sidechain<br>O-Acetate: 1 |
| 19A | 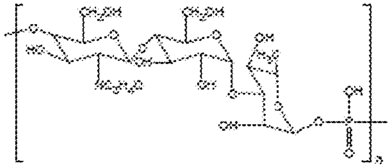<br>[$\rightarrow^{4}$D-Man$p$NAc$^{1}\rightarrow^{4}$D-Glc$p^{1}\rightarrow^{2}$L-Rha$p^{1}\rightarrow$PO$_4\rightarrow$]$_n$ | MW ($H^+$): 591.156 ($C_{20}H_{34}N_1O_{17}P_1$)<br>MW ($Na^+$): 613.138 ($C_{20}H_{33}N_1O_{17}P_1Na_1$)<br>Monosaccharides: 1 D-Glc, 1 L-Rha, 1 D-ManNac<br>Structure: Linear<br>Net Charge: -1<br>Phosphorous: 1 in polysaccharide backbone |
| 19F | 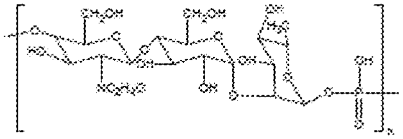<br>[$\rightarrow^{4}$D-Man$p$NAc$^{1}\rightarrow^{4}$D-Glc$p^{1}\rightarrow^{2}$L-Rha$p^{1}\rightarrow$PO$_4\rightarrow$]$_n$ | MW ($H^+$): 591.156 ($C_{20}H_{34}N_1O_{17}P_1$)<br>MW ($Na^+$): 613.138 ($C_{20}H_{33}N_1O_{17}P_1Na_1$)<br>Monosaccharides: 1 D-Glc, 1 L-Rha, 1 D-ManNac<br>Structure: Linear<br>Net Charge: -1<br>Phosphorous: 1 in polysaccharide backbone |

*Figure continued on next page*

FIG. 9 cont'd

| TYPE | STRUCTURE | ADDITIONAL INFORMATION |
|---|---|---|
| 20B | 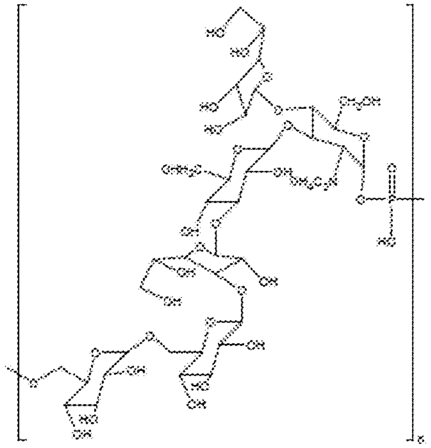<br>$[\rightarrow{}^{4}$D-Glc$p^{1}\rightarrow{}^{6}$D-Glc$p^{1}\rightarrow{}^{3}$D-Gal$f^{1}\rightarrow{}^{3}$D-Glc$p^{1}\rightarrow{}^{3}$D-Glc$p$NAc$^{1}\rightarrow PO_4\rightarrow]_n$<br>D-Gal$f^{1}\ ]^{4}$ | MW ($H^+$): 1093.875 ($C_{38}H_{64}NO_{33}P_1$)<br>MW ($Na^+$): 1115.857 ($C_{38}H_{63}NO_{33}P_1Na_1$)<br>MW ($Na^+$, OAc): 1157.894 ($C_{40}H_{65}NO_{34}P_1Na_1$)<br>Monosaccharides: 3 D-Glc, 2 D-Gal, 1 D-GlcNac<br>Structure: Branched<br>Net Charge: -1<br>Phosphorus: 1 in polysaccharide backbone<br>O-Acetate: 1 |
| 22F | 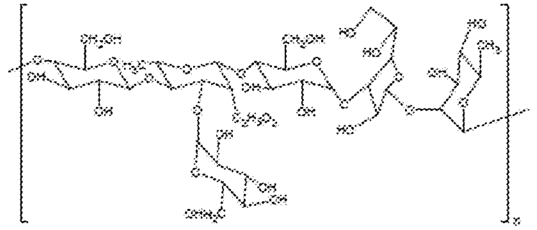<br>D-Glc$p^{1}\ ]^{3}$<br>$[\rightarrow{}^{4}$D-Glc$p$A$^{1}\rightarrow{}^{4}$L-Rha$p^{1}\rightarrow{}^{4}$D-Glc$p^{1}\rightarrow{}^{3}$D-Gal$f^{1}\rightarrow{}^{2}$L-Rha$p^{1}\rightarrow]_n$<br>OAc$\ ]^{2}$ | MW ($H^+$): 982.882 ($C_{38}H_{62}O_{29}$)<br>Monosaccharides: 2 D-Glc, 1 D-Gal, 2 L-Rha, 1 D-GlcA<br>Structure: Branched<br>Net Charge: -1<br>O-Acetate: 1 |

Figure continued on next page

FIG. 9 cont'd

| TYPE | STRUCTURE | ADDITIONAL INFORMATION |
| --- | --- | --- |
| 23F | 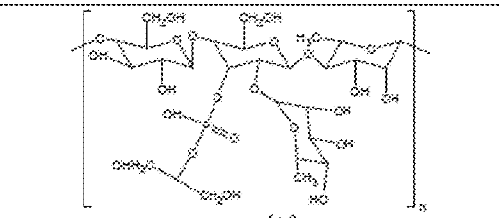<br>L-Rhap$^1$↓$^2$<br>[→$^4$D-Glcp$^1$→$^2$D-Galp$^1$→$^4$L-Rhap$^1$→]<br>Glycerol$^2$→PO$_4$⌋$^3$ | MW (H$^+$): 770.225 ($C_{27}H_{47}O_{23}P_1$)<br>MW (Na$^+$): 792.207 ($C_{27}H_{46}O_{23}P_1Na_1$)<br>Monosaccharides: 1 D-Glc, 1 D-Gal, 2 L-Rha, 1 Glycerol<br>Structure: Branched<br>Net Charge: -1<br>Phosphorous: 1 in polysaccharide sidechain |
| 33F | 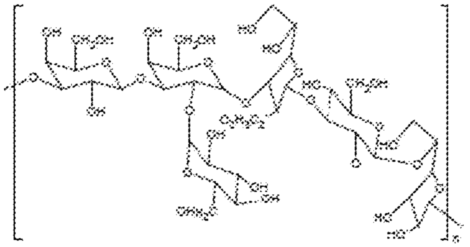<br>[→$^3$D-Galp$^1$→$^3$D-Galp$^1$→$^3$D-Galf$^1$→$^3$D-Glcp$^1$→$^5$D-Galf$^1$→]$_x$<br>D-Galp$^1$⌉$^2$ OAc⌋$^2$ | MW (H$^+$): 1014.880 ($C_{38}H_{62}O_{31}$)<br>MW (H$^+$, OAc): 1056.917 ($C_{40}H_{64}O_{32}$)<br>Monosaccharides: 1 D-Glc, 5 D-Gal<br>Structure: Branched<br>Net Charge: 0<br>O-Acetate: 1 |

Figure continued on next page

FIG. 9 cont'd

| TYPE | STRUCTURE | ADDITIONAL INFORMATION |
|---|---|---|
| 6C | 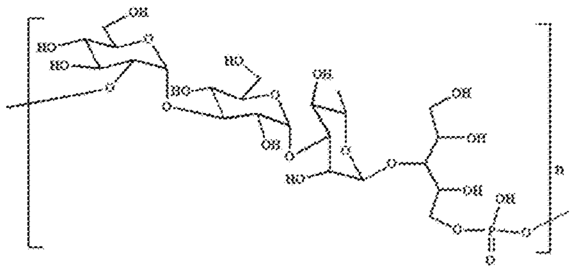<br>→2)-α-D-Glcp-(1→3)-α-D-Glcp-(1→3)-α-L-Rhap-(1→3)-D-Ribitol-(5→phosphate- | MW ($H^+$): 684.53 ($C_{23}H_{41}O_{21}P$)<br>MW ($Na^+$): 706.51 ($C_{23}H_{40}O_{21}P$ Na)<br>Composition: 2 D-Glc, 1 L-Rha, 1 Ribitol<br>Structure: Linear<br>Net Charge: -1<br>Phosphate: 1 in backbone |
| 7C | 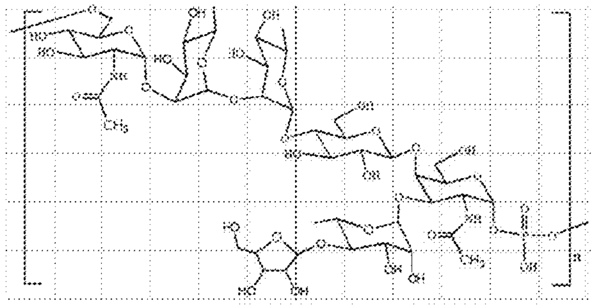<br>→6)-α-D-GlcNAc-(1→2)-α-L-Rhap-(1→2)-β-L-Rhap-(1→4)-β-D-Glcp-(1→3)-α-D-GalNAc-(1→O-P→<br>↑(1-3)<br>β-D-Ribf-(1→4)-α-L-Rhap | MW ($H^+$): 1219.04 ($C_{45}H_{75}N_2O_{34}P$)<br>MW ($Na^+$): 1241.03 ($C_{45}H_{74}N_2O_{34}PNa$)<br>Composition: 1 D-Glc, 3 L-Rha, 1 D-Rib, 1 D-GlcNAc, 1 D-GalNAc<br>Structure: Branched<br>Net Charge: -1<br>Phosphate: 1 in backbone |

*Figure continued on next page*

FIG. 9 cont'd

| TYPE | STRUCTURE | ADDITIONAL INFORMATION |
| --- | --- | --- |
| 15A | 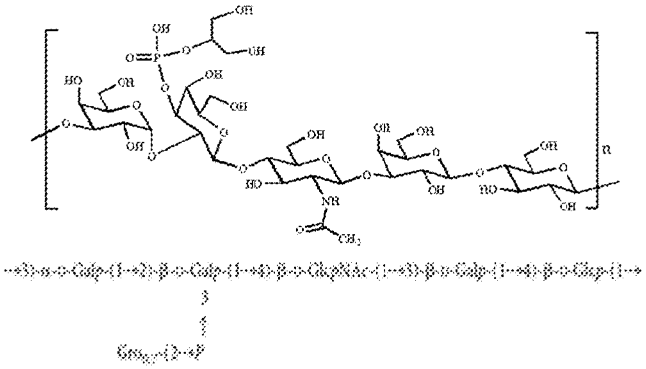 | MW ($H^+$): 1005.81 ($C_{35}H_{60}NO_{30}P$)<br>MW ($Na^+$): 1027.80 ($C_{35}H_{59}NO_{30}PNa$)<br>Composition: 1 D-Glc, 3 D-Gal, 1 D-GlcNAc, 1 Gro<br>Structure: Linear<br>Net Charge: -1<br>Phosphate: 1 in branch |
| 16F | 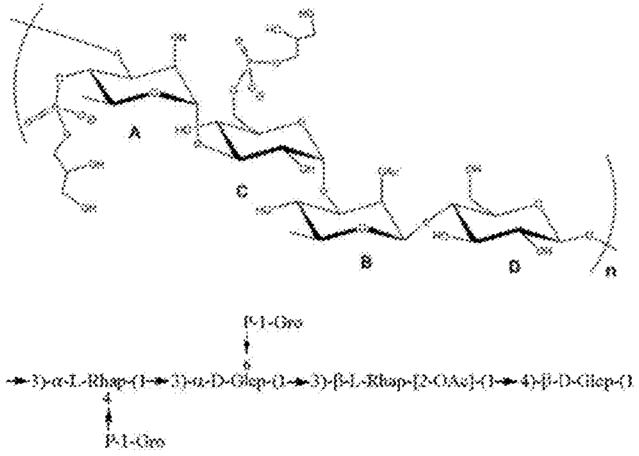 | MW ($H^+$): 966.72 ($C_{32}H_{56}O_{29}P_2$)<br>MW ($Na^+$): 988.70 ($C_{32}H_{55}O_{29}P_2Na$)<br>MW (2 $Na^+$): 1010.68 ($C_{32}H_{54}O_{29}P_2Na_2$)<br>Composition: 2 D-Glc, 2 L-Rha, 2 Gro, 1 O-Ac<br>Structure: Linear<br>Net Charge: -2<br>Phosphate: 2 in branch |

Figure continued on next page

FIG. 9 cont'd

| TYPE | STRUCTURE | ADDITIONAL INFORMATION |
|---|---|---|
| 23A | 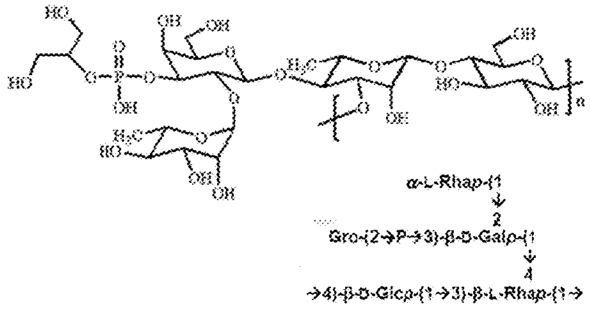 | MW ($H^+$): 770.62 ($C_{27}H_{47}O_{23}P$)<br>MW ($Na^+$): 792.60 ($C_{27}H_{46}O_{23}PNa$)<br>Composition: 1 D-Glc, 1 D-Gal, 2 L-Rha, 1 Gro<br>Structure: Branched<br>Net Charge: -1<br>Phosphate:1 in branch |
| 23B | 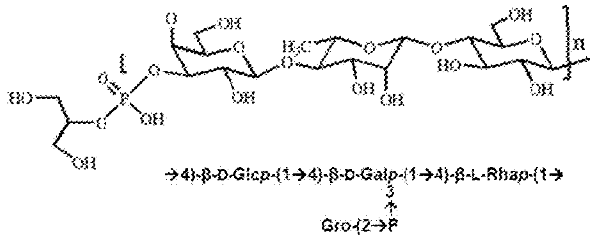 | MW ($H^+$): 624.48 ($C_{21}H_{37}O_{19}P$)<br>MW ($Na^+$): 646.46 ($C_{21}H_{36}O_{19}PNa$)<br>Composition: 1 D-Glc, 1 D-Gal, 1 L-Rha, 1 Gro<br>Structure: Linear<br>Net Charge: -1<br>Phosphate:1 in branch |
| 24F | 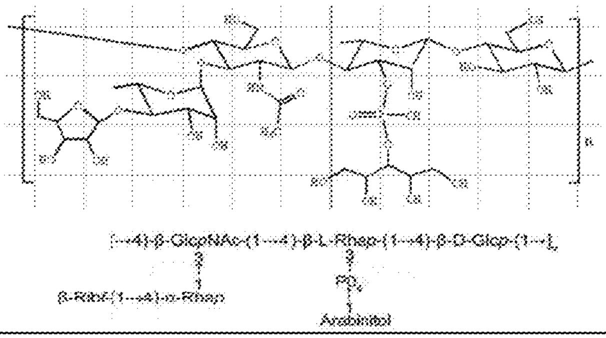 | MW ($H^+$): 1003.84 ($C_{36}H_{62}NO_{29}P$)<br>MW ($Na^+$): 1025.82 ($C_{36}H_{61}NO_{29}PNa$)<br>Composition: 1 D-Glc, 2 L-Rha, 1 D-GlcNAc, 1 D-Rib, 1 Arabinitol<br>Structure: Branched<br>Net Charge: -1<br>Phosphate: 1 in branch |

*Figure continued on next page*

FIG. 9 cont'd

| TYPE | STRUCTURE | ADDITIONAL INFORMATION |
|---|---|---|
| 31 | 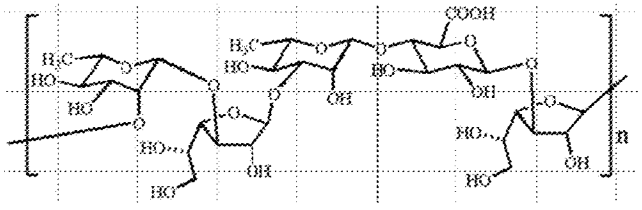<br>→2)-β-L-Rhap-(1→3)-β-D-Galf-(1→3)-β-L-Rhap-(1→4)-β-D-GlcpA-(1→3)-β-D-Galf-(1→ | MW ($H^+$): 792.69 ($C_{30}H_{48}O_{24}$)<br>MW ($Na^+$): 814.67 ($C_{30}H_{47}O_{24}Na$)<br>Composition: 2 D-Gal, 2 L-Rha, 1 GlcA, 3 O-Ac (80% each)<br>Structure: Linear<br>Net Charge: -1<br><br>3 O-acetyl sites not determined; each site with ~80% acetylation |
| 35B | 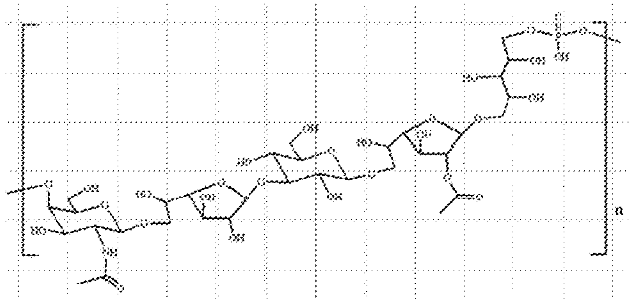<br>→4)-β-D-GalpNAc-(1→6)-β-D-Galf-(1→3)-β-D-Glcp-(1→6)-β-D-Galf2Ac$_{0.7}$-(1→1)-Rib-ol-(5→P→ | MW ($H^+$): 945.76 ($C_{33}H_{56}NO_{28}P$)<br>MW ($Na^+$): 967.74 ($C_{33}H_{55}NO_{28}PNa$)<br>Composition: 1 D-Glc, 2 D-Gal, 1 D-GalNAc, 1 Ribitol, 0.7 O-Ac<br>Structure: Linear<br>Net Charge: -1<br>Phosphate: 1 in backbone |

| Geo Means (ug/mL) | A | B | C | D | E | F | G | H |
|---|---|---|---|---|---|---|---|---|
| P1 | 52.3 | 38.0 | 56.9 | 61.7 | 48.0 | 0.4 | 58.4 | 0.4 |
| P2 | 372.7 | 264.4 | 274.0 | 356.6 | 321.1 | 1.2 | 352.1 | 0.4 |

| Geo Means (ug/mL) | A | B | C | D | E | F | G | H |
|---|---|---|---|---|---|---|---|---|
| P1 | 0.4 | 0.5 | 9.1 | 9.6 | 6.5 | 13.5 | 15.1 | 0.4 |
| P2 | 0.4 | 0.4 | 382.7 | 406.7 | 402.3 | 625.4 | 719.4 | 0.4 |

SP0435-specific IgG titers

| Geo Means (ug/mL) | A | B | C | D | E | F | G | H |
|---|---|---|---|---|---|---|---|---|
| P1 | 0.42 | 0.43 | 0.50 | 0.47 | 0.42 | 0.42 | 0.42 | 0.42 |
| P2 | 0.44 | 0.42 | 4.80 | 8.84 | 6.05 | 8.36 | 8.71 | 0.42 |

| Geo Means (IC50) | A | B | C | D | E | F | G | H |
|---|---|---|---|---|---|---|---|---|
| P0 | N/A | N/A | 437 | 564 | 478 | 529 | 642 | TBD |
| P1 | N/A | N/A | 552 | 662 | 479 | 445 | TBD | TBD |
| P2 | N/A | N/A | 4514 | 4531 | 5900 | 6525 | 4529 | TBD |

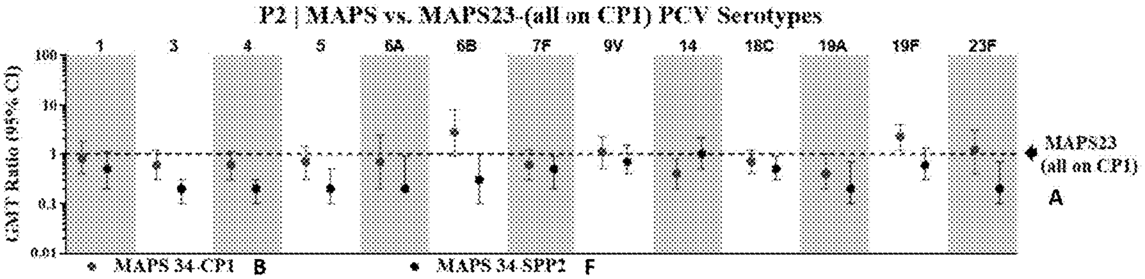
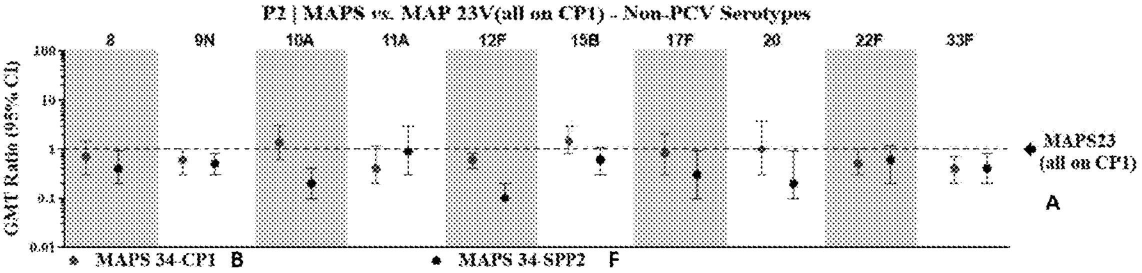
FIG. 18

| Geometric mean IC50 (serum dilution) | | | |
|---|---|---|---|
| Group | P0 | P2 | P3 |
| non-His-tagged SPP2 | 400 | 1109 | 1194 |

| Geometric mean IC50 (serum dilution) | | | |
|---|---|---|---|
| Group | P0 | P2 | P3 |
| PdT(G294P) | n/a | 500 | 1535 |

MULTIVALENT PNEUMOCOCCAL VACCINES

CROSS-REFERENCE TO RELATED APPLICATIONS

The present application is a continuation of U.S. application Ser. No. 17/942,089 filed Sep. 9, 2022, now U.S. Pat. No. 12,036,276 issued Jul. 16, 2024, which claims the benefit of U.S. Provisional Application No. 63/242,487 filed on Sep. 9, 2021 and U.S. Provisional Application No. 63/353,014 filed on Jun. 16, 2022, the contents of each of which are hereby incorporated herein in their entireties.

SEQUENCE LISTING

The present application contains a Sequence Listing which has been submitted electronically in XML file format and is hereby incorporated by reference in its entirety. Said XML copy, created on Nov. 21, 2022, is named "2011588-0193_SL.xml" and is 111,051 bytes in size.

BACKGROUND

*Streptococcus pneumoniae* remains a leading cause of serious illness, including bacteremia, sepsis, meningitis and pneumonia, among children and adults worldwide. Morbidity and mortality among infants, young children, the elderly and subjects who have certain underlying medical conditions is high.

*S. pneumoniae* is a Gram-positive encapsulated coccus that colonizes the nasopharynx in about 5-10% of healthy adults and 20-40% of healthy children. Normal colonization becomes infectious when *S. pneumoniae* is carried into the Eustachian tubes, nasal sinuses, lungs, bloodstream, meninges, joint spaces, bones and peritoneal cavity. *S. pneumoniae* infection is the most frequent cause of bacteremia, pneumonia, meningitis, sinusitis and acute otitis media [CDC, 2010].

Pneumococcal disease can be invasive or non-invasive. The most common form of non-invasive disease, non-bacteremic pneumococcal pneumonia, remains one of the most frequent causes for pneumonia hospitalizations. Invasive pneumococcal disease (IPD) is defined as *S. pneumoniae* isolated from a normally sterile site (e.g., cerebrospinal fluid, blood, joint fluid, pleural fluid or peritoneal fluid). The highest incidence of IPD is found at the extremes of age—in elderly adults and in young children younger than 2 years of age. In the U.S., prior to advent of the first pneumococcal vaccine, *S. pneumoniae* caused approximately 17,000 cases of invasive disease each year among children younger than 5 years of age, including 700 cases of meningitis and 200 deaths [CDC, 2000]. The highest morbidity and mortality rates have been reported in developing countries, but the disease burden is also considerable in industrialized countries.

*S. pneumoniae* has several virulence factors that enable the organism to evade the immune system. Examples include a polysaccharide capsule that prevents phagocytosis by host immune cells, proteases that inhibit complement-mediated opsonization, and proteins that cause lysis of host cells. In the polysaccharide capsule, the presence of complex polysaccharides forms the basis for dividing pneumococci into different serotypes. To date, close to 100 serotypes of *S. pneumoniae* have been identified.

Two vaccines for *S. pneumoniae* are currently available in the U.S.; PCV13 and PPSV23. PCV13 cannot confer protection against most of the known serotypes of *S. pneumoniae*. While PPSV23 includes polysaccharide components of more serotypes of *S. pneumoniae* than PCV13, it induces an immune response that is neither long-lasting nor anamnestic upon subsequent challenge. PPSV23 protects adults and the elderly against invasive pneumococcal disease; however, no consistent effect has been observed in the prevention of pneumonia [Gruber et al, 2008].

Thus, there is a medical need for a vaccine that provides T-cell dependent immunity against a broad range of serotypes of *S. pneumoniae*.

SUMMARY

The present disclosure addresses the lack of suitable technologies for the prevention and/or treatment of pneumococcal infection. Among other things, the present disclosure addresses challenges in providing vaccines with sufficient immunogenicity to protect against invasive pneumococcal disease and pneumonia, by inducing a T- and B-cell response providing immunity against a broad range of *S. pneumoniae* serotypes including those serotypes not included in the vaccine.

The present Applicant has previously described that a MAPS multivalent pneumococcal vaccines (e.g., in some embodiments, comprising 24-valent pneumococcal polysaccharide serotypes; see, for example, WO2020/056202) can be remarkably useful for prevention and/or treatment of pneumococcal infection when administered to subjects. Attributes of such MAPS multivalent vaccines addressed certain problems associated with standard *S. pneumoniae* vaccines such as PCV13 and PPSV23. For example, in some embodiments, a MAPS platform provides various advantages including, e.g., high affinity (dissociation constant [KD]≈10-15M), non-covalent binding between biotin and rhizavidin, a biotin-binding protein that has no significant predicted homology with human proteins. Among other things, such a MAPS multivalent pneumococcal vaccine could induce a T- and B-cell immune response against a broad range of *S. pneumoniae* serotypes; among other things, such a MAPS multivalent pneumococcal vaccine could induce immune response against *S. pneumoniae* serotypes that not included in the vaccine.

Among other things, the present disclosure provides compositions and methods for prevention and/or treatment of pneumococcal infections in patient populations in need thereof. In some embodiments, a set of pneumococcal polysaccharide serotypes to be included in compositions described herein are curated and selected based on a variety of considerations including, e.g., characteristics of diseases (e.g., epidemiology, prevalence, worldwide coverage, etc.), and/or compatibility and immunogenicity of various components in a single composition. In some embodiments, the present disclosure provides a further surprising insight that certain pneumococcal polysaccharide serotypes can induce a stronger immune response when they are non-covalently associated with a certain polypeptide antigen. For example, in some embodiments, certain pneumococcal polysaccharide serotypes (e.g., serotypes 1, 6B, 9V, 15B, 22F, 23A, 23B, 23F, and 33F) were demonstrated to induce a stronger immune response when they are non-covalently associated with a SPP2 fusion protein as described herein, as compared to the immune response observed when those serotypes were non-covalently associated with a CP1 fusion protein as described herein. In some embodiments, certain pneumococcal polysaccharide serotypes (e.g., serotypes 2, 6A, 10A, 18C and 20B) were demonstrated to induce a stronger immune response when they are non-covalently associated with a CP1 fusion protein as described herein, as compared to the immune response observed when those serotypes were non-covalently associated with a SPP2 fusion protein as described herein.

In some embodiments, the present disclosure, among other things, provides compositions of SPP2 fusion polypeptides comprising a biotin-binding protein and *S. pneumoniae* polypeptide antigens that do not induce hemolysis and hemagglutination at a detectable level. In particular, the present disclosure provides a surprising insight that the relative position of *S. pneumoniae* polypeptide antigens SP0435 and PdT (G294P) in a fusion protein can unexpectedly impact the activity of the fusion protein. Reversing the order of SP0435 and PdT (G294P) in a fusion protein, i.e., positioning SP0435 to the C-terminus of PdT (G294P) in a fusion protein, unexpectedly abolished both hemolysis and hemagglutination.

In some embodiments, the present disclosure, among other things, provides an insight that immunization with SPP2 fusion protein and *S. pneumoniae* capsular polysaccharide (CPS) of a serotype can synergistically contribute to protection against invasive pneumococcal disease (IPD) by the same serotype. In some embodiments, the serotype is of serotype 3. In some embodiments, the SPP2 fusion protein is in a MAPS complex. In some embodiments, the CPS is in a MAPS complex or in a glycoconjugate (e.g., PCV13). In some embodiments, immunization with a combination of SPP2 fusion protein and CPS of a serotype can increase protection (e.g., as measured by percent survival) against IPD by the serotype relative to a reference without the combination of SPP2 fusion protein and CPS of the serotype. In some embodiments, the protection is increased by at least 2-fold, at least 3-fold, at least 4-fold, at least 5-fold, at least 6-fold, at least 7-fold, at least 8-fold, at least 9-fold, or at least 10-fold relative to a reference. In some embodiments, such a reference is SPP2 fusion protein without CPS of the serotype. In some embodiments, such a reference is CPS of the serotype (e.g., in a MAPS complex or glycoconjugate (e.g., PCV13)) without SPP2 fusion protein.

One aspect of the present disclosure provides a multivalent pneumococcal immunogenic composition (e.g., vaccine). In some embodiments, such an immunogenic composition (e.g., vaccine) comprises one or more species of an immunogenic complexes, wherein the immunogenic complex of at least one of the species comprises: (a) a biotinylated polysaccharide antigen; and (b) a fusion protein comprising: (i) a biotin-binding moiety; and (ii) at least one polypeptide antigen; wherein the biotinylated polysaccharide antigen is non-covalently associated with the biotin-binding moiety of the fusion protein to form an immunogenic complex.

In some embodiments, where more than one species of an immunogenic complex is included in an immunogenic composition (e.g., vaccine), one or more polypeptide antigens can be utilized. In some embodiments, at least one polypeptide antigen in an immunogenic complex comprises: a pneumolysin (Ply) polypeptide or variant or antigenic fragment thereof; or an SP0435 polypeptide, or variant or antigenic fragment thereof. In some embodiments, at least one polypeptide antigen in an immunogenic complex comprises: (a) a first polypeptide antigen comprising a Ply polypeptide or variant or antigenic fragment thereof; and (b) a second polypeptide antigen comprising an SP0435 polypeptide, or variant or antigenic fragment thereof. In some embodiments, at least one polypeptide antigen in an immunogenic complex comprises: an SP1500 polypeptide or variant or antigenic fragment thereof; or an SP0785 polypeptide or variant or antigenic fragment thereof. In some embodiments, at least one polypeptide antigen in an immunogenic complex comprises: (a) a first polypeptide antigen comprising an SP1500 polypeptide or variant or antigenic fragment thereof; and (b) a second polypeptide antigen comprising an SP0785 polypeptide or variant or antigenic fragment thereof.

In some embodiments where more than one species of an immunogenic complex is included in an immunogenic composition (e.g., vaccine), one or more biotinylated polysaccharide antigens can be utilized. In some embodiments, at least one biotinylated polysaccharide antigen comprises a polysaccharide of *Streptococcus pneumoniae*. In some embodiments, a biotinylated polysaccharide antigen comprises a polysaccharide of *Streptococcus pneumoniae* having a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

In some embodiments, a biotinylated polysaccharide antigen comprises a polysaccharide of *Streptococcus pneumoniae* having a serotype selected from one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) of serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, a biotinylated polysaccharide antigen comprises a polysaccharide of *Streptococcus pneumoniae* having a serotype selected from one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33) of serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

In some embodiments, an immunogenic composition (e.g., vaccine) comprises a plurality of immunogenic complexes comprising: (a) a plurality of first biotinylated polysaccharide antigens, wherein the plurality comprises polysaccharide antigens of one or more of *Streptococcus pneumoniae* serotypes 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48; and (b) a plurality of first fusion proteins, each first fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; wherein each of the plurality of first biotinylated polysaccharide antigens is non-covalently associated with the biotin-binding moiety of one or more of the plurality of first fusion proteins to form an immunogenic complex. Additionally or alternatively, in some embodiments, immunogenic complexes in an immunogenic composition (e.g., vaccine) described herein comprise (a) a plurality of second biotinylated polysaccharide antigens, wherein the plurality comprises polysaccharide antigens of one or more of *Streptococcus pneumoniae* serotypes 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48; and (b) a plurality of second fusion proteins, each second fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; wherein each of the plurality of second biotinylated polysaccharide antigens is non-covalently associated with the biotin-binding moiety of one or more of the plurality of second fusion proteins to form an immunogenic complex.

In some embodiments, an immunogenic composition (e.g., vaccine) comprises a plurality of immunogenic complexes comprising: (a) a plurality of first biotinylated polysaccharide antigens, wherein the plurality comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38; and (b) a plurality of first fusion proteins, each first fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; wherein each of the plurality of first biotinylated polysaccharide antigens is non-covalently associated with the biotin-binding moiety of one or more of the plurality of first fusion proteins to form an immunogenic complex. Additionally or alternatively, in some embodiments, immunogenic complexes in an immunogenic composition (e.g., vaccine) described herein comprise (a) a plurality of second biotinylated polysaccharide antigens, wherein the plurality comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38; and (b) a plurality of second fusion proteins, each second fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; wherein each of the plurality of second biotinylated polysaccharide antigens is non-covalently associated with the biotin-binding moiety of one or more of the plurality of second fusion proteins to form an immunogenic complex.

In some embodiments, an immunogenic composition (e.g., vaccine) comprises a plurality of immunogenic complexes comprising: (a) a plurality of first biotinylated polysaccharide antigens, wherein the plurality comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38; and (b) a plurality of first fusion proteins, each first fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; wherein each of the plurality of first biotinylated polysaccharide antigens is non-covalently associated with the biotin-binding moiety of one or more of the plurality of first fusion proteins to form an immunogenic complex. Additionally or alternatively, in some embodiments, immunogenic complexes in an immunogenic composition (e.g., vaccine) described herein comprise (a) a plurality of second biotinylated polysaccharide antigens, wherein the plurality comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38; and (b) a plurality of second fusion proteins, each second fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; wherein each of the plurality of second biotinylated polysaccharide antigens is non-covalently associated with the biotin-binding moiety of one or more of the plurality of second fusion proteins to form an immunogenic complex.

In some embodiments, an immunogenic composition (e.g., vaccine) comprises a plurality of immunogenic complexes comprising: (a) a plurality of first biotinylated polysaccharide antigens, wherein the plurality comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38; and (b) a plurality of first fusion proteins, each first fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; wherein each of the plurality of first biotinylated polysaccharide antigens is non-covalently associated with the biotin-binding moiety of one or more of the plurality of first fusion proteins to form an immunogenic complex. Additionally or alternatively, in some embodiments, immunogenic complexes in an immunogenic composition (e.g., vaccine) described herein comprise (a) a plurality of second biotinylated polysaccharide antigens, wherein the plurality comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38; and (b) a plurality of second fusion proteins, each second fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; wherein each of the plurality of second biotinylated polysaccharide antigens is non-covalently associated with the biotin-binding moiety of one or more of the plurality of second fusion proteins to form an immunogenic complex.

In some embodiments, an immunogenic composition (e.g., vaccine) comprises a plurality of immunogenic complexes comprising: (a) a plurality of first biotinylated polysaccharide antigens, wherein the plurality comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38; and (b) a plurality of first fusion proteins, each first fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; wherein each of the plurality of first biotinylated polysaccharide antigens is non-covalently associated with the biotin-binding moiety of one or more of the plurality of first fusion proteins to form an immunogenic complex. Additionally or alternatively, in some embodiments, immunogenic complexes in an immunogenic composition (e.g., vaccine) described herein comprise (a) a plurality of second biotinylated polysaccharide antigens, wherein the plurality comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38; and (b) a plurality of second fusion proteins, each second fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; wherein each of the plurality of second biotinylated polysaccharide antigens is non-covalently associated with the biotin-binding moiety of one or more of the plurality of second fusion proteins to form an immunogenic complex.

In some embodiments, an immunogenic composition (e.g., vaccine) comprises a biotin-binding moiety, wherein the biotin-binding moiety is a polypeptide that has or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or a polypeptide that has or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof. In some embodiments, an immunogenic composition (e.g., vaccine) comprises a fusion protein that is or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 26 or SEQ ID NO: 61. In some embodiments, an immunogenic composition (e.g., vaccine) comprises a fusion protein CP1 as described herein.

In some embodiments, an immunogenic composition (e.g., vaccine) comprises a biotin-binding moiety, wherein the biotin-binding moiety is a polypeptide that has or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or a polypeptide that has or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof. In some embodiments, an immunogenic composition (e.g., vaccine) comprises a fusion protein that is or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 19 or SEQ ID NO: 58. In some embodiments, an immunogenic composition (e.g., vaccine) comprises a fusion protein SPP2 as described herein.

In some embodiments, an immunogenic composition (e.g., vaccine) comprises a plurality of immunogenic complexes comprising one or more species of immunogenic complexes, wherein a species refers to complexes comprising a polysaccharide antigen of a single *Streptococcus*

*pneumoniae* serotype (e.g., ones described herein). In some embodiments, an immunogenic composition (e.g., vaccine) comprises a plurality of immunogenic complexes comprising two or more species of immunogenic complexes, wherein a species refers to complexes comprising a polysaccharide antigen of a single *Streptococcus pneumoniae* serotype (e.g., ones described herein). In some embodiments, an immunogenic composition (e.g., vaccine) comprises a plurality of immunogenic complexes comprising thirty or more species of immunogenic complexes, wherein a species refers to complexes comprising a polysaccharide antigen of a single *Streptococcus pneumoniae* serotype (e.g., ones described herein). In some embodiments, an immunogenic composition (e.g., vaccine) comprises a plurality of immunogenic complexes comprising thirty one or more species of immunogenic complexes, wherein a species refers to complexes comprising a polysaccharide antigen of a single *Streptococcus pneumoniae* serotype (e.g., ones described herein). In some embodiments, an immunogenic composition (e.g., vaccine) comprises a plurality of immunogenic complexes comprising thirty two or more species of immunogenic complexes, wherein a species refers to complexes comprising a polysaccharide antigen of a single *Streptococcus pneumoniae* serotype (e.g., ones described herein).

In some embodiments, an immunogenic composition (e.g., vaccine) comprises a plurality of immunogenic complexes comprising thirty or more species of immunogenic complexes. In some embodiments, each species is a population of complexes comprising a polysaccharide antigen of a distinct *Streptococcus pneumoniae* serotype (e.g., ones described herein).

In some embodiments, an immunogenic composition (e.g., vaccine) comprises a plurality of immunogenic complexes comprising thirty three or more species of immunogenic complexes. In some embodiments, each species is a population of complexes comprising a polysaccharide antigen of a distinct *Streptococcus pneumoniae* serotype (e.g., ones described herein).

In some embodiments, an immunogenic composition (e.g., vaccine) comprises a plurality of immunogenic complexes comprising thirty four or more species of immunogenic complexes. In some embodiments, each species is a population of complexes comprising a polysaccharide antigen of a distinct *Streptococcus pneumoniae* serotype (e.g., ones described herein).

In some embodiments, an immunogenic composition (e.g., vaccine) comprises a plurality of immunogenic complexes comprising: a first species of immunogenic complex comprising a biotinylated polysaccharide antigen of *Streptococcus pneumoniae* serotype 6C non-covalently complexed with a biotin-binding moiety of a first fusion protein, wherein each first fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; a second species of immunogenic complex comprising a biotinylated polysaccharide antigen of *Streptococcus pneumoniae* serotype 7C non-covalently complexed with the biotin binding moiety of the first fusion protein; a third species of immunogenic complex comprising a biotinylated polysaccharide antigen of *Streptococcus pneumoniae* serotype 15A non-covalently complexed with the biotin binding moiety of the first fusion protein; a fourth species of immunogenic complex comprising a biotinylated polysaccharide antigen of *Streptococcus pneumoniae* serotype 16F non-covalently complexed with the biotin binding moiety of the first fusion protein; a fifth species of immunogenic complex comprising a biotinylated polysaccharide antigen of *Streptococcus pneumoniae* serotype 23A non-covalently complexed with the biotin binding moiety of the first fusion protein; a sixth species of immunogenic complex comprising a biotinylated polysaccharide antigen of *Streptococcus pneumoniae* serotype 23B non-covalently complexed with the biotin binding moiety of the first fusion protein; a seventh species of immunogenic complex comprising a biotinylated polysaccharide antigen of *Streptococcus pneumoniae* serotype 24F non-covalently complexed with the biotin binding moiety of the first fusion protein; an eighth species of immunogenic complex comprising a biotinylated polysaccharide antigen of *Streptococcus pneumoniae* serotype 31 non-covalently complexed with the biotin binding moiety of the first fusion protein; a ninth species of immunogenic complex comprising a biotinylated polysaccharide antigen of *Streptococcus pneumoniae* serotype 35Bnon-covalently complexed with the biotin binding moiety of the first fusion protein; a tenth species of immunogenic complex comprising a biotinylated polysaccharide antigen of *Streptococcus pneumoniae* serotype 38 non-covalently complexed with the biotin binding moiety of the first fusion protein; an eleventh species of immunogenic complex comprising a biotinylated polysaccharide antigen of *Streptococcus pneumoniae* serotype 1 non-covalently complexed with a biotin binding moiety of a second fusion protein, wherein each second fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; a twelfth species of immunogenic complex comprising a biotinylated polysaccharide antigen of *Streptococcus pneumoniae* serotype 2 non-covalently complexed with the biotin binding moiety of the second fusion protein; a thirteenth species of immunogenic complex comprising a biotinylated polysaccharide antigen of *Streptococcus pneumoniae* serotype 3 non-covalently complexed with the biotin binding moiety of the second fusion protein; a fourteenth species of immunogenic complex comprising a biotinylated polysaccharide antigen of *Streptococcus pneumoniae* serotype 4 non-covalently complexed with the biotin binding moiety of the second fusion protein; a fifteenth species of immunogenic complex comprising a biotinylated polysaccharide antigen of *Streptococcus pneumoniae* serotype 5 non-covalently complexed with the biotin binding moiety of the second fusion protein; a sixteenth species of immunogenic complex comprising a biotinylated polysaccharide antigen of *Streptococcus pneumoniae* serotype 6A non-covalently complexed with the biotin binding moiety of the second fusion protein; a seventeenth species of immunogenic complex comprising a biotinylated polysaccharide antigen of *Streptococcus pneumoniae* serotype 6B non-covalently complexed with the biotin binding moiety of the second fusion protein; an eighteenth species of immunogenic complex comprising a biotinylated polysaccharide antigen of *Streptococcus pneumoniae* serotype 7F non-covalently complexed with the biotin binding moiety of the second fusion protein; a nineteenth species of immunogenic complex comprising a biotinylated polysaccharide antigen of *Streptococcus pneumoniae* serotype 8 non-covalently complexed with the biotin binding moiety of the second fusion protein; a twentieth species of immunogenic complex comprising a biotinylated polysaccharide antigen of *Streptococcus pneumoniae* serotype 9N non-covalently complexed with the biotin binding moiety of the second fusion protein; a twenty-first species of immunogenic complex comprising a biotinylated polysaccharide antigen of *Streptococcus pneumoniae* serotype 9V non-covalently complexed with the biotin binding moiety of the second fusion protein; a twenty-second species of immunogenic complex comprising a biotinylated polysaccharide antigen of *Streptococcus pneumoniae* serotype 10A non-covalently complexed with the biotin binding moiety of the second fusion protein; a twenty-third species of immunogenic complex comprising a biotinylated polysaccharide antigen of *Streptococcus pneumoniae* serotype 11A non-covalently complexed with the biotin binding moiety of the second fusion protein; a twenty-fourth species of immunogenic complex comprising a biotinylated polysaccharide antigen of *Streptococcus pneumoniae* serotype 12F non-covalently complexed with the biotin binding moiety of the second fusion protein; a twenty-fifth species of immunogenic complex comprising a biotinylated polysaccharide antigen of *Streptococcus pneumoniae* serotype 14 non-covalently complexed with the biotin binding moiety of the second fusion protein; a twenty-sixth species of immunogenic complex comprising a biotinylated polysaccharide antigen of *Streptococcus pneumoniae* serotype 15B non-covalently complexed with the biotin binding moiety of the second fusion protein; a twenty-seventh species of immunogenic complex comprising a biotinylated polysaccharide antigen of *Streptococcus pneumoniae* serotype 17F non-covalently complexed with the biotin binding moiety of the second fusion protein; a twenty-eighth species of immunogenic complex comprising a biotinylated polysaccharide antigen of *Streptococcus pneumoniae* serotype 18C non-covalently complexed with the biotin binding moiety of the second fusion protein; a twenty-ninth species of immunogenic complex comprising a biotinylated polysaccharide antigen of *Streptococcus pneumoniae* serotype 19A non-covalently complexed with the biotin binding moiety of the second fusion protein; a thirtieth species of immunogenic complex comprising a biotinylated polysaccharide antigen of *Streptococcus pneumoniae* serotype 19F non-covalently complexed with the biotin binding moiety of the second fusion protein; a thirty-first species of immunogenic complex comprising a biotinylated polysaccharide antigen of *Streptococcus pneumoniae* serotype 20B non-covalently complexed with the biotin binding moiety of the second fusion protein; a thirty-second species of immunogenic complex comprising a biotinylated polysaccharide antigen of *Streptococcus pneumoniae* serotype 22F non-covalently complexed with the biotin binding moiety of the second fusion protein; a thirty-third species of immunogenic complex comprising a biotinylated polysaccharide antigen of *Streptococcus pneumoniae* serotype 23F non-covalently complexed with the biotin binding moiety of the second fusion protein; and a thirty-fourth species of immunogenic complex comprising a biotinylated polysaccharide antigen of *Streptococcus pneumoniae* serotype 33F non-covalently complexed with the biotin binding moiety of the second fusion protein.

In some embodiments, an immunogenic composition (e.g., vaccine) comprises a plurality of immunogenic complexes comprising: a first species of immunogenic complex comprising a biotinylated polysaccharide antigen of *Streptococcus pneumoniae* serotype 1 non-covalently complexed with a biotin-binding moiety of a first fusion protein, wherein each first fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; a second species of immunogenic complex comprising a biotinylated polysaccharide antigen of *Streptococcus pneumoniae* serotype 4 non-covalently complexed with the biotin binding moiety of the first fusion protein; a third species of immunogenic complex comprising a biotinylated polysaccharide antigen of *Streptococcus pneumoniae* serotype 6A non-covalently complexed with the biotin binding moiety of the first fusion protein; a fourth species of immunogenic complex comprising a biotinylated polysaccharide antigen of *Streptococcus pneumoniae* serotype 6B non-covalently complexed with the biotin binding moiety of the first fusion protein; a fifth species of immunogenic complex comprising a biotinylated polysaccharide antigen of *Streptococcus pneumoniae* serotype 9V non-covalently complexed with the biotin binding moiety of the first fusion protein; a sixth species of immunogenic complex comprising a biotinylated polysaccharide antigen of *Streptococcus pneumoniae* serotype 15B non-covalently complexed with the biotin binding moiety of the first fusion protein; a seventh species of immunogenic complex comprising a biotinylated polysaccharide antigen of *Streptococcus pneumoniae* serotype 18C non-covalently complexed with the biotin binding moiety of the first fusion protein; an eighth species of immunogenic complex comprising a biotinylated polysaccharide antigen of *Streptococcus pneumoniae* serotype 19A non-covalently complexed with the biotin binding moiety of the first fusion protein; a ninth species of immunogenic complex comprising a biotinylated polysaccharide antigen of *Streptococcus pneumoniae* serotype 23F non-covalently complexed with the biotin binding moiety of the first fusion protein; a tenth species of immunogenic complex comprising a biotinylated polysaccharide antigen of *Streptococcus pneumoniae* serotype 33F non-covalently complexed with the biotin binding moiety of the first fusion protein; an eleventh species of immunogenic complex comprising a biotinylated polysaccharide antigen of *Streptococcus pneumoniae* serotype 2 non-covalently complexed with a biotin binding moiety of a second fusion protein, wherein each second fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; a twelfth species of immunogenic complex comprising a biotinylated polysaccharide antigen of *Streptococcus pneumoniae* serotype 3 non-covalently complexed with the biotin binding moiety of the second fusion protein; a thirteenth species of immunogenic complex comprising a biotinylated polysaccharide antigen of *Streptococcus pneumoniae* serotype 5 non-covalently complexed with the biotin binding moiety of the second fusion protein; a fourteenth species of immunogenic complex comprising a biotinylated polysaccharide antigen of *Streptococcus pneumoniae* serotype 6C non-covalently complexed with the biotin binding moiety of the second fusion protein; a fifteenth species of immunogenic complex comprising a biotinylated polysaccharide antigen of *Streptococcus pneumoniae* serotype 7C non-covalently complexed with the biotin binding moiety of the second fusion protein; a sixteenth species of immunogenic complex comprising a biotinylated polysaccharide antigen of *Streptococcus pneumoniae* serotype 7F non-covalently complexed with the biotin binding moiety of the second fusion protein; a seventeenth species of immunogenic complex comprising a biotinylated polysaccharide antigen of *Streptococcus pneumoniae* serotype 8 non-covalently complexed with the biotin binding moiety of the second fusion protein; an eighteenth species of immunogenic complex comprising a biotinylated polysaccharide antigen of *Streptococcus pneumoniae* serotype 9N non-covalently complexed with the biotin binding moiety of the second fusion protein; a nineteenth species of immunogenic complex comprising a biotinylated polysaccharide antigen of *Streptococcus pneumoniae* serotype 10A non-covalently complexed with the biotin binding moiety of the second fusion protein; a twentieth species of immunogenic complex comprising a biotinylated polysaccharide antigen of *Streptococcus pneumoniae* serotype 11A non-covalently complexed with the biotin binding moiety of the second fusion protein; a twenty-first species of immunogenic complex comprising a biotinylated polysaccharide antigen of *Streptococcus pneumoniae* serotype 12F non-covalently complexed with the biotin binding moiety of the second fusion protein; a twenty-second species of immunogenic complex comprising a biotinylated polysaccharide antigen of *Streptococcus pneumoniae* serotype 14 non-covalently complexed with the biotin binding moiety of the second fusion protein; a twenty-third species of immunogenic complex comprising a biotinylated polysaccharide antigen of *Streptococcus pneumoniae* serotype 15A non-covalently complexed with the biotin binding moiety of the second fusion protein; a twenty-fourth species of immunogenic complex comprising a biotinylated polysaccharide antigen of *Streptococcus pneumoniae* serotype 16F non-covalently complexed with the biotin binding moiety of the second fusion protein; a twenty-fifth species of immunogenic complex comprising a biotinylated polysaccharide antigen of *Streptococcus pneumoniae* serotype 17F non-covalently complexed with the biotin binding moiety of the second fusion protein; a twenty-sixth species of immunogenic complex comprising a biotinylated polysaccharide antigen of *Streptococcus pneumoniae* serotype 19F non-covalently complexed with the biotin binding moiety of the second fusion protein; a twenty-seventh species of immunogenic complex comprising a biotinylated polysaccharide antigen of *Streptococcus pneumoniae* serotype 20B non-covalently complexed with the biotin binding moiety of the second fusion protein; a twenty-eighth species of immunogenic complex comprising a biotinylated polysaccharide antigen of *Streptococcus pneumoniae* serotype 22F non-covalently complexed with the biotin binding moiety of the second fusion protein; a twenty-ninth species of immunogenic complex comprising a biotinylated polysaccharide antigen of *Streptococcus pneumoniae* serotype 23A non-covalently complexed with the biotin binding moiety of the second fusion protein; a thirtieth species of immunogenic complex comprising a biotinylated polysaccharide antigen of *Streptococcus pneumoniae* serotype 23B non-covalently complexed with the biotin binding moiety of the second fusion protein; a thirty-first species of immunogenic complex comprising a biotinylated polysaccharide antigen of *Streptococcus pneumoniae* serotype 24F non-covalently complexed with the biotin binding moiety of the second fusion protein; a thirty-second species of immunogenic complex comprising a biotinylated polysaccharide antigen of *Streptococcus pneumoniae* serotype 31 non-covalently complexed with the biotin binding moiety of the second fusion protein; a thirty-third species of immunogenic complex comprising a biotinylated polysaccharide antigen of *Streptococcus pneumoniae* serotype 35B non-covalently complexed with the biotin binding moiety of the second fusion protein; and a thirty-fourth species of immunogenic complex comprising a biotinylated polysaccharide antigen of *Streptococcus pneumoniae* serotype 38 non-covalently complexed with the biotin binding moiety of the second fusion protein.

In some embodiments, an immunogenic composition (e.g., vaccine) comprises a plurality of immunogenic complexes comprising: a first species of immunogenic complex comprising a biotinylated polysaccharide antigen of *Streptococcus pneumoniae* serotype 1 non-covalently complexed with a biotin-binding moiety of a first fusion protein, wherein each first fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof; a second species of immunogenic complex comprising a biotinylated polysaccharide antigen of *Streptococcus pneumoniae* serotype 4 non-covalently complexed with the biotin binding moiety of the first fusion protein; a third species of immunogenic complex comprising a biotinylated polysaccharide antigen of *Streptococcus pneumoniae* serotype 6A non-covalently complexed with the biotin binding moiety of the first fusion protein; a fourth species of immunogenic complex comprising a biotinylated polysaccharide antigen of *Streptococcus pneumoniae* serotype 6B non-covalently complexed with the biotin binding moiety of the first fusion protein; a fifth species of immunogenic complex comprising a biotinylated polysaccharide antigen of *Streptococcus pneumoniae* serotype 9V non-covalently complexed with the biotin binding moiety of the first fusion protein; a sixth species of immunogenic complex comprising a biotinylated polysaccharide antigen of *Streptococcus pneumoniae* serotype 15B non-covalently complexed with the biotin binding moiety of the first fusion protein; a seventh species of immunogenic complex comprising a biotinylated polysaccharide antigen of *Streptococcus pneumoniae* serotype 18C non-covalently complexed with the biotin binding moiety of the first fusion protein; an eighth species of immunogenic complex comprising a biotinylated polysaccharide antigen of *Streptococcus pneumoniae* serotype 19A non-covalently complexed with the biotin binding moiety of the first fusion protein; a ninth species of immunogenic complex comprising a biotinylated polysaccharide antigen of *Streptococcus pneumoniae* serotype 23F non-covalently complexed with the biotin binding moiety of the first fusion protein; a tenth species of immunogenic complex comprising a biotinylated polysaccharide antigen of *Streptococcus pneumoniae* serotype 33F non-covalently complexed with the biotin binding moiety of the first fusion protein; an eleventh species of immunogenic complex comprising a biotinylated polysaccharide antigen of *Streptococcus pneumoniae* serotype 2 non-covalently complexed with a biotin binding moiety of a second fusion protein, wherein each second fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof; a twelfth species of immunogenic complex comprising a biotinylated polysaccharide antigen of *Streptococcus pneumoniae* serotype 3 non-covalently complexed with the biotin binding moiety of the second fusion protein; a thirteenth species of immunogenic complex comprising a biotinylated polysaccharide antigen of *Streptococcus pneumoniae* serotype 5 non-covalently complexed with the biotin binding moiety of the second fusion protein; a fourteenth species of immunogenic complex comprising a biotinylated polysaccharide antigen of *Streptococcus pneumoniae* serotype 6C non-covalently complexed with the biotin binding moiety of the second fusion protein; a fifteenth species of immunogenic complex comprising a biotinylated polysaccharide antigen of *Streptococcus pneumoniae* serotype 7C non-covalently complexed with the biotin binding moiety of the second fusion protein; a sixteenth species of immunogenic complex comprising a biotinylated polysaccharide antigen of *Streptococcus pneumoniae* serotype 7F non-covalently complexed with the biotin binding moiety of the second fusion protein; a seventeenth species of immunogenic complex comprising a biotinylated polysaccharide antigen of *Streptococcus pneumoniae* serotype 8 non-covalently complexed with the biotin binding moiety of the second fusion protein; an eighteenth species of immunogenic complex comprising a biotinylated polysaccharide antigen of *Streptococcus pneumoniae* serotype 9N non-covalently complexed with the biotin binding moiety of the second fusion protein; a nineteenth species of immunogenic complex comprising a biotinylated polysaccharide antigen of *Streptococcus pneumoniae* serotype 10A non-covalently complexed with the biotin binding moiety of the second fusion protein; a twentieth species of immunogenic complex comprising a biotinylated polysaccharide antigen of *Streptococcus pneumoniae* serotype 11A non-covalently complexed with the biotin binding moiety of the second fusion protein; a twenty-first species of immunogenic complex comprising a biotinylated polysaccharide antigen of *Streptococcus pneumoniae* serotype 12F non-covalently complexed with the biotin binding moiety of the second fusion protein; a twenty-second species of immunogenic complex comprising a biotinylated polysaccharide antigen of *Streptococcus pneumoniae* serotype 14 non-covalently complexed with the biotin binding moiety of the second fusion protein; a twenty-third species of immunogenic complex comprising a biotinylated polysaccharide antigen of *Streptococcus pneumoniae* serotype 15A non-covalently complexed with the biotin binding moiety of the second fusion protein; a twenty-fourth species of immunogenic complex comprising a biotinylated polysaccharide antigen of *Streptococcus pneumoniae* serotype 17F non-covalently complexed with the biotin binding moiety of the second fusion protein; a twenty-fifth species of immunogenic complex comprising a biotinylated polysaccharide antigen of *Streptococcus pneumoniae* serotype 19F non-covalently complexed with the biotin binding moiety of the second fusion protein; a twenty-sixth species of immunogenic complex comprising a biotinylated polysaccharide antigen of *Streptococcus pneumoniae* serotype 20B non-covalently complexed with the biotin binding moiety of the second fusion protein; a twenty-seventh species of immunogenic complex comprising a biotinylated polysaccharide antigen of *Streptococcus pneumoniae* serotype 22F non-covalently complexed with the biotin binding moiety of the second fusion protein; a twenty-eighth species of immunogenic complex comprising a biotinylated polysaccharide antigen of *Streptococcus pneumoniae* serotype 23A non-covalently complexed with the biotin binding moiety of the second fusion protein; a twenty-ninth species of immunogenic complex comprising a biotinylated polysaccharide antigen of *Streptococcus pneumoniae* serotype 23B non-covalently complexed with the biotin binding moiety of the second fusion protein; a thirtieth species of immunogenic complex comprising a biotinylated polysaccharide antigen of *Streptococcus pneumoniae* serotype 24F non-covalently complexed with the biotin binding moiety of the second fusion protein; a thirty-first species of immunogenic complex comprising a biotinylated polysaccharide antigen of *Streptococcus pneumoniae* serotype 31 non-covalently complexed with the biotin binding moiety of the second fusion protein; a thirty-second species of immunogenic complex comprising a biotinylated polysaccharide antigen of *Streptococcus pneumoniae* serotype 35B non-covalently complexed with the biotin binding moiety of the second fusion protein; and a thirty-third species of immunogenic complex comprising a biotinylated polysaccharide antigen of *Streptococcus pneumoniae* serotype 38 non-covalently complexed with the biotin binding moiety of the second fusion protein.

In some embodiments, an immunogenic composition (e.g., vaccine) comprises a plurality of immunogenic complexes comprising two or more species of immunogenic complexes, wherein each species of immunogenic complexes contributes a stoichiometrically equal ratio, by weight, of the polysaccharide antigen.

In some embodiments, an immunogenic composition (e.g., vaccine) comprises a plurality of immunogenic complexes comprising two or more species of immunogenic complexes, wherein at least one species of immunogenic complex contributes a stoichiometrically different ratio, by weight, of the polysaccharide antigen.

In some embodiments, an immunogenic composition (e.g., vaccine) comprises a plurality of immunogenic complexes comprising two or more species of immunogenic complexes, wherein different species of immunogenic complexes contribute a stoichiometrically different ratio, by weight, of the polysaccharide antigen.

In some embodiments, an immunogenic composition (e.g., vaccine) comprises a fusion protein comprising a biotin-binding moiety, wherein the biotin-binding moiety is a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof.

Another aspect of the present disclosure provides an immunogenic complex comprising a fusion protein comprising a biotin-binding moiety of rhizavidin and one or more *Streptococcus pneumoniae* polypeptide antigens. In some embodiments, a biotin-binding moiety is a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof.

In some embodiments, an immunogenic complex comprises a biotinylated polysaccharide antigen of *Streptococcus pneumoniae* non-covalently associated with a fusion protein described herein. In some embodiments, an immunogenic complex comprises a biotinylated polysaccharide antigen, wherein the biotinylated polysaccharide antigen comprises a polysaccharide of *Streptococcus pneumoniae* having a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

In some embodiments, an immunogenic complex comprises a biotinylated polysaccharide antigen, wherein the biotinylated polysaccharide antigen comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20, 22F, 23A, 23B, 23F, 24F, 31, 33F, 35B, and 38.

In some embodiments, an immunogenic complex comprises a biotinylated polysaccharide antigen, wherein the biotinylated polysaccharide antigen comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 17F, 18C, 19A, 19F, 20, 22F, 23A, 23B, 23F, 24F, 31, 33F, 35B, and 38.

In some embodiments, an immunogenic complex comprises at least one polypeptide antigen, wherein the at least one polypeptide antigen comprises a pneumolysin (Ply) polypeptide or variant or antigenic fragment thereof; an SP0435 polypeptide or variant or antigenic fragment thereof; or a combination thereof. In some embodiments, an immunogenic complex comprises at least one *Streptococcus pneumoniae* polypeptide antigen, wherein the at least one polypeptide antigen comprises: (a) a first polypeptide antigen comprising a pneumolysin (Ply) polypeptide, or variant or antigenic fragment thereof; and (b) a second polypeptide antigen comprising an SP0435 polypeptide or variant or antigenic fragment thereof. In some embodiments, an immunogenic complex comprises at least one polypeptide antigen, wherein the at least one polypeptide antigen comprises: (a) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (b) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof.

In some embodiments, an immunogenic complex comprises at least one polypeptide antigen, wherein the at least one polypeptide antigen comprises an SP1500 polypeptide or variant of antigenic fragment thereof; an SP0785 polypeptide or variant or antigenic fragment thereof; or a combination thereof. In some embodiments, an immunogenic complex comprises at least one polypeptide antigen, wherein the at least one polypeptide antigen comprises: (a) a first polypeptide antigen comprising an SP1500 polypeptide or variant or antigenic fragment thereof; and (b) a second polypeptide antigen comprising an SP0785 polypeptide or variant or antigenic fragment thereof. In some embodiments, an immunogenic complex comprises at least one polypeptide antigen, wherein the at least one polypeptide antigen comprises: (a) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO: 12 or variant or an antigenic fragment thereof; and (b) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or variant or an antigenic fragment thereof.

In some embodiments, an immunogenic complex comprises a biotinylated polysaccharide antigen of *Streptococcus pneumoniae* serotype 1 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 6B non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 9V non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 15B non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 22F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 23A non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 23B non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 23F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotinylated polysaccharide antigen of *Streptococcus pneumoniae* serotype 33F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or a variant or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or a variant or an antigenic fragment thereof.

In some embodiments, an immunogenic complex comprises a biotin-binding moiety, wherein the biotin-binding moiety is a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof.

In some embodiments, an immunogenic complex comprises a fusion protein (e.g., ones described herein) and a polysaccharide antigen (e.g., ones described herein), wherein the ratio of fusion protein to polysaccharide antigen in the complex is about 1:1, about 2:1, about 3:1, about 4:1, about 5:1, about 6:1, about 7:1, about 8:1, about 9:1, or about 10:1 by weight. In some embodiments, an immunogenic composition (e.g., vaccine) comprises one or more immunogenic complexes disclosed herein.

In some aspects, pharmaceutical compositions comprising immunogenic composition (e.g., vaccine) compositions are disclosed herein. In some embodiments, a pharmaceutical composition comprises an immunogenic composition (e.g., vaccine) or immunogenic composition (e.g., vaccine) composition disclosed herein, and a pharmaceutically acceptable carrier. In some embodiments, a pharmaceutical composition comprises an immunogenic complex disclosed herein, and a pharmaceutically acceptable carrier. In some embodiments, a pharmaceutical composition disclosed herein comprises one or more adjuvants. In some embodiments, the one or more adjuvants is or comprises a co-stimulation factor.

In some embodiments, the one or more adjuvants are selected from the group consisting of aluminum phosphate, aluminum hydroxide, and phosphated aluminum hydroxide. In some embodiments, wherein the one or more adjuvants is or comprises aluminum phosphate. In some embodiments, a pharmaceutical composition disclosed herein is formulated for injection.

In some embodiments, upon administration to a subject, a pharmaceutical composition disclosed herein induces an immune response. In some embodiments, the immune response comprises an innate immune response. In some embodiments, the immune response comprises an antibody or B cell response. In some embodiments, the immune response comprises a T cell response. In some embodiments, the immune response comprises a CD4+ T cell response (e.g., $T_H1$, $T_H2$, or $T_H17$ response), a CD8+ T cell response, a CD4+ and CD8+ T cell response, or a CD4−/CD8− T cell response. In some embodiments, the immune response comprises (i) an antibody or B cell response, and (ii) a T cell response. In some embodiments, the immune response comprises (i) an antibody or B cell response, (ii) a T cell response, and (iii) an innate immune response. In some embodiments, the immune response is to at least one polysaccharide antigen or at least one polypeptide antigen of a fusion protein. In some embodiments, the immune response comprises (i) an antibody or B cell response to at least one polysaccharide antigen, and (ii) a T cell response to at least one polypeptide of a fusion protein. In some embodiments, the immune response comprises (i) an antibody or B cell response to at least one polysaccharide antigen, and (ii) a CD4+ T cell response (e.g., $T_H1$, $T_H2$, or $T_H17$ response), a CD8+ T cell response, a CD4+ and CD8+ T cell response, or a CD4−/CD8− T cell response to at least one polypeptide of a fusion protein. In some embodiments, the immune response comprises (i) an antibody or B cell response to at least one polysaccharide antigen, and (ii) an antibody or B cell response to at least one polypeptide of a fusion protein. In some embodiments, the immune response comprises (i) an antibody or B cell response to at least one polysaccharide antigen, and (ii) an antibody or B cell response and a T cell response, to at least one polypeptide of a fusion protein. In some embodiments, the immune response comprises (i) an antibody or B cell response to at least one polysaccharide antigen, and (ii) an antibody or B cell response, and a CD4+ T cell response, including a $T_H1$, $T_H2$, or $T_H17$ response, a CD8+ T cell response, a CD4+ and CD8+ T cell response, or a CD4−/CD8− T cell response, to at least one polypeptide of a fusion protein.

In some embodiments, upon administration to a subject, a pharmaceutical composition disclosed herein induces an opsonic/bactericidal response against one or more serotypes of *Streptococcus pneumoniae*. In some embodiments, such an opsonic/bactericidal response may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such an opsonic/bactericidal response may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such an opsonic/bactericidal response may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, an opsonic/bactericidal response can include production of antibodies that opsonize one or more serotypes of *Streptococcus pneumoniae*, which leads to killing of such serotype(s) by one or more immune pathways. In some embodiments, such an opsonic/bactericidal response can be determined by an opsonophagocytic assay (OPA) or a concentrated opsonophagocytic assay (COPA) known in the art and/or as described herein.

In some embodiments, upon administration to a subject, a pharmaceutical composition disclosed herein inhibits transmission of one or more serotypes of *Streptococcus pneumoniae* from the subject to another subject. In some embodiments, such inhibition of transmission may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition of transmission may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of transmission may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein reduces or inhibits replication, or reduces bacterial load, of one or more serotypes of *Streptococcus pneumoniae*. In some embodiments, such reduction or inhibition of replication, or reduction of bacterial load, may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction or inhibition of replication, or reduction of bacterial load, may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction or inhibition of replication, or reduction of bacterial load, may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of Invasive Pneumonoccal Disease (IPD) associated with or induced by one or more serotypes of *Streptococcus pneumoniae*. In some embodiments, such inhibition of IPD or reduction in the rate of occurrence of IPD may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition of IPD or reduction in the rate of occurrence of IPD may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of IPD or reduction in the rate of occurrence of IPD may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of Invasive Pneumonoccal Disease (IPD) associated with or induced by one or more serotypes of *Streptococcus pneumoniae*. In some embodiments, such reduction in the severity of IPD may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of IPD may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of IPD may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of bacteremia, sepsis, and/or meningitis associated with or induced by one or more serotypes of *Streptococcus pneumoniae*. In some embodiments, such inhibition, or reduction in the rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of bacteremia, sepsis, and/or meningitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of bacteremia, sepsis, and/or meningitis associated with or induced by one or more serotypes of *Streptococcus pneumoniae*. In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of organ damage associated with or induced by one or more serotypes of *Streptococcus pneumoniae*. In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of organ damage associated with or induced by one or more serotypes of *Streptococcus pneumoniae*. In some embodiments, such reduction in the severity of organ damage may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of organ damage may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of organ damage may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of pneumonia associated with or induced by one or more serotypes of *Streptococcus pneumoniae*. In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of pneumonia associated with or induced by one or more serotypes of *Streptococcus pneumoniae*. In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of pneumonia may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of otitis media associated with or induced by one or more serotypes of *Streptococcus pneumoniae*. In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of otitis media associated with or induced by one or more serotypes of *Streptococcus pneumoniae*. In some embodiments, such reduction in the severity of otitis media may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of otitis media may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of otitis media may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of sinusitis associated with or induced by one or more serotypes of *Streptococcus pneumoniae*. In some embodiments, such inhibition, or reduction in the rate of occurrence, of sinusitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of sinusitis associated with or induced by one or more serotypes of *Streptococcus pneumoniae*. In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of sinusitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein reduces or inhibits colonization by one or more serotypes of *Streptococcus pneumoniae*. In some embodiments, such reduction or inhibition of colonization may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction or inhibition of colonization may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction or inhibition of colonization may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein reduces or inhibits colonization of mucosal surface(s) by one or more serotypes of *Streptococcus pneumoniae*. In some embodiments, such reduction or inhibition of colonization of mucosal surface(s) may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction or inhibition of colonization of mucosal surface(s) may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction or inhibition of colonization of mucosal surface(s) may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein reduces or inhibits colonization of the nasopharynx by one or more serotypes of *Streptococcus pneumoniae*. In some embodiments, such reduction or inhibition of colonization of nasopharynx may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction or inhibition of colonization of nasopharynx may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction or inhibition of colonization of nasopharynx may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces asymptomatic infection by one or more serotypes of *Streptococcus pneumoniae*. In some embodiments, such inhibition or reduction of asymptomatic infection may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition or reduction of asymptomatic infection may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition or reduction of asymptomatic infection may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

Some aspects of the present disclosure provide a method of making an immunogenic composition (e.g., vaccine), the method comprising non-covalently complexing a plurality of first biotinylated polysaccharide antigens with a plurality of a first fusion protein comprising at least one polypeptide antigen selected from: a pneumolysin polypeptide or variant or antigenic fragment thereof; an SP0435 polypeptide or antigenic fragment thereof; or a combination thereof. In some embodiments, the method further comprises non-covalently complexing a plurality of second biotinylated polysaccharide antigens with a plurality of a second fusion protein comprising at least one polypeptide antigen selected from: an SP1500 polypeptide or antigenic fragment thereof; an SP0785 polypeptide or antigenic fragment thereof; or a combination thereof. In some embodiments, the plurality of first biotinylated polysaccharide antigens comprises a polysaccharide of *Streptococcus pneumoniae* having a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48. In some embodiments, the plurality of first biotinylated polysaccharide antigens comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the plurality of first biotinylated polysaccharide antigens comprises a polysaccharide of *Streptococcus pneumoniae* having a serotype selected from each of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the plurality of first biotinylated polysaccharide antigens comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38. In some embodiments, the plurality of first biotinylated polysaccharide antigens comprises a polysaccharide of *Streptococcus pneumoniae* having a serotype selected from each of 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38. In some embodiments, the plurality of second biotinylated polysaccharide antigens comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the plurality of second biotinylated polysaccharide antigens comprises a polysaccharide of *Streptococcus pneumoniae* having a serotype selected from each of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the plurality of second biotinylated polysaccharide antigens comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38. In some embodiments, the plurality of second biotinylated polysaccharide antigens comprises a polysaccharide of *Streptococcus pneumoniae* having a serotype selected from each of 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

In some embodiments, the plurality of first biotinylated polysaccharide antigens comprises a polysaccharide of *Streptococcus pneumoniae* having a serotype selected from one or more of 6C, 7C, 15A, 16F, 23A, 23B, 24F, 31, 35B, and 38. In some embodiments, the plurality of first biotinylated polysaccharide antigens comprises a polysaccharide of *Streptococcus pneumoniae* having a serotype selected from each of 6C, 7C, 15A, 16F, 23A, 23B, 24F, 31, 35B, and 38. In some embodiments, the plurality of second biotinylated polysaccharide antigens comprises a polysaccharide of *Streptococcus pneumoniae* having a serotype selected from one or more of 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the plurality of second biotinylated polysaccharide antigens comprises a polysaccharide of *Streptococcus pneumoniae* having a serotype selected from each of 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the plurality of first biotinylated polysaccharide antigens comprises a polysaccharide of *Streptococcus pneumoniae* having a serotype selected from one or more of 1, 4, 6A, 6B, 9V, 15B, 18C, 19A, 23F, and 33F. In some embodiments, the plurality of first biotinylated polysaccharide antigens comprises a polysaccharide of *Streptococcus pneumoniae* having a serotype selected from each of 1, 4, 6A, 6B, 9V, 15B, 18C, 19A, 23F, and 33F. In some embodiments, the plurality of second biotinylated polysaccharide antigens comprises a polysaccharide of *Streptococcus pneumoniae* having a serotype selected from one or more of 2, 3, 5, 6C, 7C, 7F, 8, 9N, 10A, 11A, 12F, 14, 15A, 16F, 17F, 19F, 20B, 22F, 23A, 23B, 24F, 31, 35B, and 38. In some embodiments, the plurality of second biotinylated polysaccharide antigens comprises a polysaccharide of *Streptococcus pneumoniae* having a serotype selected from each of 2, 3, 5, 6C, 7C, 7F, 8, 9N, 10A, 11A, 12F, 14, 15A, 16F, 17F, 19F, 20B, 22F, 23A, 23B, 24F, 31, 35B, and 38. In some embodiments, the plurality of first biotinylated polysaccharide antigens comprises a polysaccharide of *Streptococcus pneumoniae* having a serotype selected from one or more of 1, 4, 6A, 6B, 9V, 15B, 18C, 19A, 23F, and 33F. In some embodiments, the plurality of first biotinylated polysaccharide antigens comprises a polysaccharide of *Streptococcus pneumoniae* having a serotype selected from each of 1, 4, 6A, 6B, 9V, 15B, 18C, 19A, 23F, and 33F. In some embodiments, the plurality of second biotinylated polysaccharide antigens comprises a polysaccharide of *Streptococcus pneumoniae* having a serotype selected from one or more of 2, 3, 5, 6C, 7C, 7F, 8, 9N, 10A, 11A, 12F, 14, 15A, 17F, 19F, 20B, 22F, 23A, 23B, 24F, 31, 35B, and 38. In some embodiments, the plurality of second biotinylated polysaccharide antigens comprises a polysaccharide of *Streptococcus pneumoniae* having a serotype selected from each of 2, 3, 5, 6C, 7C, 7F, 8, 9N, 10A, 11A, 12F, 14, 15A, 17F, 19F, 20B, 22F, 23A, 23B, 24F, 31, 35B, and 38.

Some embodiments provide for a method of immunizing a subject against *Streptococcus pneumoniae* infection and/or colonization, the method comprising administering to the subject an immunologically effective amount of an immunogenic composition (e.g., vaccine) disclosed herein. In some embodiments, a method of immunizing a subject against *Streptococcus pneumoniae* infection and/or colonization, comprises administering to a subject an immunologically effective amount of an immunogenic complex disclosed herein. In some embodiments, a method of immunizing a subject against *Streptococcus pneumoniae* infection and/or colonization, comprises administering to a subject an immunologically effective amount of a pharmaceutical composition disclosed herein.

In some embodiments, administration of the immunogenic composition (e.g., vaccine), immunogenic complex, or pharmaceutical composition induces an immune response. In some embodiments, the immune response comprises an innate immune response. In some embodiments, the immune response comprises an antibody or B cell response. In some embodiments, the immune response comprises a T cell response. In some embodiments, the immune response comprises a CD4+ T cell response (e.g., $T_H1$, $T_H2$, or $T_H17$ response), a CD8+ T cell response, a CD4+ and CD8+ T cell response, or a CD4−/CD8− T cell response. In some embodiments, the immune response comprises (i) an antibody or B cell response and (ii) a T cell response. In some embodiments, the immune response comprises (i) an antibody or B cell response, (ii) a T cell response, and (iii) an innate immune response. In some embodiments, the immune response is to at least one polysaccharide antigen or at least one polypeptide of a fusion protein. In some embodiments, the immune response comprises (i) an antibody or B cell response to at least one polysaccharide antigen, and (ii) a T cell response to at least one polypeptide of a fusion protein. In some embodiments, the immune response comprises (i) an antibody or B cell response to at least one polysaccharide antigen, and (ii) a CD4+ T cell response (e.g., $T_H1$, $T_H2$, or $T_H17$ response), a CD8+ T cell response, a CD4+ and CD8+ T cell response, or a CD4−/CD8− T cell response to at least one polypeptide of a fusion protein. In some embodiments, the immune response comprises (i) an antibody or B cell response to at least one polysaccharide antigen, and (ii) an antibody or B cell response to at least one polypeptide of a fusion protein. In some embodiments, the immune response comprises (i) an antibody or B cell response to at least one polysaccharide antigen, and (ii) an antibody or B cell response, and a T cell response, to at least one polypeptide of a fusion protein. In some embodiments, the immune response comprises (i) an antibody or B cell response to at least one polysaccharide antigen, and (ii) an antibody or B cell response, and a CD4+ T cell response, including $T_H1$, $T_H2$, or $T_H17$ response, or a CD8+ T cell response, a CD4+ and CD8+ T cell response, or a CD4−/CD8− T cell response, to at least one polypeptide of a fusion protein.

In some embodiments, administration of an immunogenic composition (e.g., vaccine), immunogenic complex, or pharmaceutical composition (e.g., ones described and/or utilized herein) induces an opsonic/bactericidal response against one or more serotypes of *Streptococcus pneumoniae*. In some embodiments, such an opsonic/bactericidal response may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such an opsonic/bactericidal response may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such an opsonic/bactericidal response may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones as described and/or utilized herein) inhibits transmission of one or more serotypes of *Streptococcus pneumoniae* from the subject to another subject. In some embodiments, such inhibition of transmission may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition of transmission may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of transmission may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of an immunogenic composition (e.g., vaccine), immunogenic complex, or pharmaceutical composition (e.g., ones described and/or utilized herein) inhibits or reduces the rate of occurrence of Invasive Pneumococcal Disease (IPD) associated with or induced by one or more serotypes of *Streptococcus pneumoniae*. In some embodiments, such inhibition, or reduction in the rate of occurrence, of IPD may be directed against one or more (e.g., 1, 2, 3, 4, 5, 6, 7, 8, 9, 10 or more) serotypes of

*Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of IPD may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of IPD may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces the severity of Invasive Pneumococcal Disease (IPD) associated with or induced by one or more serotypes of *Streptococcus pneumoniae*. In some embodiments, such reduction in the severity of IPD may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of IPD may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of IPD may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of an immunogenic composition (e.g., vaccine), immunogenic complex, or pharmaceutical composition (e.g., ones described and/or utilized herein) inhibits or reduces the rate of occurrence of bacteremia, sepsis, and/or meningitis associated with or induced by one or more serotypes of *Streptococcus pneumoniae*. In some embodiments, such inhibition, or reduction in rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in rate of occurrence, of bacteremia, sepsis, and/or meningitis may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces the severity of bacteremia, sepsis, and/or meningitis associated with or induced by one or more serotypes of *Streptococcus pneumoniae*. In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of an immunogenic composition (e.g., vaccine), immunogenic complex, or pharmaceutical composition (e.g., ones described and/or utilized herein) inhibits or reduces the rate of occurrence of organ damage associated with or induced by one or more serotypes of *Streptococcus pneumoniae*. In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces the severity of organ damage associated with or induced by one or more serotypes of *Streptococcus pneumoniae*. In some embodiments, such reduction in the severity of organ damage may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of organ damage may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of organ damage may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of an immunogenic composition (e.g., vaccine), immunogenic complex, or pharmaceutical composition (e.g., ones described and/or utilized herein) inhibits or reduces the rate of occurrence of pneumonia associated with or induced by one or more serotypes of *Streptococcus pneumoniae*. In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces the severity of pneumonia associated with or induced by one or more serotypes of *Streptococcus pneumoniae*. In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of pneumonia may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of an immunogenic composition (e.g., vaccine), immunogenic complex, or pharmaceutical composition (e.g., ones described and/or utilized herein) inhibits or reduces the rate of occurrence of otitis media associated with or induced by one or more serotypes of *Streptococcus pneumoniae*. In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against two or more (e.g., 2, 3, 4, 5, 6, 7, 8, 9, 10 or more) serotypes of *Streptococcus pneumo-*

*niae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces the severity of otitis media associated with or induced by one or more serotypes of *Streptococcus pneumoniae*. In some embodiments, such reduction in the severity of otitis media may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of otitis media may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of otitis media may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of an immunogenic composition (e.g., vaccine), immunogenic complex, or pharmaceutical composition (e.g., ones described and/or utilized herein) inhibits or reduces the rate of occurrence of sinusitis associated with or induced by one or more serotypes of *Streptococcus pneumoniae*. In some embodiments, such inhibition, or reduction in the rate of occurrence, of sinusitis may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces the severity of sinusitis associated with or induced by one or more serotypes of *Streptococcus pneumoniae*. In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of sinusitis may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of an immunogenic composition (e.g., vaccine), immunogenic complex, or pharmaceutical composition (e.g., ones described and/or utilized herein) reduces or inhibits colonization by one or more serotypes of *Streptococcus pneumoniae*. In some embodiments, such reduction or inhibition of colonization may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction or inhibition of colonization may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction or inhibition of colonization may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces or inhibits colonization of mucosal surface(s) by one or more serotypes of *Streptococcus pneumoniae*. In some embodiments, such reduction or inhibition of colonization of mucosal surface(s)

may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction or inhibition of colonization of mucosal surface(s) may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction or inhibition of colonization of mucosal surface(s) may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of an immunogenic composition (e.g., vaccine), immunogenic complex, or pharmaceutical composition (e.g., ones described and/or utilized herein) reduces or inhibits colonization of nasopharynx by one or more serotypes of *Streptococcus pneumoniae*. In some embodiments, such reduction or inhibition of colonization of nasopharynx may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction or inhibition of colonization of nasopharynx may be directed against one or more (e.g., 1, 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction or inhibition of colonization of nasopharynx may be directed against two or more (e.g., 2, 3, 4, 5, 6, 7, 8, 9, 10 or more) serotypes of *Streptococcus pneumoniae*, wherein an immunogenic composition (e.g., vaccine), immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments of the methods disclosed herein, the *Streptococcus pneumoniae* has a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48. In some embodiments, the *Streptococcus pneumoniae* has a serotype selected from one or more of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the *Streptococcus pneumoniae* has a serotype selected from one or more of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, the subject is immunized against *Streptococcus pneumoniae* infection and/or colonization with one dose of an immunogenic composition (e.g., vaccine). In some embodiments, the subject is immunized against *Streptococcus pneumoniae* infection and/or colonization with two doses of an immunogenic composition (e.g., vaccine). In some embodiments, the subject is immunized against *Streptococcus pneumoniae* infection and/or colonization with three doses of an immunogenic composition (e.g., vaccine). In some embodiments, the subject is immunized against *Streptococcus pneumoniae* infection and/or colonization with four doses of an immunogenic composition (e.g., vaccine).

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 7 is a schematic of an exemplary CP1 fusion protein. Such an exemplary CP1 fusion protein comprises a biotin-binding protein such as, e.g., a truncated rhizavidin protein (e.g., amino acids 45-179 of a wild-type rhizavidin protein), a first linker (e.g., a GGGGSSS (SEQ ID NO: 30) linker), a SP1500 polypeptide (e.g., amino acids 27-278 of a full-length *S. pneumoniae* SP1500 polypeptide), a second linker (e.g., the amino acid sequence AAA), and a SP0785 polypeptide (e.g., amino acids 33-399 of a full length *S. pneumoniae* SP0785 polypeptide). In some embodiments, a CP1 fusion protein may further comprise a detectable or purification tag (e.g., His tag). The amino acid sequence AAA can be from the Not I site on a pET21/24 plasmid, or synthesized. For a GGGGSSS (SEQ ID NO: 30) linker, the SSS amino acid sequence can be from the Sac I site on a pET21/24 plasmid, with the GGGG (SEQ ID NO: 54) amino acid sequence added to create a flexible linker with minimal steric hindrance. Alternatively, the GGGGSSS (SEQ ID NO: 30) linker can be synthesized.

FIG. 9 is a table showing exemplary structures of *S. pneumoniae* antigenic polysaccharides of serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, and 35B.

FIG. 18 shows relative antibody titers against capsular polysaccharides of various serotypes for both MAPS-34 all-on-CP1 (immunization group B, gray dot) and MAPS-34 all-on-SPP2 (immunization group F, black dot) compared to a baseline of MAPS-23 all-on-CP1 (immunization group A, dotted line) in P2 rabbit sera. The upper graph shows results for 13 serotypes common to MAPS-23, MAPS-34 and PCV13. The lower graph shows results for 10 addition serotypes common to MAPS-23 and MAPS-34. Geometric mean titer (GMT) ratio and 95% confidence intervals are shown on each graph.

FIG. 34A shows representative results for IgG titers against serotype 3 capsular polysaccharide (CPS3) in P0, P1 and P2 rabbit sera of immunization Groups D and E shown in FIG. 12 as Combo #1 and Combo #2, respectively. Each point on the graph represents serum from one rabbit. Horizontal bars are the geometric mean concentration of the groups and error bars are 95% confidence intervals. Results are expressed in arbitrary units (a.u.) of anti-CPS3 IgG. Data presented includes a subset of data for immunogenicity against capsular polysaccharide (CPS) serotypes presented in FIG. 17A. FIG. 34B shows representative titers of PdT toxoid-binding IgG (anti-PdT (G294P)) in P0, P1 and P2 rabbit sera of immunization Groups D and E shown in FIG. 12 as Combo #1 and Combo #2, respectively. Each point on the graph represents serum from one rabbit. Horizontal bars are the geometric mean concentration of the groups and error bars are 95% confidence intervals. Results are expressed in μg/ml of anti-PdT (G294P) IgG. Data presented is a subset of data for immunogenicity against PdT (G294P) presented in FIG. 14. FIG. 34C shows representative half-maximal inhibitory concentration (IC50) of pneumolysin neutralizing antibodies against the hemolytic activity of native pneumolysin in P0, P1 and P2 rabbit sera of immunization Groups D and E shown in FIG. 12 as Combo #1 and Combo #2, respectively. Each point on the graph represents serum from one rabbit. Horizontal bars are the geometric mean IC50 of the groups and error bars are 95% confidence intervals. Results are expressed as the IC50 (serum dilution). Data presented is a subset of data for functional responses against PdT (G294P) presented in FIG. 16.

FIG. 36A shows representative results for groups inoculated with His-tagged SPP2 and 1.SPP2 MAPS. FIG. 36B shows representative results for groups inoculated with non-His-tagged SPP2 and 1.SPP2 MAPS.

CERTAIN DEFINITIONS

Figure 1:
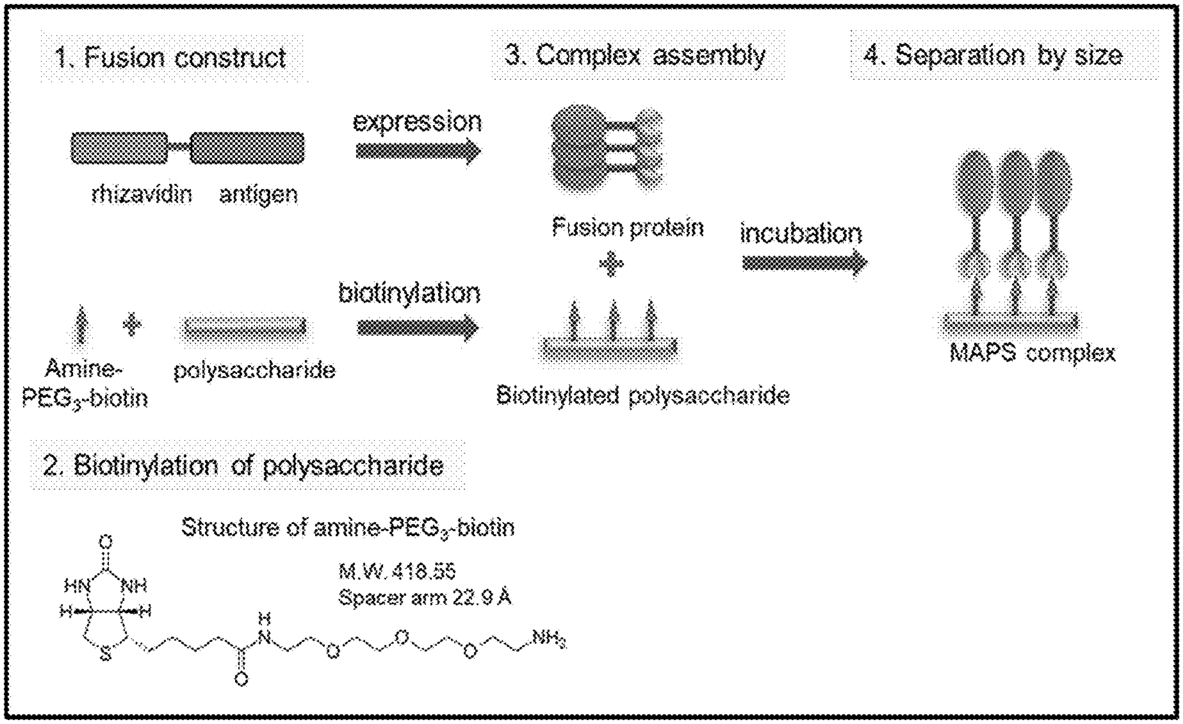
FIG. 1 is a schematic representation of an exemplary Multiple Antigen Presenting System (MAPS). In the exemplary embodiment shown, MAPS immunogenic complexes comprise one or more polypeptide antigens fused to the biotin-binding protein rhizavidin, or a biotin-binding domain or biotin-binding fragment thereof, and a biotinylated antigenic polysaccharide. In this figure, each MAPS complex is formed between one or more fusion proteins and a biotinylated polysaccharide by non-covalent binding of a truncated rhizavidin to biotin.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastrical, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively, or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amino acid: In its broadest sense, the term "amino acid", as used herein, refers to any compound and/or substance that can be incorporated into a polypeptide chain, e.g., through formation of one or more peptide bonds. In some embodiments, an amino acid has the general structure $H_2N—C(H)(R)—COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments, the term "amino acid" may be used to refer to an amino acid residue of a polypeptide.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kDa tetrameric agents comprised of two identical heavy chain polypeptides (about 50 kDa each) and two identical light chain polypeptides (about 25 kDa each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present disclosure is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BITERs; ankyrin repeat proteins or DARPINS®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., polyethylene glycol, etc.]).

Antigen: The term "antigen", as used herein, refers to (i) an agent that induces an immune response; and/or (ii) an agent that binds to a T cell receptor (e.g., when presented by an MHC molecule) or to an antibody. In some embodiments, an antigen induces a humoral response (e.g., including production of antigen-specific antibodies); in some embodiments, an antigen induces a cellular response (e.g., involving T cells whose receptors specifically interact with the antigen). In some embodiments, an antigen induces a humoral response and a cellular response. In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments, other than a biologic polymer (e.g., other than a nucleic acid or amino acid polymer)), etc. In some embodiments, an antigen is or comprises a polypeptide. In some embodiments, an antigen is or comprises a polysaccharide. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present disclosure are provided in a crude form. In some embodiments, an antigen is a recombinant antigen. In some embodiments, an antigen is a polypeptide or a polysaccharide that, upon administration to a subject, induces a specific and/or clinically relevant immune response to such polypeptide or polysaccharide. In some embodiments, an antigen is selected to induce a specific and/or clinically relevant immune response to such polypeptide or polysaccharide.

Associated with: Two entities are "associated" with one another, as that term is used herein, if the presence, level and/or form of one is correlated with that of the other. In some embodiments, two or more entities are physically "associated" with one another if they interact, directly or indirectly, so that they are and/or remain in physical proximity with one another. In some embodiments, two or more entities that are physically associated with one another are covalently linked to one another. In some embodiments, two or more entities that are physically associated with one another are not covalently linked to one another but are non-covalently associated, for example by means of affinity interactions, electrostatic interactions, hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts-including where interacting entities or moieties are studied in isolation or in the context of more complex systems (e.g., while covalently or otherwise associated with a carrier entity and/or in a biological system or cell).

Carrier protein: As used herein, the term "carrier protein" refers to a protein or peptide that is coupled, or complexed, or otherwise associated with a hapten (e.g., a small peptide or lipid) or less immunogenic antigen (e.g., a polysaccharide) and that induces or improves an immune response to such a coupled, or complexed, or otherwise associated hapten (e.g., a small peptide or lipid) or less immunogenic antigen (e.g., a polysaccharide). In some embodiments, such an immune response is or comprises a response to a hapten or less immunogenic antigen that is coupled, or complexed, or otherwise associated with such a carrier protein. In some embodiments, such an immune response is or comprises a response to both a carrier protein and a hapten or less immunogenic antigen that is coupled, or complexed, or otherwise associated with such a carrier protein. In some embodiments, no significant immune response to a carrier protein itself occurs. In some embodiments, immune response to a carrier protein may be detected; in some embodiments, immune response to such a carrier protein is strong. In some embodiments, a carrier protein is coupled, or complexed, or otherwise associated with one or more other molecules.

Colonization: As used herein, the term "colonization" generally refers to the ability of a microbe to grow at a target site or surface. For example, the terms "colonization" refers to the ability of a microbe (e.g., a bacterium) to grow at an anatomical site (e.g., a mucosal membrane, gastrointestinal tract, injury site, organ, etc.) of a host.

Combination therapy: As used herein, the term "combination therapy" refers to those situations in which a subject is exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Derivative: As used herein, the term "derivative", or grammatical equivalents thereof, refers to a structural analogue of a reference substance. That is, a "derivative" is a substance that shows significant structural similarity with the reference substance, for example sharing a core or consensus structure, but also differs in certain discrete ways. Such a substance would be said to be "derived from" said reference substance. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Fragment: A "fragment" of a material or entity as described herein has a structure that includes a discrete portion of the whole, but lacks one or more moieties found in the whole. In some embodiments, a fragment consists of such a discrete portion. In some embodiments, a fragment includes a discrete portion of the whole which discrete portion shares one or more functional characteristics found in the whole. In some embodiments, a fragment consists of such a discrete portion. In some embodiments, a fragment consists of or comprises a characteristic structural element or moiety found in the whole. In some embodiments, a fragment of a polymer, e.g., a polypeptide or a polysaccharide, comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may, in some embodiments, be referred to as the "parent" of the whole.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical. Calculation of the percent identity of two nucleic acid or polypeptide sequences, for example, can be performed by aligning the two sequences for optimal comparison purposes (e.g., gaps can be introduced in one or both of a first and a second sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 75%, at least 80%, at least 85%, at least 90%, at least 95%, at least 96%, at least 97%, at least 98%, at least 99%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller, 1989, which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, inhibit or reduce: As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single subject) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Immunologically effective amount or immunologically effective dose: As used herein, "immunologically effective amount" or "immunologically effective dose" refers to an amount of an antigenic or immunogenic substance, e.g., an antigen, immunogen, immunogenic complex, immunogenic composition, vaccine, or pharmaceutical composition, which when administered to a subject, either in a single dose or as part of a series of doses, that is sufficient to enhance a subject's own immune response against a subsequent exposure to a pathogen. In some embodiments, the pathogen is *S. pneumoniae*. In some embodiments, the immune response is against one or more different serotypes of *S. pneumoniae*. In some embodiments, the immune response is against two or more different serotypes of *S. pneumoniae*. In some embodiments, the immune response is against nine or more different serotypes of *S. pneumoniae*. In some embodiments, the immune response is against thirteen or more different serotypes of *S. pneumoniae*. In some embodiments, the immune response is against fifteen or more different serotypes of *S. pneumoniae*. In some embodiments, the immune response is against twenty-three or more different serotypes of *S. pneumoniae*. In some embodiments, the immune response is against twenty-four or more different serotypes of *S. pneumoniae*. An immunologically effective amount may vary based on the subject to be treated, the species of the subject, the degree of immune response desired to induce, etc. In some embodiments, an immunologically effective amount is sufficient for treatment or protection of a subject having or at risk of having disease. In some embodiments, an immunologically effective amount refers to a non-toxic but sufficient amount that can be an amount to treat, attenuate, or prevent infection and/or disease (e.g., bacterial infection, pneumococcal infection, bacterial colonization, pneumococcal colonization, complications associated with bacterial infection, complications associated with pneumococcal infection, etc.) in any subject. In some embodiments, an immunologically effective amount is sufficient to induce an immunoprotective response upon administration to a subject.

Immunoprotective response or protective response: As used herein, "immunoprotective response" or "protective response" refers to an immune response that mediates antigen or immunogen-induced immunological memory. In some embodiments, an immunoprotective response is induced by the administration of a substance, e.g., an antigen, immunogen, immunogenic complex, immunogenic composition, vaccine, or pharmaceutical composition to a subject. In some embodiments, immunoprotection involves one or more of active immune surveillance, a more rapid and effective response upon immune activation as compared to a response observed in a naïve subject, efficient clearance of the activating agent or pathogen, followed by rapid resolution of inflammation. In some embodiments, an immunoprotective response is an adaptive immune response. In some embodiments, an immunoprotective response is sufficient to protect an immunized subject from productive infection by a particular pathogen or pathogens to which a vaccine is directed (e.g., *S. pneumoniae* infection).

Immunization: As used herein, "immunization", or grammatical equivalents thereof, refers to a process of inducing an immune response to an infectious organism or agent in a subject ("active immunization"), or alternatively, providing immune system components against an infectious organism or agent to a subject ("passive immunization"). In some embodiments, immunization involves the administration of one or more antigens, immunogens, immunogenic complexes, vaccines, immune molecules such as antibodies, immune sera, immune cells such as T cells or B cells, or pharmaceutical compositions to a subject. In some embodiments, immunization is performed by administering an immunologically effective amount of a substance, e.g., an antigen, immunogen, immunogenic complex, immunogenic composition, vaccine, immune molecule such as an antibody, immune serum, immune cell such as a T cell or B cell, or pharmaceutical composition to a subject. In some embodiments, immunization results in an immunoprotective response in the subject. In some embodiments, active immunization is performed by administering to a subject an antigenic or immunogenic substance, e.g., an antigen, immunogen, immunogenic complex, vaccine, or pharmaceutical composition. In some embodiments, passive immunization is performed by administering to a subject an immune system component, e.g., an immune molecule such as an antibody, immune serum, or immune cell such as a T cell or B cell.

Isolated: As used herein, the term "isolated", or grammatical equivalents thereof, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polysaccharide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide or polysaccharide that is chemically synthesized or is synthesized in a cellular system different from that which produces it in nature is considered to be an "isolated" polypeptide or polysaccharide. Alternatively or additionally, in some embodiments, a polypeptide or polysaccharide that has been subjected to one or more purification techniques may be considered to be an "isolated" polypeptide or polysaccharide to the extent that it has been separated from other components a) with which it is associated in nature; and/or b) with which it was associated when initially produced.

Linker: As used herein, the term "linker" is used to refer to an entity that connects two or more elements to form a multi-element agent. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker (L). In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) are known in the art (Holliger et al, 1993; Poljak, 1994).

Non-inferior: As used herein, the term "non-inferior" in the context of evaluating a test pharmaceutical composition refers to a test pharmaceutical composition that is (e.g., in terms of immunogenicity and/or functional antibody titer generated by the test composition) at least as effective as a reference composition. In some embodiments, non-inferiority is demonstrated when the lower bound of the 95% confidence interval (CI) for the geometric mean titer (GMT) ratio of a test pharmaceutical composition over a reference composition is at least greater than or equal to 0.4 or above, including, e.g., at least 0.5, at least 0.6, at least 0.7, at least 0.8, at least 0.9, at least 0.95, at least 0.98, at least 1.0, or higher. For example, in some embodiments, an immunogenic composition (e.g., vaccine) described herein is non-inferior to a reference vaccine (e.g., PCV13, PCV20, or PPSV23) when the lower bound of the 95% confidence interval (CI) for the geometric mean titer (GMT) ratio of the immunogenic composition (e.g., vaccine) over the reference vaccine is at least greater than or equal to 0.4 or above, including, e.g., at least 0.5, at least 0.6, at least 0.7, at least 0.8, at least 0.9, at least 0.95, at least 0.98, at least 1.0, or higher. In some embodiments, an immunogenic composition (e.g., vaccine) described herein is non-inferior to a reference vaccine (e.g., PCV13, PCV20, or PPSV23) when the lower bound of the 95% confidence interval (CI) for the geometric mean titer (GMT) ratio of the immunogenic composition (e.g., vaccine) over the reference vaccine is at least greater than or equal to 0.95 or above, including, e.g., at least 0.96, at least 0.97, at least 0.98, at least 0.99, at least 1.0, at least 1.1, at least 1.3, at least 1.5, or higher. In some embodiments, an immunogenic composition (e.g., vaccine) described herein is non-inferior to a reference vaccine (e.g., PCV13, PCV20, or PPSV23) when the seroconversion rates, or percentages of vaccine recipients with immune responses, are above a pre-defined threshold, e.g., the lower bound of the 95% confidence interval for the difference between the percentage of subjects who seroconvert, following immunization with an immunogenic composition (e.g., vaccine) described herein or immunization with the reference vaccine (e.g., PCV13, PCV20, or PPSV23), is greater than-0.10.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Polysaccharide: The term "polysaccharide" as used herein refers to a polymeric carbohydrate molecule composed of long chains of monosaccharide units bound together by glycosidic, phosphodiester, or other linkages and on hydrolysis give the constituent monosaccharides or oligosaccharides. Polysaccharides range in structure from linear to highly branched. Examples include storage polysaccharides such as starch and glycogen, structural polysaccharides such as cellulose and chitin and microbial polysaccharides, and antigenic polysaccharides found in microorganisms including, but not limited to, capsular polysaccharides (CPS), O polysaccharides (OPS), core O polysaccharides (COPS), and lipopolysaccharides (LPS).

Polypeptide: The term "polypeptide", as used herein, generally has its art-recognized meaning of a polymer of at least three amino acids, e.g., linked to each other by peptide bonds. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

Prevention: The term "prevent" or "prevention", as used herein in connection with a disease, disorder, and/or medical condition, refers to reducing the risk of developing the disease, disorder and/or condition, and/or a delay of onset, and/or reduction in frequency and/or severity of one or more characteristics or symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. In some embodiments, prevention may be considered complete when onset of a disease, disorder or condition has been delayed for a pre-defined period of time.

Protein: As used herein, the term "protein" encompasses a polypeptide. Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain 1-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant: As used herein, the term "recombinant" is intended to refer to polypeptides that are designed, engineered, prepared, expressed, created, manufactured, and/or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Reference: As used herein, the term "reference" describes a standard or control relative to which a comparison is performed. For example, in some embodiments, an agent, animal, subject, population, sample, sequence or value of interest is compared with a reference or control agent, animal, subject, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a "response" to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Subject or tumor response may be measured according to a wide variety of criteria, including clinical criteria and objective criteria. Techniques for assessing response include, but are not limited to, clinical examination, positron emission tomography, chest X-ray CT scan, MRI, ultrasound, endoscopy, laparoscopy, presence or level of biomarkers in a sample obtained from a subject, cytology, and/or histology. The exact response criteria can be selected in any appropriate manner, provided that when comparing groups of subjects and/or tumors, the groups to be compared are assessed based on the same or comparable criteria for determining response rate. One of ordinary skill in the art will be able to select appropriate criteria.

Risk: As will be understood from context, "risk" of a disease, disorder, and/or condition refers to a likelihood that a particular subject will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments, risk is expressed as a risk relative to a risk associated with a reference sample or group of reference samples. In some embodiments, a reference sample or group of reference samples have a known risk of a disease, disorder, condition and/or event. In some embodiments, a reference sample or group of reference samples are from subjects comparable to a particular subject. In some embodiments, relative risk is 0, 1, 2, 3, 4, 5, 6, 7, 8, 9, 10, or more.

Serotype: As used herein, the term "serotype", also referred to as a serovar, refers to a distinct variation within a species of bacteria or virus or among immune cells of different subjects. These microorganisms, viruses, or cells are classified together based on their cell surface antigens, allowing the epidemiologic classification of organisms to the sub-species level. A group of serovars with common antigens may be referred to as a serogroup or sometimes serocomplex.

Species: As used herein, the term "species" refers to a distinct immunogenic complex comprising (i) a biotinylated polysaccharide antigen and (ii) a fusion protein comprising a biotin-binding moiety and one or more *Streptococcus pneumoniae* polypeptide antigens. In some embodiments, a distinct species can differ in one or more of (i) a biotinylated polysaccharide antigen and (ii) a fusion protein comprising a biotin-binding moiety and one or more *Streptococcus pneumoniae* polypeptide antigens.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an subject to whom diagnosis and/or therapy is and/or has been administered.

Superior: As used herein, the term "superior" in the context of evaluating a test pharmaceutical composition refers to a test pharmaceutical composition that performs (e.g., in terms of immunogenicity and/or functional antibody titer generated by the test composition) better than a reference composition. In some embodiments, superiority is demonstrated when the upper bound of the 95% confidence interval (CI) for the geometric mean titer (GMT) ratio of a test pharmaceutical composition over a reference composition is at least 1.3 or above, including, e.g., at least 1.4, at least 1.5, at least 2, at least 2.5, at least 3, at least 4, or higher. For example, in some embodiments, an immunogenic composition (e.g., vaccine) described herein is superior to a reference vaccine (e.g., PCV13, PCV20, or PPSV23) when the upper bound of the 95% confidence interval (CI) for the geometric mean titer (GMT) ratio of the immunogenic composition (e.g., vaccine) over the reference vaccine is at least 1.3 or above, including, e.g., at least 1.4, at least 1.5, at least 2, at least 2.5, at least 3, at least 4, or higher. In some embodiments, an immunogenic composition (e.g., vaccine) described herein is superior to a reference vaccine (e.g., PCV13, PCV20, or PPSV23) when the two-sided 95% confidence interval (CI) for the geometric mean titer (GMT) ratio of the immunogenic composition (e.g., vaccine) over the reference vaccine excludes zero.

Susceptible to: A subject who is "susceptible to" a disease, disorder, or condition is at risk for developing the disease, disorder, or condition. In some embodiments, a subject who is susceptible to a disease, disorder, or condition does not display any symptoms of the disease, disorder, or condition. In some embodiments, a subject who is susceptible to a disease, disorder, or condition has not been diagnosed with the disease, disorder, and/or condition. In some embodiments, a subject who is susceptible to a disease, disorder, or condition is a subject who has been exposed to conditions associated with development of the disease, disorder, or condition. In some embodiments, a risk of developing a disease, disorder, and/or condition is a population-based risk (e.g., family members of subjects suffering from the disease, disorder, or condition).

Symptoms are reduced: As used herein, "symptoms are reduced" when one or more symptoms of a particular disease, disorder or condition is reduced in magnitude (e.g., intensity, severity, etc.) and/or frequency, e.g., to a statistically and/or clinically significant or relevant level. For purposes of clarity, a delay in the onset of a particular symptom is considered one form of reducing the frequency of that symptom.

Treatment: As used herein, the term “treatment” (also “treat” or “treating”) refers to any administration of a therapy that partially or completely alleviates, ameliorates, relieves, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vaccination: As used herein, the term “vaccination” refers to the administration of a composition intended to generate an immune response, for example to a disease-causing agent. For the purposes of the present disclosure, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition. In some embodiments, vaccination initiates immunization.

Variant: As used herein in the context of molecules, e.g., nucleic acids, proteins, or small molecules, the term “variant” refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a “variant” of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a “variant” of a reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid comprises about 10, about 9, about 8, about 7, about 6, about 5, about 4, about 3, about 2, or about 1 substituted residues as compared to a reference. Often, a variant polypeptide or nucleic acid comprises a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid comprises not more than about 5, about 4, about 3, about 2, or about 1 addition or deletion, and, in some embodiments, comprises no additions or deletions, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 modifications (e.g., substitutions, additions or deletions) at the N-terminus portion, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 modifications (e.g., substitutions, additions or deletions) at the C-terminus portion, as compared to the reference. In some embodiments, a reference polypeptide or nucleic acid is one found in nature.

DETAILED DESCRIPTION OF CERTAIN EMBODIMENTS

The present disclosure relates, generally, to compositions, systems, and methods that include novel complexed proteins and polysaccharides, e.g., immunogenic compositions (e.g., vaccines) of complexed proteins and polysaccharides. Such complexes can be used, e.g., to induce and/or increase an immunoprotective response in subjects at risk of or suffering from pneumococcal infection.

Previous attempts at preparing a vaccine to protect against pneumococcal infection have had limited efficacy.

Wyeth’s first polyvalent polysaccharide conjugate vaccine, Prevnar 7 (PCV7), was licensed in 2000 in the United States and Europe. GlaxoSmithKline’s 10-valent polysaccharide conjugate vaccine Synflorix (PCV10) was licensed in Europe, but not the United States, in 2009. Synflorix was not licensed in the United States because clinical trials did not demonstrate non-inferiority in infants compared to Prevnar 7; also, despite coverage of three additional serotypes compared to Prevnar 7, Synflorix did not formally have coverage of the clinically important *S. pneumoniae* serotype 19A. Also, Synflorix had originally been designed as an 11-valent polysaccharide conjugate vaccine (PCV11), but one *S. pneumoniae* serotype (serotype 3) was removed when clinical trials suggested no efficacy against this serotype, despite immunogenicity.

Merck's polyvalent polysaccharide conjugate vaccine PCV-15 is still in clinical trials. PCV15 has undergone clinical evaluation in adults, where it appears to be non-inferior to Prevnar 13 in adults. PCV15 also appeared to be non-inferior in toddlers, but then failed to meet non-inferiority in infants, so was returned to formulation. The newly-formulated PCV15 is now being evaluated in adults and infants.

A first protein vaccine based on PspA was evaluated by Sanofi Pasteur. An early clinical trial (published in 2000, PMID: 10699322) was a Phase 1 trial with 5-125 μg recombinant PspA (rPspA), which was associated with a clear rise in antibody levels, antibodies that were reactive with heterologous rPspA molecules, and increased binding of post-immune sera to 37 pneumococcal strains expressing a variety of PspA clades and capsular serotypes. Some concerns were raised over a region of PspA that has homology with cardiac myosin, and the program was terminated by Sanofi Pasteur.

Another protein vaccine based on a combination of the three proteins, PhtD, pneumolysoid, and PcpA, was evaluated by Sanofi Pasteur from 2011 to 2014. The vaccine passed Phase 1 in adults and was then tested in toddlers (12-13 months) and infants (6 weeks). A study in Bangladesh showed immunogenicity; however, no evidence of impact on *S. pneumoniae* carriage was reported (presented at ISPPD 2014; the study was not powered to detect a small difference in prevalence of carriage). The program was terminated by Sanofi Pasteur.

A protein vaccine based on the combination of PhtD and pneumolysoid was evaluated by GlaxoSmithKline from 2012 to 2016. The vaccine was deemed safe and immunogenic in all ages (adults, toddlers, infants). However, in two further infant trials conducted in The Gambia and the Navajo Nation in the United States, there was no evidence of clinical efficacy (no impact on *S. pneumoniae* carriage in The Gambia, or on otitis media in the Navajo Nation). The program was terminated by GlaxoSmithKline.

A protein vaccine GEN-004, based on a combination of three proteins, SP0148, SP1912 and SP2108 adjuvanted with aluminum hydroxide, was developed and evaluated by Genocea Biosciences. GEN-004 was shown to be safe and immunogenic in adults in Phase 1. However, a Phase 2 trial of intentional pneumococcal challenge, conducted in the UK, showed no significant effect on *S. pneumoniae* carriage. The GEN-004 development program was suspended in 2015.

A live attenuated, engineered *Salmonella* vaccine was developed at Arizona State University. Mutant *Salmonella typhi* strains engineered to express PspA were evaluated in a Phase 1 clinical trial in adults (PMID: 23916987) from 2009 to 2011. Three different strains were evaluated. No significant adverse events were reported, but one patient had a positive blood culture for *Salmonella typhi*. No subjects shed vaccine in stool. There were no differences in pre- or post-vaccination ELISA or ELISPOT results between groups. The vaccine was deemed safe but non-immunogenic, therefore not efficacious, and development was stopped.

There are two *S. pneumoniae* vaccines currently available in the U.S. Wyeth-Pfizer's second polyvalent polysaccharide conjugate vaccine, Prevnar 13 (PCV13), was licensed in 2010 in the U.S. and Europe. PCV13 has been approved for the prevention of IPD caused by the 13 serotypes contained in the vaccine in children and for the prevention of pneumonia and IPD in adults. In this vaccine, covalent conjugation of saccharides from 13 pneumococcal serotypes to a diphtheria toxoid mutant (CRM197) protein creates saccharide-protein conjugates, which are capable of inducing a T cell-dependent immune response against one or more of the 13 pneumococcal serotypes represented by the saccharides. [PREVNAR 13 prescribing information, 2017].

PCV13 did not formally meet non-inferiority criteria compared to PCV7 and was not immunogenic against several serotypes. However, the inclusion of *S. pneumoniae* serotype 19A assisted with licensure of PCV13, since serotype 19A had emerged between 2000-2010 as a major cause of morbidity and mortality and was associated with antibiotic resistance. While infections with *S. pneumoniae* of multidrug-resistant serotypes contained in PCV13 appeared to decrease after approval of this vaccine, an increase of infections with multidrug-resistant serotypes 35B, 23A, 23B and 15B, which are just a few of the close to 100 known serotypes of *S. pneumoniae* not included in PCV13, was noted. Also, PCV13 was reported to have marginal activity against serotype 3, as its prevalence persists in the population [Richter et al, 2014].

The second vaccine, PPSV23, is a 23-valent polysaccharide vaccine developed by Merck, and is indicated for the prevention of pneumococcal disease in adults greater than 50 years of age, or in persons greater than 2 years of age at increased risk of pneumococcal disease. It is composed of purified capsular polysaccharides from 23 pneumococcal serotypes. While this vaccine has the potential to protect against more serotypes when compared to PCV13, it does not provide protection against the emerging serotypes 35B, 23A and 23B. In addition, PPSV23 elicits a T cell-independent polysaccharide immune response that stimulates mature B-lymphocytes, but not T-lymphocytes. Thus, this vaccine induces an immune response that is neither long-lasting nor anamnestic upon subsequent challenge. PPSV23 is not effective against colonization. In addition, polysaccharide-type vaccines are not used in infants and children less than 2 years of age, because these children respond poorly to T cell-independent antigens [PNEUMOVAX 23 prescribing information, 2017; CDC, 2010]. Data suggest that PPSV23 may protect adults and the elderly against IPD; however, no consistent effect has been observed in the prevention of pneumonia [Gruber et al, 2008].

The presently disclosed novel complexed proteins and polysaccharides, e.g., immunogenic compositions (e.g., vaccines) of complexed proteins and polysaccharides, and combinations thereof represent a substantial advance over the previous attempts at *S. pneumoniae* vaccine development and over the currently available options for immunizing patients against pneumococcal infection. Such novel complexes and immunogenic compositions (e.g., vaccines) can be used, e.g., to induce and/or increase an immunoprotective response in subjects, such as those at risk of or suffering from pneumococcal infection.

Immunogenic Complexes

The present disclosure encompasses immunogenic complexes that include one or more polysaccharides and/or polypeptides of *S. pneumoniae.*

In some embodiments, immunogenic complexes are, or are based on, Multiple Antigen Presenting System (MAPS) complexes. Aspects of the MAPS platform have been previously described in WO2012/155007, the contents of which are herein incorporated by reference in their entirety, and are shown schematically in FIG. 1. See also Zhang et al., 2013.

As described herein, immunogenic complexes of the disclosure include one or more antigenic polypeptides non-covalently complexed with one or more antigenic polysaccharides. In some embodiments, one or more antigenic polypeptides are complexed via affinity interaction with one or more antigenic polysaccharides. In some embodiments, immunogenic complexes of the disclosure include one or more antigenic polypeptides non-covalently complexed with one or more antigenic polysaccharides using one or more affinity molecule/complementary affinity molecule pairs. In some embodiments, an immunogenic complex includes (i) a first affinity molecule described herein conjugated to one or more antigenic polysaccharides, and (ii) a fusion protein that is or comprises a complementary affinity molecule described herein and a polypeptide. In some embodiments, an immunogenic complex includes (i) a plurality of a first affinity molecule described herein conjugated to one or more antigenic polysaccharides, and (ii) a fusion protein that is or comprises a complementary affinity molecule described herein and a polypeptide. Upon association of the first affinity molecule and the complementary affinity molecule, the one or more antigenic polypeptides are non-covalently complexed to the one or more antigenic polysaccharides.

In some embodiments, one or more antigenic polypeptides are complexed via affinity interaction with one antigenic polysaccharide. In some embodiments, immunogenic complexes of the disclosure include one or more antigenic polypeptides non-covalently complexed with one antigenic polysaccharide using one affinity molecule/complementary affinity molecule pair. In some embodiments, immunogenic complexes of the disclosure include one or more antigenic polypeptides non-covalently complexed with one antigenic polysaccharide using one or more affinity molecule/complementary affinity molecule pairs. In some embodiments, each of the affinity molecule/complementary affinity molecule pairs is the same, e.g., biotin/biotin-binding moiety pairs. In some embodiments, an immunogenic complex includes (i) a first affinity molecule described herein conjugated to one antigenic polysaccharide, and (ii) a fusion protein that is or comprises a complementary affinity molecule described herein and a polypeptide. In some embodiments, an immunogenic complex includes (i) a plurality of a first affinity molecule described herein conjugated to one antigenic polysaccharide, and (ii) a fusion protein that is or comprises a complementary affinity molecule described herein and a polypeptide. Upon association of the first affinity molecule and the complementary affinity molecule, the one or more antigenic polypeptides are non-covalently complexed to the one antigenic polysaccharide.

In some embodiments, the affinity molecule/complementary affinity molecule pair is selected from one or more of biotin/biotin-binding moiety, antibody/antigen, enzyme/substrate, receptor/ligand, metal/metal-binding protein, carbohydrate/carbohydrate binding protein, lipid/lipid-binding protein, and His tag/His tag-binding molecule.

In some embodiments, the first affinity molecule is biotin (or a derivative or fragment thereof), and the complementary affinity molecule is a moiety, e.g., a biotin-binding protein, or a biotin-binding domain or biotin-binding fragment thereof. In some embodiments, the biotin-binding moiety is rhizavidin, avidin, streptavidin, bradavidin, tamavidin, lentiavidin, zebavidin, NeutrAvidin, CaptAvidin™, or a biotin-binding domain or biotin-binding fragment thereof, or a combination thereof. In some embodiments, the biotin-binding moiety is a dimer, e.g., a non-covalent dimer. In some embodiments, the biotin-binding moiety is rhizavidin, or a biotin-binding domain or biotin-binding fragment thereof. In some embodiments, the biotin-binding moiety is or comprises a polypeptide of SEQ ID NO: 1, or a biotin-binding domain or biotin-binding fragment thereof. In some embodiments, the biotin-binding moiety is or comprises a polypeptide that comprises an amino acid sequence that is at least 80% (including, e.g., at least 90%, at least 95%, at least 98%, at least 99%, and 100%) identical to SEQ ID NO: 1, or a biotin-binding domain or biotin-binding fragment thereof. In some embodiments, the biotin-binding moiety is or comprises a polypeptide of SEQ ID NO: 2 or SEQ ID NO: 57, or a biotin-binding domain or biotin-binding fragment thereof. In some embodiments, the biotin-binding moiety is or comprises a polypeptide that comprises an amino acid sequence that is at least 80% (including, e.g., at least 90%, at least 95%, at least 98%, at least 99%, 100%) identical to SEQ ID NO: 2 or SEQ ID NO: 57, or a biotin-binding domain or biotin-binding fragment thereof.

In some embodiments, the one or more antigenic polysaccharides are, or are derived from Gram-negative bacteria and/or Gram-positive bacteria. In some embodiments, one or more bacterial antigenic polysaccharides are, or are derived from *S. pneumoniae*. In some embodiments, one or more antigenic polysaccharides are, or are derived from one or more pathogens. In some embodiments, one or more antigenic polysaccharides are, or are derived from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 serotypes or strains of a pathogen. In some embodiments, one or more antigenic polysaccharides are, or are derived from more than 35 serotypes or strains of a pathogen, e.g., 36, 37, 38, 39, 40, 45, 50, 55, or 60 serotypes or strains. In some embodiments, one or more antigenic polysaccharides are, or are derived from more than 70, 80, 90, or 100 serotypes or strains of a pathogen.

In some embodiments, the one or more antigenic polysaccharides comprise one or more affinity molecules conjugated to the antigenic polysaccharides. In some embodiments, the one or more affinity molecules comprise biotin or biotin derivatives.

In some embodiments, the antigenic polysaccharides comprise a plurality of affinity molecules conjugated to the antigenic polysaccharides. In some embodiments, the affinity molecules comprise biotin or biotin derivatives.

In some embodiments, one or more antigenic polypeptides are covalently linked (e.g., fused) to a complementary affinity molecule described herein. In some embodiments, a fusion protein comprises one or more antigenic polypeptides and a complementary affinity molecule disclosed herein. In some embodiments, the complementary affinity molecule is or comprises a biotin-binding moiety. In some embodiments, the biotin-binding moiety is a dimer, e.g., a non-covalent dimer. In some embodiments, the biotin-binding moiety comprises rhizavidin or a biotin-binding portion thereof.

In some embodiments, antigenic polysaccharides and/or antigenic polypeptides that may be included in immunogenic complexes are recombinantly or synthetically produced. In some embodiments, antigenic polysaccharides and/or antigenic polypeptides that may be included in immunogenic complexes are isolated and/or derived from natural sources. In some embodiments, antigenic polysaccharides and/or antigenic polypeptides that may be included in immunogenic complexes are isolated from bacterial cells. Exemplary polysaccharides and/or polypeptides are described below.

Antigenic Polypeptides

In some embodiments, an immunogenic complex described herein comprises one or more polypeptide antigens. In some embodiments, a polypeptide antigen is a bacterial polypeptide, a fungal polypeptide, and/or a viral polypeptide. In some embodiments, a polypeptide antigen is a polypeptide of, or derived from *S. pneumoniae*. In some embodiments, the one or more polypeptide antigen is a polypeptide of, or derived from, a pathogen other than *S. pneumoniae*. In some embodiments, the one or more polypeptide antigens comprise (i) a polypeptide of, or derived from, *S. pneumoniae*, and (ii) a polypeptide of, or derived from, a pathogen other than *S. pneumoniae*. In some embodiments, an immunogenic complex includes one or more of the following *S. pneumoniae* antigenic polypeptides, or portions thereof.

Pneumolysin Polypeptides

Pneumolysin (Ply) is a *S. pneumoniae* protein toxin. In some embodiments, Ply polypeptide is a cholesterol-dependent toxin of the thiol-activated cytolysin family. In some embodiments, a Ply polypeptide is or comprises a full-length Ply polypeptide. For example, in some embodiments, a full-length Ply polypeptide has 470 amino acids (53 kDa) and is represented by the amino acid sequence as set forth in SEQ ID NO: 3. In some embodiments, a Ply polypeptide includes a portion of a Ply polypeptide (e.g., a portion of a Ply polypeptide of SEQ ID NO: 3, which portion includes at least 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450 or more contiguous amino acids of SEQ ID NO: 3). In some embodiments, a portion of an Ply polypeptide corresponds to a protein having amino acids 2-470 of the amino acid sequence set forth in SEQ ID NO: 3. In some embodiments, a Ply polypeptide contains one or more amino acid alterations (e.g., deletion, substitution, and/or insertion) from a naturally-occurring wild-type Ply polypeptide sequence. For example, a Ply polypeptide may contain an amino acid sequence that is at least 60% or more (e.g., at least 65%, 70%, 75%, 80%, 85%, 90%, 95%, or 98%) identical to SEQ ID NO: 3 or a portion thereof (e.g., at least 7, 8, 9, 10, 11, 12, 13, 14, 15, 16, 17, 18, 19, 20, 25, 30, 35, 45, 50, 55, 60, 65, 70, 75, 80, 85, 90, 95, 100, 150, 200, 250, 300, 350, 400, 450 or more consecutive amino acids of the sequence shown in SEQ ID NO: 3). Alternatively, a Ply polypeptide may contain a portion (e.g., at least 7, 8, 9, 10, 11, 12, 13, 14, 15, 16, 17, 18, 19, 20, 25, 30, 35, 45, 50, 55, 60, 65, 70, 75, 80, 85, 90, 95, 100, 150, 200, 250, 300, 350, 400, 450 or more consecutive amino acids) of a sequence that is at least 60% or more (e.g., at least 65%, 70%, 75%, 80%, 85%, 90%, 95%, or 98%) identical to SEQ ID NO: 3. In some embodiments, a nucleotide sequence encoding a Ply polypeptide is provided herein as SEQ ID NO: 13.

Pneumolysins are exotoxins produced by bacteria that can cause hemolytic activity and complement activation. While highly immunogenic, their use in vaccines is limited because they cause lysis of red blood cells. Accordingly, in another aspect, provided herein are variants of *S. pneumoniae* pneumolysin (Ply), its fusion construct with a biotin-binding protein, and its uses. In some embodiments, such variants, designated herein as mutant Ply or "mPly" are substantially non-hemolytic. As used herein, the phrase "substantially non-hemolytic" means the ability of lysing red blood cells being reduced by at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or up to 100%, as compared to that of an equivalent concentration of a reference Ply (e.g., a wild-type Ply). In some embodiments, hemolytic activity of substantially non-hemolytic Ply is at least 5%, at least 10%, at least 15%, at least 20%, at least 20%, at least 30%, at least 30%, at least 35%, least 40%, at least 45%, at least 50%, at least 55%, at least 60%, at least 65%, at least 70%, at least 75%, at least 80%, at least 85%, at least 90%, at least 95% lower than an equivalent concentration of a reference Ply (e.g., a wild-type Ply). In some embodiments, the substantially non-hemolytic Ply has no detectable hemolytic activity. The term "wild-type Ply" is accorded the usual definition associated with such phrase, e.g., in some embodiments, a naturally occurring Ply (e.g., a Ply that is naturally secreted by a capable bacterial source). In some embodiments, a wild-type Ply protein is represented by the amino acid sequence as set forth in SEQ ID NO: 3.

In some embodiments, a mutant Ply (e.g., non-hemolytic Ply) comprises a wild-type Ply amino acid sequence (e.g., an amino acid sequence as set forth in SEQ ID NO: 3) or an antigenic fragment thereof, with one or more amino acid substitutions. In some embodiments, a mutant Ply (e.g., non-hemolytic Ply) comprises a wild-type Ply amino acid sequence (e.g., an amino acid sequence as set forth in SEQ ID NO: 3) or an antigenic fragment thereof, with one or more of the following amino acid substitutions: residue D385 substituted with N; residue C428 substituted with G, and residue W433 substituted with F. See, for example, Berry et al., "Effect of defined point mutations in the pneumolysin gene on the virulence of *Streptococcus pneumoniae*". Infect Immune 1995 63 (5): 1969-1974). In some embodiments, a mutant Ply (e.g., non-hemolytic Ply) carrying the amino acid substitutions D385N, C428G, and W433F is referred to as PdT. In some embodiments, a PdT is or comprises the amino acid sequence as set forth in SEQ ID NO: 4.

In some embodiments, a mutant Ply (e.g., non-hemolytic Ply) comprises a wild-type Ply amino acid sequence (e.g., an amino acid sequence as set forth in SEQ ID NO: 3) or an antigenic fragment thereof, with G294 substituted with P (Sec, e.g., Oloo et al., "Structure-guided antigen engineering yields pneumolysin mutants suitable for vaccination against pneumococcal disease". J Biol Chem. 2011 286 (14): 12133-12140). In some embodiments, a mutant Ply (e.g., non-hemolytic Ply) comprises a wild-type Ply amino acid sequence (e.g., an amino acid sequence as set forth in SEQ ID NO: 3) or an antigenic fragment thereof, with all of the following amino acid substitutions: residue D385 substituted with N; residue C428 substituted with G; residue W433 substituted with F; and G294 substituted with P. In some embodiments, a mutant Ply (e.g., non-hemolytic Ply) carrying the amino acid substitutions G294P, D385N, C428G, and W433F is referred to as PdT (G294P). In some embodiments, a PdT (G294P) is or comprises the amino acid sequence as set forth in SEQ ID NO: 5.

In some embodiments, a mutant Ply (e.g., non-hemolytic Ply) is a portion of a PdT (G294P) polypeptide (e.g., a portion of the PdT (G294P) polypeptide of SEQ ID NO: 5, which portion includes at least 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450 or more contiguous amino acids of SEQ ID NO: 5. In some embodiments, such a portion of PdT (G294P) polypeptide include the four amino acid substitutions described herein. In some embodiments, a portion of a PdT (G294P) polypeptide corresponds to a protein having amino acids 2-470 of the amino acid sequence set forth in SEQ ID NO: 5. In some embodiments, a mutant Ply (e.g., non-hemolytic Ply) contains one or more amino acid alterations (e.g., deletion, substitution, and/or insertion) from the PdT (G294P) polypeptide sequence of SEQ ID NO: 5. For example, a mutant Ply (e.g., non-hemolytic Ply) may contain an amino acid sequence that is at least 60% or more (e.g., at least 65%, 70%, 75%, 80%, 85%, 90%, 95%, or 98%) identical to SEQ ID NO: 5 or a portion thereof (e.g., at least 7, 8, 9, 10, 11, 12, 13, 14, 15, 16, 17, 18, 19, 20, 25, 30, 35, 45, 50, 55, 60, 65, 70, 75, 80, 85, 90, 95, 100, 150, 200, 250, 300, 350, 400, 450 or more consecutive amino acids of the sequence shown in SEQ ID NO: 5). Alternatively, a mutant Ply (e.g., non-hemolytic Ply) may contain a portion (e.g., at least 7, 8, 9, 10, 11, 12, 13, 14, 15, 16, 17, 18, 19, 20, 25, 30, 35, 45, 50, 55, 60, 65, 70, 75, 80, 85, 90, 95, 100, 150, 200, 250, 300, 350, 400, 450 or more consecutive amino acids) of a sequence that is at least 60% or more (e.g., at least 65%, 70%, 75%, 80%, 85%, 90%, 95%, or 98%) identical to SEQ ID NO: 5. In some embodiments, a mutant Ply (e.g., non-hemolytic Ply) may comprises no more than 25 (including, e.g., no more than 20, no more than 15, no more than 10, no more than 9, no more than 8, no more than 7, no more than 6, no more than 5, no more than 4, no more than 3, no more than 2) amino acid modifications (e.g., deletion, substitution, and/or insertion) within the sequence of SEQ ID NO: 5 or a portion thereof as described herein. In some embodiments, such amino acid modifications may be present in the N-terminal portion and/or C-terminal portion.

SP0435 Polypeptides

SP0435 is a *S. pneumoniae* protein. In some embodiments, an SP0435 polypeptide is an elongation factor P. In some embodiments, an SP0435 polypeptide is or comprises a full-length SP0435 polypeptide. For example, in some embodiments, a full-length SP0435 polypeptide has 186 amino acids (20 kDa) and is represented by the amino acid sequence as set forth in SEQ ID NO: 7. Without wishing to be bound by a particular theory, amino acids 1-61 of SEQ ID NO: 7 are predicted to be a dimerization domain of an SP0435 polypeptide (amino acids 1-61 of the full-length protein). Accordingly, in some embodiments, a SP0435 polypeptide may exclude such a dimerization domain, for example in some embodiments, to minimize or avoid the possibility of crosslinking or interference with a rhizavidin moiety. In some embodiments, an SP0435 polypeptide includes a portion of an SP0435 polypeptide (e.g., a portion of the SP0435 polypeptide of SEQ ID NO: 7, which portion includes at least 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, or more contiguous amino acids of SEQ ID NO: 7). In some embodiments, a portion of an SP0435 polypeptide corresponds to a protein having amino acids 62-185 of the amino acid sequence set forth in SEQ ID NO: 7. In some embodiments, an SP0435 polypeptide contains one or more amino acid alterations (e.g., deletion, substitution, and/or insertion) from a naturally-occurring wild-type SP0435 polypeptide sequence. For example, an SP0435 polypeptide may contain an amino acid sequence that is at least 60% or more (e.g., at least 65%, 70%, 75%, 80%, 85%, 90%, 95%, or 98%) identical to SEQ ID NO: 7 or a portion thereof (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, or more consecutive amino acids of the sequence shown in SEQ ID NO: 7). Alternatively, an SP0435 polypeptide may contain a portion (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, or more consecutive amino acids) of a sequence that is at least 60% or more (e.g., at least 65%, 70%, 75%, 80%, 85%, 90%, 95%, or 98%) identical to SEQ ID NO: 7. In some embodiments, a nucleotide sequence encoding an SP0435 polypeptide is provided herein as SEQ ID NO: 16. In some embodiments, an SP0434 polypeptide may comprises no more than 25 (including, e.g., no more than 20, no more than 15, no more than 10, no more than 9, no more than 8, no more than 7, no more than 6, no more than 5, no more than 4, no more than 3, no more than 2) amino acid modifications (e.g., deletion, substitution, and/or insertion) within the sequence of SEQ ID NO: 7 or a portion thereof as described herein. In some embodiments, such amino acid modifications may be present in the N-terminal portion and/or C-terminal portion. In some embodiments, an SPN0435 polypeptide is one described in WO 2011/112906, the entire content of which is incorporated herein by reference for the purposes described herein.

SP0785 Polypeptides

SP0785 is a conserved hypothetical *S. pneumoniae* protein, for example, in some embodiments as described in WO 2014/124228, the entire content of which is incorporated herein by reference for the purposes described herein. In some embodiments, an SP0785 polypeptide is an efflux transporter protein conserved across *S. pneumoniae* strains. In some embodiments, an SP0785 polypeptide is or comprises a full-length SP0785 polypeptide. For example, in some embodiments, a full-length SP0785 polypeptide has 399 amino acids (38 kDa) and is represented by the amino acid sequence as set forth in SEQ ID NO: 9. Without wishing to be bound by a particular theory, amino acids 1-32 of SEQ ID NO: 9 are predicted to be a signal sequence and transmembrane domain of an SP0785 polypeptide (amino acids 1-32 of the full-length protein). Accordingly, in some embodiments, an SP0785 polypeptide may exclude such a signal sequence and transmembrane domain. In some embodiments, an SP0785 polypeptide includes a portion of an SP0785 polypeptide (e.g., a portion of the SP0785 polypeptide of SEQ ID NO: 9, which portion includes at least 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, or more contiguous amino acids of SEQ ID NO:10). In some embodiments, a portion of an SP0785 polypeptide corresponds to a protein having amino acids 33-399 of the amino acid sequence set forth in SEQ ID NO: 9. In some embodiments, an SP0785 polypeptide contains one or more amino acid alterations (e.g., deletion, substitution, and/or insertion) from a naturally-occurring wild-type SP0785 polypeptide sequence. For example, an SP0785 polypeptide may contain an amino acid sequence that is at least 60% or more (e.g., at least 65%, 70%, 75%, 80%, 85%, 90%, 95%, or 98%) identical to SEQ ID NO: 9 or a portion thereof (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or more consecutive amino acids of the sequence shown in SEQ ID NO: 9). Alternatively, an SP0785 polypeptide may contain a portion (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids) of a sequence that is at least 60% or more (e.g., at least 65%, 70%, 75%, 80%, 85%, 90%, 95%, or 98%) identical to SEQ ID NO: 9. In some embodiments, a nucleotide sequence encoding an SP0785 polypeptide is provided herein as SEQ ID NO: 17. In some embodiments, an SP0785 polypeptide may comprises no more than 25 (including, e.g., no more than 20, no more than 15, no more than 10, no more than 9, no more than 8, no more than 7, no more than 6, no more than 5, no more than 4, no more than 3, no more than 2) amino acid modifications (e.g., deletion, substitution, and/or insertion) within the sequence of SEQ ID NO: 9 or a portion thereof as described herein. In some embodiments, such amino acid modifications may be present in the N-terminal portion and/or C-terminal portion.

SP1500 Polypeptides

SP1500 is a *S. pneumoniae* protein, for example, in some embodiments as described in WO 2014/124228, the entire content of which is incorporated herein by reference for the purposes described herein. In some embodiments, an SP1500 polypeptide is an Amino Acid ABC Transporter, amino acid-binding polypeptide conserved across *S. pneumoniae* strains. In some embodiments, an SP1500 polypeptide is or comprises a full-length SP1500 polypeptide. For example, in some embodiments, a full-length SP1500 polypeptide has 278 amino acids (28 kDa) and is represented by the amino acid sequence as set forth in SEQ ID NO: 11. Without wishing to be bound by a particular theory, amino acids 1-26 of SEQ ID NO: 11 are predicted to be a signal sequence of an SP1500 polypeptide (amino acids 1-26 of the full-length protein). Accordingly, in some embodiments, a SP1500 polypeptide may exclude such a signal sequence. In some embodiments, an SP1500 polypeptide includes a portion of an SP1500 polypeptide (e.g., a portion of the SP1500 polypeptide of SEQ ID NO: 11, which portion includes at least 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, or more contiguous amino acids of SEQ ID NO: 11). In some embodiments, a portion of an SP1500 polypeptide corresponds to a protein having amino acids 27-278 of the amino acid sequence set forth in SEQ ID NO: 11. In some embodiments, an SP1500 polypeptide contains one or more amino acid alterations (e.g., deletion, substitution, and/or insertion) from a naturally-occurring wild-type SP1500 polypeptide sequence. For example, an SP1500 polypeptide may contain an amino acid sequence that is at least 60% or more (e.g., at least 65%, 70%, 75%, 80%, 85%, 90%, 95%, or 98%) identical to SEQ ID NO: 11 or a portion thereof (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, or more consecutive amino acids of the sequence shown in SEQ ID NO: 11). Alternatively, an SP1500 polypeptide may contain a portion (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, or more consecutive amino acids) of a sequence that is at least 60% or more (e.g., at least 65%, 70%, 75%, 80%, 85%, 90%, 95%, or 98%) identical to SEQ ID NO: 11. In some embodiments, a nucleotide sequence encoding an SP1500 polypeptide is provided herein as SEQ ID NO: 18. In some embodiments, an SP1500 polypeptide may comprises no more than 25 (including, e.g., no more than 20, no more than 15, no more than 10, no more than 9, no more than 8, no more than 7, no more than 6, no more than 5, no more than 4, no more than 3, no more than 2) amino acid modifications (e.g., deletion, substitution, and/or insertion) within the sequence of SEQ ID NO: 11 or a portion thereof as described herein. In some embodiments, such amino acid modifications may be present in the N-terminal portion and/or C-terminal portion.

In some embodiments, nucleic acid sequences encoding a pneumolysin polypeptide (SEQ ID NO: 3), an SP0435 polypeptide (SEQ ID NO: 7), and an SPP2 polypeptide (SEQ ID NO: 19 or SEQ ID NO: 58) are provided as SEQ ID NO: 13, SEQ ID NO: 16, SEQ ID NO: 27, and SEQ ID NO: 62, respectively. In some embodiments, nucleic acid sequences encoding an SP0785 polypeptide (SEQ ID NO: 9), an SP1500 polypeptide (SEQ ID NO: 11), and a CP1 polypeptide (SEQ ID NO: 26 or SEQ ID NO: 61) are provided as SEQ ID NO: 17, SEQ ID NO: 18, SEQ ID NO: 29, and SEQ ID NO: 64, respectively. Due to degeneracy in the genetic code, those of ordinary skill in the art would understand that other DNA sequences (including codon-optimized sequences) could encode these polypeptides, as well as the others disclosed herein.

Fusion Proteins that Include Antigenic Polypeptides

Antigenic polypeptides described herein can be part of a fusion protein. For example, in some embodiments, an immunogenic complex described herein comprises a fusion protein that is or comprises a complementary affinity molecule and one or more antigenic polypeptides described herein. In some embodiments, a fusion protein comprises two antigenic polypeptides described herein. In some embodiments, a fusion protein comprises three antigenic polypeptides described herein. In some embodiments, a fusion protein comprises four antigenic polypeptides described herein. In some embodiments, a fusion protein comprises one or more antigenic polypeptides encoded by a nucleic acid comprising a sequence encoding the antigenic polypeptide described herein. In some embodiments, a fusion protein of the immunogenic complex has carrier properties. In some embodiments, a fusion protein of the immunogenic complex has antigenic properties. In some embodiments, a fusion protein of the immunogenic complex has carrier properties and antigenic properties.

In some embodiments, a fusion protein comprises one or more antigenic polypeptides of *S. pneumoniae* having an amino acid sequence comprising any of SEQ ID NOs: 3-12, or antigenic fragments thereof. In some embodiments, a fusion protein comprises two antigenic polypeptides having an amino acid sequence comprising any of SEQ ID NOs: 3-12, or antigenic fragments thereof. In some embodiments, a fusion protein comprises (i) two antigenic polypeptides having an amino acid sequence comprising any of SEQ ID NOs: 3-12, or antigenic fragments thereof, and (ii) a biotin-binding moiety comprising SEQ ID NO: 1, SEQ ID NO: 2, or SEQ ID NO: 57, or biotin-binding fragments thereof. In some such embodiments, at least one antigenic polypeptide is or comprises a Ply polypeptide (e.g., any one of SEQ ID NOs: 3-6). In some such embodiments, at least one antigenic polypeptide is or comprises an SP0435 polypeptide (e.g., SEQ ID NOs: 7 or 8). In some such embodiments, at least one antigenic polypeptide is or comprises an SP0785 polypeptide (e.g., SEQ ID NOs: 9 or 10). In some such embodiments, at least one antigenic polypeptide is or comprises an SP1500 polypeptide (e.g., SEQ ID NOs: 11 and 12).

In some embodiments, a fusion protein comprises one or more polypeptides homologous to the *S. pneumoniae* polypeptides described herein, e.g., a Ply polypeptide, an SP0435 polypeptide, an SP0785 polypeptide or an SP1500 polypeptide isolated from different serotypes of *S. pneumoniae*. Individual serotypes of *S. pneumoniae* contain numerous mutations relative to each other, and some of these result in different protein sequences between the different serotypes. One of skill in the art may readily substitute an amino acid sequence, or a portion thereof, with the homologous amino acid sequence from a different *S. pneumoniae* serotype. In some embodiments, antigenic polypeptides have at least 80%, at least 85%, at least 90%, at least 95%, at least 96%, at least 97%, at least 98%, at least 99%, at least 99.5%, or 100% identity to the polypeptides of any of SEQ ID NOs: 3-12, or antigenic fragments thereof. Serotypic variation may be used to design such variants of the antigenic polypeptides described herein.

In some embodiments, fusion proteins described herein comprise one or more fragments of one or more polypeptides described herein, e.g., biotin-binding fragments of rhizavidin, a Ply polypeptide or antigenic fragments thereof, an SP0435 polypeptide or antigenic fragments thereof, a SP0785 polypeptide or antigenic fragments thereof (e.g., with or without a signal sequence), or a SP1500 polypeptide or antigenic fragments thereof (e.g., with or without a signal sequence). In some embodiments, fusion proteins described herein comprise truncation mutants that are close in size to the polypeptides with amino acid sequences of SEQ ID NOs: 1-12 and 57. For example, they may lack at most one, two, three, four, five, ten, or twenty amino acids from one or both termini (referring to component polypeptides in a fusion protein). In some embodiments, a fragment is a truncated fragment of any of SEQ ID NOs: 1-12 and 57 lacking 1-5, 1-10, or 1-20 amino acid residues from the N-terminus, C-terminus, or both, of any one of SEQ ID NOs: 1-12 and 57. In some embodiments, a fragment is a truncated fragment of any of SEQ ID NOs: 1-12 and 57 lacking 1-10 amino acid residues from the N-terminus, C-terminus, or both, of any one of SEQ ID NOs: 1-12 and 57. For instance, a fragment may lack 10 amino acid residues at both the N-terminus and C-terminus of any one of SEQ ID NOs: 1-12 and 57, resulting in a protein lacking 20 amino acid residues. Internal deletions, e.g., of 1-10, 11-20, 21-30, or 31-40 amino acids, are also contemplated.

In some embodiments, a fusion protein comprises an N-terminal polypeptide and a C-terminal polypeptide. In some embodiments, one or both of the N-terminal polypeptide and the C-terminal polypeptide is an antigenic polypeptide, for example, a polypeptide having an amino acid sequence comprising one or more of SEQ ID NOs: 3-12, or an antigenic fragment or variant thereof. In some embodiments, one or both of the N-terminal polypeptide and the C-terminal polypeptide is a biotin-binding moiety, for example a polypeptide having an amino acid sequence comprising SEQ ID NO: 1, SEQ ID NO: 2, or SEQ ID NO: 57, or a biotin-binding fragment thereof. In some embodiments, one of the N-terminal polypeptide or the C-terminal polypeptide is a biotin-binding moiety, e.g., a polypeptide having an amino acid sequence comprising SEQ ID NO: 1, SEQ ID NO: 2, or SEQ ID NO: 57, or a biotin-binding fragment thereof, and the other terminal polypeptide is an antigenic polypeptide, e.g., a polypeptide having an amino acid sequence comprising one or more of SEQ ID NOs: 3-12, or an antigenic fragment or variant thereof.

In some embodiments, the N-terminal polypeptide and the C-terminal polypeptide are directly bound to each other. In some embodiments, the N-terminal polypeptide and the C-terminal polypeptide are linked via a linker peptide. The length and/or amino acids of a linker, when present, can be adjusted to obtain a more flexible, semi-rigid, or rigid linker. In some embodiments, a linker can be a GS-enriched linker. In some embodiments, a linker can be an A-enriched linker. A linker can generally be from 1-40, such as 3-10 or 10-30 and specifically 3, 4, 5, 6, 7, 8, 9, 10, 11, 12, 13, 14, 15, 16, 17, 18, 19 or 20 amino acids in length. Exemplary flexible peptide linkers are shown as SEQ ID NOs: 30-33. In some embodiments, the fusion protein comprises one linker. In some embodiments, the fusion protein comprises two linkers. In some embodiments, the one or two linkers are of SEQ ID NO: 30 (GGGGSSS). In some embodiments, the fusion protein comprises SEQ ID NO: 30 (GGGGSSS). In some embodiments, the one or two linkers are selected from SEQ ID NO: 30 (GGGGSSS) and (AAA). In some embodiments, the fusion protein comprises a linker of SEQ ID NO: 30 (GGGGSSS) and (AAA). In some embodiments, the fusion protein comprises an amino acid sequence AAA residual from a Not I restriction site. In some embodiments, the fusion protein comprises a linker of SEQ ID NO: 30 (GGGGSSS) and an amino acid sequence AAA residual from a Not I restriction site.

In some embodiments, the present disclosure provides fusion proteins with at least 80%, at least 85%, at least 90%, at least 95%, at least 96%, at least 97%, at least 98%, at least 99%, at least 99.5%, or 100% sequence identity to a fusion protein having an amino acid sequence of any one of SEQ ID NOs: 19-26 and 58-61. In some embodiments, a fusion protein is or includes an amino acid sequence having at least 80%, at least 85%, at least 90%, at least 95%, at least 96%, at least 97%, at least 98%, at least 99%, at least 99.5%, or 100% identity to SEQ ID NO: 19 or SEQ ID NO: 58. In some embodiments, a fusion protein is or includes an amino acid sequence having at least 80%, at least 85%, at least 90%, at least 95%, at least 96%, at least 97%, at least 98%, at least 99%, at least 99.5%, or 100% identity to SPP2. In some embodiments, a fusion protein is or includes an amino acid sequence having at least 80%, at least 85%, at least 90%, at least 95%, at least 96%, at least 97%, at least 98%, at least 99%, at least 99.5%, or 100% identity to SEQ ID NO: 26 or SEQ ID NO: 61. In some embodiments, a fusion protein is or includes an amino acid sequence having at least 80%, at least 85%, at least 90%, at least 95%, at least 96%, at least 97%, at least 98%, at least 99%, at least 99.5%, or 100% identity to CP1.

In some embodiments, a fusion protein described herein comprises an antigenic fragment of a fusion protein having an amino acid sequence of any one of SEQ ID NOs: 19-26 and 58-61. For example, a fusion protein may lack at most one, two three, four, five, ten, or twenty amino acids from the N-terminus, C-terminus, or both, of any one of SEQ ID NOs: 19-26 and 58-61. In some embodiments, the same number of residues is removed from the N-terminus and the C-terminus, while in other embodiments, a different number of residues is removed from the N-terminus compared to the C-terminus. In some embodiments, a fusion protein is or includes an antigenic fragment of SEQ ID NO: 19 or SEQ ID NO: 58. In some embodiments, a fusion protein is or includes an antigenic fragment of SPP2. In some embodiments, a fusion protein is or includes an antigenic fragment of SEQ ID NO: 26 or SEQ ID NO: 61. In some embodiments, a fusion protein is or includes an antigenic fragment of CP1.

In some embodiments, a fusion protein described herein comprises a biotin-binding moiety. In some embodiments, the fusion protein comprises a biotin-binding moiety, and one or more polypeptide antigens. In some embodiments, the fusion protein comprises a biotin-binding moiety and two or more polypeptide antigens. As used herein, a "biotin-binding moiety" refers to a biotin-binding polypeptide or protein, a biotin-binding fragment thereof, or a biotin-binding domain thereof. In some embodiments, the biotin-binding moiety of a fusion protein comprises rhizavidin or a biotin-binding fragment thereof, which in some embodiments as further described in WO 2012/155053, the contents of which are herein incorporated by reference in their entirety for the purposes described herein.

In some embodiments, a fusion protein described herein comprises a biotin-binding moiety that is or comprises a polypeptide having at least 80%, at least 85%, at least 90%, at least 95%, at least 96%, at least 97%, at least 98%, at least 99%, at least 99.5%, or 100% identity to the sequence of SEQ ID NO: 1 (rhizavidin), or biotin-binding fragment thereof. In some embodiments, a fusion protein comprises a biotin-binding moiety that is or comprises a polypeptide having at least 80%, 85%, 90%, 95%, 96%, 97%, 98%, 99%, or 100% identity to the sequence of SEQ ID NO: 2 (amino acids 45-179 of rhizavidin, denoted Rhavi) or SEQ ID NO: 57, or biotin-binding fragment thereof.

In some embodiments, a fusion protein comprises a pneumolysin polypeptide as described herein. For example, in some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P) polypeptide), or an antigenic fragment thereof. In some embodiments, a pneumolysin polypeptide described herein may be truncated from its N-terminal portion and/or C-terminal portion.

In some embodiments, a fusion protein comprises an SPN0435 polypeptide. For example, in some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435 polypeptide), or an antigenic fragment thereof. In some embodiments, an SPN0435 polypeptide described herein may be truncated from its N-terminal portion and/or C-terminal portion.

In some embodiments, a fusion protein comprises an SP0785 polypeptide. For example, in some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785 polypeptide), or an antigenic fragment thereof. In some embodiments, an SPN0785 polypeptide described herein may be truncated from its N-terminal portion and/or C-terminal portion.

In some embodiments, a fusion protein comprises an SP1500 polypeptide. For example, in some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500 polypeptide), or an antigenic fragment thereof. In some embodiments, an SPN1500 polypeptide described herein may be truncated from its N-terminal portion and/or C-terminal portion.

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, at least 99.5%, or 100% identity to the sequence of SEQ ID NO: 1 (rhizavidin), or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P) polypeptide), or an antigenic fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435 polypeptide) or an antigenic fragment thereof. In some embodiments, the fusion protein further comprises one or more linkers. In some embodiments, the one or more linkers are SEQ ID NO: 30 (GGGGSSS).

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, at least 99.5%, or 100% identity to the sequence of SEQ ID NO: 1 (rhizavidin), or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785 polypeptide), or an antigenic fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500 polypeptide) or an antigenic fragment thereof. In some embodiments, the fusion protein further comprises one or more linkers. In some embodiments, the one or more linkers are selected from SEQ ID NO: 30 (GGGGSSS) and (AAA). In some embodiments, the fusion protein comprises an amino acid sequence AAA residual from a Not I restriction site. In some embodiments, the fusion protein comprises a linker of SEQ ID NO: 30 (GGGGSSS) and an amino acid sequence AAA residual from a Not I restriction site.

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, at least 99.5%, or 100% identity to the sequence of SEQ ID NO: 2 (amino acids 45-179 of rhizavidin, denoted Rhavi) or SEQ ID NO: 57, or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P) polypeptide) or an antigenic fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435 polypeptide) or an antigenic fragment thereof. In some embodiments, the fusion protein further comprises one or more linkers. In some embodiments, the one or more linkers are SEQ ID NO: 30 (GGGGSSS). In some embodiments, a fusion protein described herein comprises an amino acid sequence having at least 80%, at least 85%, at least 90%, at least 91%, at least 92%, at least 93%, at least 94%, at least 95%, at least 96%, at least 97%, at least 98%, at least 99%, or 100% identity to the sequence SEQ ID NO: 19 or SEQ ID NO: 58. In some embodiments, the fusion protein comprises the amino acid sequence SEQ ID NO: 19 or SEQ ID NO: 58. In some embodiments, the fusion protein consists of the amino acid sequence SEQ ID NO: 19 (SPP2) or SEQ ID NO: 58.

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, at least 99.5%, or 100% identity to the sequence of SEQ ID NO: 2 (amino acids 45-179 of rhizavidin, denoted Rhavi) or SEQ ID NO: 57, or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785 polypeptide) or an antigenic fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500 polypeptide) or an antigenic fragment thereof. In some embodiments, the fusion protein further comprises one or more linkers. In some embodiments, the one or more linkers are selected from SEQ ID NO: 30 (GGGGSSS) and (AAA). In some embodiments, the fusion protein comprises an amino acid sequence AAA residual from a Not I restriction site. In some embodiments, the fusion protein comprises a linker of SEQ ID NO: 30 (GGGGSSS) and an amino acid sequence AAA residual from a Not I restriction site. In some embodiments, a fusion protein described herein comprises an amino acid sequence having at least 80%, at least 85%, at least 90%, at least 91%, at least 92%, at least 93%, at least 94%, at least 95%, at least 96%, at least 97%, at least 98%, at least 99%, or 100% identity to the sequence SEQ ID NO: 26 or SEQ ID NO: 61. In some embodiments, the fusion protein comprises the amino acid sequence SEQ ID NO: 26 or SEQ ID NO: 61. In some embodiments, the fusion protein consists of the amino acid sequence SEQ ID NO: 26 (CP1) or SEQ ID NO: 61.

In some embodiments, a fusion protein described herein includes a variant or fragment of a polypeptide having an amino acid sequence of SEQ ID NOs: 1-12 or 57. In some embodiments, a fusion protein described herein includes a polypeptide encoded by a variant or fragment of a gene having a nucleic acid sequence of SEQ ID NOs: 1-12 or 57. In some embodiments, a fragment included in a fusion protein described herein is close in size to a full-length polypeptide or a polypeptide having an amino acid sequence of SEQ ID NOs: 1-12 or 57. For example, they may lack at most one, two, three, four, five, ten, twenty, or thirty amino acids from one or both termini. In some embodiments, the fragment is 25-50 amino acids in length, or 50-100, or 100-150, or 150-200, or 200-250, or 250-300, or 300-350 amino acids in length. In some embodiments, the fragments result from processing, or partial processing, of signal sequences by an expression host, e.g. *E. coli*, an insect cell line (e.g., the baculovirus expression system), or a mammalian (e.g., human or Chinese Hamster Ovary) cell line. The fragments described above or sub-fragments thereof (e.g., fragments of 8-50, 8-30, or 8-20 amino acid residues) preferably have one of the biological activities described below, such as increasing the amount of IL-17 released by at least 1.5 fold or 2 fold or more (e.g., either as an absolute measure or relative to a control protein).

Linker or Spacer

In some embodiments, the fusion protein of the immunogenic complex comprises one or more linkers. In some embodiments, a linker is or comprises one or more amino acids. In some embodiments, a fusion protein comprises an antigenic polypeptide joined to a biotin-binding moiety by a linker. In some embodiments, a fusion protein comprises a first antigenic polypeptide, a second antigenic polypeptide, a biotin-binding moiety, and at least one linker. In some embodiments, the first antigenic polypeptide and the second antigenic polypeptide are joined by a linker. In some embodiments, the first antigenic polypeptide or the second antigenic polypeptide are joined to the biotin-binding moiety by a linker. In some embodiments, the first antigenic polypeptide and the second antigenic polypeptide are joined by a first linker; and the first antigenic polypeptide or the second antigenic polypeptide are joined to the biotin-binding moiety by a second linker.

In some embodiments, a fusion protein described herein comprises a first linker comprising the amino acid sequence of SEQ ID NO: 30 (GGGGSSS), and a second linker comprising the amino acid sequence of SEQ ID NO: 30 (GGGGSSS). In some embodiments, a fusion protein described herein comprises a first linker comprising the amino acid sequence of SEQ ID NO: 30 (GGGGSSS), and a second linker comprising the amino acid sequence of (AAA).

In some embodiments, a linker interposes a structure between two protein moieties. In some embodiments, the structure is or comprises an α-helix. In some embodiments, the structure is or comprises a β-strand. In some embodiments, the structure is or comprises a coil/bend. In some embodiments, the structure is or comprises a turn. In some embodiments, a linker decreases steric hindrance between two protein moieties joined by the linker. In some embodiments, a linker decreases unfavorable interactions between two protein moieties joined by the linker. In some embodiments, a linker comprises a mixture of glycine and serine residues. In some embodiments, the linker may additionally comprise threonine, proline, and/or alanine residues. In some embodiment, a linker is hydrophilic. In some embodiments, a linker is hydrophobic. In some embodiments, a linker increases the stability of the fusion protein containing the linker.

In some embodiments, a linker does not interfere with the folding of an antigenic polypeptide to which it is joined. In some embodiments, a linker does not interfere with the antigenicity of an antigenic polypeptide to which it is joined. In some embodiments, a linker does not reduce the antigenicity of an antigenic polypeptide to which it is joined. In some embodiments, a linker does not eliminate the antigenicity of an antigenic polypeptide to which it is joined. In some embodiments, the effect of the linker is determined by comparing the polypeptide with the polypeptide joined to the linker.

In some embodiments, a linker does not interfere with the folding of a biotin-binding moiety to which it is joined. In some embodiments, a linker does not interfere with the biotin-binding ability of a biotin-binding moiety to which it is joined. In some embodiments, a linker does not reduce the biotin-binding ability of a biotin-binding moiety to which it is joined. In some embodiments, a linker does not eliminate the biotin-binding ability of a biotin-binding moiety to which it is joined. In some embodiments, the effect of the linker is determined by comparing the biotin-binding moiety with the biotin-binding moiety joined to the linker.

In some embodiments, a linker is not antigenic. In some embodiments, a linker does not elicit a T cell response. In some embodiments, a linker does not elicit a B cell response. In some embodiments, a linker does not induce a T cell or a B cell response.

In some embodiments, a linker comprises two or more amino acids. In some embodiments, a linker may be 3-100, 5-100, 10-100, 20-100 30-100, 40-100, 50-100, 60-100, 70-100, 80-100, 90-100, 5-55, 10-50, 10-45, 10-40, 10-35, 10-30, 10-25, 10-20, 10-15, 3-10, 3-9, 3-8, 3-7, 3-6, 3-5, 3-4, or 2-3 amino acids in length. In some embodiments, a linker comprises between 10-100, 10-90, 10-80, 10-70, 10-60, 10-50, 10-40, 10-30, 10-20, 10-15 amino acids. In some embodiments, the linker comprises at least 10, 15, 20, 25, 30, 35, 40, 45, 50, 55, 60, 65, 70, 75, 80, 85, 90, or 95 amino acids. In some embodiments, a linker is or comprises a peptidyl linker comprising 2, 3, 4, 5, 6, 7, 8, 9, 10, 15, 20, 25, 30, 35, 40, 45, 50, 55, 60, 65, 70, 75, 80, 85, 90, 95, or 100 amino acids.

In some embodiments, a linker is a flexible linker. Flexible linkers may be useful for joining domains that require a certain degree of movement or interaction and may include small, non-polar (e.g., Gly) or polar (e.g., Ser or Thr) amino acids. Incorporation of Ser or Thr can also maintain the stability of the linker in aqueous solutions by forming hydrogen bonds with water molecules, and therefore reduce unfavorable interactions between the linker and the protein moieties. In some embodiments, a linker comprises small non-polar (e.g. Gly) or polar (e.g. Ser or Thr) amino acids. In some embodiments, a linker is a Gly-Ser linker.

In some embodiments, a linker is or comprises an amino acid sequence of GGGGSSS (SEQ ID NO: 30). In some embodiments, a linker is or comprises a sequence of (GGGGS), (SEQ ID NO: 32), where n represents the number of repeating GGGGS (SEQ ID NO: 65) units and is 1, 2, 3, 4, 5, 6, 7, 8, 9, 10, 11, 12, 13, 14, 15, 16, 17, 18, 19, 20, 25, 30 or more. In some embodiments, a polypeptide linker may have an amino acid sequence that is or comprises GGGGSGGGGSGGGGS (SEQ ID NO: 34) (i.e., (GGGGS) 3 (SEQ ID NO: 34)) or GGGGSGGGGSGGGGSGGGGSGGGGSGGGGS (SEQ ID NO: 35) (i.e., (GGGGS) 6 (SEQ ID NO: 36)). In some embodiments, a linker comprises one or more of Gly, Ser, Thr, Ala, Lys, and Glu. In some embodiments, a linker is or comprises KESGSVSSEQLAQFRSLD (SEQ ID NO: 36). In some embodiments, a linker is or comprises EGKSSGSGSESKST (SEQ ID NO: 37). In some embodiments, a linker is or comprises (Gly), (SEQ ID NO: 38) where n represents the number of repeating Gly residues and is 1, 2, 3, 4, 5, 6, 7, 8, 9, 10, 11, 12, 13, 14, 15, 16, 17, 18, 19, 20, 25, 30 or more. In some embodiments, a linker is or comprises GGG. In some embodiments, a linker is or comprises (Gly) 6 (SEQ ID NO: 33). In some embodiments, a linker is or comprises (Gly) 8 (SEQ ID NO: 39 In some embodiments, a linker is or comprises GSAGSAAGSGEF (SEQ ID NO: 40). In some embodiments, a linker is or comprises an amino acid sequence of AAA. In some embodiments, such a linker may be synthesized, or derived from amino acid residues from a restriction site (e.g., a Not I restriction site).

In some embodiments, a linker is a rigid linker. Rigid linkers are useful to keep a fixed distance between domains and to maintain their independent functions. Rigid linkers may also be useful when a spatial separation of the domains is critical to preserve the stability or bioactivity of one or more components in the fusion. In some embodiments, a linker is or comprises (EAAAK), (SEQ ID NO: 41) where n represents the number of repeating EAAAK (SEQ ID NO: 66) units and is 1, 2, 3, 4, 5, 6, 7, 8, 9, 10, 11, 12, 13, 14, 15, 16, 17, 18, 19, 20, 25, 30 or more. In some embodiments, a linker is or comprises $A(EAAAK)_nA$, (SEQ ID NO: 42) where n represents the number of repeating EAAAK (SEQ ID NO: 66) units and is 1, 2, 3, 4, 5, 6, 7, 8, 9, 10, 11, 12, 13, 14, 15, 16, 17, 18, 19, 20, 25, 30 or more. In some embodiments, a linker is or comprises $A(EAAAK)_nA$ (SEQ ID NO: 68), where n represents the number of repeating EAAAK (SEQ ID NO: 66) units and is 2, 3, 4, or 5. In some embodiments, a linker is or comprises $A(EAAAK)_4ALEA(EAAAK)_4A$ (SEQ ID NO: 43). In some embodiments, a linker is or comprises $[A(EAAAK)_nA]_m$, (SEQ ID NO: 44) wherein n is 2, 3, or 4 and m is 1 or 2. In some embodiments, a linker is or comprises AEAAAKEAAAKA (SEQ ID NO: 45).

In some embodiments, a linker is or comprises $(X\text{-}Pro)_n$ (SEQ ID NO:46), with X designating any amino acid, where n represents the number of repeating X-Pro units and is 1, 2, 3, 4, 5, 6, 7, 8, 9, 10, 11, 12, 13, 14, 15, 16, 17, 18, 19, 20, 25, 30 or more. In some embodiments, a linker is or comprises $(Ala\text{-}Pro)_n$ (SEQ ID NO: 47), where n represents the number of repeating Ala-Pro units and is 1, 2, 3, 4, 5, 6, 7, 8, 9, 10, 11, 12, 13, 14, 15, 16, 17, 18, 19, 20, 25, 30 or more. In some embodiments, a linker is or comprises $(Ala\text{-}Pro)_n$ (SEQ ID NO: 69), where n represents the number of repeating Ala-Pro units and is 5, 6, 7, 8, 9, 10, 11, 12, 13, 14, 15, 16, or 17.

In some embodiments, a linker is or comprises $(Lys\text{-}Pro)_n$ (SEQ ID NO:48), where n represents the number of repeating Lys-Pro units and is 1, 2, 3, 4, 5, 6, 7, 8, 9, 10, 11, 12, 13, 14, 15, 16, 17, 18, 19, 20, 25, 30 or more. In some embodiments, a linker is or comprises $(Glu\text{-}Pro)_n$ (SEQ ID NO: 49), where n represents the number of repeating Glu-Pro units and is 1, 2, 3, 4, 5, 6, 7, 8, 9, 10, 11, 12, 13, 14, 15, 16, 17, 18, 19, 20, 25, 30 or more. In some embodiments, a linker is or comprises $(Ala\text{-}Pro)_7$ (SEQ ID NO: 50).

In some embodiments, a linker is or comprises GAPGGGGGAAAAAGGGGGGAP (GAG linker, SEQ ID NO: 51). In some embodiments, a linker is or comprises GAPGGGGGAAAAAGGGGGGAPGGGG-GAAAAAGGGGGGAP (GAG2 linker, SEQ ID NO: 52). In some embodiments, a linker is or comprises GAPGGGG-GAAAAAGGGGGGAPGGGGGAAAAAGGGGG-GAPGGGGGAAAAAGGGGG GAP (GAG3 linker, SEQ ID NO: 53).

Suitable linkers or spacers also include those having an amino acid sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more homologous or identical to the above exemplary linkers. In some embodiments, the linker comprises a polypeptide comprising an amino acid sequence having at least 80%, at least 85%, at least 90%, at least 95%, at least 96%, at least 97%, at least 98%, at least 99%, or 100% identity to the sequence of SEQ ID NO: 30 (GGGGSSS).

Additional linkers suitable for use with some embodiments may be found in U.S. Patent Publication No. 2012/0232021, filed on Mar. 2, 2012, and [Chen, 2013] the disclosures of which is hereby incorporated by reference in their entireties.

Tags

In some embodiments, a fusion protein of the immunogenic complex may comprise one or more tags, e.g., a histidine tag. A tag may be N-terminal or C-terminal. For instance, tags may be added to a polypeptide (via additions or modifications on the encoding DNA sequence) to facilitate purification, detection, solubility, or confer other desirable characteristics on the protein. In some embodiments, a tag may be a peptide, oligopeptide, or polypeptide that may be used in affinity purification. In some embodiments, a tag is, comprises, or is derived from one or more of polyhistidine (His), Glutathione S-transferase (GST), tandem affinity purification (TAP), FLAG, myc, human influenza hemagglutinin (HA), maltose binding protein (MBP), vesicular Stomatitis viral glycoprotein (VSV-G), thioredoxin, V5, avidin, streptavidin, biotin carboxyl carrier protein (BCCP), Calmodulin, Nus, S tags, lipoprotein D, and galactosidase. In some embodiments, a His tag is or comprises an amino acid sequence of Hn (SEQ ID NO: 67), wherein n is an integer between 2 and 10. Exemplary His tags include HHHHHH (SEQ ID NO: 55) and MSYYHHHHHH (SEQ ID NO: 56). In other embodiments, a fusion protein described herein is free of tags such as protein purification tags, and is purified by a method not relying on affinity for a purification tag. In some embodiments, a fusion protein described herein comprises no more than 1, 2, 3, 4, 5, 10, or 20 additional amino acids on one or both termini of a polypeptide of amino acid sequence of any of SEQ ID NOs: 1-12 or 57 or fusion protein of amino acid sequence of any of SEQ ID NOs: 19-26 or 58-61.

In some embodiments, a fusion protein described herein may contain a membrane translocating sequence (MTS), for example, in some embodiments, to facilitate introduction of the fusion protein into a mammalian cell and subsequent stimulation of the cell-mediated immune response. Exemplary membrane translocating sequences include, but are not limited to the hydrophobic region in the signal sequence of Kaposi fibroblast growth factor, the MTS of a synuclein, the third helix of the Antennapedia homeodomain, SN50, integrin 3 h-region, HIV Tat, pAntp, PR-39, abaccin, apidaccin, Bac5, Bac7, *P. berghei* CS protein, and those MTSs described in U.S. Pat. Nos. 6,248,558, 6,432,680 and 6,248,558.

Complementary Affinity Molecules

In some embodiments, a complementary affinity molecule comprises a biotin-binding moiety. In some embodiments, a fusion protein of the immunogenic complex comprises a biotin-binding moiety, and one or more polypeptide antigens. In some embodiments, a fusion protein comprises a biotin-binding moiety and two or more polypeptide antigens. As used herein, a "biotin-binding moiety" refers to a biotin-binding protein, a biotin-binding fragment thereof, or a biotin-binding domain thereof.

In some embodiments, MAPS complexes disclosed herein utilize the high affinity (dissociation constant $[KD]\approx10^{-15}$ M) non-covalent binding between biotin and rhizavidin, a biotin-binding protein that has no significant predicted homology with human proteins. Rhizavidin, a naturally occurring dimeric protein in the avidin protein family, was first discovered in *Rhizobium etli*, a symbiotic bacterium of the common bean. Rhizavidin has only a 22% amino acid identity with chicken avidin, a protein commonly found in eggs, but with high conservation of amino acid residues involved in biotin binding. No cross-reactivity to rhizavidin is observed in human serum samples obtained from subjects exposed to avidin [Helppolainen et al, 2007], suggesting that rhizavidin antibodies may not cross-react with chicken avidin. Biotin conjugates have been used in several clinical applications without any reported adverse events [Buller et al, 2014; Paty et al, 2010; Lazzeri et al, 2004].

In some embodiments, a biotin-binding moiety that is useful in accordance with the present disclosure comprises rhizavidin or a biotin-binding domain or biotin-binding fragment thereof, for example, in some embodiments as further described in WO 2012/155053, the contents of which are herein incorporated by reference in their entirety for the purposes described herein. In some embodiments, a biotin-binding moiety is or comprises a polypeptide having at least 80%, at least 85%, at least 90%, at least 95%, at least 96%, at least 97%, at least 98%, at least 99%, or 100% identity to rhizavidin, or a biotin-binding domain or biotin-binding fragment thereof. In some embodiments, a biotin-binding moiety that is useful in accordance with the present disclosure comprises a polypeptide of SEQ ID NO: 1 or a biotin-binding domain or biotin-binding fragment thereof. In some embodiments, a biotin-binding moiety is or comprises a polypeptide having at least 80%, at least 85%, at least 90%, at least 95%, at least 96%, at least 97%, at least 98%, at least 99%, 100% identity to the sequence of SEQ ID NO: 1, or biotin-binding domain or biotin-binding fragment thereof. In some embodiments, a biotin-binding moiety that is useful in accordance with the present disclosure comprises a polypeptide of SEQ ID NO: 2 or SEQ ID NO: 57, or a biotin-binding domain or biotin-binding fragment thereof. In some embodiments, a biotin-binding moiety is or comprises a polypeptide having at least 80%, at least 85%, at least 90%, at least 95%, at least 96%, at least 97%, at least 98%, at least 99%, or 100% identity to the sequence of SEQ ID NO: 2 or SEQ ID NO: 57, or biotin-binding domain or biotin-binding fragment thereof.

Fusion Protein SPP2

In some embodiments, a fusion protein described herein is or comprises a complementary affinity molecule described herein (e.g., a biotin-binding moiety described herein), and one or more polypeptides of or derived from *S. pneumoniae*. In some embodiments, a provided fusion protein is a SPP2 described herein. In some embodiments, a SPP2 fusion protein is a fusion protein comprising a biotin-binding moiety (e.g., a biotin-binding protein), a non-hemolytic pneumolysin polypeptide comprising mutations at amino acid residues 294, 385, 428, and 433 of wild-type *Streptococcus pneumoniae* pneumolysin or an antigenic fragment thereof; and (iii) a *S. pneumoniae* elongation factor P (SP0435) polypeptide or an antigenic fragment thereof. In some embodiments, a biotin-binding moiety is or comprises a rhizavidin polypeptide or a biotin-binding portion thereof. In some embodiments, a fusion protein comprises a complementary affinity molecule described herein (e.g., a biotin-binding moiety described herein) and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P)) or an antigenic variant or fragment thereof and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435) or an antigenic variant or fragment thereof. In some embodiments, the fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 19 or SEQ ID NO: 58. In some embodiments, the fusion protein is or comprises a complementary affinity molecule described herein (e.g., a biotin-binding moiety described herein), a polypeptide having at least 80%, at least 85%, at least 90%, at least 95%, at least 96%, at least 97%, at least 98%, at least 99%, or 100% identity to pneumolysin or an antigenic variant or fragment thereof, and a polypeptide having at least 80%, at least 85%, at least 90%, at least 95%, at least 96%, at least 97%, at least 98%, at least 99%, or 100% identity to SP0435 or an antigenic variant or fragment thereof. In some embodiments, the fusion protein is or comprises a complementary affinity molecule described herein (e.g., a biotin-binding moiety described herein), a polypeptide having at least 80%, at least 85%, at least 90%, at least 95%, at least 96%, at least 97%, at least 98%, at least 99%, or 100% identity to a non-hemolytic pneumolysin comprising mutations at amino acid residues 294, 385, 428, and 433 of wild-type *S. pneumoniae* pneumolysin or an antigenic variant or fragment thereof, and a polypeptide having at least 80%, at least 85%, at least 90%, at least 95%, at least 96%, at least 97%, at least 98%, at least 99%, or 100% identity to SP0435 or an antigenic variant or fragment thereof.

In some embodiments, a fusion protein described herein comprises a complementary affinity molecule described herein (e.g., a biotin-binding moiety described herein) and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P)) or an antigenic variant or fragment thereof. In some embodiments, a fusion protein comprises a complementary affinity molecule described herein (e.g., a biotin-binding moiety described herein) and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435) or an antigenic variant or fragment thereof.

In some embodiments, a fusion protein described herein comprises a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 1 (rhizavidin), or biotin-binding fragment thereof. In some embodiments, a fusion protein comprises a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 2 (amino acids 45-179 of rhizavidin) or SEQ ID NO: 57, or biotin-binding fragment thereof. In some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P)) or an antigenic variant or fragment thereof. In some embodiments, the fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435) or an antigenic variant or fragment thereof.

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 1 (rhizavidin), or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P)) or an antigenic variant or fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435) or an antigenic variant or fragment thereof. In some embodiments, such a fusion protein further comprises one or more linkers.

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 2 (amino acids 45-179 of rhizavidin) or SEQ ID NO: 57, or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P)) or an antigenic variant or fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435) or an antigenic variant or fragment thereof. In some embodiments, such a fusion protein further comprises one or more linkers.

In some embodiments, a fusion protein described herein is or comprises a SPP2 fusion protein. In some embodiments, a SPP2 fusion protein is a fusion protein comprising, from N-terminus to C-terminus, a biotin-binding moiety (e.g., a biotin-binding protein), a first peptide linker, a pneumolysin (Ply) polypeptide described herein or an antigenic variant or fragment thereof; a second peptide linker, and an SPN0435 polypeptide described herein or an antigenic variant or fragment thereof. In some such embodiments, a biotin-binding moiety is or comprises rhizavidin or a biotin-binding portion thereof. In some embodiments, a SPP2 fusion protein comprises, from N-terminus to C-terminus, (a) a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 1 (rhizavidin) or to the sequence of SEQ ID NO: 2 (amino acids 45-179 of rhizavidin) or SEQ ID NO: 57, or biotin-binding fragment thereof; (b) a first polypeptide linker comprising the amino acid sequence of SEQ ID NO: 30 (GGGGSSS); (c) an pneumolysin (Ply) polypeptide described herein; (d) a second polypeptide linker comprising the amino acid sequence of SEQ ID NO: 30 (GGGGSSS); and (c) an SP0435 polypeptide described herein. In some embodiments, a SPP2 fusion protein comprises, from N-terminus to C-terminus, (a) a biotin-binding moiety that is or comprises the polypeptide of SEQ ID NO: 1 (rhizavidin), SEQ ID NO: 2 (amino acids 45-179 of rhizavidin), or SEQ ID NO: 57, or biotin-binding fragment thereof; (b) a first polypeptide linker comprising the amino acid sequence of SEQ ID NO: 30 (GGGGSSS); (c) an pneumolysin (Ply) polypeptide described herein; (d) a second polypeptide linker comprising the amino acid sequence of SEQ ID NO: 30 (GGGGSSS); and (e) an SP0435 polypeptide described herein. In some embodiments, such a SPP2 fusion protein may further comprise a detection or purification tag, e.g., a His tag. In some embodiments, a SPP2 fusion protein comprising a His tag is referred to as SPP2-H. In some such embodiments, a SPP2 fusion protein comprises an SP0435 polypeptide (e.g., ones described herein) between a biotin-binding moiety and a Ply polypeptide (e.g., ones described herein). In some embodiments, a SPP2 fusion protein may comprise a Ply polypeptide between a biotin-binding moiety and a SP0435 polypeptide. In some embodiments, a Ply polypeptide included in a fusion protein described herein is or comprises an amino acid sequence having at least 80%, at least 85%, at least 90%, at least 95%, at least 96%, at least 97%, at least 98%, at least 99%, at least 99.5%, or 100% identity to the sequence of SEQ ID NO: 6 (amino acids 2-470 of *S. pneumoniae* PdT (G294P)) or an antigenic variant or fragment thereof. In some embodiments, an SP0435 polypeptide included in a fusion protein described herein is or comprises an amino acid sequence having at least 80%, at least 85%, at least 90%, at least 95%, at least 96%, at least 97%, at least 98%, at least 99%, at least 99.5%, or 100% identity to the sequence of SEQ ID NO: 8 (amino acids 62-185 of *S. pneumoniae* SP0435) or an antigenic variant or fragment thereof. In some embodiments, a fusion protein described herein comprises an amino acid sequence having at least 80%, at least 85%, at least 90%, at least 95%, at least 96%, at least 97%, at least 98%, at least 99%, at least 99.5%, or 100% identity to the sequence SEQ ID NO: 19 or SEQ ID NO: 58. In some embodiments, a fusion protein described herein comprises the amino acid sequence SEQ ID NO: 19 or SEQ ID NO: 58. In some embodiments, a fusion protein described herein consists of the amino acid sequence SEQ ID NO: 19 or SEQ ID NO: 58.

Fusion Protein CP1

In some embodiments, a fusion protein described herein is or comprises a complementary affinity molecule described herein (e.g., a biotin-binding moiety described herein), and one or more polypeptides of or derived from *S. pneumoniae*. In some embodiments, a fusion protein described herein is CP1, further described in the International Patent Publication No. WO 2020/056127, the contents of which are incorporated herein by reference in their entirety for the purposes described herein. In some embodiments, a fusion protein comprises a complementary affinity molecule described herein (e.g., a biotin-binding moiety described herein) and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785) or an antigenic variant or fragment thereof and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500) or an antigenic variant or fragment thereof. In some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 26 or SEQ ID NO: 61. In some embodiments, a fusion protein is or comprises a complementary affinity molecule described herein (e.g., a biotin-binding moiety described herein), a polypeptide having at least 80%, at least 85%, at least 90%, at least 95%, at least 96%, at least 97%, at least 98%, at least 99%, or 100% identity to SP0785 or an antigenic variant or fragment thereof, and a polypeptide having at least 80%, at least 85%, at least 90%, at least 95%, at least 96%, at least 97%, at least 98%, at least 99%, or 100% identity to SP1500 or an antigenic variant or fragment thereof.

In some embodiments, a fusion protein described herein comprises a complementary affinity molecule described herein (e.g., a biotin-binding moiety described herein) and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785) or an antigenic variant or fragment thereof. In some embodiments, a fusion protein comprises a complementary affinity molecule described herein (e.g., a biotin-binding moiety described herein) and a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500) or an antigenic variant or fragment thereof.

In some embodiments, a fusion protein described herein comprises a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 1 (rhizavidin), or biotin-binding fragment thereof. In some embodiments, a fusion protein comprises a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 2 (amino acids 45-179 of rhizavidin) or SEQ ID NO: 57, or biotin-binding fragment thereof. In some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785) or an antigenic variant or fragment thereof. In some embodiments, a fusion protein comprises a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500) or an antigenic variant or fragment thereof.

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 1 (rhizavidin), or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785) or an antigenic variant or fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500) or an antigenic variant or fragment thereof. In some embodiments, such a fusion protein further comprises one or more linkers.

In some embodiments, a fusion protein described herein comprises each of: (a) a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 2 (amino acids 45-179 of rhizavidin) or SEQ ID NO: 57, or biotin-binding fragment thereof; (b) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785) or an antigenic variant or fragment thereof; and (c) a polypeptide comprising an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500) or an antigenic variant or fragment thereof. In some embodiments, such a fusion protein further comprises one or more linkers. In some embodiments, a fusion protein described herein is or comprises a CP1 fusion protein. In some embodiments, a CP1 fusion protein comprises (a) a biotin-binding moiety that is or comprises a polypeptide having at least 80%, at least 85%, at least 90%, at least 95%, at least 96%, at least 97%, at least 98%, at least 99%, or 100% identity to the sequence of SEQ ID NO: 1 (rhizavidin) or to the sequence of SEQ ID NO: 2 (amino acids 45-179 of rhizavidin) or SEQ ID NO: 57, or biotin-binding fragment thereof; (b) a first polypeptide linker comprising the amino acid sequence of SEQ ID NO: 30 (GGGGSSS); (c) an SP0785 polypeptide described herein; (d) a second polypeptide linker comprising the amino acid sequence of (AAA); and (c) an SP1500 polypeptide described herein. In some embodiments, a CP1 fusion protein comprises, from N-terminus to C-terminus, (a) a biotin-binding moiety that is or comprises the polypeptide of SEQ ID NO: 1 (rhizavidin), SEQ ID NO: 2 (amino acids 45-179 of rhizavidin), or SEQ ID NO: 57, or biotin-binding fragment thereof; (b) a first polypeptide linker comprising the amino acid sequence of SEQ ID NO: 30 (GGGGSSS); (c) an SP1500 polypeptide described herein; (d) a second polypeptide linker comprising the amino acid sequence of (AAA); and (c) an SP0785 polypeptide described herein. In some embodiments, such a CP1 fusion protein may further comprise a detection or purification tag, e.g., a His tag. In some such embodiments, a CP1 fusion protein comprises an SP1500 polypeptide between a biotin-binding moiety and an SP0785 polypeptide. In some embodiments, a CP1 fusion protein may comprise an SP0785 polypeptide between a biotin-binding moiety and a SP1500 polypeptide. In some embodiments, an SP0785 polypeptide included in a fusion protein described herein is or comprises an amino acid sequence having at least 80%, at least 85%, at least 90%, at least 95%, at least 96%, at least 97%, at least 98%, at least 99%, at least 99.5%, or 100% identity to the sequence of SEQ ID NO: 10 (amino acids 33-399 of *S. pneumoniae* SP0785) or an antigenic variant or fragment thereof. In some embodiments, an SP1500 polypeptide included in a fusion protein described herein is or comprises an amino acid sequence having at least 80%, at least 85%, at least 90%, at least 95%, at least 96%, at least 97%, at least 98%, at least 99%, at least 99.5%, or 100% identity to the sequence of SEQ ID NO: 12 (amino acids 27-278 of *S. pneumoniae* SP1500) or an antigenic variant or fragment thereof. In some embodiments, a fusion protein comprises an amino acid sequence having at least 80%, at least 85%, at least 90%, at least 95%, at least 96%, at least 97%, at least 98%, at least 99%, at least 99.5%, or 100% identity to the sequence SEQ ID NO: 26 or SEQ ID NO: 61. In some embodiments, a fusion protein comprises the amino acid sequence SEQ ID NO: 26 or SEQ ID NO: 61. In some embodiments, a fusion protein consists of the amino acid sequence SEQ ID NO: 26 or SEQ ID NO: 61.

Carrier Proteins

In some embodiments, a multivalent pneumococcal immunogenic composition (e.g., vaccine) as described herein comprises one or more carrier proteins. In some embodiments, a carrier protein is or comprises an antigenic polypeptide (e.g., ones described herein including, e.g., SP0785 as described herein, SP1500 as described herein, SP0435 as described herein, Ply as described herein or in WO 05/76696, WO 05/108580, or WO 10/71986, etc.) and/or a fusion protein that includes one or more antigenic polypeptides (e.g., ones described herein including, e.g., CP1 as described herein, SPP2 as described herein, etc.). Additional exemplary carrier proteins include, but are not limited to PspA as described in WO 19/167008; CRM197 as described in WO 14/92378; variants of CRM197 such as eCRM197 as disclosed in WO 22/178015; Diphtheria toxoid; variants of Diphtheria toxoid as described in WO18/156465; Tetanus toxoid as described in WO 19/152921; and Protein D as described in U.S. Pat. No. 5,858,677, and combinations thereof.

In some embodiments, a fusion protein described herein may comprise a carrier protein.

Antigenic Polysaccharides

In some embodiments, an immunogenic complex described herein includes one or more *S. pneumoniae* polysaccharides. In some embodiments, an immunogenic complex described herein includes one *S. pneumoniae* polysaccharide. Capsular polysaccharides are used to distinguish serotypes of *S. pneumoniae*. There are at least 97 distinct serotypes of *S. pneumoniae* polysaccharides, each having a different chemical structure. Serotype designations as used herein are designations according to Danish nomenclature [Kauffmann et al, 1960; Geno et al, 2015]. (N.B. Serotype 20 in U.S. nomenclature is referred to as serotype 20A in Danish nomenclature.)

In some embodiments, an immunogenic complex includes one or more *S. pneumoniae* capsular polysaccharides from, or derived from, one or more *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

In some embodiments, an immunogenic complex includes one or more *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, an immunogenic complex does not include a *S. pneumoniae* capsular polysaccharide from, or derived from, *S. pneumoniae* serotype 3. In some embodiments, an immunogenic complex does not include a *S. pneumoniae* capsular polysaccharide from, or derived from, *S. pneumoniae* serotype 16F. In some embodiments, an immunogenic complex does not include a *S. pneumoniae* capsular polysaccharide from, or derived from, *S. pneumoniae* serotype 31.

In some embodiments, an immunogenic complex includes one or more *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

In some embodiments, an immunogenic complex includes one or more *S. pneumoniae* capsular polysaccharides from, or derived from, one or more *S. pneumoniae* serotypes selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

Methods of Isolating and Purifying Polysaccharides

In some embodiments, the disclosure provides methods of purifying one or more polysaccharides described herein from one or more cellular components of bacteria. In some embodiments, methods comprise purifying capsular polysaccharides from one or more cellular components of bacteria.

In some embodiments, the bacteria are Gram-negative. In some embodiments, the bacteria are Gram-positive. In some embodiments, the bacteria are *S. pneumoniae.*

In some embodiments, the cellular components include protein. In some embodiments, the cellular proteins include nucleic acid. In some embodiments, the cellular components include lipids. In some embodiments, the cellular components include polysaccharides. In some embodiments, the cellular components are part of a lysate.

In some embodiments, the polysaccharide purification processes incorporate a series of ethanol precipitations, washes of crude polysaccharide preparations with ethanol, diethyl ether, and/or acetone, and drying under vacuum to furnish purified products. In some embodiments, a phenol extraction step is incorporated for polysaccharide purifications. In some embodiments, the purification process employs a CTAB (cetyltrimethyl ammonium bromide) precipitation step in addition to using ethanol and phenol precipitation steps.

FIG. 9 depicts exemplary structures and chemical information for *S. pneumoniae* capsular polysaccharides included in immunogenic complexes of the present disclosure. All structures are from European Pharmacopoeia 9.0.

Methods of Biotinylating Polysaccharides

In some embodiments, the disclosure provides methods of biotinylating one or more polysaccharides described herein. In some embodiments, the method comprises reacting purified polysaccharides with 1-cyano-4-dimethylaminopyridinium tetrafluoroborate (CDAP) for activation of hydroxyl groups in the polysaccharides followed by the addition of amine PEG biotin under conditions that result in covalent linkage of biotin to the polysaccharides. In some embodiments, the desired level of biotinylation is achieved by varying the ratio of CDAP to polysaccharide. In some embodiments, the biotinylated polysaccharides are purified by filtration to remove process residuals such as unreacted biotin, dimethylaminopyridine, acetonitrile, cyanide and unreacted glycine. In some embodiments, the level of polysaccharide biotinylation described herein is optimized to reduce the amount of accessible biotin following MAPS complexation.

Manufacture of Immunogenic Complexes

The present disclosure includes methods for manufacturing immunogenic complexes described herein. In some embodiments, a method of manufacturing immunogenic complexes comprises complexing at least one biotinylated polysaccharide with at least one biotin-binding fusion protein. In some embodiments, the fusion protein comprises an amino acid sequence having at least 80%, at least 85%, at least 90%, at least 95%, at least 96%, at least 97%, at least 98%, at least 99%, at least 99.5%, or 100% identity to SEQ ID NO: 19 or SEQ ID NO: 58. In some embodiments, the fusion protein comprises an amino acid sequence having at least 80%, at least 85%, at least 90%, at least 95%, at least 96%, at least 97%, at least 98%, at least 99%, at least 99.5%, or 100% identity to SEQ ID NO: 26 or SEQ ID NO: 61.

In some embodiments, the average (e.g., the mean) protein (e.g., antigenic protein) to polysaccharide ratio of a plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average protein to polysaccharide ratio of a plurality of immunogenic complexes is approximately 1:1 (w/w). In some embodiments, the average protein to polysaccharide ratio of a plurality of immunogenic complexes is approximately 2:1 (w/w). In some embodiments, the average protein to polysaccharide ratio of a plurality of immunogenic complexes is approximately 3:1 (w/w). In some embodiments, the average protein to polysaccharide ratio of a plurality of immunogenic complexes is approximately 4:1 (w/w). In some embodiments, the average protein to polysaccharide ratio of a plurality of immunogenic complexes is approximately 5:1 (w/w). In some embodiments, the average protein to polysaccharide ratio of a plurality of immunogenic complexes is approximately 6:1 (w/w). In some embodiments, the average protein to polysaccharide ratio of a plurality of immunogenic complexes is approximately 7:1 (w/w). In some embodiments, the average protein to polysaccharide ratio of a plurality of immunogenic complexes is approximately 8:1 (w/w). In some embodiments, the average protein to polysaccharide ratio of a plurality of immunogenic complexes is approximately 9:1 (w/w). In some embodiments, the average protein to polysaccharide ratio of a plurality of immunogenic complexes is approximately 10:1 (w/w). In some embodiments, the average protein to polysaccharide ratio of a plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a fusion protein and a capsular polysaccharide. In some embodiments, the fusion protein is a SPP2 protein. In some embodiments, the fusion protein is a CP1 protein. In some embodiments, the capsular polysaccharide is from or derived from *S. pneumoniae* having a serotype selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the capsular polysaccharide is from or derived from *S. pneumoniae* having a serotype selected a group that includes 30, 31, 32, or 33 serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the capsular polysaccharide is from or derived from *S. pneumoniae* having a serotype selected a group that does not include one or more of serotypes 3, 16F, and 31. In some embodiments, the capsular polysaccharide is from or derived from *S. pneumoniae* having a serotype selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38. In some embodiments, the capsular polysaccharide is from or derived from *S. pneumoniae* having a serotype selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the average ratio of fusion protein to capsular polysaccharide in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of fusion protein to capsular polysaccharide in the plurality of immunogenic complexes is approximately 1:1 (w/w). In some embodiments, the average ratio of fusion protein to capsular polysaccharide in the plurality of immunogenic complexes is approximately 2:1 (w/w). In some embodiments, the average ratio of fusion protein to capsular polysaccharide in the plurality of immunogenic complexes is approximately 3:1 (w/w). In some embodiments, the average ratio of fusion protein to capsular polysaccharide in the plurality of immunogenic complexes is approximately 4:1 (w/w). In some embodiments, the average ratio of fusion protein to capsular polysaccharide in the plurality of immunogenic complexes is approximately 5:1 (w/w). In some embodiments, the average ratio of fusion protein to capsular polysaccharide in the plurality of immunogenic complexes is approximately 6:1 (w/w). In some embodiments, the average ratio of fusion protein to capsular polysaccharide in the plurality of immunogenic complexes is approximately 7:1 (w/w). In some embodiments, the average ratio of fusion protein to capsular polysaccharide in the plurality of immunogenic complexes is approximately 8:1 (w/w). In some embodiments, the average ratio of fusion protein to capsular polysaccharide in the plurality of immunogenic complexes is approximately 9:1 (w/w). In some embodiments, the average ratio of fusion protein to capsular polysaccharide in the plurality of immunogenic complexes is approximately 10:1 (w/w). In some embodiments, the average ratio of fusion protein to capsular polysaccharide in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., vaccine) comprises a plurality of immunogenic complexes comprising a SPP2 protein and a capsular polysaccharide, from or derived from *S. pneumoniae* serotype 1. In some embodiments, the average ratio of SPP2 protein to capsular polysaccharide from or derived from *S. pneumoniae* serotype 1 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 1 in the plurality of immunogenic complexes is approximately 1:1 (w/w). In some embodiments, the average ratio of SPP2 protein to capsular polysaccharide from or derived from *S. pneumoniae* serotype 1 in the plurality of immunogenic complexes is approximately 2:1 (w/w). In some embodiments, the average ratio of SPP2 protein to capsular polysaccharide from or derived from *S. pneumoniae* serotype 1 in the plurality of immunogenic complexes is approximately 3:1 (w/w). In some embodiments, the average ratio of SPP2 protein to capsular polysaccharide from or derived from *S. pneumoniae* serotype 1 in the plurality of immunogenic complexes is approximately 4:1 (w/w). In some embodiments, the average ratio of SPP2 protein to capsular polysaccharide from or derived from *S. pneumoniae* serotype 1 in the plurality of immunogenic complexes is approximately 5:1 (w/w). In some embodiments, the average ratio of SPP2 protein to capsular polysaccharide from or derived from *S. pneumoniae* serotype 1 in the plurality of immunogenic complexes is approximately 6:1 (w/w). In some embodiments, the average ratio of SPP2 protein to capsular polysaccharide from or derived from *S. pneumoniae* serotype 1 in the plurality of immunogenic complexes is approximately 7:1 (w/w). In some embodiments, the average ratio of SPP2 protein to capsular polysaccharide from or derived from *S. pneumoniae* serotype 1 in the plurality of immunogenic complexes is approximately 8:1 (w/w). In some embodiments, the average ratio of SPP2 protein to capsular polysaccharide from or derived from *S. pneumoniae* serotype 1 in the plurality of immunogenic complexes is approximately 9:1 (w/w). In some embodiments, the average ratio of SPP2 protein to capsular polysaccharide from or derived from *S. pneumoniae* serotype 1 in the plurality of immunogenic complexes is approximately 10:1 (w/w). In some embodiments, the average ratio of SPP2 protein to capsular polysaccharide from or derived from *S. pneumoniae* serotype 1 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., vaccine) comprises a plurality of immunogenic complexes comprising a SPP2 protein and a capsular polysaccharide, from or derived from *S. pneumoniae* serotype 6B. In some embodiments, the average ratio of SPP2 protein to capsular polysaccharide from or derived from *S. pneumoniae* serotype 6B in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 6B in the plurality of immunogenic complexes is approximately 1:1 (w/w). In some embodiments, the average ratio of SPP2 protein to capsular polysaccharide from or derived from *S. pneumoniae* serotype 6B in the plurality of immunogenic complexes is approximately 2:1 (w/w). In some embodiments, the average ratio of SPP2 protein to capsular polysaccharide from or derived from *S. pneumoniae* serotype 6B in the plurality of immunogenic complexes is approximately 3:1 (w/w). In some embodiments, the average ratio of SPP2 protein to capsular polysaccharide from or derived from *S. pneumoniae* serotype 6B in the plurality of immunogenic complexes is approximately 4:1 (w/w). In some embodiments, the average ratio of SPP2 protein to capsular polysaccharide from or derived from *S. pneumoniae* serotype 6B in the plurality of immunogenic complexes is approximately 5:1 (w/w). In some embodiments, the average ratio of SPP2 protein to capsular polysaccharide from or derived from *S.*

*pneumoniae* serotype 6B in the plurality of immunogenic complexes is approximately 6:1 (w/w). In some embodiments, the average ratio of SPP2 protein to capsular polysaccharide from or derived from *S. pneumoniae* serotype 6B in the plurality of immunogenic complexes is approximately 7:1 (w/w). In some embodiments, the average ratio of SPP2 protein to capsular polysaccharide from or derived from *S. pneumoniae* serotype 6B in the plurality of immunogenic complexes is approximately 8:1 (w/w). In some embodiments, the average ratio of SPP2 protein to capsular polysaccharide from or derived from *S. pneumoniae* serotype 6B in the plurality of immunogenic complexes is approximately 9:1 (w/w). In some embodiments, the average ratio of SPP2 protein to capsular polysaccharide from or derived from *S. pneumoniae* serotype 6B in the plurality of immunogenic complexes is approximately 10:1 (w/w). In some embodiments, the average ratio of SPP2 protein to capsular polysaccharide from or derived from *S. pneumoniae* serotype 6B in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a SPP2 protein and a capsular polysaccharide, from or derived from *S. pneumoniae* serotype 9V. In some embodiments, the average ratio of SPP2 protein to capsular polysaccharide from or derived from *S. pneumoniae* serotype 9V in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 9V in the plurality of immunogenic complexes is approximately 1:1 (w/w). In some embodiments, the average ratio of SPP2 protein to capsular polysaccharide from or derived from *S. pneumoniae* serotype 9V in the plurality of immunogenic complexes is approximately 2:1 (w/w). In some embodiments, the average ratio of SPP2 protein to capsular polysaccharide from or derived from *S. pneumoniae* serotype 9V in the plurality of immunogenic complexes is approximately 3:1 (w/w). In some embodiments, the average ratio of SPP2 protein to capsular polysaccharide from or derived from *S. pneumoniae* serotype 9V in the plurality of immunogenic complexes is approximately 4:1 (w/w). In some embodiments, the average ratio of SPP2 protein to capsular polysaccharide from or derived from *S. pneumoniae* serotype 9V in the plurality of immunogenic complexes is approximately 5:1 (w/w). In some embodiments, the average ratio of SPP2 protein to capsular polysaccharide from or derived from *S. pneumoniae* serotype 9V in the plurality of immunogenic complexes is approximately 6:1 (w/w). In some embodiments, the average ratio of SPP2 protein to capsular polysaccharide from or derived from *S. pneumoniae* serotype 9V in the plurality of immunogenic complexes is approximately 7:1 (w/w). In some embodiments, the average ratio of SPP2 protein to capsular polysaccharide from or derived from *S. pneumoniae* serotype 9V in the plurality of immunogenic complexes is approximately 8:1 (w/w). In some embodiments, the average ratio of SPP2 protein to capsular polysaccharide from or derived from *S. pneumoniae* serotype 9V in the plurality of immunogenic complexes is approximately 9:1 (w/w). In some embodiments, the average ratio of SPP2 protein to capsular polysaccharide from or derived from *S. pneumoniae* serotype 9V in the plurality of immunogenic complexes is approximately 10:1 (w/w). In some embodiments, the average ratio of SPP2 protein to capsular polysaccharide from or derived from *S. pneumoniae* serotype 9V in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a SPP2 protein and a capsular polysaccharide, from or derived from *S. pneumoniae* serotype 15B. In some embodiments, the average ratio of SPP2 protein to capsular polysaccharide from or derived from *S. pneumoniae* serotype 15B in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 15B in the plurality of immunogenic complexes is approximately 1:1 (w/w). In some embodiments, the average ratio of SPP2 protein to capsular polysaccharide from or derived from *S. pneumoniae* serotype 15B in the plurality of immunogenic complexes is approximately 2:1 (w/w). In some embodiments, the average ratio of SPP2 protein to capsular polysaccharide from or derived from *S. pneumoniae* serotype 15B in the plurality of immunogenic complexes is approximately 3:1 (w/w). In some embodiments, the average ratio of SPP2 protein to capsular polysaccharide from or derived from *S. pneumoniae* serotype 15B in the plurality of immunogenic complexes is approximately 4:1 (w/w). In some embodiments, the average ratio of SPP2 protein to capsular polysaccharide from or derived from *S. pneumoniae* serotype 15B in the plurality of immunogenic complexes is approximately 5:1 (w/w). In some embodiments, the average ratio of SPP2 protein to capsular polysaccharide from or derived from *S. pneumoniae* serotype 15B in the plurality of immunogenic complexes is approximately 6:1 (w/w). In some embodiments, the average ratio of SPP2 protein to capsular polysaccharide from or derived from *S. pneumoniae* serotype 15B in the plurality of immunogenic complexes is approximately 7:1 (w/w). In some embodiments, the average ratio of SPP2 protein to capsular polysaccharide from or derived from *S. pneumoniae* serotype 15B in the plurality of immunogenic complexes is approximately 8:1 (w/w). In some embodiments, the average ratio of SPP2 protein to capsular polysaccharide from or derived from *S. pneumoniae* serotype 15B in the plurality of immunogenic complexes is approximately 9:1 (w/w). In some embodiments, the average ratio of SPP2 protein to capsular polysaccharide from or derived from *S. pneumoniae* serotype 15B in the plurality of immunogenic complexes is approximately 10:1 (w/w). In some embodiments, the average ratio of SPP2 protein to capsular polysaccharide from or derived from *S. pneumoniae* serotype 15B in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a SPP2 protein and a capsular polysaccharide, from or derived from *S. pneumoniae* serotype 22F. In some embodiments, the average ratio of SPP2 protein to capsular polysaccharide from or derived from *S. pneumoniae* serotype 22F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 22F in the plurality of immunogenic complexes is approximately 1:1 (w/w). In some embodiments, the average ratio of SPP2 protein to capsular polysaccharide from or derived from *S. pneumoniae* serotype 22F in the plurality of immunogenic complexes is approximately 2:1 (w/w). In some embodiments, the average ratio of SPP2 protein to capsular polysaccharide from or derived from *S. pneumoniae* serotype 22F in the plurality of immunogenic complexes is approximately 3:1 (w/w). In some embodiments, the average ratio of SPP2 protein to capsular polysaccharide from or derived from *S. pneumoniae* serotype 22F in the plurality of immunogenic complexes is approximately 4:1 (w/w). In some embodiments, the average ratio of SPP2 protein to capsular polysaccharide from or derived from *S. pneumoniae* serotype 22F in the plurality of immunogenic complexes is approximately 5:1 (w/w). In some embodiments, the average ratio of SPP2 protein to capsular polysaccharide from or derived from *S. pneumoniae* serotype 22F in the plurality of immunogenic complexes is approximately 6:1 (w/w). In some embodiments, the average ratio of SPP2 protein to capsular polysaccharide from or derived from *S. pneumoniae* serotype 22F in the plurality of immunogenic complexes is approximately 7:1 (w/w). In some embodiments, the average ratio of SPP2 protein to capsular polysaccharide from or derived from *S. pneumoniae* serotype 22F in the plurality of immunogenic complexes is approximately 8:1 (w/w). In some embodiments, the average ratio of SPP2 protein to capsular polysaccharide from or derived from *S. pneumoniae* serotype 22F in the plurality of immunogenic complexes is approximately 9:1 (w/w). In some embodiments, the average ratio of SPP2 protein to capsular polysaccharide from or derived from *S. pneumoniae* serotype 22F in the plurality of immunogenic complexes is approximately 10:1 (w/w). In some embodiments, the average ratio of SPP2 protein to capsular polysaccharide from or derived from *S. pneumoniae* serotype 22F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a SPP2 protein and a capsular polysaccharide, from or derived from *S. pneumoniae* serotype 23A. In some embodiments, the average ratio of SPP2 protein to capsular polysaccharide from or derived from *S. pneumoniae* serotype 23A in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 23A in the plurality of immunogenic complexes is approximately 1:1 (w/w). In some embodiments, the average ratio of SPP2 protein to capsular polysaccharide from or derived from *S. pneumoniae* serotype 23A in the plurality of immunogenic complexes is approximately 2:1 (w/w). In some embodiments, the average ratio of SPP2 protein to capsular polysaccharide from or derived from *S. pneumoniae* serotype 23A in the plurality of immunogenic complexes is approximately 3:1 (w/w). In some embodiments, the average ratio of SPP2 protein to capsular polysaccharide from or derived from *S. pneumoniae* serotype 23A in the plurality of immunogenic complexes is approximately 4:1 (w/w). In some embodiments, the average ratio of SPP2 protein to capsular polysaccharide from or derived from *S. pneumoniae* serotype 23A in the plurality of immunogenic complexes is approximately 5:1 (w/w). In some embodiments, the average ratio of SPP2 protein to capsular polysaccharide from or derived from *S. pneumoniae* serotype 23A in the plurality of immunogenic complexes is approximately 6:1 (w/w). In some embodiments, the average ratio of SPP2 protein to capsular polysaccharide from or derived from *S. pneumoniae* serotype 23A in the plurality of immunogenic complexes is approximately 7:1 (w/w). In some embodiments, the average ratio of SPP2 protein to capsular polysaccharide from or derived from *S. pneumoniae* serotype 23A in the plurality of immunogenic complexes is approximately 8:1 (w/w). In some embodiments, the average ratio of SPP2 protein to capsular polysaccharide from or derived from *S. pneumoniae* serotype 23A in the plurality of immunogenic complexes is approximately 9:1 (w/w). In some embodiments, the average ratio of SPP2 protein to capsular polysaccharide from or derived from *S. pneumoniae* serotype 23A in the plurality of immunogenic complexes is approximately 10:1 (w/w). In some embodiments, the average ratio of SPP2 protein to capsular polysaccharide from or derived from *S. pneumoniae* serotype 23A in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a SPP2 protein and a capsular polysaccharide, from or derived from *S. pneumoniae* serotype 23B. In some embodiments, the average ratio of SPP2 protein to capsular polysaccharide from or derived from *S. pneumoniae* serotype 23B in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 23B in the plurality of immunogenic complexes is approximately 1:1 (w/w). In some embodiments, the average ratio of SPP2 protein to capsular polysaccharide from or derived from *S. pneumoniae* serotype 23B in the plurality of immunogenic complexes is approximately 2:1 (w/w). In some embodiments, the average ratio of SPP2 protein to capsular polysaccharide from or derived from *S. pneumoniae* serotype 23B in the plurality of immunogenic complexes is approximately 3:1 (w/w). In some embodiments, the average ratio of SPP2 protein to capsular polysaccharide from or derived from *S. pneumoniae* serotype 23B in the plurality of immunogenic complexes is approximately 4:1 (w/w). In some embodiments, the average ratio of SPP2 protein to capsular polysaccharide from or derived from *S. pneumoniae* serotype 23B in the plurality of immunogenic complexes is approximately 5:1 (w/w). In some embodiments, the average ratio of SPP2 protein to capsular polysaccharide from or derived from *S. pneumoniae* serotype 23B in the plurality of immunogenic complexes is approximately 6:1 (w/w). In some embodiments, the average ratio of SPP2 protein to capsular polysaccharide from or derived from *S. pneumoniae* serotype 23B in the plurality of immunogenic complexes is approximately 7:1 (w/w). In some embodiments, the average ratio of SPP2 protein to capsular polysaccharide from or derived from *S. pneumoniae* serotype 23B in the plurality of immunogenic complexes is approximately 8:1 (w/w). In some embodiments, the average ratio of SPP2 protein to capsular polysaccharide from or derived from *S. pneumoniae* serotype 23B in the plurality of immunogenic complexes is approximately 9:1 (w/w). In some embodiments, the average ratio of SPP2 protein to capsular polysaccharide from or derived from *S. pneumoniae* serotype 23B in the plurality of immunogenic complexes is approximately 10:1 (w/w). In some embodiments, the average ratio of SPP2 protein to capsular polysaccharide from or derived from *S. pneumoniae* serotype 23B in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a SPP2 protein and a capsular polysaccharide, from or derived from *S. pneumoniae* serotype 23F. In some embodiments, the average ratio of SPP2 protein to capsular polysaccharide from or derived from *S. pneumoniae* serotype 23F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 23F in the plurality of immunogenic complexes is approximately 1:1 (w/w). In some embodiments, the average ratio of SPP2 protein to capsular polysaccharide from or derived from *S. pneumoniae* serotype 23F in the plurality of immunogenic complexes is approximately 2:1 (w/w). In some embodiments, the average ratio of SPP2 protein to capsular polysaccharide from or derived from *S. pneumoniae* serotype 23F in the plurality of immunogenic complexes is approximately 3:1 (w/w). In some embodiments, the average ratio of SPP2 protein to capsular polysaccharide from or derived from *S. pneumoniae* serotype 23F in the plurality of immunogenic complexes is approximately 4:1 (w/w). In some embodiments, the average ratio of SPP2 protein to capsular polysaccharide from or derived from *S. pneumoniae* serotype 23F in the plurality of immunogenic complexes is approximately 5:1 (w/w). In some embodiments, the average ratio of SPP2 protein to capsular polysaccharide from or derived from *S. pneumoniae* serotype 23F in the plurality of immunogenic complexes is approximately 6:1 (w/w). In some embodiments, the average ratio of SPP2 protein to capsular polysaccharide from or derived from *S. pneumoniae* serotype 23F in the plurality of immunogenic complexes is approximately 7:1 (w/w). In some embodiments, the average ratio of SPP2 protein to capsular polysaccharide from or derived from *S. pneumoniae* serotype 23F in the plurality of immunogenic complexes is approximately 8:1 (w/w). In some embodiments, the average ratio of SPP2 protein to capsular polysaccharide from or derived from *S. pneumoniae* serotype 23F in the plurality of immunogenic complexes is approximately 9:1 (w/w). In some embodiments, the average ratio of SPP2 protein to capsular polysaccharide from or derived from *S. pneumoniae* serotype 23F in the plurality of immunogenic complexes is approximately 10:1 (w/w). In some embodiments, the average ratio of SPP2 protein to capsular polysaccharide from or derived from *S. pneumoniae* serotype 23F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises a plurality of immunogenic complexes comprising a SPP2 protein and a capsular polysaccharide, from or derived from *S. pneumoniae* serotype 33F. In some embodiments, the average ratio of SPP2 protein to capsular polysaccharide from or derived from *S. pneumoniae* serotype 33F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of SPP2 protein to capsular polysaccharide from or derived from *S. pneumoniae* serotype 33F in the plurality of immunogenic complexes is approximately 1:1 (w/w). In some embodiments, the average ratio of SPP2 protein to capsular polysaccharide from or derived from *S. pneumoniae* serotype 33F in the plurality of immunogenic complexes is approximately 2:1 (w/w). In some embodiments, the average ratio of SPP2 protein to capsular polysaccharide from or derived from *S. pneumoniae* serotype 33F in the plurality of immunogenic complexes is approximately 3:1 (w/w). In some embodiments, the average ratio of SPP2 protein to capsular polysaccharide from or derived from *S. pneumoniae* serotype 33F in the plurality of immunogenic complexes is approximately 4:1 (w/w). In some embodiments, the average ratio of SPP2 protein to capsular polysaccharide from or derived from *S. pneumoniae* serotype 33F in the plurality of immunogenic complexes is approximately 5:1 (w/w). In some embodiments, the average ratio of SPP2 protein to capsular polysaccharide from or derived from *S. pneumoniae* serotype 33F in the plurality of immunogenic complexes is approximately 6:1 (w/w). In some embodiments, the average ratio of SPP2 protein to capsular polysaccharide from or derived from *S. pneumoniae* serotype 33F in the plurality of immunogenic complexes is approximately 7:1 (w/w). In some embodiments, the average ratio of SPP2 protein to capsular polysaccharide from or derived from *S. pneumoniae* serotype 33F in the plurality of immunogenic complexes is approximately 8:1 (w/w). In some embodiments, the average ratio of SPP2 protein to capsular polysaccharide from or derived from *S. pneumoniae* serotype 33F in the plurality of immunogenic complexes is approximately 9:1 (w/w). In some embodiments, the average ratio of SPP2 protein to capsular polysaccharide from or derived from *S. pneumoniae* serotype 33F in the plurality of immunogenic complexes is approximately 10:1 (w/w). In some embodiments, the average ratio of SPP2 protein to capsular polysaccharide from or derived from *S. pneumoniae* serotype 33F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions (e.g., vaccines) of the present disclosure may comprise mixtures of immunogenic complexes with different average protein to polysaccharide ratios.

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 6C, wherein the average ratio of SPP2 protein to capsular polysaccharide from or derived from *S. pneumoniae* serotype 6C in the plurality of immunogenic complexes is between about 2.5:1 and about 3.5:1 (w/w);

(2) a plurality of immunogenic complexes comprising a SPP2 protein and a capsular polysaccharide, from or derived from *S. pneumoniae* serotype 7C, wherein the average ratio of SPP2 protein to capsular polysaccharide from or derived from *S. pneumoniae* serotype 7C in the plurality of immunogenic complexes is between about 2.5:1 and about 3.5:1 (w/w);

(3) a plurality of immunogenic complexes comprising a SPP2 protein and a capsular polysaccharide, from or derived from *S. pneumoniae* serotype 15A, wherein the average ratio of SPP2 protein to capsular polysaccharide from or derived from *S. pneumoniae* serotype 15A in the plurality of immunogenic complexes is between about 2.5:1 and about 3.5:1 (w/w);

(4) a plurality of immunogenic complexes comprising a SPP2 protein and a capsular polysaccharide, from or derived from *S. pneumoniae* serotype 16F, wherein the average ratio of SPP2 protein to capsular polysaccharide from or derived from *S. pneumoniae* serotype 16F in the plurality of immunogenic complexes is between about 2.5:1 and about 3.5:1 (w/w);

(5) a plurality of immunogenic complexes comprising a SPP2 protein and a capsular polysaccharide, from or derived from *S. pneumoniae* serotype 23A, wherein the average ratio of SPP2 protein to capsular polysaccharide from or derived from *S. pneumoniae* serotype 23A in the plurality of immunogenic complexes is between about 2.5:1 and about 3.5:1 (w/w);

(6) a plurality of immunogenic complexes comprising a SPP2 protein and a capsular polysaccharide, from or derived from *S. pneumoniae* serotype 23B, wherein the average ratio of SPP2 protein to capsular polysaccharide from or derived from *S. pneumoniae* serotype 23B in the plurality of immunogenic complexes is between about 2.5:1 and about 3.5:1 (w/w);

(7) a plurality of immunogenic complexes comprising a SPP2 protein and a capsular polysaccharide, from or derived from *S. pneumoniae* serotype 24F, wherein the average ratio of SPP2 protein to capsular polysaccharide from or derived from *S. pneumoniae* serotype 24F in the plurality of immunogenic complexes is between about 2.5:1 and about 3.5:1 (w/w);

(8) a plurality of immunogenic complexes comprising a SPP2 protein and a capsular polysaccharide, from or derived from *S. pneumoniae* serotype 31, wherein the average ratio of SPP2 protein to capsular polysaccharide from or derived from *S. pneumoniae* serotype 31 in the plurality of immunogenic complexes is between about 2.5:1 and about 3.5:1 (w/w);

(9) a plurality of immunogenic complexes comprising a SPP2 protein and a capsular polysaccharide, from or derived from *S. pneumoniae* serotype 35B, wherein the average ratio of SPP2 protein to capsular polysaccharide from or derived from *S. pneumoniae* serotype 35B in the plurality of immunogenic complexes is between about 2.5:1 and about 3.5:1 (w/w);

(10) a plurality of immunogenic complexes comprising a SPP2 protein and a capsular polysaccharide, from or derived from *S. pneumoniae* serotype 38, wherein the average ratio of SPP2 protein to capsular polysaccharide from or derived from *S. pneumoniae* serotype 38 in the plurality of immunogenic complexes is between about 2.5:1 and about 3.5:1 (w/w);

(11) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.5:1 and about 3.5:1 (w/w);

(12) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.5:1 and about 3.5:1 (w/w);

(13) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.5:1 and about 3.5:1 (w/w);

(14) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.5:1 and about 3.5:1 (w/w);

(15) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.5:1 and about 3.5:1 (w/w);

(16) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.5:1 and about 3.5:1 (w/w);

(17) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.5:1 and about 3.5:1 (w/w);

(18) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.5:1 and about 3.5:1 (w/w);

(19) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.5:1 and about 3.5:1 (w/w);

(20) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.5:1 and about 3.5:1 (w/w);

(21) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.5:1 and about 3.5:1 (w/w);

(22) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.5:1 and about 3.5:1 (w/w);

(23) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.5:1 and about 3.5:1 (w/w);

(24) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.5:1 and about 3.5:1 (w/w);

(25) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.5:1 and about 3.5:1 (w/w);

(26) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is between about 2.5:1 and about 3.5:1 (w/w);

(27) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.5:1 and about 3.5:1 (w/w);

(28) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.5:1 and about 3.5:1 (w/w);

(29) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is between about 2.5:1 and about 3.5:1 (w/w);

(30) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.5:1 and about 3.5:1 (w/w);

(31) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.5:1 and about 3.5:1 (w/w);

(32) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.5:1 and about 3.5:1 (w/w);

(33) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.5:1 and about 3.5:1 (w/w); and

(34) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.5:1 and about 3.5:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is between about 2.5:1 and about 3.5:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is between about 2.5:1 and about 3.5:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is between about 2.5:1 and about 3.5:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is between about 2.5:1 and about 3.5:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is between about 2.5:1 and about 3.5:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is between about 2.5:1 and about 3.5:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is between about 2.5:1 and about 3.5:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is between about 2.5:1 and about 3.5:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is between about 2.5:1 and about 3.5:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is between about 2.5:1 and about 3.5:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.5:1 and about 3.5:1 (w/w);

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.5:1 and about 3.5:1 (w/w);

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.5:1 and about 3.5:1 (w/w);

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.5:1 and about 3.5:1 (w/w);

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.5:1 and about 3.5:1 (w/w);

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.5:1 and about 3.5:1 (w/w);

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.5:1 and about 3.5:1 (w/w);

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.5:1 and about 3.5:1 (w/w);

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.5:1 and about 3.5:1 (w/w);

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.5:1 and about 3.5:1 (w/w);

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.5:1 and about 3.5:1 (w/w);

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.5:1 and about 3.5:1 (w/w);

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is between about 2.5:1 and about 3.5:1 (w/w);

(24) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is between about 2.5:1 and about 3.5:1 (w/w);

(25) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.5:1 and about 3.5:1 (w/w);

(26) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.5:1 and about 3.5:1 (w/w);

(27) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.5:1 and about 3.5:1 (w/w);

(28) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.5:1 and about 3.5:1 (w/w);

(29) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.5:1 and about 3.5:1 (w/w);

(30) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.5:1 and about 3.5:1 (w/w);

(31) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is between about 2.5:1 and about 3.5:1 (w/w);

(32) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.5:1 and about 3.5:1 (w/w);

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is between about 2.5:1 and about 3.5:1 (w/w); and

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.5:1 and about 3.5:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is between about 2.5:1 and about 3.5:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is between about 2.5:1 and about 3.5:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is between about 2.5:1 and about 3.5:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is between about 2.5:1 and about 3.5:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is between about 2.5:1 and about 3.5:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is between about 2.5:1 and about 3.5:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is between about 2.5:1 and about 3.5:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is between about 2.5:1 and about 3.5:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is between about 2.5:1 and about 3.5:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is between about 2.5:1 and about 3.5:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.5:1 and about 3.5:1 (w/w);

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.5:1 and about 3.5:1 (w/w);

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.5:1 and about 3.5:1 (w/w);

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.5:1 and about 3.5:1 (w/w);

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.5:1 and about 3.5:1 (w/w);

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.5:1 and about 3.5:1 (w/w);

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.5:1 and about 3.5:1 (w/w);

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.5:1 and about 3.5:1 (w/w);

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.5:1 and about 3.5:1 (w/w);

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.5:1 and about 3.5:1 (w/w);

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.5:1 and about 3.5:1 (w/w);

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.5:1 and about 3.5:1 (w/w);

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is between about 2.5:1 and about 3.5:1 (w/w);

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.5:1 and about 3.5:1 (w/w);

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.5:1 and about 3.5:1 (w/w);

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.5:1 and about 3.5:1 (w/w);

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.5:1 and about 3.5:1 (w/w);

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.5:1 and about 3.5:1 (w/w);

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.5:1 and about 3.5:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is between about 2.5:1 and about 3.5:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.5:1 and about 3.5:1 (w/w);

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is between about 2.5:1 and about 3.5:1 (w/w); and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.5:1 and about 3.5:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is between about 2.5:1 and about 3.5:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is between about 2.5:1 and about 3.5:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is between about 2.5:1 and about 3.5:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is between about 2.5:1 and about 3.5:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is between about 2.5:1 and about 3.5:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is between about 2.5:1 and about 3.5:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is between about 2.5:1 and about 3.5:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is between about 2.5:1 and about 3.5:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is between about 2.5:1 and about 3.5:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is between about 2.5:1 and about 3.5:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.5:1 and about 3.5:1 (w/w);

(12) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.5:1 and about 3.5:1 (w/w);

(13) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.5:1 and about 3.5:1 (w/w);

(14) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.5:1 and about 3.5:1 (w/w);

(15) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.5:1 and about 3.5:1 (w/w);

(16) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.5:1 and about 3.5:1 (w/w);

(17) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.5:1 and about 3.5:1 (w/w);

(18) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.5:1 and about 3.5:1 (w/w);

(19) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.5:1 and about 3.5:1 (w/w);

(20) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.5:1 and about 3.5:1 (w/w);

(21) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.5:1 and about 3.5:1 (w/w);

(22) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is between about 2.5:1 and about 3.5:1 (w/w);

(23) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is between about 2.5:1 and about 3.5:1 (w/w);

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.5:1 and about 3.5:1 (w/w);

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.5:1 and about 3.5:1 (w/w);

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.5:1 and about 3.5:1 (w/w);

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.5:1 and about 3.5:1 (w/w);

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.5:1 and about 3.5:1 (w/w);

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.5:1 and about 3.5:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is between about 2.5:1 and about 3.5:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.5:1 and about 3.5:1 (w/w);

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is between about 2.5:1 and about 3.5:1 (w/w); and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.5:1 and about 3.5:1 (w/w).

In some embodiments, an immunogenic composition (e.g., a vaccine) comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.5:1 and about 3.5:1 (w/w);

(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.5:1 and about 3.5:1 (w/w);

(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.5:1 and about 3.5:1 (w/w);

(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.5:1 and about 3.5:1 (w/w);

(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.5:1 and about 3.5:1 (w/w);

(6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.5:1 and about 3.5:1 (w/w);

(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.5:1 and about 3.5:1 (w/w);

(8) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.5:1 and about 3.5:1 (w/w);

(9) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.5:1 and about 3.5:1 (w/w);

(10) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.5:1 and about 3.5:1 (w/w);

(11) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.5:1 and about 3.5:1 (w/w);

(12) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.5:1 and about 3.5:1 (w/w);

(13) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.5:1 and about 3.5:1 (w/w);

(14) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.5:1 and about 3.5:1 (w/w);

(15) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.5:1 and about 3.5:1 (w/w);

(16) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.5:1 and about 3.5:1 (w/w);

(17) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.5:1 and about 3.5:1 (w/w);

(18) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is between about 2.5:1 and about 3.5:1 (w/w);

(19) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is between about 2.5:1 and about 3.5:1 (w/w);

(20) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is between about 2.5:1 and about 3.5:1 (w/w);

(21) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.5:1 and about 3.5:1 (w/w);

(22) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.5:1 and about 3.5:1 (w/w);

(23) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is between about 2.5:1 and about 3.5:1 (w/w);

(24) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.5:1 and about 3.5:1 (w/w);

(25) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.5:1 and about 3.5:1 (w/w);

(26) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.5:1 and about 3.5:1 (w/w);

(27) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.5:1 and about 3.5:1 (w/w);

(28) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.5:1 and about 3.5:1 (w/w);

(29) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.5:1 and about 3.5:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is between about 2.5:1 and about 3.5:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.5:1 and about 3.5:1 (w/w);

(32) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.5:1 and about 3.5:1 (w/w);

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is between about 2.5:1 and about 3.5:1 (w/w); and

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.5:1 and about 3.5:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 6C, wherein the average ratio of SPP2 protein to capsular polysaccharide from or derived from *S. pneumoniae* serotype 6C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a SPP2 protein and a capsular polysaccharide, from or derived from *S. pneumoniae* serotype 7C, wherein the average ratio of SPP2 protein to capsular polysaccharide from or derived from *S. pneumoniae* serotype 7C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a SPP2 protein and a capsular polysaccharide, from or derived from *S. pneumoniae* serotype 15A, wherein the average ratio of SPP2 protein to capsular polysaccharide from or derived from *S. pneumoniae* serotype 15A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a SPP2 protein and a capsular polysaccharide, from or derived from *S. pneumoniae* serotype 16F, wherein the average ratio of SPP2 protein to capsular polysaccharide from or derived from *S. pneumoniae* serotype 16F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a SPP2 protein and a capsular polysaccharide, from or derived from *S. pneumoniae* serotype 23A, wherein the average ratio of SPP2 protein to capsular polysaccharide from or derived from *S. pneumoniae* serotype 23A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a SPP2 protein and a capsular polysaccharide, from or derived from *S. pneumoniae* serotype 23B, wherein the average ratio of SPP2 protein to capsular polysaccharide from or derived from *S. pneumoniae* serotype 23B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a SPP2 protein and a capsular polysaccharide, from or derived from *S. pneumoniae* serotype 24F, wherein the average ratio of SPP2 protein to capsular polysaccharide from or derived from *S. pneumoniae* serotype 24F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(8) a plurality of immunogenic complexes comprising a SPP2 protein and a capsular polysaccharide, from or derived from *S. pneumoniae* serotype 31, wherein the average ratio of SPP2 protein to capsular polysaccharide from or derived from *S. pneumoniae* serotype 31 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(9) a plurality of immunogenic complexes comprising a SPP2 protein and a capsular polysaccharide, from or derived from *S. pneumoniae* serotype 35B, wherein the average ratio of SPP2 protein to capsular polysaccharide from or derived from *S. pneumoniae* serotype 35B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(10) a plurality of immunogenic complexes comprising a SPP2 protein and a capsular polysaccharide, from or derived from *S. pneumoniae* serotype 38, wherein the average ratio of SPP2 protein to capsular polysaccharide from or derived from *S. pneumoniae* serotype 38 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(11) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(12) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(13) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(14) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(15) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(16) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(17) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(18) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(19) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(20) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(21) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(22) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(23) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(24) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(25) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(26) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(27) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(28) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(29) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(30) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(31) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(32) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(33) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and

(34) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(24) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(25) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(26) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(27) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(28) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(29) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(30) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(31) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(32) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(12) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(13) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(14) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(15) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(16) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(17) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(18) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(19) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(20) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(21) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(22) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(23) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w).

In some embodiments, an immunogenic composition (e.g., a vaccine) comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(8) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(9) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(10) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(11) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(12) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(13) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(14) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(15) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(16) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(17) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(18) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(19) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(20) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(21) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(22) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(23) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(24) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(25) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(26) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(27) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(28) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(29) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(32) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w). In some embodiments, an immunogenic composition (e.g., a vaccine) comprises:

(1) a plurality of immunogenic complexes comprising a SPP2 protein and a capsular polysaccharide, from or derived from *S. pneumoniae* serotype 6C, wherein the average ratio of SPP2 protein to capsular polysaccharide from or derived from *S. pneumoniae* serotype 6C in the (2) a plurality of immunogenic complexes comprising a SPP2 protein and a capsular polysaccharide, from or derived from *S. pneumoniae* serotype 7C, wherein the average ratio of SPP2 protein to capsular polysaccharide from or derived from *S. pneumoniae* serotype 7C in the plurality of immunogenic complexes is between about 2.9:1 and about 3.1:1 (w/w);

(3) a plurality of immunogenic complexes comprising a SPP2 protein and a capsular polysaccharide, from or derived from *S. pneumoniae* serotype 15A, wherein the average ratio of SPP2 protein to capsular polysaccharide from or derived from *S. pneumoniae* serotype 15A in the plurality of immunogenic complexes is between about 2.9:1 and about 3.1:1 (w/w);

(4) a plurality of immunogenic complexes comprising a SPP2 protein and a capsular polysaccharide, from or derived from *S. pneumoniae* serotype 16F, wherein the average ratio of SPP2 protein to capsular polysaccharide from or derived from *S. pneumoniae* serotype 16F in the plurality of immunogenic complexes is between about 2.9:1 and about 3.1:1 (w/w);

(5) a plurality of immunogenic complexes comprising a SPP2 protein and a capsular polysaccharide, from or derived from *S. pneumoniae* serotype 23A, wherein the average ratio of SPP2 protein to capsular polysaccharide from or derived from *S. pneumoniae* serotype 23A in the plurality of immunogenic complexes is between about 2.9:1 and about 3.1:1 (w/w);

(6) a plurality of immunogenic complexes comprising a SPP2 protein and a capsular polysaccharide, from or derived from *S. pneumoniae* serotype 23B, wherein the average ratio of SPP2 protein to capsular polysaccharide from or derived from *S. pneumoniae* serotype 23B in the plurality of immunogenic complexes is between about 2.9:1 and about 3.1:1 (w/w);

(7) a plurality of immunogenic complexes comprising a SPP2 protein and a capsular polysaccharide, from or derived from *S. pneumoniae* serotype 24F, wherein the average ratio of SPP2 protein to capsular polysaccharide from or derived from *S. pneumoniae* serotype 24F in the plurality of immunogenic complexes is between about 2.9:1 and about 3.1:1 (w/w);

(8) a plurality of immunogenic complexes comprising a SPP2 protein and a capsular polysaccharide, from or derived from *S. pneumoniae* serotype 31, wherein the average ratio of SPP2 protein to capsular polysaccharide from or derived from *S. pneumoniae* serotype 31 in the (9) a plurality of immunogenic complexes comprising a SPP2 protein and a capsular polysaccharide, from or derived from *S. pneumoniae* serotype 35B, wherein the average ratio of SPP2 protein to capsular polysaccharide from or derived from *S. pneumoniae* serotype 35B in the plurality of immunogenic complexes is between about 2.9:1 and about 3.1:1 (w/w);

(10) a plurality of immunogenic complexes comprising a SPP2 protein and a capsular polysaccharide, from or derived from *S. pneumoniae* serotype 38, wherein the average ratio of SPP2 protein to capsular polysaccharide from or derived from *S. pneumoniae* serotype 38 in the plurality of immunogenic complexes is between about 2.9:1 and about 3.1:1 (w/w);

(11) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.9:1 and about 3.1:1 (w/w);

(12) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.9:1 and about 3.1:1 (w/w);

(13) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.9:1 and about 3.1:1 (w/w);

(14) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.9:1 and about 3.1:1 (w/w);

(15) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the

(16) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.9:1 and about 3.1:1 (w/w);

(17) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.9:1 and about 3.1:1 (w/w);

(18) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.9:1 and about 3.1:1 (w/w);

(19) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.9:1 and about 3.1:1 (w/w);

(20) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.9:1 and about 3.1:1 (w/w);

(21) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.9:1 and about 3.1:1 (w/w);

(22) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the

(23) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.9:1 and about 3.1:1 (w/w);

(24) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.9:1 and about 3.1:1 (w/w);

(25) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.9:1 and about 3.1:1 (w/w);

(26) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is between about 2.9:1 and about 3.1:1 (w/w);

(27) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.9:1 and about 3.1:1 (w/w);

(28) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.9:1 and about 3.1:1 (w/w);

(29) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the

(30) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.9:1 and about 3.1:1 (w/w);

(31) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.9:1 and about 3.1:1 (w/w);

(32) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.9:1 and about 3.1:1 (w/w);

(33) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.9:1 and about 3.1:1 (w/w); and

(34) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.9:1 and about 3.1:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is between about 2.9:1 and about 3.1:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is between about 2.9:1 and about 3.1:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is between about 2.9:1 and about 3.1:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is between about 2.9:1 and about 3.1:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is between about 2.9:1 and about 3.1:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is between about 2.9:1 and about 3.1:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is between about 2.9:1 and about 3.1:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is between about 2.9:1 and about 3.1:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is between about 2.9:1 and about 3.1:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is between about 2.9:1 and about 3.1:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.9:1 and about 3.1:1 (w/w);

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.9:1 and about 3.1:1 (w/w);

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.9:1 and about 3.1:1 (w/w);

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.9:1 and about 3.1:1 (w/w);

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.9:1 and about 3.1:1 (w/w);

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.9:1 and about 3.1:1 (w/w);

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.9:1 and about 3.1:1 (w/w);

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.9:1 and about 3.1:1 (w/w);

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.9:1 and about 3.1:1 (w/w);

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.9:1 and about 3.1:1 (w/w);

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.9:1 and about 3.1:1 (w/w);

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.9:1 and about 3.1:1 (w/w);

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is between about 2.9:1 and about 3.1:1 (w/w);

(24) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is between about 2.9:1 and about 3.1:1 (w/w);

(25) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.9:1 and about 3.1:1 (w/w);

(26) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.9:1 and about 3.1:1 (w/w);

(27) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.9:1 and about 3.1:1 (w/w);

(28) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.9:1 and about 3.1:1 (w/w);

(29) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.9:1 and about 3.1:1 (w/w);

(30) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.9:1 and about 3.1:1 (w/w);

(31) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is between about 2.9:1 and about 3.1:1 (w/w);

(32) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.9:1 and about 3.1:1 (w/w);

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is between about 2.9:1 and about 3.1:1 (w/w); and

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.9:1 and about 3.1:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is between about 2.9:1 and about 3.1:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the (3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is between about 2.9:1 and about 3.1:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is between about 2.9:1 and about 3.1:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is between about 2.9:1 and about 3.1:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is between about 2.9:1 and about 3.1:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is between about 2.9:1 and about 3.1:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is between about 2.9:1 and about 3.1:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is between about 2.9:1 and about 3.1:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.9:1 and about 3.1:1 (w/w);

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.9:1 and about 3.1:1 (w/w);

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.9:1 and about 3.1:1 (w/w);

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.9:1 and about 3.1:1 (w/w);

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.9:1 and about 3.1:1 (w/w);

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.9:1 and about 3.1:1 (w/w);

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.9:1 and about 3.1:1 (w/w);

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.9:1 and about 3.1:1 (w/w);

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.9:1 and about 3.1:1 (w/w);

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.9:1 and about 3.1:1 (w/w);

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.9:1 and about 3.1:1 (w/w);

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.9:1 and about 3.1:1 (w/w);

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.9:1 and about 3.1:1 (w/w);

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.9:1 and about 3.1:1 (w/w);

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.9:1 and about 3.1:1 (w/w);

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.9:1 and about 3.1:1 (w/w);

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.9:1 and about 3.1:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.9:1 and about 3.1:1 (w/w);

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is between about 2.9:1 and about 3.1:1 (w/w); and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.9:1 and about 3.1:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is between about 2.9:1 and about 3.1:1 (w/w);

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is between about 2.9:1 and about 3.1:1 (w/w);

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is between about 2.9:1 and about 3.1:1 (w/w);

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is between about 2.9:1 and about 3.1:1 (w/w);

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is between about 2.9:1 and about 3.1:1 (w/w);

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is between about 2.9:1 and about 3.1:1 (w/w);

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is between about 2.9:1 and about 3.1:1 (w/w);

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is between about 2.9:1 and about 3.1:1 (w/w);

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is between about 2.9:1 and about 3.1:1 (w/w);

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is between about 2.9:1 and about 3.1:1 (w/w);

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.9:1 and about 3.1:1 (w/w);

(12) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.9:1 and about 3.1:1 (w/w);

(13) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.9:1 and about 3.1:1 (w/w);

(14) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.9:1 and about 3.1:1 (w/w);

(15) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.9:1 and about 3.1:1 (w/w);

(16) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.9:1 and about 3.1:1 (w/w);

(17) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.9:1 and about 3.1:1 (w/w);

(18) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.9:1 and about 3.1:1 (w/w);

(19) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.9:1 and about 3.1:1 (w/w);

(20) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.9:1 and about 3.1:1 (w/w);

(21) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.9:1 and about 3.1:1 (w/w);

(22) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is between about 2.9:1 and about 3.1:1 (w/w);

(23) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is between about 2.9:1 and about 3.1:1 (w/w);

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.9:1 and about 3.1:1 (w/w);

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.9:1 and about 3.1:1 (w/w);

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.9:1 and about 3.1:1 (w/w);

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.9:1 and about 3.1:1 (w/w);

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.9:1 and about 3.1:1 (w/w);

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.9:1 and about 3.1:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is between about 2.9:1 and about 3.1:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.9:1 and about 3.1:1 (w/w);

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is between about 2.9:1 and about 3.1:1 (w/w); and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.9:1 and about 3.1:1 (w/w).

In some embodiments, an immunogenic composition (e.g., a vaccine) comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.9:1 and about 3.1:1 (w/w);

(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.9:1 and about 3.1:1 (w/w);

(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.9:1 and about 3.1:1 (w/w);

(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.9:1 and about 3.1:1 (w/w);

(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the (6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.9:1 and about 3.1:1 (w/w);

(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.9:1 and about 3.1:1 (w/w);

(8) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is between about 2.9:1 and about 3.1:1 (w/w);

(9) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is between about 2.9:1 and about 3.1:1 (w/w);

(10) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.9:1 and about 3.1:1 (w/w);

(11) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.9:1 and about 3.1:1 (w/w);

(12) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the

(13) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.9:1 and about 3.1:1 (w/w);

(14) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.9:1 and about 3.1:1 (w/w);

(15) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.9:1 and about 3.1:1 (w/w);

(16) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.9:1 and about 3.1:1 (w/w);

(17) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.9:1 and about 3.1:1 (w/w);

(18) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is between about 2.9:1 and about 3.1:1 (w/w);

(19) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the

(20) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is between about 2.9:1 and about 3.1:1 (w/w);

(21) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.9:1 and about 3.1:1 (w/w);

(22) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.9:1 and about 3.1:1 (w/w);

(23) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is between about 2.9:1 and about 3.1:1 (w/w);

(24) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.9:1 and about 3.1:1 (w/w);

(25) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.9:1 and about 3.1:1 (w/w);

(26) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the

(27) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is between about 2.9:1 and about 3.1:1 (w/w);

(28) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is between about 2.9:1 and about 3.1:1 (w/w);

(29) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.9:1 and about 3.1:1 (w/w);

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is between about 2.9:1 and about 3.1:1 (w/w);

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is between about 2.9:1 and about 3.1:1 (w/w);

(32) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.9:1 and about 3.1:1 (w/w);

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is between about 2.9:1 and about 3.1:1 (w/w).

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 6C, wherein the average ratio of SPP2 protein to capsular polysaccharide from or derived from *S. pneumoniae* serotype 6C in the plurality of immunogenic complexes is about 3:1;

(2) a plurality of immunogenic complexes comprising a SPP2 protein and a capsular polysaccharide, from or derived from *S. pneumoniae* serotype 7C, wherein the average ratio of SPP2 protein to capsular polysaccharide from or derived from *S. pneumoniae* serotype 7C in the plurality of immunogenic complexes is about 3:1;

(3) a plurality of immunogenic complexes comprising a SPP2 protein and a capsular polysaccharide, from or derived from *S. pneumoniae* serotype 15A, wherein the average ratio of SPP2 protein to capsular polysaccharide from or derived from *S. pneumoniae* serotype 15A in the plurality of immunogenic complexes is about 3:1;

(4) a plurality of immunogenic complexes comprising a SPP2 protein and a capsular polysaccharide, from or derived from *S. pneumoniae* serotype 16F, wherein the average ratio of SPP2 protein to capsular polysaccharide from or derived from *S. pneumoniae* serotype 16F in the plurality of immunogenic complexes is about 3:1;

(5) a plurality of immunogenic complexes comprising a SPP2 protein and a capsular polysaccharide, from or derived from *S. pneumoniae* serotype 23A, wherein the average ratio of SPP2 protein to capsular polysaccharide from or derived from *S. pneumoniae* serotype 23A in the plurality of immunogenic complexes is about 3:1;

(6) a plurality of immunogenic complexes comprising a SPP2 protein and a capsular polysaccharide, from or derived from *S. pneumoniae* serotype 23B, wherein the average ratio of SPP2 protein to capsular polysaccharide from or derived from *S. pneumoniae* serotype 23B in the plurality of immunogenic complexes is about 3:1;

(7) a plurality of immunogenic complexes comprising a SPP2 protein and a capsular polysaccharide, from or derived from *S. pneumoniae* serotype 24F, wherein the average ratio of SPP2 protein to capsular polysaccharide from or derived from *S. pneumoniae* serotype 24F in the plurality of immunogenic complexes is about 3:1;

(8) a plurality of immunogenic complexes comprising a SPP2 protein and a capsular polysaccharide, from or derived from *S. pneumoniae* serotype 31, wherein the average ratio of SPP2 protein to capsular polysaccharide from or derived from *S. pneumoniae* serotype 31 in the plurality of immunogenic complexes is about 3:1;

(9) a plurality of immunogenic complexes comprising a SPP2 protein and a capsular polysaccharide, from or derived from *S. pneumoniae* serotype 35B, wherein the average ratio of SPP2 protein to capsular polysaccharide from or derived from *S. pneumoniae* serotype 35B in the plurality of immunogenic complexes is about 3:1;

(10) a plurality of immunogenic complexes comprising a SPP2 protein and a capsular polysaccharide, from or derived from *S. pneumoniae* serotype 38, wherein the average ratio of SPP2 protein to capsular polysaccharide from or derived from *S. pneumoniae* serotype 38 in the plurality of immunogenic complexes is about 3:1;

(11) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is about 3:1;

(12) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is about 3:1;

(13) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is about 3:1;

(14) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is about 3:1;

(15) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is about 3:1;

(16) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is about 3:1;

(17) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is about 3:1;

(18) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is about 3:1;

(19) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is about 3:1;

(20) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is about 3:1;

(21) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is about 3:1;

(22) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is about 3:1;

(23) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is about 3:1;

(24) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is about 3:1;

(25) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is about 3:1;

(26) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is about 3:1;

(27) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is about 3:1;

(28) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is about 3:1;

(29) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is about 3:1;

(30) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is about 3:1;

(31) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is about 3:1;

(32) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is about 3:1;

(33) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is about 3:1; and

(34) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is about 3:1.

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is about 3:1;

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is about 3:1;

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is about 3:1;

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is about 3:1;

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is about 3:1;

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is about 3:1;

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is about 3:1;

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is about 3:1;

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is about 3:1;

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is about 3:1;

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is about 3:1;

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is about 3:1;

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is about 3:1;

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is about 3:1;

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is about 3:1;

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is about 3:1;

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is about 3:1;

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is about 3:1;

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is about 3:1;

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is about 3:1;

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is about 3:1;

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is about 3:1;

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is about 3:1;

(24) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is about 3:1;

(25) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is about 3:1;

(26) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is about 3:1;

(27) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is about 3:1;

(28) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is about 3:1;

(29) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is about 3:1;

(30) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is about 3:1;

(31) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is about 3:1;

(32) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is about 3:1;

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is about 3:1; and

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is about 3:1.

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is about 3:1;

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is about 3:1;

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is about 3:1;

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is about 3:1;

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is about 3:1;

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is about 3:1;

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is about 3:1;

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is about 3:1;

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is about 3:1;

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is about 3:1;

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is about 3:1;

(12) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is about 3:1;

(13) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is about 3:1;

(14) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is about 3:1;

(15) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is about 3:1;

(16) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is about 3:1;

(17) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is about 3:1;

(18) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is about 3:1;

(19) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is about 3:1;

(20) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is about 3:1;

(21) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is about 3:1;

(22) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is about 3:1;

(23) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is about 3:1;

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is about 3:1;

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is about 3:1;

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is about 3:1;

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is about 3:1;

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is about 3:1;

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is about 3:1;

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is about 3:1;

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is about 3:1;

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is about 3:1; and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is about 3:1.

In some embodiments, an immunogenic composition (e.g., a vaccine) comprises:

(1) a plurality of immunogenic complexes comprising a SPP2 protein and a capsular polysaccharide, from or derived from *S. pneumoniae* serotype 1, wherein the average ratio of SPP2 protein to capsular polysaccharide from or derived from *S. pneumoniae* serotype 1 in the plurality of immunogenic complexes is about 3:1;

(2) a plurality of immunogenic complexes comprising a SPP2 protein and a capsular polysaccharide, from or derived from *S. pneumoniae* serotype 4, wherein the average ratio of SPP2 protein to capsular polysaccharide from or derived from *S. pneumoniae* serotype 4 in the plurality of immunogenic complexes is about 3:1;

(3) a plurality of immunogenic complexes comprising a SPP2 protein and a capsular polysaccharide, from or derived from *S. pneumoniae* serotype 6A, wherein the average ratio of SPP2 protein to capsular polysaccharide from or derived from *S. pneumoniae* serotype 6A in the plurality of immunogenic complexes is about 3:1;

(4) a plurality of immunogenic complexes comprising a SPP2 protein and a capsular polysaccharide, from or derived from *S. pneumoniae* serotype 6B, wherein the average ratio of SPP2 protein to capsular polysaccharide from or derived from *S. pneumoniae* serotype 6B in the plurality of immunogenic complexes is about 3:1;

(5) a plurality of immunogenic complexes comprising a SPP2 protein and a capsular polysaccharide, from or derived from *S. pneumoniae* serotype 9V, wherein the average ratio of SPP2 protein to capsular polysaccharide from or derived from *S. pneumoniae* serotype 9V in the plurality of immunogenic complexes is about 3:1;

(6) a plurality of immunogenic complexes comprising a SPP2 protein and a capsular polysaccharide, from or derived from *S. pneumoniae* serotype 15B, wherein the average ratio of SPP2 protein to capsular polysaccharide from or derived from *S. pneumoniae* serotype 15B in the plurality of immunogenic complexes is about 3:1;

(7) a plurality of immunogenic complexes comprising a SPP2 protein and a capsular polysaccharide, from or derived from *S. pneumoniae* serotype 18C, wherein the average ratio of SPP2 protein to capsular polysaccharide from or derived from *S. pneumoniae* serotype 18C in the plurality of immunogenic complexes is about 3:1;

(8) a plurality of immunogenic complexes comprising a SPP2 protein and a capsular polysaccharide, from or derived from *S. pneumoniae* serotype 19A, wherein the average ratio of SPP2 protein to capsular polysaccharide from or derived from *S. pneumoniae* serotype 19A in the plurality of immunogenic complexes is about 3:1;

(9) a plurality of immunogenic complexes comprising a SPP2 protein and a capsular polysaccharide, from or derived from *S. pneumoniae* serotype 23F, wherein the average ratio of SPP2 protein to capsular polysaccharide from or derived from *S. pneumoniae* serotype 23F in the plurality of immunogenic complexes is about 3:1;

(10) a plurality of immunogenic complexes comprising a SPP2 protein and a capsular polysaccharide, from or derived from *S. pneumoniae* serotype 33F, wherein the average ratio of SPP2 protein to capsular polysaccharide from or derived from *S. pneumoniae* serotype 33F in the plurality of immunogenic complexes is about 3:1;

(11) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is about 3:1;

(12) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is about 3:1;

(13) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is about 3:1;

(14) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is about 3:1;

(15) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is about 3:1;

(16) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is about 3:1;

(17) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is about 3:1;

(18) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is about 3:1;

(19) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is about 3:1;

(20) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is about 3:1;

(21) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is about 3:1;

(22) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is about 3:1;

(23) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is about 3:1;

(24) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is about 3:1;

(25) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is about 3:1;

(26) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is about 3:1;

(27) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is about 3:1;

(28) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is about 3:1;

(29) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is about 3:1;

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is about 3:1;

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is about 3:1;

(32) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is about 3:1; and

(33) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is about 3:1.

In some embodiments, an immunogenic composition (e.g., a vaccine) comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is about 3:1;

(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is about 3:1;

(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is about 3:1;

(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is about 3:1;

(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is about 3:1;

(6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is about 3:1;

(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is about 3:1;

(8) a plurality of immunogenic complexes comprising a CP1 protein and a capsular polysaccharide, from or derived from *S. pneumoniae* serotype 6C, wherein the average ratio of CP1 protein to capsular polysaccharide from or derived from *S. pneumoniae* serotype 6C in the plurality of immunogenic complexes is about 3:1;

(9) a plurality of immunogenic complexes comprising a CP1 protein and a capsular polysaccharide, from or derived from *S. pneumoniae* serotype 7C, wherein the average ratio of CP1 protein to capsular polysaccharide from or derived from *S. pneumoniae* serotype 7C in the plurality of immunogenic complexes is about 3:1;

(10) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is about 3:1;

(11) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is about 3:1;

(12) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is about 3:1;

(13) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is about 3:1;

(14) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is about 3:1;

(15) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is about 3:1;

(16) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is about 3:1;

(17) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is about 3:1;

(18) a plurality of immunogenic complexes comprising a CP1 protein and a capsular polysaccharide, from or derived from *S. pneumoniae* serotype 15A, wherein the average ratio of CP1 protein to capsular polysaccharide from or derived from *S. pneumoniae* serotype 15A in the plurality of immunogenic complexes is about 3:1;

(19) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is about 3:1;

(29) a plurality of immunogenic complexes comprising a CP1 protein and a capsular polysaccharide, from or derived from *S. pneumoniae* serotype 16F, wherein the average ratio of CP1 protein to capsular polysaccharide from or derived from *S. pneumoniae* serotype 16F in the plurality of immunogenic complexes is about 3:1;

(21) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is about 3:1;

(22) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is about 3:1;

(23) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is about 3:1;

(24) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is about 3:1;

(25) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is about 3:1;

(26) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is about 3:1;

(27) a plurality of immunogenic complexes comprising a CP1 protein and a capsular polysaccharide, from or derived from *S. pneumoniae* serotype 23A, wherein the average ratio of CP1 protein to capsular polysaccharide from or derived from *S. pneumoniae* serotype 23A in the plurality of immunogenic complexes is about 3:1;

(28) a plurality of immunogenic complexes comprising a CP1 protein and a capsular polysaccharide, from or derived from *S. pneumoniae* serotype 23B, wherein the average ratio of CP1 protein to capsular polysaccharide from or derived from *S. pneumoniae* serotype 23B in the plurality of immunogenic complexes is about 3:1;

(29) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is about 3:1;

(30) a plurality of immunogenic complexes comprising a CP1 protein and a capsular polysaccharide, from or derived from *S. pneumoniae* serotype 24F, wherein the average ratio of CP1 protein to capsular polysaccharide from or derived from *S. pneumoniae* serotype 24F in the plurality of immunogenic complexes is about 3:1;

(31) a plurality of immunogenic complexes comprising a CP1 protein and a capsular polysaccharide, from or derived from *S. pneumoniae* serotype 31, wherein the average ratio of CP1 protein to capsular polysaccharide from or derived from *S. pneumoniae* serotype 31 in the plurality of immunogenic complexes is about 3:1;

(32) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is about 3:1;

(33) a plurality of immunogenic complexes comprising a CP1 protein and a capsular polysaccharide, from or derived from *S. pneumoniae* serotype 35B, wherein the average ratio of CP1 protein to capsular polysaccharide from or derived from *S. pneumoniae* serotype 35B in the plurality of immunogenic complexes is about 3:1; and

(34) a plurality of immunogenic complexes comprising a CP1 protein and a capsular polysaccharide, from or derived from *S. pneumoniae* serotype 38, wherein the average ratio of CP1 protein to capsular polysaccharide from or derived from *S. pneumoniae* serotype 38 in the plurality of immunogenic complexes is about 3:1.

Immunogenic Compositions (e.g., Vaccines)

Another aspect of the disclosure provides compositions that include one or more immunogenic complexes described herein. For example, an immunogenic composition, e.g., vaccine composition, can include one or more immunogenic complexes described herein. In some embodiments, such compositions can include a plurality of one type or species of immunogenic complex described herein. For example, a composition can include a population of one type or species of immunogenic complex, where all of the immunogenic complexes include the same antigenic polypeptide and the same antigenic polysaccharide. Additionally or alternatively, such compositions can include a plurality of more than one type or species of immunogenic complex described herein. For example, a composition can include populations of different types or species of immunogenic complexes. In some embodiments, a composition can include a population of a first type or species of immunogenic complex and a population of a second type or species of immunogenic complex, where the first type or species and the second type or species of the immunogenic complex have different antigenic polypeptides and/or different antigenic polysaccharides. In some embodiments, a composition can include a population of a first type or species of immunogenic complex and a population of a second type or species of immunogenic complex, where the first type and the second type or species of the immunogenic complex include different antigenic polypeptides and different antigenic polysaccharides (e.g., polysaccharides of different serotypes). In some embodiments, a composition can include a population of a first type or species of immunogenic complex and a population of a second type or species of immunogenic complex, where the first type and the second type or species of the immunogenic complex include the same antigenic polypeptide and different antigenic polysaccharides (e.g., polysaccharides of different serotypes). In some embodiments, immunogenic complexes described herein are formulated into a pharmaceutical composition. In some embodiments, a pharmaceutical composition may be a vaccine. In some embodiments, a pharmaceutical composition comprises a pharmaceutically acceptable carrier. In some embodiments, a pharmaceutical composition comprises an adjuvant.

In some embodiments, an immunogenic composition comprises one or more (e.g., 1, 2, 3, 4, 5, 6, 7, 8, 9, 10, 15, 20, 25, 30, 40, 50, or more) species of immunogenic complexes selected from:

(1) an immunogenic complex comprising a biotinylated *S. pneumoniae* serotype 1 capsular polysaccharide, and one or more CP1 or SPP2 fusion proteins non-covalently complexed to the biotinylated polysaccharide;

(2) an immunogenic complex comprising a biotinylated *S. pneumoniae* serotype 2 capsular polysaccharide, and one or more CP1 or SPP2 fusion proteins non-covalently complexed to the biotinylated polysaccharide;

(3) an immunogenic complex comprising a biotinylated *S. pneumoniae* serotype 3 capsular polysaccharide, and one or more CP1 or SPP2 fusion proteins non-covalently complexed to the biotinylated polysaccharide;

(4) an immunogenic complex comprising a biotinylated *S. pneumoniae* serotype 4 capsular (5) an immunogenic complex comprising a biotinylated *S. pneumoniae* serotype 5 capsular polysaccharide, and one or more CP1 SPP2 fusion proteins non-covalently complexed to the biotinylated polysaccharide;

(6) an immunogenic complex comprising a biotinylated *S. pneumoniae* serotype 6A capsular polysaccharide, and one or more CP1 or SPP2 fusion proteins non-covalently complexed to the biotinylated polysaccharide;

(7) an immunogenic complex comprising a biotinylated *S. pneumoniae* serotype 6B capsular polysaccharide, and one or more or SPP2 fusion proteins non-covalently complexed to the biotinylated polysaccharide;

(8) an immunogenic complex comprising a biotinylated *S. pneumoniae* serotype 6C capsular polysaccharide, and one or more CP1 or SPP2 fusion proteins non-covalently complexed to the biotinylated polysaccharide;

(9) an immunogenic complex comprising a biotinylated *S. pneumoniae* serotype 6D capsular polysaccharide, and one or more CP1 or SPP2 fusion proteins non-covalently complexed to the biotinylated polysaccharide;

(10) an immunogenic complex comprising a biotinylated *S. pneumoniae* serotype 6E capsular polysaccharide, and one or more CP1 or SPP2 fusion proteins non-covalently complexed to the biotinylated polysaccharide;

(11) an immunogenic complex comprising a biotinylated *S. pneumoniae* serotype 6F capsular polysaccharide, and one or more CP1 or SPP2 fusion proteins non-covalently complexed to the biotinylated polysaccharide;

(12) an immunogenic complex comprising a biotinylated *S. pneumoniae* serotype 6G capsular polysaccharide, and one or more CP1 or SPP2 fusion proteins non-covalently complexed to the biotinylated polysaccharide;

(13) an immunogenic complex comprising a biotinylated *S. pneumoniae* serotype 6H capsular

(14) an immunogenic complex comprising a biotinylated *S. pneumoniae* serotype 7A capsular polysaccharide, and one or more CP1 or SPP2 fusion proteins non-covalently complexed to the biotinylated polysaccharide;

(15) an immunogenic complex comprising a biotinylated *S. pneumoniae* serotype 7B capsular polysaccharide, and one or more CP1 or SPP2 fusion proteins non-covalently complexed to the biotinylated polysaccharide;

(16) an immunogenic complex comprising a biotinylated *S. pneumoniae* serotype 7C capsular polysaccharide, and one or more CP1 or SPP2 fusion proteins non-covalently complexed to the biotinylated polysaccharide;

(17) an immunogenic complex comprising a biotinylated *S. pneumoniae* serotype 7F capsular polysaccharide, and one or more CP1 or SPP2 fusion proteins non-covalently complexed to the biotinylated polysaccharide;

(18) an immunogenic complex comprising a biotinylated *S. pneumoniae* serotype 8 capsular polysaccharide, and one or more CP1 or SPP2 fusion proteins non-covalently complexed to the biotinylated polysaccharide;

(19) an immunogenic complex comprising a biotinylated *S. pneumoniae* serotype 9A capsular polysaccharide, and one or more CP1 or SPP2 fusion proteins non-covalently complexed to the biotinylated polysaccharide;

(20) an immunogenic complex comprising a biotinylated *S. pneumoniae* serotype 9L capsular polysaccharide, and one or more CP1 or SPP2 fusion proteins non-covalently complexed to the biotinylated polysaccharide;

(21) an immunogenic complex comprising a biotinylated *S. pneumoniae* serotype 9N capsular polysaccharide, and one or more CP1 or SPP2 fusion proteins non-covalently complexed to the biotinylated polysaccharide;

(22) an immunogenic complex comprising a biotinylated *S. pneumoniae* serotype 9V capsular

(23) an immunogenic complex comprising a biotinylated *S. pneumoniae* serotype 10A capsular polysaccharide, and one or more CP1 or SPP2 fusion proteins non-covalently complexed to the biotinylated polysaccharide;

(24) an immunogenic complex comprising a biotinylated *S. pneumoniae* serotype 10B capsular polysaccharide, and one or more CP1 or SPP2 fusion proteins non-covalently complexed to the biotinylated polysaccharide;

(25) an immunogenic complex comprising a biotinylated *S. pneumoniae* serotype 10C capsular polysaccharide, and one or more CP1 or SPP2 fusion proteins non-covalently complexed to the biotinylated polysaccharide;

(26) an immunogenic complex comprising a biotinylated *S. pneumoniae* serotype 10F capsular polysaccharide, and one or more CP1 or SPP2 fusion proteins non-covalently complexed to the biotinylated polysaccharide;

(27) an immunogenic complex comprising a biotinylated *S. pneumoniae* serotype 11A capsular polysaccharide, and one or more CP1 or SPP2 fusion proteins non-covalently complexed to the biotinylated polysaccharide;

(28) an immunogenic complex comprising a biotinylated *S. pneumoniae* serotype 11B capsular polysaccharide, and one or more CP1 or SPP2 fusion proteins non-covalently complexed to the biotinylated polysaccharide;

(29) an immunogenic complex comprising a biotinylated *S. pneumoniae* serotype 11C capsular polysaccharide, and one or more CP1 or SPP2 fusion proteins non-covalently complexed to the biotinylated polysaccharide;

(30) an immunogenic complex comprising a biotinylated *S. pneumoniae* serotype 11D capsular polysaccharide, and one or more CP1 or SPP2 fusion proteins non-covalently complexed to the biotinylated polysaccharide;

(31) an immunogenic complex comprising a biotinylated *S. pneumoniae* serotype 11E

(32) an immunogenic complex comprising a biotinylated *S. pneumoniae* serotype 11F capsular polysaccharide, and one or more CP1 or SPP2 fusion proteins non-covalently complexed to the biotinylated polysaccharide;

(33) an immunogenic complex comprising a biotinylated *S. pneumoniae* serotype 12A capsular polysaccharide, and one or more CP1 or SPP2 fusion proteins non-covalently complexed to the biotinylated polysaccharide;

(34) an immunogenic complex comprising a biotinylated *S. pneumoniae* serotype 12B capsular polysaccharide, and one or more CP1 or SPP2 fusion proteins non-covalently complexed to the biotinylated polysaccharide;

(35) an immunogenic complex comprising a biotinylated *S. pneumoniae* serotype 12F capsular polysaccharide, and one or more CP1 or SPP2 fusion proteins non-covalently complexed to the biotinylated polysaccharide;

(36) an immunogenic complex comprising a biotinylated *S. pneumoniae* serotype 13 capsular polysaccharide, and one or more CP1 or SPP2 fusion proteins non-covalently complexed to the biotinylated polysaccharide;

(37) an immunogenic complex comprising a biotinylated *S. pneumoniae* serotype 14 capsular polysaccharide, and one or more CP1 or SPP2 fusion proteins non-covalently complexed to the biotinylated polysaccharide;

(38) an immunogenic complex comprising a biotinylated *S. pneumoniae* serotype 15A capsular polysaccharide, and one or more CP1 or SPP2 fusion proteins non-covalently complexed to the biotinylated polysaccharide;

(39) an immunogenic complex comprising a biotinylated *S. pneumoniae* serotype 15B capsular polysaccharide, and one or more CP1 or SPP2 fusion proteins non-covalently complexed to the biotinylated polysaccharide;

(40) an immunogenic complex comprising a biotinylated *S. pneumoniae* serotype 15C

(41) an immunogenic complex comprising a biotinylated *S. pneumoniae* serotype 15F capsular polysaccharide, and one or more CP1 or SPP2 fusion proteins non-covalently complexed to the biotinylated polysaccharide;

(42) an immunogenic complex comprising a biotinylated *S. pneumoniae* serotype 16A capsular polysaccharide, and one or more CP1 or SPP2 fusion proteins non-covalently complexed to the biotinylated polysaccharide;

(43) an immunogenic complex comprising a biotinylated *S. pneumoniae* serotype 16F capsular polysaccharide, and one or more CP1 or SPP2 fusion proteins non-covalently complexed to the biotinylated polysaccharide;

(44) an immunogenic complex comprising a biotinylated *S. pneumoniae* serotype 17A capsular polysaccharide, and one or more CP1 or SPP2 fusion proteins non-covalently complexed to the biotinylated polysaccharide;

(45) an immunogenic complex comprising a biotinylated *S. pneumoniae* serotype 17F capsular polysaccharide, and one or more CP1 or SPP2 fusion proteins non-covalently complexed to the biotinylated polysaccharide;

(46) an immunogenic complex comprising a biotinylated *S. pneumoniae* serotype 18A capsular polysaccharide, and one or more CP1 or SPP2 fusion proteins non-covalently complexed to the biotinylated polysaccharide;

(47) an immunogenic complex comprising a biotinylated *S. pneumoniae* serotype 18B capsular polysaccharide, and one or more CP1 or SPP2 fusion proteins non-covalently complexed to the biotinylated polysaccharide;

(48) an immunogenic complex comprising a biotinylated *S. pneumoniae* serotype 18C capsular polysaccharide, and one or more CP1 or SPP2 fusion proteins non-covalently complexed to the biotinylated polysaccharide;

(49) an immunogenic complex comprising a biotinylated *S. pneumoniae* serotype 18F

(50) an immunogenic complex comprising a biotinylated *S. pneumoniae* serotype 19A capsular polysaccharide, and one or more CP1 SPP2 fusion proteins non-covalently complexed to the biotinylated polysaccharide;

(51) an immunogenic complex comprising a biotinylated *S. pneumoniae* serotype 19B capsular polysaccharide, and one or more CP1 or SPP2 fusion proteins non-covalently complexed to the biotinylated polysaccharide;

(52) an immunogenic complex comprising a biotinylated *S. pneumoniae* serotype 19C capsular polysaccharide, and one or more CP1 or SPP2 fusion proteins non-covalently complexed to the biotinylated polysaccharide;

(53) an immunogenic complex comprising a biotinylated *S. pneumoniae* serotype 19F capsular polysaccharide, and one or more CP1 or SPP2 fusion proteins non-covalently complexed to the biotinylated polysaccharide;

(54) an immunogenic complex comprising a biotinylated *S. pneumoniae* serotype 20A capsular polysaccharide, and one or more CP1 or SPP2 fusion proteins non-covalently complexed to the biotinylated polysaccharide;

(55) an immunogenic complex comprising a biotinylated *S. pneumoniae* serotype 20B capsular polysaccharide, and one or more CP1 or SPP2 fusion proteins non-covalently complexed to the biotinylated polysaccharide;

(56) an immunogenic complex comprising a biotinylated *S. pneumoniae* serotype 21 capsular polysaccharide, and one or more CP1 or SPP2 fusion proteins non-covalently complexed to the biotinylated polysaccharide;

(57) an immunogenic complex comprising a biotinylated *S. pneumoniae* serotype 22A capsular polysaccharide, and one or more CP1 or SPP2 fusion proteins non-covalently complexed to the biotinylated polysaccharide;

(58) an immunogenic complex comprising a biotinylated *S. pneumoniae* serotype 22F

(59) an immunogenic complex comprising a biotinylated *S. pneumoniae* serotype 23A capsular polysaccharide, and one or more CP1 or SPP2 fusion proteins non-covalently complexed to the biotinylated polysaccharide;

(60) an immunogenic complex comprising a biotinylated *S. pneumoniae* serotype 23B capsular polysaccharide, and one or more CP1 or SPP2 fusion proteins non-covalently complexed to the biotinylated polysaccharide;

(61) an immunogenic complex comprising a biotinylated *S. pneumoniae* serotype 23F capsular polysaccharide, and one or more CP1 or SPP2 fusion proteins non-covalently complexed to the biotinylated polysaccharide;

(62) an immunogenic complex comprising a biotinylated *S. pneumoniae* serotype 24A capsular polysaccharide, and one or more CP1 or SPP2 fusion proteins non-covalently complexed to the biotinylated polysaccharide;

(63) an immunogenic complex comprising a biotinylated *S. pneumoniae* serotype 24B capsular polysaccharide, and one or more CP1 or SPP2 fusion proteins non-covalently complexed to the biotinylated polysaccharide;

(64) an immunogenic complex comprising a biotinylated *S. pneumoniae* serotype 24F capsular polysaccharide, and one or more CP1 or SPP2 fusion proteins non-covalently complexed to the biotinylated polysaccharide;

(65) an immunogenic complex comprising a biotinylated *S. pneumoniae* serotype 25A capsular polysaccharide, and one or more CP1 or SPP2 fusion proteins non-covalently complexed to the biotinylated polysaccharide;

(66) an immunogenic complex comprising a biotinylated *S. pneumoniae* serotype 25F capsular polysaccharide, and one or more CP1 or SPP2 fusion proteins non-covalently complexed to the biotinylated polysaccharide;

(67) an immunogenic complex comprising a biotinylated *S. pneumoniae* serotype 27 capsular

(68) an immunogenic complex comprising a biotinylated *S. pneumoniae* serotype 28A capsular polysaccharide, and one or more CP1 or SPP2 fusion proteins non-covalently complexed to the biotinylated polysaccharide;

(69) an immunogenic complex comprising a biotinylated *S. pneumoniae* serotype 28F capsular polysaccharide, and one or more CP1 or SPP2 fusion proteins non-covalently complexed to the biotinylated polysaccharide;

(70) an immunogenic complex comprising a biotinylated *S. pneumoniae* serotype 29 capsular polysaccharide, and one or more CP1 or SPP2 fusion proteins non-covalently complexed to the biotinylated polysaccharide;

(71) an immunogenic complex comprising a biotinylated *S. pneumoniae* serotype 31 capsular polysaccharide, and one or more CP1 or SPP2 fusion proteins non-covalently complexed to the biotinylated polysaccharide;

(72) an immunogenic complex comprising a biotinylated *S. pneumoniae* serotype 32A capsular polysaccharide, and one or more CP1 or SPP2 fusion proteins non-covalently complexed to the biotinylated polysaccharide;

(73) an immunogenic complex comprising a biotinylated *S. pneumoniae* serotype 32F capsular polysaccharide, and one or more CP1 or SPP2 fusion proteins non-covalently complexed to the biotinylated polysaccharide;

(74) an immunogenic complex comprising a biotinylated *S. pneumoniae* serotype 33A capsular polysaccharide, and one or more CP1 or SPP2 fusion proteins non-covalently complexed to the biotinylated polysaccharide;

(75) an immunogenic complex comprising a biotinylated *S. pneumoniae* serotype 33B capsular polysaccharide, and one or more CP1 or SPP2 fusion proteins non-covalently complexed to the biotinylated polysaccharide;

(76) an immunogenic complex comprising a biotinylated *S. pneumoniae* serotype 33C

(77) an immunogenic complex comprising a biotinylated *S. pneumoniae* serotype 33D capsular polysaccharide, and one or more CP1 or SPP2 fusion proteins non-covalently complexed to the biotinylated polysaccharide;

(78) an immunogenic complex comprising a biotinylated *S. pneumoniae* serotype 33E capsular polysaccharide, and one or more CP1 or SPP2 fusion proteins non-covalently complexed to the biotinylated polysaccharide;

(79) an immunogenic complex comprising a biotinylated *S. pneumoniae* serotype 33F capsular polysaccharide, and one or more CP1 or SPP2 fusion proteins non-covalently complexed to the biotinylated polysaccharide;

(80) an immunogenic complex comprising a biotinylated *S. pneumoniae* serotype 34 capsular polysaccharide, and one or more CP1 or SPP2 fusion proteins non-covalently complexed to the biotinylated polysaccharide;

(81) an immunogenic complex comprising a biotinylated *S. pneumoniae* serotype 35A capsular polysaccharide, and one or more CP1 or SPP2 fusion proteins non-covalently complexed to the biotinylated polysaccharide;

(82) an immunogenic complex comprising a biotinylated *S. pneumoniae* serotype 35B capsular polysaccharide, and one or more CP1 or SPP2 fusion proteins non-covalently complexed to the biotinylated polysaccharide;

(83) an immunogenic complex comprising a biotinylated *S. pneumoniae* serotype 35C capsular polysaccharide, and one or more CP1 or SPP2 fusion proteins non-covalently complexed to the biotinylated polysaccharide;

(84) an immunogenic complex comprising a biotinylated *S. pneumoniae* serotype 35F capsular polysaccharide, and one or more CP1 or SPP2 fusion proteins non-covalently complexed to the biotinylated polysaccharide;

(85) an immunogenic complex comprising a biotinylated *S. pneumoniae* serotype 36 capsular

(86) an immunogenic complex comprising a biotinylated *S. pneumoniae* serotype 37 capsular polysaccharide, and one or more CP1 or SPP2 fusion proteins non-covalently complexed to the biotinylated polysaccharide;

(87) an immunogenic complex comprising a biotinylated *S. pneumoniae* serotype 38 capsular polysaccharide, and one or more CP1 or SPP2 fusion proteins non-covalently complexed to the biotinylated polysaccharide;

(88) an immunogenic complex comprising a biotinylated *S. pneumoniae* serotype 39 capsular polysaccharide, and one or more CP1 or SPP2 fusion proteins non-covalently complexed to the biotinylated polysaccharide;

(89) an immunogenic complex comprising a biotinylated *S. pneumoniae* serotype 40 capsular polysaccharide, and one or more CP1 or SPP2 fusion proteins non-covalently complexed to the biotinylated polysaccharide;

(90) an immunogenic complex comprising a biotinylated *S. pneumoniae* serotype 41A capsular polysaccharide, and one or more CP1 or SPP2 fusion proteins non-covalently complexed to the biotinylated polysaccharide;

(91) an immunogenic complex comprising a biotinylated *S. pneumoniae* serotype 41F capsular polysaccharide, and one or more CP1 or SPP2 fusion proteins non-covalently complexed to the biotinylated polysaccharide;

(92) an immunogenic complex comprising a biotinylated *S. pneumoniae* serotype 42 capsular polysaccharide, and one or more CP1 or SPP2 fusion proteins non-covalently complexed to the biotinylated polysaccharide;

(93) an immunogenic complex comprising a biotinylated *S. pneumoniae* serotype 43 capsular polysaccharide, and one or more CP1 or SPP2 fusion proteins non-covalently complexed to the biotinylated polysaccharide;

(94) an immunogenic complex comprising a biotinylated *S. pneumoniae* serotype 44 capsular

(95) an immunogenic complex comprising a biotinylated *S. pneumoniae* serotype 45 capsular polysaccharide, and one or more CP1 or SPP2 fusion proteins non-covalently complexed to the biotinylated polysaccharide;

(96) an immunogenic complex comprising a biotinylated *S. pneumoniae* serotype 46 capsular polysaccharide, and one or more CP1 or SPP2 fusion proteins non-covalently complexed to the biotinylated polysaccharide;

(97) an immunogenic complex comprising a biotinylated *S. pneumoniae* serotype 47A capsular polysaccharide, and one or more CP1 or SPP2 fusion proteins non-covalently complexed to the biotinylated polysaccharide;

(98) an immunogenic complex comprising a biotinylated *S. pneumoniae* serotype 47F capsular polysaccharide, and one or more CP1 f or SPP2 fusion proteins non-covalently complexed to the biotinylated polysaccharide; and

(99) an immunogenic complex comprising a biotinylated *S. pneumoniae* serotype 48 capsular polysaccharide, and one or more CP1 or SPP2 fusion proteins non-covalently complexed to the biotinylated polysaccharide.

In some embodiments, an immunogenic composition comprises one or more (e.g., 1, 2, 3, 4, 5, 6, 7, 8, 9, 10, 15, 20, 21, 22, 23, 24, 25, 26, 27, 28, 29, 30, 31, 32, 33, or 34) species of immunogenic complexes selected from:

(1) an immunogenic complex comprising a biotinylated *S. pneumoniae* serotype 1 capsular polysaccharide, and one or more CP1 or SPP2 fusion proteins non-covalently complexed to the biotinylated polysaccharide;

(2) an immunogenic complex comprising a biotinylated *S. pneumoniae* serotype 2 capsular polysaccharide, and one or more CP1 or SPP2 fusion proteins non-covalently complexed to the biotinylated polysaccharide;

(3) an immunogenic complex comprising a biotinylated *S. pneumoniae* serotype 3 capsular (4) an immunogenic complex comprising a biotinylated *S. pneumoniae* serotype 4 capsular polysaccharide, and one or more CP1 or SPP2 fusion proteins non-covalently complexed to the biotinylated polysaccharide;

(5) an immunogenic complex comprising a biotinylated *S. pneumoniae* serotype 5 capsular polysaccharide, and one or more CP1 or SPP2 fusion proteins non-covalently complexed to the biotinylated polysaccharide;

(6) an immunogenic complex comprising a biotinylated *S. pneumoniae* serotype 6A capsular polysaccharide, and one or more CP1 or SPP2 fusion proteins non-covalently complexed to the biotinylated polysaccharide;

(7) an immunogenic complex comprising a biotinylated *S. pneumoniae* serotype 6B capsular polysaccharide, and one or more CP1 or SPP2 fusion proteins non-covalently complexed to the biotinylated polysaccharide;

(8) an immunogenic complex comprising a biotinylated *S. pneumoniae* serotype 6C capsular polysaccharide, and one or more CP1 or SPP2 fusion proteins non-covalently complexed to the biotinylated polysaccharide;

(9) an immunogenic complex comprising a biotinylated *S. pneumoniae* serotype 7C capsular polysaccharide, and one or more CP1 or SPP2 fusion proteins non-covalently complexed to the biotinylated polysaccharide;

(10) an immunogenic complex comprising a biotinylated *S. pneumoniae* serotype 7F capsular polysaccharide, and one or more CP1 or SPP2 fusion proteins non-covalently complexed to the biotinylated polysaccharide;

(11) an immunogenic complex comprising a biotinylated *S. pneumoniae* serotype 8 capsular polysaccharide, and one or more CP1 or SPP2 fusion proteins non-covalently complexed to the biotinylated polysaccharide;

(12) an immunogenic complex comprising a biotinylated *S. pneumoniae* serotype 9N capsular

(13) an immunogenic complex comprising a biotinylated *S. pneumoniae* serotype 9V capsular polysaccharide, and one or more CP1 or SPP2 fusion proteins non-covalently complexed to the biotinylated polysaccharide;

(14) an immunogenic complex comprising a biotinylated *S. pneumoniae* serotype 10A capsular polysaccharide, and one or more CP1 or SPP2 fusion proteins non-covalently complexed to the biotinylated polysaccharide;

(15) an immunogenic complex comprising a biotinylated *S. pneumoniae* serotype 11A capsular polysaccharide, and one or more CP1 or SPP2 fusion proteins non-covalently complexed to the biotinylated polysaccharide;

(16) an immunogenic complex comprising a biotinylated *S. pneumoniae* serotype 12F capsular polysaccharide, and one or more CP1 or SPP2 fusion proteins non-covalently complexed to the biotinylated polysaccharide;

(17) an immunogenic complex comprising a biotinylated *S. pneumoniae* serotype 14 capsular polysaccharide, and one or more CP1 or SPP2 fusion proteins non-covalently complexed to the biotinylated polysaccharide;

(18) an immunogenic complex comprising a biotinylated *S. pneumoniae* serotype 15A capsular polysaccharide, and one or more CP1 or SPP2 fusion proteins non-covalently complexed to the biotinylated polysaccharide;

(19) an immunogenic complex comprising a biotinylated *S. pneumoniae* serotype 15B capsular polysaccharide, and one or more CP1 or SPP2 fusion proteins non-covalently complexed to the biotinylated polysaccharide;

(20) an immunogenic complex comprising a biotinylated *S. pneumoniae* serotype 16F capsular polysaccharide, and one or more CP1 or SPP2 fusion proteins non-covalently complexed to the biotinylated polysaccharide;

(21) an immunogenic complex comprising a biotinylated *S. pneumoniae* serotype 17F

(22) an immunogenic complex comprising a biotinylated *S. pneumoniae* serotype 18C capsular polysaccharide, and one or more CP1 or SPP2 fusion proteins non-covalently complexed to the biotinylated polysaccharide;

(23) an immunogenic complex comprising a biotinylated *S. pneumoniae* serotype 19A capsular polysaccharide, and one or more CP1 or SPP2 fusion proteins non-covalently complexed to the biotinylated polysaccharide;

(24) an immunogenic complex comprising a biotinylated *S. pneumoniae* serotype 19F capsular polysaccharide, and one or more CP1 or SPP2 fusion proteins non-covalently complexed to the biotinylated polysaccharide;

(25) an immunogenic complex comprising a biotinylated *S. pneumoniae* serotype 20B capsular polysaccharide, and one or more CP1 or SPP2 fusion proteins non-covalently complexed to the biotinylated polysaccharide;

(26) an immunogenic complex comprising a biotinylated *S. pneumoniae* serotype 22F capsular polysaccharide, and one or more CP1 or SPP2 fusion proteins non-covalently complexed to the biotinylated polysaccharide;

(27) an immunogenic complex comprising a biotinylated *S. pneumoniae* serotype 23A capsular polysaccharide, and one or more CP1 or SPP2 fusion proteins non-covalently complexed to the biotinylated polysaccharide;

(28) an immunogenic complex comprising a biotinylated *S. pneumoniae* serotype 23B capsular polysaccharide, and one or more CP1 or SPP2 fusion proteins non-covalently complexed to the biotinylated polysaccharide;

(29) an immunogenic complex comprising a biotinylated *S. pneumoniae* serotype 23F capsular polysaccharide, and one or more CP1 or SPP2 fusion proteins non-covalently complexed to the biotinylated polysaccharide;

(30) an immunogenic complex comprising a biotinylated *S. pneumoniae* serotype 24F

(31) an immunogenic complex comprising a biotinylated *S. pneumoniae* serotype 31 capsular polysaccharide, and one or more CP1 or SPP2 fusion proteins non-covalently complexed to the biotinylated polysaccharide;

(32) an immunogenic complex comprising a biotinylated *S. pneumoniae* serotype 33F capsular polysaccharide, and one or more CP1 or SPP2 fusion proteins non-covalently complexed to the biotinylated polysaccharide;

(33) an immunogenic complex comprising a biotinylated *S. pneumoniae* serotype 35B capsular polysaccharide, and one or more CP1 or SPP2 fusion proteins non-covalently complexed to the biotinylated polysaccharide; and

(34) an immunogenic complex comprising a biotinylated *S. pneumoniae* serotype 38 capsular polysaccharide, and one or more CP1 or SPP2 fusion proteins non-covalently complexed to the biotinylated polysaccharide.

In some embodiments, an immunogenic composition comprises one or more (e.g., 1, 2, 3, 4, 5, 6, 7, 8, 9, 10, 15, 20, 21, 22, 23, 24, 25, 26, 27, 28, 29, 30, 31, 32, or 33) species of immunogenic complexes selected from:

(1) an immunogenic complex comprising a biotinylated *S. pneumoniae* serotype 1 capsular polysaccharide, and one or more CP1 or SPP2 fusion proteins non-covalently complexed to the biotinylated polysaccharide;

(2) an immunogenic complex comprising a biotinylated *S. pneumoniae* serotype 2 capsular polysaccharide, and one or more CP1 or SPP2 fusion proteins non-covalently complexed to the biotinylated polysaccharide;

(3) an immunogenic complex comprising a biotinylated *S. pneumoniae* serotype 3 capsular polysaccharide, and one or more CP1 or SPP2 fusion proteins non-covalently complexed to the biotinylated polysaccharide;

(4) an immunogenic complex comprising a biotinylated *S. pneumoniae* serotype 4 capsular (5) an immunogenic complex comprising a biotinylated *S. pneumoniae* serotype 5 capsular polysaccharide, and one or more CP1 or SPP2 fusion proteins non-covalently complexed to the biotinylated polysaccharide;

(6) an immunogenic complex comprising a biotinylated *S. pneumoniae* serotype 6A capsular polysaccharide, and one or more CP1 or SPP2 fusion proteins non-covalently complexed to the biotinylated polysaccharide;

(7) an immunogenic complex comprising a biotinylated *S. pneumoniae* serotype 6B capsular polysaccharide, and one or more CP1 or SPP2 fusion proteins non-covalently complexed to the biotinylated polysaccharide;

(8) an immunogenic complex comprising a biotinylated *S. pneumoniae* serotype 6C capsular polysaccharide, and one or more CP1 or SPP2 fusion proteins non-covalently complexed to the biotinylated polysaccharide;

(9) an immunogenic complex comprising a biotinylated *S. pneumoniae* serotype 7C capsular polysaccharide, and one or more CP1 or SPP2 fusion proteins non-covalently complexed to the biotinylated polysaccharide;

(10) an immunogenic complex comprising a biotinylated *S. pneumoniae* serotype 7F capsular polysaccharide, and one or more CP1 or SPP2 fusion proteins non-covalently complexed to the biotinylated polysaccharide;

(11) an immunogenic complex comprising a biotinylated *S. pneumoniae* serotype 8 capsular polysaccharide, and one or more CP1 or SPP2 fusion proteins non-covalently complexed to the biotinylated polysaccharide;

(12) an immunogenic complex comprising a biotinylated *S. pneumoniae* serotype 9N capsular polysaccharide, and one or more CP1 or SPP2 fusion proteins non-covalently complexed to the biotinylated polysaccharide;

(13) an immunogenic complex comprising a biotinylated *S. pneumoniae* serotype 9V capsular

(14) an immunogenic complex comprising a biotinylated *S. pneumoniae* serotype 10A capsular polysaccharide, and one or more CP1 or SPP2 fusion proteins non-covalently complexed to the biotinylated polysaccharide;

(15) an immunogenic complex comprising a biotinylated *S. pneumoniae* serotype 11A capsular polysaccharide, and one or more CP1 or SPP2 fusion proteins non-covalently complexed to the biotinylated polysaccharide;

(16) an immunogenic complex comprising a biotinylated *S. pneumoniae* serotype 12F capsular polysaccharide, and one or more CP1 or SPP2 fusion proteins non-covalently complexed to the biotinylated polysaccharide;

(17) an immunogenic complex comprising a biotinylated *S. pneumoniae* serotype 14 capsular polysaccharide, and one or more CP1 or SPP2 fusion proteins non-covalently complexed to the biotinylated polysaccharide;

(18) an immunogenic complex comprising a biotinylated *S. pneumoniae* serotype 15A capsular polysaccharide, and one or more CP1 or SPP2 fusion proteins non-covalently complexed to the biotinylated polysaccharide;

(19) an immunogenic complex comprising a biotinylated *S. pneumoniae* serotype 15B capsular polysaccharide, and one or more CP1 or SPP2 fusion proteins non-covalently complexed to the biotinylated polysaccharide;

(20) an immunogenic complex comprising a biotinylated *S. pneumoniae* serotype 17F capsular polysaccharide, and one or more CP1 or SPP2 fusion proteins non-covalently complexed to the biotinylated polysaccharide;

(21) an immunogenic complex comprising a biotinylated *S. pneumoniae* serotype 18C capsular polysaccharide, and one or more CP1 or SPP2 fusion proteins non-covalently complexed to the biotinylated polysaccharide;

(22) an immunogenic complex comprising a biotinylated *S. pneumoniae* serotype 19A

(23) an immunogenic complex comprising a biotinylated *S. pneumoniae* serotype 19F capsular polysaccharide, and one or more CP1 or SPP2 fusion proteins non-covalently complexed to the biotinylated polysaccharide;

(24) an immunogenic complex comprising a biotinylated *S. pneumoniae* serotype 20B capsular polysaccharide, and one or more CP1 or SPP2 fusion proteins non-covalently complexed to the biotinylated polysaccharide;

(25) an immunogenic complex comprising a biotinylated *S. pneumoniae* serotype 22F capsular polysaccharide, and one or more CP1 or SPP2 fusion proteins non-covalently complexed to the biotinylated polysaccharide;

(26) an immunogenic complex comprising a biotinylated *S. pneumoniae* serotype 23A capsular polysaccharide, and one or more CP1 or SPP2 fusion proteins non-covalently complexed to the biotinylated polysaccharide;

(27) an immunogenic complex comprising a biotinylated *S. pneumoniae* serotype 23B capsular polysaccharide, and one or more CP1 or SPP2 fusion proteins non-covalently complexed to the biotinylated polysaccharide;

(28) an immunogenic complex comprising a biotinylated *S. pneumoniae* serotype 23F capsular polysaccharide, and one or more CP1 or SPP2 fusion proteins non-covalently complexed to the biotinylated polysaccharide;

(29) an immunogenic complex comprising a biotinylated *S. pneumoniae* serotype 24F capsular polysaccharide, and one or more CP1 or SPP2 fusion proteins non-covalently complexed to the biotinylated polysaccharide;

(30) an immunogenic complex comprising a biotinylated *S. pneumoniae* serotype 31 capsular polysaccharide, and one or more CP1 or SPP2 fusion proteins non-covalently complexed to the biotinylated polysaccharide;

(31) an immunogenic complex comprising a biotinylated *S. pneumoniae* serotype 33F

(32) an immunogenic complex comprising a biotinylated *S. pneumoniae* serotype 35B capsular polysaccharide, and one or more CP1 or SPP2 fusion proteins non-covalently complexed to the biotinylated polysaccharide; and

(33) an immunogenic complex comprising a biotinylated *S. pneumoniae* serotype 38 capsular polysaccharide, and one or more CP1 or SPP2 fusion proteins non-covalently complexed to the biotinylated polysaccharide.

In some embodiments, an immunogenic composition comprises one or more (e.g., 1, 2, 3, 4, 5, 6, 7, 8, 9, 10, 15, 20, 21, 22, 23, 24, 25, 26, 27, 28, 29, 30, 31, 32, or 33) species of immunogenic complexes selected from:

(1) an immunogenic complex comprising a biotinylated *S. pneumoniae* serotype 1 capsular polysaccharide, and one or more CP1 or SPP2 fusion proteins non-covalently complexed to the biotinylated polysaccharide;

(2) an immunogenic complex comprising a biotinylated *S. pneumoniae* serotype 2 capsular polysaccharide, and one or more CP1 or SPP2 fusion proteins non-covalently complexed to the biotinylated polysaccharide;

(3) an immunogenic complex comprising a biotinylated *S. pneumoniae* serotype 4 capsular polysaccharide, and one or more CP1 or SPP2 fusion proteins non-covalently complexed to the biotinylated polysaccharide;

(4) an immunogenic complex comprising a biotinylated *S. pneumoniae* serotype 5 capsular polysaccharide, and one or more CP1 or SPP2 fusion proteins non-covalently complexed to the biotinylated polysaccharide;

(5) an immunogenic complex comprising a biotinylated *S. pneumoniae* serotype 6A capsular polysaccharide, and one or more CP1 or SPP2 fusion proteins non-covalently complexed to the biotinylated polysaccharide;

(6) an immunogenic complex comprising a biotinylated *S. pneumoniae* serotype 6B capsular (7) an immunogenic complex comprising a biotinylated *S. pneumoniae* serotype 6C capsular polysaccharide, and one or more CP1 or SPP2 fusion proteins non-covalently complexed to the biotinylated polysaccharide;

(8) an immunogenic complex comprising a biotinylated *S. pneumoniae* serotype 7C capsular polysaccharide, and one or more CP1 or SPP2 fusion proteins non-covalently complexed to the biotinylated polysaccharide;

(9) an immunogenic complex comprising a biotinylated *S. pneumoniae* serotype 7F capsular polysaccharide, and one or more CP1 or SPP2 fusion proteins non-covalently complexed to the biotinylated polysaccharide;

(10) an immunogenic complex comprising a biotinylated *S. pneumoniae* serotype 8 capsular polysaccharide, and one or more CP1 or SPP2 fusion proteins non-covalently complexed to the biotinylated polysaccharide;

(11) an immunogenic complex comprising a biotinylated *S. pneumoniae* serotype 9N capsular polysaccharide, and one or more CP1 or SPP2 fusion proteins non-covalently complexed to the biotinylated polysaccharide;

(12) an immunogenic complex comprising a biotinylated *S. pneumoniae* serotype 9V capsular polysaccharide, and one or more CP1 or SPP2 fusion proteins non-covalently complexed to the biotinylated polysaccharide;

(13) an immunogenic complex comprising a biotinylated *S. pneumoniae* serotype 10A capsular polysaccharide, and one or more CP1 or SPP2 fusion proteins non-covalently complexed to the biotinylated polysaccharide;

(14) an immunogenic complex comprising a biotinylated *S. pneumoniae* serotype 11A capsular polysaccharide, and one or more CP1 or SPP2 fusion proteins non-covalently complexed to the biotinylated polysaccharide;

(15) an immunogenic complex comprising a biotinylated *S. pneumoniae* serotype 12F

(16) an immunogenic complex comprising a biotinylated *S. pneumoniae* serotype 14 capsular polysaccharide, and one or more CP1 or SPP2 fusion proteins non-covalently complexed to the biotinylated polysaccharide;

(17) an immunogenic complex comprising a biotinylated *S. pneumoniae* serotype 15A capsular polysaccharide, and one or more CP1 or SPP2 fusion proteins non-covalently complexed to the biotinylated polysaccharide;

(18) an immunogenic complex comprising a biotinylated *S. pneumoniae* serotype 15B capsular polysaccharide, and one or more CP1 or SPP2 fusion proteins non-covalently complexed to the biotinylated polysaccharide;

(18) an immunogenic complex comprising a biotinylated *S. pneumoniae* serotype 16F capsular polysaccharide, and one or more CP1 or SPP2 fusion proteins non-covalently complexed to the biotinylated polysaccharide;

(20) an immunogenic complex comprising a biotinylated *S. pneumoniae* serotype 17F capsular polysaccharide, and one or more CP1 or SPP2 fusion proteins non-covalently complexed to the biotinylated polysaccharide;

(21) an immunogenic complex comprising a biotinylated *S. pneumoniae* serotype 18C capsular polysaccharide, and one or more CP1 or SPP2 fusion proteins non-covalently complexed to the biotinylated polysaccharide;

(22) an immunogenic complex comprising a biotinylated *S. pneumoniae* serotype 19A capsular polysaccharide, and one or more CP1 or SPP2 fusion proteins non-covalently complexed to the biotinylated polysaccharide;

(23) an immunogenic complex comprising a biotinylated *S. pneumoniae* serotype 19F capsular polysaccharide, and one or more CP1 or SPP2 fusion proteins non-covalently complexed to the biotinylated polysaccharide;

(24) an immunogenic complex comprising a biotinylated *S. pneumoniae* serotype 20B

(25) an immunogenic complex comprising a biotinylated *S. pneumoniae* serotype 22F capsular polysaccharide, and one or more CP1 or SPP2 fusion proteins non-covalently complexed to the biotinylated polysaccharide;

(26) an immunogenic complex comprising a biotinylated *S. pneumoniae* serotype 23A capsular polysaccharide, and one or more CP1 or SPP2 fusion proteins non-covalently complexed to the biotinylated polysaccharide;

(27) an immunogenic complex comprising a biotinylated *S. pneumoniae* serotype 23B capsular polysaccharide, and one or more CP1 or SPP2 fusion proteins non-covalently complexed to the biotinylated polysaccharide;

(28) an immunogenic complex comprising a biotinylated *S. pneumoniae* serotype 23F capsular polysaccharide, and one or more CP1 or SPP2 fusion proteins non-covalently complexed to the biotinylated polysaccharide;

(29) an immunogenic complex comprising a biotinylated *S. pneumoniae* serotype 24F capsular polysaccharide, and one or more CP1 or SPP2 fusion proteins non-covalently complexed to the biotinylated polysaccharide;

(30) an immunogenic complex comprising a biotinylated *S. pneumoniae* serotype 31 capsular polysaccharide, and one or more CP1 or SPP2 fusion proteins non-covalently complexed to the biotinylated polysaccharide;

(31) an immunogenic complex comprising a biotinylated *S. pneumoniae* serotype 33F capsular polysaccharide, and one or more CP1 or SPP2 fusion proteins non-covalently complexed to the biotinylated polysaccharide;

(32) an immunogenic complex comprising a biotinylated *S. pneumoniae* serotype 35B capsular polysaccharide, and one or more CP1 or SPP2 fusion proteins non-covalently complexed to the biotinylated polysaccharide; and

(33) an immunogenic complex comprising a biotinylated *S. pneumoniae* serotype 38 capsular polysaccharide, and one or more CP1 or SPP2 fusion proteins non-covalently complexed to the biotinylated polysaccharide.

Vaccine Compositions

In some embodiments, a vaccine composition is a polyvalent or multivalent vaccine. In some embodiments, the valency of a vaccine composition refers to the number of species of immunogenic complexes present in the vaccine composition. The valency of a vaccine described herein is not limiting with respect to the total antigens present in said pharmaceutical composition, immunogenic complex, or vaccine, or to the number of pathogen strains for which administration of said pharmaceutical composition, immunogenic complex, immunogenic composition, or vaccine composition may induce an immune-protective response. In a non-limiting example, a 34-valent vaccine composition may comprise more than 34 antigenic components (e.g., peptide and/or polysaccharide components) and may induce an immunoprotective response against more than 34 pathogens, or pathogenic serotypes or strains.

In some embodiments, a vaccine composition comprises between 1-60 species of immunogenic complexes described herein. In some embodiments, a vaccine composition comprises between 1-50 species of immunogenic complexes described herein. In some embodiments, a vaccine composition comprises between 1-45 species of immunogenic complexes described herein. In some embodiments, a vaccine composition comprises between 1-40 species of immunogenic complexes described herein. In some embodiments, a vaccine composition comprises between 1-40 species of immunogenic complexes described herein. In some embodiments, a vaccine composition comprises between 1-34 species of immunogenic complexes described herein. In some embodiments, a vaccine composition comprises between 1-33 species of immunogenic complexes described herein. In some embodiments, a vaccine composition comprises between 1-32, 1-31, or 1-30 species of immunogenic complexes described herein. In some embodiments, a vaccine is a polyvalent vaccine. In some embodiments, a vaccine composition comprises at least 30 (including, e.g., at least 31, at least 32, at least 33, at least 34) species of immunogenic complexes described herein. In some embodiments, a vaccine composition comprises 30-40 species of immunogenic complexes described herein. In some embodiments, a vaccine composition comprises 30-35 species of immunogenic complexes described herein.

In some embodiments, a multivalent pneumococcal composition comprises between 1-60 serotypes of *S. pneumoniae* capsular polysaccharides described herein. In some embodiments, a multivalent pneumococcal composition comprises between 1-50 serotypes of *S. pneumoniae* capsular polysaccharides described herein. In some embodiments, a multivalent pneumococcal composition comprises between 1-45 serotypes of *S. pneumoniae* capsular polysaccharides described herein. In some embodiments, a multivalent pneumococcal composition comprises between 1-40 serotypes of *S. pneumoniae* capsular polysaccharides described herein. In some embodiments, a multivalent pneumococcal composition comprises between 1-34 serotypes of *S. pneumoniae* capsular polysaccharides described herein. In some embodiments, a multivalent pneumococcal composition comprises between 1-33 serotypes of *S. pneumoniae* capsular polysaccharides described herein. In some embodiments, a multivalent pneumococcal composition comprises between 1-32, 1-31, or 1-30 serotypes of *S. pneumoniae* capsular polysaccharides described herein. In some embodiments, a multivalent pneumococcal composition comprises at least 30 (including, e.g., at least 31, at least 32, at least 33, at least 34) serotypes of *S. pneumoniae* capsular polysaccharides described herein. In some embodiments, a multivalent pneumococcal composition comprises 30-40 serotypes of *S. pneumoniae* capsular polysaccharides described herein. In some embodiments, a multivalent pneumococcal composition comprises 30-35 serotypes of *S. pneumoniae* capsular polysaccharides described herein. In some embodiments, one or more serotypes of *S. pneumoniae* capsular polysaccharides described herein in a multivalent pneumococcal composition are non-covalently associated with one or more carrier proteins, antigenic polypeptides, and/or fusion proteins described herein. In some embodiments, one or more serotypes of *S. pneumoniae* capsular polysaccharides described herein in a multivalent pneumococcal composition are covalently associated with one or more carrier proteins, antigenic polypeptides and/or fusion proteins described herein.

In some embodiments, a vaccine composition comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 species of immunogenic complexes described herein. In some embodiments, a vaccine composition comprises 1 species of immunogenic complex described herein. In some embodiments, a vaccine composition comprises 2 species of immunogenic complexes described herein. In some embodiments, a vaccine composition comprises 4 species of immunogenic complexes described herein. In some embodiments, a vaccine composition comprises 6 species of immunogenic complexes described herein. In some embodiments, a vaccine composition comprises 7 species of immunogenic complexes described herein. In some embodiments, a vaccine composition comprises 8 species of immunogenic complexes described herein. In some embodiments, a vaccine composition comprises 9 species of immunogenic complexes described herein. In some embodiments, a vaccine composition comprises 10 species of immunogenic complexes described herein. In some embodiments, a vaccine composition comprises 11 species of immunogenic complexes described herein. In some embodiments, a vaccine composition comprises 12 species of immunogenic complexes described herein. In some embodiments, a vaccine composition comprises 13 species of immunogenic complexes described herein. In some embodiments, a vaccine composition comprises 14 species of immunogenic complexes described herein. In some embodiments, a vaccine composition comprises 15 species of immunogenic complexes described herein. In some embodiments, a vaccine composition comprises 16 species of immunogenic complexes described herein. In some embodiments, a vaccine composition comprises 17 species of immunogenic complexes described herein. In some embodiments, a vaccine composition comprises 18 species of immunogenic complexes described herein. In some embodiments, a vaccine composition comprises 19 species of immunogenic complexes described herein. In some embodiments, a vaccine composition comprises 20 species of immunogenic complexes described herein. In some embodiments, a vaccine composition comprises 21 species of immunogenic complexes described herein. In some embodiments, a vaccine composition comprises 22 species of immunogenic complexes described herein. In some embodiments, a vaccine composition comprises 23 species of immunogenic complexes described herein. In some embodiments, a vaccine composition comprises 24 species of immunogenic complexes described herein. In some embodiments, a vaccine composition comprises 25 species of immunogenic complexes described herein. In some embodiments, a vaccine composition comprises 26 species of immunogenic complexes described herein. In some embodiments, a vaccine composition comprises 27 species of immunogenic complexes described herein. In some embodiments, a vaccine composition comprises 28 species of immunogenic complexes described herein. In some embodiments, a vaccine composition comprises 29 species of immunogenic complexes described herein. In some embodiments, a vaccine composition comprises 30 species of immunogenic complexes described herein. In some embodiments, a vaccine composition comprises 31 species of immunogenic complexes described herein. In some embodiments, a vaccine composition comprises 32 species of immunogenic complexes described herein. In some embodiments, a vaccine composition comprises 33 species of immunogenic complexes described herein. In some embodiments, a vaccine composition comprises 34 species of immunogenic complexes described herein. In some embodiments, a vaccine composition comprises 35 species of immunogenic complexes described herein. In some embodiments, a vaccine composition comprises 36 species of immunogenic complexes described herein. In some embodiments, a vaccine composition comprises 37 species of immunogenic complexes described herein. In some embodiments, a vaccine composition comprises 38 species of immunogenic complexes described herein. In some embodiments, a vaccine composition comprises 39 species of immunogenic complexes described herein. In some embodiments, a vaccine composition comprises 40 species of immunogenic complexes described herein. In some embodiments, a vaccine composition comprises 45 species of immunogenic complexes described herein. In some embodiments, a vaccine composition comprises 50 species of immunogenic complexes described herein. In some embodiments, a vaccine composition comprises 55 species of immunogenic complexes described herein. In some embodiments, a vaccine composition comprises 60 species of immunogenic complexes described herein.

In some embodiments, a vaccine composition comprises two or more species of immunogenic complexes (e.g., in immunogenic compositions) in amounts such that the weight of polysaccharides in the vaccine composition from each immunogenic complex is about the same, e.g., present in a w/w ratio of about 1:1. In some embodiments, the weight of polysaccharides in the vaccine contributed by each immunogenic complex is about 0.20 μg. In some embodiments, the weight of polysaccharides in the vaccine contributed by each immunogenic complex is about 0.25 μg. In some embodiments, the weight of polysaccharides in the vaccine contributed by each immunogenic complex is about 0.5 μg. In some embodiments, the weight of polysaccharides in the vaccine contributed by each immunogenic complex is about 1 μg. In some embodiments, the weight of polysaccharides in the vaccine contributed by each immunogenic complex is about 1.5 μg. In some embodiments, the weight of polysaccharides in the vaccine contributed by each immunogenic complex is about 2 μg. In some embodiments, the weight of polysaccharides in the vaccine contributed by each immunogenic complex is about 2.5 μg. In some embodiments, the weight of polysaccharides in the vaccine contributed by each immunogenic complex is about 3 μg. In some embodiments, the weight of polysaccharides in the vaccine contributed by each immunogenic complex is about 3.5 μg. In some embodiments, the weight of polysaccharides in the vaccine contributed by each immunogenic complex is about 4 μg. In some embodiments, the weight of polysaccharides in the vaccine contributed by each immunogenic complex is about 4.5 μg. In some embodiments, the weight of polysaccharides in the vaccine contributed by each immunogenic complex is about 5 μg. In some embodiments, the weight of polysaccharides in the vaccine contributed by each immunogenic complex is about 5.5 μg. In some embodiments, the weight of polysaccharides in the vaccine contributed by each immunogenic complex is about 6 μg. In some embodiments, the weight of polysaccharides in the vaccine contributed by each immunogenic complex is about 7 μg. In some embodiments, the weight of polysaccharides in the vaccine contributed by each immunogenic complex is about 8 μg. In some embodiments, the weight of polysaccharides in the vaccine contributed by each immunogenic complex is about 9 μg. In some embodiments, the weight of polysaccharides in the vaccine contributed by each immunogenic complex is about 10 μg. In some embodiments, the weight of polysaccharides in the vaccine contributed by each immunogenic complex is about 11 μg. In some embodiments, the weight of polysaccharides in the vaccine contributed by each immunogenic complex is about 12 μg. In some embodiments, the weight of polysaccharides in the vaccine contributed by each immunogenic complex is more than 12 μg, e.g., 13 μg, 14 μg, 15 μg, 16 μg, 17 μg, 18 μg, 19 μg, 20 μg, 21 μg, 22 μg, 23 μg, 24 μg, 25 μg, or more.

In some embodiments, a vaccine composition comprises two or more species of immunogenic complexes (e.g., in immunogenic compositions) in amounts such that the weight of polysaccharides in the vaccine composition contributed by each immunogenic complex is different, e.g., present in a w/w ratio that is not about 1:1. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:2. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:3. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:4. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:5. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:6. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:7. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:8. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:9. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:10. In some embodiments, the vaccine composition comprises a mixture of immunogenic complexes, such that the weight of polysaccharide in a vaccine contributed by an immunogenic complex ranges from about 0.20 μg to about 6 μg. In some embodiments, the vaccine composition comprises a mixture of immunogenic complexes, such that the weight of polysaccharide in a vaccine contributed by an immunogenic complex ranges from about 0.20 μg to about 12 μg. In some embodiments, the vaccine composition comprises a mixture of immunogenic complexes, such that the weight of polysaccharides in the vaccine contributed by each immunogenic complex ranges from about 0.20 μg to about 20 μg. In some embodiments, the vaccine composition comprises a mixture of immunogenic complexes, such that the weight of polysaccharides in the vaccine contributed by each immunogenic complex ranges from about 0.20 μg to about 40 μg.

In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is about the same, e.g., present in a w/w protein: PS ratio of about 1:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 2:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 3:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 4:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 5:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 6:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 7:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 8:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 9:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein: PS ratio of about 10:1.

In some embodiments, the combined weight of polysaccharides and polypeptides in the vaccine contributed by each immunogenic complex is about 0.20 μg. In some embodiments, the combined weight of polysaccharides and polypeptides in the vaccine contributed by each immunogenic complex is about 0.40 μg. In some embodiments, the combined weight of polysaccharides and polypeptides in the vaccine contributed by each immunogenic complex is about 1 μg. In some embodiments, the combined weight of polysaccharides and polypeptides in the vaccine contributed by each immunogenic complex is about 2 μg. In some embodiments, the combined weight of polysaccharides and polypeptides in the vaccine contributed by each immunogenic composition is about 3 μg. In some embodiments, the combined weight of polysaccharides and polypeptides in the vaccine contributed by each immunogenic composition is about 4 μg. In some embodiments, the combined weight of polysaccharides and polypeptides in the vaccine contributed by each immunogenic composition is about 5 μg. In some embodiments, the combined weight of polysaccharides and polypeptides in the vaccine contributed by each immunogenic composition is about 6 μg. In some embodiments, the combined weight of polysaccharides and polypeptides in the vaccine contributed by each immunogenic composition is about 7 μg. In some embodiments, the combined weight of polysaccharides and polypeptides in the vaccine contributed by each immunogenic composition is about 8 μg. In some embodiments, the combined weight of polysaccharides and polypeptides in the vaccine contributed by each immunogenic composition is about 9 μg. In some embodiments, the combined weight of polysaccharides and polypeptides in the vaccine contributed by each immunogenic composition is about 10 μg. In some embodiments, the combined weight of polysaccharides and polypeptides in the vaccine contributed by each immunogenic composition is about 11 μg. In some embodiments, the combined weight of polysaccharides and polypeptides in the vaccine contributed by each immunogenic composition is about 12 μg. In some embodiments, the combined weight of polysaccharides and polypeptides in the vaccine contributed by each immunogenic composition is about 14 μg. In some embodiments, the combined weight of polysaccharides and polypeptides in the vaccine contributed by each immunogenic composition is about 16 μg. In some embodiments, the combined weight of polysaccharides and polypeptides in the vaccine contributed by each immunogenic composition is about 18 μg. In some embodiments, the combined weight of polysaccharides and polypeptides in the vaccine contributed by each immunogenic composition is about 20 μg. In some embodiments, the combined weight of polysaccharides and polypeptides in the vaccine contributed by each immunogenic composition is about 21 μg. In some embodiments, the combined weight of polysaccharides and polypeptides in the vaccine contributed by each immunogenic composition is about 22 μg. In some embodiments, the combined weight of polysaccharides and polypeptides in the vaccine contributed by each immunogenic composition is about 23 μg. In some embodiments, the combined weight of polysaccharides and polypeptides in the vaccine contributed by each immunogenic composition is about 24 μg. In some embodiments, the combined weight of polysaccharides and polypeptides in the vaccine contributed by each immunogenic composition is about 25 μg. In some embodiments, the combined weight of polysaccharides and polypeptides in the vaccine contributed by each immunogenic composition is about 30 μg. In some embodiments, the combined weight of polysaccharides and polypeptides in the vaccine contributed by each immunogenic composition is about 40 μg. In some embodiments, the combined weight of polysaccharides and polypeptides in the vaccine contributed by each immunogenic composition is about 50 μg. In some embodiments, the combined weight of polysaccharides and polypeptides in the vaccine contributed by each immunogenic composition is about 60 μg. In some embodiments, the combined weight of polysaccharides and polypeptides in the vaccine contributed by each immunogenic composition is about 70 μg. In some embodiments, the combined weight of polysaccharides and polypeptides in the vaccine contributed by each immunogenic composition is about 80 μg. In some embodiments, the combined weight of polysaccharides and polypeptides in the vaccine contributed by each immunogenic composition is about 90 μg. In some embodiments, the combined weight of polysaccharides and polypeptides in the vaccine contributed by each immunogenic composition is about 100 μg. In some embodiments, the combined weight of polysaccharides and polypeptides in the vaccine contributed by each immunogenic composition is about 110 μg.

In some embodiments, a vaccine composition comprises two or more species of immunogenic complexes (e.g., in immunogenic compositions) in amounts such that the combined weight of polysaccharides and polypeptides in the vaccine composition contributed by each immunogenic complex is different, e.g., present in a w/w protein: PS ratio that is not about 1:1, e.g., a protein: PS ratio that is 2:1, 3:1, 4:1, 5:1, 6:1, 7:1, 8:1, 9:1, or 10:1. In some embodiments, the vaccine composition comprises a mixture of immunogenic complexes, such that the combined weight of polysaccharides and polypeptides in the vaccine contributed by each immunogenic complex ranges from about 0.4 μg to about 110 μg.

In some embodiments, a vaccine composition comprises one or more (e.g., 1, 2, 3, 4, 5, 6, 7, 8, 9, 10, 15, 20, 25, 30, 35, 40, 50, or more) species of immunogenic complexes selected from:

(1) an immunogenic complex comprising a biotinylated *S. pneumoniae* serotype 1 capsular
(2) an immunogenic complex comprising a biotinylated *S. pneumoniae* serotype 2 capsular polysaccharide, and one or more CP1 or SPP2 fusion proteins non-covalently complexed to the biotinylated polysaccharide;
(3) an immunogenic complex comprising a biotinylated *S. pneumoniae* serotype 3 capsular polysaccharide, and one or more CP1 or SPP2 fusion proteins non-covalently complexed to the biotinylated polysaccharide;
(4) an immunogenic complex comprising a biotinylated *S. pneumoniae* serotype 4 capsular polysaccharide, and one or more CP1 or SPP2 fusion proteins non-covalently complexed to the biotinylated polysaccharide;
(5) an immunogenic complex comprising a biotinylated *S. pneumoniae* serotype 5 capsular polysaccharide, and one or more CP1 or SPP2 fusion proteins non-covalently complexed to the biotinylated polysaccharide;
(6) an immunogenic complex comprising a biotinylated *S. pneumoniae* serotype 6A capsular polysaccharide, and one or more CP1 or SPP2 fusion proteins non-covalently complexed to the biotinylated polysaccharide;
(7) an immunogenic complex comprising a biotinylated *S. pneumoniae* serotype 6B capsular polysaccharide, and one or more CP1 or SPP2 fusion proteins non-covalently complexed to the biotinylated polysaccharide;
(8) an immunogenic complex comprising a biotinylated *S. pneumoniae* serotype 6C capsular polysaccharide, and one or more CP1 or SPP2 fusion proteins non-covalently complexed to the biotinylated polysaccharide;
(9) an immunogenic complex comprising a biotinylated *S. pneumoniae* serotype 6D capsular polysaccharide, and one or more CP1 or SPP2 fusion proteins non-covalently complexed to the biotinylated polysaccharide;
(10) an immunogenic complex comprising a biotinylated *S. pneumoniae* serotype 6E capsular
(11) an immunogenic complex comprising a biotinylated *S. pneumoniae* serotype 6F capsular polysaccharide, and one or more CP1 or SPP2 fusion proteins non-covalently complexed to the biotinylated polysaccharide;
(12) an immunogenic complex comprising a biotinylated *S. pneumoniae* serotype 6G capsular polysaccharide, and one or more CP1 or SPP2 fusion proteins non-covalently complexed to the biotinylated polysaccharide;
(13) an immunogenic complex comprising a biotinylated *S. pneumoniae* serotype 6H capsular polysaccharide, and one or more CP1 or SPP2 fusion proteins non-covalently complexed to the biotinylated polysaccharide;
(14) an immunogenic complex comprising a biotinylated *S. pneumoniae* serotype 7A capsular polysaccharide, and one or more CP1 or SPP2 fusion proteins non-covalently complexed to the biotinylated polysaccharide;
(15) an immunogenic complex comprising a biotinylated *S. pneumoniae* serotype 7B capsular polysaccharide, and one or more CP1 or SPP2 fusion proteins non-covalently complexed to the biotinylated polysaccharide;
(16) an immunogenic complex comprising a biotinylated *S. pneumoniae* serotype 7C capsular polysaccharide, and one or more CP1 or SPP2 fusion proteins non-covalently complexed to the biotinylated polysaccharide;

(17) an immunogenic complex comprising a biotinylated *S. pneumoniae* serotype 7F capsular polysaccharide, and one or more CP1 or SPP2 fusion proteins non-covalently complexed to the biotinylated polysaccharide;

(18) an immunogenic complex comprising a biotinylated *S. pneumoniae* serotype 8 capsular polysaccharide, and one or more CP1 or SPP2 fusion proteins non-covalently complexed to the biotinylated polysaccharide;

(19) an immunogenic complex comprising a biotinylated *S. pneumoniae* serotype 9A capsular

(20) an immunogenic complex comprising a biotinylated *S. pneumoniae* serotype 9L capsular polysaccharide, and one or more CP1 or SPP2 fusion proteins non-covalently complexed to the biotinylated polysaccharide;

(21) an immunogenic complex comprising a biotinylated *S. pneumoniae* serotype 9N capsular polysaccharide, and one or more CP1 or SPP2 fusion proteins non-covalently complexed to the biotinylated polysaccharide;

(22) an immunogenic complex comprising a biotinylated *S. pneumoniae* serotype 9V capsular polysaccharide, and one or more CP1 or SPP2 fusion proteins non-covalently complexed to the biotinylated polysaccharide;

(23) an immunogenic complex comprising a biotinylated *S. pneumoniae* serotype 10A capsular polysaccharide, and one or more CP1 or SPP2 fusion proteins non-covalently complexed to the biotinylated polysaccharide;

(24) an immunogenic complex comprising a biotinylated *S. pneumoniae* serotype 10B capsular polysaccharide, and one or more CP1 or SPP2 fusion proteins non-covalently complexed to the biotinylated polysaccharide;

(25) an immunogenic complex comprising a biotinylated *S. pneumoniae* serotype 10C capsular polysaccharide, and one or more CP1 or SPP2 fusion proteins non-covalently complexed to the biotinylated polysaccharide;

(26) an immunogenic complex comprising a biotinylated *S. pneumoniae* serotype 10F capsular polysaccharide, and one or more CP1 or SPP2 fusion proteins non-covalently complexed to the biotinylated polysaccharide;

(27) an immunogenic complex comprising a biotinylated *S. pneumoniae* serotype 11A capsular polysaccharide, and one or more CP1 or SPP2 fusion proteins non-covalently complexed to the biotinylated polysaccharide;

(28) an immunogenic complex comprising a biotinylated *S. pneumoniae* serotype 11B

(29) an immunogenic complex comprising a biotinylated *S. pneumoniae* serotype 11C capsular polysaccharide, and one or more CP1 or SPP2 fusion proteins non-covalently complexed to the biotinylated polysaccharide;

(30) an immunogenic complex comprising a biotinylated *S. pneumoniae* serotype 11D capsular polysaccharide, and one or more CP1 or SPP2 fusion proteins non-covalently complexed to the biotinylated polysaccharide;

(31) an immunogenic complex comprising a biotinylated *S. pneumoniae* serotype 11E capsular polysaccharide, and one or more CP1 or SPP2 fusion proteins non-covalently complexed to the biotinylated polysaccharide;

(32) an immunogenic complex comprising a biotinylated *S. pneumoniae* serotype 11F capsular polysaccharide, and one or more CP1 or SPP2 fusion proteins non-covalently complexed to the biotinylated polysaccharide;

(33) an immunogenic complex comprising a biotinylated *S. pneumoniae* serotype 12A capsular polysaccharide, and one or more CP1 or SPP2 fusion proteins non-covalently complexed to the biotinylated polysaccharide;

(34) an immunogenic complex comprising a biotinylated *S. pneumoniae* serotype 12B capsular polysaccharide, and one or more CP1 or SPP2 fusion proteins non-covalently complexed to the biotinylated polysaccharide;

(35) an immunogenic complex comprising a biotinylated *S. pneumoniae* serotype 12F capsular polysaccharide, and one or more CP1 or SPP2 fusion proteins non-covalently complexed to the biotinylated polysaccharide;

(36) an immunogenic complex comprising a biotinylated *S. pneumoniae* serotype 13 capsular polysaccharide, and one or more CP1 or SPP2 fusion proteins non-covalently complexed to the biotinylated polysaccharide;

(37) an immunogenic complex comprising a biotinylated *S. pneumoniae* serotype 14 capsular

(38) an immunogenic complex comprising a biotinylated *S. pneumoniae* serotype 15A capsular polysaccharide, and one or more CP1 or SPP2 fusion proteins non-covalently complexed to the biotinylated polysaccharide;

(39) an immunogenic complex comprising a biotinylated *S. pneumoniae* serotype 15B capsular polysaccharide, and one or more CP1 or SPP2 fusion proteins non-covalently complexed to the biotinylated polysaccharide;

(40) an immunogenic complex comprising a biotinylated *S. pneumoniae* serotype 15C capsular polysaccharide, and one or more CP1 or SPP2 fusion proteins non-covalently complexed to the biotinylated polysaccharide;

(41) an immunogenic complex comprising a biotinylated *S. pneumoniae* serotype 15F capsular polysaccharide, and one or more CP1 or SPP2 fusion proteins non-covalently complexed to the biotinylated polysaccharide;

(42) an immunogenic complex comprising a biotinylated *S. pneumoniae* serotype 16A capsular polysaccharide, and one or more CP1 or SPP2 fusion proteins non-covalently complexed to the biotinylated polysaccharide;

(43) an immunogenic complex comprising a biotinylated *S. pneumoniae* serotype 16F capsular polysaccharide, and one or more CP1 or SPP2 fusion proteins non-covalently complexed to the biotinylated polysaccharide;

(44) an immunogenic complex comprising a biotinylated *S. pneumoniae* serotype 17A capsular polysaccharide, and one or more CP1 or SPP2 fusion proteins non-covalently complexed to the biotinylated polysaccharide;

(45) an immunogenic complex comprising a biotinylated *S. pneumoniae* serotype 17F capsular polysaccharide, and one or more CP1 or SPP2 fusion proteins non-covalently complexed to the biotinylated polysaccharide;

(46) an immunogenic complex comprising a biotinylated *S. pneumoniae* serotype 18A

(47) an immunogenic complex comprising a biotinylated *S. pneumoniae* serotype 18B capsular polysaccharide, and one or more CP1 or SPP2 fusion proteins non-covalently complexed to the biotinylated polysaccharide;

(48) an immunogenic complex comprising a biotinylated *S. pneumoniae* serotype 18C capsular polysaccharide, and one or more CP1 or SPP2 fusion proteins non-covalently complexed to the biotinylated polysaccharide;

(49) an immunogenic complex comprising a biotinylated *S. pneumoniae* serotype 18F capsular polysaccharide, and one or more CP1 or SPP2 fusion proteins non-covalently complexed to the biotinylated polysaccharide;

(50) an immunogenic complex comprising a biotinylated *S. pneumoniae* serotype 19A capsular polysaccharide, and one or more CP1 or SPP2 fusion proteins non-covalently complexed to the biotinylated polysaccharide;

(51) an immunogenic complex comprising a biotinylated *S. pneumoniae* serotype 19B capsular polysaccharide, and one or more CP1 or SPP2 fusion proteins non-covalently complexed to the biotinylated polysaccharide;

(52) an immunogenic complex comprising a biotinylated *S. pneumoniae* serotype 19C capsular polysaccharide, and one or more CP1 or SPP2 fusion proteins non-covalently complexed to the biotinylated polysaccharide;

(53) an immunogenic complex comprising a biotinylated *S. pneumoniae* serotype 19F capsular polysaccharide, and one or more CP1 or SPP2 fusion proteins non-covalently complexed to the biotinylated polysaccharide;

(54) an immunogenic complex comprising a biotinylated *S. pneumoniae* serotype 20A capsular polysaccharide, and one or more CP1 or SPP2 fusion proteins non-covalently complexed to the biotinylated polysaccharide;

(55) an immunogenic complex comprising a biotinylated *S. pneumoniae* serotype 20B

(56) an immunogenic complex comprising a biotinylated *S. pneumoniae* serotype 21 capsular polysaccharide, and one or more CP1 or SPP2 fusion proteins non-covalently complexed to the biotinylated polysaccharide;

(57) an immunogenic complex comprising a biotinylated *S. pneumoniae* serotype 22A capsular polysaccharide, and one or more CP1 or SPP2 fusion proteins non-covalently complexed to the biotinylated polysaccharide;

(58) an immunogenic complex comprising a biotinylated *S. pneumoniae* serotype 22F capsular polysaccharide, and one or more CP1 or SPP2 fusion proteins non-covalently complexed to the biotinylated polysaccharide;

(59) an immunogenic complex comprising a biotinylated *S. pneumoniae* serotype 23A capsular polysaccharide, and one or more CP1 or SPP2 fusion proteins non-covalently complexed to the biotinylated polysaccharide;

(60) an immunogenic complex comprising a biotinylated *S. pneumoniae* serotype 23B capsular polysaccharide, and one or more CP1 or SPP2 fusion proteins non-covalently complexed to the biotinylated polysaccharide;

(61) an immunogenic complex comprising a biotinylated *S. pneumoniae* serotype 23F capsular polysaccharide, and one or more CP1 or SPP2 fusion proteins non-covalently complexed to the biotinylated polysaccharide;

(62) an immunogenic complex comprising a biotinylated *S. pneumoniae* serotype 24A capsular polysaccharide, and one or more CP1 or SPP2 fusion proteins non-covalently complexed to the biotinylated polysaccharide;

(63) an immunogenic complex comprising a biotinylated *S. pneumoniae* serotype 24B capsular polysaccharide, and one or more CP1 or SPP2 fusion proteins non-covalently complexed to the biotinylated polysaccharide;

(64) an immunogenic complex comprising a biotinylated *S. pneumoniae* serotype 24F

(65) an immunogenic complex comprising a biotinylated *S. pneumoniae* serotype 25A capsular polysaccharide, and one or more CP1 or SPP2 fusion proteins non-covalently complexed to the biotinylated polysaccharide;

(66) an immunogenic complex comprising a biotinylated *S. pneumoniae* serotype 25F capsular polysaccharide, and one or more CP1 or SPP2 fusion proteins non-covalently complexed to the biotinylated polysaccharide;

(67) an immunogenic complex comprising a biotinylated *S. pneumoniae* serotype 27 capsular polysaccharide, and one or more CP1 or SPP2 fusion proteins non-covalently complexed to the biotinylated polysaccharide;

(68) an immunogenic complex comprising a biotinylated *S. pneumoniae* serotype 28A capsular polysaccharide, and one or more CP1 or SPP2 fusion proteins non-covalently complexed to the biotinylated polysaccharide;

(69) an immunogenic complex comprising a biotinylated *S. pneumoniae* serotype 28F capsular polysaccharide, and one or more CP1 or SPP2 fusion proteins non-covalently complexed to the biotinylated polysaccharide;

(70) an immunogenic complex comprising a biotinylated *S. pneumoniae* serotype 29 capsular polysaccharide, and one or more CP1 or SPP2 fusion proteins non-covalently complexed to the biotinylated polysaccharide;

(71) an immunogenic complex comprising a biotinylated *S. pneumoniae* serotype 31 capsular polysaccharide, and one or more CP1 or SPP2 fusion proteins non-covalently complexed to the biotinylated polysaccharide;

(72) an immunogenic complex comprising a biotinylated *S. pneumoniae* serotype 32A capsular polysaccharide, and one or more CP1 or SPP2 fusion proteins non-covalently complexed to the biotinylated polysaccharide;

(73) an immunogenic complex comprising a biotinylated *S. pneumoniae* serotype 32F

(74) an immunogenic complex comprising a biotinylated *S. pneumoniae* serotype 33A capsular polysaccharide, and one or more CP1 or SPP2 fusion proteins non-covalently complexed to the biotinylated polysaccharide;

(75) an immunogenic complex comprising a biotinylated *S. pneumoniae* serotype 33B capsular polysaccharide, and one or more CP1 or SPP2 fusion proteins non-covalently complexed to the biotinylated polysaccharide;

(76) an immunogenic complex comprising a biotinylated *S. pneumoniae* serotype 33C capsular polysaccharide, and one or more CP1 or SPP2 fusion proteins non-covalently complexed to the biotinylated polysaccharide;

(77) an immunogenic complex comprising a biotinylated *S. pneumoniae* serotype 33D capsular polysaccharide, and one or more CP1 or SPP2 fusion proteins non-covalently complexed to the biotinylated polysaccharide;

(78) an immunogenic complex comprising a biotinylated *S. pneumoniae* serotype 33E capsular polysaccharide, and one or more CP1 or SPP2 fusion proteins non-covalently complexed to the biotinylated polysaccharide;

(79) an immunogenic complex comprising a biotinylated *S. pneumoniae* serotype 33F capsular polysaccharide, and one or more CP1 or SPP2 fusion proteins non-covalently complexed to the biotinylated polysaccharide;

(80) an immunogenic complex comprising a biotinylated *S. pneumoniae* serotype 34 capsular polysaccharide, and one or more CP1 or SPP2 fusion proteins non-covalently complexed to the biotinylated polysaccharide;

(81) an immunogenic complex comprising a biotinylated *S. pneumoniae* serotype 35A capsular polysaccharide, and one or more CP1 or SPP2 fusion proteins non-covalently complexed to the biotinylated polysaccharide;

(82) an immunogenic complex comprising a biotinylated *S. pneumoniae* serotype 35B

(83) an immunogenic complex comprising a biotinylated *S. pneumoniae* serotype 35C capsular polysaccharide, and one or more CP1 or SPP2 fusion proteins non-covalently complexed to the biotinylated polysaccharide;

(84) an immunogenic complex comprising a biotinylated *S. pneumoniae* serotype 35F capsular polysaccharide, and one or more CP1 or SPP2 fusion proteins non-covalently complexed to the biotinylated polysaccharide;

(85) an immunogenic complex comprising a biotinylated *S. pneumoniae* serotype 36 capsular polysaccharide, and one or more CP1 or SPP2 fusion proteins non-covalently complexed to the biotinylated polysaccharide;

(86) an immunogenic complex comprising a biotinylated *S. pneumoniae* serotype 37 capsular polysaccharide, and one or more CP1 or SPP2 fusion proteins non-covalently complexed to the biotinylated polysaccharide;

(87) an immunogenic complex comprising a biotinylated *S. pneumoniae* serotype 38 capsular polysaccharide, and one or more CP1 or SPP2 fusion proteins non-covalently complexed to the biotinylated polysaccharide;

(88) an immunogenic complex comprising a biotinylated *S. pneumoniae* serotype 39 capsular polysaccharide, and one or more CP1 or SPP2 fusion proteins non-covalently complexed to the biotinylated polysaccharide;

(89) an immunogenic complex comprising a biotinylated *S. pneumoniae* serotype 40 capsular polysaccharide, and one or more CP1 or SPP2 fusion proteins non-covalently complexed to the biotinylated polysaccharide;

(90) an immunogenic complex comprising a biotinylated *S. pneumoniae* serotype 41A capsular polysaccharide, and one or more CP1 or SPP2 fusion proteins non-covalently complexed to the biotinylated polysaccharide;

(91) an immunogenic complex comprising a biotinylated *S. pneumoniae* serotype 41F

(92) an immunogenic complex comprising a biotinylated *S. pneumoniae* serotype 42 capsular polysaccharide, and one or more CP1 or SPP2 fusion proteins non-covalently complexed to the biotinylated polysaccharide;

(93) an immunogenic complex comprising a biotinylated *S. pneumoniae* serotype 43 capsular polysaccharide, and one or more CP1 or SPP2 fusion proteins non-covalently complexed to the biotinylated polysaccharide;

(94) an immunogenic complex comprising a biotinylated *S. pneumoniae* serotype 44 capsular polysaccharide, and one or more CP1 or SPP2 fusion proteins non-covalently complexed to the biotinylated polysaccharide;

(95) an immunogenic complex comprising a biotinylated *S. pneumoniae* serotype 45 capsular polysaccharide, and one or more CP1 or SPP2 fusion proteins non-covalently complexed to the biotinylated polysaccharide;

(96) an immunogenic complex comprising a biotinylated *S. pneumoniae* serotype 46 capsular polysaccharide, and one or more CP1 or SPP2 fusion proteins non-covalently complexed to the biotinylated polysaccharide;

(97) an immunogenic complex comprising a biotinylated *S. pneumoniae* serotype 47A capsular polysaccharide, and one or more CP1 or SPP2 fusion proteins non-covalently complexed to the biotinylated polysaccharide;

(98) an immunogenic complex comprising a biotinylated *S. pneumoniae* serotype 47F capsular polysaccharide, and one or more CP1 or SPP2 fusion proteins non-covalently complexed to the biotinylated polysaccharide; and

(99) an immunogenic complex comprising a biotinylated *S. pneumoniae* serotype 48 capsular polysaccharide, and one or more CP1 or SPP2 fusion proteins non-covalently complexed to the biotinylated polysaccharide.

In some embodiments, a vaccine composition comprises two or more (e.g., 2, 3, 4, 5, 6, 7, 8, 9, 10, 15, 20, 25, 30, 31, 32, 33, or 34) species of immunogenic complexes selected from:

(1) an immunogenic complex comprising a biotinylated *S. pneumoniae* serotype 6C capsular polysaccharide, and one or more SPP2 fusion proteins non-covalently complexed to the biotinylated polysaccharide;

(2) an immunogenic complex comprising a biotinylated *S. pneumoniae* serotype 7C capsular polysaccharide, and one or more SPP2 fusion proteins non-covalently complexed to the biotinylated polysaccharide;

(3) an immunogenic complex comprising a biotinylated *S. pneumoniae* serotype 15A capsular polysaccharide, and one or more SPP2 fusion proteins non-covalently complexed to the biotinylated polysaccharide;

(4) an immunogenic complex comprising a biotinylated *S. pneumoniae* serotype 16F capsular polysaccharide, and one or more SPP2 fusion proteins non-covalently complexed to the biotinylated polysaccharide;

(5) an immunogenic complex comprising a biotinylated *S. pneumoniae* serotype 23A capsular polysaccharide, and one or more SPP2 fusion proteins non-covalently complexed to the biotinylated polysaccharide;

(6) an immunogenic complex comprising a biotinylated *S. pneumoniae* serotype 23B capsular polysaccharide, and one or more SPP2 fusion proteins non-covalently complexed to the biotinylated polysaccharide;

(7) an immunogenic complex comprising a biotinylated *S. pneumoniae* serotype 24F capsular polysaccharide, and one or more SPP2 fusion proteins non-covalently complexed to the biotinylated polysaccharide;

(8) an immunogenic complex comprising a biotinylated *S. pneumoniae* serotype 31 capsular polysaccharide, and one or more SPP2 fusion proteins non-covalently complexed to the biotinylated polysaccharide;

(9) an immunogenic complex comprising a biotinylated *S. pneumoniae* serotype 35B capsular polysaccharide, and one or more SPP2 fusion proteins non-covalently complexed to the

(10) an immunogenic complex comprising a biotinylated *S. pneumoniae* serotype 38 capsular polysaccharide, and one or more SPP2 fusion proteins non-covalently complexed to the biotinylated polysaccharide;

(11) an immunogenic complex comprising a biotinylated *S. pneumoniae* serotype 1 capsular polysaccharide, and one or more CP1 fusion proteins non-covalently complexed to the biotinylated polysaccharide;

(12) an immunogenic complex comprising a biotinylated *S. pneumoniae* serotype 2 capsular polysaccharide, and one or more CP1 fusion proteins non-covalently complexed to the biotinylated polysaccharide;

(13) an immunogenic complex comprising a biotinylated *S. pneumoniae* serotype 3 capsular polysaccharide, and one or more CP1 fusion proteins non-covalently complexed to the biotinylated polysaccharide;

(14) an immunogenic complex comprising a biotinylated *S. pneumoniae* serotype 4 capsular polysaccharide, and one or more CP1 fusion proteins non-covalently complexed to the biotinylated polysaccharide;

(15) an immunogenic complex comprising a biotinylated *S. pneumoniae* serotype 5 capsular polysaccharide, and one or more CP1 fusion proteins non-covalently complexed to the biotinylated polysaccharide;

(16) an immunogenic complex comprising a biotinylated *S. pneumoniae* serotype 6A capsular polysaccharide, and one or more CP1 fusion proteins non-covalently complexed to the biotinylated polysaccharide;

(17) an immunogenic complex comprising a biotinylated *S. pneumoniae* serotype 6B capsular polysaccharide, and one or more CP1 fusion proteins non-covalently complexed to the biotinylated polysaccharide;

(18) an immunogenic complex comprising a biotinylated *S. pneumoniae* serotype 7F capsular polysaccharide, and one or more CP1 fusion proteins non-covalently complexed to the

(19) an immunogenic complex comprising a biotinylated *S. pneumoniae* serotype 8 capsular polysaccharide, and one or more CP1 fusion proteins non-covalently complexed to the biotinylated polysaccharide;

(20) an immunogenic complex comprising a biotinylated *S. pneumoniae* serotype 9N capsular polysaccharide, and one or more CP1 fusion proteins non-covalently complexed to the biotinylated polysaccharide;

(21) an immunogenic complex comprising a biotinylated *S. pneumoniae* serotype 9V capsular polysaccharide, and one or more CP1 fusion proteins non-covalently complexed to the biotinylated polysaccharide;

(22) an immunogenic complex comprising a biotinylated *S. pneumoniae* serotype 10A capsular polysaccharide, and one or more CP1 fusion proteins non-covalently complexed to the biotinylated polysaccharide;

(23) an immunogenic complex comprising a biotinylated *S. pneumoniae* serotype 11A capsular polysaccharide, and one or more CP1 fusion proteins non-covalently complexed to the biotinylated polysaccharide;

(24) an immunogenic complex comprising a biotinylated *S. pneumoniae* serotype 12F capsular polysaccharide, and one or more CP1 fusion proteins non-covalently complexed to the biotinylated polysaccharide;

(25) an immunogenic complex comprising a biotinylated *S. pneumoniae* serotype 14 capsular polysaccharide, and one or more CP1 fusion proteins non-covalently complexed to the biotinylated polysaccharide;

(26) an immunogenic complex comprising a biotinylated *S. pneumoniae* serotype 15B capsular polysaccharide, and one or more CP1 fusion proteins non-covalently complexed to the biotinylated polysaccharide;

(27) an immunogenic complex comprising a biotinylated *S. pneumoniae* serotype 17F

(28) an immunogenic complex comprising a biotinylated *S. pneumoniae* serotype 18C capsular polysaccharide, and one or more CP1 fusion proteins non-covalently complexed to the biotinylated polysaccharide;

(29) an immunogenic complex comprising a biotinylated *S. pneumoniae* serotype 19A capsular polysaccharide, and one or more CP1 fusion proteins non-covalently complexed to the biotinylated polysaccharide;

(30) an immunogenic complex comprising a biotinylated *S. pneumoniae* serotype 19F capsular polysaccharide, and one or more CP1 fusion proteins non-covalently complexed to the biotinylated polysaccharide;

(31) an immunogenic complex comprising a biotinylated *S. pneumoniae* serotype 20B capsular polysaccharide, and one or more CP1 fusion proteins non-covalently complexed to the biotinylated polysaccharide;

(32) an immunogenic complex comprising a biotinylated *S. pneumoniae* serotype 22F capsular polysaccharide, and one or more CP1 fusion proteins non-covalently complexed to the biotinylated polysaccharide;

(33) an immunogenic complex comprising a biotinylated *S. pneumoniae* serotype 23F capsular polysaccharide, and one or more CP1 fusion proteins non-covalently complexed to the biotinylated polysaccharide; and

(34) an immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises two or more (e.g., 2, 3, 4, 5, 6, 7, 8, 9, 10, 15, 20, 25, 30, 31, 32, 33, or 34) species of immunogenic complexes selected from:

(1) an immunogenic complex comprising a biotinylated *S. pneumoniae* serotype 1 capsular polysaccharide, and one or more SPP2 fusion proteins non-covalently complexed to the (2) an immunogenic complex comprising a biotinylated *S. pneumoniae* serotype 4 capsular polysaccharide, and one or more SPP2 fusion proteins non-covalently complexed to the biotinylated polysaccharide;

(3) an immunogenic complex comprising a biotinylated *S. pneumoniae* serotype 6A capsular polysaccharide, and one or more SPP2 fusion proteins non-covalently complexed to the biotinylated polysaccharide;

(4) an immunogenic complex comprising a biotinylated *S. pneumoniae* serotype 6B capsular polysaccharide, and one or more SPP2 fusion proteins non-covalently complexed to the biotinylated polysaccharide;

(5) an immunogenic complex comprising a biotinylated *S. pneumoniae* serotype 9V capsular polysaccharide, and one or more SPP2 fusion proteins non-covalently complexed to the biotinylated polysaccharide;

(6) an immunogenic complex comprising a biotinylated *S. pneumoniae* serotype 15B capsular polysaccharide, and one or more SPP2 fusion proteins non-covalently complexed to the biotinylated polysaccharide;

(7) an immunogenic complex comprising a biotinylated *S. pneumoniae* serotype 18C capsular polysaccharide, and one or more SPP2 fusion proteins non-covalently complexed to the biotinylated polysaccharide;

(8) an immunogenic complex comprising a biotinylated *S. pneumoniae* serotype 19A capsular polysaccharide, and one or more SPP2 fusion proteins non-covalently complexed to the biotinylated polysaccharide;

(9) an immunogenic complex comprising a biotinylated *S. pneumoniae* serotype 23F capsular polysaccharide, and one or more SPP2 fusion proteins non-covalently complexed to the biotinylated polysaccharide;

(10) an immunogenic complex comprising a biotinylated *S. pneumoniae* serotype 33F capsular polysaccharide, and one or more SPP2 fusion proteins non-covalently complexed to the biotinylated polysaccharide;

(11) an immunogenic complex comprising a biotinylated *S. pneumoniae* serotype 2 capsular polysaccharide, and one or more CP1 fusion proteins non-covalently complexed to the

(12) an immunogenic complex comprising a biotinylated *S. pneumoniae* serotype 3 capsular polysaccharide, and one or more CP1 fusion proteins non-covalently complexed to the biotinylated polysaccharide;

(13) an immunogenic complex comprising a biotinylated *S. pneumoniae* serotype 5 capsular polysaccharide, and one or more CP1 fusion proteins non-covalently complexed to the biotinylated polysaccharide;

(14) an immunogenic complex comprising a biotinylated *S. pneumoniae* serotype 6C capsular polysaccharide, and one or more CP1 fusion proteins non-covalently complexed to the biotinylated polysaccharide;

(15) an immunogenic complex comprising a biotinylated *S. pneumoniae* serotype 7C capsular polysaccharide, and one or more CP1 fusion proteins non-covalently complexed to the biotinylated polysaccharide;

(16) an immunogenic complex comprising a biotinylated *S. pneumoniae* serotype 7F capsular polysaccharide, and one or more CP1 fusion proteins non-covalently complexed to the biotinylated polysaccharide;

(17) an immunogenic complex comprising a biotinylated *S. pneumoniae* serotype 8 capsular polysaccharide, and one or more CP1 fusion proteins non-covalently complexed to the biotinylated polysaccharide;

(18) an immunogenic complex comprising a biotinylated *S. pneumoniae* serotype 9N capsular polysaccharide, and one or more CP1 fusion proteins non-covalently complexed to the biotinylated polysaccharide;

(19) an immunogenic complex comprising a biotinylated *S. pneumoniae* serotype 10A capsular polysaccharide, and one or more CP1 fusion proteins non-covalently complexed to the biotinylated polysaccharide;

(20) an immunogenic complex comprising a biotinylated *S. pneumoniae* serotype 11A capsular polysaccharide, and one or more CP1 fusion proteins non-covalently complexed to the biotinylated polysaccharide;

(21) an immunogenic complex comprising a biotinylated *S. pneumoniae* serotype 12F

(22) an immunogenic complex comprising a biotinylated *S. pneumoniae* serotype 14 capsular polysaccharide, and one or more CP1 fusion proteins non-covalently complexed to the biotinylated polysaccharide;

(23) an immunogenic complex comprising a biotinylated *S. pneumoniae* serotype 15A capsular polysaccharide, and one or more CP1 fusion proteins non-covalently complexed to the biotinylated polysaccharide;

(24) an immunogenic complex comprising a biotinylated *S. pneumoniae* serotype 16F capsular polysaccharide, and one or more CP1 fusion proteins non-covalently complexed to the biotinylated polysaccharide;

(25) an immunogenic complex comprising a biotinylated *S. pneumoniae* serotype 17F capsular polysaccharide, and one or more CP1 fusion proteins non-covalently complexed to the biotinylated polysaccharide;

(26) an immunogenic complex comprising a biotinylated *S. pneumoniae* serotype 19F capsular polysaccharide, and one or more CP1 fusion proteins non-covalently complexed to the biotinylated polysaccharide;

(27) an immunogenic complex comprising a biotinylated *S. pneumoniae* serotype 20B capsular polysaccharide, and one or more CP1 fusion proteins non-covalently complexed to the biotinylated polysaccharide;

(28) an immunogenic complex comprising a biotinylated *S. pneumoniae* serotype 22F capsular polysaccharide, and one or more CP1 fusion proteins non-covalently complexed to the biotinylated polysaccharide;

(29) an immunogenic complex comprising a biotinylated *S. pneumoniae* serotype 23A capsular polysaccharide, and one or more CP1 fusion proteins non-covalently complexed to the biotinylated polysaccharide;

(30) an immunogenic complex comprising a biotinylated *S. pneumoniae* serotype 23B capsular polysaccharide, and one or more CP1 fusion proteins non-covalently complexed to the biotinylated polysaccharide;

(31) an immunogenic complex comprising a biotinylated *S. pneumoniae* serotype 24F

(32) an immunogenic complex comprising a biotinylated *S. pneumoniae* serotype 31 capsular polysaccharide, and one or more CP1 fusion proteins non-covalently complexed to the biotinylated polysaccharide;

(33) an immunogenic complex comprising a biotinylated *S. pneumoniae* serotype 35B capsular polysaccharide, and one or more CP1 fusion proteins non-covalently complexed to the biotinylated polysaccharide; and

(34) an immunogenic complex comprising a biotinylated *S. pneumoniae* serotype 38 capsular polysaccharide, and one or more CP1 fusion proteins non-covalently complexed to the biotinylated polysaccharide.

In some embodiments, a vaccine composition comprises two or more (e.g., 2, 3, 4, 5, 6, 7, 8, 9, 10, 15, 20, 25, 30, 31, 32, or 33) species of immunogenic complexes selected from:

(1) an immunogenic complex comprising a biotinylated *S. pneumoniae* serotype 1 capsular polysaccharide, and one or more SPP2 fusion proteins non-covalently complexed to the biotinylated polysaccharide;

(2) an immunogenic complex comprising a biotinylated *S. pneumoniae* serotype 4 capsular polysaccharide, and one or more SPP2 fusion proteins non-covalently complexed to the biotinylated polysaccharide;

(3) an immunogenic complex comprising a biotinylated *S. pneumoniae* serotype 6A capsular polysaccharide, and one or more SPP2 fusion proteins non-covalently complexed to the biotinylated polysaccharide;

(4) an immunogenic complex comprising a biotinylated *S. pneumoniae* serotype 6B capsular polysaccharide, and one or more SPP2 fusion proteins non-covalently complexed to the biotinylated polysaccharide;

(5) an immunogenic complex comprising a biotinylated *S. pneumoniae* serotype 9V capsular polysaccharide, and one or more SPP2 fusion proteins non-covalently complexed to the biotinylated polysaccharide;

(6) an immunogenic complex comprising a biotinylated *S. pneumoniae* serotype 15B capsular polysaccharide, and one or more SPP2 fusion proteins non-covalently complexed to the (7) an immunogenic complex comprising a biotinylated *S. pneumoniae* serotype 18C capsular polysaccharide, and one or more SPP2 fusion proteins non-covalently complexed to the biotinylated polysaccharide;

(8) an immunogenic complex comprising a biotinylated *S. pneumoniae* serotype 19A capsular polysaccharide, and one or more SPP2 fusion proteins non-covalently complexed to the biotinylated polysaccharide;

(9) an immunogenic complex comprising a biotinylated *S. pneumoniae* serotype 23F capsular polysaccharide, and one or more SPP2 fusion proteins non-covalently complexed to the biotinylated polysaccharide;

(10) an immunogenic complex comprising a biotinylated *S. pneumoniae* serotype 33F capsular polysaccharide, and one or more SPP2 fusion proteins non-covalently complexed to the biotinylated polysaccharide;

(11) an immunogenic complex comprising a biotinylated *S. pneumoniae* serotype 2 capsular polysaccharide, and one or more CP1 fusion proteins non-covalently complexed to the biotinylated polysaccharide;

(12) an immunogenic complex comprising a biotinylated *S. pneumoniae* serotype 3 capsular polysaccharide, and one or more CP1 fusion proteins non-covalently complexed to the biotinylated polysaccharide;

(13) an immunogenic complex comprising a biotinylated *S. pneumoniae* serotype 5 capsular polysaccharide, and one or more CP1 fusion proteins non-covalently complexed to the biotinylated polysaccharide;

(14) an immunogenic complex comprising a biotinylated *S. pneumoniae* serotype 6C capsular polysaccharide, and one or more CP1 fusion proteins non-covalently complexed to the biotinylated polysaccharide;

(15) an immunogenic complex comprising a biotinylated *S. pneumoniae* serotype 7C capsular polysaccharide, and one or more CP1 fusion proteins non-covalently complexed to the biotinylated polysaccharide;

(16) an immunogenic complex comprising a biotinylated *S. pneumoniae* serotype 7F capsular polysaccharide, and one or more CP1 fusion proteins non-covalently complexed to the

(17) an immunogenic complex comprising a biotinylated *S. pneumoniae* serotype 8 capsular polysaccharide, and one or more CP1 fusion proteins non-covalently complexed to the biotinylated polysaccharide;

(18) an immunogenic complex comprising a biotinylated *S. pneumoniae* serotype 9N capsular polysaccharide, and one or more CP1 fusion proteins non-covalently complexed to the biotinylated polysaccharide;

(19) an immunogenic complex comprising a biotinylated *S. pneumoniae* serotype 10A capsular polysaccharide, and one or more CP1 fusion proteins non-covalently complexed to the biotinylated polysaccharide;

(20) an immunogenic complex comprising a biotinylated *S. pneumoniae* serotype 11A capsular polysaccharide, and one or more CP1 fusion proteins non-covalently complexed to the biotinylated polysaccharide;

(21) an immunogenic complex comprising a biotinylated *S. pneumoniae* serotype 12F capsular polysaccharide, and one or more CP1 fusion proteins non-covalently complexed to the biotinylated polysaccharide;

(22) an immunogenic complex comprising a biotinylated *S. pneumoniae* serotype 14 capsular polysaccharide, and one or more CP1 fusion proteins non-covalently complexed to the biotinylated polysaccharide;

(23) an immunogenic complex comprising a biotinylated *S. pneumoniae* serotype 15A capsular polysaccharide, and one or more CP1 fusion proteins non-covalently complexed to the biotinylated polysaccharide;

(24) an immunogenic complex comprising a biotinylated *S. pneumoniae* serotype 17F capsular polysaccharide, and one or more CP1 fusion proteins non-covalently complexed to the biotinylated polysaccharide;

(25) an immunogenic complex comprising a biotinylated *S. pneumoniae* serotype 19F capsular polysaccharide, and one or more CP1 fusion proteins non-covalently complexed to the biotinylated polysaccharide;

(26) an immunogenic complex comprising a biotinylated *S. pneumoniae* serotype 20B

(27) an immunogenic complex comprising a biotinylated *S. pneumoniae* serotype 22F capsular polysaccharide, and one or more CP1 fusion proteins non-covalently complexed to the biotinylated polysaccharide;

(28) an immunogenic complex comprising a biotinylated *S. pneumoniae* serotype 23A capsular polysaccharide, and one or more CP1 fusion proteins non-covalently complexed to the biotinylated polysaccharide;

(29) an immunogenic complex comprising a biotinylated *S. pneumoniae* serotype 23B capsular polysaccharide, and one or more CP1 fusion proteins non-covalently complexed to the biotinylated polysaccharide;

(30) an immunogenic complex comprising a biotinylated *S. pneumoniae* serotype 24F capsular polysaccharide, and one or more CP1 fusion proteins non-covalently complexed to the biotinylated polysaccharide;

(31) an immunogenic complex comprising a biotinylated *S. pneumoniae* serotype 31 capsular polysaccharide, and one or more CP1 fusion proteins non-covalently complexed to the biotinylated polysaccharide;

(32) an immunogenic complex comprising a biotinylated *S. pneumoniae* serotype 35B capsular polysaccharide, and one or more CP1 fusion proteins non-covalently complexed to the biotinylated polysaccharide; and

(33) an immunogenic complex comprising a biotinylated *S. pneumoniae* serotype 38 capsular polysaccharide, and one or more CP1 fusion proteins non-covalently complexed to the biotinylated polysaccharide.

In some embodiments, a vaccine composition comprises two or more (e.g., 2, 3, 4, 5, 6, 7, 8, 9, 10, 15, 20, 25, 30, 31, 32, or 33) species of immunogenic complexes selected from:

(1) an immunogenic complex comprising a biotinylated *S. pneumoniae* serotype 1 capsular polysaccharide, and one or more SPP2 fusion proteins non-covalently complexed to the biotinylated polysaccharide;

(2) an immunogenic complex comprising a biotinylated *S. pneumoniae* serotype 4 capsular polysaccharide, and one or more SPP2 fusion proteins non-covalently complexed to the (3) an immunogenic complex comprising a biotinylated *S. pneumoniae* serotype 6A capsular polysaccharide, and one or more SPP2 fusion proteins non-covalently complexed to the biotinylated polysaccharide;

(4) an immunogenic complex comprising a biotinylated *S. pneumoniae* serotype 6B capsular polysaccharide, and one or more SPP2 fusion proteins non-covalently complexed to the biotinylated polysaccharide;

(5) an immunogenic complex comprising a biotinylated *S. pneumoniae* serotype 9V capsular polysaccharide, and one or more SPP2 fusion proteins non-covalently complexed to the biotinylated polysaccharide;

(6) an immunogenic complex comprising a biotinylated *S. pneumoniae* serotype 15B capsular polysaccharide, and one or more SPP2 fusion proteins non-covalently complexed to the biotinylated polysaccharide;

(7) an immunogenic complex comprising a biotinylated *S. pneumoniae* serotype 18C capsular polysaccharide, and one or more SPP2 fusion proteins non-covalently complexed to the biotinylated polysaccharide;

(8) an immunogenic complex comprising a biotinylated *S. pneumoniae* serotype 19A capsular polysaccharide, and one or more SPP2 fusion proteins non-covalently complexed to the biotinylated polysaccharide;

(9) an immunogenic complex comprising a biotinylated *S. pneumoniae* serotype 23F capsular polysaccharide, and one or more SPP2 fusion proteins non-covalently complexed to the biotinylated polysaccharide;

(10) an immunogenic complex comprising a biotinylated *S. pneumoniae* serotype 33F capsular polysaccharide, and one or more SPP2 fusion proteins non-covalently complexed to the biotinylated polysaccharide;

(11) an immunogenic complex comprising a biotinylated *S. pneumoniae* serotype 2 capsular polysaccharide, and one or more CP1 fusion proteins non-covalently complexed to the biotinylated polysaccharide;

(12) an immunogenic complex comprising a biotinylated *S. pneumoniae* serotype 5 capsular polysaccharide, and one or more CP1 fusion proteins non-covalently complexed to the

(13) an immunogenic complex comprising a biotinylated *S. pneumoniae* serotype 6C capsular polysaccharide, and one or more CP1 fusion proteins non-covalently complexed to the biotinylated polysaccharide;

(14) an immunogenic complex comprising a biotinylated *S. pneumoniae* serotype 7C capsular polysaccharide, and one or more CP1 fusion proteins non-covalently complexed to the biotinylated polysaccharide;

(15) an immunogenic complex comprising a biotinylated *S. pneumoniae* serotype 7F capsular polysaccharide, and one or more CP1 fusion proteins non-covalently complexed to the biotinylated polysaccharide;

(16) an immunogenic complex comprising a biotinylated *S. pneumoniae* serotype 8 capsular polysaccharide, and one or more CP1 fusion proteins non-covalently complexed to the biotinylated polysaccharide;

(17) an immunogenic complex comprising a biotinylated *S. pneumoniae* serotype 9N capsular polysaccharide, and one or more CP1 fusion proteins non-covalently complexed to the biotinylated polysaccharide;

(18) an immunogenic complex comprising a biotinylated *S. pneumoniae* serotype 10A capsular polysaccharide, and one or more CP1 fusion proteins non-covalently complexed to the biotinylated polysaccharide;

(19) an immunogenic complex comprising a biotinylated *S. pneumoniae* serotype 11A capsular polysaccharide, and one or more CP1 fusion proteins non-covalently complexed to the biotinylated polysaccharide;

(20) an immunogenic complex comprising a biotinylated *S. pneumoniae* serotype 12F capsular polysaccharide, and one or more CP1 fusion proteins non-covalently complexed to the biotinylated polysaccharide;

(21) an immunogenic complex comprising a biotinylated *S. pneumoniae* serotype 14 capsular polysaccharide, and one or more CP1 fusion proteins non-covalently complexed to the biotinylated polysaccharide;

(22) an immunogenic complex comprising a biotinylated *S. pneumoniae* serotype 15A

(23) an immunogenic complex comprising a biotinylated *S. pneumoniae* serotype 16F capsular polysaccharide, and one or more CP1 fusion proteins non-covalently complexed to the biotinylated polysaccharide;

(24) an immunogenic complex comprising a biotinylated *S. pneumoniae* serotype 17F capsular polysaccharide, and one or more CP1 fusion proteins non-covalently complexed to the biotinylated polysaccharide;

(25) an immunogenic complex comprising a biotinylated *S. pneumoniae* serotype 19F capsular polysaccharide, and one or more CP1 fusion proteins non-covalently complexed to the biotinylated polysaccharide;

(26) an immunogenic complex comprising a biotinylated *S. pneumoniae* serotype 20B capsular polysaccharide, and one or more CP1 fusion proteins non-covalently complexed to the biotinylated polysaccharide;

(27) an immunogenic complex comprising a biotinylated *S. pneumoniae* serotype 22F capsular polysaccharide, and one or more CP1 fusion proteins non-covalently complexed to the biotinylated polysaccharide;

(28) an immunogenic complex comprising a biotinylated *S. pneumoniae* serotype 23A capsular polysaccharide, and one or more CP1 fusion proteins non-covalently complexed to the biotinylated polysaccharide;

(29) an immunogenic complex comprising a biotinylated *S. pneumoniae* serotype 23B capsular polysaccharide, and one or more CP1 fusion proteins non-covalently complexed to the biotinylated polysaccharide;

(30) an immunogenic complex comprising a biotinylated *S. pneumoniae* serotype 24F capsular polysaccharide, and one or more CP1 fusion proteins non-covalently complexed to the biotinylated polysaccharide;

(31) an immunogenic complex comprising a biotinylated *S. pneumoniae* serotype 31 capsular polysaccharide, and one or more CP1 fusion proteins non-covalently complexed to the biotinylated polysaccharide;

(32) an immunogenic complex comprising a biotinylated *S. pneumoniae* serotype 35B capsular polysaccharide, and one or more CP1 fusion proteins non-covalently complexed to the biotinylated polysaccharide; and

(33) an immunogenic complex comprising a biotinylated *S. pneumoniae* serotype 38 capsular polysaccharide, and one or more CP1 fusion proteins non-covalently complexed to the biotinylated polysaccharide.

In some embodiments, a vaccine composition comprises two or more (e.g., 2, 3, 4, 5, 6, 7, 8, 9, 10, 15, 20, 25, 30, 31, 32, 33, or 34) species of immunogenic complexes selected from:

(1) an immunogenic complex comprising a biotinylated *S. pneumoniae* serotype 1 capsular polysaccharide, and one or more CP1 fusion proteins non-covalently complexed to the biotinylated polysaccharide;

(2) an immunogenic complex comprising a biotinylated *S. pneumoniae* serotype 2 capsular polysaccharide, and one or more CP1 fusion proteins non-covalently complexed to the biotinylated polysaccharide;

(3) an immunogenic complex comprising a biotinylated *S. pneumoniae* serotype 3 capsular polysaccharide, and one or more CP1 fusion proteins non-covalently complexed to the biotinylated polysaccharide;

(4) an immunogenic complex comprising a biotinylated *S. pneumoniae* serotype 4 capsular polysaccharide, and one or more CP1 fusion proteins non-covalently complexed to the biotinylated polysaccharide;

(5) an immunogenic complex comprising a biotinylated *S. pneumoniae* serotype 5 capsular polysaccharide, and one or more CP1 fusion proteins non-covalently complexed to the biotinylated polysaccharide;

(6) an immunogenic complex comprising a biotinylated *S. pneumoniae* serotype 6A capsular polysaccharide, and one or more CP1 fusion proteins non-covalently complexed to the biotinylated polysaccharide;

(7) an immunogenic complex comprising a biotinylated *S. pneumoniae* serotype 6B capsular polysaccharide, and one or more CP1 fusion proteins non-covalently complexed to the biotinylated polysaccharide;

(8) an immunogenic complex comprising a biotinylated *S. pneumoniae* serotype 6C capsular polysaccharide, and one or more CP1 fusion proteins non-covalently complexed to the (9) an immunogenic complex comprising a biotinylated *S. pneumoniae* serotype 7C capsular polysaccharide, and one or more CP1 fusion proteins non-covalently complexed to the biotinylated polysaccharide;

(10) an immunogenic complex comprising a biotinylated *S. pneumoniae* serotype 7F capsular polysaccharide, and one or more CP1 fusion proteins non-covalently complexed to the biotinylated polysaccharide;

(11) an immunogenic complex comprising a biotinylated *S. pneumoniae* serotype 8 capsular polysaccharide, and one or more CP1 fusion proteins non-covalently complexed to the biotinylated polysaccharide;

(12) an immunogenic complex comprising a biotinylated *S. pneumoniae* serotype 9N capsular polysaccharide, and one or more CP1 fusion proteins non-covalently complexed to the biotinylated polysaccharide;

(13) an immunogenic complex comprising a biotinylated *S. pneumoniae* serotype 9V capsular polysaccharide, and one or more CP1 fusion proteins non-covalently complexed to the biotinylated polysaccharide;

(14) an immunogenic complex comprising a biotinylated *S. pneumoniae* serotype 10A capsular polysaccharide, and one or more CP1 fusion proteins non-covalently complexed to the biotinylated polysaccharide;

(15) an immunogenic complex comprising a biotinylated *S. pneumoniae* serotype 11A capsular polysaccharide, and one or more CP1 fusion proteins non-covalently complexed to the biotinylated polysaccharide;

(16) an immunogenic complex comprising a biotinylated *S. pneumoniae* serotype 12F capsular polysaccharide, and one or more CP1 fusion proteins non-covalently complexed to the biotinylated polysaccharide;

(17) an immunogenic complex comprising a biotinylated *S. pneumoniae* serotype 14 capsular polysaccharide, and one or more CP1 fusion proteins non-covalently complexed to the biotinylated polysaccharide;

(18) an immunogenic complex comprising a biotinylated *S. pneumoniae* serotype 15A

(19) an immunogenic complex comprising a biotinylated *S. pneumoniae* serotype 15B capsular polysaccharide, and one or more CP1 fusion proteins non-covalently complexed to the biotinylated polysaccharide;

(20) an immunogenic complex comprising a biotinylated *S. pneumoniae* serotype 16F capsular polysaccharide, and one or more CP1 fusion proteins non-covalently complexed to the biotinylated polysaccharide;

(21) an immunogenic complex comprising a biotinylated *S. pneumoniae* serotype 17F capsular polysaccharide, and one or more CP1 fusion proteins non-covalently complexed to the biotinylated polysaccharide;

(22) an immunogenic complex comprising a biotinylated *S. pneumoniae* serotype 18C capsular polysaccharide, and one or more CP1 fusion proteins non-covalently complexed to the biotinylated polysaccharide;

(23) an immunogenic complex comprising a biotinylated *S. pneumoniae* serotype 19A capsular polysaccharide, and one or more CP1 fusion proteins non-covalently complexed to the biotinylated polysaccharide;

(24) an immunogenic complex comprising a biotinylated *S. pneumoniae* serotype 19F capsular polysaccharide, and one or more CP1 fusion proteins non-covalently complexed to the biotinylated polysaccharide;

(25) an immunogenic complex comprising a biotinylated *S. pneumoniae* serotype 20B capsular polysaccharide, and one or more CP1 fusion proteins non-covalently complexed to the biotinylated polysaccharide;

(26) an immunogenic complex comprising a biotinylated *S. pneumoniae* serotype 22F capsular polysaccharide, and one or more CP1 fusion proteins non-covalently complexed to the biotinylated polysaccharide;

(27) an immunogenic complex comprising a biotinylated *S. pneumoniae* serotype 23A capsular polysaccharide, and one or more CP1 fusion proteins non-covalently complexed to the biotinylated polysaccharide;

(28) an immunogenic complex comprising a biotinylated *S. pneumoniae* serotype 23B

(29) an immunogenic complex comprising a biotinylated *S. pneumoniae* serotype 23F capsular polysaccharide, and one or more CP1 fusion proteins non-covalently complexed to the biotinylated polysaccharide;

(30) an immunogenic complex comprising a biotinylated *S. pneumoniae* serotype 24F capsular polysaccharide, and one or more CP1 fusion proteins non-covalently complexed to the biotinylated polysaccharide;

(31) an immunogenic complex comprising a biotinylated *S. pneumoniae* serotype 31 capsular polysaccharide, and one or more CP1 fusion proteins non-covalently complexed to the biotinylated polysaccharide;

(32) an immunogenic complex comprising a biotinylated *S. pneumoniae* serotype 33F capsular polysaccharide, and one or more CP1 fusion proteins non-covalently complexed to the biotinylated polysaccharide;

(33) an immunogenic complex comprising a biotinylated *S. pneumoniae* serotype 35B capsular polysaccharide, and one or more CP1 fusion proteins non-covalently complexed to the biotinylated polysaccharide; and

(34) an immunogenic complex comprising a biotinylated *S. pneumoniae* serotype 38 capsular polysaccharide, and one or more CP1 fusion proteins non-covalently complexed to the biotinylated polysaccharide.

In some embodiments, a vaccine composition comprises:

(1) a first immunogenic complex comprising a biotinylated *S. pneumoniae* serotype 6C capsular polysaccharide, and one or more SPP2 fusion proteins non-covalently complexed to the biotinylated polysaccharide;

(2) a second immunogenic complex comprising a biotinylated *S. pneumoniae* serotype 7C capsular polysaccharide, and one or more SPP2 fusion proteins non-covalently complexed to the biotinylated polysaccharide;

(3) a third immunogenic complex comprising a biotinylated *S. pneumoniae* serotype 15A capsular polysaccharide, and one or more SPP2 fusion proteins non-covalently complexed to the (4) a fourth immunogenic complex comprising a biotinylated *S. pneumoniae* serotype 16F capsular polysaccharide, and one or more SPP2 fusion proteins non-covalently complexed to the biotinylated polysaccharide;

(5) a fifth immunogenic complex comprising a biotinylated *S. pneumoniae* serotype 23A capsular polysaccharide, and one or more SPP2 fusion proteins non-covalently complexed to the biotinylated polysaccharide;

(6) a sixth immunogenic complex comprising a biotinylated *S. pneumoniae* serotype 23B capsular polysaccharide, and one or more SPP2 fusion proteins non-covalently complexed to the biotinylated polysaccharide;

(7) a seventh immunogenic complex comprising a biotinylated *S. pneumoniae* serotype 24F capsular polysaccharide, and one or more SPP2 fusion proteins non-covalently complexed to the biotinylated polysaccharide;

(8) an eighth immunogenic complex comprising a biotinylated *S. pneumoniae* serotype 31 capsular polysaccharide, and one or more SPP2 fusion proteins non-covalently complexed to the biotinylated polysaccharide;

(9) a ninth immunogenic complex comprising a biotinylated *S. pneumoniae* serotype 35B capsular polysaccharide, and one or more SPP2 fusion proteins non-covalently complexed to the biotinylated polysaccharide;

(10) a tenth immunogenic complex comprising a biotinylated *S. pneumoniae* serotype 38 capsular polysaccharide, and one or more SPP2 fusion proteins non-covalently complexed to the biotinylated polysaccharide;

(11) an eleventh immunogenic complex comprising a biotinylated *S. pneumoniae* serotype 1 capsular polysaccharide, and one or more CP1 fusion proteins non-covalently complexed to the biotinylated polysaccharide;

(12) a twelfth immunogenic complex comprising a biotinylated *S. pneumoniae* serotype 2

(13) a thirteenth immunogenic complex comprising a biotinylated *S. pneumoniae* serotype 3 capsular polysaccharide, and one or more CP1 fusion proteins non-covalently complexed to the biotinylated polysaccharide;

(14) a fourteenth immunogenic complex comprising a biotinylated *S. pneumoniae* serotype 4 capsular polysaccharide, and one or more CP1 fusion proteins non-covalently complexed to the biotinylated polysaccharide;

(15) a fifteenth immunogenic complex comprising a biotinylated *S. pneumoniae* serotype 5 capsular polysaccharide, and one or more CP1 fusion proteins non-covalently complexed to the biotinylated polysaccharide;

(16) a sixteenth immunogenic complex comprising a biotinylated *S. pneumoniae* serotype 6A capsular polysaccharide, and one or more CP1 fusion proteins non-covalently complexed to the biotinylated polysaccharide;

(17) a seventeenth immunogenic complex comprising a biotinylated *S. pneumoniae* serotype 6B capsular polysaccharide, and one or more CP1 fusion proteins non-covalently complexed to the biotinylated polysaccharide;

(18) an eighteenth immunogenic complex comprising a biotinylated *S. pneumoniae* serotype 7F capsular polysaccharide, and one or more CP1 fusion proteins non-covalently complexed to the biotinylated polysaccharide;

(19) a nineteenth immunogenic complex comprising a biotinylated *S. pneumoniae* serotype 8 capsular polysaccharide, and one or more CP1 fusion proteins non-covalently complexed to the biotinylated polysaccharide;

(20) a twentieth immunogenic complex comprising a biotinylated *S. pneumoniae* serotype 9N capsular polysaccharide, and one or more CP1 fusion proteins non-covalently complexed to the biotinylated polysaccharide;

(21) a twenty-first immunogenic complex comprising a biotinylated *S. pneumoniae* serotype 9V capsular polysaccharide, and one or more CP1 fusion proteins non-covalently complexed to the biotinylated polysaccharide;

(22) a twenty-second immunogenic complex comprising a biotinylated *S. pneumoniae* serotype 10A capsular polysaccharide, and one or more CP1 fusion proteins non-covalently complexed to the biotinylated polysaccharide;

(23) a twenty-third immunogenic complex comprising a biotinylated *S. pneumoniae* serotype 11A capsular polysaccharide, and one or more CP1 fusion proteins non-covalently complexed to the biotinylated polysaccharide;

(24) a twenty-fourth immunogenic complex comprising a biotinylated *S. pneumoniae* serotype 12F capsular polysaccharide, and one or more CP1 fusion proteins non-covalently complexed to the biotinylated polysaccharide;

(25) a twenty-fifth immunogenic complex comprising a biotinylated *S. pneumoniae* serotype 14 capsular polysaccharide, and one or more CP1 fusion proteins non-covalently complexed to the biotinylated polysaccharide;

(26) a twenty-sixth immunogenic complex comprising a biotinylated *S. pneumoniae* serotype 15B capsular polysaccharide, and one or more CP1 fusion proteins non-covalently complexed to the biotinylated polysaccharide;

(27) a twenty-seventh immunogenic complex comprising a biotinylated *S. pneumoniae* serotype 17F capsular polysaccharide, and one or more CP1 fusion proteins non-covalently complexed to the biotinylated polysaccharide;

(28) a twenty-eighth immunogenic complex comprising a biotinylated *S. pneumoniae* serotype 18C capsular polysaccharide, and one or more CP1 fusion proteins non-covalently complexed to the biotinylated polysaccharide;

(29) a twenty-ninth immunogenic complex comprising a biotinylated *S. pneumoniae* serotype 19A capsular polysaccharide, and one or more CP1 fusion proteins non-covalently complexed to the biotinylated polysaccharide;

(30) a thirtieth immunogenic complex comprising a biotinylated *S. pneumoniae* serotype 19F

(31) a thirty-first immunogenic complex comprising a biotinylated *S. pneumoniae* serotype 20B capsular polysaccharide, and one or more CP1 fusion proteins non-covalently complexed to the biotinylated polysaccharide;

(32) a thirty-second immunogenic complex comprising a biotinylated *S. pneumoniae* serotype 22F capsular polysaccharide, and one or more CP1 fusion proteins non-covalently complexed to the biotinylated polysaccharide;

(33) a thirty-third immunogenic complex comprising a biotinylated *S. pneumoniae* serotype 23F capsular polysaccharide, and one or more CP1 fusion proteins non-covalently complexed to the biotinylated polysaccharide; and

(34) a thirty-fourth immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises:

(1) a first immunogenic complex comprising a biotinylated *S. pneumoniae* serotype 1 capsular polysaccharide, and one or more SPP2 fusion proteins non-covalently complexed to the biotinylated polysaccharide;

(2) a second immunogenic complex comprising a biotinylated *S. pneumoniae* serotype 4 capsular polysaccharide, and one or more SPP2 fusion proteins non-covalently complexed to the biotinylated polysaccharide;

(3) a third immunogenic complex comprising a biotinylated *S. pneumoniae* serotype 6A capsular polysaccharide, and one or more SPP2 fusion proteins non-covalently complexed to the biotinylated polysaccharide;

(4) a fourth immunogenic complex comprising a biotinylated *S. pneumoniae* serotype 6B capsular polysaccharide, and one or more SPP2 fusion proteins non-covalently complexed to the biotinylated polysaccharide;

(5) a fifth immunogenic complex comprising a biotinylated *S. pneumoniae* serotype 9V capsular polysaccharide, and one or more SPP2 fusion proteins non-covalently complexed to the (6) a sixth immunogenic complex comprising a biotinylated *S. pneumoniae* serotype 15B capsular polysaccharide, and one or more SPP2 fusion proteins non-covalently complexed to the biotinylated polysaccharide;

(7) a seventh immunogenic complex comprising a biotinylated *S. pneumoniae* serotype 18C capsular polysaccharide, and one or more SPP2 fusion proteins non-covalently complexed to the biotinylated polysaccharide;

(8) an eighth immunogenic complex comprising a biotinylated *S. pneumoniae* serotype 19A capsular polysaccharide, and one or more SPP2 fusion proteins non-covalently complexed to the biotinylated polysaccharide;

(9) a ninth immunogenic complex comprising a biotinylated *S. pneumoniae* serotype 23F capsular polysaccharide, and one or more SPP2 fusion proteins non-covalently complexed to the biotinylated polysaccharide;

(10) a tenth immunogenic complex comprising a biotinylated *S. pneumoniae* serotype 33F capsular polysaccharide, and one or more SPP2 fusion proteins non-covalently complexed to the biotinylated polysaccharide;

(11) an eleventh immunogenic complex comprising a biotinylated *S. pneumoniae* serotype 2 capsular polysaccharide, and one or more CP1 fusion proteins non-covalently complexed to the biotinylated polysaccharide;

(12) a twelfth immunogenic complex comprising a biotinylated *S. pneumoniae* serotype 3 capsular polysaccharide, and one or more CP1 fusion proteins non-covalently complexed to the biotinylated polysaccharide;

(13) a thirteenth immunogenic complex comprising a biotinylated *S. pneumoniae* serotype 5 capsular polysaccharide, and one or more CP1 fusion proteins non-covalently complexed to the biotinylated polysaccharide;

(14) a fourteenth immunogenic complex comprising a biotinylated *S. pneumoniae* serotype 6C

(15) a fifteenth immunogenic complex comprising a biotinylated *S. pneumoniae* serotype 7C capsular polysaccharide, and one or more CP1 fusion proteins non-covalently complexed to the biotinylated polysaccharide;

(16) a sixteenth immunogenic complex comprising a biotinylated *S. pneumoniae* serotype 7F capsular polysaccharide, and one or more CP1 fusion proteins non-covalently complexed to the biotinylated polysaccharide;

(17) a seventeenth immunogenic complex comprising a biotinylated *S. pneumoniae* serotype 8 capsular polysaccharide, and one or more CP1 fusion proteins non-covalently complexed to the biotinylated polysaccharide;

(18) an eighteenth immunogenic complex comprising a biotinylated *S. pneumoniae* serotype 9N capsular polysaccharide, and one or more CP1 fusion proteins non-covalently complexed to the biotinylated polysaccharide;

(19) a nineteenth immunogenic complex comprising a biotinylated *S. pneumoniae* serotype 10A capsular polysaccharide, and one or more CP1 fusion proteins non-covalently complexed to the biotinylated polysaccharide;

(20) a twentieth immunogenic complex comprising a biotinylated *S. pneumoniae* serotype 11A capsular polysaccharide, and one or more CP1 fusion proteins non-covalently complexed to the biotinylated polysaccharide;

(21) a twenty-first immunogenic complex comprising a biotinylated *S. pneumoniae* serotype 12F capsular polysaccharide, and one or more CP1 fusion proteins non-covalently complexed to the biotinylated polysaccharide;

(22) a twenty-second immunogenic complex comprising a biotinylated *S. pneumoniae* serotype 14 capsular polysaccharide, and one or more CP1 fusion proteins non-covalently complexed to the biotinylated polysaccharide;

(23) a twenty-third immunogenic complex comprising a biotinylated *S. pneumoniae* serotype 15A capsular polysaccharide, and one or more CP1 fusion proteins non-covalently complexed to the biotinylated polysaccharide;

(24) a twenty-fourth immunogenic complex comprising a biotinylated *S. pneumoniae* serotype 16F capsular polysaccharide, and one or more CP1 fusion proteins non-covalently complexed to the biotinylated polysaccharide;

(25) a twenty-fifth immunogenic complex comprising a biotinylated *S. pneumoniae* serotype 17F capsular polysaccharide, and one or more CP1 fusion proteins non-covalently complexed to the biotinylated polysaccharide;

(26) a twenty-sixth immunogenic complex comprising a biotinylated *S. pneumoniae* serotype 19F capsular polysaccharide, and one or more CP1 fusion proteins non-covalently complexed to the biotinylated polysaccharide;

(27) a twenty-seventh immunogenic complex comprising a biotinylated *S. pneumoniae* serotype 20B capsular polysaccharide, and one or more CP1 fusion proteins non-covalently complexed to the biotinylated polysaccharide;

(28) a twenty-eighth immunogenic complex comprising a biotinylated *S. pneumoniae* serotype 22F capsular polysaccharide, and one or more CP1 fusion proteins non-covalently complexed to the biotinylated polysaccharide;

(29) a twenty-ninth immunogenic complex comprising a biotinylated *S. pneumoniae* serotype 23A capsular polysaccharide, and one or more CP1 fusion proteins non-covalently complexed to the biotinylated polysaccharide;

(30) a thirtieth immunogenic complex comprising a biotinylated *S. pneumoniae* serotype 23B capsular polysaccharide, and one or more CP1 fusion proteins non-covalently complexed to the biotinylated polysaccharide;

(31) a thirty-first immunogenic complex comprising a biotinylated *S. pneumoniae* serotype 24F capsular polysaccharide, and one or more CP1 fusion proteins non-covalently complexed to the biotinylated polysaccharide;

(32) a thirty-second immunogenic complex comprising a biotinylated *S. pneumoniae* serotype 31 capsular polysaccharide, and one or more CP1 fusion proteins non-covalently complexed to the biotinylated polysaccharide;

(33) a thirty-third immunogenic complex comprising a biotinylated *S. pneumoniae* serotype 35B capsular polysaccharide, and one or more CP1 fusion proteins non-covalently complexed to the biotinylated polysaccharide; and

(34) a thirty-fourth immunogenic complex comprising a biotinylated *S. pneumoniae* serotype 38 capsular polysaccharide, and one or more CP1 fusion proteins non-covalently complexed to the biotinylated polysaccharide.

In some embodiments, a vaccine composition comprises:

(1) a first immunogenic complex comprising a biotinylated *S. pneumoniae* serotype 1 capsular polysaccharide, and one or more SPP2 fusion proteins non-covalently complexed to the biotinylated polysaccharide;

(2) a second immunogenic complex comprising a biotinylated *S. pneumoniae* serotype 4 capsular polysaccharide, and one or more SPP2 fusion proteins non-covalently complexed to the biotinylated polysaccharide;

(3) a third immunogenic complex comprising a biotinylated *S. pneumoniae* serotype 6A capsular polysaccharide, and one or more SPP2 fusion proteins non-covalently complexed to the biotinylated polysaccharide;

(4) a fourth immunogenic complex comprising a biotinylated *S. pneumoniae* serotype 6B capsular polysaccharide, and one or more SPP2 fusion proteins non-covalently complexed to the biotinylated polysaccharide;

(5) a fifth immunogenic complex comprising a biotinylated *S. pneumoniae* serotype 9V capsular polysaccharide, and one or more SPP2 fusion proteins non-covalently complexed to the biotinylated polysaccharide;

(6) a sixth immunogenic complex comprising a biotinylated *S. pneumoniae* serotype 15B capsular polysaccharide, and one or more SPP2 fusion proteins non-covalently complexed to the biotinylated polysaccharide;

(7) a seventh immunogenic complex comprising a biotinylated *S. pneumoniae* serotype 18C capsular polysaccharide, and one or more SPP2 fusion proteins non-covalently complexed to the (8) an eighth immunogenic complex comprising a biotinylated *S. pneumoniae* serotype 19A capsular polysaccharide, and one or more SPP2 fusion proteins non-covalently complexed to the biotinylated polysaccharide;

(9) a ninth immunogenic complex comprising a biotinylated *S. pneumoniae* serotype 23F capsular polysaccharide, and one or more SPP2 fusion proteins non-covalently complexed to the biotinylated polysaccharide;

(10) a tenth immunogenic complex comprising a biotinylated *S. pneumoniae* serotype 33F capsular polysaccharide, and one or more SPP2 fusion proteins non-covalently complexed to the biotinylated polysaccharide;

(11) an eleventh immunogenic complex comprising a biotinylated *S. pneumoniae* serotype 2 capsular polysaccharide, and one or more CP1 fusion proteins non-covalently complexed to the biotinylated polysaccharide;

(12) a twelfth immunogenic complex comprising a biotinylated *S. pneumoniae* serotype 3 capsular polysaccharide, and one or more CP1 fusion proteins non-covalently complexed to the biotinylated polysaccharide;

(13) a thirteenth immunogenic complex comprising a biotinylated *S. pneumoniae* serotype 5 capsular polysaccharide, and one or more CP1 fusion proteins non-covalently complexed to the biotinylated polysaccharide;

(14) a fourteenth immunogenic complex comprising a biotinylated *S. pneumoniae* serotype 6C capsular polysaccharide, and one or more CP1 fusion proteins non-covalently complexed to the biotinylated polysaccharide;

(15) a fifteenth immunogenic complex comprising a biotinylated *S. pneumoniae* serotype 7C capsular polysaccharide, and one or more CP1 fusion proteins non-covalently complexed to the biotinylated polysaccharide;

(16) a sixteenth immunogenic complex comprising a biotinylated *S. pneumoniae* serotype 7F

(17) a seventeenth immunogenic complex comprising a biotinylated *S. pneumoniae* serotype 8 capsular polysaccharide, and one or more CP1 fusion proteins non-covalently complexed to the biotinylated polysaccharide;

(18) an eighteenth immunogenic complex comprising a biotinylated *S. pneumoniae* serotype 9N capsular polysaccharide, and one or more CP1 fusion proteins non-covalently complexed to the biotinylated polysaccharide;

(19) a nineteenth immunogenic complex comprising a biotinylated *S. pneumoniae* serotype 10A capsular polysaccharide, and one or more CP1 fusion proteins non-covalently complexed to the biotinylated polysaccharide;

(20) a twentieth immunogenic complex comprising a biotinylated *S. pneumoniae* serotype 11A capsular polysaccharide, and one or more CP1 fusion proteins non-covalently complexed to the biotinylated polysaccharide;

(21) a twenty-first immunogenic complex comprising a biotinylated *S. pneumoniae* serotype 12F capsular polysaccharide, and one or more CP1 fusion proteins non-covalently complexed to the biotinylated polysaccharide;

(22) a twenty-second immunogenic complex comprising a biotinylated *S. pneumoniae* serotype 14 capsular polysaccharide, and one or more CP1 fusion proteins non-covalently complexed to the biotinylated polysaccharide;

(23) a twenty-third immunogenic complex comprising a biotinylated *S. pneumoniae* serotype 15A capsular polysaccharide, and one or more CP1 fusion proteins non-covalently complexed to the biotinylated polysaccharide;

(24) a twenty-fourth immunogenic complex comprising a biotinylated *S. pneumoniae* serotype 17F capsular polysaccharide, and one or more CP1 fusion proteins non-covalently complexed to the biotinylated polysaccharide;

(25) a twenty-fifth immunogenic complex comprising a biotinylated *S. pneumoniae* serotype 19F capsular polysaccharide, and one or more CP1 fusion proteins non-covalently complexed to the biotinylated polysaccharide;

(26) a twenty-sixth immunogenic complex comprising a biotinylated *S. pneumoniae* serotype 20B capsular polysaccharide, and one or more CP1 fusion proteins non-covalently complexed to the biotinylated polysaccharide;

(27) a twenty-seventh immunogenic complex comprising a biotinylated *S. pneumoniae* serotype 22F capsular polysaccharide, and one or more CP1 fusion proteins non-covalently complexed to the biotinylated polysaccharide;

(28) a twenty-eighth immunogenic complex comprising a biotinylated *S. pneumoniae* serotype 23A capsular polysaccharide, and one or more CP1 fusion proteins non-covalently complexed to the biotinylated polysaccharide;

(29) a twenty-ninth immunogenic complex comprising a biotinylated *S. pneumoniae* serotype 23B capsular polysaccharide, and one or more CP1 fusion proteins non-covalently complexed to the biotinylated polysaccharide;

(30) a thirtieth immunogenic complex comprising a biotinylated *S. pneumoniae* serotype 24F capsular polysaccharide, and one or more CP1 fusion proteins non-covalently complexed to the biotinylated polysaccharide;

(31) a thirty-first immunogenic complex comprising a biotinylated *S. pneumoniae* serotype 31 capsular polysaccharide, and one or more CP1 fusion proteins non-covalently complexed to the biotinylated polysaccharide;

(32) a thirty-second immunogenic complex comprising a biotinylated *S. pneumoniae* serotype 35B capsular polysaccharide, and one or more CP1 fusion proteins non-covalently complexed to the biotinylated polysaccharide; and

(33) a thirty-third immunogenic complex comprising a biotinylated *S. pneumoniae* serotype 38 capsular polysaccharide, and one or more CP1 fusion proteins non-covalently complexed to the biotinylated polysaccharide.

In some embodiments, a vaccine composition comprises:

(1) a first immunogenic complex comprising a biotinylated *S. pneumoniae* serotype 1 capsular polysaccharide, and one or more SPP2 fusion proteins non-covalently complexed to the (2) a second immunogenic complex comprising a biotinylated *S. pneumoniae* serotype 4 capsular polysaccharide, and one or more SPP2 fusion proteins non-covalently complexed to the biotinylated polysaccharide;

(3) a third immunogenic complex comprising a biotinylated *S. pneumoniae* serotype 6A capsular polysaccharide, and one or more SPP2 fusion proteins non-covalently complexed to the biotinylated polysaccharide;

(4) a fourth immunogenic complex comprising a biotinylated *S. pneumoniae* serotype 6B capsular polysaccharide, and one or more SPP2 fusion proteins non-covalently complexed to the biotinylated polysaccharide;

(5) a fifth immunogenic complex comprising a biotinylated *S. pneumoniae* serotype 9V capsular polysaccharide, and one or more SPP2 fusion proteins non-covalently complexed to the biotinylated polysaccharide;

(6) a sixth immunogenic complex comprising a biotinylated *S. pneumoniae* serotype 15B capsular polysaccharide, and one or more SPP2 fusion proteins non-covalently complexed to the biotinylated polysaccharide;

(7) a seventh immunogenic complex comprising a biotinylated *S. pneumoniae* serotype 18C capsular polysaccharide, and one or more SPP2 fusion proteins non-covalently complexed to the biotinylated polysaccharide;

(8) an eighth immunogenic complex comprising a biotinylated *S. pneumoniae* serotype 19A capsular polysaccharide, and one or more SPP2 fusion proteins non-covalently complexed to the biotinylated polysaccharide;

(9) a ninth immunogenic complex comprising a biotinylated *S. pneumoniae* serotype 23F capsular polysaccharide, and one or more SPP2 fusion proteins non-covalently complexed to the biotinylated polysaccharide;

(10) a tenth immunogenic complex comprising a biotinylated *S. pneumoniae* serotype 33F capsular polysaccharide, and one or more SPP2 fusion proteins non-covalently complexed to the

(11) an eleventh immunogenic complex comprising a biotinylated *S. pneumoniae* serotype 2 capsular polysaccharide, and one or more CP1 fusion proteins non-covalently complexed to the biotinylated polysaccharide;

(12) a twelfth immunogenic complex comprising a biotinylated *S. pneumoniae* serotype 5 capsular polysaccharide, and one or more CP1 fusion proteins non-covalently complexed to the biotinylated polysaccharide;

(13) a thirteenth immunogenic complex comprising a biotinylated *S. pneumoniae* serotype 6C capsular polysaccharide, and one or more CP1 fusion proteins non-covalently complexed to the biotinylated polysaccharide;

(14) a fourteenth immunogenic complex comprising a biotinylated *S. pneumoniae* serotype 7C capsular polysaccharide, and one or more CP1 fusion proteins non-covalently complexed to the biotinylated polysaccharide;

(15) a fifteenth immunogenic complex comprising a biotinylated *S. pneumoniae* serotype 7F capsular polysaccharide, and one or more CP1 fusion proteins non-covalently complexed to the biotinylated polysaccharide;

(16) a sixteenth immunogenic complex comprising a biotinylated *S. pneumoniae* serotype 8 capsular polysaccharide, and one or more CP1 fusion proteins non-covalently complexed to the biotinylated polysaccharide;

(17) a seventeenth immunogenic complex comprising a biotinylated *S. pneumoniae* serotype 9N capsular polysaccharide, and one or more CP1 fusion proteins non-covalently complexed to the biotinylated polysaccharide;

(18) an eighteenth immunogenic complex comprising a biotinylated *S. pneumoniae* serotype 10A capsular polysaccharide, and one or more CP1 fusion proteins non-covalently complexed to the biotinylated polysaccharide;

(19) a nineteenth immunogenic complex comprising a biotinylated *S. pneumoniae* serotype 11A capsular polysaccharide, and one or more CP1 fusion proteins non-covalently complexed to the biotinylated polysaccharide;

(20) a twentieth immunogenic complex comprising a biotinylated *S. pneumoniae* serotype 12F capsular polysaccharide, and one or more CP1 fusion proteins non-covalently complexed to the biotinylated polysaccharide;

(21) a twenty-first immunogenic complex comprising a biotinylated *S. pneumoniae* serotype 14 capsular polysaccharide, and one or more CP1 fusion proteins non-covalently complexed to the biotinylated polysaccharide;

(22) a twenty-second immunogenic complex comprising a biotinylated *S. pneumoniae* serotype 15A capsular polysaccharide, and one or more CP1 fusion proteins non-covalently complexed to the biotinylated polysaccharide;

(23) a twenty-third immunogenic complex comprising a biotinylated *S. pneumoniae* serotype 16F capsular polysaccharide, and one or more CP1 fusion proteins non-covalently complexed to the biotinylated polysaccharide;

(24) a twenty-fourth immunogenic complex comprising a biotinylated *S. pneumoniae* serotype 17F capsular polysaccharide, and one or more CP1 fusion proteins non-covalently complexed to the biotinylated polysaccharide;

(25) a twenty-fifth immunogenic complex comprising a biotinylated *S. pneumoniae* serotype 19F capsular polysaccharide, and one or more CP1 fusion proteins non-covalently complexed to the biotinylated polysaccharide;

(26) a twenty-sixth immunogenic complex comprising a biotinylated *S. pneumoniae* serotype 20B capsular polysaccharide, and one or more CP1 fusion proteins non-covalently complexed to the biotinylated polysaccharide;

(27) a twenty-seventh immunogenic complex comprising a biotinylated *S. pneumoniae* serotype 22F capsular polysaccharide, and one or more CP1 fusion proteins non-covalently complexed to the biotinylated polysaccharide;

(28) a twenty-eighth immunogenic complex comprising a biotinylated *S. pneumoniae* serotype 23A capsular polysaccharide, and one or more CP1 fusion proteins non-covalently complexed to the biotinylated polysaccharide;

(29) a twenty-ninth immunogenic complex comprising a biotinylated *S. pneumoniae* serotype 23B capsular polysaccharide, and one or more CP1 fusion proteins non-covalently complexed to the biotinylated polysaccharide;

(30) a thirtieth immunogenic complex comprising a biotinylated *S. pneumoniae* serotype 24F capsular polysaccharide, and one or more CP1 fusion proteins non-covalently complexed to the biotinylated polysaccharide;

(31) a thirty-first immunogenic complex comprising a biotinylated *S. pneumoniae* serotype 31 capsular polysaccharide, and one or more CP1 fusion proteins non-covalently complexed to the biotinylated polysaccharide;

(32) a thirty-second immunogenic complex comprising a biotinylated *S. pneumoniae* serotype 35B capsular polysaccharide, and one or more CP1 fusion proteins non-covalently complexed to the biotinylated polysaccharide; and

(33) a thirty-third immunogenic complex comprising a biotinylated *S. pneumoniae* serotype 38 capsular polysaccharide, and one or more CP1 fusion proteins non-covalently complexed to the biotinylated polysaccharide.

In some embodiments, a vaccine composition comprises:

(1) a first immunogenic complex comprising a biotinylated *S. pneumoniae* serotype 1 capsular polysaccharide, and one or more CP1 fusion proteins non-covalently complexed to the biotinylated polysaccharide;

(2) a second immunogenic complex comprising a biotinylated *S. pneumoniae* serotype 2 capsular polysaccharide, and one or more CP1 fusion proteins non-covalently complexed to the biotinylated polysaccharide;

(3) a third immunogenic complex comprising a biotinylated *S. pneumoniae* serotype 3 capsular polysaccharide, and one or more CP1 fusion proteins non-covalently complexed to the biotinylated polysaccharide;

(4) a fourth immunogenic complex comprising a biotinylated *S. pneumoniae* serotype 4

(5) a fifth immunogenic complex comprising a biotinylated *S. pneumoniae* serotype 5 capsular polysaccharide, and one or more CP1 fusion proteins non-covalently complexed to the biotinylated polysaccharide;

(6) a sixth immunogenic complex comprising a biotinylated *S. pneumoniae* serotype 6A capsular polysaccharide, and one or more CP1 fusion proteins non-covalently complexed to the biotinylated polysaccharide;

(7) a seventh immunogenic complex comprising a biotinylated *S. pneumoniae* serotype 6B capsular polysaccharide, and one or more CP1 fusion proteins non-covalently complexed to the biotinylated polysaccharide;

(8) an eighth immunogenic complex comprising a biotinylated *S. pneumoniae* serotype 6C capsular polysaccharide, and one or more SPP2 fusion proteins non-covalently complexed to the biotinylated polysaccharide;

(9) a ninth immunogenic complex comprising a biotinylated *S. pneumoniae* serotype 7C capsular polysaccharide, and one or more SPP2 fusion proteins non-covalently complexed to the biotinylated polysaccharide;

(10) a tenth immunogenic complex comprising a biotinylated *S. pneumoniae* serotype 7F capsular polysaccharide, and one or more CP1 fusion proteins non-covalently complexed to the biotinylated polysaccharide;

(11) an eleventh immunogenic complex comprising a biotinylated *S. pneumoniae* serotype 8 capsular polysaccharide, and one or more CP1 fusion proteins non-covalently complexed to the biotinylated polysaccharide;

(12) a twelfth immunogenic complex comprising a biotinylated *S. pneumoniae* serotype 9N capsular polysaccharide, and one or more CP1 fusion proteins non-covalently complexed to the biotinylated polysaccharide;

(13) a thirteenth immunogenic complex comprising a biotinylated *S. pneumoniae* serotype 9V

(14) a fourteenth immunogenic complex comprising a biotinylated *S. pneumoniae* serotype 10A capsular polysaccharide, and one or more CP1 fusion proteins non-covalently complexed to the biotinylated polysaccharide;

(15) a fifteenth immunogenic complex comprising a biotinylated *S. pneumoniae* serotype 11A capsular polysaccharide, and one or more CP1 fusion proteins non-covalently complexed to the biotinylated polysaccharide;

(16) a sixteenth immunogenic complex comprising a biotinylated *S. pneumoniae* serotype 12F capsular polysaccharide, and one or more CP1 fusion proteins non-covalently complexed to the biotinylated polysaccharide;

(17) a seventeenth immunogenic complex comprising a biotinylated *S. pneumoniae* serotype 14 capsular polysaccharide, and one or more CP1 fusion proteins non-covalently complexed to the biotinylated polysaccharide;

(18) an eighteenth immunogenic complex comprising a biotinylated *S. pneumoniae* serotype 15A capsular polysaccharide, and one or more SPP2 fusion proteins non-covalently complexed to the biotinylated polysaccharide;

(19) a nineteenth immunogenic complex comprising a biotinylated *S. pneumoniae* serotype 15B capsular polysaccharide, and one or more CP1 fusion proteins non-covalently complexed to the biotinylated polysaccharide;

(20) a twentieth immunogenic complex comprising a biotinylated *S. pneumoniae* serotype 16F capsular polysaccharide, and one or more SPP2 fusion proteins non-covalently complexed to the biotinylated polysaccharide;

(21) a twenty-first immunogenic complex comprising a biotinylated *S. pneumoniae* serotype 17F capsular polysaccharide, and one or more CP1 fusion proteins non-covalently complexed to the biotinylated polysaccharide;

(22) a twenty-second immunogenic complex comprising a biotinylated *S. pneumoniae* serotype 18C capsular polysaccharide, and one or more CP1 fusion proteins non-covalently

(23) a twenty-third immunogenic complex comprising a biotinylated *S. pneumoniae* serotype 19A capsular polysaccharide, and one or more CP1 fusion proteins non-covalently complexed to the biotinylated polysaccharide;

(24) a twenty-fourth immunogenic complex comprising a biotinylated *S. pneumoniae* serotype 19F capsular polysaccharide, and one or more CP1 fusion proteins non-covalently complexed to the biotinylated polysaccharide;

(25) a thirty-fifth immunogenic complex comprising a biotinylated *S. pneumoniae* serotype 20B capsular polysaccharide, and one or more CP1 fusion proteins non-covalently complexed to the biotinylated polysaccharide;

(26) a thirty-sixth immunogenic complex comprising a biotinylated *S. pneumoniae* serotype 22F capsular polysaccharide, and one or more CP1 fusion proteins non-covalently complexed to the biotinylated polysaccharide;

(27) a twenty-seventh immunogenic complex comprising a biotinylated *S. pneumoniae* serotype 23A capsular polysaccharide, and one or more SPP2 fusion proteins non-covalently complexed to the biotinylated polysaccharide;

(28) a twenty-eighth immunogenic complex comprising a biotinylated *S. pneumoniae* serotype 23B capsular polysaccharide, and one or more SPP2 fusion proteins non-covalently complexed to the biotinylated polysaccharide;

(29) a twenty-ninth immunogenic complex comprising a biotinylated *S. pneumoniae* serotype 23F capsular polysaccharide, and one or more CP1 fusion proteins non-covalently complexed to the biotinylated polysaccharide;

(30) a thirtieth immunogenic complex comprising a biotinylated *S. pneumoniae* serotype 24F capsular polysaccharide, and one or more SPP2 fusion proteins non-covalently complexed to the biotinylated polysaccharide;

(31) an thirty-first immunogenic complex comprising a biotinylated *S. pneumoniae* serotype 31 capsular polysaccharide, and one or more SPP2 fusion proteins non-covalently complexed to the biotinylated polysaccharide;

(32) a thirty-second immunogenic complex comprising a biotinylated *S. pneumoniae* serotype 33F capsular polysaccharide, and one or more CP1 fusion proteins non-covalently complexed to the biotinylated polysaccharide;

(33) a thirty-third immunogenic complex comprising a biotinylated *S. pneumoniae* serotype 35B capsular polysaccharide, and one or more SPP2 fusion proteins non-covalently complexed to the biotinylated polysaccharide; and

(34) a thirty-fourth immunogenic complex comprising a biotinylated *S. pneumoniae* serotype 38 capsular polysaccharide, and one or more SPP2 fusion proteins non-covalently complexed to the biotinylated polysaccharide.

Conjugated Immunogenic Complexes; Immunogenic Compositions (e.g., Vaccine Compositions) Comprising Same As described herein, a conjugated immunogenic complex comprises one or more polypeptides described herein (e.g., antigenic polypeptides, fusion proteins, or carrier proteins) conjugated (e.g., covalently conjugated) to one or more antigenic polysaccharides described herein. In some embodiments, one or more conjugated polysaccharides comprise a capsular polysaccharide of *S. pneumoniae* (e.g., ones described herein). In some embodiments, one or more polypeptides of conjugated immunogenic complex comprise a carrier protein (e.g., ones described herein). In some embodiments, one or more polypeptides of conjugated immunogenic complex comprise an antigenic polypeptide of *S. pneumoniae* (e.g., ones described herein). In some embodiments, one or more polypeptides of conjugated immunogenic complex comprise a fusion protein (e.g., ones described herein). In some such embodiments, a fusion protein of a conjugated immunogenic complex is or comprises SPP2 fusion protein. In some such embodiments, a fusion protein of a conjugated immunogenic complex is or comprises CP1 fusion protein. In some embodiments, an antigenic polypeptide or a fusion protein of a conjugated immunogenic complex is or comprises a carrier protein.

In some embodiments, a conjugated immunogenic complex comprises one or more *S. pneumoniae* capsular polysaccharides from, or derived from, one or more *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48. In some embodiments, a conjugated immunogenic complex comprises one or more *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, a conjugated immunogenic complex comprises one or more *S. pneumoniae* capsular polysaccharides from, or derived from, one or more *S. pneumoniae* serotypes selected from a group that includes 30, 31, 32, or 33 serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, a conjugated immunogenic complex comprises one or more *S. pneumoniae* capsular polysaccharides from, or derived from, one or more *S. pneumoniae* serotypes selected from a group that does not include one or more of serotypes 3, 16F, and 31. In some embodiments, a conjugated immunogenic complex comprises one or more *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38. In some embodiments, a conjugated immunogenic complex comprises one or more *S. pneumoniae* capsular polysaccharides from, or derived from, one or more *S. pneumoniae* serotypes selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, a conjugated immunogenic complex comprises:

(a) one or more carrier proteins described herein; and (b) one or more *S. pneumoniae* capsular polysaccharides from, or derived from, one or more (e.g., at least 1, 2, 3, 4, 5, 6, 7, 8, 9, 10, 15, 20, 25, 30, 31, 32, 33, 34, or more) *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more SPP2 proteins are covalently attached to the one or more polysaccharides.

In some embodiments, a conjugated immunogenic complex comprises:

(a) one or more carrier proteins described herein; and (b) one or more (e.g., at least 1, 2, 3, 4, 5, 6, 7, 8, 9, 10, 15, 20, 25, 30, 31, 32, 33, or 34) *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, wherein the one or more SPP2 proteins are covalently attached to the one or more polysaccharides.

In some embodiments, a conjugated immunogenic complex comprises:

(a) one or more carrier proteins described herein; and (b) one or more (e.g., at least 1, 2, 3, 4, 5, 6, 7, 8, 9, 10, 15, 20, 25, 30, 31, 32, or 33) *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38, wherein the one or more SPP2 proteins are covalently attached to the one or more polysaccharides.

In some embodiments, a conjugated immunogenic complex comprises:

(a) one or more carrier proteins described herein; and (b) one or more (e.g., at least 1, 2, 3, 4, 5, 6, 7, 8, 9, 10, 15, 20, 25, 30, 31, 32, or 33) *S. pneumoniae* capsular polysaccharides from, or derived from, one or more *S.*

*pneumoniae* serotypes selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, wherein the one or more SPP2 proteins are covalently attached to the one or more polysaccharides.

In some embodiments, a conjugated immunogenic complex comprises:

(a) one or more SPP2 proteins; and (b) one or more *S. pneumoniae* capsular polysaccharides from, or derived from, one or more (e.g., at least 1, 2, 3, 4, 5, 6, 7, 8, 9, 10, 15, 20, 25, 30, 31, 32, 33, 34, or more) *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more SPP2 proteins are covalently attached to the one or more polysaccharides.

In some embodiments, a conjugated immunogenic complex comprises:

(a) one or more SPP2 proteins; and (b) one or more (e.g., at least 1, 2, 3, 4, 5, 6, 7, 8, 9, 10, 15, 20, 25, 30, 31, 32, 33, or 34) *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, wherein the one or more SPP2 proteins are covalently attached to the one or more polysaccharides.

In some embodiments, a conjugated immunogenic complex comprises:

(a) one or more SPP2 proteins; and (b) one or more (e.g., at least 1, 2, 3, 4, 5, 6, 7, 8, 9, 10, 15, 20, 25, 30, 31, 32, or 33) *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38, wherein the one or more SPP2 proteins are covalently attached to the one or more polysaccharides.

In some embodiments, a conjugated immunogenic complex comprises:

(a) one or more SPP2 proteins; and (b) one or more (e.g., at least 1, 2, 3, 4, 5, 6, 7, 8, 9, 10, 15, 20, 25, 30, 31, 32, or 33) *S. pneumoniae* capsular polysaccharides from, or derived from, one or more *S. pneumoniae* serotypes selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, wherein the one or more SPP2 proteins are covalently attached to the one or more polysaccharides.

In some embodiments, an immunogenic composition comprises one or more conjugated immunogenic complexes comprising:

(a) one or more SPP2 proteins; and (b) one or more first *S. pneumoniae* capsular polysaccharides from, or derived from, one or more *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more SPP2 proteins are covalently attached to the one or more first polysaccharides; or (c) one or more CP1 proteins; and (d) one or more second *S. pneumoniae* capsular polysaccharides from, or derived from, one or more *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more CP1 proteins are covalently attached to the one or more second polysaccharides.

In some embodiments, an immunogenic composition comprises one or more conjugated immunogenic complexes comprising:

(a) one or more SPP2 proteins; and (b) one or more first *S. pneumoniae* capsular polysaccharides from, or derived from, one or more *S. pneumoniae* serotypes selected from 6C, 7C, 15A, 16F, 23A, 23B, 24F, 31, 35B, and 38, wherein the one or more SPP2 proteins are covalently attached to the one or more first polysaccharides; or (c) one or more CP1 proteins; and (d) one or more second *S. pneumoniae* capsular polysaccharides from, or derived from, one or more *S. pneumoniae* serotypes selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, wherein the one or more CP1 proteins are covalently attached to the one or more second polysaccharides.

In some embodiments, an immunogenic composition comprises one or more conjugated immunogenic complexes comprising:

(a) one or more SPP2 proteins; and (b) one or more first *S. pneumoniae* capsular polysaccharides from, or derived from, one or more *S. pneumoniae* serotypes selected from 1, 4, 6A, 6B, 9V, 15B, 18C, 19A, 23F, and 33F, wherein the one or more SPP2 proteins are covalently attached to the one or more first polysaccharides; or (c) one or more CP1 proteins; and (d) one or more second *S. pneumoniae* capsular polysaccharides from, or derived from, one or more *S. pneumoniae* serotypes selected from 2, 3, 5, 6C, 7C, 7F, 8, 9N, 10A, 11A, 12F, 14, 15A, 16F, 17F, 19F, 20B, 22F, 23A, 23B, 24F, 31, 35B, and 38, wherein the one or more CP1 proteins are covalently attached to the one or more second polysaccharides.

In some embodiments, an immunogenic composition comprises one or more conjugated immunogenic complexes comprising:

(a) one or more SPP2 proteins; and
(b) one or more first *S. pneumoniae* capsular polysaccharides from, or derived from, one or more *S. pneumoniae* serotypes selected from 1, 4, 6A, 6B, 9V, 15B, 18C, 19A, 23F, and 33F, wherein the one or more SPP2 proteins are covalently attached to the one or more first polysaccharides; or
(c) one or more CP1 proteins; and
(d) one or more second *S. pneumoniae* capsular polysaccharides from, or derived from, one or more *S. pneumoniae* serotypes selected from 2, 3, 5, 6C, 7C, 7F, 8, 9N, 10A, 11A, 12F, 14, 15A, 17F, 19F, 20B, 22F, 23A, 23B, 24F, 31, 35B, and 38, wherein the one or more CP1 proteins are covalently attached to the one or more second polysaccharides.

In some embodiments, an immunogenic composition comprises one or more conjugated immunogenic complexes comprising:

(a) one or more SPP2 proteins; and
(b) one or more first *S. pneumoniae* capsular polysaccharides from, or derived from, one or more *S. pneumoniae* serotypes selected from 1, 4, 6A, 6B, 9V, 15B, 18C, 19A, 23F, and 33F, wherein the one or more SPP2 proteins are covalently attached to the one or more first polysaccharides; or
(c) one or more CP1 proteins; and
(d) one or more second *S. pneumoniae* capsular polysaccharides from, or derived from, one or more *S. pneumoniae* serotypes selected from 2, 5, 6C, 7C, 7F, 8, 9N, 10A, 11A, 12F, 14, 15A, 16F, 17F, 19F, 20B, 22F, 23A, 23B, 24F, 31, 35B, and 38, wherein the one or more CP1 proteins are covalently attached to the one or more second polysaccharides.

In some embodiments, an immunogenic composition comprises one or more conjugated immunogenic complexes comprising:

(a) one or more CP1 proteins; and
(b) one or more *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, wherein the one or more CP1 proteins are covalently attached to the one or more polysaccharides.

In some embodiments, a vaccine composition comprises one or more conjugated immunogenic complexes comprising:

(a) one or more SPP2 proteins; and
(b) one or more first *S. pneumoniae* capsular polysaccharides from, or derived from, one or more *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more SPP2 proteins are covalently attached to the one or more first polysaccharides; or
(c) one or more CP1 proteins; and
(d) one or more second *S. pneumoniae* capsular polysaccharides from, or derived from, one or more *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more CP1 proteins are covalently attached to the one or more second polysaccharides.

In some embodiments, a vaccine composition comprises one or more conjugated immunogenic complexes comprising:

(a) one or more SPP2 proteins; and
(b) one or more first *S. pneumoniae* capsular polysaccharides from, or derived from, one or more *S. pneumoniae* serotypes selected from 6C, 7C, 15A, 16F, 23A, 23B, 24F, 31, 35B, and 38, wherein the one or more SPP2 proteins are covalently attached to the one or more first polysaccharides; or
(c) one or more CP1 proteins; and
(d) one or more second *S. pneumoniae* capsular polysaccharides from, or derived from, one or more *S. pneumoniae* serotypes selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, wherein the one or more CP1 proteins are covalently attached to the one or more second polysaccharides.

In some embodiments, a vaccine composition comprises one or more conjugated immunogenic complexes comprising:

(a) one or more SPP2 proteins; and
(b) one or more first *S. pneumoniae* capsular polysaccharides from, or derived from, one or more *S. pneumoniae* serotypes selected from 1, 4, 6A, 6B, 9V, 15B, 18C, 19A, 23F, and 33F, wherein the one or more SPP2 proteins are covalently attached to the one or more first polysaccharides; or
(c) one or more CP1 proteins; and
(d) one or more second *S. pneumoniae* capsular polysaccharides from, or derived from, one or more *S. pneumoniae* serotypes selected from 2, 3, 5, 6C, 7C, 7F, 8, 9N, 10A, 11A, 12F, 14, 15A, 16F, 17F, 19F, 20B, 22F, 23A, 23B, 24F, 31, 35B, and 38, wherein the one or more CP1 proteins are covalently attached to the one or more second polysaccharides.

In some embodiments, a vaccine composition comprises one or more conjugated immunogenic complexes comprising:

(a) one or more SPP2 proteins; and
(b) one or more first *S. pneumoniae* capsular polysaccharides from, or derived from, one or more *S. pneumoniae* serotypes selected from 1, 4, 6A, 6B, 9V, 15B, 18C, 19A, 23F, and 33F, wherein the one or more SPP2 proteins are covalently attached to the one or more first polysaccharides; or
(c) one or more CP1 proteins; and
(d) one or more second *S. pneumoniae* capsular polysaccharides from, or derived from, one or more *S. pneumoniae* serotypes selected from 2, 3, 5, 6C, 7C, 7F, 8, 9N, 10A, 11A, 12F, 14, 15A, 17F, 19F, 20B, 22F, 23A, 23B, 24F, 31, 35B, and 38, wherein the one or more CP1 proteins are covalently attached to the one or more second polysaccharides.

In some embodiments, a vaccine composition comprises one or more conjugated immunogenic complexes comprising:

(a) one or more SPP2 proteins; and
(b) one or more first *S. pneumoniae* capsular polysaccharides from, or derived from, one or more *S. pneumoniae* serotypes selected from 1, 4, 6A, 6B, 9V, 15B, 18C, 19A, 23F, and 33F, wherein the one or more SPP2 proteins are covalently attached to the one or more first polysaccharides; or
(c) one or more CP1 proteins; and
(d) one or more second *S. pneumoniae* capsular polysaccharides from, or derived from, one or more *S. pneumoniae* serotypes selected from 2, 5, 6C, 7C, 7F, 8, 9N, 10A, 11A, 12F, 14, 15A, 16F, 17F, 19F, 20B, 22F, 23A, 23B, 24F, 31, 35B, and 38, wherein the one or more CP1 proteins are covalently attached to the one or more second polysaccharides.

In some embodiments, a vaccine composition comprises one or more conjugated immunogenic complexes comprising:

(a) one or more CP1 proteins; and
(b) one or more *S. pneumoniae* capsular polysaccharides from, or derived from, one or more *S. pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, wherein the one or more CP1 proteins are covalently attached to the one or more polysaccharides.

Uses of Immunogenic Compositions (e.g., Vaccine Compositions)

In some embodiments, an immunogenic complex or an immunogenic composition (e.g., vaccine) described herein that includes one or more antigenic polysaccharides is characterized in that one or more of the opsonization potential, or immune response to one or more antigenic polysaccharides is increased relative to a predetermined level, as measured by ELISA and or by a functional antibody assay. In some embodiments, one or more of the opsonization potential, immune response to the one or more antigenic polysaccharides is increased at least 1-fold, 2-fold, 3-fold, 4-fold, or 5-fold relative to a predetermined level, as measured by ELISA and or by a functional antibody assay. In some embodiments, the predetermined level is a pre-immune level. In some embodiments, the predetermined level is a pre-immune level. In some embodiments, one or more polypeptide antigens are carrier proteins for one or more antigenic polysaccharides.

In some embodiments, an immunogenic complex or an immunogenic composition (e.g., vaccine) described herein, upon administration to a subject, induces an immune response against one or more pathogens in the subject at a level greater than a composition comprising an antigenic polysaccharide alone. In some embodiments, an immunogenic complex or an immunogenic composition (e.g., vaccine) described herein, upon administration to a subject, induces an immune response against one or more pathogens in the subject at a level greater than a composition comprising a polypeptide antigen alone. In some embodiments, an immunogenic complex or an immunogenic composition (e.g., vaccine) described herein, upon administration to a subject, induces a protective immune response.

In some embodiments, an immunogenic complex or an immunogenic composition (e.g., vaccine) described herein, upon administration to a subject, induces an immune response against *S. pneumoniae*. In some embodiments, an immunogenic complex or an immunogenic composition (e.g., vaccine) described herein, upon administration to a subject, induces an immune response against one or more serotypes of *S. pneumoniae*. In some embodiments, such an immune response may be directed against one or more (e.g., 1, 2, 3, 4, 5, 6, 7, 8, 9, 10 or more) serotypes of *Streptococcus pneumoniae*, wherein an immunogenic complex or an immunogenic composition (e.g., vaccine) described herein includes polysaccharide(s) present in at least one or more (e.g., 1, 2, 3, 4, 5, 6, 7, 8, 9, 10 or more) of such serotype(s). In some embodiments, such an immune response may be directed against one or more (e.g., 1, 2, 3, 4, 5, 6, 7, 8, 9, 10 or more) serotypes of *Streptococcus pneumoniae*, wherein an immunogenic complex or an immunogenic composition (e.g., vaccine) described herein does not include polysaccharide(s) present in at least one or more (e.g., 1, 2, 3, 4, 5, 6, 7, 8, 9, 10 or more) of such serotype(s). In some embodiments, such an immune response may be directed against two or more (e.g., 2, 3, 4, 5, 6, 7, 8, 9, 10 or more) serotypes of *Streptococcus pneumoniae*, wherein an immunogenic complex or an immunogenic composition (e.g., vaccine) described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, an immunogenic complex or an immunogenic composition (e.g., vaccine) described herein, upon administration to a subject, induces a protective immune response against one or more serotypes of *S. pneumoniae*. In some embodiments, such a protective response may be directed against one or more (e.g., 1, 2, 3, 4, 5, 6, 7, 8, 9, 10 or more) serotypes of *Streptococcus pneumoniae*, wherein an immunogenic complex or an immunogenic composition (e.g., vaccine) described herein includes polysaccharide(s) present in at least one or more (e.g., 1, 2, 3, 4, 5, 6, 7, 8, 9, 10 or more) of such serotype(s). In some embodiments, such a protective response may be directed against one or more (e.g., 1, 2, 3, 4, 5, 6, 7, 8, 9, 10 or more) serotypes of *Streptococcus pneumoniae*, wherein an immunogenic complex or an immunogenic composition (e.g., vaccine) described herein does not include polysaccharide(s) present in at least one or more (e.g., 1, 2, 3, 4, 5, 6, 7, 8, 9, 10 or more) of such serotype(s). In some embodiments, such a protective response may be directed against two or more (e.g., 2, 3, 4, 5, 6, 7, 8, 9, 10 or more) serotypes of *Streptococcus pneumoniae*, wherein an immunogenic complex or an immunogenic composition (e.g., vaccine) described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, the immune response is an antibody or B cell response. In some embodiments, the immune response is a T cell response. In some embodiments, the immune response is an innate immune response. In some embodiments, the immune response is a CD4+ T cell response, including $T_H1$, $T_H2$, or $T_H17$ response, or a CD8+ T cell response, or a CD4+ and CD8+ T cell response, or a CD4−/CD8− T cell response. In some embodiments, the immune response is an antibody or B cell response, and a T cell response. In some embodiments, the immune response is an antibody or B cell response, a T cell response, and an innate immune response. In some embodiments, the immune response is a protective immune response.

In some embodiments, an immunogenic complex or an immunogenic composition (e.g., vaccine) described herein, upon administration to a subject, induces antibody production against one or more pathogens in the subject at a level greater than a composition comprising an antigenic polysaccharide alone. In some embodiments, an immunogenic complex or an immunogenic composition (e.g., vaccine) described herein, upon administration to a subject, induces antibody production against one or more pathogens in the subject at level greater than a composition comprising a polypeptide antigen alone.

In some embodiments, an immunogenic composition (e.g., vaccine) described herein, upon administration to a subject, induces an immune response against one or more pathogens in the subject at a level greater than a composition comprising an antigenic polysaccharide alone. In some embodiments, an immunogenic composition (e.g., vaccine) described herein, upon administration to a subject, induces an immune response against one or more pathogens in the subject at a level greater than a composition comprising a polypeptide antigen alone. In some embodiments, an immunogenic complex or an immunogenic composition (e.g., vaccine) described herein, upon administration to a subject, induces a protective immune response.

The *S. pneumoniae* immunogenic compositions and vaccines described herein may be used for prophylactic and/or therapeutic treatment of *S. pneumoniae*. Accordingly, this application provides a method for immunizing a subject suffering from or susceptible to *S. pneumoniae* infection, comprising administering an immunologically effective amount of any of the immunogenic compositions or vaccine formulations described herein. The subject receiving the vaccination may be a male or a female, and may be an infant, child, adolescent, or adult. In some embodiments, the subject being treated is a human. In other embodiments, the subject is a non-human animal. In some embodiments, an immunogenic complex or an immunogenic composition (e.g., vaccine) described herein, upon administration to a subject, induces a protective immune response against one or more serotypes of *S. pneumoniae.*

In prophylactic embodiments, an immunogenic composition described herein (including, e.g., vaccine composition (e.g., ones as described and/or utilized herein)) is administered to a subject to induce an immune response that can help protect against the establishment of *S. pneumoniae*, for example by protecting against colonization, the first and necessary step in disease. In some embodiments, such an immune response may be directed against one or more (e.g., 1, 2, 3, 4, 5, 6, 7, 8, 9, 10 or more) serotypes of *Streptococcus pneumoniae*, wherein an immunogenic composition described herein (including, e.g., vaccine composition (e.g., ones as described and/or utilized herein)) includes polysaccharide(s) present in at least one or more (e.g., 1, 2, 3, 4, 5, 6, 7, 8, 9, 10 or more) of such serotype(s). In some embodiments, such an immune response may be directed against one or more (e.g., 1, 2, 3, 4, 5, 6, 7, 8, 9, 10 or more) serotypes of *Streptococcus pneumoniae*, wherein an immunogenic composition described herein (including, e.g., vaccine composition (e.g., ones as described and/or utilized herein)) does not include polysaccharide(s) present in at least one or more (e.g., 1, 2, 3, 4, 5, 6, 7, 8, 9, 10 or more) of such serotype(s) (non-vaccine types, NVTs). In some embodiments, such an immune response may be directed against two or more (e.g., 2, 3, 4, 5, 6, 7, 8, 9, 10 or more) serotypes of *Streptococcus pneumoniae*, wherein an immunogenic composition described herein (including, e.g., vaccine composition (e.g., ones as described and/or utilized herein)) (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). Thus, in some aspects, the method inhibits infection by *S. pneumoniae* in a non-colonized or uninfected subject. In another aspect, the method may reduce the duration of colonization in a subject who is already colonized.

In therapeutic embodiments, an immunogenic composition described herein (including, e.g., vaccine composition (e.g., ones as described and/or utilized herein)) may be administered to a subject suffering from *S. pneumoniae* infection, in an amount sufficient to treat the subject. Treating the subject, in this case, refers to reducing *S. pneumoniae* symptoms and/or bacterial load and/or sequelae in an infected subject. In some embodiments, treating the subject refers to reducing the duration of symptoms or sequelae, or reducing the intensity of symptoms or sequelae. In some embodiments, an immunogenic composition described herein (including, e.g., vaccine composition (e.g., ones as described and/or utilized herein)) reduces transmissibility of *S. pneumoniae* from the vaccinated subject. In certain embodiments, the reductions described above are at least 25%, 30%, 40%, 50%, 60%, 70%, 80%, or 90%.

In therapeutic embodiments, an immunogenic composition described herein (including, e.g., vaccine composition (e.g., ones as described and/or utilized herein)) is administered to a subject post-infection. In some embodiments, an immunogenic composition described herein (including, e.g., vaccine composition (e.g., ones as described and/or utilized herein)) may be administered shortly after infection, e.g. before symptoms or sequelae manifest, or may be administered during or after manifestation of symptoms or sequelae.

In some embodiments, an immunogenic composition described herein (including, e.g., vaccine composition (e.g., ones as described and/or utilized herein)) confer protective immunity, allowing a vaccinated subject to exhibit delayed onset of symptoms or sequelae, or reduced severity of symptoms or sequelae, as the result of his or her exposure to the immunogenic composition. In certain embodiments, the reduction in severity of symptoms or sequelae is at least 25%, 40%, 50%, 60%, 70%, 80%, or 90%. In particular embodiments, vaccinated subjects may display no symptoms or sequelae upon contact with *S. pneumoniae*, do not become colonized by *S. pneumoniae*, or both. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ or $T_H17$ cells.

In some embodiments, an immunogenic composition (e.g., vaccine) described herein, upon administration to a subject, induces an immune response against *S. pneumoniae*. In some embodiments, an immunogenic composition (e.g., vaccine) described herein, upon administration to a subject, induces an immune response against one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or more) serotypes of *S. pneumoniae*. In some embodiments, an immunogenic composition (e.g., vaccine) described herein, upon administration to a subject, induces an immune response against all serotypes of *S. pneumoniae* comprised in such immunogenic composition (e.g., vaccine). In some embodiments, an immunogenic complex or an immunogenic composition (e.g., vaccine) described herein, upon administration to a subject, induces a protective immune response against one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or more) serotypes of *S. pneumoniae*. In some embodiments, an immunogenic complex or an immunogenic composition (e.g., vaccine) described herein, upon administration to a subject, induces a protective immune response against all serotypes of *S. pneumoniae* comprised in such immunogenic composition (e.g., vaccine).

In some embodiments, the immune response is an antibody or B cell response. In some embodiments, the immune response is a T cell response. In some embodiments, the immune response is an innate immune response. In some embodiments, the immune response is a CD4+ T cell response, including $T_H1$, $T_H2$, or $T_H17$ response, or a CD8+ T cell response, or a CD4+ and CD8+ T cell response, or CD4−/CD8− T cell response. In some embodiments, the immune response is an antibody or B cell response, and a T cell response. In some embodiments, the immune response is an antibody or B cell response, a T cell response, and an innate immune response. In some embodiments, the immune response is a protective immune response.

In some embodiments, an immunogenic composition (e.g., vaccine) described herein, upon administration to a subject, induces an antibody or B cell response against one or more pathogens in the subject at a level greater than a composition comprising an antigenic polysaccharide alone. In some embodiments, an immunogenic composition (e.g., vaccine) described herein, upon administration to a subject, induces an antibody or B cell response against one or more pathogens in the subject at level greater than a composition comprising a polypeptide antigen alone. In some embodiments, the immune response is a protective immune response.

In some embodiments, an immunogenic composition (e.g., vaccine) described herein, upon administration to a subject, induces a T cell response against one or more pathogens in the subject at a level greater than a composition comprising an antigenic polysaccharide alone. In some embodiments, an immunogenic composition (e.g., vaccine) described herein, upon administration to a subject, induces a T cell response against one or more pathogens in the subject at level greater than a composition comprising a polypeptide antigen alone. In some embodiments, the immune response is a protective immune response.

In some embodiments, upon administration to a subject, an immunogenic composition (e.g., vaccine) described herein treats or prevents infection by *S. pneumoniae*. In some embodiments, upon administration to a subject, an immunogenic composition (e.g., vaccine) described herein treats or prevents Invasive Pneumococcal Disease (IPD) due to infection by *S. pneumoniae*. In some embodiments, upon administration to a subject, an immunogenic composition (e.g., vaccine) described herein treats or prevents bacteremia due to infection by *S. pneumoniae*. In some embodiments, upon administration to a subject, an immunogenic composition (e.g., vaccine) described herein treats or prevents sepsis due to infection by *S. pneumoniae*. In some embodiments, upon administration to a subject, an immunogenic composition (e.g., vaccine) described herein treats or prevents organ damage due to infection by *S. pneumoniae*. In some embodiments, upon administration to a subject, an immunogenic composition (e.g., vaccine) described herein treats or prevents meningitis due to infection by *S. pneumoniae*. In some embodiments, upon administration to a subject, an immunogenic composition (e.g., vaccine) described herein treats or prevents pneumonia due to infection by *S. pneumoniae*. In some embodiments, upon administration to a subject, an immunogenic composition (e.g., vaccine) described herein treats or prevents otitis media due to infection by *S. pneumoniae*. In some embodiments, upon administration to a subject, an immunogenic composition (e.g., vaccine) described herein treats or prevents sinusitis due to infection by *S. pneumoniae*.

In some embodiments, upon administration to a subject, an immunogenic composition (e.g., vaccine) described herein inhibits or reduces the rate of occurrence of infection by *S. pneumoniae*. In some embodiments, upon administration to a subject, an immunogenic composition (e.g., vaccine) described herein inhibits or reduces the rate of occurrence of Invasive Pneumococcal Disease (IPD) due to infection by *S. pneumoniae*. In some embodiments, upon administration to a subject, an immunogenic composition (e.g., vaccine) described herein inhibits or reduces the rate of occurrence of bacteremia due to infection by *S. pneumoniae*. In some embodiments, upon administration to a subject, an immunogenic composition (e.g., vaccine) described herein inhibits or reduces the rate of occurrence of sepsis due to infection by *S. pneumoniae*. In some embodiments, upon administration to a subject, an immunogenic composition (e.g., vaccine) described herein inhibits or reduces the rate of occurrence of organ damage due to infection by *S. pneumoniae*. In some embodiments, upon administration to a subject, an immunogenic composition (e.g., vaccine) described herein inhibits or reduces the rate of occurrence of meningitis due to infection by *S. pneumoniae*. In some embodiments, upon administration to a subject, an immunogenic composition (e.g., vaccine) described herein inhibits or reduces the rate of occurrence of pneumonia due to infection by *S. pneumoniae*. In some embodiments, upon administration to a subject, an immunogenic composition (e.g., vaccine) described herein inhibits or reduces the rate of occurrence of otitis media due to infection by *S. pneumoniae*. In some embodiments, upon administration to a subject, an immunogenic composition (e.g., vaccine) described herein inhibits or reduces the rate of occurrence of sinusitis due to infection by *S. pneumoniae*.

In some embodiments, upon administration to a subject, an immunogenic composition (e.g., vaccine) described herein reduces the severity of infection by *S. pneumoniae*. In some embodiments, upon administration to a subject, an immunogenic composition (e.g., vaccine) described herein reduces the severity of Invasive Pneumococcal Disease (IPD) due to infection by *S. pneumoniae*. In some embodiments, upon administration to a subject, an immunogenic composition (e.g., vaccine) described herein reduces the severity of bacteremia due to infection by *S. pneumoniae*. In some embodiments, upon administration to a subject, an immunogenic composition (e.g., vaccine) described herein reduces the severity of sepsis due to infection by *S. pneumoniae*. In some embodiments, upon administration to a subject, an immunogenic composition (e.g., vaccine)

described herein reduces the severity of organ damage due to infection by *S. pneumoniae*. In some embodiments, upon administration to a subject, an immunogenic composition (e.g., vaccine) described herein reduces the severity of meningitis due to infection by *S. pneumoniae*. In some embodiments, upon administration to a subject, an immunogenic composition (e.g., vaccine) described herein reduces the severity of pneumonia due to infection by *S. pneumoniae*. In some embodiments, upon administration to a subject, an immunogenic composition (e.g., vaccine) described herein reduces the severity of otitis media due to infection by *S. pneumoniae*. In some embodiments, upon administration to a subject, an immunogenic composition (e.g., vaccine) described herein reduces the severity of sinusitis due to infection by *S. pneumoniae*.

In some embodiments, upon administration to a subject, an immunogenic composition (e.g., vaccine) described herein inhibits transmission of *S. pneumoniae* from the subject to another subject. In some embodiments, upon administration to a subject, an immunogenic composition (e.g., vaccine) described herein inhibits colonization by *S. pneumoniae* in the subject. In some embodiments, upon administration to a subject, an immunogenic composition (e.g., vaccine) described herein inhibits colonization by *S. pneumoniae* of a mucosal surface of the subject. In some embodiments, upon administration to a subject, an immunogenic composition (e.g., vaccine) described herein inhibits colonization by *S. pneumoniae* in the nasopharynx of the subject. In some embodiments, upon administration to a subject, an immunogenic composition (e.g., vaccine) described herein inhibits or reduces asymptomatic infection by *S. pneumoniae* in the subject.

In some embodiments, an immunogenic composition (e.g., vaccine) described herein, upon administration to a subject, induces an immune response against one or more pathogens in the subject at a level greater than a control composition. In some embodiments, an immunogenic composition (e.g., vaccine) described herein, upon administration to a subject, induces a protective immune response against one or more pathogens in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, an immunogenic composition (e.g., vaccine) described herein, upon administration to a subject, elicits immunogenicity non-inferior to (e.g., immunogenicity at least as effective as) that elicited by administration of PCV13. In some embodiments, an immunogenic composition (e.g., vaccine) described herein, upon administration to a subject, elicits immunogenicity non-inferior to (e.g., immunogenicity at least as effective as) that elicited by administration of PCV13 against one or more of *S. pneumoniae* serotypes 1, 3, 4, 5, 6A, 6B, 7F, 9V, 14, 18C, 19A, 19F and 23F. In some embodiments, an immunogenic composition (e.g., vaccine) described herein, upon administration to a subject, elicits immunogenicity non-inferior to (e.g., immunogenicity at least as effective as) that elicited by administration of PCV13 against each of *S. pneumoniae* serotypes 1, 3, 4, 5, 6A, 6B, 7F, 9V, 14, 18C, 19A, 19F and 23F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity superior to that elicited by administration of PCV13. In some embodiments, an immunogenic composition (e.g., vaccine) described herein, upon administration to a subject, elicits immunogenicity superior to that elicited by administration of PCV13 against one or more of *S. pneumoniae* serotypes 1, 3, 4, 5, 6A, 6B, 7F 9V, 14, 18C, 19A, 19F, and 23F. In some embodiments, an immunogenic composition (e.g., vaccine) described herein, upon administration to a subject, elicits immunogenicity superior to that elicited by administration of PCV13 against each of *S. pneumoniae* serotypes 1, 3, 4, 5, 6A, 6B, 7F 9V, 14, 18C, 19A, 19F, and 23F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity non-inferior to (e.g., immunogenicity at least as effective as) that elicited by administration of PCV20. In some embodiments, an immunogenic composition (e.g., vaccine) described herein, upon administration to a subject, elicits immunogenicity non-inferior to (e.g., immunogenicity at least as effective as) that elicited by administration of PCV20 against one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine) described herein, upon administration to a subject, elicits immunogenicity non-inferior to (e.g., immunogenicity at least as effective as) that elicited by administration of PCV20 against each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity superior to that elicited by administration of PCV20. In some embodiments, an immunogenic composition (e.g., vaccine) described herein, upon administration to a subject, elicits immunogenicity superior to that elicited by administration of PCV20 against one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine) described herein, upon administration to a subject, elicits immunogenicity superior to that elicited by administration of PCV20 against each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity non-inferior to (e.g., immunogenicity at least as effective as) that elicited by administration of PPSV23. In some embodiments, an immunogenic composition (e.g., vaccine) described herein, upon administration to a subject, elicits immunogenicity non-inferior to (e.g., immunogenicity at least as effective as) that elicited by administration of PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits immunogenicity non-inferior to (e.g., immunogenicity at least as effective as) that elicited by administration of PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity superior to that elicited by administration of PPSV23. In some embodiments, an immunogenic composition (e.g., vaccine) described herein, upon administration to a subject, elicits immunogenicity superior to that elicited by administration of PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits immunogenicity superior to that elicited by administration of PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity non-inferior to (e.g., immunogenicity at least as effective as) that elicited by administration of PCV13 in combination with PPSV23 against one or more of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits immunogenicity non-inferior to (e.g., immunogenicity at least as effective as) that elicited by administration of PCV13 in combination with PPSV23 against each of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits immunogenicity non-inferior to (e.g., immunogenicity at least as effective as) that elicited by administration of PCV13 in combination with PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits immunogenicity non-inferior to (e.g., immunogenicity at least as effective as) that elicited by administration of PCV13 in combination with PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, elicits immunogenicity superior to that elicited by administration of PCV13 in combination with PPSV23 against one or more of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits immunogenicity superior to that elicited by administration of PCV13 in combination with PPSV23 against each of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits immunogenicity superior to that elicited by administration of PCV13 in combination with PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits immunogenicity superior to that elicited by administration of PCV13 in combination with PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, the immunogenicity is determined by measuring the amount of anti-capsular polysaccharide antibody of one or more *S. pneumoniae* serotypes. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, elicits a functional antibody titer non-inferior to (e.g., a functional antibody titer at least as effective as) that elicited by administration of PCV13 against one or more of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits a functional antibody titer non-inferior to (e.g., a functional antibody titer at least as effective as) that elicited by administration of PCV13 against each of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits a functional antibody titer non-inferior to (e.g., a functional antibody titer at least as effective as) that elicited by administration of PCV13 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PCV13 against (i) one or more of *S. pneumoniae* serotypes 1, 3, 4, 5, 6A, 6B, 7F, 9V, 14, 18C, 19A, 19F, and 23F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer non-inferior to (e.g., a functional antibody titer at least as effective as) that elicited by administration of PCV13 against one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PCV13 against each of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PCV13 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PCV13 against (i) one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer non-inferior to (e.g., a functional antibody titer at least as effective as) that elicited by administration of PCV20 against one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine) described herein, upon administration to a subject, elicits a functional antibody titer non-inferior to (e.g., a functional antibody titer at least as effective as) that elicited by administration of PCV20 against each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine)

described herein, upon administration to a subject, elicits a functional antibody titer non-inferior to (e.g., a functional antibody titer at least as effective as) that elicited by administration of PCV20 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PCV20 against (i) one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer non-inferior to (e.g., a functional antibody titer at least as effective as) that elicited by administration of PCV20 against one or more of *S. pneumoniae* serotypes 2, 6C, 7C, 9N, 15A, 16F, 17F, 20B, 23A, 23B, 24F, 31, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PCV20 against each of *S. pneumoniae* serotypes 2, 6C, 7C, 9N, 15A, 16F, 17F, 20B, 23A, 23B, 24F, 31, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PCV20 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PCV20 against (i) one or more of *S. pneumoniae* serotypes 2, 6C, 7C, 9N, 15A, 16F, 17F, 20B, 23A, 23B, 24F, 31, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against (i) one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against one or more of *S. pneumoniae* serotypes 6A, 6C, 7C, 15A, 16F, 20B, 23A, 23B, 24F, 31, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against each of *S. pneumoniae* serotypes 6A, 6C, 7C, 15A, 16F, 20B, 23A, 23B, 24F, 31, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PPSV23 against (i) one or more of *S. pneumoniae* serotypes 6A, 6C, 7C, 15A, 16F, 20B, 23A, 23B, 24F, 31, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer superior to that elicited by administration of PCV13 against one or more of *S. pneumoniae* serotypes 1, 3, 4, 5, 6A, 6B, 7F 9V, 14, 18C, 19A, 19F, and 23F. In some embodiments, an immunogenic composition (e.g., vaccine) described herein, upon administration to a subject, elicits a functional antibody titer superior to that elicited by administration of PCV13 against each of *S. pneumoniae* serotypes 1, 3, 4, 5, 6A, 6B, 7F 9V, 14, 18C, 19A, 19F, and 23F. In some embodiments, an immunogenic composition (e.g., vaccine) described herein, upon administration to a subject, elicits a functional antibody titer superior to that elicited by administration of PCV13 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PCV13 against (i) one or more of *S. pneumoniae* serotypes 1, 3, 4, 5, 6A, 6B, 7F, 9V, 14, 18C, 19A, 19F, and 23F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer superior to that elicited by administration of PCV13 against one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer superior to that elicited by administration of PCV13 against each of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer superior to that elicited by administration of PCV13 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PCV13 against (i) one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer superior to that elicited by administration of PCV20 against one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine) described herein, upon administration to a subject, elicits a functional antibody titer superior to that elicited by administration of PCV20 against each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine) described herein, upon administration to a subject, elicits a functional antibody titer superior to that elicited by administration of PCV20 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PCV20 against (i) one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer superior to that elicited by administration of PCV20 against one or more of *S. pneumoniae* serotypes 2, 6C, 7C, 9N, 15A, 16F, 17F, 20B, 23A, 23B, 24F, 31, 35B, and 38. In some embodiments, an immunogenic composition (e.g., vaccine) described herein, upon administration to a subject, elicits a functional antibody titer superior to that elicited by administration of PCV20 against each of *S. pneumoniae* serotypes 2, 6C, 7C, 9N, 15A, 16F, 17F, 20B, 23A, 23B, 24F, 31, 35B, and 38. In some embodiments, an immunogenic composition (e.g., vaccine) described herein, upon administration to a subject, elicits a functional antibody titer superior to that elicited by administration of PCV20 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PCV20 against (i) one or more of *S. pneumoniae* serotypes 2, 6C, 7C, 9N, 15A, 16F, 17F, 20B, 23A, 23B, 24F, 31, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer superior to that elicited by administration of PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer superior to that elicited by administration of PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer superior to that elicited by administration of PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PPSV23 against (i) one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer superior to that elicited by administration of PPSV23 against one or more of *S. pneumoniae* serotypes 6A, 6C, 7C, 15A, 16F, 20B, 23A, 23B, 24F, 31, 35B, and 38. In some embodiments, an immunogenic composition (e.g., vaccine) described herein, upon administration to a subject, elicits a functional antibody titer superior to that elicited by administration of PPSV23 against each of *S. pneumoniae* serotypes 6A, 6C, 7C, 15A, 16F, 20B, 23A, 23B, 24F, 31, 35B, and 38. In some embodiments, an immunogenic composition (e.g., vaccine) described herein, upon administration to a subject, elicits a functional antibody titer superior to that elicited by administration of PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PPSV23 against (i) one or more of *S. pneumoniae* serotypes 6A, 6C, 7C, 15A, 16F, 20B, 23A, 23B, 24F, 31, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against one or more of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against each of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against (i) one or more of *S. pneumoniae* serotypes 1, 3, 4, 5, 6A, 6B, 7F, 9V, 14, 18C, 19A, 19F and 23F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against (i) one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against each of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer non-inferior to (e.g., a functional antibody titer at least as effective as) that elicited by administration of PCV13 in combination with PPSV23 against (i) one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, elicits a functional antibody titer superior to that elicited by administration of PCV13 in combination with PPSV23 against one or more of *S. pneumoniae* serotypes 1, 3, 4, 5, 6A, 6B, 7F, 9V, 14, 18C, 19A, 19F, and 23F. In some embodiments, an immunogenic composition (e.g., vaccine)

described herein, upon administration to a subject, elicits a functional antibody titer superior to that elicited by administration of PCV13 in combination with PPSV23 against each of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits a functional antibody titer superior to that elicited by administration of PCV13 in combination with PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer superior to that elicited by administration of PCV13 in combination with PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits a functional antibody titer superior to that elicited by administration of PCV13 in combination with PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PCV13 in combination with PPSV23 against (i) one or more of *S. pneumoniae* serotypes 1, 3, 4, 5, 6A, 6B, 7F, 9V, 14, 18C, 19A, 19F, and 23F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, an immunogenic composition (e.g., vaccine) described herein, upon administration to a subject, elicits a functional antibody titer superior to that elicited by administration of PCV13 in combination with PPSV23 against (i) one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, elicits a functional antibody titer superior to that elicited by administration of PCV13 in combination with PPSV23 against one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer superior to that elicited by administration of PCV13 in combination with PPSV23 against each of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38. In some embodiments, an immunogenic composition (e.g., vaccine) described herein, upon administration to a subject, elicits a functional antibody titer superior to that elicited by administration of PCV13 in combination with PPSV23 against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits a functional antibody titer superior to that elicited by administration of PCV13 in combination with PPSV23 against (i) one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, elicits immunogenicity against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits immunogenicity against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits immunogenicity against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits immunogenicity against (i) one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against one or more *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the immunogenicity is determined by measuring the amount of anti-capsular polysaccharide antibody against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the amount of anti-capsular polysaccharide antibody measured is an amount that meets a pre-determined threshold. In some embodiments, the total amount of anti-capsular polysaccharide antibody measured is an amount that meets a pre-determined threshold. In some embodiments, the pre-determined threshold is a blood serum or plasma concentration between about 0.20 μg/mL to about 0.35 μg/mL. In some embodiments, the pre-determined threshold is at least about 0.35 μg/mL. In some embodiments, the functional antibody titer is measured by an opsonophagocytic assay. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity against one or more of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits immunogenicity against each of *S. pneumoniae* serotypes 1, 3, 4, 5, 6A, 6B, 7F, 9V, 14, 18C, 19A, 19F, and 23F. In some embodiments, an immunogenic composition (e.g., vaccine) described herein, upon administration to a subject, elicits immunogenicity against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits immunogenicity against (i) one or more of *S. pneumoniae* serotypes 1, 3, 4, 5, 6A, 6B, 7F, 9V, 14, 18C, 19A, 19F, and 23F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against one or more *S. pneumoniae* serotypes 1, 3, 4, 5, 6A, 6B, 7F, 9V, 14, 18C, 19A, 19F, and 23F. In some embodiments, the immunogenicity is determined by measuring the amount of anti-capsular polysaccharide antibody against each of *S. pneumoniae* serotypes 1, 3, 4, 5, 6A, 6B, 7F, 9V, 14, 18C, 19A, 19F, and 23F. In some embodiments, the amount of anti-capsular polysaccharide antibody measured is an amount that meets a pre-determined threshold. In some embodiments, the total amount of anti-capsular polysaccharide antibody measured is an amount that meets a pre-determined threshold. In some embodiments, the pre-determined threshold is a blood serum or plasma concentration between about 0.20 μg/mL to about 0.35 μg/mL. In some embodiments, the pre-determined threshold is at least about 0.35 μg/mL. In some embodiments, the functional antibody titer is measured by an opsonophagocytic assay. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity against one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine) described herein, upon administration to a subject, elicits immunogenicity against each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, an immunogenic composition (e.g., vaccine) described herein, upon administration to a subject, elicits immunogenicity against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits immunogenicity against (i) one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against one or more *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, the immunogenicity is determined by measuring the amount of anti-capsular polysaccharide antibody against each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F. In some embodiments, the amount of anti-capsular polysaccharide antibody measured is an amount that meets a predetermined threshold. In some embodiments, the total amount of anti-capsular polysaccharide antibody measured is an amount that meets a pre-determined threshold. In some embodiments, the pre-determined threshold is a blood serum or plasma concentration between about 0.20 μg/mL to about 0.35 μg/mL. In some embodiments, the pre-determined threshold is at least about 0.35 μg/mL. In some embodiments, the functional antibody titer is measured by an opsonophagocytic assay. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, elicits immunogenicity against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits immunogenicity against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, an immunogenic composition (e.g., vaccine) described herein, upon administration to a subject, elicits immunogenicity against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits immunogenicity against (i) one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against one or more *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, the immunogenicity is determined by measuring the amount of anti-capsular polysaccharide antibody against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F. In some embodiments, the amount of anti-capsular polysaccharide antibody measured is an amount that meets a pre-determined threshold. In some embodiments, the total amount of anti-capsular polysaccharide antibody measured is an amount that meets a pre-determined threshold. In some embodiments, the pre-determined threshold is a blood serum or plasma concentration between about 0.20 g/mL to about 0.35 μg/mL. In some embodiments, the pre-determined threshold is at least about 0.35 μg/mL. In some embodiments, the functional antibody titer is measured by an opsonophagocytic assay. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, (i) elicits a functional antibody titer superior to that elicited by administration of PCV13 against one or more of *S. pneumoniae* serotypes 1, 3, 4, 5, 6A, 6B, 7F, 9V, 14, 18C, 19A, 19F, and 23F; and (ii) elicits immunogenicity against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, (i) elicits a functional antibody titer superior to that elicited by administration of PCV13 against each of *S. pneumoniae* serotypes 1, 3, 4, 5, 6A, 6B, 7F, 9V, 14, 18C, 19A, 19F, and 23F; and (ii) elicits immunogenicity against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits (i) a functional antibody titer superior to that elicited by administration of PCV13 and (ii) immunogenicity (e.g., an innate immune response, an antibody or B cell response, and/or a T cell response), against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits (i) a functional antibody titer superior to that elicited by administration of PCV13 and (ii) immunogenicity (e.g., an innate immune response, an antibody or B cell response, and/or a T cell response), against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and also against one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the functional antibody titer is measured by an opsonophagocytic assay (e.g., ones as described herein). In some embodiments, the amount of anti-capsular polysaccharide antibody measured is an amount that meets a pre-determined threshold. In some embodiments, the total amount of anti-capsular polysaccharide antibody measured is an amount that meets a pre-determined threshold. In some embodiments, the pre-determined threshold is a blood serum or plasma concentration between about 0.20 μg/mL to about 0.35 μg/mL. In some embodiments, the pre-determined threshold is at least about 0.35 μg/mL. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, (i) elicits a functional antibody titer superior to that elicited by administration of PCV20 against one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F; and (ii) elicits immunogenicity against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38v. In some embodiments, an immunogenic composition (e.g., vaccine)

described herein, upon administration to a subject, (i) elicits a functional antibody titer superior to that elicited by administration of PCV20 against each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F; and (ii) elicits immunogenicity against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits (i) a functional antibody titer superior to that elicited by administration of PCV20 and (ii) immunogenicity (e.g., an innate immune response, an antibody or B cell response, and/or a T cell response), against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits (i) a functional antibody titer superior to that elicited by administration of PCV20 and (ii) immunogenicity (e.g., an innate immune response, an antibody or B cell response, and/or a T cell response), against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and also against one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the functional antibody titer is measured by an opsonophagocytic assay (e.g., ones as described herein). In some embodiments, the amount of anti-capsular polysaccharide antibody measured is an amount that meets a pre-determined threshold. In some embodiments, the total amount of anti-capsular polysaccharide antibody measured is an amount that meets a pre-determined threshold. In some embodiments, the pre-determined threshold is a blood serum or plasma concentration between about 0.20 μg/mL to about 0.35 μg/mL. In some embodiments, the pre-determined threshold is at least about 0.35 μg/mL. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, (i) elicits a functional antibody titer superior to that elicited by administration of PPSV23 against one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F; and (ii) elicits immunogenicity against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, (i) elicits a functional antibody titer superior to that elicited by administration of PPSV23 against each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F; and (ii) elicits immunogenicity against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits (i) a functional antibody titer superior to that elicited by administration of PPSV23 and (ii) immunogenicity (e.g., an innate immune response, an antibody or B cell response, and/or a T cell response), against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits (i) a functional antibody titer superior to that elicited by administration of PPSV23 and (ii) immunogenicity (e.g., an innate immune response, an antibody or B cell response, and/or a T cell response), against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and also against one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the functional antibody titer is measured by an opsonophagocytic assay (e.g., ones as described herein). In some embodiments, the amount of anti-capsular polysaccharide antibody measured is an amount that meets a pre-determined threshold. In some embodiments, the total amount of anti-capsular polysaccharide antibody measured is an amount that meets a pre-determined threshold. In some embodiments, the pre-determined threshold is a blood serum or plasma concentration between about 0.20 μg/mL to about 0.35 μg/mL. In some embodiments, the pre-determined threshold is at least about 0.35 μg/mL. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, (i) elicits a functional antibody titer superior to that elicited by administration of PCV13 in combination with PPSV23 against one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38; and (ii) elicits immunogenicity against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, (i) elicits a functional antibody titer superior to that elicited by administration of PCV13 in combination with PPSV23 against each of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38; and (ii) elicits immunogenicity against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits (i) a functional antibody titer superior to that elicited by administration of PCV13 in combination with PPSV23 and (ii) immunogenicity (e.g., an innate immune response, an antibody or B cell response, and/or a T cell response), against one or more *S. pneumoniae* serotypes, wherein such an immunogenic composition (e.g., vaccine) does not include polysaccharide(s) present in at least one or more of such *S. pneumoniae* serotypes (non-vaccine types, NVTs). In some embodiments, an immunogenic composition (e.g., vaccine) described herein, upon administration to a subject, elicits (i) a functional antibody titer superior to that elicited by administration of PCV13 in combination with PPSV23 and (ii) immunogenicity (e.g., an innate immune response, an antibody or B cell response, and/or a T cell response), against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and also against one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, the functional antibody titer is measured by an opsonophagocytic assay (e.g., ones as described herein). In some embodiments, the amount of anti-capsular polysaccharide antibody measured is an amount that meets a pre-determined threshold. In some embodiments, the total amount of anti-capsular polysaccharide antibody measured is an amount that meets a pre-determined threshold. In some embodiments, the pre-determined threshold is a blood serum or plasma concentration between about 0.20 μg/mL to about 0.35 μg/mL. In some embodiments, the pre-determined threshold is at least about 0.35 μg/mL. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, elicits an immunoprotective response against one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits an immunoprotective response against each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38. In some embodiments, an immunogenic composition (e.g., vaccine) described herein, upon administration to a subject, elicits an immunoprotective response against (i) at least one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs).

In some embodiments, an immunogenic composition (e.g., vaccine) described herein, upon administration to a subject, reduces *S. pneumoniae* colonization to a greater degree than administration of PCV13. In some embodiments, an immunogenic composition (e.g., vaccine) described herein, upon administration to a subject, reduces *S. pneumoniae* colonization by one or more of *S. pneumoniae* serotypes 1, 3, 4, 5, 6A, 6B, 7F, 9V, 14, 18C, 19A, 19F, and 23F to a greater degree than administration of PCV13. In some embodiments, an immunogenic composition (e.g., vaccine) described herein, upon administration to a subject, reduces *S. pneumoniae* colonization by each of *S. pneumoniae* serotypes 1, 3, 4, 5, 6A, 6B, 7F, 9V, 14, 18C, 19A, 19F, and 23F to a greater degree than administration of PCV13. In some embodiments, an immunogenic composition (e.g., vaccine) described herein, upon administration to a subject, reduces *S. pneumoniae* colonization to a greater degree than administration of PCV13 by (i) at least one or more of *S. pneumoniae* serotypes 1, 3, 4, 5, 6A, 6B, 7F, 9V, 14, 18C, 19A, 19F, and 23F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PCV13. In some embodiments, an immunogenic composition (e.g., vaccine) described herein, upon administration to a subject, reduces *S. pneumoniae* colonization by one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38 to a greater degree than administration of PCV13. In some embodiments, an immunogenic composition (e.g., vaccine)

described herein, upon administration to a subject, reduces *S. pneumoniae* colonization by each of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38 to a greater degree than administration of PCV13. In some embodiments, an immunogenic composition (e.g., vaccine) described herein, upon administration to a subject, reduces *S. pneumoniae* colonization to a greater degree than administration of PCV13 by (i) at least one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PCV13. In some embodiments, an immunogenic composition (e.g., vaccine) described herein, upon administration to a subject, reduces *S. pneumoniae* colonization by one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PCV13. In some embodiments, an immunogenic composition (e.g., vaccine) described herein, upon administration to a subject, reduces *S. pneumoniae* colonization by each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PCV13. In some embodiments, an immunogenic composition (e.g., vaccine) described herein, upon administration to a subject, reduces *S. pneumoniae* colonization to a greater degree than administration of PCV13 by (i) at least one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PCV20. In some embodiments, an immunogenic composition (e.g., vaccine) described herein, upon administration to a subject, reduces *S. pneumoniae* colonization by one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F to a greater degree than administration of PCV20. In some embodiments, an immunogenic composition (e.g., vaccine) described herein, upon administration to a subject, reduces *S. pneumoniae* colonization by each of *S. pneumoniae* serotypes 1, 3, 4, 5, 6A, 6B, 7F, 8, 9V, 10A, 11A, 12F, 14, 15B, 18C, 19A, 19F, 22F, 23F, and 33F to a greater degree than administration of PCV20. In some embodiments, an immunogenic composition (e.g., vaccine) described herein, upon administration to a subject, reduces *S. pneumoniae* colonization to a greater degree than administration of PCV20 by (i) at least one or more of *S. pneumoniae* serotypes 1, 3, 4, 5, 6A, 6B, 7F, 8, 9V, 10A, 11A, 12F, 14, 15B, 18C, 19A, 19F, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PCV20. In some embodiments, an immunogenic composition (e.g., vaccine) described herein, upon administration to a subject, reduces *S. pneumoniae* colonization by one or more of *S. pneumoniae* serotypes 2, 6C, 7C, 9N, 15A, 16F, 17F, 20B, 23A, 23B, 24F, 31, 35B, and 38 to a greater degree than administration of PCV20. In some embodiments, an immunogenic composition (e.g., vaccine) described herein, upon administration to a subject, reduces *S. pneumoniae* colonization by each of *S. pneumoniae* serotypes 2, 6C, 7C, 9N, 15A, 16F, 17F, 20B, 23A, 23B, 24F, 31, 35B, and 38 to a greater degree than administration of PCV20. In some embodiments, an immunogenic composition (e.g., vaccine) described herein, upon administration to a subject, reduces *S. pneumoniae* colonization to a greater degree than administration of PCV20 by (i) at least one or more of *S. pneumoniae* serotypes 2, 6C, 7C, 9N, 15A, 16F, 17F, 20B, 23A, 23B, 24F, 31, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PCV20. In some embodiments, an immunogenic composition (e.g., vaccine) described herein, upon administration to a subject, reduces *S. pneumoniae* colonization by one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PCV20. In some embodiments, an immunogenic composition (e.g., vaccine) described herein, upon administration to a subject, reduces *S. pneumoniae* colonization by each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PCV20. In some embodiments, an immunogenic composition (e.g., vaccine) described herein, upon administration to a subject, reduces *S. pneumoniae* colonization to a greater degree than administration of PCV20 by (i) at least one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PPSV23. In some embodiments, an immunogenic composition (e.g., vaccine) described herein, upon administration to a subject, reduces *S. pneumoniae* colonization by one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F to a greater degree than administration of PPSV23. In some embodiments, an immunogenic composition (e.g., vaccine) described herein, upon administration to a subject, reduces *S. pneumoniae* colonization by each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F to a greater degree than administration of PPSV23. In some embodiments, an immunogenic composition (e.g., vaccine) described herein, upon administration to a subject, reduces *S. pneumoniae* colonization to a greater degree than administration of PPSV23 by (i) at least one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PPSV23. In some embodiments, an immunogenic composition (e.g., vaccine) described herein, upon administration to a subject, reduces *S. pneumoniae* colonization by one or more of *S. pneumoniae* serotypes 6A, 6C, 7C, 15A, 16F, 20B, 23A, 23B, 24F, 31, 35B, and 38 to a greater degree than administration of PPSV23. In some embodiments, an immunogenic composition (e.g., vaccine) described herein, upon administration to a subject, reduces *S. pneumoniae* colonization by each of *S. pneumoniae* serotypes 6A, 6C, 7C, 15A, 16F, 20B, 23A, 23B, 24F, 31, 35B, and 38 to a greater degree than administration of PPSV23. In some embodiments, an immunogenic composition (e.g., vaccine) described herein, upon administration to a subject, reduces *S. pneumoniae* colonization to a greater degree than administration of PPSV23 by (i) at least one or more of *S. pneumoniae* serotypes 6A, 6C, 7C, 15A, 16F, 20B, 23A, 23B, 24F, 31, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PPSV23. In some embodiments, an immunogenic composition (e.g., vaccine) described herein, upon administration to a subject, reduces *S. pneumoniae* colonization by one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PPSV23. In some embodiments, an immunogenic composition (e.g., vaccine) described herein, upon administration to a subject, reduces *S. pneumoniae* colonization by each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PPSV23. In some embodiments, an immunogenic composition (e.g., vaccine) described herein, upon administration to a subject, reduces *S. pneumoniae* colonization to a greater degree than administration of PPSV23 by (i) at least one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older.

In some embodiments, an immunogenic composition (e.g., vaccine) described herein, upon administration to a subject, reduces *S. pneumoniae* colonization to a greater degree than administration of PCV13 in combination with PPSV23. In some embodiments, an immunogenic composition (e.g., vaccine) described herein, upon administration to a subject, reduces *S. pneumoniae* colonization by one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F to a greater degree than administration of PCV13 in combination with PPSV23. In some embodiments, an immunogenic composition (e.g., vaccine) described herein, upon administration to a subject, reduces *S. pneumoniae* colonization by each of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F to a greater degree than administration of PCV13 in combination with PPSV23. In some embodiments, an immunogenic composition (e.g., vaccine) described herein, upon administration to a subject, reduces *S. pneumoniae* colonization to a greater degree than administration of PCV13 in combination with PPSV23 by (i) at least one or more of *S. pneumoniae* serotypes 1, 2, 3, 4, 5, 6B, 7F, 8, 9N, 9V, 10A, 11A, 12F, 14, 15B, 17F, 18C, 19A, 19F, 20A, 22F, 23F, and 33F, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, reduces *S. pneumoniae* colonization to a greater degree than administration of PCV13 in combination with PPSV23. In some embodiments, an immunogenic composition (e.g., vaccine) described herein, upon administration to a subject, reduces *S. pneumoniae* colonization by one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38 to a greater degree than administration of PCV13 in combination with PPSV23. In some embodiments, an immunogenic composition (e.g., vaccine) described herein, upon administration to a subject, reduces *S. pneumoniae* colonization by each of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38 to a greater degree than administration of PCV13 in combination with PPSV23. In some embodiments, an immunogenic composition (e.g., vaccine) described herein, upon administration to a subject, reduces *S. pneumoniae* colonization to a greater degree than administration of PCV13 in combination with PPSV23 by (i) at least one or more of *S. pneumoniae* serotypes 2, 6C, 7C, 8, 9N, 10A, 11A, 12F, 15A, 15B, 16F, 17F, 20B, 22F, 23A, 23B, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, reduces *S. pneumoniae* colonization to a greater degree than administration of PCV13 in combination with PPSV23. In some embodiments, an immunogenic composition (e.g., vaccine) described herein, upon administration to a subject, reduces *S. pneumoniae* colonization by one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PCV13 in combination with PPSV23. In some embodiments, an immunogenic composition (e.g., vaccine) described herein, upon administration to a subject, reduces *S. pneumoniae* colonization by each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38 to a greater degree than administration of PCV13 in combination with PPSV23. In some embodiments, an immunogenic composition (e.g., vaccine) described herein, upon administration to a subject, reduces *S. pneumoniae* colonization to a greater degree than administration of PCV13 in combination with PPSV23 by (i) at least one or more of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38, and (ii) one or more additional *S. pneumoniae* serotypes, wherein such an immunogenic composition (e.g., vaccine) does not include polysaccharide(s) present in at least one or more of such additional *S. pneumoniae* serotypes (non-vaccine types, NVTs). In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition (e.g., vaccine) described herein, upon administration to a subject, induces an immune response that can help protect against the establishment of *S. pneumoniae*, at a level greater than a control composition. In some embodiments, an immunogenic composition (e.g., vaccine) described herein protects against colonization at a level greater than a control composition. In some embodiments, an immunogenic composition (e.g., vaccine) described herein inhibits infection by *S. pneumoniae* in a non-colonized or uninfected subject at a level greater than a control composition. In some embodiments, an immunogenic composition (e.g., vaccine) described herein reduces the duration of colonization by *S. pneumoniae* in a subject who is already colonized at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, an immunogenic composition (e.g., vaccine) described herein, upon administration to a subject, induces an immune response against *S. pneumoniae* at a level greater than a control composition. In some embodiments, an immunogenic composition (e.g., vaccine) described herein, upon administration to a subject, induces an immune response against one or more serotypes of *S. pneumoniae* at a level greater than a control composition. In some embodiments, the immune response is an antibody or B cell response. In some embodiments, the immune response is a T cell response. In some embodiments, the immune response is an innate immune response. In some embodiments, the immune response is a CD4+ T cell response, including $T_H1$, $T_H2$, or $T_H17$ response, or a CD8+ T cell response, or a CD4+ and CD8+ T cell response, or CD4−/CD8− T cell response. In some embodiments, the immune response is an antibody or B cell response, and a T cell response. In some embodiments, the immune response is an antibody or B cell response, a T cell response, and an innate immune response. In some embodiments, the immune response is a protective immune response. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, an immunogenic composition (e.g., vaccine) described herein, upon administration to a subject, induces an antibody or B cell response against one or more pathogens in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, an immunogenic composition (e.g., vaccine) described herein, upon administration to a subject, induces an antibody or B cell response against one or more pathogens in the subject at level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, an immunogenic composition (e.g., vaccine) described herein, upon administration to a subject, induces a T cell response against one or more pathogens in the subject at a level greater than a control composition. In some embodiments, an immunogenic composition (e.g., vaccine) described herein, upon administration to a subject, induces a T cell response against one or more pathogens in the subject at level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, upon administration to a subject, an immunogenic composition (e.g., vaccine) described herein treats or prevents infection by *S. pneumoniae* in the subject at a level greater than a control composition. In some embodiments, upon administration to a subject, an immunogenic composition (e.g., vaccine) described herein treats or prevents Invasive Pneumococcal Disease (IPD) due to infection by *S. pneumoniae* in the subject at a level greater than a control composition. In some embodiments, upon administration to a subject, an immunogenic composition (e.g., vaccine) described herein treats or prevents bacteremia due to infection by *S. pneumoniae* in the subject at a level greater than a control composition. In some embodiments, upon administration to a subject, an immunogenic composition (e.g., vaccine) described herein treats or prevents sepsis due to infection by *S. pneumoniae* in the subject at a level greater than a control composition. In some embodiments, upon administration to a subject, an immunogenic composition (e.g., vaccine) described herein treats or prevents organ damage due to infection by *S. pneumoniae* in the subject at a level greater than a control composition. In some embodiments, upon administration to a subject, an immunogenic composition (e.g., vaccine) described herein treats or prevents meningitis due to infection by *S. pneumoniae* in the subject at a level greater than a control composition. In some embodiments, upon administration to a subject, an immunogenic composition (e.g., vaccine) described herein treats or prevents pneumonia due to infection by *S. pneumoniae* in the subject at a level greater than a control composition. In some embodiments, upon administration to a subject, an immunogenic composition (e.g., vaccine) described herein treats or prevents otitis media due to infection by *S. pneumoniae* in the subject at a level greater than a control composition. In some embodiments, upon administration to a subject, an immunogenic composition (e.g., vaccine) described herein treats or prevents sinusitis due to infection by *S. pneumoniae* in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, upon administration to a subject, an immunogenic composition (e.g., vaccine) described herein inhibits or reduces the rate of occurrence of infection by *S. pneumoniae* in the subject at a level greater than a control composition. In some embodiments, upon administration to a subject, an immunogenic composition (e.g., vaccine) described herein inhibits or reduces the rate of occurrence of Invasive Pneumococcal Disease (IPD) due to infection by *S. pneumoniae* in the subject at a level greater than a control composition. In some embodiments, upon administration to a subject, an immunogenic composition (e.g., vaccine) described herein inhibits or reduces the rate of occurrence of bacteremia due to infection by *S. pneumoniae* in the subject at a level greater than a control composition. In some embodiments, upon administration to a subject, an immunogenic composition (e.g., vaccine) described herein inhibits or reduces the rate of occurrence of sepsis due to infection by *S. pneumoniae* in the subject at a level greater than a control composition. In some embodiments, upon administration to a subject, an immunogenic composition (e.g., vaccine) described herein inhibits or reduces the rate of occurrence of organ damage due to infection by *S. pneumoniae* in the subject at a level greater than a control composition. In some embodiments, upon administration to a subject, an immunogenic composition (e.g., vaccine) described herein inhibits or reduces the rate of occurrence of meningitis due to infection by *S. pneumoniae* in the subject at a level greater than a control composition. In some embodiments, upon administration to a subject, an immunogenic composition (e.g., vaccine) described herein inhibits or reduces the rate of occurrence of pneumonia due to infection by *S. pneumoniae* in the subject at a level greater than a control composition. In some embodiments, upon administration to a subject, an immunogenic composition (e.g., vaccine) described herein inhibits or reduces the rate of occurrence of otitis media due to infection by *S. pneumoniae* in the subject at a level greater than a control composition. In some embodiments, upon administration to a subject, an immunogenic composition (e.g., vaccine) described herein inhibits or reduces the rate of occurrence of sinusitis due to infection by *S. pneumoniae* in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, upon administration to a subject, an immunogenic composition (e.g., vaccine) described herein reduces the severity of infection by *S. pneumoniae* in the subject at a level greater than a control composition. In some embodiments, upon administration to a subject, an immunogenic composition (e.g., vaccine) described herein reduces the severity of Invasive Pneumococcal Disease (IPD) due to infection by *S. pneumoniae* in the subject at a level greater than a control composition. In some embodiments, upon administration to a subject, an immunogenic composition (e.g., vaccine) described herein reduces the severity of bacteremia due to infection by *S. pneumoniae* in the subject at a level greater than a control composition. In some embodiments, upon administration to a subject, an immunogenic composition (e.g., vaccine) described herein reduces the severity of sepsis due to infection by *S. pneumoniae* in the subject at a level greater than a control composition. In some embodiments, upon administration to a subject, an immunogenic composition (e.g., vaccine) described herein reduces the severity of organ damage due to infection by *S. pneumoniae* in the subject at a level greater than a control composition. In some embodiments, the control composition may be PCV13, PCV20, or PPSV23. In some embodiments, upon administration to a subject, an immunogenic composition (e.g., vaccine) described herein reduces the severity of meningitis due to infection by *S. pneumoniae* in the subject at a level greater than a control composition. In some embodiments, upon administration to a subject, an immunogenic composition (e.g., vaccine) described herein reduces the severity of pneumonia due to infection by *S. pneumoniae* in the subject at a level greater than a control composition. In some embodiments, upon administration to a subject, an immunogenic composition (e.g., vaccine) described herein reduces the severity of otitis media due to infection by *S. pneumoniae* in the subject at a level greater than a control composition. In some embodiments, upon administration to a subject, an immunogenic composition (e.g., vaccine) described herein reduces the severity of sinusitis due to infection by *S. pneumoniae* in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, upon administration to a subject, an immunogenic composition (e.g., vaccine) described herein inhibits transmission of *S. pneumoniae* from the subject to another subject at a level greater than a control composition. In some embodiments, upon administration to a subject, an immunogenic composition (e.g., vaccine) described herein inhibits colonization by *S. pneumoniae* in the subject at a level greater than a control composition. In some embodiments, upon administration to a subject, an immunogenic composition (e.g., vaccine) described herein inhibits colonization by *S. pneumoniae* in the nasopharynx of the subject at a level greater than a control composition.

In some embodiments, upon administration to a subject, an immunogenic composition (e.g., vaccine) described herein inhibits or reduces asymptomatic infection by *S. pneumoniae* of the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13, PCV20, or PPSV23.

In some embodiments, an immunogenic composition (e.g., vaccine) described herein is administered to a subject between about 6 weeks and about 5 years (e.g., prior to the $6^{th}$ birthday) for active immunization for the prevention of invasive disease caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, a MAPS30+ vaccine (e.g., a MAPS33 or MAPS34 vaccine) is administered to a subject between about 6 weeks and about 5 years (e.g., prior to the $6^{th}$ birthday) for active immunization for the prevention of invasive disease caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, an immunogenic composition (e.g., vaccine) described herein is administered to a subject between about 6 years and about 17 years (e.g., prior to the $18^{th}$ birthday) for active immunization for the prevention of invasive disease caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, a MAPS30+ vaccine (e.g., a MAPS33 or MAPS34 vaccine) is administered to a subject between about 6 years and about 17 years (e.g., prior to the $18^{th}$ birthday) for active immunization for the prevention of invasive disease caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, an immunogenic composition (e.g., vaccine) described herein is administered to a subject 18 years or older for active immunization for the prevention of invasive disease caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, a MAPS30+ vaccine (e.g., a MAPS33 or MAPS34 vaccine) is administered to a subject 18 years or older for active immunization for the prevention of invasive disease caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, an immunogenic composition (e.g., vaccine) described herein is administered to a subject 18 years or older for active immunization for the prevention of pneumonia caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, a MAPS30+ vaccine (e.g., a MAPS33 or MAPS34 vaccine) is administered to a subject 18 years or older for active immunization for the prevention of pneumonia caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, an immunogenic composition (e.g., vaccine) described herein is administered to a subject 18 years or older for active immunization for the prevention of invasive disease and pneumonia caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

In some embodiments, a MAPS30+ vaccine (e.g., a MAPS33 or MAPS34 vaccine) is administered to a subject 18 years or older for active immunization for the prevention of invasive disease and pneumonia caused by *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

Antibody Compositions

One aspect of the present disclosure provides for an antibody composition comprising antibodies raised in a mammal immunized with an immunogenic complex of the invention. In some embodiments, an antibody comprises at least one antibody selected from the group consisting of mAbs and anti-idiotype antibodies. In some embodiments, an antibody composition comprises an isolated gamma globulin fraction. In some embodiments, an antibody composition comprises polyclonal antibodies. In some embodiments, the antibody composition is administered to a subject. In some embodiments, the antibody composition administered to a subject confers passive immunization.

Immunogenic Composition (e.g., Vaccine) Formulations

Optimal amounts of components for a particular immunogenic composition (e.g., vaccine) can be ascertained by standard studies involving observation of appropriate immune responses in subjects. Following an initial vaccination, subjects can receive one or several booster immunizations adequately spaced in time.

The immunogenic complexes described herein, and/or preparations thereof may be formulated in a unit dosage form for ease of administration and uniformity of dosage. The specific therapeutically effective dose level for any particular subject or organism may depend upon a variety of factors including the severity or degree of risk of infection; the activity of the specific immunogenic composition (e.g., vaccine composition) employed; other characteristics of the specific immunogenic composition (e.g., vaccine composition) employed; the age, body weight, general health, sex of the subject, diet of the subject, pharmacokinetic condition of the subject, the time of administration (e.g., with regard to other activities of the subject such as eating, sleeping, receiving other medicines including other vaccine doses, etc.), route of administration, rate of excretion of the specific immunogenic composition (e.g., vaccine composition) employed; vaccines used in combination or coincidental with the immunogenic composition (e.g., vaccine composition) employed; and like factors well known in the medical arts.

Immunogenic complexes for use in accordance with the present disclosure may be formulated into compositions (e.g., pharmaceutical compositions) according to known techniques. Vaccine preparation is generally described in Vaccine Design (Powell and Newman, 1995). For example, an immunologically amount of a vaccine product can be formulated together with one or more organic or inorganic, liquid or solid, pharmaceutically suitable carrier materials. Preparation of pneumococcal polysaccharide and conjugate vaccines is described, for example, in U.S. Ser. No. 11/395,593, filed Mar. 31, 2006, the contents of which are incorporated herein by reference.

In general, pharmaceutically acceptable carrier(s) include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (Martin, 1975).

Immunogenic compositions (e.g., vaccines) may be formulated by combining one or more of the immunogenic complexes disclosed herein with carriers and/or other optional components by any available means including, for example, conventional mixing, granulating, dissolving, lyophilizing, or similar processes.

Vaccine compositions useful in the provided methods may be lyophilized up until they are about to be used, at which point they are extemporaneously reconstituted with diluent. In some embodiments, immunogenic (e.g., vaccine) components or compositions are lyophilized in the presence of one or more other components (e.g., adjuvants), and are extemporaneously reconstituted with saline solution. Alternatively, individual components, or sets of components may be separately lyophilized and/or stored (e.g., in a vaccination kit), the components being reconstituted and either mixed prior to use or administered separately to the subject.

Lyophilization can produce a more stable composition (for instance by preventing or reducing breakdown of polysaccharide antigens). Lyophilizing of immunogenic compositions (e.g., vaccine compositions) or immunogenic components (e.g., vaccine components) is well known in the art. Typically, a liquid immunogenic composition (e.g., vaccine) or component(s) thereof is freeze dried, often in the presence of an anti-caking agent (such as, for example, sugars such as sucrose or lactose). In some embodiments, the anti-caking agent is present, for example, at an initial concentration of 10-200 mg/ml. Lyophilization typically occurs over a series of steps, for instance a cycle starting at −69° C., gradually adjusting to −24° C. over 3 h, then retaining this temperature for 18 h, then gradually adjusting to −16° C. over 1 h, then retaining this temperature for 6 h, then gradually adjusting to +34° C. over 3 h, and finally retaining this temperature over 9 h.

In some embodiments, an immunogenic composition (e.g., vaccine) is a liquid. In some embodiments, the liquid is a reconstituted lyophilate. In some embodiments, an immunogenic composition (e.g., vaccine) has a pH of about 5, about 6, about 7, or about 8. In some embodiments, an immunogenic composition (e.g., vaccine) has a pH between about 5 and about 7.5. In some embodiments, an immunogenic composition (e.g., vaccine) has a pH between 5 and 7.5. In some embodiments, an immunogenic composition (e.g., vaccine) has a pH between about 5.3 and about 6.3. In some embodiments, an immunogenic composition (e.g., vaccine) has a pH between 5.3 and 6.3. In some embodiments, an immunogenic composition (e.g., vaccine) has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

Immunogenic compositions (e.g., vaccines) or components thereof for use in accordance with the present disclosure invention may be incorporated into liposomes, cochleates, biodegradable polymers such as poly-lactide, polyglycolide and poly-lactide-co-glycolides, or immune-stimulating complexes (ISCOMs).

In certain situations, it may be desirable to prolong the effect of an immunogenic composition (e.g., vaccine) or for use in accordance with the present disclosure, for example by slowing the absorption of one or more components of immunogenic compositions (e.g., vaccines). Such delay of absorption may be accomplished, for example, by the use of a liquid suspension of crystalline or amorphous material with poor water solubility. The rate of absorption of the product then depends upon its rate of dissolution, which in turn, may depend upon size and form. Alternatively, or additionally, delayed absorption may be accomplished by dissolving or suspending one or more components of immunogenic compositions (e.g., vaccines) in an oil vehicle. Injectable depot forms can also be employed to delay absorption. Such depot forms can be prepared by forming microcapsule matrices of one or more components of immunogenic compositions (e.g., vaccines) a biodegradable polymers network. Depending upon the ratio of polymer to component(s) of immunogenic compositions (e.g., vaccines), and the nature of the particular polymer(s) employed, the rate of release can be controlled.

Examples of biodegradable polymers that can be employed in accordance with the present disclosure include, for example, poly(orthoesters) and poly(anhydrides). One particular exemplary polymer is polylactide-polyglycolide.

Depot injectable formulations may also be prepared by entrapping the product in liposomes or microemulsions, which are compatible with body tissues.

Polymeric delivery systems can also be employed in non-depot formulations including, for example, oral formulations. For example, biodegradable, biocompatible polymers such as ethylene vinyl acetate, polyanhydrides, polyglycolic acid, collagen, polyorthoesters, and polylactic acid, etc., can be used in oral formulations. Polysaccharide antigens or conjugates may be formulated with such polymers, for example to prepare particles, microparticles, extrudates, solid dispersions, admixtures, or other combinations in order to facilitate preparation of useful formulations (e.g., oral).

Immunogenic compositions (e.g., vaccines) for use in accordance with the present disclosure include immunogenic compositions, and may additionally include one or more additional active agents (i.e., agents that exert a biological effect—not inert ingredients). For example, it is common in immunogenic composition (e.g., vaccine) preparation to include one or more adjuvants. It will be appreciated that such additional agents may be formulated together with one or more other components of immunogenic compositions (e.g., vaccines), or may be maintained separately and combined at or near the time of administration. In some embodiments, such additional components may be administered separately from some or all of the other components of immunogenic compositions (e.g., vaccines), within an appropriate time window for the relevant effect to be achieved.

Adjuvants

The vaccine formulations and immunogenic compositions described herein may include an adjuvant. Adjuvants, generally, are agents that enhance the immune response to an antigen. Adjuvants can be broadly separated into two classes, based on their principal mechanisms of action: vaccine delivery systems and immunostimulatory adjuvants (see, e.g., Singh et al, 2003). In most vaccine formulations, the adjuvant provides a signal to the immune system so that it generates a response to the antigen, and the antigen is required for driving the specificity of the response to the pathogen. Vaccine delivery systems are often particulate formulations, e.g., emulsions, microparticles, immune-stimulating complexes (ISCOMs), nanoparticles, which may be, for example, particles and/or matrices, and liposomes. In contrast, immunostimulatory adjuvants are sometimes from or derived from pathogens and can represent pathogen associated molecular patterns (PAMP), e.g., lipopolysaccharides (LPS), monophosphoryl lipid A (MPL), or CpG-containing DNA, which activate cells of the innate immune system.

Alternatively, adjuvants may be classified as organic and inorganic. Inorganic adjuvants include alum salts such as aluminum phosphate, amorphous aluminum hydroxyphosphate sulfate, and aluminum hydroxide, which are commonly used in human vaccines. Organic adjuvants comprise organic molecules including macromolecules. Non-limiting examples of organic adjuvants include cholera toxin/toxoids, other enterotoxins/toxoids or labile toxins/toxoids of Gram-negative bacteria, interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), and tumor necrosis factor (TNF).

Adjuvants may also be classified by the response they induce. In some embodiments, the adjuvant induces the generation, proliferation, or activation of $T_H1$ cells or $T_H2$ cells. In other embodiments, the adjuvant induces the generation, proliferation, or activation of B cells. In yet other embodiments, the adjuvant induces the activation of antigen-presenting cells. These categories are not mutually exclusive; in some cases, an adjuvant activates more than one type of cell.

In certain embodiments, the adjuvant induces the generation, proliferation, or activation of $T_H17$ cells. The adjuvant may promote the CD4+ or CD8+ T cells to secrete IL-17. In some embodiments, an adjuvant that induces the generation, proliferation, or activation of $T_H17$ cells is one that produces at least a 2-fold, and in some cases a 10-fold, experimental sample to control ratio in the following assay. In the assay, an experimenter compares the IL-17 levels secreted by two populations of cells: (1) cells from animals immunized with the adjuvant and a polypeptide known to induce $T_H17$ generation, proliferation, or activation, and (2) cells from animals treated with the adjuvant and an irrelevant (control) polypeptide. An adjuvant that induces the generation, proliferation, or activation of $T_H17$ cells may cause the cells of population (1) to produce more than 2-fold, or more than 10-fold more IL-17 than the cells of population (2). IL-17 may be measured, for example, by ELISA or ELISPOT. Certain toxins, such as cholera toxin and labile toxin (produced by enterotoxigenic *E. coli*, or ETEC), activate a $T_H17$ response. Thus, in some embodiments, the adjuvant is a toxin or toxoid. One form of labile toxin is produced by Intercell. Mutant derivates of labile toxin (toxoids) that are active as adjuvants but significantly less toxic can be used as well. Exemplary detoxified mutant derivatives of labile toxin include mutants lacking ADP-ribosyltransferase activity. Particular detoxified mutant derivatives of labile toxin include LTK7 (Douce et al, 1995) and LTK63 (Williams et al, 2004), LT-G192 (Douce et al, 1999), and LTR72 (Giuliani et al, 1998).

In some embodiments, the adjuvant comprises a VLP (virus-like particle). One such adjuvant platform, Alphavirus replicons, induces the activation of $T_H17$ cells using alphavirus and is produced by Alphavax. In certain embodiments of the Alphavirus replicon system, alphavirus may be engineered to express an antigen of interest, a cytokine of interest (for example, IL-17 or a cytokine that stimulates IL-17 production), or both, and may be produced in a helper cell line. More detailed information may be found in U.S. Pat. Nos. 5,643,576 and 6,783,939. In some embodiments, an immunogenic composition (e.g., vaccine) formulation is administered to a subject in combination with a nucleic acid encoding a cytokine.

Certain classes of adjuvants activate toll-like receptors (TLRs) in order to activate a $T_H17$ response. TLRs are well known proteins that may be found on leukocyte membranes, and recognize foreign antigens (including microbial antigens). Administering a known TLR ligand together with an antigen of interest (for instance, as a fusion protein) can promote the development of an immune response specific to the antigen of interest. One exemplary adjuvant that activates TLRs comprises Monophosphoryl Lipid A (MPL). Traditionally, MPL has been produced as a detoxified lipopolysaccharide (LPS) endotoxin obtained from Gram-negative bacteria, such as *S. minnesota*. In particular, sequential acid and base hydrolysis of LPS produces an immunoactive lipid A fraction (which is MPL), and lacks the saccharide groups and all but one of the phosphates present in LPS. A number of synthetic TLR agonists (in particular, TLR-4 agonists) are disclosed in Evans et al, 2003. Like MPL adjuvants, these synthetic compounds activate the innate immune system via TLR. Another type of TLR agonist is a synthetic phospholipid dimer, for example E6020 (Ishizaka et al, 2007). Various TLR agonists (including TLR-4 agonists) have been produced and/or sold by, for example, the Infectious Disease Research Institute (IRDI), Corixa, Esai, Avanti Polar Lipids, Inc., and Sigma Aldrich. Another exemplary adjuvant that activates TLRs comprises a mixture of MPL, Trehalose Dicoynomycolate (TDM), and dioctadecyldimethylammonium bromide (DDA). Another TLR-activating adjuvant is R848 (resiquimod).

In some embodiments, the adjuvant is or comprises a saponin. Typically, the saponin is a triterpene glycoside, such as those isolated from the bark of the Quillaja *saponaria* tree. A saponin extract from a biological source can be further fractionated (e.g., by chromatography) to isolate the portions of the extract with the best adjuvant activity and with acceptable toxicity. Typical fractions of extract from Quillaja *saponaria* tree used as adjuvants are known as fractions A and C.

In certain embodiments, combinations of adjuvants are used. Three exemplary combinations of adjuvants are MPL and alum, E6020 and alum, and MPL and an ISCOM.

Adjuvants may be covalently or non-covalently bound to antigens. In some embodiments, the adjuvant may comprise a protein which induces inflammatory responses through activation of antigen-presenting cells (APCs). In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (e.g., see Wu et al, 2005).

In some embodiments, immunogenic complexes described herein are formulated and/or administered in combination with an adjuvant. In some embodiments, the adjuvant is selected from the group consisting of aluminum phosphate, aluminum hydroxide, and phosphate aluminum hydroxide. In some embodiments, the adjuvant comprises aluminum phosphate. In some embodiments, the adjuvant is aluminum phosphate.

Typically, the same adjuvant or mixture of adjuvants is present in each dose of an immunogenic composition (e.g., vaccine). Optionally, however, an adjuvant may be administered with the first dose of immunogenic composition (e.g., vaccine) and not with subsequent doses (i.e., booster shots). Alternatively, a strong adjuvant may be administered with the first dose of immunogenic composition (e.g., vaccine) and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human subjects, non-human animals, or both.

Immunogenic compositions (e.g., vaccines) for use in accordance with the present disclosure may include, or be administered concurrently with, other antimicrobial therapy. For example, such immunogenic compositions (e.g., vaccines) may include or be administered with one or more agents that kills or retards growth of a pathogen. Such agents include, for example, penicillin, vancomycin, erythromycin, azithromycin, and clarithromycin, cefotaxime, ceftriaxone, levoflaxin, gatifloxacin.

Alternatively or additionally, immunogenic compositions (e.g., vaccines) for use in accordance with the present disclosure may include, or be administered with, one or more other vaccines or therapies. For example, one or more non-pneumococcal antigens may be included in or administered with the immunogenic compositions (e.g., vaccines).

Additional Components and Excipients

In addition to the antigens and the adjuvants described above, a vaccine formulation or immunogenic composition may include one or more additional components.

In certain embodiments, the vaccine formulation or immunogenic composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or immunogenic composition includes one or more buffers such as a mixture of sodium bicarbonate and ascorbic acid. In some embodiments, the vaccine formulation may be administered in saline, such as phosphate buffered saline (PBS), or distilled water.

In certain embodiments, the vaccine formulation or immunogenic composition includes one or more surfactants, for example, but not limited to, polysorbate 80 (TWEEN 80), polysorbate 20 (TWEEN 20), Polyethylene glycol p-(1,1,3,3-tetramethylbutyl)-phenyl ether (TRITON X-100), and 4-(1,1,3,3-Tetramethylbutyl) phenol polymer with formaldehyde and oxirane (TYLOXAPOL). A surfactant can be ionic or non-ionic.

In certain embodiments, the vaccine formulation or immunogenic composition includes one or more salts such as sodium chloride, ammonium chloride, calcium chloride, or potassium chloride.

In certain embodiments, a preservative is included in the vaccine or immunogenic composition. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

Methods of Administration

In some embodiments, immunogenic complexes and/or immunogenic compositions described herein (including, e.g., vaccine compositions (e.g., ones as described and/or utilized herein)) are administered to a subject at risk of developing pneumococcal disease, e.g. an infant, a toddler, a juvenile, or an older adult. In some embodiments, the subject is a human. In some embodiments, the human is between about 2 weeks of age and about 6 weeks of age. In some embodiments, the human is between about 6 weeks of age and about 6 years of age. In some embodiments, the human is between about 6 years of age and about 18 years of age. In some embodiments, the human is between about 18 years of age and about 50 years of age. In some embodiments, the human is about 50 years of age or older. In some embodiments, and/or immunogenic compositions described herein (including, e.g., vaccine compositions (e.g., ones as described and/or utilized herein)) are administered to a subject at elevated risk of developing pneumococcal disease, e.g., immunocompromised subjects, subjects having sickle cell disease or other hemoglobinopathies, congenital or acquired asplenia, splenic dysfunction, chronic renal failure or nephrotic syndrome, diseases associated with treatment with immunosuppressive drugs or radiation therapy (including malignant neoplasm, leukemia, lymphomas, Hodgkin's disease, or solid organ transplantation), congenital or acquired immunodeficiency, HIV infection, cerebrospinal fluid leaks, cochlear implant(s), chronic heart disease, chronic lung disease, diabetes mellitus, alcoholism, chronic liver disease, cigarette smoking, asthma, generalized malignancy, multiple myeloma, or solid organ transplantation. It will be appreciated that a subject can be considered at risk for developing a disease without having been diagnosed with any symptoms of the disease. For example, if the subject is known to have been, or to be intended to be, in situations with relatively high risk of infection, that subject will be considered at risk for developing the disease.

Any effective route of administration may be utilized such as, for example, oral, nasal, enteral, parenteral, intramuscular or intravenous, subcutaneous, transdermal, intradermal, rectal, vaginal, topical, ocular, pulmonary, or by contact application. In some embodiments, immunogenic compositions described herein (including, e.g., vaccine compositions (e.g., ones as described and/or utilized herein)) may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments, it may be desirable to administer different doses of an immunogenic composition described herein (including, e.g., vaccine composition (e.g., ones as described and/or utilized herein)) by different routes; in some embodiments, it may be desirable to administer different components of one dose via different routes. In some embodiments, an immunogenic composition (e.g., vaccine) disclosed herein is administered intramuscularly. In some embodiments, an immunogenic composition (e.g., vaccine) disclosed herein is administered subcutaneously.

In some embodiments, pharmaceutical compositions (e.g., vaccines) are administered intradermally. Conventional technique of intradermal injection, the "Mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced while providing a slight pressure to elevate it under the skin. The liquid is then injected very slowly thereby forming a bleb or bump on the skin surface, followed by slow withdrawal of the needle.

Devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Other methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

As described above, pharmaceutical compositions (e.g., vaccines) may be administered as a single dose or as multiple doses. It will be appreciated that an administration is a single "dose" so long as all relevant components are administered to a subject within a window of time; it is not necessary that every component be present in a single composition. For example, administration of two different immunogenic compositions, within a period of less than 24 h, is considered a single dose. To give but one example, immunogenic compositions having different antigenic components may be administered in separate compositions, but as part of a single dose. As noted above, such separate compositions may be administered via different routes or via the same route. Alternatively or additionally, in embodiments wherein a vaccine comprises a combination of immunogenic compositions and additional types of active agents, immunogenic compositions may be administered via one route, and a second active agent may be administered by the same route or by a different route.

Pharmaceutical compositions (e.g., vaccines) are administered in such amounts and for such time as is necessary to achieve a desired result. In certain embodiments of the present disclosure, a vaccine composition comprises an immunologically effective amount of at least immunogenic composition. The exact amount required to achieve an immunologically effective amount may vary, depending on the immunogenic composition, and from subject to subject, depending on the species, age, and general condition of the subject, the stage of the disease, the particular pharmaceutical mixture, its mode of administration, and the like.

The amount of polypeptide antigen(s), polysaccharide antigen(s) or conjugate(s) in each pharmaceutical composition (e.g., vaccine) dose is selected to allow the vaccine, when administered as described herein, to induce an appropriate immune-protective response without significant, adverse side effects.

In some embodiments, a pharmaceutical composition comprising an immunogenic complex disclosed herein induces a $T_H1$ and/or $T_H17$ cell response upon administration to a subject. In some embodiments, a pharmaceutical composition comprising an immunogenic complex disclosed herein induces an opsonic/bactericidal response against *S. pneumoniae* upon administration to a subject. In some embodiments, a pharmaceutical composition comprising an immunogenic complex disclosed herein reduces rate of transmission and/or colonization by *S. pneumoniae* upon administration to a subject. In some embodiments, a pharmaceutical composition comprising an immunogenic complex disclosed herein reduces rate of transmission and/or colonization of the mucosal surfaces by *S. pneumoniae* upon administration to a subject.

In some embodiments, a pharmaceutical composition comprising an immunogenic complex disclosed herein reduces rate of transmission and/or colonization of the nasopharynx or the lungs by *S. pneumoniae* upon transmission. In some embodiments, a pharmaceutical composition comprising an immunogenic complex disclosed herein inhibits or reduces asymptomatic infection by *S. pneumoniae* upon administration to a subject.

Some embodiments provide for a method of immunizing a subject against *S. pneumoniae* infection comprising administering to the subject an immunologically effective amount of an immunogenic complex described herein. Some embodiments provide for a method of immunizing a subject against *S. pneumoniae* infection comprising administering to the subject an immunologically effective amount of an immunogenic composition described herein. Some embodiments provide for a method of immunizing a subject against *S. pneumoniae* infection comprising administering to the subject an immunologically effective amount of a vaccine composition described herein. Some embodiments provide for a method of immunizing a subject against *S. pneumoniae* infection comprising administering to the subject an immunologically effective amount of a pharmaceutical composition described herein.

Some embodiments provide an immunogenic complex, immunogenic composition (e.g., vaccine), or pharmaceutical composition as described herein for use in therapy. For example, a vaccine as described herein for use in the treatment or prevention of *Streptococcus pneumoniae* infection and/or colonization in a subject such as a human subject. Some embodiments provide an immunogenic complex, immunogenic composition (e.g., vaccine), or pharmaceutical composition as described herein for use in the treatment or prevention of *Streptococcus pneumoniae* infection and/or colonization in a subject such as a human subject. Further embodiments provide a use of an immunogenic complex, immunogenic composition (e.g., vaccine), or pharmaceutical composition as described herein in the manufacture of a medicament for the treatment or prevention of *Streptococcus pneumoniae* infection and/or colonization. The characteristics of methods of treatment or prevention disclosed herein are equally applicable to an immunogenic complex, immunogenic composition (e.g., vaccine), or pharmaceutical composition for use, or a use of an immunogenic complex, immunogenic composition (e.g., vaccine), or pharmaceutical composition, in the manufacture of a medicament.

Combination Prophylaxis or Combination Therapy

In some embodiments, an immunogenic complex, immunogenic composition, vaccine, or pharmaceutical composition disclosed herein may be administered in combination with one or more additional agents. In some embodiments, the agents are additional vaccines. In some embodiments, the agent is or comprises PCV13. In some embodiments, the agent is or comprises PCV20. In some embodiments, the agent is or comprises PPSV23. In some embodiments, the agent is or comprises an antibiotic.

Dosing

In some embodiments, administration of an immunogenic composition (e.g., vaccine) described herein may involve the delivery of a single dose. In some embodiments, administration may involve an initial dose followed by one or several additional immunization doses, adequately spaced. An immunization schedule is a program for the administration of one or more specified doses of one or more specified pneumococcal vaccines, by one or more specified routes of administration, at one or more specified ages of a subject.

The present disclosure provides immunization methods that involve administering at least one dose of a vaccine to an infant subject. In some embodiments, the infant subject is 18 months old or younger. In some embodiments, the infant subject is 12 months old or younger. In some embodiments, the infant subject has previously received one or more doses of a conjugated pneumococcal polysaccharide vaccine; in other embodiments, the infant subject is naïve to pneumococcal vaccines. In some embodiments, the infant subject has previously been infected with, or exposed to infection by *S. pneumoniae.*

The present disclosure provides immunization methods that involve administering at least one dose of a vaccine to a toddler subject. In some embodiments, the toddler subject is 5 years old or younger. In some embodiments, the toddler subject is 4 years old or younger. In some embodiments, the toddler subject has previously received one or more doses of a conjugated pneumococcal polysaccharide vaccine; in other embodiments, the toddler subject is naïve to pneumococcal vaccines. In some embodiments, the toddler subject has previously been infected with, or exposed to infection by *S. pneumoniae.*

The present disclosure provides immunization methods that involve administering at least one dose of a vaccine to a juvenile subject. In some embodiments, the juvenile subject is 18 years old or younger. In some embodiments, the juvenile subject is 15 years old or younger. In some embodiments, the juvenile subject has previously received one or more doses of a conjugated pneumococcal polysaccharide vaccine; in other embodiments, the juvenile subject is naïve to pneumococcal vaccines. In some embodiments, the juvenile subject has previously been infected with, or exposed to infection by *S. pneumoniae.*

The present disclosure provides immunization methods that involve administering at least one dose of a vaccine to an adult subject. In some embodiments, the adult subject is older than about 50 years of age. In some embodiments, the adult subject is older than about 65 years of age. In some embodiments, the adult subject has previously received one or more doses of a conjugated pneumococcal polysaccharide vaccine; in other embodiments, the adult subject is naïve to pneumococcal vaccines. In some embodiments, the adult subject has previously been infected with, or exposed to infection by *S. pneumoniae.*

Immunization schedules of the present disclosure are provided to induce an immune response (e.g., an immunoprotective response) in a subject sufficient to reduce at least one measure selected from the group consisting of incidence, prevalence, frequency, and/or severity of at least one infection, disease, or disorder, and/or at least one surrogate marker of the infection, disease, or disorder, in a population and/or subpopulation of the subject(s). A supplemental immunization schedule is one which has this effect relative to the standard schedule which it supplements. A supplemental schedule may call for additional administrations and/or supra-immunogenic doses of the immunogenic compositions disclosed herein, found in the standard schedule, or for the administration of vaccines not part of the standard schedule. A full immunization schedule of the present disclosure may comprise both a standard schedule and a supplemental schedule. Exemplary sample vaccination schedules are provided for illustrative purposes. Detailed descriptions of methods to assess immunogenic response discussed herein allow one to develop alterations to the sample immunization schedules without undue experimentation.

In some embodiments of the present disclosure, a first administration of a pneumococcal immunogenic composition (e.g., vaccine) occurs when a subject is more than about 2 weeks old, more than about 5 weeks old, more than about 1 year old, more than about 2 years old, more than about 15 years old, or more than about 18 years old.

In some embodiments, a first administration of a pneumococcal immunogenic composition (e.g., vaccine) occurs when a subject is about two months old. In some embodiments, a second administration of a pneumococcal immunogenic composition (e.g., vaccine) occurs when a subject is about four months old. In some embodiments, a third administration of a pneumococcal immunogenic composition (e.g., vaccine) occurs when a subject is about six months old. In some embodiments, a fourth administration of a pneumococcal immunogenic composition (e.g., vaccine) occurs when a subject is between about twelve months old and about fifteen months old.

In some embodiments of the present disclosure, a first administration of a pneumococcal immunogenic composition (e.g., vaccine) occurs when a subject is more than about 50 years old, more than about 55 years old, more than about 60 years old, more than about 65 years old, or more than about 70 years old.

In some embodiments of the disclosure, a single administration of immunogenic composition (e.g., vaccine) is employed. It is possible that the purposes of the present disclosure can be served with a single administration, especially when one or more utilized immunogenic composition (e.g., vaccine) polypeptide(s), polysaccharide(s) and/or immunogenic complex(es) or combinations thereof is/are strong, and in such a situation a single dose schedule is sufficient to induce a lasting immune-protective response.

In certain embodiments, it is desirable to administer two or more doses of immunogenic composition (e.g., vaccine), for greater immune-protective efficacy and coverage. Thus, in some embodiments, a number of doses is at least two, at least three, at least four or more doses. There is no set maximum number of doses; however, it is good clinical practice not to immunize more often than necessary to achieve the desired effect.

Without being bound by theory, a first dose of immunogenic composition (e.g., vaccine) administered according to the disclosure may be considered a "priming" dose. When administered in a regimen as a priming dose the immunogenic composition (e.g., vaccine) may be considered a "priming vaccine". In certain embodiments, more than one dose is included in an immunization schedule. In such a scenario, a subsequent dose may be considered a "boosting" dose. When administered in a regimen as a boosting dose the immunogenic composition (e.g., vaccine) may be considered a "booster vaccine". In some embodiments, the immunogenic composition (e.g., vaccine) can be administered in a regimen as a prime vaccine and as a booster vaccine.

A priming dose may be administered to a naïve subject (a subject who has never previously received a conjugated polysaccharide vaccine). In some embodiments, a priming dose may be administered to a subject who has previously received conjugated polysaccharide vaccine at least five or more years prior to administration of an initial vaccine dose according to the disclosure. In other embodiments, a priming dose may be administered to a subject who has previously received a conjugated polysaccharide vaccine at least twenty or more years prior to administration of a priming vaccine according to the disclosure.

When an immunization schedule calls for two or more separate doses, the interval between doses is considered. The interval between two successive doses may be the same throughout an immunization schedule, or it may change as the subject ages. In immunization schedules of the present disclosure, once a first vaccine dose has been administered, there is a first interval before administration of a subsequent dose. A first interval is generally at least about 2 weeks, 1 month, 6 weeks, 2 months, 3 months, 6 months, 9 months, 12 months, or longer. Where more than one subsequent dose(s) are administered, second (or higher) intervals may be provided between such subsequent doses. In some embodiments, all intervals between subsequent doses are of the same length; in other embodiments, second intervals may vary in length. In some embodiments, the interval between subsequent doses may be at least about 12 months, at least about 15 months, at least about 18 months, at least about 21 months or at least about 2 years. In certain embodiments, the interval between doses may be up to 3 years, up to about 4 years, or up to about 5 years or 10 years or more. In certain embodiments, intervals between subsequent doses may decrease as the subject ages.

It will be appreciated by those skilled in the art that a variety of possible combinations and sub-combinations of the various conditions of timing of the first administration, shortest interval, largest interval and total number of administrations (in absolute terms, or within a stated period) exist, and all of these combinations and sub-combinations should be considered to be within the inventor's contemplation though not explicitly enumerated here.

Assays for Determining Immune Response

In some embodiments, a method of assessing the immunogenicity of an immunogenic composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by opsonophagocytic killing (OPK), serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, inhibition or reduction of asymptomatic infection, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the immunogenic composition and not comprise an antigenic polypeptide present in the immunogenic composition. In some embodiments, a control composition may comprise an antigenic polypeptide present in the immunogenic composition and not comprise an antigenic polysaccharide present in the immunogenic composition. In some embodiments, a control composition may comprise an adjuvant present in the immunogenic composition, and not comprise an antigenic polysaccharide and/or an immunogenic polypeptide present in the immunogenic composition.

In some embodiments, a method of assessing the potency of an immunogenic composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), internalization, activity neutralization, agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance or reduction from mucosal surfaces or bloodstream, reduction or prevention of bacteremia, meningitis, sepsis, or otitis media, reduction or prevention of colonization of the nasopharynx, inhibition or reduction of asymptomatic infection, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the immunogenic composition and not comprise an antigenic polypeptide present in the immunogenic composition. In some embodiments, a control composition may comprise an antigenic polypeptide present in the immunogenic composition and not comprise an antigenic polysaccharide present in the immunogenic composition. In some embodiments, a control composition may comprise an adjuvant present in the immunogenic composition, and not comprise an antigenic polysaccharide and/or an immunogenic polypeptide present in the immunogenic composition.

In some embodiments, a method of assessing the immunogenicity of a vaccine composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, inhibition or reduction of asymptomatic infection, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the vaccine composition and not comprise an antigenic polypeptide present in the vaccine composition. In some embodiments, a control composition may comprise an antigenic polypeptide present in the vaccine composition and not comprise an antigenic polysaccharide present in the vaccine composition. In some embodiments, a control composition may comprise an adjuvant present in the vaccine composition, and not comprise an antigenic polysaccharide and/or an immunogenic polypeptide present in the vaccine composition.

In some embodiments, a method of assessing the potency of a vaccine composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, inhibition or reduction of asymptomatic infection, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the vaccine composition and not comprise an antigenic polypeptide present in the vaccine composition. In some embodiments, a control composition may comprise an antigenic polypeptide present in the vaccine composition and not comprise an antigenic polysaccharide present in the vaccine composition. In some embodiments, a control composition may comprise an adjuvant present in the vaccine composition, and not comprise an antigenic polysaccharide and/or an immunogenic polypeptide present in the vaccine composition.

In some embodiments, a method of assessing the immunogenicity of a pharmaceutical composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, inhibition or reduction of asymptomatic infection, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the pharmaceutical composition and not comprise an antigenic polypeptide present in the pharmaceutical composition. In some embodiments, a control composition may comprise an antigenic polypeptide present in the pharmaceutical composition and not comprise an antigenic polysaccharide present in the pharmaceutical composition. In some embodiments, a control composition may comprise an adjuvant present in the pharmaceutical composition, and not comprise an antigenic polysaccharide and/or an immunogenic polypeptide present in the pharmaceutical composition.

In some embodiments, a method of assessing the potency of a pharmaceutical composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, inhibition or reduction of asymptomatic infection, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the pharmaceutical composition and not comprise an antigenic polypeptide present in the pharmaceutical composition. In some embodiments, a control composition may comprise an antigenic polypeptide present in the pharmaceutical composition and not comprise an antigenic polysaccharide present in the pharmaceutical composition. In some embodiments, a control composition may comprise an adjuvant present in the pharmaceutical composition, and not comprise an antigenic polysaccharide and/or an immunogenic polypeptide present in the pharmaceutical composition.

In some embodiments, a method of assessing the immunogenicity and/or potency of an immunogenic complex comprises evaluating an immune response to immunogenic or vaccine compositions comprising one or more immunogenic complexes. In some embodiments, the method of assessing the immunogenicity and/or potency of an immunogenic complex described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, inhibition or reduction of asymptomatic infection, reduction in mortality, and passive and active protection following challenge with the pneumococcal pathogens that are the targets of the immunogenic composition.

Generally speaking, it may be desirable to assess humoral responses, cellular responses, and/or interactions between the two. Where humoral responses are being assessed, antibody titers and/or types (e.g., total IgG, IgG1, IgG2, IgM, IgA, etc.) to specific pathogen polysaccharides or polypeptides (either serotype-specific or conserved across two or more serotypes) may be determined, for example before and/or after administration of an initial or a boosting dose of vaccine (and/or as compared with antibody levels in the absence of antigenic stimulation). Cellular responses may be assessed by monitoring reactions such as delayed type hypersensitivity responses, etc. to the carrier protein. Cellular responses can also be measured directly by evaluating the response of peripheral blood mononuclear cells (PBMCs) monocytes to stimulation with the antigens of interest. Precursor and memory B cell populations may be assessed in enzyme linked immunospot (ELISpot) assays directed against specific pathogen polysaccharides or polypeptides.

Any of a variety of assays may be employed to detect levels and/or activity of antibodies in subject sera. Suitable assays include, for example, ligand binding assays, such as radioimmunoassay (RIAs), ELISAs, and multiplex assays (Luminex, Bioplex, MSD); functional assays, such as opsonophagocytic assays or internalization assays; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, inhibition or reduction of asymptomatic infection, reduction in mortality, and passive and active protection following challenge with the pneumococcal pathogens that are the targets of the immunogenic composition.

The RIA method detects specific antibodies through incubation of sera with radiolabeled polysaccharides or polypeptides in suspension (e.g., Schiffiman et al, 1980). The antigen-antibody complexes are then precipitated with ammonium sulfate and the radiolabeled pellets assayed for counts per minute (cpm).

In the ELISA detection method, specific antibodies from the sera of vaccinated subjects are quantitated by incubation with polysaccharides or polypeptides (either serotype-specific or conserved across two or more serotypes) which have been adsorbed to a solid support (e.g., Koskela and Leinonen (1981); Kojima et al, 1990; Concepcion and Frasch, 2001). The bound antibody is detected using enzyme-conjugated secondary detection antibodies. The ELISA also allows isotyping and subclassing of the immune response (i.e., IgM vs. IgG or IgG1 vs. IgG2) by using isotype- or subclass-specific secondary antibodies and can be adapted to evaluate the avidity of the antibodies (Anttila et al, 1998; Romero-Steiner et al, 2005). Multiplex assays (e.g., Luminex) facilitate simultaneous detection of antibodies to multiple antigens. Capsular polysaccharide(s) or polypeptides are conjugated to spectrally distinct microspheres that are mixed and incubated with serum. The antibodies bound to the polysaccharides or polypeptides on the coated microspheres are detected using a secondary antibody (e.g., R-Phycocrythrin-conjugated goat anti-human IgG).

An approach for assessing functional antibody in serum is an opsonophagocytic assay (OPA) or a concentrated opsonophagocytic assay (COPA), which quantitates only the antibodies that can opsonize the bacteria, leading to ingestion and killing of the bacteria. The standard assay utilizes a human phagocytic effector cell, a source of complement, bacteria, and diluted sera. The assay readout is the serum endpoint titer at which there is >50% killing compared to bacteria incubated with complement and human cells alone (Romero-Steiner et al, 1997). This killing OPA can also be multiplexed by utilizing target strains of pathogen that carry different antibiotic resistance markers (Kim et al, 2003). Another type of multiplex opsonic assay is a nonkilling assay in which the uptake by phagocytic effector cells of fluorescent stained encapsulated pathogen or fluorescent microspheres conjugated with antigenic polysaccharides or polypeptides from a target pathogen in the presence of diluted sera plus a complement source is evaluated by flow cytometry (Martinez et al, 1999). Opsonic activity of serum antibody plus complement can also be evaluated by measuring the oxidative response of phagocytic human effector cells to ingested pathogen (Munro et al. 1985; Ojo-Amaize et al. 1995).

Certain in vivo model systems can be used to evaluate the protection afforded by serum antibodies induced by vaccines of the present disclosure. In such passive protection systems, mice or rats are challenged with the pathogen plus diluted sera, and the endpoint titer of the sera which provides protection against pneumonia, bacteremia, colonization of organs or tissues, or mortality is determined (Stack et al. 1998; Sacland et al. 2000).

In some embodiments, efficacy of vaccination may be determined by assaying one or more cytokine levels by stimulating T cells from a subject after vaccination. The one or more cytokine levels may be compared to the one or more cytokine levels in the same subject before vaccination. Increased levels of the one or more cytokine, such as a 1.5 fold, 2-fold, 5-fold, 10-fold, 20-fold, 50-fold or 100-fold or more increase over pre-immunization cytokine levels, would indicate an increased response to the vaccine. In some embodiments, the one or more cytokines are selected from GM-CSP; IL-1a; IL-1B; IL-2; IL-3; IL-4; IL-5; IL-6; IL-7; IL-8; IL-10; IL-12; IL-17A, IL-17F or other members of the IL-17 family; IL-22; IL-23; IFN-α; IFN-β; IFN-γ; MIP-1α; MIP-1β; TGF-β; TNFα, or TNF-β. In a non-limiting example, efficacy of vaccination may be determined by assaying IL-17 levels (particularly IL-17A) by stimulating T cells from a subject after vaccination. The IL-17 levels may be compared to IL-17 levels in the same subject before vaccination. Increased IL-17 (e.g., IL-17A) levels, such as a 1.5 fold, 2-fold, 5-fold, 10-fold, 20-fold, 50-fold or 100-fold or more increase, would indicate an increased response to the vaccine.

In some embodiments, one may assay neutrophils in the presence of T cells or antibodies from the patient for pneumococcal killing. Increased pneumococcal killing, such as a 1.5 fold, 2-fold, 5-fold, 10-fold, 20-fold, 50-fold or 100-fold or more increase, would indicate an increased response to the vaccine. For example, one may measure $T_H17$ cell activation, where increased $T_H17$ cell activation, such as a 1.5 fold, 2-fold, 5-fold, 10-fold, 20-fold, 50-fold or 100-fold or more increase, correlates with an increased response to the vaccine. In another non-limiting example, one may measure $T_H1$ cell activation, where increased $T_H1$ cell activation, such as a 1.5 fold, 2-fold, 5-fold, 10-fold, 20-fold, 50-fold or 100-fold or more increase, correlates with an increased response to the vaccine. One may also measure levels of an antibody specific to the vaccine, where increased levels of the specific antibody, such as a 1.5 fold, 2-fold, 5-fold, 10-fold, 20-fold, 50-fold or 100-fold or more increase, are correlated with increased vaccine efficacy. In certain embodiments, two or more of these assays are used. For example, one may measure IL-17 levels and the levels of vaccine-specific antibody. Alternatively, one may follow epidemiological markers such as incidence of, severity of, or duration of pneumococcal infection in vaccinated individuals compared to unvaccinated individuals.

Vaccine efficacy may also be assayed in various model systems such as the mouse challenge model. For instance, BALB/c or C57BL/6 strains of mice may be used. After administering the test vaccine to a subject (as a single dose or multiple doses), the experimenter administers a challenge dose of *S. pneumoniae*. In some cases, a challenge dose administered intranasally is sufficient to cause *S. pneumoniae* colonization (especially nasal colonization) in an unvaccinated animal, and in some cases a challenge dose administered via aspiration is sufficient to cause sepsis and a high rate of lethality in unvaccinated animals. In some cases, a challenge dose administered via intraperitoneal injection is sufficient to cause sepsis and a high rate of lethality in unvaccinated animals. In some cases, a challenge dose administered via intravenous injection is sufficient to cause sepsis and a high rate of lethality in unvaccinated animals. One can then measure the reduction in colonization or the reduction in lethality in vaccinated animals.

Certain in vivo model systems can be used to evaluate the protection afforded by serum antibodies induced by vaccines of the present disclosure. In such passive protection systems, mice or rats are challenged with the pathogen plus diluted sera, and the endpoint titer of the sera which provides protection against bacteremia, colonization of organs or tissues, or mortality is determined (Stack et al. 1998; Saeland et al. 2000).

Kits

The present disclosure also provides for kits for producing an immunogenic complex as disclosed herein which is useful for an investigator to tailor an immunogenic complex with their preferred antigens, e.g., for research purposes to assess the effect of an antigen, or a combination of antigens on immune response. Such kits can be prepared from readily available materials and reagents. For example, such kits can comprise any one or more of the following materials: a container comprising a polysaccharide cross-linked with a plurality of first affinity molecules; a container comprising a complementary affinity molecule which associates with the first affinity molecule, wherein the complementary affinity molecule associates with an antigen or carrier protein; a container comprising an antigen; a container comprising a carrier protein; a container comprising an antigen associated with a complementary affinity molecule; a container comprising a carrier protein associated with a complementary affinity molecule.

In another embodiment, the kit comprises a container comprising a polysaccharide; a container comprising a plurality of first affinity molecules; and a container comprising a cross-linking reagent for cross-linking the first affinity molecules to the polysaccharide, for example, but not limited to, CDAP (1-cyano-4-dimethylaminopyridinium tetrafluoroborate), and EDC (1-Ethyl-3-[3-dimethylaminopropyl] carbodiimide hydrochloride).

In another embodiment, the kit comprises a container comprising an antigen or carrier protein, and a container comprising a complementary affinity molecule which associates with a first affinity molecule. In some embodiments, the kit further comprises a means to attach the complementary affinity molecule to the antigen or carrier protein, where the means can be by a cross-linking reagent or by some intermediary fusion protein.

In some embodiments, the kit can comprise at least one co-stimulation factor which can be added to the polymer. In some embodiments, the kit comprises a cross-linking reagent, for example, but not limited to, CDAP (1-cyano-4-dimethylaminopyridinium tetrafluoroborate); EDC (1-Ethyl-3-[3-dimethylaminopropyl] carbodiimide hydrochloride); sodium cyanoborohydride; cyanogen bromide; and ammonium bicarbonate/iodoacetic acid, for linking the co-factor to the polymer.

A variety of kits and components can be prepared for use in the methods described herein, depending upon the intended use of the kit, the particular target antigen and the needs of the user.

EXEMPLARY EMBODIMENTS

Exemplary embodiments as described below are also within the scope of the present disclosure:

1. A vaccine comprising one or more species of immunogenic complexes, wherein the immunogenic complex of at least one of the species comprises:
   (a) a biotinylated polysaccharide antigen; and
   (b) a fusion protein comprising:
      (i) a biotin-binding moiety;
      (ii) a non-hemolytic pneumolysin (Ply) polypeptide comprising mutations at amino acid residues 294, 385, 428, and 433 of wild-type *Streptococcus pneumoniae* pneumolysin or antigenic fragment thereof; and
      (iii) an SP0435 polypeptide or antigenic fragment thereof;
   wherein the biotinylated polysaccharide antigen is non-covalently associated with the biotin-binding moiety of the fusion protein to form an immunogenic complex.
2. The vaccine of embodiment 1, wherein the biotinylated polysaccharide antigen comprises a polysaccharide of *Streptococcus pneumoniae*.
3. The vaccine of embodiment 1 or embodiment 2, wherein the biotinylated polysaccharide antigen comprises a polysaccharide of *Streptococcus pneumoniae* having a serotype selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.
4. The vaccine of any one of embodiments 1-3, wherein the biotinylated polysaccharide antigen comprises a polysaccharide of *Streptococcus pneumoniae* having a serotype selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

5. The vaccine of any one of embodiments 1-3, wherein the biotinylated polysaccharide antigen comprises a polysaccharide of *Streptococcus pneumoniae* having a serotype selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

6. The vaccine of any one of embodiments 1-3, wherein the biotinylated polysaccharide antigen comprises a polysaccharide of *Streptococcus pneumoniae* having a serotype selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

7. The vaccine of any one of embodiments 1-3, wherein the biotinylated polysaccharide antigen comprises a polysaccharide of *Streptococcus pneumoniae* having a serotype selected from 1, 3, 4, 5, 6A, 6B, 7F, 8, 9N, 9V, 10A, 11A, 12F, 14, 15B, 17F, 18C, 19A, 19F, 20B, 22F, 23F, and 33F.

8. The vaccine of any one of embodiments 1-3, wherein the biotinylated polysaccharide antigen comprises a polysaccharide of *Streptococcus pneumoniae* having a serotype selected from 6C, 7C, 15A, 16F, 23A, 23B, 24F, 31, 35B, and 38.

9. A vaccine comprising:
 a plurality of immunogenic complexes comprising:
 (a) a plurality of first biotinylated polysaccharide antigens, wherein the plurality comprises polysaccharide antigens of one or more of *Streptococcus pneumoniae* serotypes 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48; and
 (b) a plurality of first fusion proteins, wherein each first fusion protein comprises:
 (i) a biotin-binding moiety;
 (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and
 (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof;
 wherein each of the plurality of first biotinylated polysaccharide antigens is non-covalently associated with the biotin-binding moiety of one or more of the plurality of first fusion proteins to form an immunogenic complex.

10. The vaccine of embodiment 9, wherein the plurality of immunogenic complexes further comprises:
 (a) a plurality of second biotinylated polysaccharide antigens, wherein the plurality comprises polysaccharide antigens of one or more of *Streptococcus pneumoniae* serotypes 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48; and
 (b) a plurality of second fusion proteins, wherein each second fusion protein comprises:
 (i) a biotin-binding moiety;
 (ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and
 (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof;
 wherein each of the plurality of second biotinylated polysaccharide antigens is non-covalently associated with the biotin-binding moiety of one or more of the plurality of second fusion proteins to form an immunogenic complex.

11. The vaccine of embodiment 10, wherein the plurality of second biotinylated polysaccharide antigens comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

12. The vaccine of embodiment 11, wherein the plurality of second biotinylated polysaccharide antigens comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

13. The vaccine of any one of embodiments 9-12, wherein the plurality of first biotinylated polysaccharide antigens comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

14. The vaccine of embodiment 13, wherein the plurality of first biotinylated polysaccharide antigens comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

15. The vaccine of embodiment 10, wherein the plurality of second biotinylated polysaccharide antigens comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

16. The vaccine of embodiment 15, wherein the plurality of second biotinylated polysaccharide antigens comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

17. The vaccine of any one of embodiments 9, 10, 15, and 16, wherein the plurality of first biotinylated polysaccharide antigens comprises polysaccharide antigens of one or more of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

18. The vaccine of embodiment 17, wherein the plurality of first biotinylated polysaccharide antigens comprises polysaccharide antigens of each of *Streptococcus pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

19. The vaccine of embodiment 10, wherein the plurality of second biotinylated polysaccharide antigens comprises polysaccharide antigens of one or more of *Streptococcus pneumoniae* serotypes 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

20. The vaccine of embodiment 19, wherein the plurality of second biotinylated polysaccharide antigens comprises polysaccharide antigens of each of *Streptococcus pneumoniae* serotypes 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

21. The vaccine of any one of embodiments 9, 10, 19, and 20, wherein the plurality of first biotinylated polysaccharide antigens comprises polysaccharide antigens of one or more of *Streptococcus pneumoniae* serotypes 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

22. The vaccine of embodiment 21, wherein the plurality of first biotinylated polysaccharide antigens comprises polysaccharide antigens of each of *Streptococcus pneumoniae* serotypes 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

23. The vaccine of embodiment 10, wherein the plurality of second biotinylated polysaccharide antigens comprises polysaccharide antigens of one or more of *Streptococcus pneumoniae* serotypes 1, 3, 4, 5, 6A, 6B, 7F, 8, 9N, 9V, 10A, 11A, 12F, 14, 15B, 17F, 18C, 19A, 19F, 20B, 22F, 23F, and 33F.

24. The vaccine of embodiment 23, wherein the plurality of second biotinylated polysaccharide antigens comprises polysaccharide antigens of each of *Streptococcus pneumoniae* serotypes 1, 3, 4, 5, 6A, 6B, 7F, 8, 9N, 9V, 10A, 11A, 12F, 14, 15B, 17F, 18C, 19A, 19F, 20B, 22F, 23F, and 33F.

25. The vaccine of any one of embodiments 9, 10, 23, and 24, wherein the plurality of first biotinylated polysaccharide antigens comprises polysaccharide antigens of one or more of *Streptococcus pneumoniae* serotypes 1, 3, 4, 5, 6A, 6B, 7F, 8, 9N, 9V, 10A, 11A, 12F, 14, 15B, 17F, 18C, 19A, 19F, 20B, 22F, 23F, and 33F.

26. The vaccine of embodiment 25, wherein the plurality of first biotinylated polysaccharide antigens comprises polysaccharide antigens of each of *Streptococcus pneumoniae* serotypes 1, 3, 4, 5, 6A, 6B, 7F, 8, 9N, 9V, 10A, 11A, 12F, 14, 15B, 17F, 18C, 19A, 19F, 20B, 22F, 23F, and 33F.

27. The vaccine of embodiment 10, wherein the plurality of second biotinylated polysaccharide antigens comprises polysaccharide antigens of one or more of *Streptococcus pneumoniae* serotypes 6C, 7C, 15A, 16F, 23A, 23B, 24F, 31, 35B, and 38.

28. The vaccine of embodiment 27, wherein the plurality of second biotinylated polysaccharide antigens comprises polysaccharide antigens of each of *Streptococcus pneumoniae* serotypes 6C, 7C, 15A, 16F, 23A, 23B, 24F, 31, 35B, and 38.

29. The vaccine of any one of embodiments 9, 10, 27 and 28, wherein the plurality of first biotinylated polysaccharide antigens comprises polysaccharide antigens of one or more of *Streptococcus pneumoniae* serotypes 6C, 7C, 15A, 16F, 23A, 23B, 24F, 31, 35B, and 38.

30. The vaccine of embodiment 29, wherein the plurality of first biotinylated polysaccharide antigens comprises polysaccharide antigens of each of *Streptococcus pneumoniae* serotypes 6C, 7C, 15A, 16F, 23A, 23B, 24F, 31, 35B, and 38.

31. The vaccine of embodiment 10, wherein the plurality of second biotinylated polysaccharide comprises polysaccharide antigens from one or more of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F.

32. The vaccine of embodiment 31, wherein the plurality of second biotinylated polysaccharide antigens comprises polysaccharide antigens of each of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F.

33. The vaccine of any one of embodiments 9, 10, 31, and 32, wherein the plurality of first biotinylated polysaccharide antigens comprises polysaccharide antigens from one or more of *Streptococcus pneumoniae* serotypes 6C, 7C, 15A, 16F, 23A, 23B, 24F, 31, 35B, and 38.

34. The vaccine of embodiment 33, wherein the plurality of first biotinylated polysaccharide antigens comprises polysaccharide antigens of each of *Streptococcus pneumoniae* serotypes 6C, 7C, 15A, 16F, 23A, 23B, 24F, 31, 35B, and 38.

35. The vaccine of embodiment 10, wherein the plurality of second biotinylated polysaccharide antigens comprises polysaccharide antigens from one or more of *Streptococcus pneumoniae* serotypes 2, 3, 5, 6C, 7C, 7F, 8, 9N, 10A, 11A, 12F, 14, 15A, 16F, 17F, 19F, 20B, 22F, 23A, 23B, 24F, 31, 35B, and 38.

36. The vaccine of embodiment 35, wherein the plurality of second biotinylated polysaccharide antigens comprises polysaccharide antigens of each of *Streptococcus pneumoniae* serotypes 2, 3, 5, 6C, 7C, 7F, 8, 9N, 10A, 11A, 12F, 14, 15A, 16F, 17F, 19F, 20B, 22F, 23A, 23B, 24F, 31, 35B, and 38.

37. The vaccine of any one of embodiments 9, 10, 35, and 36, wherein the plurality of first biotinylated polysaccharide antigens comprises polysaccharide antigens from one or more of *Streptococcus pneumoniae* serotypes 1, 4, 6A, 6B, 9V, 15B, 18C, 19A, 23F, and 33F.

38. The vaccine of embodiment 37, wherein the plurality of first biotinylated polysaccharide antigens comprises polysaccharide antigens of each of *Streptococcus pneumoniae* serotypes 1, 4, 6A, 6B, 9V, 15B, 18C, 19A, 23F, and 33F.

39. The vaccine of embodiment 10, wherein the plurality of second biotinylated polysaccharide antigens comprises polysaccharide antigens from one or more of *Streptococcus pneumoniae* serotypes 2, 3, 5, 6A, 7F, 8, 9N, 10A, 11A, 12F, 14, 17F, 18C, 19A, 19F, 20B, and 22F.

40. The vaccine of embodiment 39, wherein the plurality of second biotinylated polysaccharide antigens comprises polysaccharide antigens of each of *Streptococcus pneumoniae* serotypes 2, 3, 5, 6A, 7F, 8, 9N, 10A, 11A, 12F, 14, 17F, 18C, 19A, 19F, 20B, and 22F.

41. The vaccine of embodiment 9, 10, 39, and 40, wherein the plurality of first biotinylated polysaccharide antigens comprises polysaccharide antigens from one or more of *Streptococcus pneumoniae* serotypes 1, 4, 6B, 6C, 7C, 9V, 15A, 15B, 16F, 23A, 23B, 23F, 24F, 31, 33F, 35B, and 38.

42. The vaccine of embodiment 41, wherein the plurality of first biotinylated polysaccharide antigens comprises polysaccharide antigens of each of *Streptococcus pneumoniae* serotypes 1, 4, 6B, 6C, 7C, 9V, 15A, 15B, 16F, 23A, 23B, 23F, 24F, 31, 33F, 35B, and 38.

43. The vaccine of embodiment 10, wherein the plurality of second biotinylated polysaccharide antigens comprises polysaccharide antigens from one or more of *Streptococcus pneumoniae* serotypes 1, 4, 6B, 6C, 7C, 9V, 15A, 15B, 16F, 23A, 23B, 23F, 24F, 31, 33F, 35B, and 38.

44. The vaccine of embodiment 43, wherein the plurality of second biotinylated polysaccharide antigens comprises polysaccharide antigens of each of *Streptococcus pneumoniae* serotypes 1, 4, 6B, 6C, 7C, 9V, 15A, 15B, 16F, 23A, 23B, 23F, 24F, 31, 33F, 35B, and 38.

45. The vaccine of any one of embodiment 9, 10, 43, and 44, wherein the plurality of first biotinylated polysaccharide antigens comprises polysaccharide antigens from one or more of *Streptococcus pneumoniae* serotypes 2, 3, 5, 6A, 7F, 8, 9N, 10A, 11A, 12F, 14, 17F, 18C, 19A, 19F, 20B, and 22F.

46. The vaccine of embodiment 45, wherein the plurality of first biotinylated polysaccharide antigens comprises polysaccharide antigens of each of *Streptococcus pneumoniae* serotypes 2, 3, 5, 6A, 7F, 8, 9N, 10A, 11A, 12F, 14, 17F, 18C, 19A, 19F, 20B, and 22F.

47. The vaccine of embodiment 10, wherein the plurality of second biotinylated polysaccharide antigens comprises polysaccharide antigens from one or more of *Streptococcus pneumoniae* serotypes 2, 3, 5, 6C, 7C, 7F, 8, 9N, 10A, 11A, 12F, 14, 15A, 17F, 19F, 20B, 22F, 23A, 23B, 24F, 31, 35B, and 38.

48. The vaccine of embodiment 47, wherein the plurality of second biotinylated polysaccharide antigens comprises polysaccharide antigens of each of *Streptococcus pneumoniae* serotypes 2, 3, 5, 6C, 7C, 7F, 8, 9N, 10A, 11A, 12F, 14, 15A, 17F, 19F, 20B, 22F, 23A, 23B, 24F, 31, 35B, and 38.

49. The vaccine of any one of embodiments 9, 10, 47, and 48, wherein the plurality of first biotinylated polysaccharide antigens comprises polysaccharide antigens from one or more of *Streptococcus pneumoniae* serotypes 1, 4, 6A, 6B, 9V, 15B, 18C, 19A, 23F, and 33F.

50. The vaccine of embodiment 49, wherein the plurality of first biotinylated polysaccharide antigens comprises polysaccharide antigens of each of *Streptococcus pneumoniae* serotypes 1, 4, 6A, 6B, 9V, 15B, 18C, 19A, 23F, and 33F.

51. The vaccine of embodiment 10, wherein the plurality of second biotinylated polysaccharide antigens comprises polysaccharide antigens from one or more of *Streptococcus pneumoniae* serotypes 2, 5, 6C, 7C, 7F, 8, 9N, 10A, 11A, 12F, 14, 15A, 16F, 17F, 19F, 20B, 22F, 23A, 23B, 24F, 31, 35B, and 38.

52. The vaccine of embodiment 51, wherein the plurality of second biotinylated polysaccharide antigens comprises polysaccharide antigens of each of *Streptococcus pneumoniae* serotypes 2, 5, 6C, 7C, 7F, 8, 9N, 10A, 11A, 12F, 14, 15A, 16F, 17F, 19F, 20B, 22F, 23A, 23B, 24F, 31, 35B, and 38.

53. The vaccine of any one of embodiments 9, 10, 51, and 52, wherein the plurality of first biotinylated polysaccharide antigens comprises polysaccharide antigens from one or more of *Streptococcus pneumoniae* serotypes 1, 4, 6A, 6B, 9V, 15B, 18C, 19A, 23F, and 33F.

54. The vaccine of embodiment 53, wherein the plurality of first biotinylated polysaccharide antigens comprises polysaccharide antigens of each of *Streptococcus pneumoniae* serotypes 1, 4, 6A, 6B, 9V, 15B, 18C, 19A, 23F, and 33F.

55. The vaccine of any one of embodiments 10-12, 15, 16, 19, 20, 23, 24, 27, 28, 31, 32, 35, 36, 39, 40, 43, 44, 47, 48, 51, and 52, wherein each of the plurality of second fusion proteins, is or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 26 or SEQ ID NO: 61.

56. The vaccine of any one of embodiments 10-12, 15, 16, 19, 20, 23, 24, 27, 28, 31, 32, 35, 36, 39, 40, 43, 44, 47, 48, 51, 52, and 55, wherein each of the plurality of second fusion proteins is SEQ ID NO: 26 or SEQ ID NO: 61.

57. The vaccine of any one of the preceding embodiments, wherein the fusion protein, or each of the plurality of first fusion proteins, is or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 19, SEQ ID NO: 20, SEQ ID NO: 58, or SEQ ID NO: 59.

58. The vaccine of any one of the preceding embodiments, wherein the fusion protein, or each of the plurality of first fusion proteins, is SEQ ID NO: 19, SEQ ID NO: 20, SEQ ID NO: 58, or SEQ ID NO: 59.

59. The vaccine of any one of embodiments 9-58, wherein the plurality of immunogenic complexes comprises one species of immunogenic complexes, wherein the species comprises a polysaccharide antigen of a single *Streptococcus pneumoniae* serotype.

60. The vaccine of any one of embodiments 9-59, wherein the plurality of immunogenic complexes comprises two or more different species of immunogenic complexes, wherein each species comprises a polysaccharide antigen of a single *Streptococcus pneumoniae* serotype.

61. The vaccine of any one of embodiments 9-60, wherein the plurality of immunogenic complexes comprises thirty or more, thirty one or more, or thirty two or more different species of immunogenic complexes, wherein each species comprises a polysaccharide antigen of a single *Streptococcus pneumoniae* serotype.

62. The vaccine of any one of embodiments 9-61, wherein the plurality of immunogenic complexes comprises thirty three or more different species of immunogenic complexes, wherein each species comprises a polysaccharide antigen of a single *Streptococcus pneumoniae* serotype.

63. The vaccine of any one of embodiments 9-62, wherein the plurality of immunogenic complexes comprises thirty four or more different species of immunogenic complexes, wherein each species comprises a polysaccharide antigen of a single *Streptococcus pneumoniae* serotype.

64. A vaccine comprising a plurality of different species of immunogenic complexes, wherein the different species comprise:

a biotinylated polysaccharide antigen of *Streptococcus pneumoniae* serotype 6C non-covalently complexed with a biotin binding moiety of a first fusion protein;

wherein the first fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof;

a biotinylated polysaccharide antigen of *Streptococcus pneumoniae* serotype 7C non-covalently complexed with the biotin-binding moiety of the first fusion protein;

a biotinylated polysaccharide antigen of *Streptococcus pneumoniae* serotype 15A non-covalently complexed with the biotin-binding moiety of the first fusion protein;

a biotinylated polysaccharide antigen of *Streptococcus pneumoniae* serotype 16F non-covalently complexed with the biotin-binding moiety of the first fusion protein;

a biotinylated polysaccharide antigen of *Streptococcus pneumoniae* serotype 23A non-covalently complexed with the biotin-binding moiety of the first fusion protein;

a biotinylated polysaccharide antigen of *Streptococcus pneumoniae* serotype 23B non-covalently complexed with the biotin-binding moiety of the first fusion protein;

a biotinylated polysaccharide antigen of *Streptococcus pneumoniae* serotype 24F non-covalently complexed with the biotin-binding moiety of the first fusion protein;

a biotinylated polysaccharide antigen of *Streptococcus pneumoniae* serotype 31 non-covalently complexed with the biotin-binding moiety of the first fusion protein;

a biotinylated polysaccharide antigen of *Streptococcus pneumoniae* serotype 35B non-covalently complexed with the biotin-binding moiety of the first fusion protein; and a biotinylated polysaccharide antigen of *Streptococcus pneumoniae* serotype 38 non-covalently complexed with the biotin-binding moiety of the first fusion protein;

a biotinylated polysaccharide antigen of *Streptococcus pneumoniae* serotype 1 non-covalently complexed with a second fusion protein;

wherein the second fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof;

a biotinylated polysaccharide antigen of *Streptococcus pneumoniae* serotype 2 non-covalently complexed with the biotin-binding moiety of the second fusion protein;

a biotinylated polysaccharide antigen of *Streptococcus pneumoniae* serotype 3 non-covalently complexed with the biotin-binding moiety of the second fusion protein;

a biotinylated polysaccharide antigen of *Streptococcus pneumoniae* serotype 4 non-covalently complexed with the biotin-binding moiety of the second fusion protein;

a biotinylated polysaccharide antigen of *Streptococcus pneumoniae* serotype 5 non-covalently complexed with the biotin-binding moiety of the second fusion protein;

a biotinylated polysaccharide antigen of *Streptococcus pneumoniae* serotype 6A non-covalently complexed with the biotin-binding moiety of the second fusion protein;

a biotinylated polysaccharide antigen of *Streptococcus pneumoniae* serotype 6B non-covalently complexed with the biotin-binding moiety of the second fusion protein;

a biotinylated polysaccharide antigen of *Streptococcus pneumoniae* serotype 7F non-covalently complexed with the biotin-binding moiety of the second fusion protein;

a biotinylated polysaccharide antigen of *Streptococcus pneumoniae* serotype 8 non-covalently complexed with the biotin-binding moiety of the second fusion protein;

a biotinylated polysaccharide antigen of *Streptococcus pneumoniae* serotype 9N non-covalently complexed with the biotin-binding moiety of the second fusion protein;

a biotinylated polysaccharide antigen of *Streptococcus pneumoniae* serotype 9V non-covalently complexed with the biotin-binding moiety of the second fusion protein;

a biotinylated polysaccharide antigen of *Streptococcus pneumoniae* serotype 10A non-covalently complexed with the biotin-binding moiety of the second fusion protein;

a biotinylated polysaccharide antigen of *Streptococcus pneumoniae* serotype 11A non-covalently complexed with the biotin-binding moiety of the second fusion protein;

a biotinylated polysaccharide antigen of *Streptococcus pneumoniae* serotype 12F non-covalently complexed with the biotin-binding moiety of the second fusion protein;

a biotinylated polysaccharide antigen of *Streptococcus pneumoniae* serotype 14 non-covalently complexed with the biotin-binding moiety of the second fusion protein;

a biotinylated polysaccharide antigen of *Streptococcus pneumoniae* serotype 15B non-covalently complexed with the biotin-binding moiety of the second fusion protein;

a biotinylated polysaccharide antigen of *Streptococcus pneumoniae* serotype 17F non-covalently complexed with the biotin-binding moiety of the second fusion protein;

a biotinylated polysaccharide antigen of *Streptococcus pneumoniae* serotype 18C non-covalently complexed with the biotin-binding moiety of the second fusion protein;

a biotinylated polysaccharide antigen of *Streptococcus pneumoniae* serotype 19A non-covalently complexed with the biotin-binding moiety of the second fusion protein;

a biotinylated polysaccharide antigen of *Streptococcus pneumoniae* serotype 19F non-covalently complexed with the biotin-binding moiety of the second fusion protein;

a biotinylated polysaccharide antigen of *Streptococcus pneumoniae* serotype 20B non-covalently complexed with the biotin-binding moiety of the second fusion protein;

a biotinylated polysaccharide antigen of *Streptococcus pneumoniae* serotype 22F non-covalently complexed with the biotin-binding moiety of the second fusion protein;

a biotinylated polysaccharide antigen of *Streptococcus pneumoniae* serotype 23F non-covalently complexed with the biotin-binding moiety of the second fusion protein; and a biotinylated polysaccharide antigen of *Streptococcus pneumoniae* serotype 33F non-covalently complexed with the biotin-binding moiety of the second fusion protein.

65. A vaccine comprising a plurality of different species of immunogenic complexes, wherein the different species comprise:

a biotinylated polysaccharide antigen of *Streptococcus pneumoniae* serotype 1 non-covalently complexed with a biotin binding moiety of a first fusion protein;

wherein the first fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof;

a biotinylated polysaccharide antigen of *Streptococcus pneumoniae* serotype 4 non-covalently complexed with the biotin-binding moiety of the first fusion protein;

a biotinylated polysaccharide antigen of *Streptococcus pneumoniae* serotype 6A non-covalently complexed with the biotin-binding moiety of the first fusion protein;

a biotinylated polysaccharide antigen of *Streptococcus pneumoniae* serotype 6B non-covalently complexed with the biotin-binding moiety of the first fusion protein;

a biotinylated polysaccharide antigen of *Streptococcus pneumoniae* serotype 9V non-covalently complexed with the biotin-binding moiety of the first fusion protein;

a biotinylated polysaccharide antigen of *Streptococcus pneumoniae* serotype 15B non-covalently complexed with the biotin-binding moiety of the first fusion protein;

a biotinylated polysaccharide antigen of *Streptococcus pneumoniae* serotype 18C non-covalently complexed with the biotin-binding moiety of the first fusion protein;

a biotinylated polysaccharide antigen of *Streptococcus pneumoniae* serotype 19A non-covalently complexed with the biotin-binding moiety of the first fusion protein;

a biotinylated polysaccharide antigen of *Streptococcus pneumoniae* serotype 23F non-covalently complexed with the biotin-binding moiety of the first fusion protein; and a biotinylated polysaccharide antigen of *Streptococcus pneumoniae* serotype 33F non-covalently complexed with the biotin-binding moiety of the first fusion protein;

a biotinylated polysaccharide antigen of *Streptococcus pneumoniae* serotype 2 non-covalently complexed with a second fusion protein;

wherein the second fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof;

a biotinylated polysaccharide antigen of *Streptococcus pneumoniae* serotype 3 non-covalently complexed with the biotin-binding moiety of the second fusion protein;

a biotinylated polysaccharide antigen of *Streptococcus pneumoniae* serotype 5 non-covalently complexed with the biotin-binding moiety of the second fusion protein;

a biotinylated polysaccharide antigen of *Streptococcus pneumoniae* serotype 6C non-covalently complexed with the biotin-binding moiety of the second fusion protein;

a biotinylated polysaccharide antigen of *Streptococcus pneumoniae* serotype 7C non-covalently complexed with the biotin-binding moiety of the second fusion protein;

a biotinylated polysaccharide antigen of *Streptococcus pneumoniae* serotype 7F non-covalently complexed with the biotin-binding moiety of the second fusion protein;

a biotinylated polysaccharide antigen of *Streptococcus pneumoniae* serotype 8 non-covalently complexed with the biotin-binding moiety of the second fusion protein;

a biotinylated polysaccharide antigen of *Streptococcus pneumoniae* serotype 9N non-covalently complexed with the biotin-binding moiety of the second fusion protein;

a biotinylated polysaccharide antigen of *Streptococcus pneumoniae* serotype 10A non-covalently complexed with the biotin-binding moiety of the second fusion protein;

a biotinylated polysaccharide antigen of *Streptococcus pneumoniae* serotype 11A non-covalently complexed with the biotin-binding moiety of the second fusion protein;

a biotinylated polysaccharide antigen of *Streptococcus pneumoniae* serotype 12F non-covalently complexed with the biotin-binding moiety of the second fusion protein;

a biotinylated polysaccharide antigen of *Streptococcus pneumoniae* serotype 14 non-covalently complexed with the biotin-binding moiety of the second fusion protein;

a biotinylated polysaccharide antigen of *Streptococcus pneumoniae* serotype 15A non-covalently complexed with the biotin-binding moiety of the second fusion protein;

a biotinylated polysaccharide antigen of *Streptococcus pneumoniae* serotype 16F non-covalently complexed with the biotin-binding moiety of the second fusion protein;

a biotinylated polysaccharide antigen of *Streptococcus pneumoniae* serotype 17F non-covalently complexed with the biotin-binding moiety of the second fusion protein;

a biotinylated polysaccharide antigen of *Streptococcus pneumoniae* serotype 19F non-covalently complexed with the biotin-binding moiety of the second fusion protein;

a biotinylated polysaccharide antigen of *Streptococcus pneumoniae* serotype 20B non-covalently complexed with the biotin-binding moiety of the second fusion protein;

a biotinylated polysaccharide antigen of *Streptococcus pneumoniae* serotype 22F non-covalently complexed with the biotin-binding moiety of the second fusion protein;

a biotinylated polysaccharide antigen of *Streptococcus pneumoniae* serotype 23A non-covalently complexed with the biotin-binding moiety of the second fusion protein;

a biotinylated polysaccharide antigen of *Streptococcus pneumoniae* serotype 23B non-covalently complexed with the biotin-binding moiety of the second fusion protein;

a biotinylated polysaccharide antigen of *Streptococcus pneumoniae* serotype 24F non-covalently complexed with the biotin-binding moiety of the second fusion protein;

a biotinylated polysaccharide antigen of *Streptococcus pneumoniae* serotype 31 non-covalently complexed with the biotin-binding moiety of the second fusion protein;

a biotinylated polysaccharide antigen of *Streptococcus pneumoniae* serotype 35B non-covalently complexed with the biotin-binding moiety of the second fusion protein; and a biotinylated polysaccharide antigen of *Streptococcus pneumoniae* serotype 38 non-covalently complexed with the biotin-binding moiety of the second fusion protein.

66. A vaccine comprising a plurality of different species of immunogenic complexes, wherein the different species comprise:

a biotinylated polysaccharide antigen of *Streptococcus pneumoniae* serotype 1 non-covalently complexed with a biotin binding moiety of a fusion protein;

wherein the fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof;

a biotinylated polysaccharide antigen of *Streptococcus pneumoniae* serotype 2 non-covalently complexed with the biotin-binding moiety of the fusion protein;

a biotinylated polysaccharide antigen of *Streptococcus pneumoniae* serotype 3 non-covalently complexed with the biotin-binding moiety of the fusion protein;

a biotinylated polysaccharide antigen of *Streptococcus pneumoniae* serotype 4 non-covalently complexed with the biotin-binding moiety of the fusion protein;

a biotinylated polysaccharide antigen of *Streptococcus pneumoniae* serotype 5 non-covalently complexed with the biotin-binding moiety of the fusion protein;

a biotinylated polysaccharide antigen of *Streptococcus pneumoniae* serotype 6A non-covalently complexed with the biotin-binding moiety of the fusion protein;

a biotinylated polysaccharide antigen of *Streptococcus pneumoniae* serotype 6B non-covalently complexed with the biotin-binding moiety of the fusion protein;

a biotinylated polysaccharide antigen of *Streptococcus pneumoniae* serotype 6C non-covalently complexed with the biotin-binding moiety of the fusion protein;

a biotinylated polysaccharide antigen of *Streptococcus pneumoniae* serotype 7C non-covalently complexed with the biotin-binding moiety of the fusion protein;

a biotinylated polysaccharide antigen of *Streptococcus pneumoniae* serotype 7F non-covalently complexed with the biotin-binding moiety of the fusion protein;

a biotinylated polysaccharide antigen of *Streptococcus pneumoniae* serotype 8 non-covalently complexed with the biotin-binding moiety of the fusion protein;

a biotinylated polysaccharide antigen of *Streptococcus pneumoniae* serotype 9N non-covalently complexed with the biotin-binding moiety of the fusion protein;

a biotinylated polysaccharide antigen of *Streptococcus pneumoniae* serotype 9V non-covalently complexed with the biotin-binding moiety of the fusion protein;

a biotinylated polysaccharide antigen of *Streptococcus pneumoniae* serotype 10A non-covalently complexed with the biotin-binding moiety of the fusion protein;

a biotinylated polysaccharide antigen of *Streptococcus pneumoniae* serotype 11A non-covalently complexed with the biotin-binding moiety of the fusion protein;

a biotinylated polysaccharide antigen of *Streptococcus pneumoniae* serotype 12F non-covalently complexed with the biotin-binding moiety of the fusion protein;

a biotinylated polysaccharide antigen of *Streptococcus pneumoniae* serotype 14 non-covalently complexed with the biotin-binding moiety of the fusion protein;

a biotinylated polysaccharide antigen of *Streptococcus pneumoniae* serotype 15A non-covalently complexed with the biotin-binding moiety of the fusion protein;

a biotinylated polysaccharide antigen of *Streptococcus pneumoniae* serotype 15B non-covalently complexed with the biotin-binding moiety of the fusion protein;

a biotinylated polysaccharide antigen of *Streptococcus pneumoniae* serotype 16F non-covalently complexed with the biotin-binding moiety of the fusion protein;

a biotinylated polysaccharide antigen of *Streptococcus pneumoniae* serotype 17F non-covalently complexed with the biotin-binding moiety of the fusion protein;

a biotinylated polysaccharide antigen of *Streptococcus pneumoniae* serotype 18C non-covalently complexed with the biotin-binding moiety of the fusion protein;

a biotinylated polysaccharide antigen of *Streptococcus pneumoniae* serotype 19A non-covalently complexed with the biotin-binding moiety of the fusion protein;

a biotinylated polysaccharide antigen of *Streptococcus pneumoniae* serotype 19F non-covalently complexed with the biotin-binding moiety of the fusion protein;

a biotinylated polysaccharide antigen of *Streptococcus pneumoniae* serotype 20B non-covalently complexed with the biotin-binding moiety of the fusion protein;

a biotinylated polysaccharide antigen of *Streptococcus pneumoniae* serotype 22F non-covalently complexed with the biotin-binding moiety of the fusion protein;

a biotinylated polysaccharide antigen of *Streptococcus pneumoniae* serotype 23A non-covalently complexed with the biotin-binding moiety of the fusion protein;

a biotinylated polysaccharide antigen of *Streptococcus pneumoniae* serotype 23B non-covalently complexed with the biotin-binding moiety of the fusion protein;

a biotinylated polysaccharide antigen of *Streptococcus pneumoniae* serotype 23F non-covalently complexed with the biotin-binding moiety of the fusion protein; and a biotinylated polysaccharide antigen of *Streptococcus pneumoniae* serotype 24F non-covalently complexed with the biotin-binding moiety of the fusion protein;

a biotinylated polysaccharide antigen of *Streptococcus pneumoniae* serotype 31 non-covalently complexed with the biotin-binding moiety of the fusion protein;

a biotinylated polysaccharide antigen of *Streptococcus pneumoniae* serotype 33F non-covalently complexed with the biotin-binding moiety of the fusion protein;

a biotinylated polysaccharide antigen of *Streptococcus pneumoniae* serotype 35B non-covalently complexed with the biotin-binding moiety of the fusion protein; and a biotinylated polysaccharide antigen of *Streptococcus pneumoniae* serotype 38 non-covalently complexed with the biotin-binding moiety of the fusion protein.

67. A vaccine comprising a plurality of different species of immunogenic complexes, wherein the different species comprise:

a biotinylated polysaccharide antigen of *Streptococcus pneumoniae* serotype 1 non-covalently complexed with a biotin binding moiety of a first fusion protein;

wherein the first fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof;

a biotinylated polysaccharide antigen of *Streptococcus pneumoniae* serotype 4 non-covalently complexed with the biotin-binding moiety of the first fusion protein;

a biotinylated polysaccharide antigen of *Streptococcus pneumoniae* serotype 6A non-covalently complexed with the biotin-binding moiety of the first fusion protein;

a biotinylated polysaccharide antigen of *Streptococcus pneumoniae* serotype 6B non-covalently complexed with the biotin-binding moiety of the first fusion protein;

a biotinylated polysaccharide antigen of *Streptococcus pneumoniae* serotype 9V non-covalently complexed with the biotin-binding moiety of the first fusion protein;

a biotinylated polysaccharide antigen of *Streptococcus pneumoniae* serotype 15B non-covalently complexed with the biotin-binding moiety of the first fusion protein;

a biotinylated polysaccharide antigen of *Streptococcus pneumoniae* serotype 18C non-covalently complexed with the biotin-binding moiety of the first fusion protein;

a biotinylated polysaccharide antigen of *Streptococcus pneumoniae* serotype 19A non-covalently complexed with the biotin-binding moiety of the first fusion protein;

a biotinylated polysaccharide antigen of *Streptococcus pneumoniae* serotype 23F non-covalently complexed with the biotin-binding moiety of the first fusion protein; and a biotinylated polysaccharide antigen of *Streptococcus pneumoniae* serotype 33F non-covalently complexed with the biotin-binding moiety of the first fusion protein;

a biotinylated polysaccharide antigen of *Streptococcus pneumoniae* serotype 2 non-covalently complexed with a second fusion protein;

wherein the second fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at 100% identical to SEQ ID NO: 10 or an antigenic fragment thereof;

a biotinylated polysaccharide antigen of *Streptococcus pneumoniae* serotype 3 non-covalently complexed with the biotin-binding moiety of the second fusion protein;

a biotinylated polysaccharide antigen of *Streptococcus pneumoniae* serotype 5 non-covalently complexed with the biotin-binding moiety of the second fusion protein;

a biotinylated polysaccharide antigen of *Streptococcus pneumoniae* serotype 6C non-covalently complexed with the biotin-binding moiety of the second fusion protein;

a biotinylated polysaccharide antigen of *Streptococcus pneumoniae* serotype 7C non-covalently complexed with the biotin-binding moiety of the second fusion protein;

a biotinylated polysaccharide antigen of *Streptococcus pneumoniae* serotype 7F non-covalently complexed with the biotin-binding moiety of the second fusion protein;

a biotinylated polysaccharide antigen of *Streptococcus pneumoniae* serotype 8 non-covalently complexed with the biotin-binding moiety of the second fusion protein;

a biotinylated polysaccharide antigen of *Streptococcus pneumoniae* serotype 9N non-covalently complexed with the biotin-binding moiety of the second fusion protein;

a biotinylated polysaccharide antigen of *Streptococcus pneumoniae* serotype 10A non-covalently complexed with the biotin-binding moiety of the second fusion protein;

a biotinylated polysaccharide antigen of *Streptococcus pneumoniae* serotype 11A non-covalently complexed with the biotin-binding moiety of the second fusion protein;

a biotinylated polysaccharide antigen of *Streptococcus pneumoniae* serotype 12F non-covalently complexed with the biotin-binding moiety of the second fusion protein;

a biotinylated polysaccharide antigen of *Streptococcus pneumoniae* serotype 14 non-covalently complexed with the biotin-binding moiety of the second fusion protein;

a biotinylated polysaccharide antigen of *Streptococcus pneumoniae* serotype 15A non-covalently complexed with the biotin-binding moiety of the second fusion protein;

a biotinylated polysaccharide antigen of *Streptococcus pneumoniae* serotype 17F non-covalently complexed with the biotin-binding moiety of the second fusion protein;

a biotinylated polysaccharide antigen of *Streptococcus pneumoniae* serotype 19F non-covalently complexed with the biotin-binding moiety of the second fusion protein;

a biotinylated polysaccharide antigen of *Streptococcus pneumoniae* serotype 20B non-covalently complexed with the biotin-binding moiety of the second fusion protein;

a biotinylated polysaccharide antigen of *Streptococcus pneumoniae* serotype 22F non-covalently complexed with the biotin-binding moiety of the second fusion protein;

a biotinylated polysaccharide antigen of *Streptococcus pneumoniae* serotype 23A non-covalently complexed with the biotin-binding moiety of the second fusion protein;

a biotinylated polysaccharide antigen of *Streptococcus pneumoniae* serotype 23B non-covalently complexed with the biotin-binding moiety of the second fusion protein;

a biotinylated polysaccharide antigen of *Streptococcus pneumoniae* serotype 24F non-covalently complexed with the biotin-binding moiety of the second fusion protein;

a biotinylated polysaccharide antigen of *Streptococcus pneumoniae* serotype 31 non-covalently complexed with the biotin-binding moiety of the second fusion protein;

a biotinylated polysaccharide antigen of *Streptococcus pneumoniae* serotype 35B non-covalently complexed with the biotin-binding moiety of the second fusion protein; and a biotinylated polysaccharide antigen of *Streptococcus pneumoniae* serotype 38 non-covalently complexed with the biotin-binding moiety of the second fusion protein.

68. A vaccine comprising a plurality of different species of immunogenic complexes, wherein the different species comprise:

a biotinylated polysaccharide antigen of *Streptococcus pneumoniae* serotype 1 non-covalently complexed with a biotin binding moiety of a first fusion protein;

wherein the first fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof;

a biotinylated polysaccharide antigen of *Streptococcus pneumoniae* serotype 4 non-covalently complexed with the biotin-binding moiety of the first fusion protein;

a biotinylated polysaccharide antigen of *Streptococcus pneumoniae* serotype 6A non-covalently complexed with the biotin-binding moiety of the first fusion protein;

a biotinylated polysaccharide antigen of *Streptococcus pneumoniae* serotype 6B non-covalently complexed with the biotin-binding moiety of the first fusion protein;

a biotinylated polysaccharide antigen of *Streptococcus pneumoniae* serotype 9V non-covalently complexed with the biotin-binding moiety of the first fusion protein;

a biotinylated polysaccharide antigen of *Streptococcus pneumoniae* serotype 15B non-covalently complexed with the biotin-binding moiety of the first fusion protein;

a biotinylated polysaccharide antigen of *Streptococcus pneumoniae* serotype 18C non-covalently complexed with the biotin-binding moiety of the first fusion protein;

a biotinylated polysaccharide antigen of *Streptococcus pneumoniae* serotype 19A non-covalently complexed with the biotin-binding moiety of the first fusion protein;

a biotinylated polysaccharide antigen of *Streptococcus pneumoniae* serotype 23F non-covalently complexed with the biotin-binding moiety of the first fusion protein; and a biotinylated polysaccharide antigen of *Streptococcus pneumoniae* serotype 33F non-covalently complexed with the biotin-binding moiety of the first fusion protein;

a biotinylated polysaccharide antigen of *Streptococcus pneumoniae* serotype 2 non-covalently complexed with a second fusion protein;

wherein the second fusion protein comprises:

(a) a biotin-binding moiety;

(b) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof;

a biotinylated polysaccharide antigen of *Streptococcus pneumoniae* serotype 5 non-covalently complexed with the biotin-binding moiety of the second fusion protein;

a biotinylated polysaccharide antigen of *Streptococcus pneumoniae* serotype 6C non-covalently complexed with the biotin-binding moiety of the second fusion protein;

a biotinylated polysaccharide antigen of *Streptococcus pneumoniae* serotype 7C non-covalently complexed with the biotin-binding moiety of the second fusion protein;

a biotinylated polysaccharide antigen of *Streptococcus pneumoniae* serotype 7F non-covalently complexed with the biotin-binding moiety of the second fusion protein;

a biotinylated polysaccharide antigen of *Streptococcus pneumoniae* serotype 8 non-covalently complexed with the biotin-binding moiety of the second fusion protein;

a biotinylated polysaccharide antigen of *Streptococcus pneumoniae* serotype 9N non-covalently complexed with the biotin-binding moiety of the second fusion protein;

a biotinylated polysaccharide antigen of *Streptococcus pneumoniae* serotype 10A non-covalently complexed with the biotin-binding moiety of the second fusion protein;

a biotinylated polysaccharide antigen of *Streptococcus pneumoniae* serotype 11A non-covalently complexed with the biotin-binding moiety of the second fusion protein;

a biotinylated polysaccharide antigen of *Streptococcus pneumoniae* serotype 12F non-covalently complexed with the biotin-binding moiety of the second fusion protein;

a biotinylated polysaccharide antigen of *Streptococcus pneumoniae* serotype 14 non-covalently complexed with the biotin-binding moiety of the second fusion protein;

a biotinylated polysaccharide antigen of *Streptococcus pneumoniae* serotype 15A non-covalently complexed with the biotin-binding moiety of the second fusion protein;

a biotinylated polysaccharide antigen of *Streptococcus pneumoniae* serotype 16F non-covalently complexed with the biotin-binding moiety of the second fusion protein;

a biotinylated polysaccharide antigen of *Streptococcus pneumoniae* serotype 17F non-covalently complexed with the biotin-binding moiety of the second fusion protein;

a biotinylated polysaccharide antigen of *Streptococcus pneumoniae* serotype 19F non-covalently complexed with the biotin-binding moiety of the second fusion protein;

a biotinylated polysaccharide antigen of *Streptococcus pneumoniae* serotype 20B non-covalently complexed with the biotin-binding moiety of the second fusion protein;

a biotinylated polysaccharide antigen of *Streptococcus pneumoniae* serotype 22F non-covalently complexed with the biotin-binding moiety of the second fusion protein;

a biotinylated polysaccharide antigen of *Streptococcus pneumoniae* serotype 23A non-covalently complexed with the biotin-binding moiety of the second fusion protein;

a biotinylated polysaccharide antigen of *Streptococcus pneumoniae* serotype 23B non-covalently complexed with the biotin-binding moiety of the second fusion protein;
a biotinylated polysaccharide antigen of *Streptococcus pneumoniae* serotype 24F non-covalently complexed with the biotin-binding moiety of the second fusion protein;
a biotinylated polysaccharide antigen of *Streptococcus pneumoniae* serotype 31 non-covalently complexed with the biotin-binding moiety of the second fusion protein;
a biotinylated polysaccharide antigen of *Streptococcus pneumoniae* serotype 35B non-covalently complexed with the biotin-binding moiety of the second fusion protein; and
a biotinylated polysaccharide antigen of *Streptococcus pneumoniae* serotype 38 non-covalently complexed with the biotin-binding moiety of the second fusion protein.

69. The vaccine of embodiment 68, further comprising:
a biotinylated polysaccharide antigen of *Streptococcus pneumoniae* serotype 3 non-covalently complexed with the biotin-binding moiety of the second fusion protein 70. The vaccine of any one of embodiments 60-69, wherein the vaccine comprises a stoichiometrically equal ratio, by weight, of each of the polysaccharide antigens of the different species.

71. The vaccine of any one of embodiments 60-69, wherein the vaccine comprises at least one of the polysaccharide antigens of the different species at a stoichiometrically different ratio, by weight.

72. The vaccine of any one of embodiments 60-69, wherein the vaccine comprises a stoichiometrically different ratio, by weight, of each of the polysaccharide antigens of the different species.

73. The vaccine of any one of the preceding embodiments, wherein the biotin-binding moiety is (i) a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or (ii) a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof.

74. A non-hemolytic pneumolysin (Ply) protein comprising mutations at amino acid residues 294, 385, 428, and 433 of wild-type *Streptococcus pneumoniae* pneumolysin 75. The non-hemolytic pneumolysin of embodiment 74, wherein the non-hemolytic pneumolysin has lower hemolytic activity than an equivalent concentration of wild-type pneumolysin 76. The non-hemolytic pneumolysin of embodiment 75, wherein the hemolytic activity of the non-hemolytic pneumolysin is at least 25%, at least 35%, at least 45%, at least 55%, at least 65%, at least 75%, at least 85%, or at least 95% lower than an equivalent concentration of wild-type pneumolysin.

77. The non-hemolytic pneumolysin of any one of embodiments 74-76, wherein amino acid residues 1-470 of wild-type pneumolysin has the amino acid sequence of SEQ ID NO: 3.

78. The non-hemolytic pneumolysin of any one of embodiments 74-77, wherein the non-hemolytic pneumolysin comprises the following mutations in the wild-type *Streptococcus pneumoniae* pneumolysin: (i) residue 294 G to P; (ii) residue 385 D to N; (iii) residue 428 C to G; and (iv) residue 433 W to F.

79. The non-hemolytic pneumolysin of any one of embodiments 74-78, wherein the non-hemolytic pneumolysin comprises an amino acid sequence of SEQ ID NO: 5 or SEQ ID NO: 6.

80. A nucleic acid that comprises a nucleotide sequence encoding the non-hemolytic pneumolysin of any one of embodiments 62-65.

81. The nucleic acid of embodiment 80, wherein the nucleotide sequence is at least 80%, at least 85%, at least 90%, at least 95%, at least 97%, at least 98%, at least 99%, at least 99.5%, or 100% identical to SEQ ID NO: 14 or SEQ ID NO: 15.

82. A fusion protein comprising:
(i) a biotin-binding moiety;
(ii) a non-hemolytic pneumolysin (Ply) polypeptide comprising mutations at amino acid residues 294, 385, 428, and 433 of wild-type *Streptococcus pneumoniae* pneumolysin or an antigenic fragment thereof; and
(iii) an SP0435 polypeptide or an antigenic portion thereof.

83. A fusion protein comprising:
(i) a biotin-binding moiety comprising an amino acid sequence at least 80%, at least 85%, at least 90%, or 100% identical to SEQ ID NO: 2 or SEQ ID NO: 57, or a biotin binding portion thereof;
(ii) a polypeptide comprising an amino acid sequence at least 80%, at least 85%, at least 90%, or 100% identical to SEQ ID NO: 5 or SEQ ID NO: 6 or an antigenic portion thereof; and
(iii) a polypeptide comprising an amino acid sequence at least 80%, at least 85%, at least 90%, or 100% identical to SEQ ID NO: 8 or an antigenic portion thereof.

84. A fusion protein comprising:
(i) a biotin-binding moiety comprising an amino acid sequence at least 80%, at least 85%, at least 90%, or 100% identical to SEQ ID NO: 2 or SEQ ID NO: 57, or a biotin binding portion thereof;
(ii) a first polypeptide comprising an amino acid sequence at least 80%, at least 85%, at least 90%, or 100% identical to SEQ ID NO: 5 or SEQ ID NO: 6 or an antigenic portion thereof;
(iii) a second polypeptide comprising an amino acid sequence at least 80%, at least 85%, at least 90%, or 100% identical to SEQ ID NO: 8 or an antigenic portion thereof; and
(iv) a first linker positioned between the biotin-binding moiety and the first polypeptide and/or a second linker positioned between the first polypeptide and the second polypeptide.

85. The fusion protein of embodiment 84 wherein the first linker and/or the second linker comprises the amino acid sequence GGGGSSS (SEQ ID NO: 30).

86. The fusion protein of any one of embodiments 82-85, wherein the biotin-binding moiety is C-terminally linked to the first polypeptide.

87. The fusion protein of any one of embodiments 82-85, wherein the biotin-binding moiety is N-terminally linked to the first polypeptide.
88. The fusion protein of any one of embodiments 82-87, wherein the first polypeptide is C-terminally linked to the second polypeptide.
89. The fusion protein of any one of embodiments 82-87, wherein the first polypeptide is N-terminally linked to the second polypeptide.
90. The fusion protein of any one of embodiments 82-89, wherein the second polypeptide is C-terminally linked to the biotin-binding moiety.
91. The fusion protein of any one of embodiments 82-89, wherein the second polypeptide is N-terminally linked to the biotin-binding moiety.
92. The fusion protein of any one of embodiments 82-91, further comprising a His tag.
93. The fusion protein of any one of embodiments 82-92, comprising the amino acid sequence of SEQ ID NO: 2.
94. The fusion protein of any one of embodiments 82-93, comprising the amino acid sequence of SEQ ID NO: 5 or SEQ ID NO: 6.
95. The fusion protein of any one of embodiments 82-94, comprising the amino acid sequence of SEQ ID NO: 8.
96. The fusion protein of any one of embodiments 82-95, comprising the amino acid sequence at least 80%, at least 85%, at least 90%, or 100% identical to SEQ ID NO: 19 or SEQ ID NO: 58.
97. The fusion protein of any one of embodiments 82-96, comprising the amino acid sequence at least 80%, at least 85%, at least 90%, at least 95%, or 100% identical to SEQ ID NO: 20 or SEQ ID NO: 59.
98. The fusion protein of any one of embodiments 82-97, wherein the fusion protein is SPP2.
99. A nucleic acid that comprises a sequence encoding the fusion protein of any one of embodiments 80-98.
100. The nucleic acid of embodiment 99, wherein the sequence is at least 80%, at least 85%, at least 90%, at least 95%, at least 97%, at least 98%, at least 99%, at least 99.5%, or 100% identical to SEQ ID NO: 27 or SEQ ID NO: 62.
101. An immunogenic complex comprising a biotinylated polysaccharide antigen non-covalently associated with the fusion protein of any one of embodiments 68-84.
102. The immunogenic complex of embodiment 101, wherein the biotinylated polysaccharide antigen comprises a polysaccharide of *Streptococcus pneumoniae*.
103. The immunogenic complex of embodiment 101 or embodiment 102, wherein the biotinylated polysaccharide antigen comprises a polysaccharide of *Streptococcus pneumoniae* having a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.
104. The immunogenic complex of any one of embodiments 101-102, wherein the biotinylated polysaccharide antigen comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.
105. The immunogenic complex of any one of embodiments 101-102, wherein the biotinylated polysaccharide antigen comprises a polysaccharide of *Streptococcus pneumoniae* having a serotype selected from one or more of 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.
106. The immunogenic complex of any one of embodiments 101-102, wherein the biotinylated polysaccharide antigen comprises a polysaccharide of *Streptococcus pneumoniae* having a serotype selected from one or more of 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.
107. The immunogenic complex of any one of embodiments 101-102, wherein the biotinylated polysaccharide antigen comprises a polysaccharide of *Streptococcus pneumoniae* having a serotype selected from one or more of 1, 3, 4, 5, 6A, 6B, 7F, 8, 9N, 9V, 10A, 11A, 12F, 14, 15B, 17F, 18C, 19A, 19F, 20B, 22F, 23F, and 33F.
108. The immunogenic complex of any one of embodiments 101-102, wherein the biotinylated polysaccharide antigen comprises a polysaccharide of *Streptococcus pneumoniae* having a serotype selected from one or more of 6C, 7C, 15A, 16F, 23A, 23B, 24F, 31, 35B, and 38.
109. The immunogenic complex of any one of embodiments 101-102, wherein the biotinylated polysaccharide antigen is of *Streptococcus pneumoniae* serotype 1.
110. The immunogenic complex of any one of embodiments 101-102, wherein the biotinylated polysaccharide antigen is of *Streptococcus pneumoniae* serotype 6B.
111. The immunogenic complex of any one of embodiments 101-102, wherein the biotinylated polysaccharide antigen is of *Streptococcus pneumoniae* serotype 9V.
112. The immunogenic complex of any one of embodiments 101-102, wherein the biotinylated polysaccharide antigen is of *Streptococcus pneumoniae* serotype 15B.
113. The immunogenic complex of any one of embodiments 101-102, wherein the biotinylated polysaccharide antigen is of *Streptococcus pneumoniae* serotype 22F.
114. The immunogenic complex of any one of embodiments 101-102, wherein the biotinylated polysaccharide antigen is of *Streptococcus pneumoniae* serotype 23A.
115. The immunogenic complex of any one of embodiments 101-102, wherein the biotinylated polysaccharide antigen is of *Streptococcus pneumoniae* serotype 23B.
116. The immunogenic complex of any one of embodiments 101-102, wherein the biotinylated polysaccharide antigen is of *Streptococcus pneumoniae* serotype 23F.
117. The immunogenic complex of any one of embodiments 101-102, wherein the biotinylated polysaccharide antigen is of *Streptococcus pneumoniae* serotype 33F.
118. The immunogenic complex of any one of embodiments 101-117, wherein the biotin-binding moiety is a polypeptide comprising (i) an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or (ii) an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof.

119. The immunogenic complex of any one of embodiments 101-118, comprising a ratio of fusion protein to polysaccharide antigen of about 1:1, about 2:1, about 3:1, about 4:1, about 5:1, about 6:1, about 7:1, about 8:1, about 9:1, or about 10:1, by weight.

120. A vaccine comprising one or more immunogenic complexes of any one of embodiments 101-119.

121. A pharmaceutical composition comprising the vaccine of any one of embodiments 1-73 and 120, and a pharmaceutically acceptable carrier.

122. A pharmaceutical composition comprising the immunogenic complex of any one of embodiments 101-119, and a pharmaceutically acceptable carrier.

123. The pharmaceutical composition of embodiment 121 or embodiment 122, further comprising one or more adjuvants.

124. The pharmaceutical composition of embodiment 123, wherein the one or more adjuvants is or comprises a co-stimulation factor.

125. The pharmaceutical composition of embodiment 123 or embodiment 124, wherein the one or more adjuvants are selected from the group consisting of aluminum phosphate, aluminum hydroxide, and phosphated aluminum hydroxide.

126. The pharmaceutical composition of any one of embodiments 123-125, wherein the one or more adjuvants is or comprises aluminum phosphate.

127. The pharmaceutical composition of any one of embodiments 121-126, wherein the pharmaceutical composition is formulated for injection.

128. The pharmaceutical composition of any one of embodiments 121-127, wherein upon administration to a subject, the pharmaceutical composition induces an immune response.

129. The pharmaceutical composition of embodiment 128, wherein the immune response comprises an antibody and/or B cell response.

130. The pharmaceutical composition of embodiment 128 or embodiment 129, wherein the immune response comprises a CD4+ T cell response (e.g., $T_H1$, $T_H2$, or $T_H17$ response); a CD8+ T cell response; a CD4+ and CD8+ T cell response; or a CD4−/CD8− T cell response.

131. The pharmaceutical composition of any one of embodiments 128-130, wherein the immune response comprises (i) an antibody or B cell response and (ii) a T cell response.

132. The pharmaceutical composition of any one of embodiments 128-131, wherein the immune response is to (i) at least one polysaccharide antigen of the vaccine or immunogenic complex, and/or (ii) at least one polypeptide antigen of the vaccine or immunogenic complex.

133. The pharmaceutical composition of any one of embodiments 128-132, wherein the immune response comprises (i) an antibody or B cell response to at least one polysaccharide antigen of the vaccine or immunogenic complex, and (ii) a CD4+ T cell response (e.g., $T_H1$, $T_H2$, or $T_H17$ response), a CD8+ T cell response, a CD4+ and CD8+ T cell response, or a CD4−/CD8− T cell response to at least one polypeptide antigen of the vaccine or immunogenic complex.

134. The pharmaceutical composition of any one of embodiments 128-133, wherein the immune response comprises (i) an antibody or B cell response to at least one polysaccharide antigen of the vaccine or immunogenic complex, and (ii) an antibody or B cell response to at least one polypeptide antigen of the vaccine or immunogenic complex.

135. The pharmaceutical composition of any one of embodiments 128-134, wherein the immune response comprises (i) an antibody or B cell response to at least one polysaccharide antigen of the vaccine or immunogenic complex, and (ii) an antibody or B cell response; and a CD4+ T cell response (including $T_H1$, $T_H2$, or $T_H17$ response), a CD8+ T cell response, a CD4+ and CD8+ T cell response, or a CD4−/CD8− T cell response to at least one polypeptide antigen of the vaccine or immunogenic complex.

136. The pharmaceutical composition of any one of embodiments 121-135, wherein upon administration to a subject, the pharmaceutical composition induces an opsonic/bactericidal response against one or more serotypes of *Streptococcus pneumoniae.*

137. The pharmaceutical composition of any one of embodiments 121-136, wherein upon administration to a subject, the pharmaceutical composition reduces or inhibits transmission of one or more serotypes of *Streptococcus pneumoniae* from the subject to another subject.

138. The pharmaceutical composition of any one of embodiments 121-137, wherein upon administration to a subject, the pharmaceutical composition reduces or inhibits colonization by one or more serotypes of *Streptococcus pneumoniae.*

139. The pharmaceutical composition of embodiment 138, wherein upon administration to a subject, the pharmaceutical composition reduces or inhibits colonization of mucosal surfaces by one or more serotypes of *Streptococcus pneumoniae.*

140. The pharmaceutical composition of embodiment 139, wherein upon administration to a subject, the pharmaceutical composition reduces or inhibits colonization of the nasopharynx by one or more serotypes of *Streptococcus pneumoniae.*

141. The pharmaceutical composition of any one of embodiments 121-140, wherein upon administration to a subject, the pharmaceutical composition reduces bacterial load of one or more serotypes of *Streptococcus pneumoniae.*

142. The pharmaceutical composition of any one of embodiments 121-141, wherein upon administration to a subject, the pharmaceutical composition inhibits, or reduces the rate of occurrence of, Invasive Pneumococcal Disease (IPD) associated with or induced by one or more serotypes of *Streptococcus pneumoniae.*

143. The pharmaceutical composition of any one of embodiments 121-142, wherein upon administration to a subject, the pharmaceutical composition reduces the severity of Invasive Pneumococcal Disease (IPD) associated with or induced by one or more serotypes of *Streptococcus pneumoniae.*

144. The pharmaceutical composition of any one of embodiments 121-143, wherein upon administration to a subject, the pharmaceutical composition inhibits, or reduces the rate of occurrence of, bacteremia, sepsis, and/or meningitis associated with or induced by one or more serotypes of *Streptococcus pneumoniae.*

145. The pharmaceutical composition of any one of embodiments 121-144, wherein upon administration to a subject, the pharmaceutical composition reduces the severity of bacteremia, sepsis, and/or meningitis associated with or induced by one or more serotypes of *Streptococcus pneumoniae.*

146. The pharmaceutical composition of any one of embodiments 121-145, wherein upon administration to a subject, the pharmaceutical composition inhibits, or reduces the rate of occurrence of, organ damage associated with or induced by one or more serotypes of *Streptococcus pneumoniae.*

147. The pharmaceutical composition of any one of embodiments 121-146, wherein upon administration to a subject, the pharmaceutical composition reduces the severity of organ damage associated with or induced by one or more serotypes of *Streptococcus pneumoniae.*

148. The pharmaceutical composition of any one of embodiments 121-147, wherein upon administration to a subject, the pharmaceutical composition inhibits, or reduces the rate of occurrence of, pneumonia associated with or induced by one or more serotypes of *Streptococcus pneumoniae.*

149. The pharmaceutical composition of any one of embodiments 121-148, wherein upon administration to a subject, the pharmaceutical composition reduces the severity of pneumonia associated with or induced by one or more serotypes of *Streptococcus pneumoniae.*

150. The pharmaceutical composition of any one of embodiments 121-149, wherein upon administration to a subject, the pharmaceutical composition inhibits, or reduces the rate of occurrence of, otitis media associated with or induced by one or more serotypes of *Streptococcus pneumoniae.*

151. The pharmaceutical composition of any one of embodiments 121-150, wherein upon administration to a subject, the pharmaceutical composition reduces the severity of otitis media associated with or induced by one or more serotypes of *Streptococcus pneumoniae.*

152. The pharmaceutical composition of any one of embodiments 121-151, wherein upon administration to a subject, the pharmaceutical composition inhibits, or reduces the rate of occurrence of, sinusitis associated with or induced by one or more serotypes of *Streptococcus pneumoniae.*

153. The pharmaceutical composition of any one of embodiments 121-152, wherein upon administration to a subject, the pharmaceutical composition reduces the severity of sinusitis associated with or induced by one or more serotypes of *Streptococcus pneumoniae.*

154. A method of making a vaccine, comprising non-covalently complexing a plurality of first biotinylated polysaccharide antigens with a plurality of first fusion proteins, wherein each first fusion protein comprises:
(a) a biotin-binding moiety;
(b) a pneumolysin (Ply) polypeptide or antigenic fragment thereof; and
(c) an SP0435 polypeptide or antigenic fragment thereof.

155. The method of embodiment 154, further comprising non-covalently complexing a plurality of second biotinylated polysaccharide antigens with a plurality of second fusion proteins, wherein each second fusion protein comprises:
(a) a biotin-binding moiety;
(b) an SP1500 polypeptide or antigenic fragment thereof; and
(c) an SP0785 polypeptide or antigenic fragment thereof.

156. The method of embodiment 155, wherein the plurality of second biotinylated polysaccharide antigens comprises polysaccharides of one or more *Streptococcus pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

157. The method of embodiment 155 or embodiment 156, wherein the plurality of second biotinylated polysaccharide antigens comprises polysaccharides of one or more *Streptococcus pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

158. The method of embodiment 155 or embodiment 156, wherein the plurality of second biotinylated polysaccharide antigens comprises polysaccharides of one or more *Streptococcus pneumoniae* serotypes selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

159. The method of embodiment 155 or embodiment 156, wherein the plurality of second biotinylated polysaccharide antigens comprises polysaccharides of one or more *Streptococcus pneumoniae* serotypes selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

160. The method of embodiment 155 or embodiment 156, wherein the plurality of second biotinylated polysaccharide antigens comprises polysaccharides of one or more *Streptococcus pneumoniae* serotypes selected from 1, 3, 4, 5, 6A, 6B, 7F, 8, 9N, 9V, 10A, 11A, 12F, 14, 15B, 17F, 18C, 19A, 19F, 20B, 22F, 23F, and 33F.

161. The method of embodiment 155 or embodiment 156, wherein the plurality of second biotinylated polysaccharide antigens comprises polysaccharides of one or more *Streptococcus pneumoniae* serotypes selected from 6C, 7C, 15A, 16F, 23A, 23B, 24F, 31, 35B, and 38.

162. The method of embodiment 154 or embodiment 155, wherein the plurality of first biotinylated polysaccharide antigens comprises polysaccharides of one or more *Streptococcus pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

163. The method of any one of embodiments 154, 155, and 162, wherein the plurality of first biotinylated polysaccharide antigens comprises polysaccharides of one or more *Streptococcus pneumoniae* serotypes selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

164. The method of any one of embodiments 154, 155, and 162, wherein the plurality of first biotinylated polysaccharide antigens comprises polysaccharides of one or more *Streptococcus pneumoniae* serotypes selected from 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.

165. The method of any one of embodiments 154, 155, and 162, wherein the plurality of first biotinylated polysaccharide antigens comprises polysaccharides of one or more *Streptococcus pneumoniae* serotypes selected from 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

166. The method of any one of embodiments 154, 155, and 162, wherein the plurality of first biotinylated polysaccharide antigens comprises polysaccharides of one or more *Streptococcus pneumoniae* serotypes selected from 1, 3, 4, 5, 6A, 6B, 7F, 8, 9N, 9V, 10A, 11A, 12F, 14, 15B, 17F, 18C, 19A, 19F, 20B, 22F, 23F, and 33F.

167. The method of any one of embodiments 154, 155, and 162, wherein the plurality of first biotinylated polysaccharide antigens comprises polysaccharides of one or more *Streptococcus pneumoniae* serotypes selected from 6C, 7C, 15A, 16F, 23A, 23B, 24F, 31, 35B, and 38.

168. A method of immunizing a subject against *Streptococcus pneumoniae* infection and/or colonization comprising administering to the subject an immunologically effective amount of the vaccine of any one of embodiments 1-73 and 120.

169. A method of immunizing a subject against *Streptococcus pneumoniae* infection and/or colonization comprising administering to the subject an immunologically effective amount of the immunogenic complex of any one of embodiments 101-119.

170. A method of immunizing a subject against *Streptococcus pneumoniae* infection and/or colonization comprising administering to the subject an immunologically effective amount of the pharmaceutical composition of any one of embodiments 121-153.

171. The method of any one of embodiments 168-170, wherein the vaccine, immunogenic composition, or pharmaceutical composition induces an immune response.

172. The method of embodiment 171, wherein the immune response comprises an antibody or B cell response.

173. The method of embodiment 171 or embodiment 172, wherein the immune response comprises a CD4+ T cell response (e.g., $T_H1$, $T_H2$, or $T_H17$ response), a CD8+ T cell response, a CD4+ and CD8+ T cell response, or a CD4−/CD8− T cell response.

174. The method of any one of embodiments 171-173, wherein the immune response comprises (i) an antibody or B cell response and (ii) a T cell response.

175. The method of any one of embodiments 171-174, wherein the immune response is to at least one polysaccharide antigen or at least one polypeptide of a fusion protein.

176. The method of any one of embodiments 171-175, wherein the immune response comprises (i) an antibody or B cell response to at least one polysaccharide antigen, and (ii) a CD4+ T cell response (e.g., $T_H1$, $T_H2$, or $T_H17$ response), a CD8+ T cell response, a CD4+ and CD8+ T cell response, or a CD4−/CD8− T cell response to at least one polypeptide of a fusion protein.

177. The method of any one of embodiments 171-176, wherein the immune response comprises (i) an antibody or B cell response to at least one polysaccharide antigen, and (ii) an antibody or B cell response to at least one polypeptide of a fusion protein.

178. The method of any one of embodiments 171-177, wherein the immune response comprises (i) an antibody or B cell response to at least one polysaccharide antigen, and (ii) an antibody or B cell response and a CD4+ T cell response, including $T_H1$, $T_H2$, or $T_H17$ response, or a CD8+ T cell response, a CD4+ and CD8+ T cell response, or a CD4−/CD8− T cell response to at least one polypeptide of a fusion protein.

179. The method of any one of embodiments 168-178, wherein the vaccine induces an opsonic/bactericidal response against one or more serotypes of *Streptococcus pneumoniae*.

180. The method of any one of embodiments 168-179, wherein the vaccine inhibits transmission of one or more serotypes of *Streptococcus pneumoniae* from the subject to another subject.

181. The method of any one of embodiments 168-180, wherein the vaccine inhibits or reduces replication, or reduces bacterial load, of one or more serotypes of *Streptococcus pneumoniae*.

182. The method of any one of embodiments 168-181, wherein the vaccine inhibits or reduces the rate of occurrence of Invasive Pneumococcal Disease (IPD) associated with or induced by one or more serotypes of *Streptococcus pneumoniae*.

183. The method of any one of embodiments 168-182, wherein the vaccine reduces the severity of Invasive Pneumococcal Disease (IPD) associated with or induced by one or more serotypes of *Streptococcus pneumoniae*.

184. The method of any one of embodiments 168-183, wherein the vaccine inhibits or reduces the rate of occurrence of bacteremia, sepsis, and/or meningitis associated with or induced by one or more serotypes of *Streptococcus pneumoniae*.

185. The method of any one of embodiments 168-184, wherein the vaccine reduces the severity of bacteremia, sepsis, and/or meningitis associated with or induced by one or more serotypes of *Streptococcus pneumoniae*.

186. The method of any one of embodiments 168-185, wherein the vaccine inhibits or reduces the rate of occurrence of organ damage associated with or induced by one or more serotypes of *Streptococcus pneumoniae*.

187. The method of any one of embodiments 168-186, wherein the vaccine reduces the severity of organ damage associated with or induced by one or more serotypes of *Streptococcus pneumoniae*.

188. The method of any one of embodiments 168-187, wherein the vaccine inhibits or reduces the rate of occurrence of pneumonia associated with or induced by one or more serotypes of *Streptococcus pneumoniae*.

189. The method of any one of embodiments 168-188, wherein the vaccine reduces the severity of pneumonia associated with or induced by one or more serotypes of *Streptococcus pneumoniae*.

190. The method of any one of embodiments 168-189, wherein the vaccine inhibits or reduces the rate of occurrence of otitis media associated with or induced by one or more serotypes of *Streptococcus pneumoniae.*
191. The method of any one of embodiments 168-190, wherein the vaccine reduces the severity of otitis media associated with or induced by one or more serotypes of *Streptococcus pneumoniae.*
192. The method of any one of embodiments 168-191, wherein the vaccine inhibits or reduces the rate of occurrence of sinusitis associated with or induced by one or more serotypes of *Streptococcus pneumoniae.*
193. The method of any one of embodiments 168-192, wherein the vaccine reduces the severity of sinusitis associated with or induced by one or more serotypes of *Streptococcus pneumoniae.*
194. The method of any one of embodiments 168-193, wherein the vaccine inhibits colonization of mucosal surfaces by one or more serotypes of *Streptococcus pneumoniae.*
195. The method of any one of embodiments 168-194, wherein the vaccine inhibits colonization of the nasopharynx by one or more serotypes of *Streptococcus pneumoniae.*
196. The method of any one of embodiments 168-195, wherein the vaccine inhibits or reduces asymptomatic infection by one or more serotypes of *Streptococcus pneumoniae.*
197. The method of any one of embodiments 168-196, wherein the *Streptococcus pneumoniae* has a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.
198. The method of any one of embodiments 168-197, wherein the *Streptococcus pneumoniae* has a serotype selected from one or more of 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.
199. The method of any one of embodiments 168-198, wherein the *Streptococcus pneumoniae* has a serotype selected from one or more of 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 33F, 35B, and 38.
200. The method of any one of embodiments 168-199, wherein the *Streptococcus pneumoniae* has a serotype selected from one or more of 1, 2, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.
201. The method of any one of embodiments 168-200, wherein the *Streptococcus pneumoniae* has a serotype selected from one or more of 1, 3, 4, 5, 6A, 6B, 7F, 8, 9N, 9V, 10A, 11A, 12F, 14, 15B, 17F, 18C, 19A, 19F, 20B, 22F, 23F, and 33F.
202. The method of any one of embodiments 168-201, wherein the *Streptococcus pneumoniae* has a serotype selected from one or more of 6C, 7C, 15A, 16F, 23A, 23B, 24F, 31, 35B, and 38.
203. The method of any one of embodiments 168-202, wherein the subject is immunized against *Streptococcus pneumoniae* infection and/or colonization with one dose of a vaccine.
204. The method of any one of embodiments 168-203, wherein the subject is immunized against *Streptococcus pneumoniae* infection and/or colonization with two doses of a vaccine.
205. The method of any one of embodiments 168-204, wherein the subject is immunized against *Streptococcus pneumoniae* infection and/or colonization with three doses of a vaccine.
206. The method of any one of embodiments 168-205, wherein the subject is immunized against *Streptococcus pneumoniae* infection and/or colonization with four doses of a vaccine.
207. The method of any one of embodiments 168-206, wherein the vaccine is administered in a regimen as a priming vaccine.
208. The method of any one of embodiments 168-207, wherein the vaccine is administered in a regimen as a booster vaccine.
209. The method of any one of embodiments 168-208, wherein the vaccine is administered in a regimen as a priming vaccine and a booster vaccine.
210. The method of any one of embodiments 168-209, wherein the regimen comprises administration of one or more additional vaccines.
211. The vaccine of any one of embodiments 1-73 and 120, the immunogenic complex of any one of embodiments 101-119, or the pharmaceutical composition of any one of embodiments 121-153, for use in the treatment or prevention of *Streptococcus pneumoniae* infection and/or colonization in a subject.
212. A use of the vaccine of any one of embodiments 1-73 and 120, the immunogenic complex of any one of embodiments 101-119, or the pharmaceutical composition of any one of embodiments 121-153 in the manufacture of a medicament for the treatment or prevention of *Streptococcus pneumoniae* infection and/or colonization.
213. A multivalent pneumococcal immunogenic composition comprising *S. pneumoniae* capsular polysaccharides from at least 25, 26, 27, 28, 29, 30, 31, 32, 33, or 34 different pneumococcal serotypes, each associated with a carrier protein.
214. A multivalent pneumococcal immunogenic composition comprising a *S. pneumoniae* serotype 38 capsular polysaccharide associated with a carrier protein, wherein said immunogenic composition comprises at least 20, 24, 25, 26, 27, 28, 29, 30, 31, 32, or 33 different *S. pneumoniae* capsular polysaccharides, each associated with a carrier protein.
215. A multivalent pneumococcal immunogenic composition comprising a *S. pneumoniae* serotype 7C capsular polysaccharide associated with a carrier protein, wherein said immunogenic composition comprises at least 20, 24, 25, 26, 27, 28, 29, 30, 31, 32, or 33 different *S. pneumoniae* capsular polysaccharides, each associated with a carrier protein.
216. The multivalent pneumococcal immunogenic composition of embodiment 214 or embodiment 215, comprising serotype 7C and 38 capsular polysaccharide each associated with a carrier protein, wherein said immunogenic composition comprises at least 20, 24, 25, 26, 27, 28, 29, 30, 31, 32, or 33 different *S. pneumoniae* capsular polysaccharides, each associated with a carrier protein.

217. The multivalent pneumococcal immunogenic composition of any one of embodiments 213-216, comprising up to 60, 50, 40, or 35 different *S. pneumoniae* capsular polysaccharides each associated with a carrier protein, optionally 20-60, 25-60, 30-60, 20-50, 25-50, 30-50, 15-40, 20-40, 25-40, 30-40, or 30-35 different *S. pneumoniae* capsular polysaccharides, each associated with a carrier protein.

218. The multivalent pneumococcal immunogenic composition of any one of embodiments 213-217, comprising at least or exactly two different antigenic polypeptides or fusion proteins associated with the *S. pneumoniae* capsular polysaccharides.

219. The multivalent pneumococcal immunogenic composition of any one of embodiments 213-218, wherein the carrier protein is or comprises an antigenic polypeptide or a fusion protein.

220. The multivalent pneumococcal immunogenic composition of embodiment 219, wherein the antigenic polypeptide or fusion protein is or comprises CP1, SPP2, SP0785, SP1500, SP0435, Ply, and combinations thereof.

221. The multivalent pneumococcal immunogenic composition of any one of embodiments 213-219, wherein the carrier protein is or comprises PspA, CRM197, variants of CRM197, Diphtheria toxoid, variants of Diphtheria toxoid, Tetanus toxoid, Protein D, and combinations thereof.

222. The multivalent pneumococcal immunogenic composition of any one of embodiments 213-221, comprising *S. pneumoniae* capsular polysaccharides from serotypes 1, 3, 4, 5, 6A, 6B, 7F, 9V, 14, 18C, 19A, 19F, and 23F.

223. The multivalent pneumococcal immunogenic composition of any one of embodiments 213-221, comprising *S. pneumoniae* capsular polysaccharides from serotypes 1, 3, 4, 5, 6A, 6B, 7F, 8, 9N, 9V, 10A, 11A, 12F, 14, 15B, 18C, 19A, 19F, 22F, 23F, and 33F.

224. The multivalent pneumococcal immunogenic composition of any one of embodiments 213-221, comprising *S. pneumoniae* capsular polysaccharides from serotypes 1, 3, 4, 5, 6A, 6B, 7F, 8, 9V, 10A, 11A, 12F, 14, 15B, 18C, 19A, 19F, 22F, 23F, and 33F.

225. The multivalent pneumococcal immunogenic composition of embodiment 223 or 224, wherein the carrier protein is selected from CRM197, variants of CRM197, and Tetanus toxoid.

226. The multivalent pneumococcal immunogenic composition of any one of embodiments 213-225, comprising *S. pneumoniae* capsular polysaccharides from serotypes 6C, 7C, 15A, 16F, 23A, 23B, 24F, 31, 35B, and 38.

227. The multivalent pneumococcal immunogenic composition of any one of embodiments 213-226, comprising *S. pneumoniae* serotype 23A capsular polysaccharide.

228. The multivalent pneumococcal immunogenic composition of any one of embodiments 213-227, comprising a *S. pneumoniae* serotype 23B capsular polysaccharide.

229. The multivalent pneumococcal immunogenic composition of any one of embodiments 213-228, comprising a *S. pneumoniae* serotype 24F capsular polysaccharide.

230. The multivalent pneumococcal immunogenic composition of any one of embodiments 213-229, comprising a *S. pneumoniae* serotype 31 capsular polysaccharide.

231. The multivalent pneumococcal immunogenic composition of any one of embodiments 213-230, comprising a *S. pneumoniae* serotype 35B capsular polysaccharide 232. The multivalent pneumococcal immunogenic composition of any one of embodiments 213-231, comprising a *S. pneumoniae* serotype 17F capsular polysaccharide.

233. The multivalent pneumococcal immunogenic composition of any one of embodiments 213-232, comprising a *S. pneumoniae* serotype 20 (e.g., 20B) capsular polysaccharide.

234. The multivalent pneumococcal immunogenic composition of any one of embodiments 213-233, comprising a *S. pneumoniae* serotype 15 capsular polysaccharide, optionally 15A and 15B capsular polysaccharides.

235. The multivalent pneumococcal immunogenic composition of any one of embodiments 213-234, comprising a *S. pneumoniae* serotype 6C capsular polysaccharide.

236. The multivalent pneumococcal immunogenic composition of any one of embodiments 213-235, comprising a *S. pneumoniae* serotype 16F capsular polysaccharide.

237. The multivalent pneumococcal immunogenic composition of any one of embodiments 213-236, comprising a *S. pneumoniae* serotype 2 capsular polysaccharide.

238. The multivalent pneumococcal immunogenic composition of any one of embodiments 213-237, comprising a *S. pneumoniae* serotype 9N capsular polysaccharide.

239. The multivalent pneumococcal immunogenic composition of any one of embodiments 216-238, wherein the *S. pneumoniae* capsular polysaccharides comprise at least 30, 31, 32, 33, or 34 capsular polysaccharides selected from *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20 (e.g., 20B), 22F, 23A, 23B, 23F, 24F, 31, 33F, 35B, and 38.

240. The multivalent pneumococcal immunogenic composition of any one of embodiments 213-239, comprising capsular polysaccharide from *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20 (e.g., 20B), 22F, 23A, 23B, 23F, 24F, 31, 33F, 35B, and 38.

241. The multivalent pneumococcal immunogenic composition of any one of embodiments 213-240, for use in the treatment or prevent of *Streptococcus pneumoniae* infection and/or colonization in a subject.

242. The multivalent pneumococcal immunogenic composition of any one of embodiments 213-240, containing the features of the vaccine of any one of embodiments 1-73 and 120.

243. A use of the multivalent pneumococcal immunogenic composition of any one of embodiments 213-242 in the manufacture of a medicament for the treatment or prevention of *Streptococcus pneumoniae* infection and/or colonization.

244. A vaccine comprising the multivalent pneumococcal immunogenic composition of any one of embodiments 213-242.

245. A pharmaceutical composition comprising the multivalent pneumococcal immunogenic composition of any one of embodiments 213-242 or the vaccine of embodiment 244, and a pharmaceutically acceptable carrier and/or excipient.

246. The pharmaceutical composition of embodiment 245, further comprising one or more adjuvants.

247. The vaccine of embodiment 244 or the pharmaceutical composition of embodiment 245 or embodiment 246, for use in the treatment or prevent of *Streptococcus pneumoniae* infection and/or colonization in a subject.

248. A method of immunizing a subject against *Streptococcus pneumoniae* infection and/or colonization comprising administering to the subject an immunologically effective amount of the multivalent pneumococcal immunogenic composition of any one of embodiments 213-242, the vaccine of embodiment 244, or the pharmaceutical composition of embodiment 245 or embodiment 246.

EXEMPLIFICATION

Example 1: Exemplary SPP2 Fusion Protein Construct Design

SPP2 is a fusion protein comprising a biotin-binding moiety (e.g., a biotin-binding protein), a non-hemolytic pneumolysin polypeptide comprising mutations at amino acid residues 294, 385, 428, and 433 of wild-type *Streptococcus pneumoniae* pneumolysin or an antigenic fragment thereof; and (iii) a *S. pneumoniae* elongation factor P (SP0435) polypeptide or an antigenic fragment thereof. In some embodiments, a biotin-binding moiety is or comprises rhizavidin or a biotin-binding portion thereof.

Figure 2A:
FIG. 2A is a schematic of an exemplary mutant pneumolysin (Ply) polypeptide. Such an exemplary mutant Ply polypeptide comprises a Ply polypeptide (e.g., amino acids 2-470 of a full-length *S. pneumoniae* Ply polypeptide) comprising mutations G294P, D385N, C428G, and W433F, denoted as PdT (G294P). In some embodiments, a mutant Ply polypeptide (e.g., a PdT (G294P) polypeptide) may further comprise a detection or purification tag (e.g., a His tag). Figure discloses SEQ ID NO: 30 as "GGGGSSS".
Figure 2B:
FIG. 2B is a schematic of an exemplary SPP2 fusion protein. Such an exemplary SPP2 fusion protein comprises a biotin-binding protein, such as e.g., a truncated rhizavidin protein (e.g., amino acids 45-179 of a wild-type rhizavidin protein, denoted as Rhavi), a first linker (e.g., a GGGGSSS (SEQ ID NO: 30) linker), a pneumolysin (Ply) polypeptide (e.g., amino acids 2-470 of a full-length *S. pneumoniae* Ply polypeptide comprising mutations G294P, D385N, C428G, and W433F, denoted as PdT (G294P)), a second linker (e.g., a GGGGSSS (SEQ ID NO: 30) linker), and a SP0435 polypeptide (e.g., amino acids 62-185 of a full length *S. pneumoniae* SP0435 polypeptide). In some embodiments, a SPP2 fusion protein may further comprise a detection or purification tag (e.g., a His tag). For a GGGGSSS (SEQ ID NO: 30) linker, the SSS amino acid sequence can be from the Sac I site on a pET21/24 plasmid, with the GGGG (SEQ ID NO: 54) amino acid sequence added to create a flexible linker with minimal steric hindrance. Alternatively, the GGGGSSS (SEQ ID NO: 30) linker can be synthesized.
Figure 3:
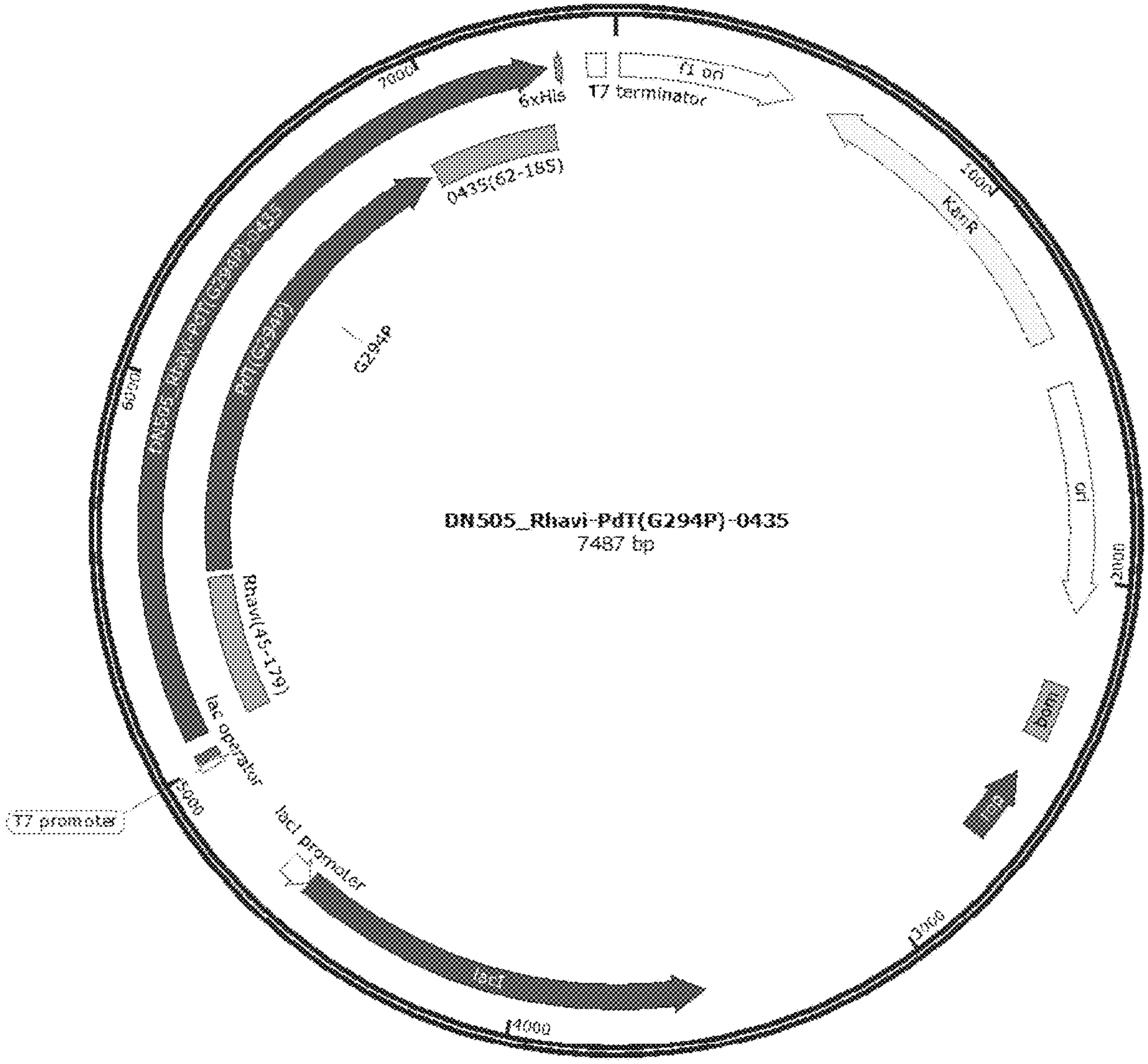
FIG. 3 is a schematic of a plasmid construct composed of the pET-24a (+) vector containing a sequence encoding an exemplary SPP2 fusion protein. Figure discloses SEQ ID NO: 55 as "6×His".

In some embodiments, SPP2 is a fusion protein comprising rhizavidin residues 45-179 (denoted Rhavi), pneumolysin residues 2-470 comprising mutations at amino acid residues 294, 385, 428, and 433 of wild-type *Streptococcus pneumoniae* pneumolysin (denoted PdT (G294P)), and *S. pneumoniae* elongation factor P (SP0435) residues 62-185. In some embodiments, such a SPP2 fusion protein comprises a first GGGGSSS (SEQ ID NO: 30) linker positioned between a Rhavi polypeptide and a PdT (G294P) polypeptide, and a second GGGGSSS (SEQ ID NO: 30) linker positioned between the PdT (G294P) polypeptide and a SP0435 polypeptide. In some embodiments, a SPP2 fusion protein includes one or more His tags. An exemplary SPP2 fusion protein construct is shown schematically in FIG. 2B. An exemplary plasmid map for an exemplary SPP2 fusion protein is shown in FIG. 3.

First Precursor to an Exemplary SPP2

Pneumolysin (Ply) is a cholesterol-dependent, thiol-activated cytolysin that has been identified as a virulence factor of *S. pneumoniae*. Ply has two independent functions, hemolytic activity and complement activation. The structure of Ply can be conveniently separated into four domains. Three well-characterized amino acid substitutions of Ply (D385N, C428G, and W433F) have been shown to reduce both hemolytic activity and complement activation (Berry et al., "Effect of defined point mutations in the pneumolysin gene on the virulence of *Streptococcus pneumoniae*". Infect Immun. 1996 63 (5): 1969-1974). A Ply polypeptide carrying these three amino acid substitutions (D385N, C428G, and W433F) is referred to as PdT. In some embodiments, a first precursor to an exemplary SPP2 comprising Rhavi, SP0435, and PdT was constructed, but showed residual hemolytic activity.

Novel Mutant Pneumolysin PdT (G294P) and Second Precursor to an Exemplary SPP2

Figure 4:
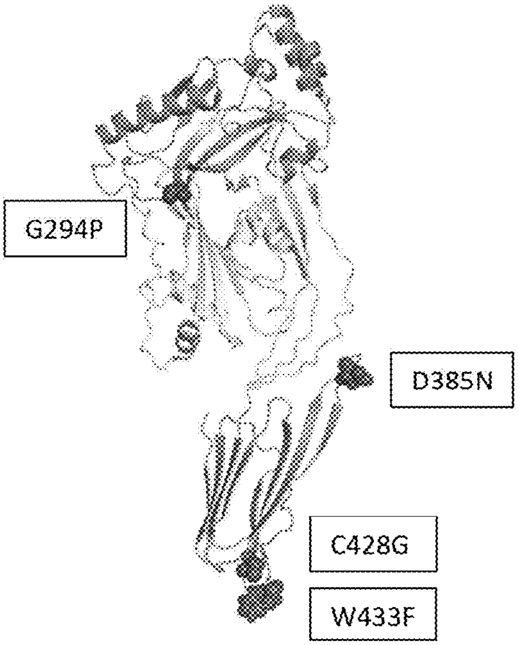
FIG. 4 is a model depicting the tertiary structure of an exemplary pneumolysin polypeptide containing the mutations G294P, D385N, C428G, and W433F (denoted as PdT (G294P)).

In an effort to eliminate residual hemolytic activity of the first precursor, a modified PdT was generated by adding a further amino acid substitution. In particular, the present disclosure observes that single residue changes in the oligomerization domain of Domain 3 of Ply can greatly reduce native hemolytic activity of Ply (Oloo et al., "Structure-guided antigen engineering yields pneumolysin mutants suitable for vaccination against pneumococcal disease". J Biol Chem. 2011 286 (14): 12133-12140). Thus, a second precursor (Precursor 2) to an exemplary SPP2 was generated, which comprises, from the N-terminus to C-terminus, Rhavi, SP0435, and a PdT polypeptide with the addition of a G294P amino acid substitution (denoted as PdT (G294P)). To the inventors' knowledge, this is the first reported instance of a pneumolysin polypeptide combining the amino acid substitution G294P and the amino acid substitutions of PdT (D385N, C428G, and W433F). An exemplary PdT (G294P) polypeptide is shown schematically in FIG. 2A. PdT (G294P) may further comprise a detection or purification tag (e.g., a His tag). The tertiary structure of an exemplary PdT (G294P) polypeptide is shown in FIG. 4. Hemolytic activity was not detected for PdT (G294P) or Precursor 2 (FIG. 5A); however, Precursor 2 unexpectedly showed red blood cell agglutination (hemagglutination) (FIGS. 6A and 6B).

Exemplary SPP2 Construct

The present disclosure provides a surprising insight that the relative position of SP0435 and PdT (G294P) in a fusion protein can unexpectedly impact hemagglutination activity of the fusion protein. In particular, reversing the order of SP0435 and PdT (G294P) in Precursor 2 described above, i.e., positioning SP0435 to the C-terminus of PdT (G294P) in a fusion protein, unexpectedly abolished hemagglutination (FIGS. 6A and 6B). In an exemplary SPP2 construct, which comprises Rhavi, PdT (G294P), and SP0435, with optional His tags, neither hemolysis (FIG. 5A) nor hemagglutination (FIGS. 6A and 6B) were detected. SPP2 fusion protein in MAPS complexes with *Streptococcus pneumoniae* polysaccharide PS1 (1.SPP2 MAPS) also showed no evidence of either hemolysis (FIG. 5B) or hemagglutination (FIG. 6C).

Hemolysis Assay

Figure 5A:
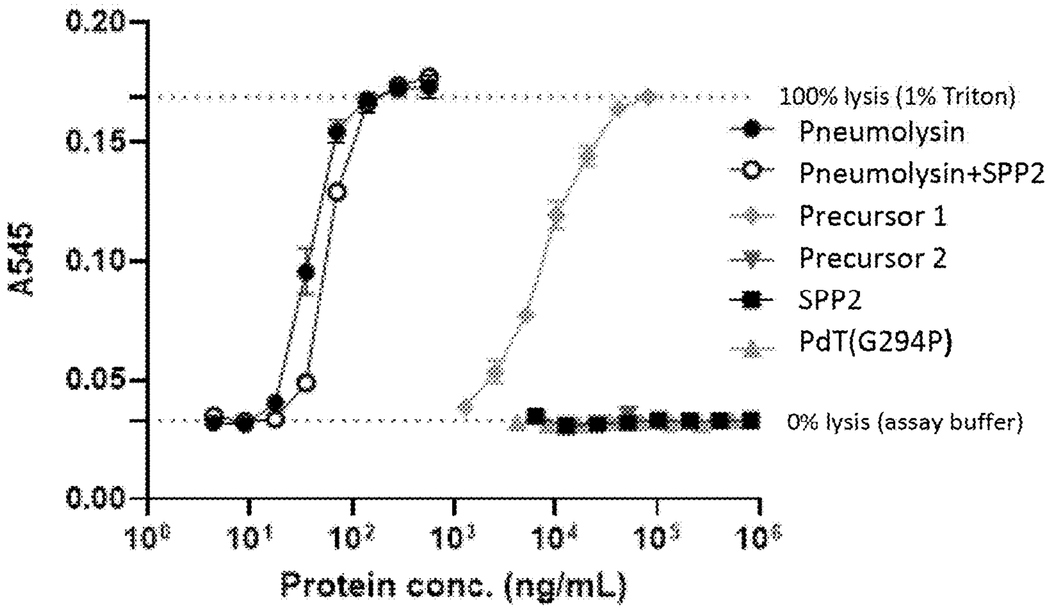
FIG. 5A illustrates the hemolytic activity of pneumolysin, pneumolysin plus SPP2 fusion protein, a PdT (G294P) polypeptide, and fusion proteins (Precursor 1, Precursor 2, and SPP2) as measured using a rabbit red blood cell hemolysis assay. No hemolysis was observed for PdT (G294P), Precursor 2, or SPP2.
Figure 5B:
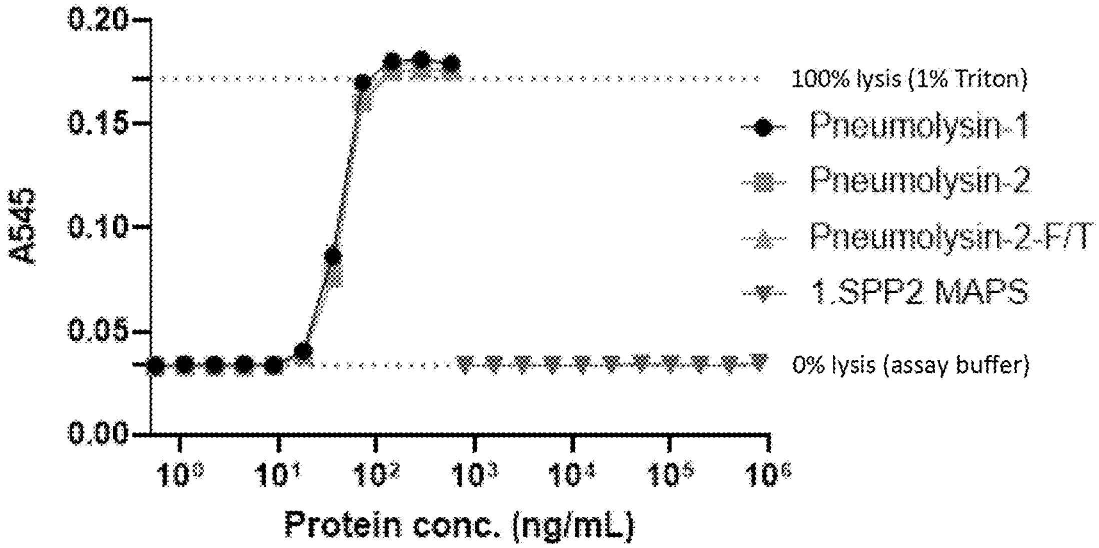
FIG. 5B illustrates the hemolytic activity, as measured using a rabbit red blood cell hemolysis assay, of fusion protein SPP2 in MAPS complexes with *Streptococcus pneumoniae* polysaccharide SP1 (1.SPP2 MAPS), and of pneumolysin prepared from standard 0.5 mg/mL stock (Pneumolysin-1), pneumolysin prepared from diluted 0.1 mg/mL stock (Pneumolysin-2), and pneumolysin prepared from diluted 0.1 mg/mL stock, then subjected to one freeze-thaw cycle (Pneumolysin-2-F/T). No hemolysis was observed for 1.SPP2 MAPS.
Figure 6A:
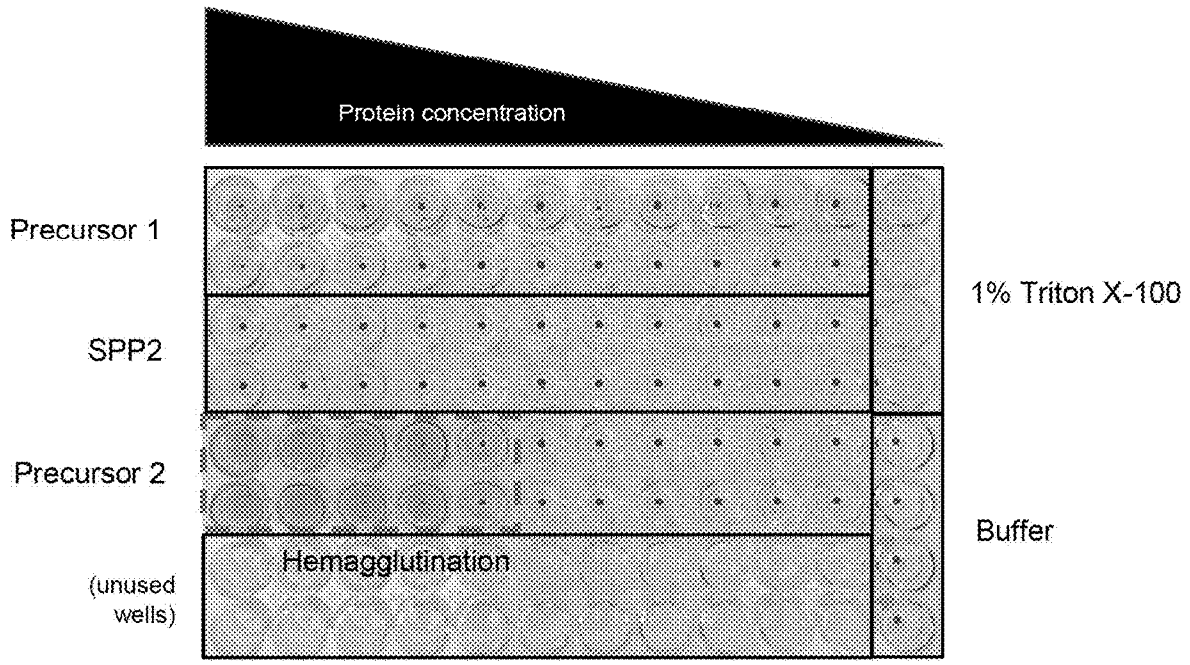
FIG. 6A illustrates hemagglutination activity of fusion proteins (Precursor 1, Precursor 2, and SPP2), as measured using a rabbit red blood cell assay. Precursor 2 wells denoted by the dashed line show evidence of hemagglutination. No hemagglutination was observed in Precursor 1 or SPP2 wells.
Figure 6B:
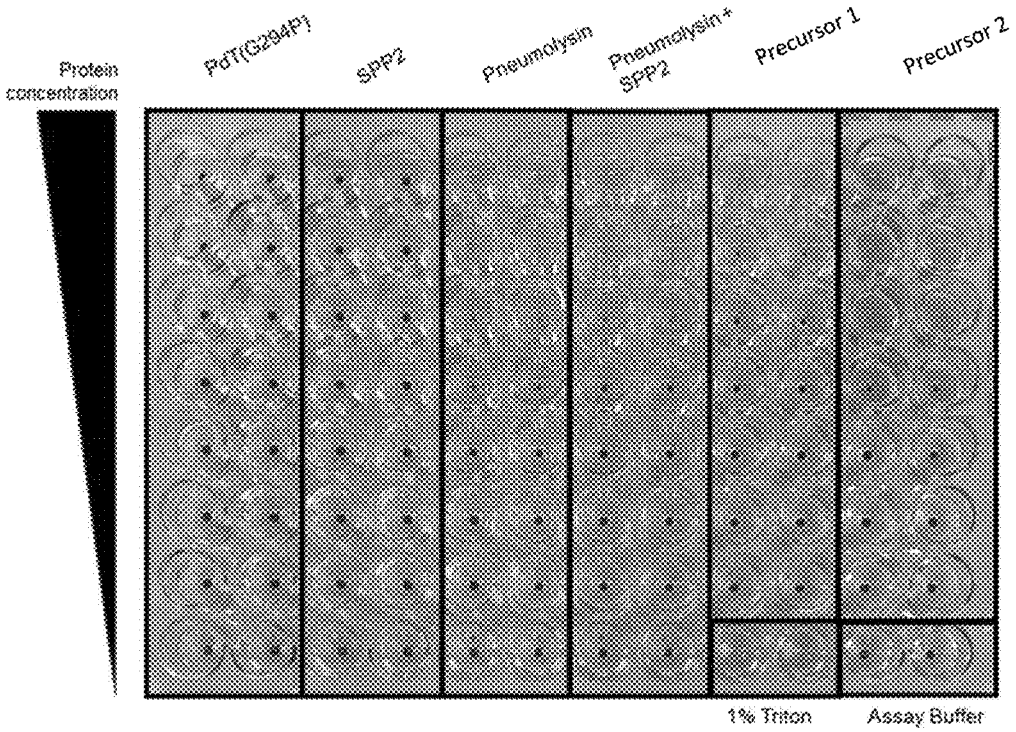
FIG. 6B illustrates hemagglutination activity of pneumolysin, pneumolysin plus fusion protein SPP2, a PdT (G294P) polypeptide, and fusion proteins (Precursor 1, Precursor 2, and SPP2), as measured using a rabbit red blood cell assay. Precursor 2 wells denoted by the dashed lines show evidence of hemagglutination. In this experiment, Precursor 1 wells may show a small amount of hemagglutination. No hemagglutination was observed in PdT (G294P) or SPP2 wells.
Figure 6C:
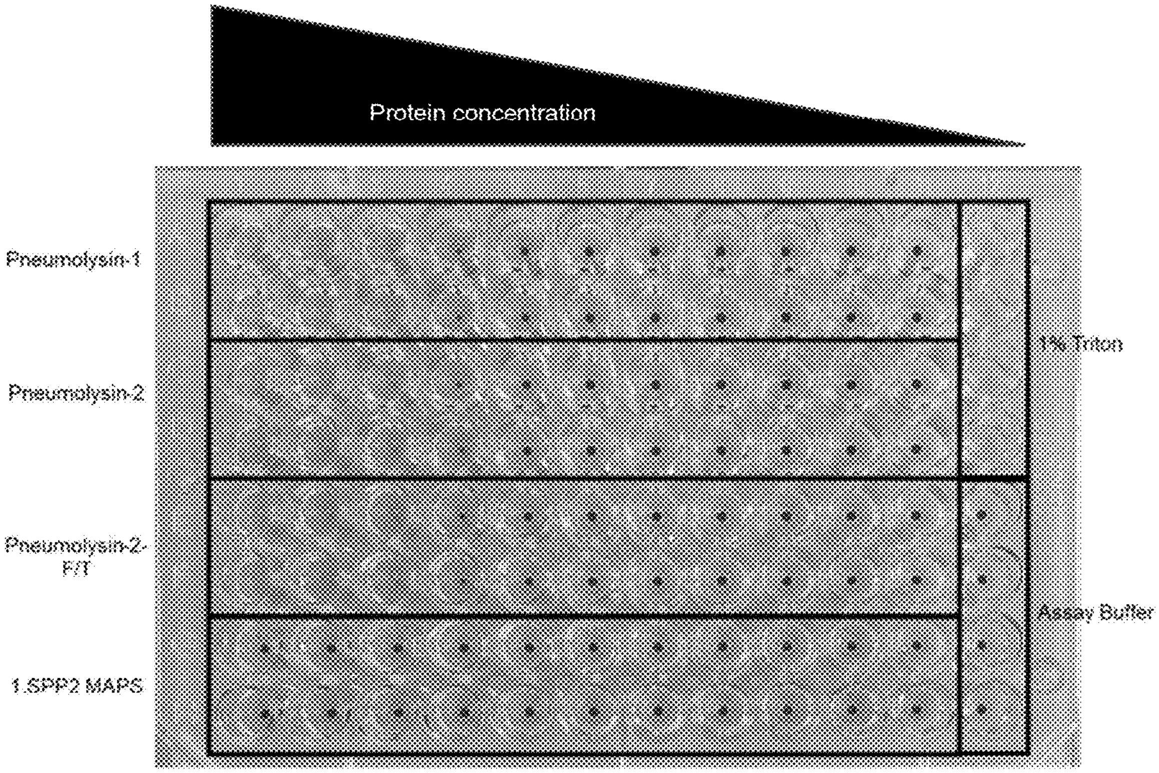
FIG. 6C illustrates hemagglutination activity, as measured using a rabbit red blood cell assay, of fusion protein SPP2 in MAPS complexes with *Streptococcus pneumoniae* polysaccharide PS1 (1.SPP2 MAPS), and of pneumolysin prepared from standard 0.5 mg/mL stock (Pneumolysin-1), pneumolysin prepared from diluted 0.1 mg/mL stock (Pneumolysin-2), and pneumolysin prepared from diluted 0.1 mg/mL stock, then subjected to one freeze-thaw cycle (Pneumolysin-2-F/T). No hemagglutination was observed in 1.SPP2 MAPS wells.

FIG. 5A shows comparative hemolytic activity of purified proteins pneumolysin, pneumolysin plus SPP2 fusion protein, a PdT (G294P) polypeptide, and fusion proteins (Precursor 1, Precursor 2, and SPP2), as measured using a rabbit red blood cell hemolysis assay. FIG. 5B shows comparative hemolytic activity, as measured using a rabbit red blood cell hemolysis assay, of fusion protein SPP2 in MAPS complexes with *Streptococcus pneumoniae* polysaccharide SP1 (1.SPP2 MAPS), and of pneumolysin prepared from standard 0.5 mg/mL stock (Pneumolysin-1), pneumolysin prepared from diluted 0.1 mg/mL stock (Pneumolysin-2), and pneumolysin prepared from diluted 0.1 mg/mL stock, then subjected to one freeze-thaw cycle (Pneumolysin-2-F/T).

Briefly, the indicated proteins (FIG. 5A: Pneumolysin, Pneumolysin+SPP2, PdT (G294P), Precursor 1, Precursor 2, and SPP2; FIG. 5B: 1.SPP2 MAPS, pneumolysin prepared from standard 0.5 mg/mL stock (Pneumolysin-1), pneumolysin prepared from diluted 0.1 mg/mL stock (Pneumolysin-2), and pneumolysin prepared from diluted 0.1 mg/mL stock, then subjected to one freeze-thaw cycle (Pneumolylin-2-F/T)) were incubated at various concentrations with dilute rabbit red blood cells (2% vol/vol in DPBS, 0.1% BSA, +10 mM DTT) for 30 minutes at 37° C. Intact red blood cells were removed by centrifugation, and the supernatants containing red blood cell lysate were collected. The % lysis of red blood cells was determined by comparing the absorbance of the supernatant at 545 nm (A545) to (i) a 100% lysis control (1% Triton X-100 in DPBS, 0.1% BSA, +10 mM DTT), and (ii) a 0% lysis control (DPBS, 0.1% BSA, +10 mM DTT). The normalized % hemolysis data was then fit using a 4PL model, and the concentration of protein required to achieve 50% hemolysis was reported (EC50). For samples that did not reach 50% hemolysis, the EC50 was reported as greater than the highest concentration tested. The range for the A545 values and averages was plotted against the protein concentrations. Values shown are averages of two replicates with the error bars representing the range. Complete lysis of red blood cells accomplished by incubation with 1% Triton is indicated by the dotted top line, while background absorbance of the assay buffer is indicated by dotted bottom line.

In FIG. 5A, complete lysis is observed with pneumolysin between 100-1,000 ng/ml protein. Co-incubation of pneumolysin with SPP2 fusion protein did not reduce the hemolytic activity of pneumolysin, indicating that SPP2 fusion protein, or other constituents of the SPP2 sample, did not mask hemolytic activity. Reduced hemolytic activity was observed with Precursor 1. Notably, no hemolytic activity was seen with PdT (G294P), Precursor 2, or SPP2 fusion protein at approximately 10,000-fold higher protein concentration than pneumolysin.

Results for FIG. 5A are shown quantitatively in Table 1 below:

TABLE 1

Results of Hemolysis Assay

| Protein | EC50 (μM) | Fold-reduction |
|---|---|---|
| Pneumolysin | 0.0007 | 1 (baseline) |
| Pneumolysin + SPP2 | 0.0011 | 1.6 |
| Precursor 1 | 0.0964 | 138/0.0007 |
| Precursor 2 | >10 | >14,000 |
| SPP2 | >10 | >14,000 |
| PdT(G294P) | >10 | >14,000 |

In FIG. 5B, SPP2 fusion protein in MAPS complexes with SP1 (1.SPP2 MAPS) displayed no hemolytic activity at concentrations up to $8.05\times10^5$ ng/mL, an approximately 10,000-fold higher protein concentration than Pneumolysin-1. Preparing pneumolysin from different stock concentrations (Pneumolysin-1 and Pneumolysin-2) and freeze-thawing (Pneumolysin-2 F/T) did not impact hemolytic activity.

Hemagglutination Assay

FIGS. 6A, 6B, and 6C shows comparative hemagglutination activity of purified proteins using a rabbit red blood cell assay. Briefly, the indicated proteins (FIG. 6A: Precursor 1, Precursor 2, SPP2; FIG. 6B: Pneumolysin, Pneumolysin+ SPP2, PdT (G294P), Precursor 1, Precursor 2, and SPP2; FIG. 6C: 1.SPP2 MAPS, pneumolysin prepared from standard 0.5 mg/mL stock (Pneumolysin-1), pneumolysin prepared from diluted 0.1 mg/mL stock (Pneumolysin-2), and pneumolysin prepared from diluted 0.1 mg/mL stock, then subjected to one freeze-thaw cycle (Pneumolysin-2-F/T) were incubated at various concentrations with dilute rabbit red blood cells (RBCs) (2% vol/vol in DPBS, 0.1% BSA, +10 mM DTT) for 30 minutes at 37° C. The assay plate was directly visualized for evidence of red blood cell clumping (hemagglutination). In control wells, rabbit red blood cells were incubated with (i) 1% Triton X-100 in DPBS, 0.1% BSA, +10 mM DTT (100% lysis), or (ii) DPBS, 0.1% BSA, +10 mM DTT (0% lysis). In FIG. 6A, only the wells indicated by a dashed line in Precursor 2 rows showed evidence of hemagglutination. In FIG. 6B, wells indicated by a dashed line in Precursor 2 rows also showed evidence of hemagglutination. In all cases, wells in PdT (G294P), SPP2 and 1.SPP2 MAPS rows were free of hemagglutination.

Example 2: Preparation of Exemplary Fusion Proteins CP1 and SPP2

Vector Constructions

In some embodiments, fusion proteins CP1 and SPP2 each comprise a biotin-binding portion of rhizavidin spanning amino acids 45 to 179 of the full-length protein, wherein the predicted signal sequences (amino acids 1-44) of rhizavidin were not incorporated. To optimize the expression level of CP1 in *E. coli*, in some embodiments, the gene sequence that encodes rhizavidin polypeptide (e.g., in some embodiments, amino acids 45-179; SEQ ID NO: 2) was redesigned using *E. coli*-preferred expression codons, synthesized and cloned into plasmid pET24a (+). This synthetic rhizavidin gene was designated Rhavi.

To construct the fusion proteins CP1 and SPP2, in some embodiments, a DNA sequence encoding a flexible linker (e.g., in some embodiments, a flexible linker of GGGGSSS; SEQ ID NO: 30) was directly inserted into the 3' end of the synthetic Rhavi gene to provide separation from Rhavi and promote proper folding of the subsequent fusion protein.

For CP1, the genes encoding desired portions of SP1500 and SP0785 protein (not including predicted signal sequences; nucleic acid sequences encoding the polypeptides of SEQ ID NO: 12 and SEQ ID NO: 10, respectively) were synthesized and inserted into the Rhavi expression vector just beyond the linker region. Three residual amino acids (AAA) from a Not I restriction site of pET24a (+) separate SP1500 and SP0785, and may be referred to as the second linker of CP1. Stop codons were included at the 3'-end of the CP1 coding sequences. After cloning was complete, DNA sequencing of the pET-24a (+): CP1 plasmid was performed to confirm the presence, orientation and sequence of the CP1 DNA insert in the pET-24a (+) vector. A schematic of fusion protein CP1 is shown in FIG. 7.

For SPP2, a DNA sequence encoding an exemplary fusion protein SPP2 (Rhavi-GGGGSSS-PdT (G294P)-GGGGSSS-SP0435; e.g., SEQ ID NO: 27 or SEQ ID NO: 62) was cloned into the pET-24a (+) vector using PCR cloning. Stop codons were included at the 3'-end of the coding sequences. After cloning was complete, DNA sequencing of the pET-24a (+): SPP2 plasmid was performed to confirm the presence, orientation and sequence of the SPP2 DNA insert in the pET-24a (+) vector. A schematic of fusion protein SPP2 is shown in FIG. 2. The map of plasmid pET24a (+): SPP2 is shown in FIG. 3.

Establishment of Master Cell Banks (MCB)

To generate the Research Cell Banks (RCB), the pET-24a (+): CP1 and pET24a (+): SPP2 plasmids were transformed into an *E. coli* expression strain. Transformed *E. coli* cells were plated in culture plates containing Kanamycin. A single colony from the plate was selected and used to inoculate into liquid medium in a shaker flask. The flasks were placed in an incubator shaker for overnight culture and grown to the desired OD. The bacterial culture was then mixed with glycerol solution. The mixed solution was aliquoted into vials to make RCB.

To generate the MCB, RCB was inoculated into liquid medium in shaker flasks and grown to the desired OD. The bacterial culture was then brought to 15% glycerol, mixed and aliquoted into vials. The MCB vials were then placed at −80° C. (−70° C. to −90° C.) and selected vials were taken for quality assurance testing.

Manufacturing Process Overview

The CP1 and SPP2 fusion proteins were expressed in *E. coli*. The expressed CP1 and SPP2 fusion proteins were released from *E. coli* cells and purified in a series of chromatographic and filtration steps. The following section describes the 300 L culture scale CP1 manufacturing process.

The process was initiated by thawing and inoculating cells from a MCB vial into cell medium. Initial cell expansion was performed in flask and then the bacterial culture was transferred to a 300 L fermenter. Bacteria were harvested by centrifugation. The recovered cell paste was resuspended in a lysis buffer and fluidized by a microfluidizer. Bulk CP1 fusion protein in the fluidized cell lysate was purified by precipitation and chromatography steps. The final process stream was concentration and buffer exchange into 20 mM Tris, 150 mM NaCl at pH 8.0±0.1 via ultrafiltration membranes. Lastly, the CP1 fusion protein was 0.22 μm filtered immediately prior to bottling and stored at −80° C. No raw materials contained animal- or human-derived components.

Upstream Process

Figure 8:
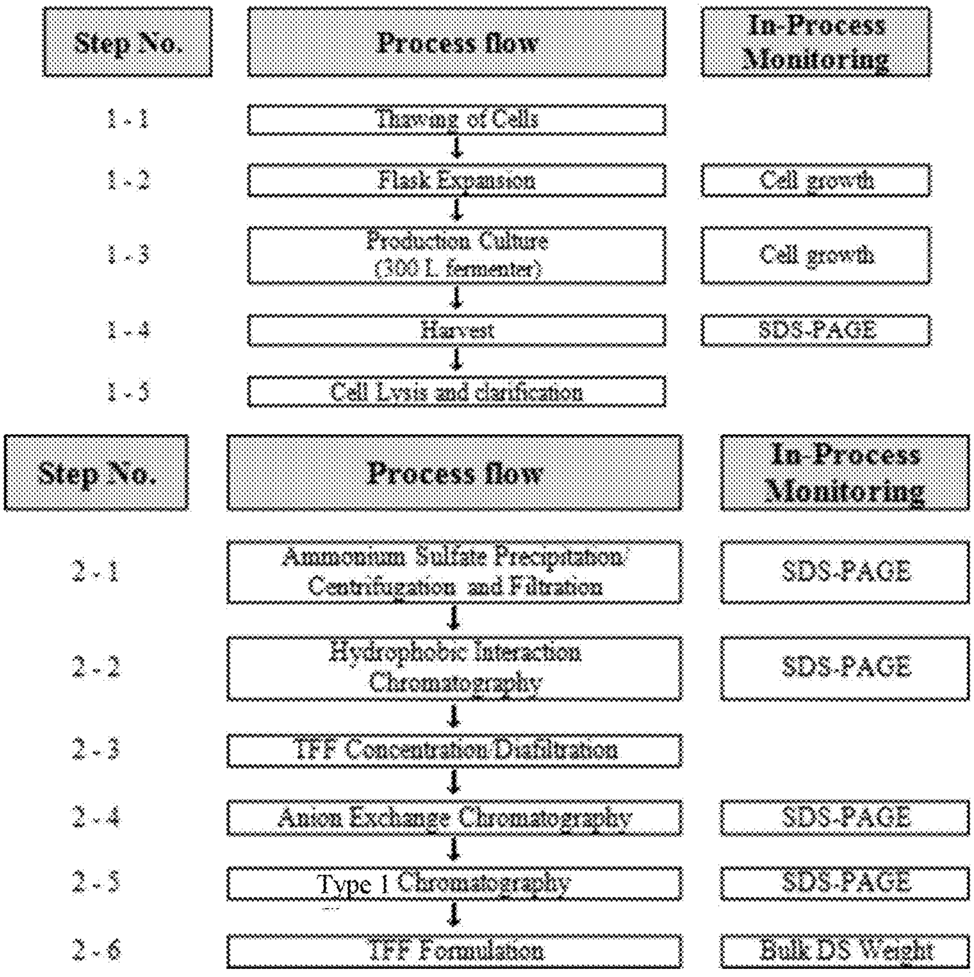
FIG. 8 are flow-charts depicting an exemplary upstream (upper panel) and downstream (lower panel) manufacturing process for fusion proteins as described herein (e.g., CP1 and SPP2). An exemplary SPP2 polypeptide is a fusion protein comprising a truncated rhizavidin [amino acids 45-179 of a full-length rhizavidin protein], a first linker (e.g., a GGGGSSS (SEQ ID NO: 30) linker), a pneumolysin (Ply) polypeptide, a second linker (e.g., a GGGGSSS (SEQ ID NO: 30) linker), and a SP0435 polypeptide. An exemplary CP1 polypeptide is a fusion protein comprising a truncated rhizavidin [amino acids 45-179 of a full-length rhizavidin protein], a first linker (e.g., a GGGGSSS (SEQ ID NO: 30) linker), a SP1500 polypeptide, a second linker (e.g., the amino acid sequence AAA), and a SP0785 polypeptide. SDS-PAGE: Sodium dodecyl sulfate polyacrylamide gel electrophoresis; TFF: tangential flow filtration; DS: drug substance.

A flow chart of a representative upstream manufacturing process for fusion proteins CP1 and SPP2 is provided in FIG. 8, upper panel, and details for the individual steps follow.

The cell culture utilized chemically defined media and components depending on the manufacturing step. The media used were cell media, production media, feed 1 media and feed 2 media. These media were used in inoculum expansion, production culture, and feeding, respectively.

Step 1-1: Thawing of Cells

Sufficient cell medium was prepared and transferred into an appropriate culture flask and then frozen MCB is thawed.

Step 1-2: Flask Expansion

Thawed MCB was inoculated and grown in a 2.5 L flask. Cell growth was monitored by a spectrophotometer at OD600.

Step 1-3: Production Culture

The production culture was run in fed-batch mode. To support product generation and to prolong the cell culture production period, feed 1 and feed 2 media were added after appropriate cell growth. Once the fermenter temperature reached the set point, isopropyl β-D-1-thiogalactopyranoside was added to induce fusion protein expression. After approximately 18 hours from induction, harvest was begun by centrifugation.

Step 1-4: Harvest

Bacterial culture was harvested by continuous flow centrifugation.

Step 1-5: Cell Lysis and Clarification

The recovered cell paste was resuspended in lysis buffer and fluidized by a microfluidizer. The fluidized cell lysate, including bulk fusion protein, was centrifuged and the supernatant was recovered.

Alternative upstream processes may be employed to manufacture the CP1 and SPP2 fusion proteins.

Downstream Process

After harvest and cell lysis, fusion proteins CP1 and SPP2 were purified by several chromatography steps. A flow chart of a representative fusion protein purification process is provided in FIG. 8, lower panel. Details for the individual steps follow.

Step 2-1: Ammonium Sulfate Precipitation/Centrifugation and Filtration

Ammonium sulfate solution was added to the clarified lysate and adjusted to a final concentration of 0.8 M. After mixing at room temperature, the clarified lysate with ammonium sulfate was centrifuged and the supernatant was recovered. The recovered supernatant was filtered through 0.22 μm filter and collected in an appropriate container.

Step 2-2: Hydrophobic Interaction Chromatography

The purpose of this step is to remove process-related contaminants. Fusion protein bound to the resin was washed with high concentration ammonium sulfate buffer then eluted with elution buffer (the concentration of NaCl in the buffer was gradually reduced). A sodium dodecyl sulfate polyacrylamide gel electrophoresis (SDS-PAGE) analysis was performed with each fraction to confirm the presence of fusion protein.

Step 2-3: Tangential Flow Filtration Concentration/Filtration

The elution pool was concentrated and then buffer exchanged with several-fold volumes of Tris-buffered saline using a 30 kDa filtration membrane. The filtrated tangential flow filtration (TFF) retentate was filtered by 0.22 μm filter.

Step 2-4: Anion Exchange Chromatography

The purpose of this step is to remove process-related contaminants. Fusion protein bound to the resin was washed with NaCl wash buffer then eluted with NaCl elution buffer (the concentration of NaCl in the buffer was gradually increased). SDS-PAGE analysis was performed with each fraction to confirm the presence of fusion protein.

Step 2-5: Type 1 Chromatography

The purpose of this step is to further remove process-related contaminants. Fusion protein bound to the resin was washed with phosphate wash buffer then eluted with phosphate elution buffer (the concentration of phosphate in the buffer was gradually increased). SDS-PAGE analysis was performed with each fraction to confirm the presence of fusion protein.

Step 2-6: TFF Formulation

The Type 1 chromatography fraction pool was concentrated and then buffer exchanged with several-fold volumes of formulation buffer (20 mM Tris, 150 mM sodium chloride, pH 8.0±0.1) using a 30 kDa filtration membrane. The formulated fusion protein was filtered through 0.22 μm filter.

Alternative downstream processes may be employed to manufacture the CP1 and SPP2 fusion proteins.

Container Closure System

CP1 and SPP2 fusion proteins were stored at −80° C. (−70° C. to −90° C.) in sterile polyethylene terephthalate bottles.

Example 3: *S. pneumoniae* Capsular Polysaccharides (PS) and Preparations of the Same Preparation and Purification Methods of culturing pneumococci are well known in the art (e.g. Chase, 1967, Methods of Immunology and Immunochemistry 1:52). Methods of preparing pneumococcal capsular polysaccharides are also well known in the art (e.g., European Patent No. EP0497524). Isolates of pneumococcal serotypes are available from the ATCC, the National Collection of Type Cultures operated by Public Health England, and other repositories.

*S. pneumoniae* is identified as non-motile, Gram-positive, lancet-shaped diplococci that are alpha-hemolytic on blood agar. Most but not all strains are encapsulated. Serotypes are differentiated on the basis of Neufeld Test (Quelling reaction) using specific antisera (e.g., U.S. Pat. No. 5,847,112), latex agglutination, or multilocus sequence typing.

A frozen vial representing each of the *S. pneumoniae* serotypes present in MAPS vaccine candidates of the present disclosure was thawed and used to generate a seed culture in appropriate pre-sterilized growth media. The seed culture was grown with temperature and pH control. The seed culture was transferred to a production fermenter that contained pre-sterilized growth media. The production culture was grown with temperature, pH and agitation rate control. The growth process was terminated with addition of an inactivating agent with a controlled temperature hold.

The purification process was initiated by removal of cell debris using a combination of centrifugation and filtration. The material was filtered followed by solvent-based fractionations to remove impurities and recover PS.

Exemplary Polysaccharide Structures

Representative polysaccharide (PS) structures are shown in FIG. 9. All PS specifications in Table 2 were obtained from European Pharmacopoeia 9.0 Table 0966.-1, except for molecular size and serotype 6A, which are based on the manufacturer's certificate of analysis.

TABLE 2

Exemplary Polysaccharide (PS) Specifications

| Molecular type† | Protein | Nucleic acids | Total nitrogen | Phosphorus | Molecular size ($K_D$) ‡ | Molecular size ($K_D$) § | Uronic acids | Hex-osamines | Methyl-pentoses | O-acetyl Groups |
|---|---|---|---|---|---|---|---|---|---|---|
| 1 | ≤2 | ≤2 | 3.5-6 | 0-1.5 | ≤0.15 | | ≥45 | | | ≥1.8 |
| 2 | ≤2 | ≤2 | 0-1 | 0-1.0 | ≤0.15 | | ≥15 | | ≥38 | |
| 3 | ≤5 | ≤2 | 0-1 | 0-1.0 | ≤0.15 | | ≥40 | | | |
| 4 | ≤3 | ≤2 | 4-6 | 0-1.5 | ≤0.15 | | | ≥40 | | |
| 5 | ≤7.5 | ≤2 | 2.5-6.0 | ≤2 | | ≤0.60 | ≥12 | ≥20 | | |
| 6A | ≤1.5 | ≤1.5 | 0-2 | 2.5-5.0 | | ≤0.50 | | | ≥15 | |
| 6B | ≤2 | ≤2 | 0-2 | 2.5-5.0 | | ≤0.50 | | | ≥15 | |
| 6C | ≤3 | ≤2 | | | | | | | | |
| 7C | ≤3 | ≤2 | | | | | | | | |
| 7F | ≤5 | ≤2 | 1.5-4.0 | 0-1.0 | ≤0.20 | | | | ≥13 | |
| 8 | ≤2 | ≤2 | 0-1 | 0-1.0 | ≤0.15 | | ≥25 | | | |
| 9N | ≤2 | ≤1 | 2.2-4 | 0-1.0 | ≤0.20 | | ≥20 | ≥28 | | |
| 9V | ≤2 | ≤2 | 0.5-3 | 0-1.0 | | ≤0.45 | ≥15 | ≥13 | | |
| 10A | ≤7 | ≤2 | 0.5-3.5 | 1.5-3.5 | | ≤0.65 | | ≥12 | | |
| 11A | ≤3 | ≤2 | 0-2.5 | 2.0-5.0 | | ≤0.40 | | | | ≥9 |
| 12F | ≤3 | ≤2 | 3-5 | 0-1.0 | ≤0.25 | | | ≥25 | | |
| 14 | ≤5 | ≤2 | 1.5-4 | 0-1.0 | ≤0.30 | | | ≥20 | | |
| 15A | ≤3 | ≤2 | | | | | | | | |
| 15B | ≤3 | ≤2 | 1-3 | 2.0-4.5 | | ≤0.55 | | ≥15 | | |
| 16F | ≤3 | ≤2 | | | | | | | | |
| 17F | ≤2 | ≤2 | 0-1.5 | 0-3.5 | | ≤0.45 | | | ≥20 | |
| 18C | ≤3 | ≤2 | 0-1 | 2.4-4.9 | ≤0.15 | | | | ≥14 | |
| 19A | ≤2 | ≤2 | 0.6-3.5 | 3.0-7.0 | ≤0.45 | | | ≥12 | ≥20 | |
| 19F | ≤3 | ≤2 | 1.4-3.5 | 3.0-5.5 | ≤0.20 | | | ≥12.5 | ≥20 | |
| 20 | ≤2 | ≤2 | 0.5-2.5 | 1.5-4.0 | | ≤0.60 | | ≥12 | | |
| 22F | ≤2 | ≤2 | 0-2 | 0-1.0 | | ≤0.55 | ≥15 | | ≥25 | |
| 23A | ≤3 | ≤2 | | | | | | | | |
| 23B | ≤3 | ≤2 | | | | | | | | |
| 23F | ≤2 | ≤2 | 0-1 | 3.0-4.5 | ≤0.15 | | | | ≥37 | |
| 24F | ≤3 | ≤2 | | | | | | | | |
| 31 | | | | | | | | | | |
| 33F | ≤2.5 | ≤2 | 0-2 | 0-1.0 | | ≤0.50 | | | | |
| 35B | ≤3 | ≤2 | | | | | | | | |
| 38 | ≤3 | ≤2 | | | | | | | | |

Values shown are percentage contents of components of monovalent bulk PS.

†The different types are indicated using the Danish nomenclature.

‡ Cross-linked agarose for chromatography R.

§ Cross-linked agarose for chromatography R1.

Example 4: Preparation of MAPS Immunogenic Complexes

Overview

The MAPS platform provides various advantages including, e.g., high affinity (dissociation constant [KD]≈$10^{-15}$M), non-covalent binding between biotin and rhizavidin, a biotin-binding protein that has no significant predicted homology with human proteins. Rhizavidin, a naturally occurring dimeric protein in the avidin protein family, was first discovered in *Rhizobium etli*, a symbiotic bacterium of the common bean. Rhizavidin has only 22% amino acid identity with chicken avidin, a protein commonly found in eggs, but with high conservation of amino acid residues involved in biotin binding. No cross-reactivity to rhizavidin was observed in human serum samples obtained from subjects exposed to avidin [Helppolainen et al, 2007], suggesting that rhizavidin antibodies may not cross-react with chicken avidin. Biotin conjugates have been used in several clinical applications without any reported adverse events [Buller et al, 2014; Paty et al, 2010; Lazzeri et al, 2004]. The biotinylation of the PS and MAPS immunogenic complexing process in MAPS24 were optimized to consistently show no free biotin, thus reducing the potential for generating anti-biotin antibodies.

MAPS vaccine candidates comprise genetically constructed fusion proteins of a biotin-binding moiety (e.g., rhizavidin, or a biotin-binding domain or biotin-binding fragment thereof), and a protein antigens of interest, which are then complexed with biotinylated PS of interest, leading to specific assembly into integrated macromolecular immunogenic complexes that, when processed by the immune system, result in the activation of protective B- and T-cell immune responses, as shown schematically in FIG. 1.

MAPS33 and MAPS34 are novel pneumococcal vaccine candidates based on the proprietary MAPS platform. MAPS34 is a 34-valent MAPS vaccine candidate comprising 34 pneumococcal capsular polysaccharides of serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 35B, and 38, individually biotinylated and complexed with either SPP2 or CP1 fusion protein. MAPS33 comprises 33 of the same 34 pneumococcal capsular polysaccharides as in MAPS34. In some embodiments, MAPS33 does not include pneumococcal capsular polysaccharide of scrotype 16F (i.e., MAPS33 comprises pneumococcal capsular polysaccharides of serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 35B, and 38). MAPS vaccine candidates comprising at least 30 (e.g., 30 [MAPS30], 31 [MAPS31], 32 [MAPS32]) of the same 34 pneumococcal capsular polysaccharides as in MAPS34 are also contemplated. MAPS30+ refers to any one of MAPS30, MAPS31, MAPS32, MAPS33 or MAPS34 pneumococcal vaccine candidates.

In some embodiments, an exemplary SPP2 comprises a genetic fusion construct of truncated rhizavidin plus pneumococcal proteins pneumolysin (with a combination of four amino acid substitutions as described herein, denoted PdT (G294P)) and SP0435, joined by linkers, as shown in FIG. 2. In some embodiments, an exemplary CP1 comprises a genetic fusion construct of truncated rhizavidin plus pneumococcal proteins SP1500 and SP0785 joined by linkers, as shown in FIG. 7. No available vaccines contain these unique combinations of PS and polypeptide antigens which are capable of eliciting an immune response against such a broad range of pneumococcal serotypes.

Assembly of MAPS Immunogenic Complexes

Drug substance (MAPS immunogenic complexes) comprises PS and CP1 and SPP2 fusion protein. In some embodiments, since the PS are biotinylated and CP1 and SPP2 fusion protein have a rhizavidin biotin-binding domain, they are linked by the high affinity biotin-rhizavidin interaction. MAPS immunogenic complexation was conducted individually for each PS serotype.

In some embodiments, each MAPS immunogenic complex was made from 2 key intermediates: PS of each of up to 34 *S. pneumoniae* serotypes, and rhizavidin fusion proteins CP1 or SPP2. PS of each serotype were activated, for example, by creation of a cyanate ester and then biotinylated. The biotinylated PS were mixed with CP1 or SPP2 fusion protein to create MAPS immunogenic complexes of defined PS serotype and fusion protein, linked by the high affinity biotin-rhizavidin interaction. MAPS immunogenic complexes of defined PS serotype and fusion protein are referred to as a species.

MAPS immunogenic complexes of each species were formulated with 150 mM sodium chloride and surfactant buffer, then 0.2 μm filtered immediately prior to bottling and storing at 2° C. to 8° C. Formulated MAPS immunogenic complexes of each species are referred to as MAPS drug substance.

No raw materials contained animal- or human-derived components.

Figure 10:
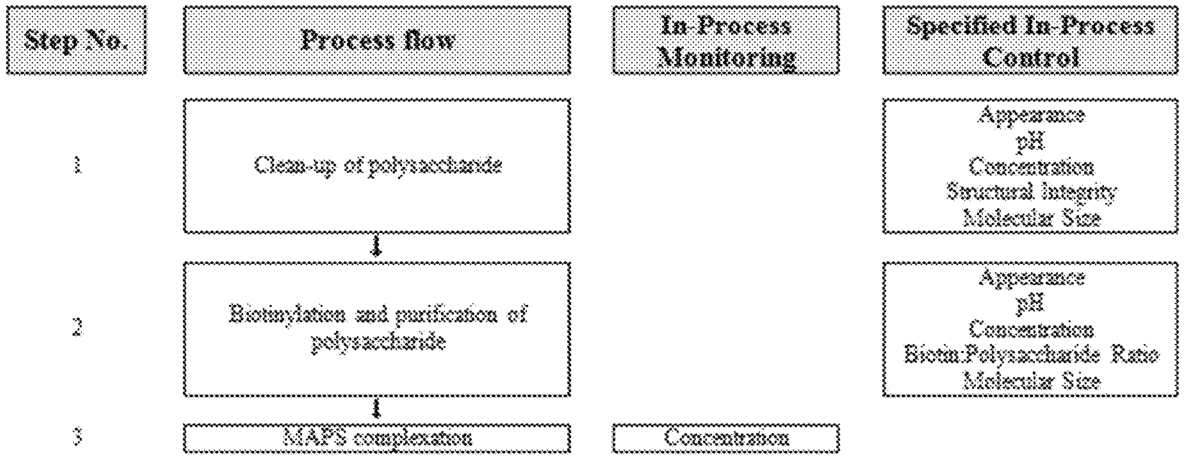
FIG. 10 is a flow-chart depicting an exemplary manufacturing process for MAPS immunogenic complexes, comprising biotinylation of antigenic polysaccharides and assembly with fusion protein(s) as described herein (e.g., CP1 or SPP2). MAPS: Multiple Antigen Presenting System.

A flow chart of a representative MAPS complexation process is provided in FIG. 10, and details for the individual steps follow.

Step 1: Clean-Up of Polysaccharide

The purpose of this step is to remove process residuals. Dissolved PS was purified by filtration then exchanged with several-fold volumes of water for injection, followed by ultra-filtration to concentrate the PS. The cleaned-up PS was filtered by a 0.22 μm filter membrane.

Step 2: Biotinylation and Purification of Polysaccharide

The hydroxyl group on the PS was activated with a 1-cyano-4-dimethylamino-pyridinium tetrafluoroborate (CDAP) to create a highly active cyanoester. The cyanoesters were reacted with amine-PEG3-biotin and unreacted cyanoesters were capped with glycine. The biotinylated PS was buffer exchanged into 1 mM PBS in order to remove unreacted CDAP, amine-PEG3-biotin, glycine and residuals. After buffer exchange, the biotinylated PS was filtered with a 0.22 μm filter.

Step 3: MAPS Immunogenic Complexation

The biotinylated PS was mixed with CP1 or SPP2 fusion protein in order to create the desired species of MAPS immunogenic complexes, linked by a high affinity biotin-rhizavidin interaction. The MAPS immunogenic complexes were purified to remove uncomplexed PS and protein by using a filtration membrane. After purification, the MAPS immunogenic complexes were filtered with a 0.22 μm filter and stored at 2° C. to 8° C.

Specifications

Exemplary MAPS immunogenic complex/MAPS drug substance specifications are set forth in Table 3.

TABLE 3

| Exemplary MAPS Drug Substance Specifications PS Serotype (1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38) | |
|---|---|
| Quality Attribute | Acceptance Criteria |
| Appearance | Clear, colorless, no particulate matter |
| pH | 5-7.5 |
| PS Identity | Positive |
| PS Concentration | >0.25 mg/mL |
| Protein Concentration | FIO |
| Free Protein | FIO |
| Free PS | <30% |
| Endotoxin | <1.25 × $10^{-2}$ EU/μg PS |
| Bioburden | ≤1 CFU/mL |

FIO: for information only; MAPS: multiple antigen-presenting system; PS: polysaccharide.

Example 5: MAPS33 and MAPS34 Vaccines-Exemplary MAPS30+ Vaccines

Drug Product

MAPS34 is a 34-valent MAPS vaccine candidate comprising 34 pneumococcal capsular polysaccharides of serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 35B, and 38, individually biotinylated and complexed with either SPP2 or CP1 fusion protein. MAPS33 comprises 33 of the same 34 pneumococcal capsular polysaccharides as in MAPS34. In some embodiments, MAPS33 does not include pneumococcal capsular polysaccharide of serotype 16F (i.e., MAPS33 comprises pneumococcal capsular polysaccharides of serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 35B, and 38). MAPS vaccine candidates comprising at least 30 (e.g., 30 [MAPS30], 31 [MAPS31], 32 [MAPS32]) of the same 34 pneumococcal capsular polysaccharides as in MAPS34 are also contemplated. MAPS30+ refers to any one of MAPS30, MAPS31, MAPS32, MAPS33, or MAPS34 pneumococcal vaccine candidates.

Figure 11:
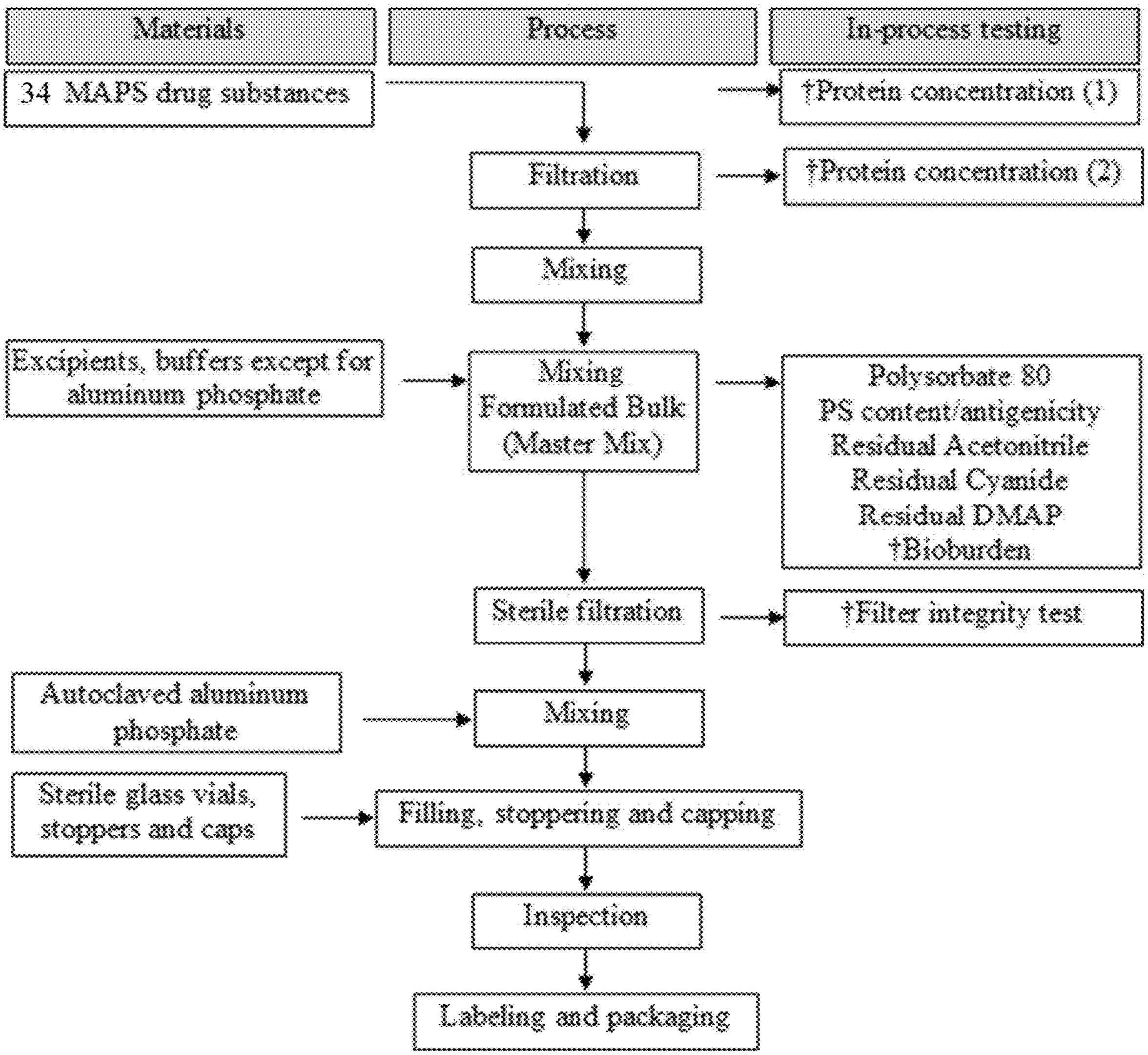
FIG. 11 is a flow-chart depicting exemplary manufacturing processes for a MAPS vaccine. For example, such exemplary processes can be used to manufacture a MAPS34 vaccine, comprising MAPS immunogenic complexes that comprise capsular polysaccharides from 34 different *S. pneumoniae* serotypes. DMAP: 4-Dimethylaminopyridine; MAPS: Multiple Antigen Presenting System; PS: polysaccharide. † In-process tests

In a representative formulation, a MAPS33 or MAPS34 vaccine candidate is formulated so that each 0.5-mL dose of MAPS33 or MAPS34 drug product comprises 1, 2 or 5 μg of each PS (for MAPS34, from each of *S. pneumoniae* serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 35B, and 38; and for MAPS33, from each of *S. pneumoniae* serotypes 1, 2, 3, 4, 5, 6A, 6B, 6C, 7C, 7F, 8, 9N, 9V, 10A, 11A, 12F, 14, 15A, 15B, 17F, 18C, 19A, 19F, 20B, 22F, 23A, 23B, 23F, 24F, 31, 35B, and 38) contributed by each species of MAPS immunogenic complex. MAPS33 or MAPS34 is formulated for IM administration with aluminum phosphate adjuvant. The total amount of aluminum per dose is 0.625 mg, which is below the FDA/WHO maximum recommended dose of 0.85 mg to 1.25 mg. FIG. 11 shows a representative scheme for MAPS33 or MAPS34 drug product manufacturing.

Example 6: Serotype Distribution Study

Figure 12:
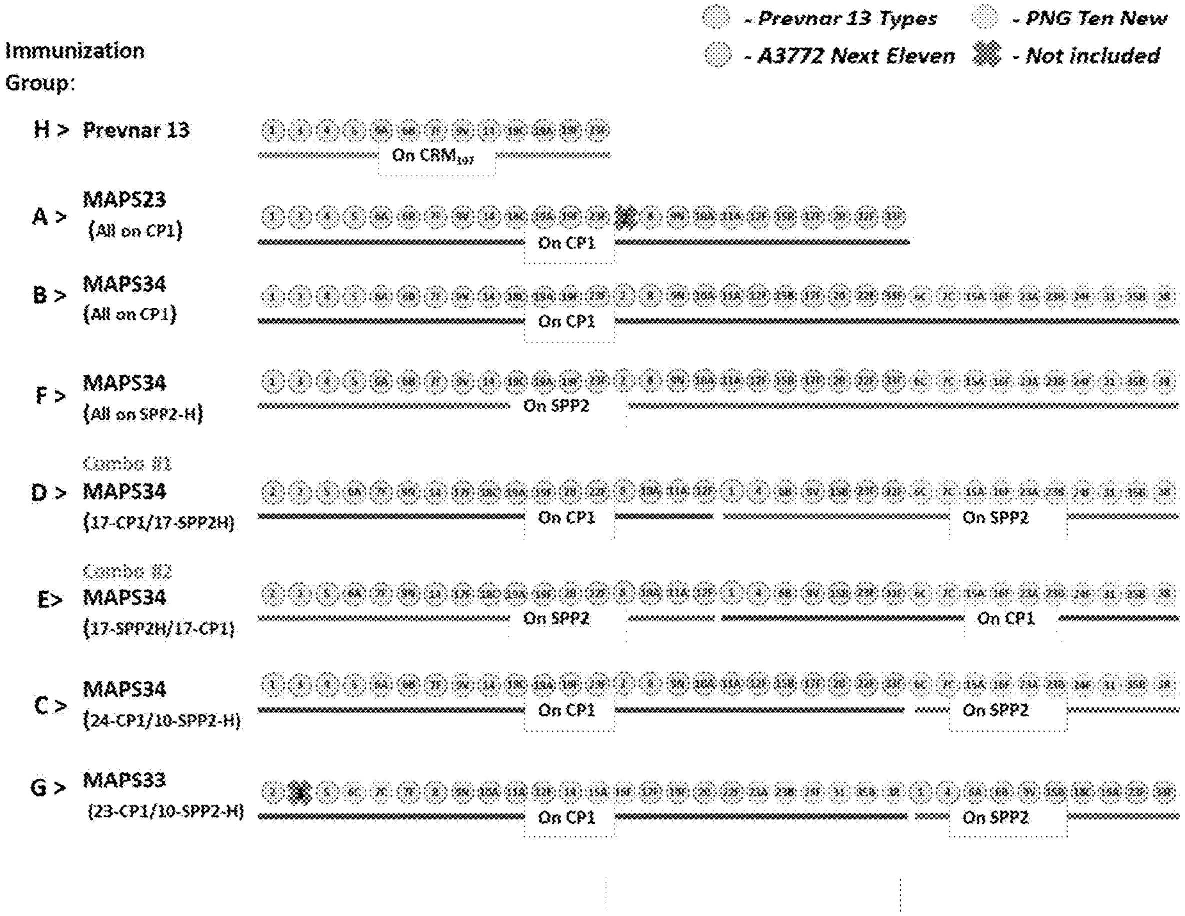
FIG. 12 is a schematic depicting various multi-valent vaccine candidates with different combinations of *S. pneumoniae* polysaccharides (serotypes) with antigenic fusion proteins CP1 and SPP2. The immunization group (A-H) corresponding to each vaccine candidate is indicated. While the figure illustrates certain multivalent vaccine candidates in a MAPS format as described herein, in some embodiments, such multivalent vaccine candidates can be provided in a conjugated format where a *S. pneumoniae* polysaccharide is covalently conjugated to an antigenic polypeptide and/or a fusion protein as described herein (e.g., CP1 and/or SPP2).

The goal of this study was to define the preferred combinations of *S. pneumoniae* polysaccharides (serotypes) with antigenic fusion proteins CP1 and SPP2, in order to optimize the immune response profile of 33- and 34-valent MAPS vaccine candidates. The vaccine candidates used in this study comprised different combinations of the *S. pneumoniae* polysaccharides and fusion proteins CP1 only, SPP2 only, or both SPP2 and CP1, as shown in FIG. 12.

Production of Rabbit Hyperimmune Sera

Hyperimmune sera were obtained using 8 groups of New Zealand White rabbits (Cocalico Biologicals). Groups A-F and H included 10 rabbits; group G included 5 rabbits. On Day 0, groups of rabbits were immunized intramuscularly according to Table 4 below. A second immunization was administered on Day 14. Serum was collected on Day 0 prior to first immunization (P0 serum), on Day 14 prior to second immunization (post-first immunization production bleed; P1 serum), and on Day 28 (post-second immunization production bleed; P2 serum).

TABLE 4

| Immunization Groups for Production of Rabbit Hyperimmune Sera | | |
|---|---|---|
| Group | Adjuvant | Buffer |
| A: 23 V MAPS CP1 1.2 μg dose | $AlPO_4$ | 0.625 mg/dose aluminum phosphate in 20 mM histidine, pH 5.5, 150 mM Sodium Chloride, 1 mM Sodium Phosphate monobasic, 0.02% Tween 80 |
| B: 34 V MAPS CP1 1.2 μg dose | $AlPO_4$ | 0.625 mg/dose aluminum phosphate in 20 mM histidine, pH 5.5, 150 mM Sodium Chloride, 1 mM Sodium Phosphate monobasic, 0.02% Tween 80 |
| C: 24 V MAPS CP1 10 V MAPS SPP2 1.2 μg dose | $AlPO_4$ | 0.625 mg/dose aluminum phosphate in 20 mM histidine, pH 5.5, 150 mM Sodium Chloride, 1 mM Sodium Phosphate monobasic, 0.02% Tween 80 |
| D: 17 V MAPS CP1 17 V MAPS SPP2 (Combo #1) 1.2 μg dose | $AlPO_4$ | 0.625 mg/dose aluminum phosphate in 20 mM histidine, pH 5.5, 150 mM Sodium Chloride, 1 mM Sodium Phosphate monobasic, 0.02% Tween 80 |
| E: 17 V MAPS SPP2 17 V MAPS CP1 (Combo #2) 1.2 μg dose | $AlPO_4$ | 0.625 mg/dose aluminum phosphate in 20 mM histidine, pH 5.5, 150 mM Sodium Chloride, 1 mM Sodium Phosphate monobasic, 0.02% Tween 80 |
| F: 34 V MAPS SPP2 1.2 μg dose | $AlPO_4$ | 0.625 mg/dose aluminum phosphate in 20 mM histidine, pH 5.5, 150 mM Sodium Chloride, 1 mM Sodium Phosphate monobasic, 0.02% Tween 80 |
| G: 23 V MAPS CP1 10 V MAPS SPP2 (MAPS-33) 1.2 μg dose | $AlPO_4$ | 0.625 mg/dose aluminum phosphate in 20 mM histidine, pH 5.5, 150 mM Sodium Chloride, 1 mM Sodium Phosphate monobasic, 0.02% Tween 80 |
| H: Prevnar 13 1.1 μg dose | $AlPO_4$ | 0.125 mg/dose aluminum phosphate, 590 μg/mL Succinate pH 5.5, 200 μg/mL Tween 80 |

IgG Responses to Proteins

To measure titers of rabbit IgG antibody against the *S. pneumoniae* portions of the fusion proteins CP1 and SPP2, an Enzyme-Linked Immunosorbent Assays (ELISA) specific for each fusion protein were performed. For CP1, IgG response was assessed against the SP1500-SP0785 fusion. For SPP2, IgG responses were separately assessed against PdT (G294P) and SP0435 proteins.

MaxiSorp 96-well plates (ThermoFisher Scientific, Waltham, MA, USA) were coated with 100 μl per well of 2.0 μg/ml SP1500-SP0785, or PdT (G294P), or SP0435 in 1× Dulbecco's phosphate-buffered saline (DPBS) overnight at room temperature. Plates were washed with 1×DPBS with 0.05% Tween 20 (DPBS-T) and then blocked with 200 μl per well of 1% BSA in DPBS-T for 1 hour. The plate was washed with 1×DPBS-T prior to the addition of rabbit sera for testing diluted in DPBS-T. Primary antisera dilutions were incubated for 1 hour at room temperature followed by washing with DPBS-T. Goat anti-rabbit IgG (Fc)-HRP (Jackson ImmunoResearch, West Grove, PA, USA) was diluted 1:100,000 and 100 μl added per well followed by a 1-hour incubation at room temperature. The plate was washed with DPBS-T and 100 μl of tetramethylbenzidine (TMB peroxidase substrate-KPL) was added per well and incubated for 30 minutes before stopping with 100 μl of 1 N HCl. The absorbance was read on a SpectraMax i3x at $OD_{450}$. Absorbance values were analyzed using SoftMax Pro and Microsoft Excel utilizing a 4-parameter logistic curve fit for a standard with known concentration. Geometric mean titers (GMTs) were calculated by transforming individual antibody titers to their logo concentrations, taking the means of the transformed concentrations from each animal group at each time point, and subsequently transforming those means to GMTs by taking their anti-log 10. The asymmetric 95% confidence intervals (CI) were calculated by the GraphPad Prism Software (version 7, La Jolla, CA, USA) together with the GMTs.

Figure 13:
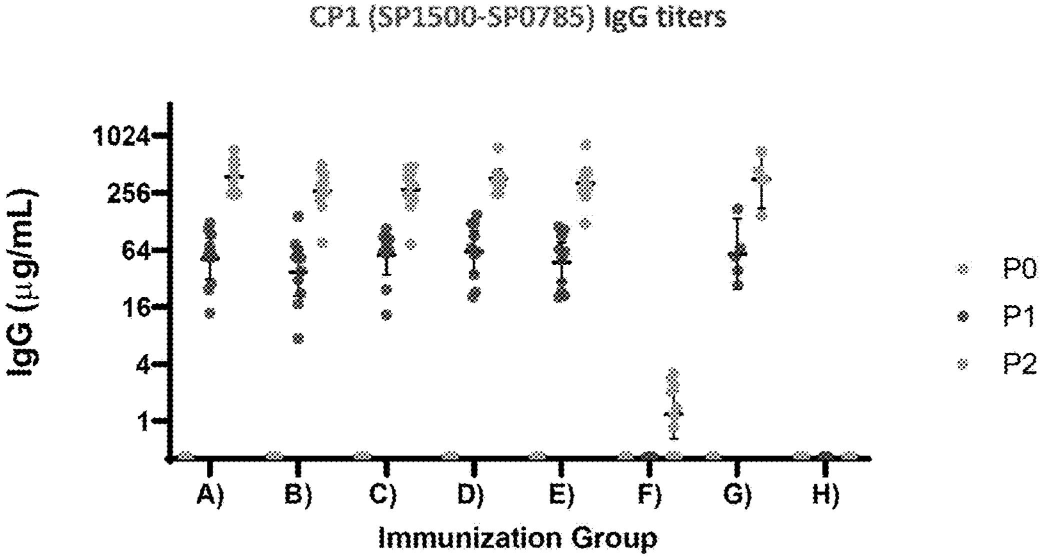
FIG. 13 shows representative IgG levels against CP1 fusion protein in P0, P1 and P2 rabbit sera from each of rabbit immunization groups A-H. Each dot on the graph represents one rabbit. Results are expressed in μg/ml with 95% confidence intervals on the graph and tabulated as geometric means (μg/ml) below the graph.
Figure 14:
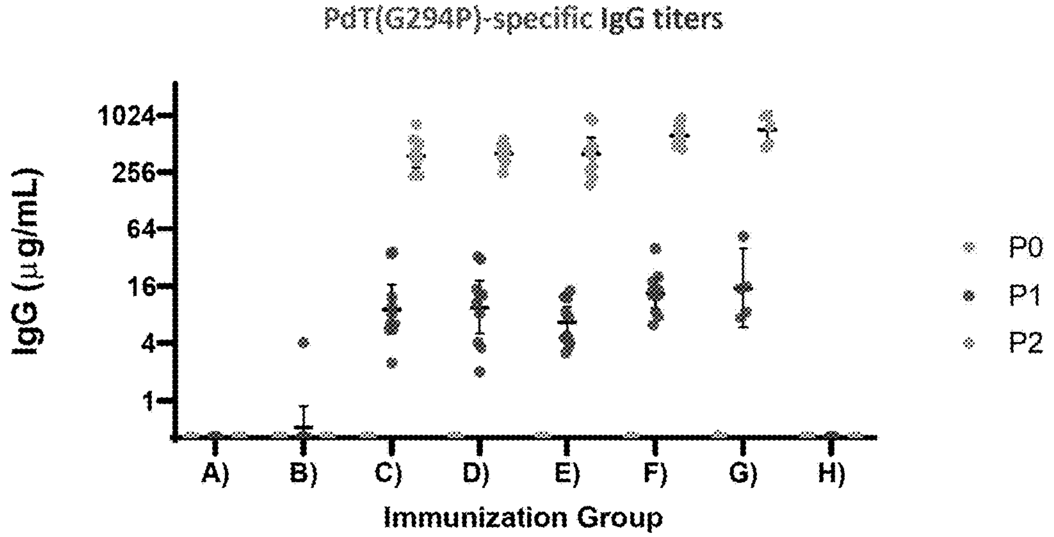
FIG. 14 shows representative IgG levels against the PdT (G294P) component of SPP2 fusion protein in P0, P1 and P2 rabbit sera from each of immunization groups A-H. Each dot on the graph represents one rabbit. Results are expressed in μg/ml with 95% confidence intervals on the graph and tabulated as geometric means (μg/ml) below the graph.
Figure 15:
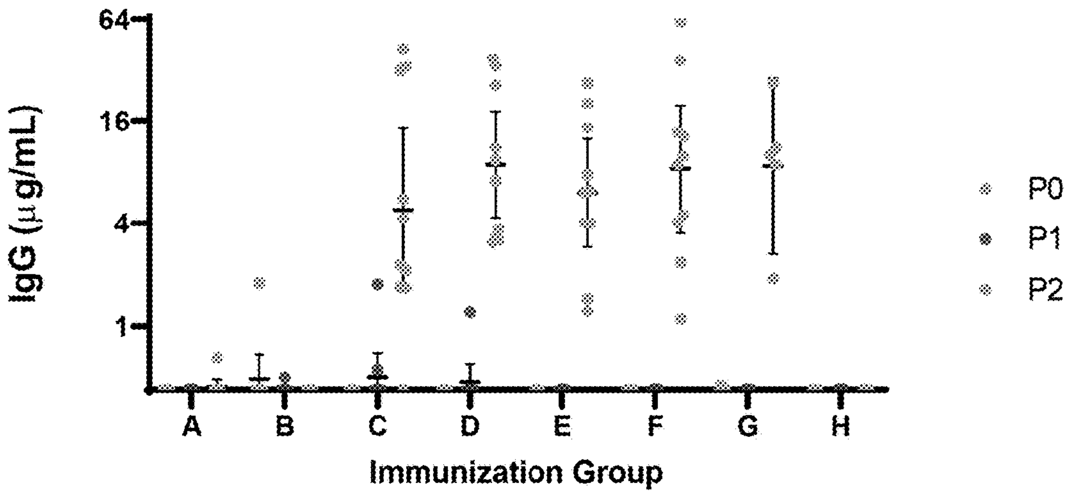
FIG. 15 shows representative IgG levels against the SP0435 component of SPP2 fusion protein in P0, P1 and P2 rabbit sera from each of immunization groups A-H. Each dot on the graph represents one rabbit. Results are expressed in μg/ml with 95% confidence intervals on the graph and tabulated as geometric means (μg/ml) below the graph.

Representative IgG levels against CP1, PdT (G294P), and SP0435 in P0, P1, and P2 rabbit sera from each of rabbit immunization groups A-H are shown in FIGS. 13-15. Immunization groups A-E and G, which all received MAPS-23, MAPS-33, or MAPS-34 vaccines comprising CP1, showed robust IgG responses to CP1 (FIG. 13). Immunization group F, which received MAPS-34 vaccine on fusion protein SPP2 only, showed background IgG levels against CP1; control immunization group H, which received Prevnar 13, showed no IgG response to CP1 (FIG. 13). Immunization groups C-G, which all received MAPS-33 or MAPS-34 vaccines comprising SPP2, showed robust IgG responses to PdT (G294P) (FIG. 14) and SP0435 (FIG. 15). Immunization groups A and B, which received MAPS-23 and MAPS-34 vaccines on fusion protein CP1 only, showed either no response or background IgG levels against PdT (G294P) and SP0435; control immunization group H, which received Prevnar 13, showed no IgG response to PdT (G294P) and SP0435 (FIGS. 14 and 15).

Neutralizing Antibody Responses to Proteins

Pneumolysin neutralization assays were performed to determine whether antibodies against fusion protein SPP2 (specifically, the PdT (G294P) portion of SPP2) are able to neutralize the hemolytic activity of native pneumolysin (red blood cell lysis). Briefly, 50 μl of a 200 ng/ml pneumolysin solution in 1×PBS, 0.1% bovine serum albumin and 10 mM dithiothreitol (DTT) was incubated with 50 μl of serum serial dilutions from rabbits in a V-bottom 96-microwell plate for 30 min at 37° C. with 5% $CO_2$ and shaking at 350 rpm. Following the initial incubation period, 50 μl of 2% rabbit red blood cells was added and incubated for an additional 30 min using the same conditions. After centrifugation at 1000×g for 5 min to pellet intact red blood cells, the supernatants were harvested and the absorbance at 545 nm was measured to quantify the extent of hemolysis. The absorbance was read on a SpectraMax i3× at OD545. Absorbance values were analyzed using SoftMax Pro and Microsoft Excel utilizing a 4-parameter logistic curve fit to determine the serum dilution at which 50% of the hemolytic activity of pneumolysin was inhibited (IC50). For samples that did not achieve 50% neutralization, the lowest dilution tested was recorded. Geometric mean titers (GMTs) were calculated by transforming individual IC50s to their $log_{10}$ concentrations, taking the means of the transformed concentrations from each animal group at each time point, and subsequently transforming those means to GMTs by taking their anti-log 10. The asymmetric 95% confidence intervals (CI) were calculated by the GraphPad Prism Software (version 7, La Jolla, CA, USA) together with the GMTs.

Figure 16:
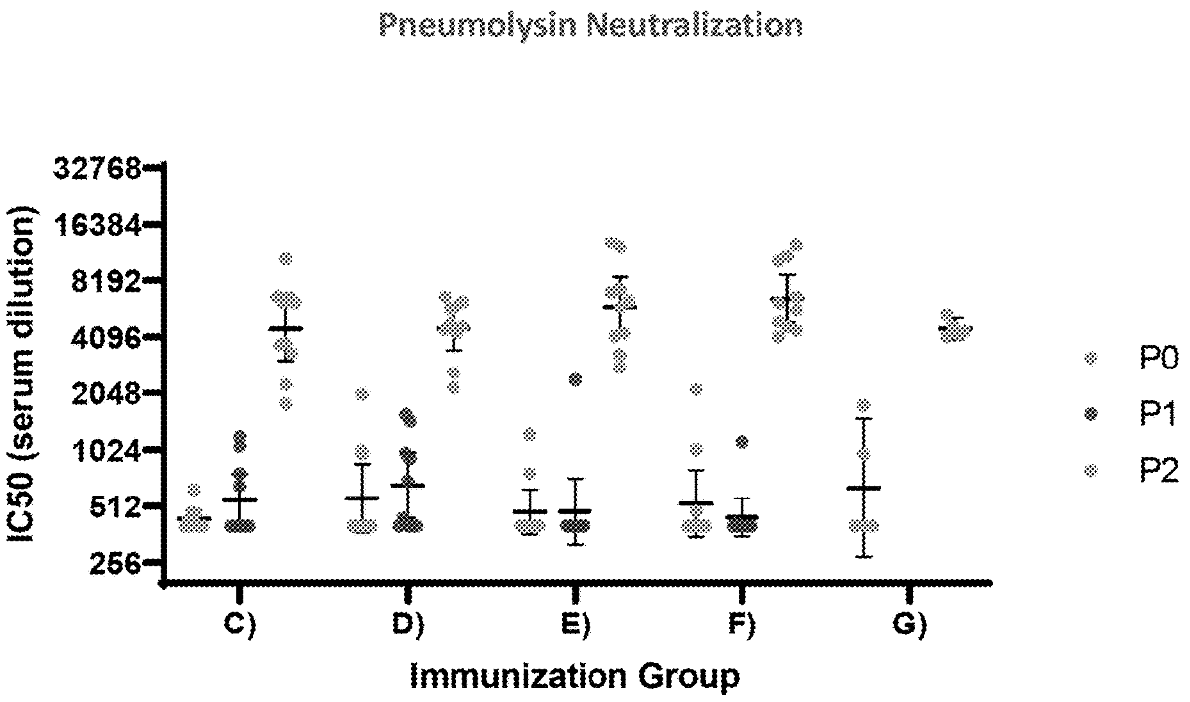
FIG. 16 shows representative half-maximal inhibitory concentration (IC50) of neutralizing antibodies against the hemolytic activity of native pneumolysin, in P0, P1 and P2 rabbit sera from each of immunization groups C-G. Each dot on the graph represents one rabbit. Results are expressed as the IC50 (serum dilution) with 95% confidence intervals on the graph and tabulated as geometric means (IC50) below the graph.

Representative titers of neutralizing antibodies against the hemolytic activity of native pneumolysin, in P0, P1 and P2 rabbit sera from each of immunization groups C-G are shown in FIG. 16. Immunization groups C-G, which all received MAPS-33 or MAPS-34 vaccines comprising SPP2, showed robust neutralizing antibody response against the hemolytic activity of pneumolysin.

IgG and Functional (OPA) Antibody Responses to S. *Pneumoniae* Polysaccharides

To evaluate IgG antibody levels specific for the 24 polysaccharide serotypes 1, 2, 3, 4, 5, 6A, 6B, 7F, 8, 9V, 9N, 10A, 11A, 12F, 14, 15B, 17F, 18C, 19A, 19F, 22F, 23F, and 33F in immunized rabbits, an electro-chemiluminescent-based Meso Scale Discovery immunoassay (MSD) was developed using a reference standard. Briefly, 5-fold serial dilutions were created starting with a ~1:200 dilution of the reference standard in PBS-T, 1% BSA, and 5 μg/mL CWPS. The control and experimental rabbit serum samples were diluted 1000-fold, 5000-fold, and 25000-fold with PBS-T, 1% BSA, and 5 μg/mL CWPS, respectively. Plates were washed with 1×PBS-T prior to adding the reference standard, control serum and experimental rabbit sera. After incubating at room temperature for one hour, plates were washed with PBS-T and secondary anti-rabbit SULFO-conjugated antibody was added. The plates were washed with PBS-T and 1× Read Buffer was added and the plates were read using an MSD Meso QuickPlex SQ 120 Model No. 1300. IgG antibody levels for the additional 10 polysaccharide serotypes 6C, 7C, 15A, 16F, 23A, 23B, 24F, 31, 35B, and 38 were determined using an MSD-based assay in end-point dilution format.

To evaluate functional (opsonophagocytic) antibody levels specific for the polysaccharide serotypes in immunized rabbits, a multiplex opsonophagocytic assay (MOPA) was used. The MOPA measures the level of serum antibodies specific to 4 *S. pneumoniae* capsular serotypes simultaneously in the same reaction. To do so, *S. pneumoniae* serotypes were selected and propagated based on their unique antibiotic resistance to 4 antibiotics (e.g., optochin, spectinomycin, streptomycin and trimethoprim). Heat-inactivated rabbit serum samples were serially diluted and mixed with *S. pneumoniae* bacteria organized in different cassettes (opsonization step). After an incubation period, complement (baby rabbit complement, BRC) and phagocytes (HL-60) were added to the reaction (complement-mediated phagocytosis step). After a second incubation period, an aliquot of the mixture was evaluated to determine the number of surviving bacteria using appropriate antibiotic-containing media. Titers of functional antibodies (OPA) were calculated per standard protocol.

In a first analysis, antibody levels were graphed as arbitrary units (a.u., for IgG) and titers (for functional antibodies) for comparison across all immunization groups. In another analysis, IgG levels measured in sera from each immunization group were compared pair-wise to a baseline and expressed as geometric mean titer ratios.

Figure 17A:
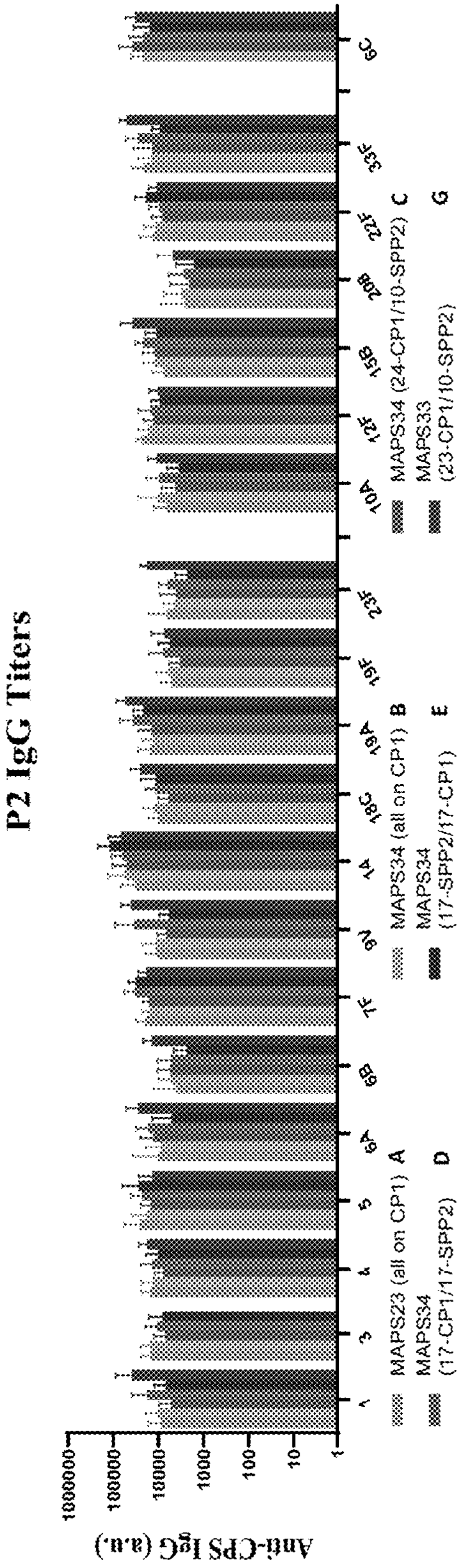
FIG. 17A shows representative IgG levels against 20 capsular polysaccharide (CPS) serotypes in P2 rabbit sera from each of immunization groups A-E and G. Results are expressed as IgG level in arbitrary units (a.u.) for comparison across the immunization groups.
Figure 17B:
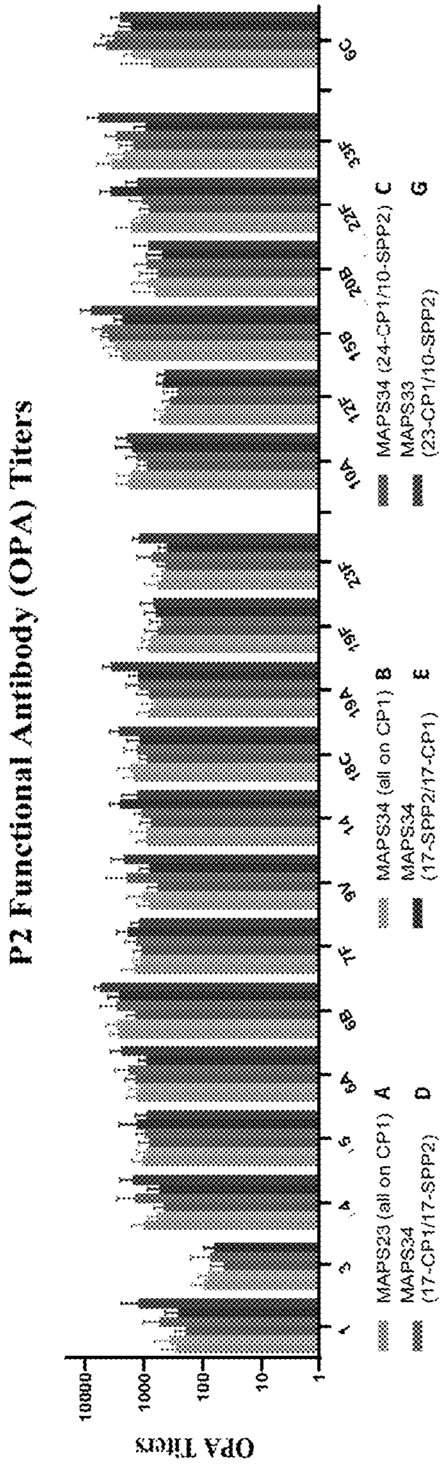
FIG. 17B shows representative functional antibody (OPA) levels against 20 capsular polysaccharide (CPS) serotypes in P2 rabbit sera from each of immunization groups A-E and G. Results are expressed as OPA titers for comparison across the immunization groups.

Results for IgG and Functional Antibody Levels Across Multiple Immunization Groups Representative IgG levels and functional antibody (OPA) levels against 20 capsular polysaccharide (CPS) serotypes, in P2 rabbit sera form each of immunization groups A-E and G are shown in FIGS. 17A and 17B. A trend towards higher IgG levels (FIG. 17A) and higher functional antibody levels (FIG. 17B) against polysaccharides of serotype 1, 6A, 6B, 9V, 15B, 18C, 19A, 23F, and 33F was observed in immunization group G (MAPS-33 on CP1 and SPP2). In this vaccine formulation, the above-listed serotypes (i.e., serotypes 1, 6A, 6B, 9V, 15B, 18C, 19A, 23F, and 33F) were all presented in MAPS complexes on SPP2 (FIG. 12). (For serotype 4, also presented on SPP2, the levels of IgG and functional antibody titers were equivalent across all groups.)

Results for Pair-Wise Comparisons of IgG Levels

For each comparison, IgG levels against *S. pneumoniae* polysaccharides were expressed as geometric mean titer (GMT) ratio at 95% confidence interval, relative to a baseline represented as a dotted line at GMT ratio of 1. If the point estimate of the GMT ratio >1, then anti-polysaccharide antibody levels for a given immunization group are higher. If the point estimate of the GMT ratio <1, then anti-polysaccharide antibody levels for a given immunization group are lower.

Figure 19:
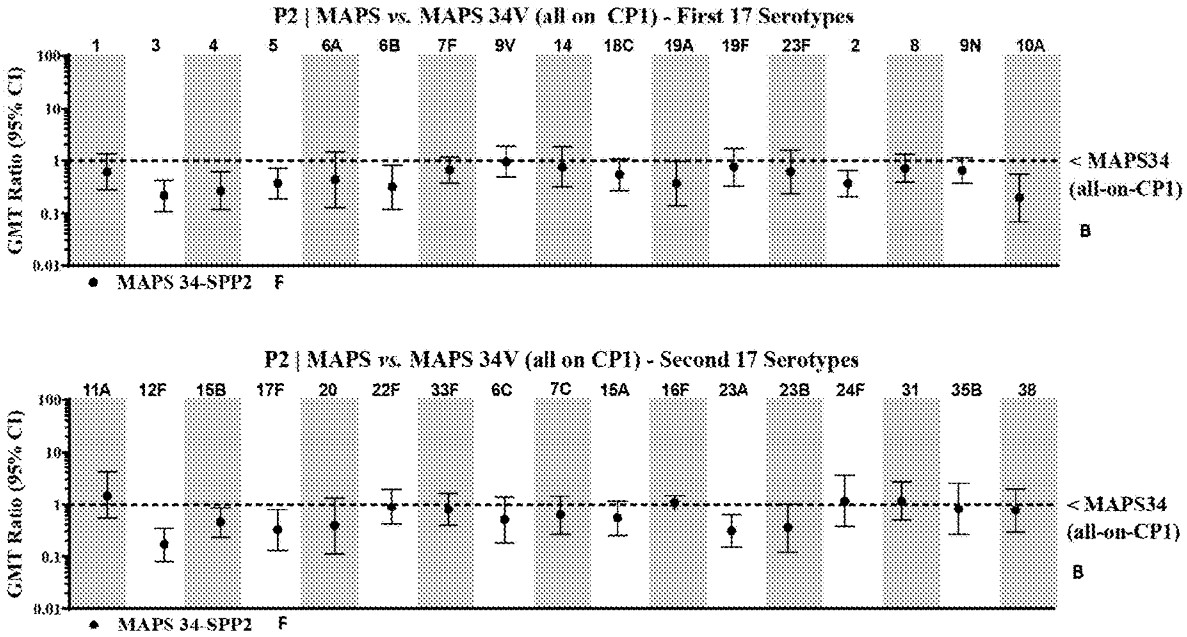
FIG. 19 shows relative antibody titers against capsular polysaccharides of various serotypes for MAPS-34 all-on-SPP2 (immunization group F) compared to a baseline of MAPS-34 all-on-CP1 (immunization group B, dotted line) in P2 rabbit sera. The upper graph shows results for the first 17 serotypes of MAPS-34, and the lower graph shows results for the next 17 serotypes, as shown graphically in FIG. 12. Geometric mean titer (GMT) ratio and 95% confidence intervals are shown on the graph.
Figure 20:
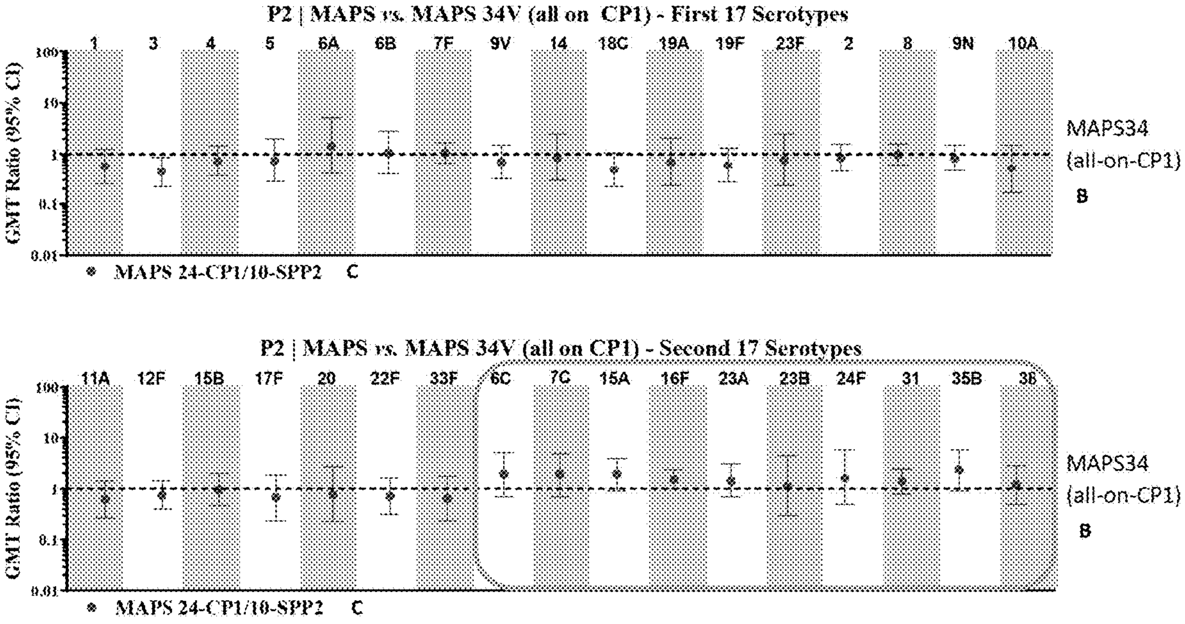
FIG. 20 shows relative antibody titers against capsular polysaccharides of various serotypes for MAPS-34 on CP1 and SPP2 (immunization group C) compared to a baseline of MAPS-34 all-on-CP1 (immunization group B, dotted line) in P2 rabbit sera. The upper graph shows results for the first 17 serotypes of MAPS-34, and the lower graph shows results for the next 17 serotypes, as shown graphically in FIG. 12. Geometric mean titer (GMT) ratio and 95% confidence intervals are shown on the graph. For MAPS-34 on CP1 and SPP2 (immunization group C), the boxed subset of polysaccharides are present in MAPS complexes on SPP2.

Representative IgG levels against *S. pneumoniae* polysaccharides of various serotypes for pair-wise comparisons of immunization groups are shown in FIGS. 18-24. The results show a slight trend towards decreased antibody responses to the tested *S. pneumoniae* polysaccharides with increased valency (34 vs. 23 serotypes) (FIG. 18). Further, MAPS-34 all-on-SPP2 (immunization group F) yielded an overall lower antibody response than MAPS-34 all-on-CP1 (immunization group B) (FIGS. 18 and 19). However, when MAPS-34 all-on-CP1 (immunization group B) is compared to MAPS-34 on CP1 and SPP2 (immunization group C), in which a subset of the serotypes are in MAPS complexes with SPP2 as opposed to CP1, it was unexpected to observe a trend towards increased antibody responses for the subset of *S. pneumoniae* polysaccharides (i.e., serotypes 6C, 7C, 15A, 16F, 23A, 23B, 24F, 31, 35B, and 38) (FIG. 20). These unexpected results suggest that for a given set of serotypes, presenting a subset of the serotypes in MAPS complexes comprising SPP2 and presenting the remaining serotypes in MAPS complexes comprising CP1, can enhance antibody responses relative to presenting all serotypes in MAPS complexes comprising a single fusion protein.

Figure 21:
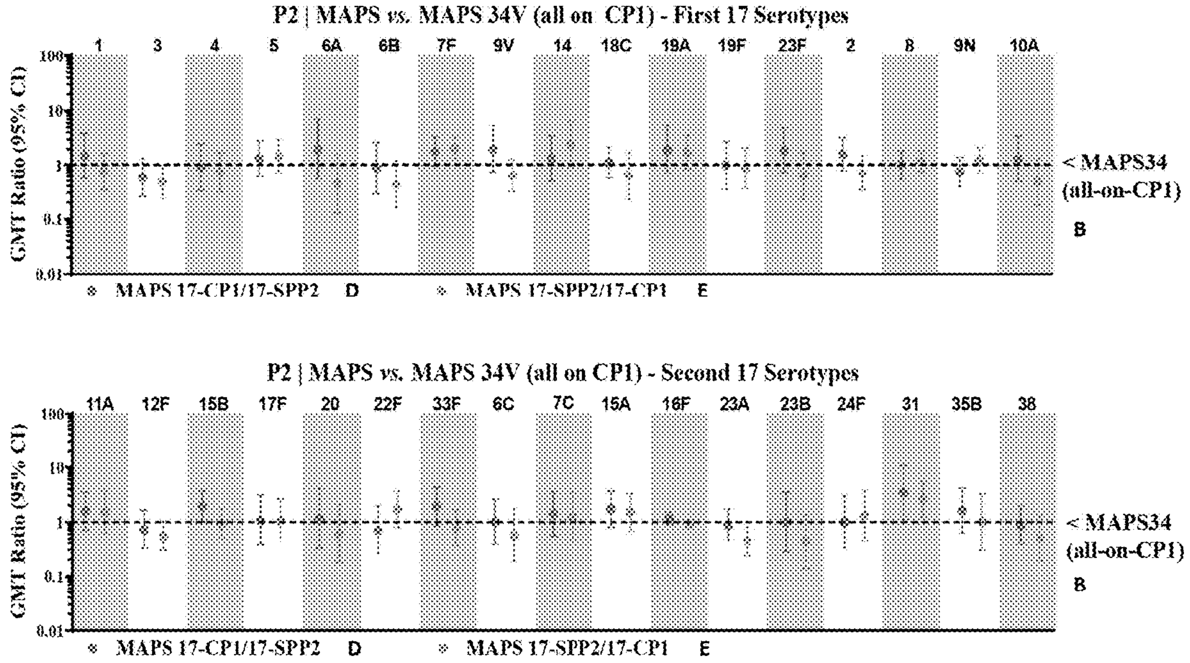
FIG. 21 shows relative antibody titers against capsular polysaccharides of various serotypes for both MAPS-34 on CP1 and SPP2 (Combo #1, immunization group D, gray dot) and MAPS-34 on SPP2 and CP1 (Combo #2, immunization group E, black dot) compared to a baseline of MAPS-34 all-on-CP1 (immunization group B, dotted line) in P2 rabbit sera. The upper graph shows results for the first 17 serotypes of MAPS-34, and the lower graph shows results for the next 17 serotypes, as shown graphically in FIG. 12. Geometric mean titer (GMT) ratio and 95% confidence intervals are shown on the graph.
Figure 22:
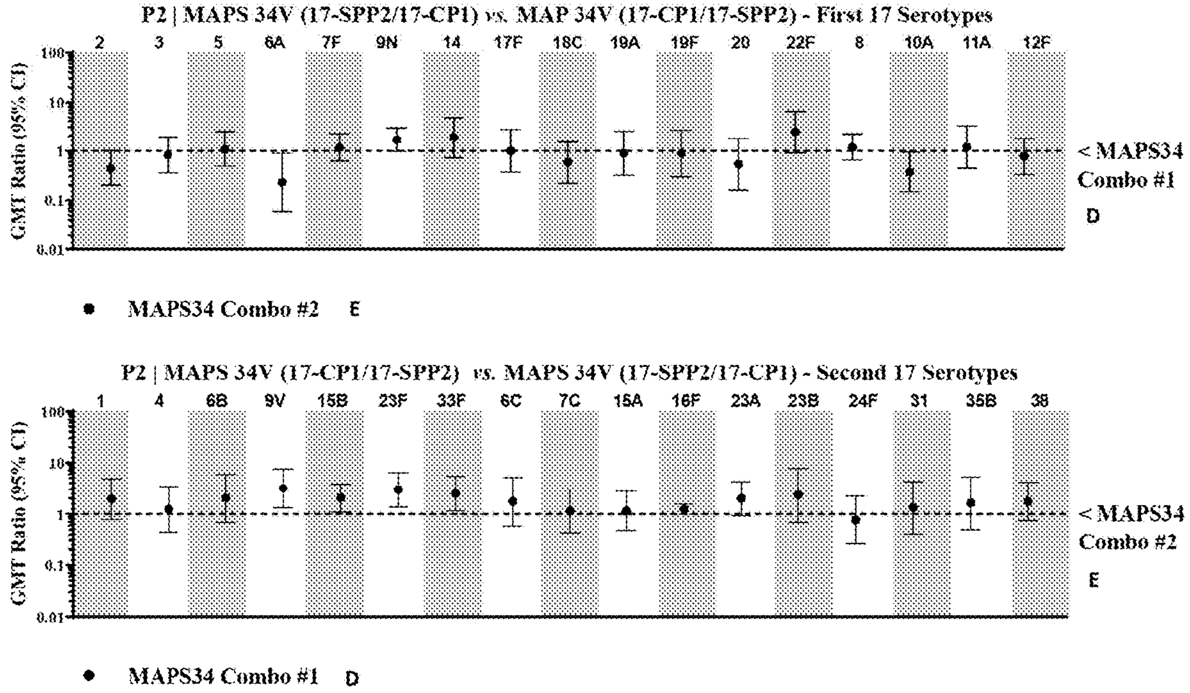
FIG. 22 shows relative antibody titers against capsular polysaccharides of various serotypes for MAPS-34 on CP1 and SPP2 (Combo #1, immunization group D) compared to MAPS-34 on SPP2 and CP1 (Combo #2, immunization group E) in P2 rabbit sera. The upper graph shows results comparing Combo #2 (on SPP2) to Combo #1 (on CP1) for the first 17 serotypes of MAPS-34, as shown graphically in FIG. 12. The lower graph shows results comparing Combo #1 (on SPP2) to Combo #2 (on CP1) for the next 17 serotypes of MAPS-34, as shown graphically in FIG. 12. Geometric mean titer (GMT) ratio and 95% confidence intervals are shown on the graph.
Figure 23:
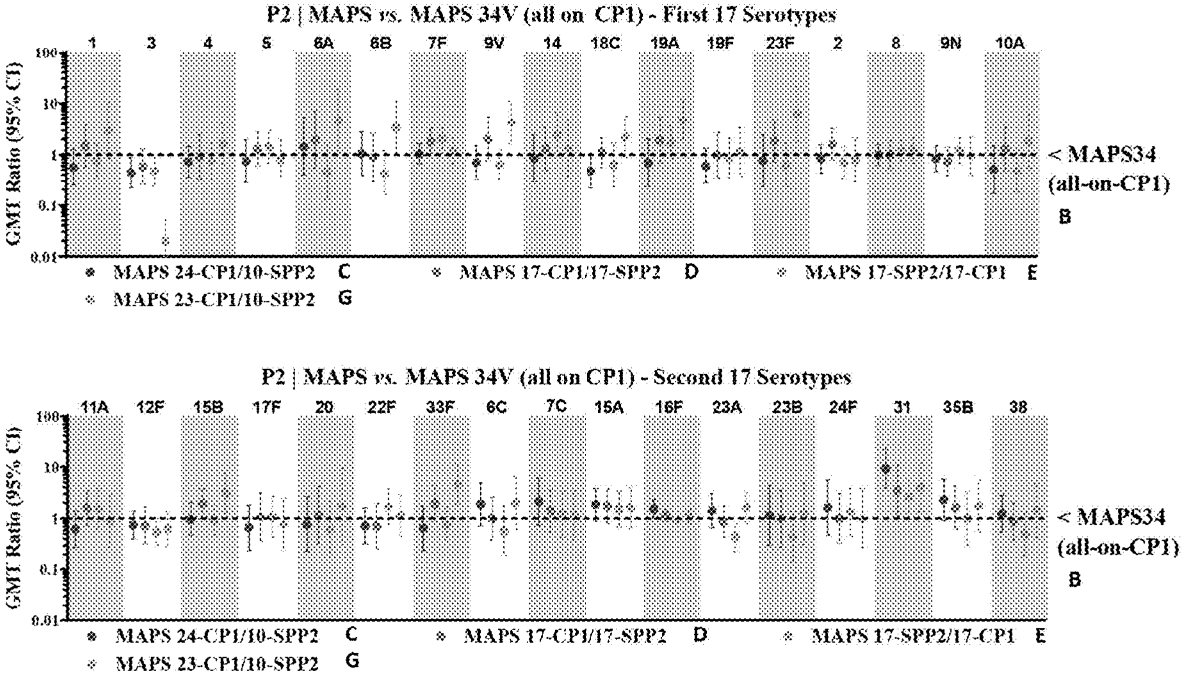
FIG. 23 shows relative antibody titers against capsular polysaccharides of various serotypes for MAPS-34 on CP1 and SPP2 (immunization group C), MAPS-34 on CP1 and SPP2 (Combo #1, immunization group D), MAPS-34 on SPP2 and CP1 (Combo #2, immunization group E), and MAPS-33 on CP1 and SPP2 (immunization group G) compared to a baseline of MAPS-34 all-on-CP1 (immunization group B). The upper graph shows results for the first 17 serotypes of MAPS-34 and the lower graph shows results for the next 17 serotypes. Geometric mean titer (GMT) ratio and 95% confidence intervals are shown on the graph.
Figure 24:
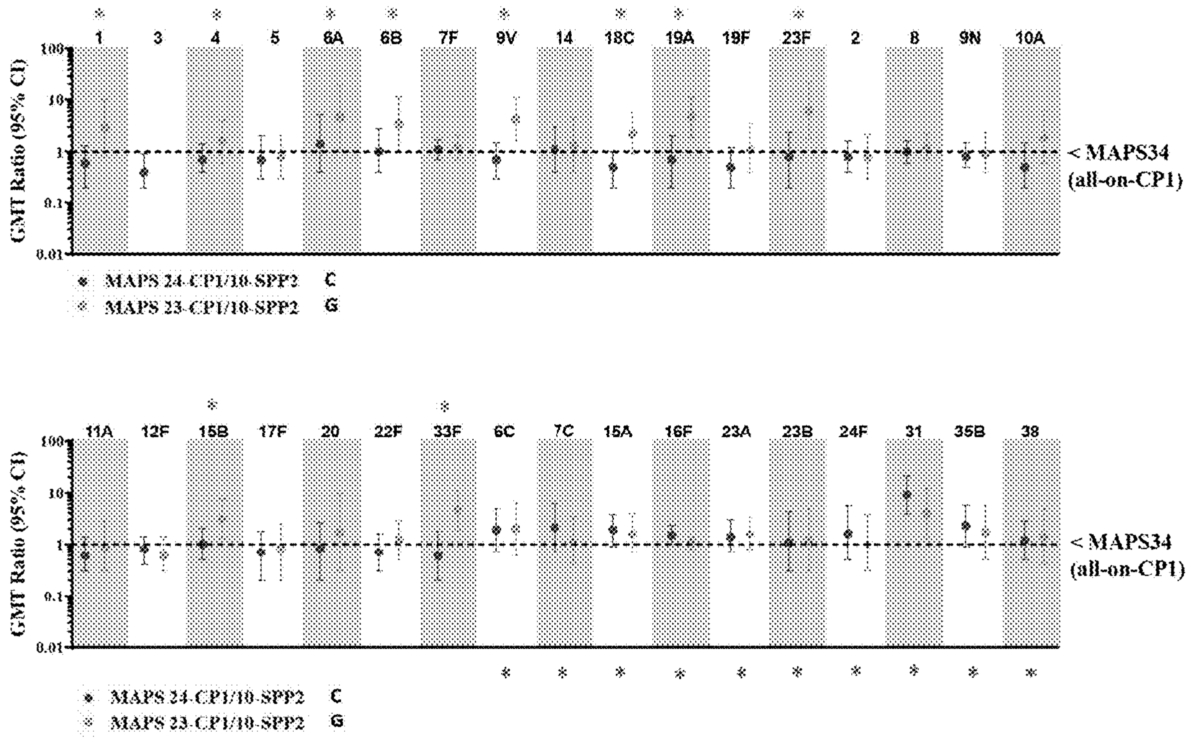
FIG. 24 is based on the same data as FIG. 23, but shows only the comparison of MAPS-34 on CP1 and SPP2 (immunization group C) and MAPS-33 on CP1 and SPP2 (immunization group G) compared to a baseline of MAPS-34 all-on-CP1 (immunization group B) in P2 rabbit sera. The upper graph shows results for the first 17 serotypes of MAPS-34 and the lower graph shows results for the next 17 serotypes. Geometric mean titer (GMT) ratio and 95% confidence intervals are shown on the graph. The star symbol denotes polysaccharides that are presented in MAPS complexes comprising SPP2 for immunization group C (below the graph) or immunization group G (above the graph).

To evaluate whether particular serotypes favored presentation in MAPS complexes comprising SPP2 or in MAPS complexes comprising CP1, IgG levels against *S. pneumoniae* polysaccharides of various serotypes for MAPS-34 on CP1 and SPP2 (Combo #1, immunization group D) and MAPS-34 on SPP2 and CP1 (Combo #2, immunization group E) were examined. The results show a trend towards overall increased antibody responses for MAPS-34 Combo #1, compared to both MAPS-34 Combo #2 and MAPS-34 all-on-CP1 (FIG. 21). For most serotypes, the antibody response when the polysaccharide is present in MAPS complexes comprising SPP2 was observed to be similar as when the polysaccharide is present in MAPS complexes comprising CP1 (FIG. 22). However, unexpectedly, several serotypes appeared to favor presentation in MAPS complexes comprising either SPP2 or CP1. In particular, serotypes 1, 6B, 9V, 15B, 22F, 23A, 23B, 23F, 33F and potentially 14 appear to favor presentation in MAPS complexes comprising SPP2; and serotypes 2, 6A, 10A, 18C and 20B appear to favor presentation in MAPS complexes comprising CP1 (FIG. 22). Taken together, these results suggest that certain *S. pneumoniae* polysaccharides elicit greater immune responses when presented in MAPS complexes comprising SPP2 rather than CP1, and vice-versa.

Example 7: Active Immunization and Sepsis Challenge I

The objective of this study was to test immunogenicity and protection against lethal *Streptococcus pneumoniae* sepsis challenge in a mouse model, following immunization with vaccines comprising isolated proteins SPP2, or SPP2 plus CP1, or with vaccines comprising SPP2 plus CP1 both in MAPS complexes with *Streptococcus pneumoniae* polysaccharide PS1. Control groups were immunized with isolated protein Rhavi (negative control) or with Prevnar 13 (positive control). Vaccines were adjuvanted with Aluminum Phosphate. SPP2 is described in Example 1. CP1 is a fusion protein comprising rhizavidin residues 45-179 (denoted Rhavi), *S. pneumoniae* protein SP1500, and *S. pneumoniae* hypothetical protein SP0785, with each of the three domains separated by a linker. Optionally, CP1 includes His tags. See WO2020/056127 and WO2020/056202 for detailed description of CP1 and MAPS complexes.

Methods

The vaccines formulations examined in this study are provided below. The total volume prepared for each vaccine was 2.4 mL, which is sufficient for 10 doses of 0.2 mL each.

| | |
|---|---|
| **A: Rhavi (5 μg/dose) + AlPO4 (0.250 mg/dose)** | |
| 1685.2 μl | Sterile Water |
| 24.0 μl | 0.1M Phosphate, pH 5.8 (1 mM, final) |
| 71.4 μl | 5M Sodium Chloride (150 mM final) |
| 600.0 μl | 5 mg/ml AdjuPhos, Aluminum Phosphate (1.25 mg/ml, final) |
| 19.4 μl | Rhavi, protein conc. 25 μg/ml final |
| 2400.0 μl | Final Volume |
| **B: Prevnar 13 (0.88 μg/PS/dose)** | |
| 2400.0 μl | 0.88 μg/PS, 0.2 ml of undiluted Prevnar 13 per mouse |
| 2400.0 μl | Final Volume |
| **C: SPP2 (15 μg/dose) + AlPO4 (0.250 mg/dose)** | |
| 1393.3 μl | Sterile Water |
| 24.0 μl | 0.1M Phosphate, pH 5.8 (1 mM, final) |
| 62.4 μl | 5M Sodium Chloride (150 mM final) |
| 600.0 μl | 5 mg/ml AdjuPhos, Aluminum Phosphate (1.25 mg/ml, final) |
| 320.3 μl | SPP2, protein conc. 75 μg/ml final |
| 2400.0 μl | Final Volume |
| **D: CP1 (15 μg/dose) + SPP2 (15 μg/dose) + AlPO4 (0.250 mg/dose)** | |
| 1351.2 μl | Sterile Water |
| 24.0 μl | 0.1M Phosphate, pH 5.8 (1 mM, final) |
| 61.1 μl | 5M Sodium Chloride (150 mM final) |
| 600.0 μl | 5 mg/ml AdjuPhos, Aluminum Phosphate (1.25 mg/ml, final) |
| 320.3 μl | SPP2, protein conc. 75 μg/ml final |
| 43.4 μl | CP1, protein conc. 75 μg/ml final |
| 2400.0 μl | Final Volume |
| **E: PS1.CP1 (15 μg/dose) + PS1.SPP2 (15 μg/dose) + AlPO4 (0.250 mg/dose)** | |
| 657.6 μl | Sterile Water |
| 24.0 μl | 0.1M Phosphate, pH 5.8 (1 mM, final) |
| 39.6 μl | 5M Sodium Chloride (150 mM final) |
| 600.0 μl | 5 mg/ml AdjuPhos, Aluminum Phosphate (1.25 mg/ml, final) |
| 652.2 μl | PS1.SPP2 (MAPS complexes: protein conc. 75 μg/ml final) |
| 426.5 μl | PS1.CP1 (MAPS complexes: protein conc. 75 μg/ml final) |
| 2400.0 μl | Final Volume |

The study was conducted using 5 groups each with 10 wild type C57BL/6 mice (Charles River labs). All procedures involving mice were approved by the Mispro Biotech Animal Care and Use Committee (IACUC protocol no. 2018 May 1-AF2), following the National Institutes of Health guidelines for animal housing and care. On Day 0 of the study, groups of 10 mice were immunized subcutaneously according to Table 5 below. A first booster dose was administered on Day 14. A second booster dose was administered on Day 28. Blood was collected on Day 42 and immunogenicity was assessed by ELISA.

TABLE 5

Immunization Groups for Study 006

| Vaccine | AlPO4 adjuvant conc. (mg/ml) | Adjuvant dose (μg) | Immunogen dose | Dose volume |
|---|---|---|---|---|
| A. Rhavi | 1.25 | 250 | 5 μg Rhavi | 0.2 mL s.c. |
| B. Prevnar 13 | 0.25 | 50 | 200 μl undiluted (2/5th of human dose; 0.88 μg/PS) | 0.2 mL s.c. |
| C. SPP2 (protein) | 1.25 | 250 | 15 μg SPP2 | 0.2 mL s.c. |
| D. SPP2 + CP1 (proteins) | 1.25 | 250 | 15 μg each protein | 0.2 mL s.c. |
| E. PS1.SPP2 + PS1.CP1 (MAPS complexes) | 1.25 | 250 | 15 μg each protein | 0.2 mL s.c |

On Day 49 following first immunization, mice were inoculated in the intraperitoneal (IP) cavity with a 3×10^4 CFU/mouse target dose of *S. pneumoniae* AR003 (serotype 3 strain) in 0.2 mL 1× saline. Mice were monitored for any signs of illness following challenge with *S. pneumoniae*; any ill-appearing animal (e.g., presenting with signs of ruffled fur, slow moving, and/or with closed eyes) was immediately and humanely euthanized. Following the IP challenge, a daily body weight and twice daily observations were gathered from all mice on Days 50-63 (i.e., days 1-14 post-challenge). The study was concluded on Day 63 (i.e., day 14 post-challenge) with all remaining mice being humanely sacrificed.

Results

Figure 25:
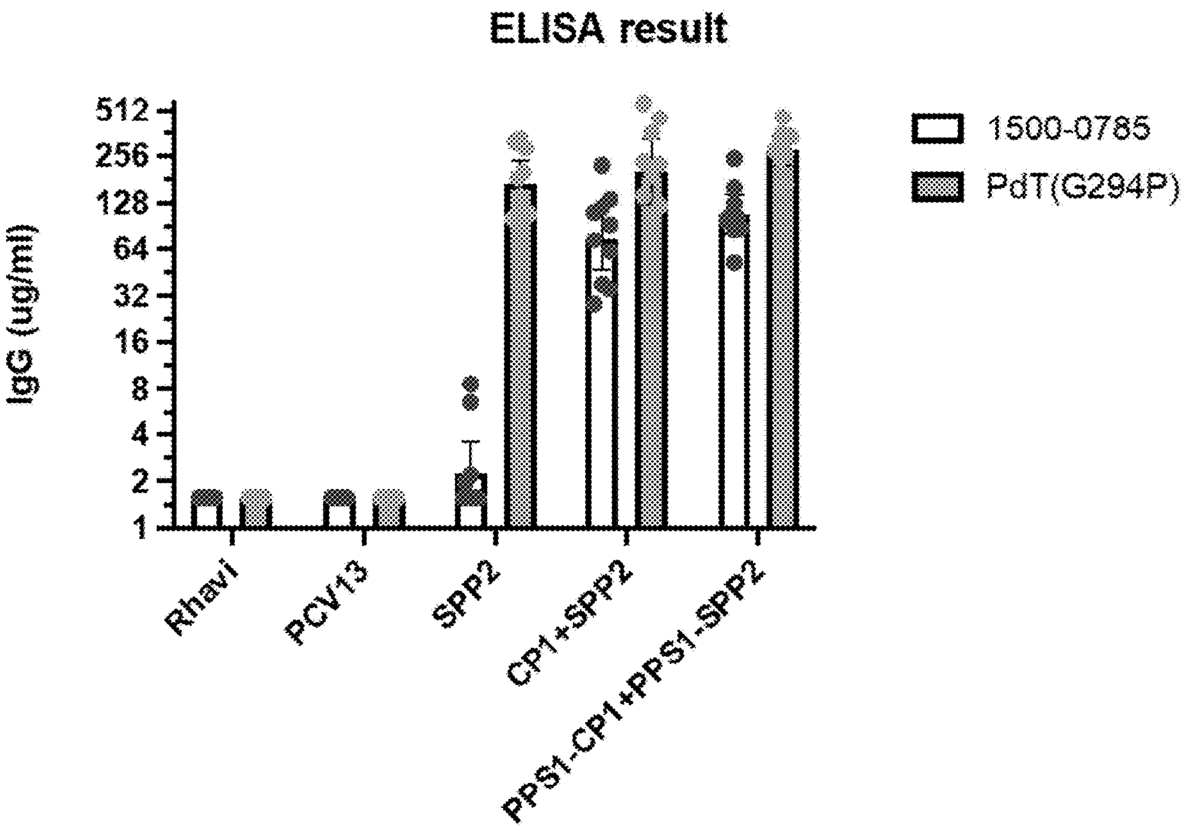
FIG. 25 shows total IgG levels against SP1500-SP0785 and PdT (G294P) for mice immunized with vaccines comprising isolated proteins SPP2, or SPP2 plus CP1, or with vaccines comprising SPP2 plus CP1 both in MAPS complexes with *Streptococcus pneumoniae* polysaccharide PS1 (PPS1). Mice immunized with rhizavidin polypeptide (Rhavi) and PCV13 are shown as controls. Each dot on the graph represents an individual mouse. Geometric mean titer and 95% confidence intervals are shown on the graph.

Mouse sera collected on Day 42 of the study were analyzed by ELISA against PdT (G294P) and SP1500-SP0785, which are components of SPP2 and CP1, respectively. Comparable specific IgG titers against PdT (G294P) were raised in mice immunized with vaccines comprising isolated proteins SPP2, or SPP2 plus CP1, or with vaccines comprising SPP2 plus CP1 both in MAPS complexes (FIG. 25). The addition of CP1 to SPP2 was not observed to significantly impact IgG titers against PdT (G294P).

Figure 26:
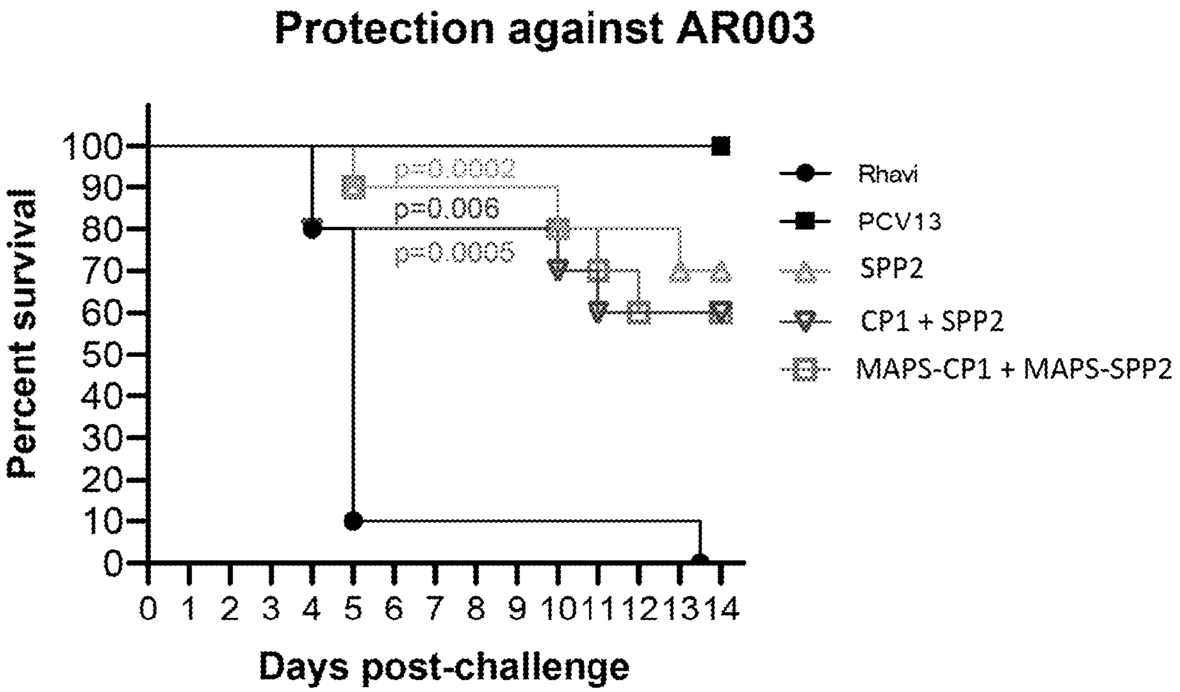
FIG. 26 shows percent survival at indicated time points for groups of mice immunized with vaccines comprising isolated proteins SPP2, or SPP2 plus CP1, or with vaccines comprising SPP2 plus CP1 both in MAPS complexes with *Streptococcus pneumoniae* polysaccharide PS1, and challenged with *S. pneumoniae* strain AR003. Mice immunized with Rhavi and Prevnar 13 (PCV13) are shown as negative and positive controls, respectively.
Figure 27:
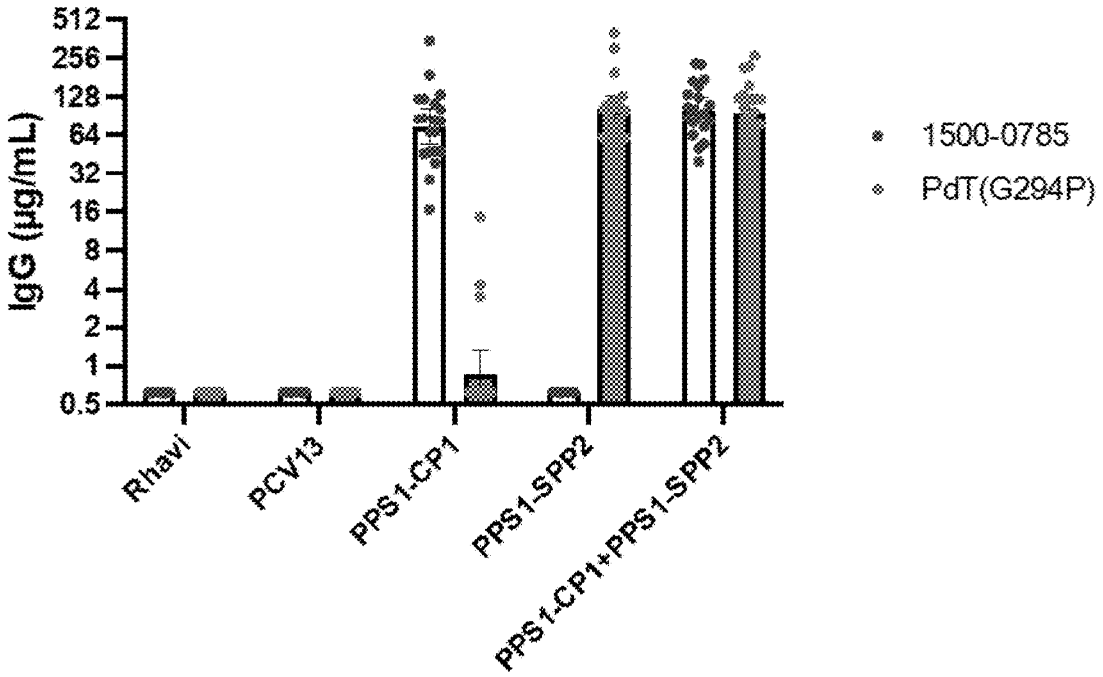
FIG. 27 shows total IgG levels against SP1500-SP0785 and PdT (G294P) for mice immunized with vaccines comprising CP1, SPP2, or CP1 plus SPP2, all in MAPS complexes with *Streptococcus pneumoniae* polysaccharide PS1 (PPS1). Mice immunized with Rhavi and PCV13 are shown as controls. Each dot on the graph represents an individual mouse. Geometric mean titer and 95% confidence intervals are shown on the graph.

Percent survival for each group of immunized mice was examined at time points after challenge with *S. pneumoniae* (FIG. 26). Statistical analysis for survival rates was performed using the log-rank (Mantel-Cox) test. By day 14 post-challenge, surprisingly, mice immunized with vaccines comprising isolated proteins SPP2, or SPP2 plus CP1, or with vaccines comprising SPP2 plus CP1 in MAPS complexes reached comparable survival rates of >=60%. Mice immunized with positive control Prevnar13 maintained 100% survival throughout the study; the negative control group of mice immunized with Rhavi exhibited no survival by the end of the study. These results show that SPP2 protein alone can confer protection in a sepsis challenge model using serotype 3 *S. pneumoniae* strain AR003. The addition of CP1 to SPP2 did not significantly impact survival in this assay.

Example 8: Active Immunization and Sepsis Challenge II

This study tested immunogenicity and protection against lethal *Streptococcus pneumoniae* sepsis challenge in a mouse model, following immunization with vaccines comprising proteins SPP2, CP1, or SPP2 plus CP1, all in MAPS complexes with *Streptococcus pneumoniae* polysaccharide PS1. Control groups were immunized with isolated protein Rhavi (negative control) or with Prevnar 13 (positive control). Vaccines were adjuvanted with Aluminum Phosphate. SPP2 is described in Example 1. CP1 is a fusion protein comprising rhizavidin residues 45-179 (denoted Rhavi), *S. pneumoniae* protein SP1500, and *S. pneumoniae* hypothetical protein SP0785, with each of the three domains separated by a linker. Optionally, CP1 includes His tags. See WO2020/056127 and WO2020/056202 for detailed description of CP1 and MAPS complexes, the entire contents of each of which are incorporated herein by reference for the purposes described herein.

Methods

The vaccines formulations examined in this study are provided below. The total volume prepared for each vaccine was sufficient for at least the indicated number of doses, with each dose being 0.2 mL.

| 1. Rhavi (5 μg/dose) + AlPO4 (0.250 mg/dose); (Doses, n = 30) | |
|---|---|
| 4911.6 μl | Sterile Water |
| 72.0 μl | 1% thimerosal (0.01%, final) |
| 144.0 μl | 1M Phosphate, pH 5.8 (20 mM, final) |
| 214.3 μl | 5M Sodium Chloride (150 mM final) |
| 1800.0 μl | 5 mg/ml AdjuPhos, Aluminum Phosphate (1.25 mg/ml, final) |
| 58.2 μl | Rhavi, protein conc. 25 μg/ml final |
| 7200.0 μl | Final Volume |

| 2. Prevnar13 (0.88 μg/PS/dose); (Doses, n = 10) | |
|---|---|
| 2500.0 μl | 0.88 μg/PS, 0.2 ml of undiluted Prevnar13 per mouse |
| 2500.0 μl | Final Volume |

| 3. PS1.CP1 (15 μg/dose) + AlPO4 (0.250 mg/dose); (Doses, n = 20) | |
|---|---|
| 2383.3 μl | Sterile Water |
| 48.0 μl | 1% thimerosal (0.01%, final) |
| 96.0 μl | 1M Phosphate, pH 5.8 (20 mM, final) |
| 115.3 μl | 5M Sodium Chloride (150 mM final) |
| 1200.0 μl | 5 mg/ml AdjuPhos, Aluminum Phosphate (1.25 mg/ml, final) |
| 957.4 μl | PS1.CP1, MAPS complexes: protein conc. 75 μg/ml final |
| 4800.0 μl | Final Volume |

| 4. PS1.SPP2 (15 μg/dose) + AlPO4 (0.250 mg/dose); (Doses, n = 20) | |
|---|---|
| 2766.4 μl | Sterile Water |
| 48.0 μl | 1% thimerosal (0.01%, final) |
| 96.0 μl | 1M Phosphate, pH 5.8 (20 mM, final) |
| 127.1 μl | 5M Sodium Chloride (150 mM final) |
| 1200.0 μl | 5 mg/ml AdjuPhos, Aluminum Phosphate (1.25 mg/ml, final) |
| 562.5 μl | PS1.SPP2, MAPS complexes: protein conc. 75 μg/ml final |
| 4800.0 μl | Final Volume |

| 5. PS1.CP1 (15 μg/dose) + PS1.SPP2 (15 μg/dose) + AlPO4 (0.250 mg/dose); (Doses, n = 20) | |
|---|---|
| 1901.5 μl | Sterile Water |
| 48.0 μl | 1% thimerosal (0.01%, final) |
| 96.0 μl | 1M Phosphate, pH 5.8 (20 mM, final) |

-continued

| | |
|---|---|
| 110.0 μl | 5M Sodium Chloride (150 mM final) |
| 1200.0 μl | 5 mg/ml AdjuPhos, Aluminum Phosphate (1.25 mg/ml, final) |
| 562.5 μl | PS1.SPP2, MAPS complexes: protein conc. 75 μg/ml final |
| 312.0 μl | PS1.CP1 MAPS complexes: protein conc. 75 μg/ml final |
| 4800.0 μl | Final Volume |

The study was conducted using 5 groups, each with 10-30 wild type C57BL/6 mice (Charles River Labs). All procedures involving mice were approved by the Mispro Biotech Animal Care and Use Committee (IACUC protocol no. 2018 May 1-AF2), following the National Institutes of Health guidelines for animal housing and care. On Day 0 of the study, groups of mice were immunized subcutaneously according to Table 6 below. A first booster dose was administered on Day 14. A second booster dose was administered on Day 28. Blood was collected on Day 42 and immunogenicity was assessed by ELISA.

TABLE 6

Immunization Groups for Study 015

| Vaccine | AlPO4 adjuvant conc. (mg/ml) | Adjuvant dose (μg) | Immunogen dose | Dose volume |
|---|---|---|---|---|
| A. Rhavi (n = 20) (protein) | 1.25 | 250 | 5 μg | 0.2 mL s.c. |
| B. Prevnar13 (n = 10) | | N/A | 200 μl undiluted (2/5$^{th}$ of human dose) | 0.2 mL s.c. |
| C. PS1.CP1 (n = 20) (MAPS complexes) | 1.25 | 250 | 15 μg | 0.2 mL s.c. |
| D. PS1.SPP2 (n = 20) (MAPS complexes) | 1.25 | 250 | 15 μg | 0.2 mL s.c. |
| E. PS1.CP1 + PS1.SPP2 (n = 20) (MAPS complexes) | 1.25 | 250 | 15 μg each protein | 0.2 mL s.c. |

On Day 49 following first immunization, mice were inoculated in the intraperitoneal (IP) cavity with 3x10^4 CFU/mouse target dose of *S. pneumoniae* AR003 (serotype 3 strain) in 0.2 mL 1× saline. Mice were monitored for any signs of illness following challenge with *S. pneumoniae*; any ill-appearing animal (presenting with signs of ruffled fur, slow moving, and/or with closed eyes) was immediately and humanely euthanized. Following the IP challenge, a daily body weight and twice daily observations were gathered from all mice on Days 50-63 (i.e., days 1-14 post-challenge). The study was concluded on Day 63 (i.e., day 14 post-challenge) with all remaining mice being humanely sacrificed.

Results

Mouse sera collected on Day 42 of the study were analyzed by ELISA against PdT (G294P) and SP1500-SP0785, components of SPP2 and CP1 respectively. Comparable specific IgG titers were raised in mice immunized with vaccines comprising SPP2, CP1, and SPP2 plus CP1 all in MAPS complexes. The addition of MAPS complexes with CP1 to MAPS complexes with SPP2 did not significantly impact IgG titers against PdT (G294P).

Figure 28A:
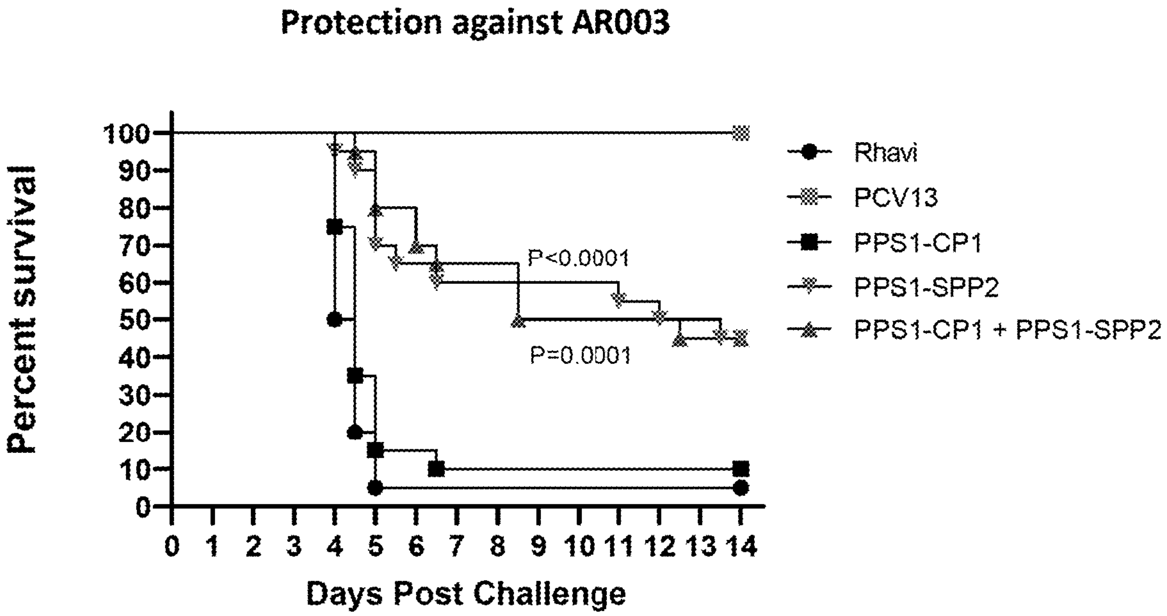
FIG. 28A shows the percent survival at indicated time points for groups of mice immunized with vaccines comprising CP1, SPP2, or CP1 plus SPP2, all in MAPS complexes with *Streptococcus pneumoniae* polysaccharide PS1, and challenged with *S. pneumoniae* strain AR003. Mice immunized with Rhavi and Prevnar 13 (PCV13) are shown as negative and positive controls, respectively.
Figure 28B:
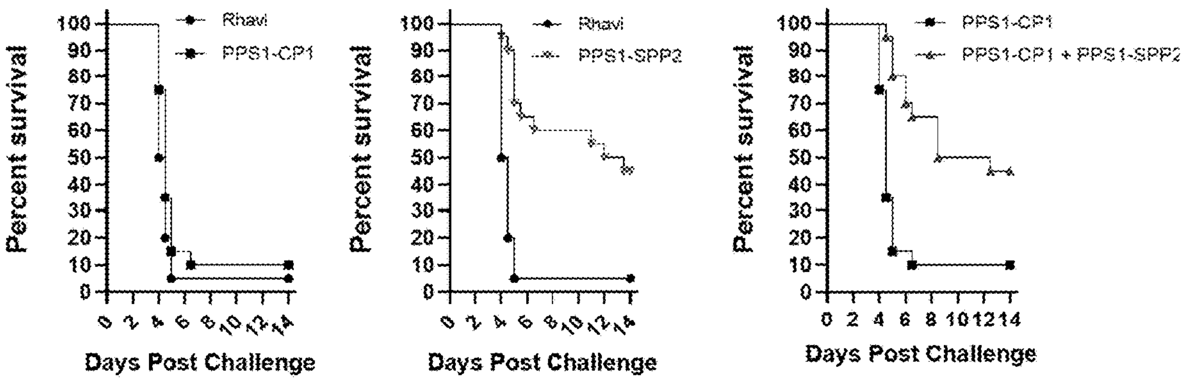
FIG. 28B shows the same results as in FIG. 28A but separating survival curves for the immunization groups onto different graphs.

Percent survival for each group of immunized mice was examined at time points after challenge with *S. pneumoniae* (FIGS. 28A and 28B). Statistical analysis for survival rates was performed using the log-rank (Mantel-Cox) test. By day 14 post-challenge, mice immunized with positive control Prevnar 13 maintained 100% survival throughout the study; the negative control group of mice immunized with Rhavi exhibited 5% survival by the end of the study (FIGS. 28A and 28B). Mice immunized with CP1 in MAPS complexes showed a modest increase in survival rate (10%) compared to the negative control (FIGS. 28A and 28B). Surprisingly, mice immunized with vaccines comprising either SPP2 or SPP2 plus CP1 in MAPS complexes reached an identical survival rate of 45% that was statistically significant (p=0.0001) (FIG. 28A). These results confirm the unexpected protective efficacy of SPP2 protein in a sepsis challenge model using serotype 3 *S. pneumoniae* strain AR003 as demonstrated in Example 7. SPP2 was protective whether administered as an isolated protein (Example 7) or in MAPS complexes (this Example).

Example 9: Passive Immunization and Sepsis Protection

The goal of this study was to evaluate the protection of MAPS-33 and MAPS-34 antisera against lethal *Streptococcus pneumoniae* sepsis challenge in a mouse model, where PCV13 antisera were known to be not completely protective. The MAPS-33 and MAPS-34 vaccines used to generate antisera comprised different combinations of polysaccharides and fusion proteins CP1, SPP2, or SPP2 and CP1, as shown in FIG. 12. These antisera were compared to PCV13 antisera.

Methods

Hyperimmune sera was produced using New Zealand White rabbits as described in Example 6. Immunogenicity was assessed by ELISA and OPA. Four study groups (A-D), each with 10 wild type C57BL/6 mice (Charles River Labs) were used. All procedures involving mice were approved by the Mispro Biotech Animal Care and Use Committee (IACUC protocol no. 2018 May 1-AF2), following the National Institutes of Health guidelines for animal housing and care. Heat inactivated rabbit sera were administered intraperitoneally to the mice at 0.2 mL/mouse one day prior to challenge (Day-1 of the study). Group A mice received saline control. Group B mice received PCV13 P2 sera of rabbit immunization group H, shown as Prevnar 13 in FIG. 12. Group C mice received MAPS-34 P2 sera of rabbit immunization group E: 17V MAPS SPP2/17V MAPS CP1, shown as Combo #2 in FIG. 12. Group D mice received MAPS-34 P2 sera of rabbit immunization group D: 17V MAPS CP1/17V MAPS SPP2, shown as Combo #1 in FIG. 12.

On Day 0 of the study, all mice were weighed and challenged by intraperitoneal (IP) injection with a $3\times10^4$ CFU/mouse target dose (high dose) of *S. pneumoniae* AR003 (serotype 3 strain) in 0.2 mL 1× saline. Following the challenge with *S. pneumoniae*, a daily body weight and twice daily observations were collected from all mice on days 1-14. Mice were monitored for any signs of illness; any ill-appearing animal (presenting with signs of ruffled fur, slow moving, and/or with closed eyes) was immediately and humanely euthanized. The study was concluded on Day 14 with all mice being humanely sacrificed. Upon completion of the challenge, the stock was enumerated in triplicate to verify a true infection dose of $3.84\times10^4$ CFU/mouse.

OPA protocol: To demonstrate presence of functional antibodies against *S. pneumoniae*, an opsonophagocytic assay (OPA) was established. In such an assay, the presence of functional antibodies is shown by killing of *S. pneumoniae* following incubation with immune sera. Briefly, frozen stocks of *S. pneumoniae* were thawed and resuspended at $2\times10^5$ CFU/ml in assay buffer (Hank's buffered saline with 10% heat-inactivated FBS, and 0.1% gelatin). To each well of a 96-well plate, 20 μl of heat-inactivated rabbit serum diluted in assay buffer was added, followed by 10 μl of bacterial suspension in assay buffer. The bacteria and rabbit sera were incubated at room temperature for 30 minutes with shaking at 650 rpm. Differentiated HL60 cells (ATCC) were washed with assay buffer and resuspended to $1\times10^7$ cells/ml in assay buffer. To each well, 40 μl of this HL60 suspension was added (200 to 1, HL60 to bacteria ratio) followed by 10 μl of baby rabbit complement (Pel-Freeze Biologicals). The assay plates were incubated at 37° C. with 5% $CO_2$ and shaken at 650 rpm for 45 minutes. Each plate was transferred to ice and incubated for 20 minutes. Contents of each well were diluted in water 1/5 and 1/25, and each dilution was then plated on 5% blood agar plates. After overnight incubation at 37° C. with 5% $CO_2$, the CFU were counted for each sample and dilution, discarding data points with colony counts greater than 250 CFU. The percent killing at each serum dilution was calculated by subtracting the remaining CFU/mL from each sample from the CFU/mL of a control without rabbit serum. The difference was then normalized by the CFU/mL of the control without rabbit serum.

Results

Figure 29:
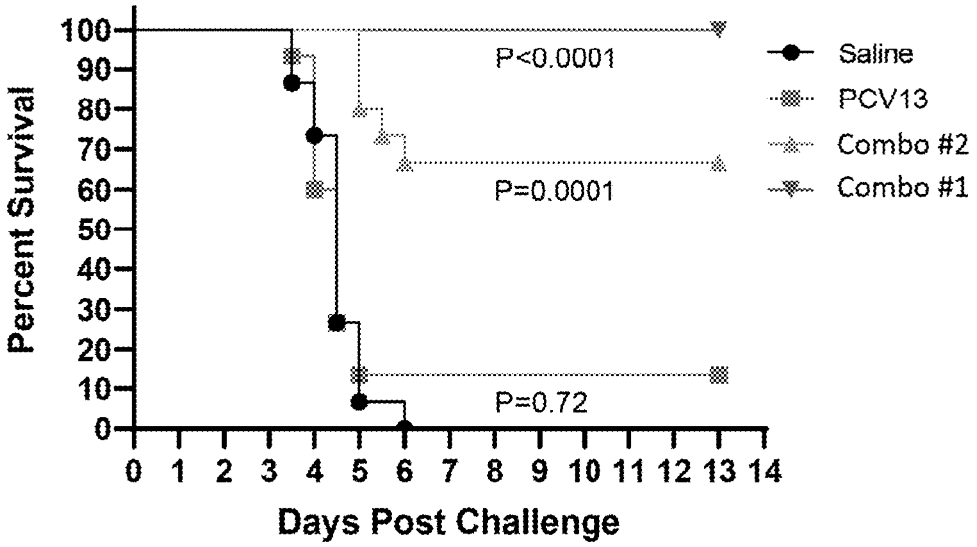
FIG. 29 shows percent survival at the indicated time points for groups of mice passively immunized with P2 sera from rabbits immunized with MAPS34 vaccines, and challenged with high dose *S. pneumoniae* strain AR003. Mice passively immunized with saline or with P2 sera from rabbits immunized with Prevnar 13 (PCV13) are shown as controls.

Percent survival for each group of passively immunized mice was examined at time points after challenge with *S. pneumoniae* (FIG. 29). Statistical analysis for survival rates was performed using the log-rank (Mantel-Cox) test in comparison to the saline group. By Day 13 post-challenge, mice passively immunized with PCV13 P2 sera had a survival rate of 13% (2/15 mice). In contrast, by Day 13 post-challenge, mice passively immunized with MAPS-34 P2 sera had a survival rate of 67% (10/15 mice) for Combo #2, and 100% (15/15 mice) for Combo #1. In previous work, mice passively immunized with PCV13 P2 sera and challenged with true doses of $9.4\times10^3$ (medium dose) and $3.32\times10^3$ CFU/mouse (low dose) completed the study with 100% survival (data not shown). These results demonstrate the efficacy of MAPS-34 vaccine in providing passive protection.

Figure 30:
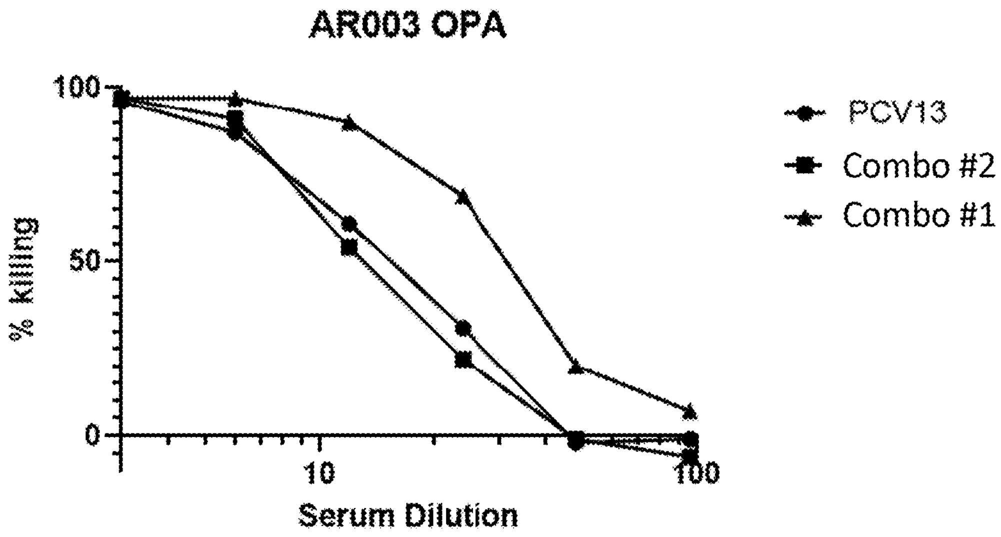
FIG. 30 shows killing activity of representative P2 sera from rabbits immunized with MAPS-34 on CP1 and SPP2 (Combo #1, immunization group D), MAPS-34 on SPP2 and CP1 (Combo #2, immunization group E), and PCV13 (immunization group H). Killing activity was measured by an opsonophagocytic assay (OPA) against *S. pneumoniae* AR003. Results are expressed as % killing activity relative to serum dilution.

FIG. 30 shows killing activity of representative rabbit sera against S. *pneumoniae* AR003 measured by an opsonophagocytic assay (OPA). Representative Combo #2 and pooled PCV13 rabbit sera had equivalent IgG titers (approximately 30,000 a.u. each) against *S. pneumoniae* serotype 3 polysaccharides and demonstrated similar levels of killing activity. Combo #1 rabbit serum had a higher IgG titer (approximately two-fold higher) against serotype 3 polysaccharides than Combo #1 or PCV13 sera and showed a greater level of killing activity.

The lack of protection observed in mice passively immunized with PCV13 P2 sera was therefore not due to lower functional IgG levels against serotype 3 polysaccharides or to lower killing activity. Taken together, these results indicate that for mice passively immunized and subjected to a high dose challenge with *S. pneumoniae* AR003: 1) the protection afforded by PCV13 sera against *S. pneumoniae* AR003 challenge at low and medium doses can be overcome with a high dose; 2) the protection afforded by MAPS-34 sera is maintained; and 3) the difference in protection between PCV13 and Combo #2 MAPS-34 sera in particular is not attributable to a difference in IgG titers against *S. pneumoniae* serotype 3 polysaccharides, or to a difference in killing activity against AR003. The greater degree of protection achieved with Combo #2 MAPS-34 sera may be attributed instead to the presence of antibodies directed not only to *S. pneumoniae* serotype 3 polysaccharides (common to the PCV13, Combo #1 and Combo #2 rabbit sera), but also antibodies to one or more additional antigenic components specific to MAPS-34 vaccines. The results presented in Examples 7 and 8 suggest that this additional antigenic component could be SPP2.

Example 10: Active Immunization and Sepsis Challenge III

This study tested immunogenicity and protection against lethal *Streptococcus pneumoniae* sepsis challenge in a mouse model, following immunization with MAPS-34 on CP1 and SPP2, MAPS-33 on CP1 and SPP2, or with SPP2 in MAPS complexes with *Streptococcus pneumoniae* polysaccharide PS1. Control groups were immunized with isolated protein Rhavi (negative control) or with Prevnar 13 at 2 different doses (positive control). Vaccines were adjuvanted with aluminum phosphate. SPP2 is described in Example 1. CP1 is a fusion protein comprising rhizavidin residues 45-179 (denoted Rhavi), *S. pneumoniae* protein SP1500, and *S. pneumoniae* hypothetical protein SP0785, with each of the three domains separated by a linker. Optionally, CP1 includes His tags. See WO2020/056127 and WO2020/056202 for detailed description of CP1 and MAPS complexes.

Methods

The vaccines formulations examined in this study are provided below. The total volume prepared for each vaccine was sufficient for at least the indicated number of doses, with each dose being 0.2 mL.

| A. Rhavi (5 μg/dose) + AlPO4 (0.250 mg/dose); (Doses, n = 19) | |
|---|---|
| 3120.8 μl | Sterile Water |
| 48.0 μl | 1% thimerosal (0.01%, final) |
| 9.6 μl | 10% Tween 80 (0.02%, final) |
| 240.0 μl | 0.4M Histidine, pH 5.5 (20 mM, final) |
| 142.8 μl | 5M Sodium Chloride (150 mM final) |
| 1200.0 μl | 5 mg/ml AdjuPhos, Aluminum Phosphate (1.25 mg/ml, final) |
| 38.8 μl | Rhavi, protein conc. 25 μg/ml final |
| 4.8 μl | 1M Sodium phosphate, pH 5.5 (1 mM, final) |
| 4800.0 μl | Final Volume |

| B. Prevnar 13 (0.88 μg/PS/dose); (Doses, n = 10) | |
|---|---|
| 2500.0 μl | 0.88 μg/PS, 0.2 ml of undiluted Prevnar 13 per mouse (= 2/5$^{th}$ human dose) |
| 2500.0 μl | Final Volume |

| C. PPS1-SPP2 (15 μg/dose) + AlPO4 (0.250 mg/dose); (Doses, n = 10) | |
|---|---|
| 1242.0 μl | Sterile Water |
| 24.0 μl | 1% thimerosal (0.01%, final) |
| 4.8 μl | 10% Tween 80 (0.02%, final) |
| 120.0 μl | 0.4M Histidine, pH 5.5 (20 mM, final) |
| 61.6 μl | 5M Sodium Chloride (150 mM final) |
| 600.0 μl | 5 mg/ml AdjuPhos, Aluminum Phosphate (1.25 mg/ml, final) |

-continued

| | |
|---|---|
| 347.6 µl | PS1.SPP2 (MAPS complexes, SPP2 conc. 75 µg/ml final |
| 2.1 µl | 1M Sodium phosphate, pH 5.5 (1 mM, final) |
| 2400.0 µl | Final Volume |
| D. Prevnar 13 (PPS3, 0.04 µg/dose); (Doses, n = 10) | |
| 2136.9 µl | Sterile Water |
| 43.7 µl | 0.25M Succinate buffer, pH 5.5 (5 mM, final) |
| 4.4 µl | 10% Tween 80 (0.02%, final) |
| 115.0 µl | Prevnar 13, PPS3 conc. 0.2 µg/ml final (= 1/50$^{th}$ human dose) |
| 2400.0 µl | Final Volume |
| E: MAPS33 (SPP2, 1.5 µg, no PPS3/dose) + AlPO4 (0.250 mg/dose); (Doses, n = 10) | |
| 1371.5 | Sterile Water |
| 24.0 µl | 1% thimerosal (0.01%, final) |
| 4.8 µl | 10% Tween 80 (0.02%, final) |
| 120.0 µl | 0.4M Histidine, pH 5.5 (20 mM, final) |
| 65.6 µl | 5M Sodium Chloride (150 mM final) |
| 600.0 µl | 5 mg/ml AdjuPhos, Aluminum Phosphate (1.25 mg/ml, final) |
| 211.9 µl | MAPS33, SPP2 conc. 7.5 µg/ml final |
| 2.2 µl | 1M Sodium phosphate, pH 5.5 (1 mM, final) |
| 2400.0 µl | Final Volume |
| F: MAPS34 (SPP2, 1.5 µg/dose + PPS3, 0.04 µg/dose) + AlPO4 (0.250 mg/dose); (Doses, n = 10) | |
| 1371.5 | Sterile Water |
| 24.0 µl | 1% thimerosal (0.01%, final) |
| 4.8 µl | 10% Tween 80 (0.02%, final) |
| 120.0 µl | 0.4M Histidine, pH 5.5 (20 mM, final) |
| 65.6 µl | 5M Sodium Chloride (150 mM final) |
| 600.0 µl | 5 mg/ml AdjuPhos, Aluminum Phosphate (1.25 mg/ml, final) |
| 211.9 µl | MAPS33, SPP2 conc. 7.5 µg/ml final; PPS3 conc. 0.2 µg/ml final |
| 2.2 µl | 1M Sodium phosphate, pH 5.5 (1 mM, final) |
| 2400.0 µl | Final Volume |

The study was conducted using 6 groups, each comprising 10 wild-type C57BL/6 mice (Charles River Labs). All procedures involving mice were approved by the Mispro Biotech Animal Care and Use Committee (IACUC protocol no. 2018 May 1-AF2), following the National Institutes of Health guidelines for animal housing and care. On Day 0 of the study, groups of mice were immunized subcutaneously according to Table 7 below. A first booster dose was administered on Day 14. A second booster dose was administered on Day 28. Blood was collected on Day 41 and immunogenicity was assessed by ELISA.

TABLE 7

Immunization Groups for Study 021

| Groups | AlPO4 adjuvant conc. (mg/ml) | Adjuvant dose (µg) | Immunogen dose | Dose volume |
|---|---|---|---|---|
| A. Rhavi-His (n = 10) | 1.25 | 250 | 5 µg | 0.2 mL s.c. |
| B. Prevnar 13 (2/5$^{th}$ human dose; n = 10) | 0.25 | 50 | 200 µl undiluted | 0.2 mL s.c. |
| C. PPS1-SPP2 (n = 10) | 1.25 | 250 | 15 µg | 0.2 mL s.c. |
| D. Prevnar 13 (1/50$^{th}$ human dose; n = 10) | 0.0125 | 2.5 | 0.04 µg PPS3 | 0.2 mL s.c. |
| E. MAPS33 (23 on CP1 + 10 on SPP2) (n = 10) | 1.25 | 250 | 1.5 µg SPP2 | 0.2 mL s.c. |
| F. MAPS34 (24 on CP1 + 10 on SPP2) (n = 10) | 1.25 | 250 | 1.5 µg SPP2 + 0.04 µg PPS3 = 1/50$^{th}$ Prevnar 13 human dose | 0.2 mL s.c. |

On Day 42 following first immunization, mice were inoculated in the intraperitoneal (IP) cavity with a 3×10^4 CFU/mouse target dose of *S. pneumoniae* AR003 (serotype 3 strain) in 0.2 mL 1× saline. Mice were monitored for any signs of illness following challenge with *S. pneumoniae*; any ill-appearing animal (presenting with signs of ruffled fur, slow moving, and/or with closed eyes) was immediately and humanely euthanized. Following the IP challenge, a daily body weight and twice daily observations were gathered from all mice for 14 days post-challenge. The study was concluded on Day 56 (i.e., day 14 post-challenge) with all remaining mice being humanely sacrificed.

Example 11: Correlation of Anti-PdT (G294P) IgG to Pneumolysin Neutralization Titers The goal of this study was to determine the relationship between anti-PdT (G294P) IgG titers and pneumolysin neutralization activity induced by immunization with fusion protein SPP2. New Zealand White rabbits (2 studies: n=5 and n=3) were immunized intramuscularly with 100 µg of SPP2 protein on Day 0 and again on Day 14 (two weeks apart). Serum was collected on Day 0 prior to first immunization (P0 serum), on Day 14 prior to second immunization (post-first immunization production bleed; P1 serum), and on Day 28 (post-second immunization production bleed; P2 serum). Sera were evaluated for titers of PdT toxoid-binding IgG (anti-PdT (G294P)) by ELISA, and titers of pneumolysin neutralizing antibodies (IC50). Evaluation methods were as described in Example 6.

Figure 31:
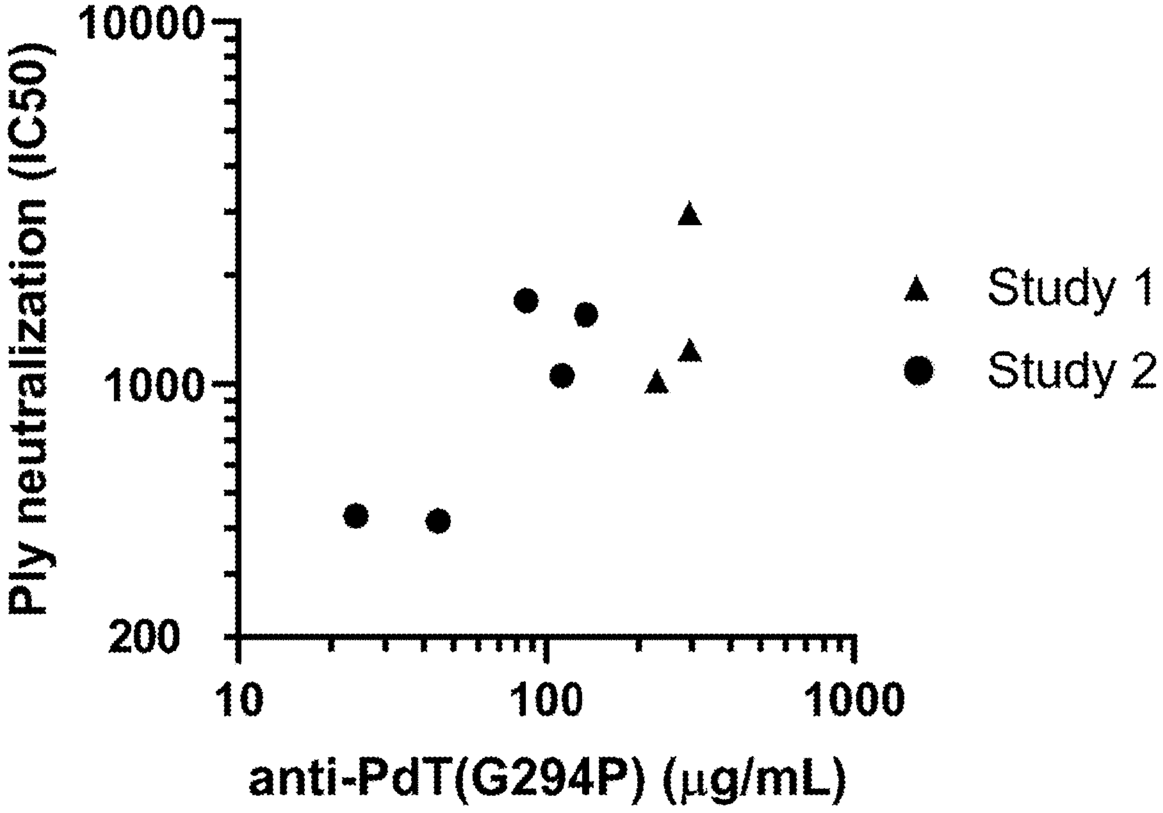
FIG. 31 shows representative half-maximal inhibitory concentration (IC50) of pneumolysin neutralizing antibodies (Ply neutralization (IC50)) in P2 sera from rabbits immunized with SPP2 fusion protein, graphed against anti-PdT (G294P) IgG titers (μg/mL). Results of two studies were combined (n=5 and n=3).

FIG. 31 shows representative P2 pneumolysin neutralization antibody titers (the P2 serum dilution factor required to abolish 50% of the hemolytic activity of pneumolysin (Ply neutralization (IC50)) graphed against anti-PdT (G294P) IgG titers (µg/mL). In this figure, results of two studies (n=5 and n=3) were combined. Results show positive correlation between pneumolysin neutralization titers and anti-PdT (G294P) IgG titers.

Example 12: Synergistic Protection of SPP2 and Serotype 3 Polysaccharide Against Sepsis Serotype 3 invasive pneumococcal disease (IPD) incidence rates have not significantly declined despite the introduction of a 13-valent pneumococcal vaccine (PCV13) in children worldwide and adults in the United States. The relative failure of the serotype 3 capsular polysaccharide (CPS3) component of PCV13 remains unexplained, although hypotheses regarding lack of covalent attachment of the CPS3 to the bacterial cell wall and/or insufficient immunogenicity of the type 3 component of PCV13 have been advanced. The studies of the present Example examined immunogenicity and protection conferred by separate components of MAPS30+ vaccine candidates, i.e., polysaccharides and, in particular, the fusion protein SPP2.

A highly lethal serotype 3 pneumococcal invasive disease (sepsis) model, in which antibodies to CPS3 alone are not sufficient to confer protection against serotype 3 invasive pneumococcal disease, was developed to evaluate whether inclusion of two fusion proteins (e.g., CP1 and SPP2) can provide synergistic protection. Results of the present Example show a synergistic protective effect of anti-fusion protein and anti-CPS3 antibodies against lethal *S. pneumoniae* serotype 3 challenge. These data strongly support a vaccine approach that includes both pneumococcal polysaccharides and proteins to overcome the clinical resistance of serotype 3 pneumococcal disease to traditional glycoconjugate vaccines.

In the first study, on Day 0 and Day 14, groups of mice were administered prime and booster doses, respectively, of Rhavi (n=15, 5 μg Rhavi/dose), SPP2 fusion protein (n=15, 15 μg SPP2/dose), or SPP2 fusion protein in MAPS complexes with *S. pneumoniae* capsular polysaccharide 1 (CPS1) (denoted "1.SPP2"; n=15, 15 μg SPP2/dose). At week 4 (on or about Day 28 of the study), naïve mice received a prime dose of PCV13 (n=15, 0.88 μg/PS/dose) and mice that had previously received prime and booster doses of 1.SPP2 were administered a booster dose of PCV13 (0.88 μg/PS/dose). Vaccines were adjuvanted with aluminum phosphate. "Rhavi" refers to a polypeptide comprising residues 45-179 of rhizavidin. SPP2 fusion protein is described in Example 1.

At week 7 (on or about Day 49) following the first immunization, mice were inoculated in the intraperitoneal (IP) cavity with a $1\times10^7$ CFU/mouse dose of *S. pneumoniae* strain AR003 (serotype 3) in 0.2 mL 1× saline. Following the IP challenge, a daily body weight and twice-daily observations were gathered from all mice for 14 days post-challenge. The study was concluded on or about Day 63 (i.e., day 14 post-challenge) with all remaining mice being humanely sacrificed. The percent survival of each group over the 14 days post-challenge was plotted. Results of this first study are shown in FIG. 32.

In the second study, on Day 0 and Day 14, groups of mice were administered prime and booster doses, respectively, of Rhavi (n=15, 5 μg Rhavi/dose) or SPP2 fusion protein in MAPS complexes with *S. pneumoniae* capsular polysaccharide 1 (CPS1) (denoted "1.SPP2"; n=15, 15 μg SPP2/dose). At week 4 (on or about Day 28 of the study), naïve mice received a prime dose of PCV13 (n=15, 0.88 μg/PS/dose) and mice that had previously received prime and booster doses of 1.SPP2 were administered a booster dose of CP1 fusion protein in MAPS complexes with *S. pneumoniae* capsular polysaccharide 3 (CPS3) (denoted "3.CP1", 0.88 μg CPS3/dose). Vaccines were adjuvanted with aluminum phosphate. "Rhavi" refers to a polypeptide comprising residues 45-179 of Rhizavidin. SPP2 fusion protein is described in Example 1. CP1 is a fusion protein comprising Rhizavidin residues 45-179 (i.e., Rhavi), *S. pneumoniae* protein SP1500, and *S. pneumoniae* hypothetical protein SP0785, with each of the three domains separated by a linker. Optionally, CP1 includes His tags. See WO2020/056127 and WO2020/056202, incorporated herein by reference, for detailed description of CP1 fusion protein and MAPS complexes.

Figure 33:
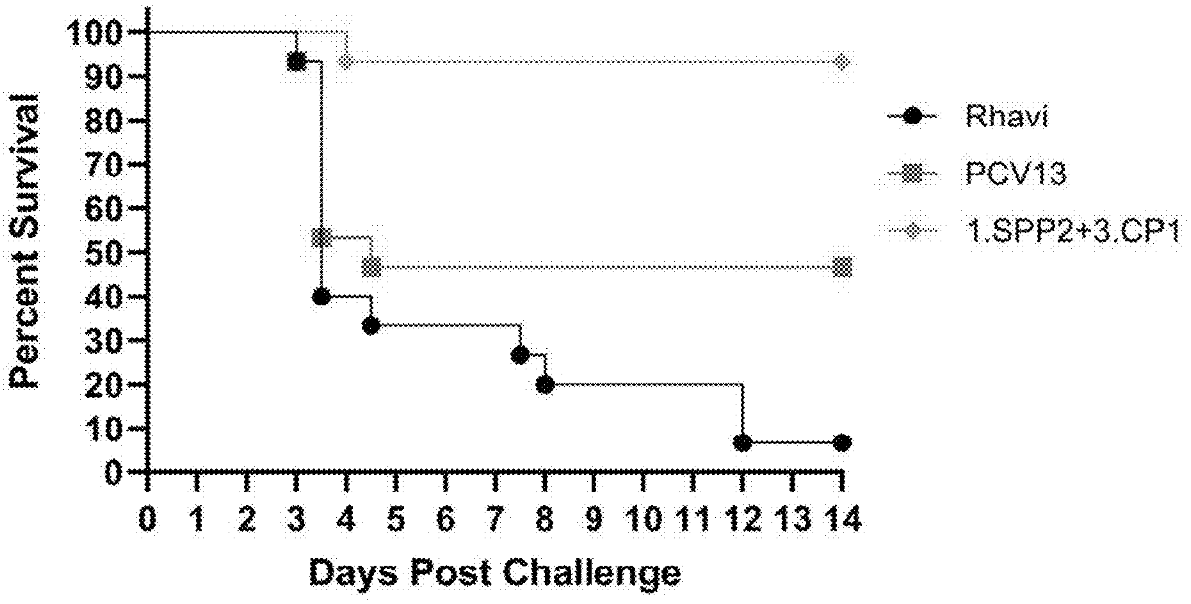
FIG. 33 shows the percent survival at indicated time points for the indicated groups of immunized mice, challenged with $6.7\times10^6$ CFU of *S. pneumoniae* strain AR003 (serotype 3). Rhavi: primed and boosted with Rhavi. PCV13: primed with Prevnar 13 (PCV13). 1.SPP2+3.CP1: primed and boosted with SPP2 fusion protein in MAPS complexes with *S. pneumoniae* capsular polysaccharide 1 (CPS1) (denoted "1.SPP2"), and re-boosted with CP1 fusion protein in MAPS complexes with *S. pneumoniae* capsular polysaccharide 3 (CPS3) (denoted "3.CP1").

At week 7 (on or about Day 49) following the first immunization, mice were inoculated in the intraperitoneal (IP) cavity with a $6.7\times10^6$ CFU/mouse dose of *S. pneumoniae* strain AR003 (serotype 3) in 0.2 mL 1× saline. Following the IP challenge, a daily body weight and twice-daily observations were gathered from all mice for 14 days post-challenge. The study was concluded on or about Day 63 (i.e., day 14 post-challenge) with all remaining mice being humanely sacrificed. The percent survival of each group over the 14 days post-challenge was plotted. Results of this second study are shown in FIG. 33.

Figure 32:
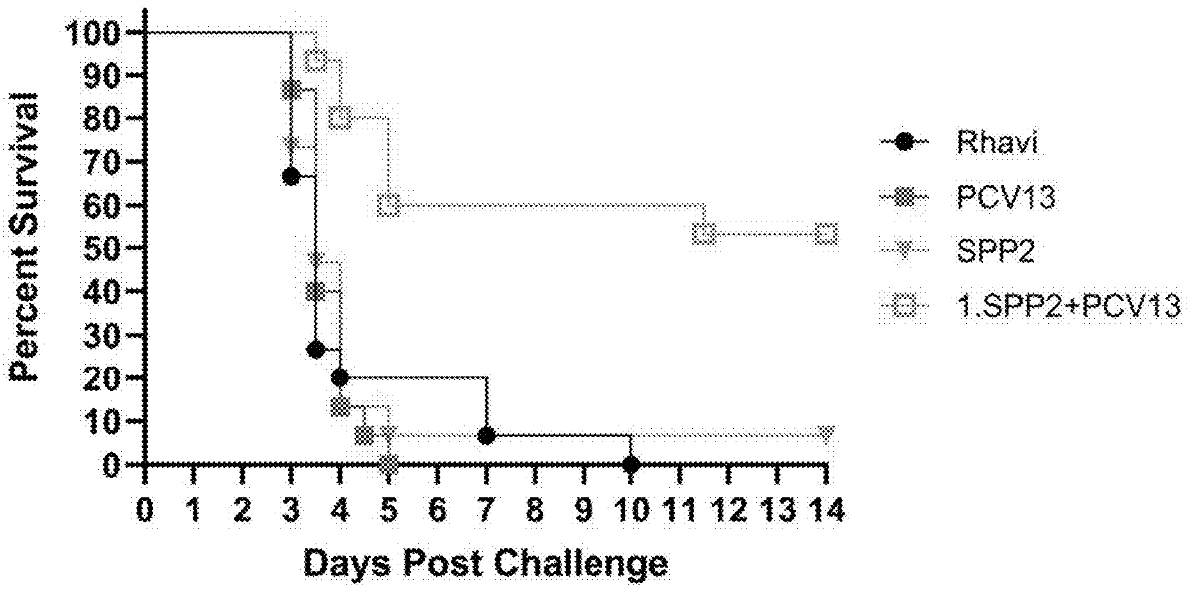
FIG. 32 shows the percent survival at indicated time points for the indicated groups of immunized mice, challenged with $1.0\times10^7$ CFU of *S. pneumoniae* strain AR003 (serotype 3) per mouse. Rhavi: primed and boosted with Rhavi. PCV13: primed with Prevnar 13 (PCV13). SPP2: primed and boosted with SPP2 fusion protein. 1.SPP2+PCV13: primed and boosted with SPP2 fusion protein in MAPS complexes with *S. pneumoniae* capsular polysaccharide 1 (CPS1) (denoted "1.SPP2"), and re-boosted with PCV13.

FIG. 32 shows that immunization with SPP2 fusion protein or PCV13 alone is not protective at high challenge doses (e.g., $1\times10^7$ CFU/mouse), but the combination of 1.SPP2+PCV13 significantly protects from sepsis ($p<0.001$, Mantel-Cox). Additionally, FIG. 33 shows partial protection in the PCV13 group and significantly better (approximately double) protection in the 1.SPP2+3.CP1 group ($p<0.01$, Mantel-Cox) when animals were challenged with a slightly lower dose of AR003 (e.g., $6.7\times10^6$ CFU/mouse). Together these results show that protection offered by traditional *S. pneumoniae* glycoconjugate vaccines such as PCV13 can be overcome with sufficiently high challenge doses of bacteria. Additionally, the results indicate that SPP2 fusion protein (e.g., in MAPS complexes) and CPS3 (e.g., in MAPS complexes, or in the context of glycoconjugates, such as PCV13) can synergize to confer immune protection in a stringent, high-dose model of type 3 pneumococcal sepsis.

Figure 34A:
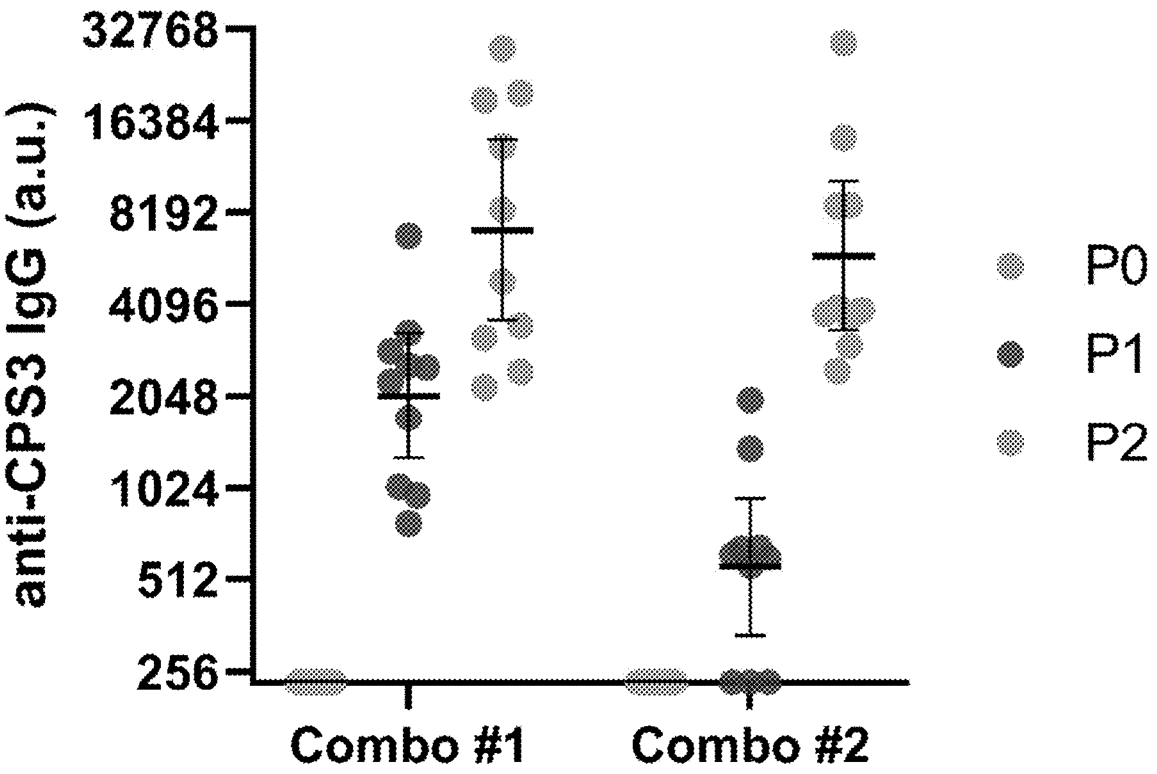
FIGS. 34A-34C show immunogenicity and functional antibody responses against antigens relevant to the *S. pneumoniae* strain AR003 (serotype 3) sepsis model.
Figure 34B:
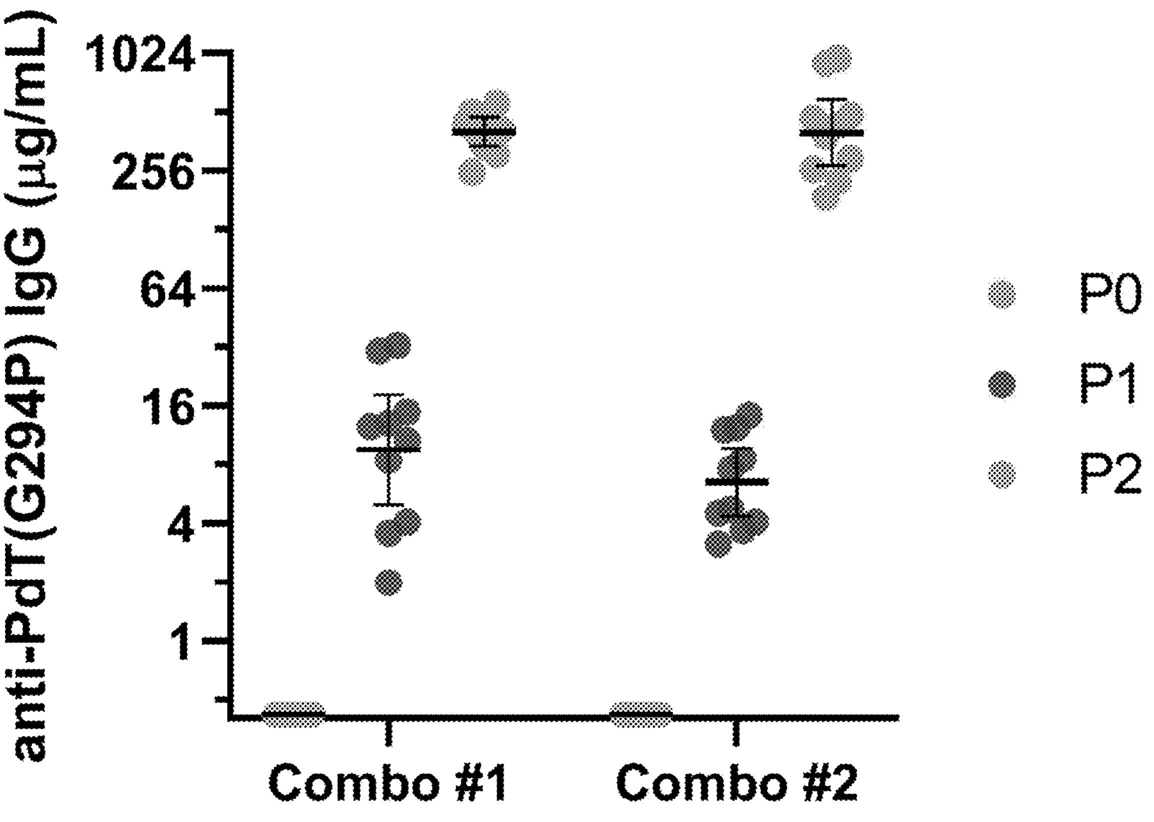
Figure 34C:
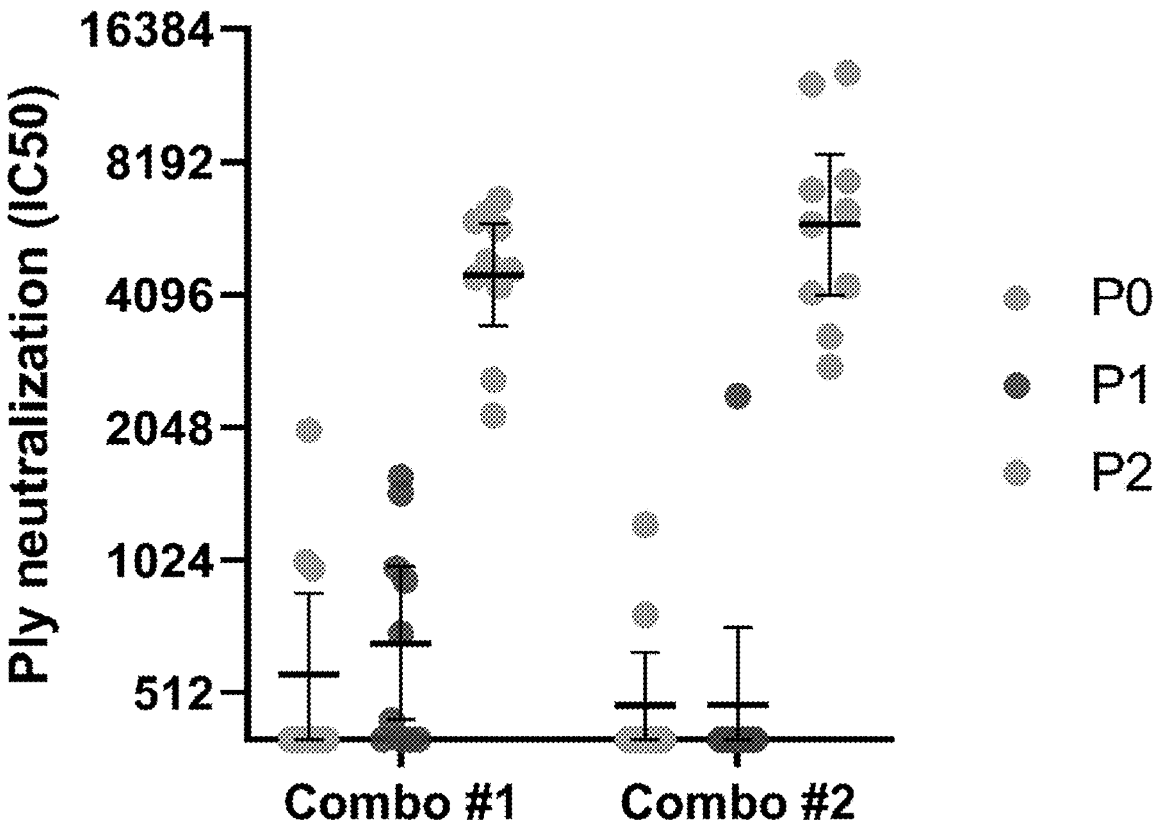

In the third study, rabbit sera from immunization Groups D and E of Example 6 (Serotype Distribution Study) were further evaluated for immunogenicity against capsular polysaccharide 3 (CPS3). Results are shown in FIG. 34A. Results obtained for immunogenicity and functional responses against PdT (G294P) in rabbit sera from immunization Groups D and E are shown in FIGS. 34B and 34C (same data as presented for Groups D and E in FIGS. 14 and 16, respectively). Briefly, in Example 6, different combinations of fusion proteins CP1 and SPP2 with *S. pneumoniae* polysaccharides from more than 30 serotypes (MAPS30+ series of vaccine candidates) were evaluated. Group D and group E rabbits each received a different 34-valent vaccine comprising capsular polysaccharides of 17 serotypes in MAPS complexes with SPP2 and capsular polysaccharides of 17 further serotypes in MAPS complexes with CP1, as shown in FIG. 12. Serum was collected on Day 0 prior to first immunization (P0 serum), on Day 14 prior to second immunization (post-first immunization production bleed; P1 serum), and on Day 28 (post-second immunization production bleed; P2 serum).

Anti-CPS3 IgG titers were measured by electrochemiluminescence. Biotinylated CPS3 was coated on plates, blocked, and incubated with rabbit serum samples at various dilutions. The serum samples were quantified as arbitrary units (a.u.) of anti-CPS3 IgG by comparing the serum samples to a common reference standard on each assay plate. The lower limit of quantification (LLOQ) for this assay was 235 a.u..

FIG. 34A shows representative results for IgG titers against CPS3 in rabbit sera of immunization Groups D and E. Data presented includes a subset of IgG titers against capsular polysaccharide (CPS) serotypes presented in FIG. 17A. FIGS. 34B and 34C show immunogenicity and functional antibody responses against PdT (G294P) in rabbit sera of immunization Groups D and E, which are the same data as presented for Groups D and E in FIGS. 14 and 16, respectively. FIG. 34B shows representative titers of PdT toxoid-binding IgG (anti-PdT (G294P)) for rabbit sera of Groups D and E; FIG. 34C shows representative titers of pneumolysin neutralizing antibodies (IC50), also for rabbit sera of Groups D and E. Each point represents serum from one rabbit. Horizontal bars are the geometric mean concentrations of the groups and error bars are 95% CIs.

Conclusions:

- SPP2 is a non-hemolytic fusion protein that can generate pneumolysin (Ply)-neutralizing antibodies (Example 1 and Example 11).
- Neither immunization with SPP2 fusion protein alone nor with PCV13 alone are protective in a stringent serotype 3 IPD model, at high challenge doses of $1.0\times10^7$ CFU; however, immunization with SPP2 in MAPS complexes with CPS1 followed by immunization with PCV13 (which comprises CPS3) significantly protects from IPD. At intermediate challenge doses of $6.7\times10^6$ CFU, immunization with SPP2 in MAPS complexes with CPS1 followed by immunization with fusion protein CP1 in MAPS complexes with CPS3 approximately doubles the protection from IPD observed after immunization with PCV13 alone (Example 12).
- Taken together, the results indicate SPP2 fusion protein (e.g., in MAPS complexes) and CPS3 (e.g., in MAPS complexes, or in the context of glycoconjugates, such as PCV13) can synergize to confer immune protection from IPD.
- This synergistic effect is also observed in a passive immunization model with matched anti-CPS3 titers, suggesting the antibody response elicited by SPP2 fusion protein (e.g., Ply-neutralizing antibodies) is a significant factor for protection from IPD (Example 8 and Example 9).

Example 13. Pneumolysin Neutralization Activity in Rabbits Immunized with Non-His-Tagged SPP2 or PdT(G294P)

The goal of this study was to determine whether immunization with either non-His-tagged SPP2 fusion protein or PdT(G294P) protein induced neutralization activity against native pneumolysin. New Zealand White rabbits (n=3 for non-His-tagged SPP2, and n=5 for PdT(G294P) were immunized intramuscularly with 100 μg of protein on Day 0, Day 14, and Day 28 (two weeks apart). Serum was collected on Day 0 prior to first immunization (P0 serum), Day 14 prior to second immunization (P1 serum), Day 28 (two weeks post-second immunization; P2 serum), and Day 42 (two weeks post-third immunization; P3 serum). Sera were evaluated for IgG titers against PdT (G294P) and titers of pneumolysin neutralizing antibodies (IC50).

Briefly, 80 μL of a 200 ng/mL pneumolysin solution in 1×PBS, 0.1% bovine serum albumin and 10 mM dithiothreitol (DTT) was incubated with 80 μL of serum serial dilutions from rabbits in a V-bottom 96-microwell plate for 1 hour at 37° C., shaking at 350 rpm. Following the initial incubation period, 100 μL of the serum+pneumolysin solution was transferred to a second V-bottom 96-microwell plate and incubated with 100 μL of 2% rabbit red blood cells for an additional 30 minutes at 37° C., shaking at 450 rpm. After centrifugation at 1000×g for 5 minutes to pellet intact red blood cells, the supernatants were harvested, and the absorbance at 545 nm was measured to quantify the extent of hemolysis. Absorbance values were analyzed using SoftMax Pro and Microsoft Excel utilizing a 4-parameter logistic curve fit to determine the serum dilution at which 50% of the hemolytic activity of pneumolysin was inhibited (IC50). The asymmetric 95% confidence intervals were calculated by the GraphPad Prism Software (version 7, La Jolla, CA, USA) together with the geometric means.

Figure 35A:
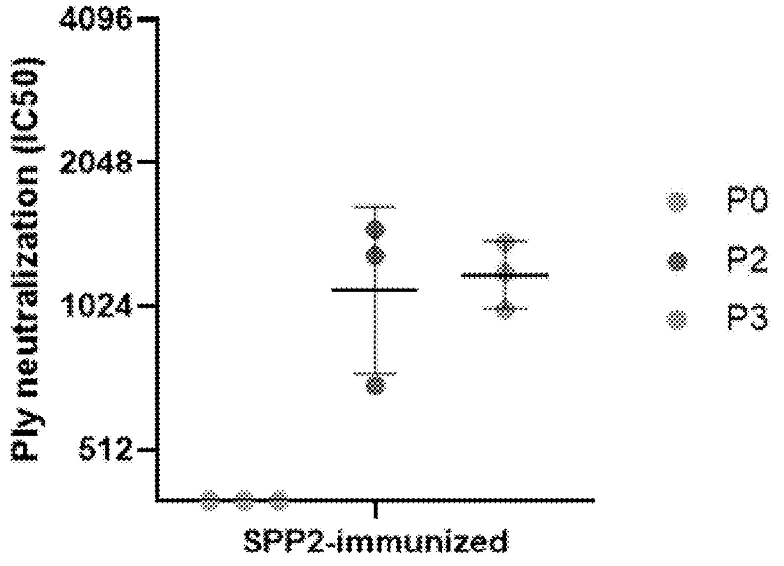
FIGS. 35A and 35B show representative half-maximal inhibitory concentration (IC50) of pneumolysin neutralizing antibodies against the hemolytic activity of native pneumolysin, in sera from rabbits immunized with non-His-tagged SPP2 (FIG. 35A) or PdT (G294P) (FIG. 35B). Each dot on the graph represents one rabbit. Results are expressed as the IC50 (serum dilution) with 95% confidence intervals on the graphs and tabulated as geometric means (IC50) below each graph.
Figure 35B:
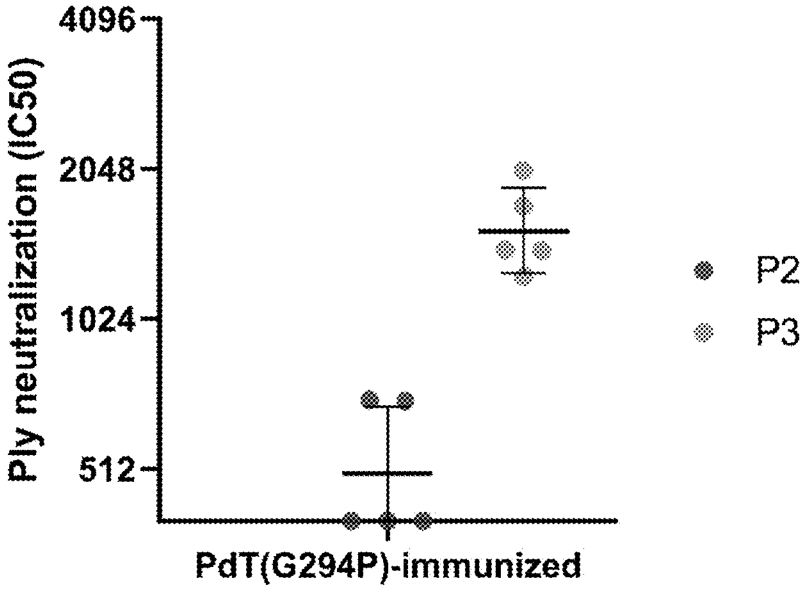

FIGS. 35A and 35B shows representative half-maximal inhibitory concentration (IC50) of pneumolysin neutralizing antibodies against the hemolytic activity of native pneumolysin, in sera from rabbits immunized with non-His-tagged SPP2 (FIG. 35A), or PdT (G294P) (FIG. 35B). Each dot on the graph represents one rabbit. Results are expressed as the IC50 (serum dilution) with 95% confidence intervals on the graphs and tabulated as geometric means (IC50) below each graph. Non-His-tagged SPP2 generated robust pneumolysin neutralizing antibodies, similar to His-tagged SPP2 (FIG. 31, y-axis). The 3-fold increase in IC50 values between P2 and P3 sera for the PdT (G294P) group correlated with a 3-fold boost in IgG titers against PdT (G294P) (data not shown).

Example 14: Toxicity Studies of SPP2 Fusion Protein

The goal of these studies was to determine whether mice receiving SPP2 fusion protein alone or SPP2 fusion protein in MAPS complexes with *Streptococcus pneumoniae* polysaccharide PS1 (1.SPP2 MAPS) by intranasal inhalation exhibit signs of toxicity. The SPP2 fusion protein was either His-tagged or non-His-tagged. Survival of the SPP2-dosed mice was compared to that of mice receiving wild-type Pneumolysin (Ply). SPP2 fusion protein is described in Example 1. Female wild type C57BL/6 mice, 9-11 weeks old, were purchased from Jackson Laboratories. All procedures involving mice were approved by the Mispro Biotech Animal Care and Use Committee (IACUC protocol no. 2021-AF-05), following the National Institutes of Health guidelines for animal housing and care. Each study group consisted of n=10 mice.

TABLE 8

| Study Groups | | |
|---|---|---|
| Group | Test Article | Dose (μg/mouse) |
| Study 1: His-tagged SPP2 fusion protein | | |
| A | Pneumolysin (Ply) | 10 μg |
| B | SPP2 His-tagged | 20 μg |
| C | 1.SPP2 MAPS His-tagged | 20 μg |
| D | SPP2 His-tagged | 100 μg |
| Study 2: non-His-tagged SPP2 fusion protein | | |
| A | Pneumolysin (Ply) | 2 μg |
| B | 1.SPP2 MAPS non-His-tagged | 30 μg |
| C | SPP2 non-His-tagged | 30 μg |

On day 0, all mice were anesthetized and dosed with Ply, SPP2, or SPP2 in MAPS complexes with PS1 (1.SPP2 MAPS) intranasally in the indicated amounts, at a total volume of 50 μL (25 μL/nare). Animals were anesthetized prior to dosing. Following the intranasal dose, the mice were monitored for clinical signs including signs of labored breathing, hunched posture, and ruffled fur at 15-minute intervals for 2 hours, and thereafter every 30 minutes for up to 6 hours after intranasal inoculation. Twenty-four hours after the intranasal dose, all surviving mice were euthanized. Survival of Ply, SPP2 and 1.SPP2 MAPS groups was plotted using GraphPad PRISM.

Figure 36A:
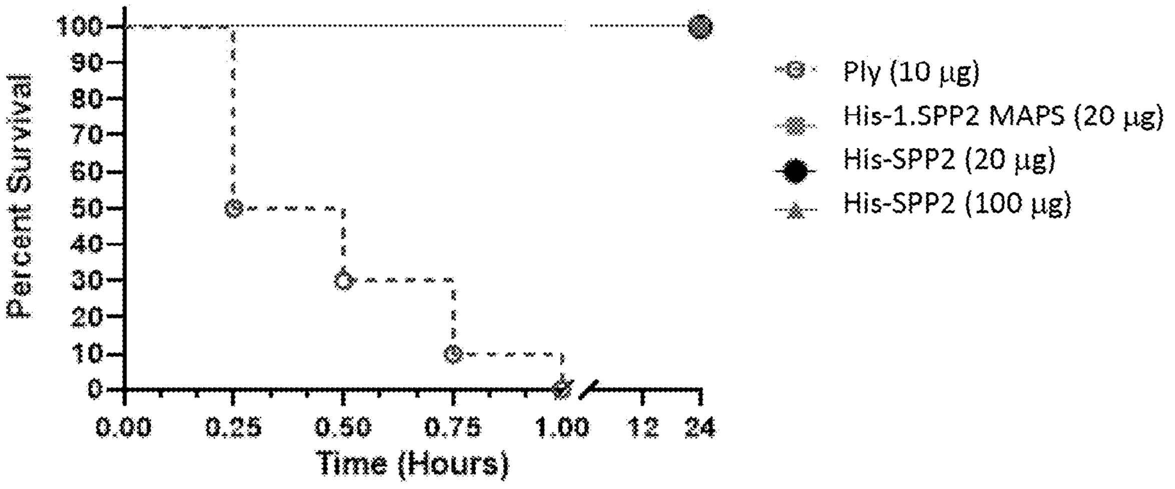
FIGS. 36A and 36B show representative survival curves, up to 24 hours after dosing, for groups of mice receiving the indicated amounts of pneumolysin (Ply), SPP2 fusion protein alone, or SPP2 fusion protein in MAPS complexes with *Streptococcus pneumoniae* polysaccharide SP1 (1.SPP2 MAPS) by intranasal inoculation.
Figure 36B:
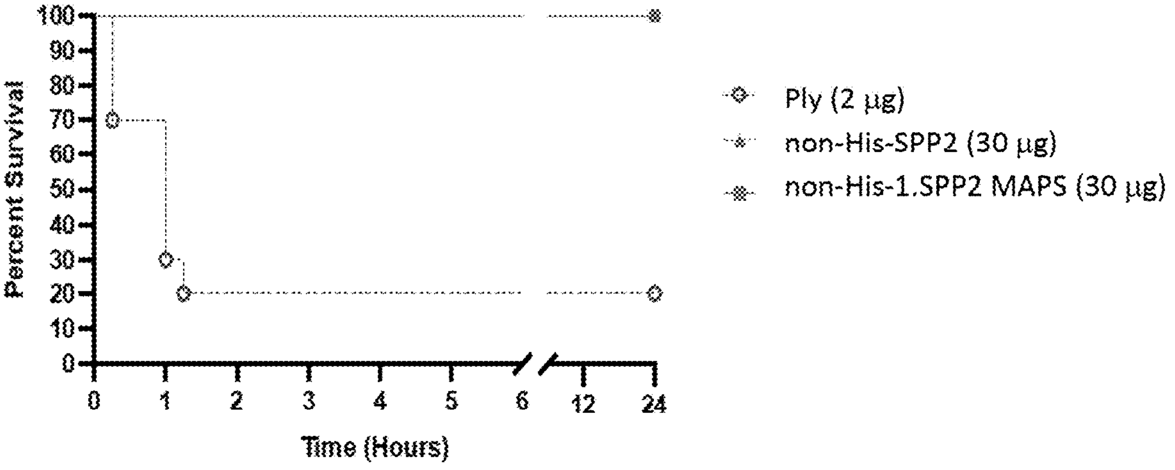

FIGS. 36A and 36B show representative survival curves, up to 24 hours after dosing, for groups of mice receiving Ply, SPP2 and 1.SPP2 MAPS at the indicated amounts by intranasal inoculation. FIG. 36A shows representative results for groups inoculated with His-tagged SPP2 and 1.SPP2 MAPS. Mice receiving 20 μg or 100 μg of His-tagged SPP2 or 20 μg His-tagged 1.SPP2 MAPS displayed no signs of toxicity and exhibited 100% survival at 24 hours post-dose. FIG. 36B shows representative results for groups inoculated with non-His-tagged SPP2 and 1.SPP2 MAPS. Mice receiving 30 μg non-His-tagged SPP2 or 30 μg non-His-tagged 1.SPP2 MAPS displayed no signs of toxicity and exhibited 100% survival at 24 hours post-dose. Control groups receiving 10 μg or 2 μg Ply displayed overt toxicity and exhibited 100% and 80% lethality, respectively, by 1-hour post-dose. In summary, the data demonstrate no inhalation toxicity of SPP2 or 1.SPP2 MAPS in mice, whether the fusion protein is His-tagged or non-His-tagged.

Example 15: Serotype Distribution Study (II)

Figure 37:
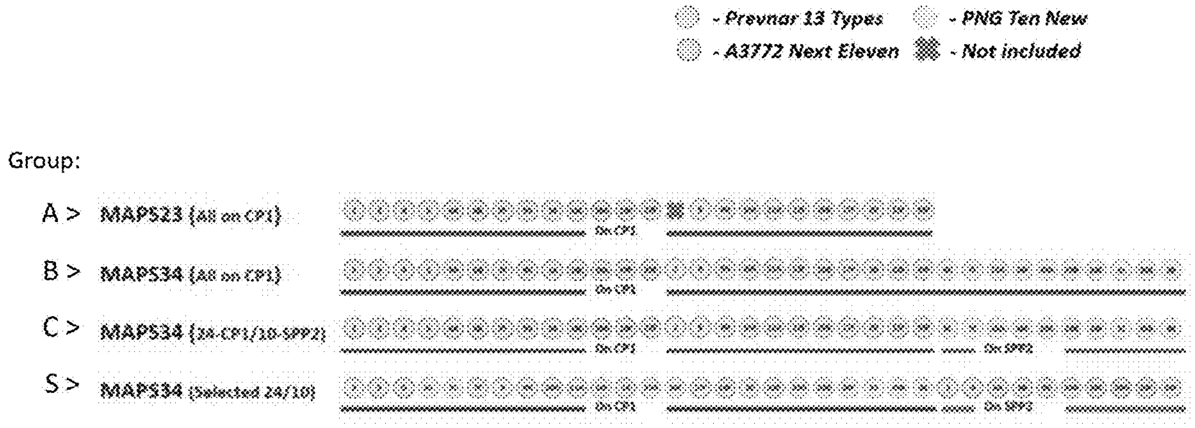
FIG. 37 is a schematic depicting various exemplary multi-valent vaccine candidates with different combinations of *S. pneumoniae* polysaccharides (serotypes) with antigenic fusion proteins CP1 and SPP2. The immunization group (A, B, C, and S) corresponding to each vaccine candidate is indicated. While the figure illustrates these multivalent vaccine candidates in a MAPS format as described herein, in some embodiments, such multivalent vaccine candidates can be provided in a conjugated format where a *S. pneumoniae* polysaccharide is conjugated to an antigenic polypeptide or a fusion protein as described herein (e.g., CP1 and/or SPP2).

The goal of this study is to further define the preferred combinations of *S. pneumoniae* polysaccharides (serotypes) with antigenic fusion proteins CP1 and SPP2, in order to optimize the immune response profile of 34-valent MAPS vaccine candidates. The vaccine candidates used in this study comprise different combinations of the *S. pneumoniae* polysaccharides and fusion proteins CP1 only, SPP2 only, or both SPP2 and CP1, as shown in FIG. 37 and Table 9.

Production of Rabbit Hyperimmune Sera

Hyperimmune sera are obtained using 4 or more groups of New Zealand White rabbits (Cocalico Biologicals), each comprising up to 20 rabbits. On Day 0, groups of rabbits are immunized intramuscularly according to Table 9 below. A second immunization is administered on Day 14. Serum is collected on Day 0 prior to first immunization (P0 serum), on Day 14 prior to second immunization (post-first immunization production bleed; P1 serum), and on Day 28 (post-second immunization production bleed; P2 serum).

TABLE 9

Immunization Groups for Production of Rabbit Hyperimmune Sera

| Group | Adjuvant |
|---|---|
| A: 23 V MAPS CP1 (All on CP1) | $AlPO_4$ |
| B: 34 V MAPS CP1 (All on CP1) | $AlPO_4$ |
| C: 24 V MAPS CP1/10 V MAPS SPP2 (24-CP1/10-SPP2) | $AlPO_4$ |
| S: 24 V MAPS CP1/10 V MAPS SPP2 (Selected 24/10) | $AlPO_4$ |

IgG Responses to Proteins

To measure titers of rabbit IgG antibody against the *S. pneumoniae* portions of the fusion proteins CP1 and SPP2, an Enzyme-Linked Immunosorbent Assays (ELISA) specific for each fusion protein is performed. For CP1, IgG response is assessed against the SP1500-SP0785 fusion. For SPP2, IgG responses are separately assessed against PdT (G294P) and SP0435 polypeptides.

MaxiSorp 96-well plates (ThermoFisher Scientific, Waltham, MA, USA) are coated with 100 μL per well of 2.0 g/ml SP1500-SP0785, or PdT (G294P), or SP0435 in 1× Dulbecco's phosphate-buffered saline (DPBS) overnight at room temperature. Plates are washed with 1×DPBS with 0.05% Tween 20 (DPBS-T) and then blocked with 200 μL per well of 1% BSA in DPBS-T for 1 hour. Plates are washed with 1×DPBS-T prior to the addition of rabbit sera for testing diluted in DPBS-T. Primary antisera dilutions are incubated for 1 hour at room temperature followed by washing with DPBS-T. Goat anti-rabbit IgG (Fc)-HRP (Jackson ImmunoResearch, West Grove, PA, USA) is diluted 1:100,000 and 100 μl is added to each well, followed by a 1-hour incubation at room temperature. Plates are washed with DPBS-T; 100 μL of tetramethylbenzidine (TMB peroxidase substrate-KPL) is added to each well, incubated for 30 minutes, and stopped with 100 μL of 1 N HCl. Absorbance is read on a SpectraMax i3× at $OD_{450}$. Absorbance values are analyzed using SoftMax Pro and Microsoft Excel utilizing a 4-parameter logistic curve fit for a standard with known concentration. Geometric mean titers (GMTs) are calculated by transforming individual antibody titers to their $\log_{10}$ concentrations, taking the means of the transformed concentrations from each animal group at each time point, and subsequently transforming those means to GMTs by taking their anti-$\log_{10}$. The asymmetric 95% confidence intervals (CI) are calculated by the GraphPad Prism Software (version 7, La Jolla, CA, USA) together with the GMTs.

Neutralizing Antibody Responses to Proteins

Pneumolysin neutralization assays are performed to determine whether antibodies against fusion protein SPP2 (specifically, the PdT(G294P) portion of SPP2) are able to neutralize the hemolytic activity of native pneumolysin (red blood cell lysis). Briefly, 50 μL of a 200 ng/mL pneumolysin solution in 1×PBS, 0.1% bovine serum albumin and 10 mM dithiothreitol (DTT) is incubated with 50 μL of serum serial dilutions from rabbits in a V-bottom 96-microwell plate for 30 minutes at 37° C. with 5% $CO_2$ and shaking at 350 rpm. Following the initial incubation period, 50 μL of 2% rabbit red blood cells is added and incubated for an additional 30 minutes using the same conditions. After centrifugation at 1000×g for 5 min to pellet intact red blood cells, the supernatants are harvested and the absorbance at 545 nm is measured to quantify the extent of hemolysis. Absorbance is read on a SpectraMax i3× at OD545. Absorbance values are analyzed using SoftMax Pro and Microsoft Excel utilizing a 4-parameter logistic curve fit to determine the serum dilution at which 50% of the hemolytic activity of pneumolysin is inhibited (IC50). For samples that do not achieve 50% neutralization, the lowest dilution tested is recorded. Geometric mean titers (GMTs) are calculated by transforming individual IC50s to their $\log_{10}$ concentrations, taking the means of the transformed concentrations from each animal group at each time point, and subsequently transforming those means to GMTs by taking their anti-log 10. The asymmetric 95% confidence intervals (CI) are calculated by the GraphPad Prism Software (version 7, La Jolla, CA, USA) together with the GMTs.

IgG and Functional (OPA) Antibody Responses to S. *Pneumoniae* Polysaccharides

To evaluate IgG antibody levels specific for the 24 polysaccharide serotypes 1, 2, 3, 4, 5, 6A, 6B, 7F, 8, 9V, 9N, 10A, 11A, 12F, 14, 15B, 17F, 18C, 19A, 19F, 22F, 23F, and 33F in immunized rabbits, an electro-chemiluminescent-based Meso Scale Discovery immunoassay (MSD) is performed using a reference standard. Briefly, 5-fold serial dilutions are created starting with a ~1:200 dilution of the reference standard in PBS-T, 1% BSA, and 5 μg/mL CWPS. The control and experimental rabbit serum samples are diluted 1000-fold, 5000-fold, and 25000-fold with PBS-T, 1% BSA, and 5 μg/mL CWPS, respectively. Plates are washed with 1×PBS-T prior to adding the reference standard, control serum and experimental rabbit sera. After incubating at room temperature for one hour, plates are washed with PBS-T and secondary anti-rabbit SULFO-conjugated antibody is added. The plates are washed with PBS-T; 1× Read Buffer is added and the plates are read using an MSD Meso QuickPlex SQ 120 Model No. 1300. IgG antibody levels for the additional 10 polysaccharide serotypes 6C, 7C, 15A, 16F, 23A, 23B, 24F, 31, 35B, and 38 are determined using an MSD-based assay in end-point dilution format.

To evaluate functional (opsonophagocytic) antibody levels specific for the polysaccharide serotypes in immunized rabbits, a multiplex opsonophagocytic assay (MOPA) is used. The MOPA measures the level of serum antibodies specific to 4 *S. pneumoniae* capsular serotypes simultaneously in the same reaction. To do so, *S. pneumoniae* serotypes are selected and propagated based on their unique antibiotic resistance to 4 antibiotics (e.g., optochin, spectinomycin, streptomycin and trimethoprim). Heat-inactivated rabbit serum samples are serially diluted and mixed with *S. pneumoniae* bacteria organized in different cassettes (opsonization step). After an incubation period, complement (baby rabbit complement, BRC) and phagocytes (HL-60) are added to the reaction (complement-mediated phagocytosis step). After a second incubation period, an aliquot of the mixture is evaluated to determine the number of surviving bacteria using appropriate antibiotic-containing media. Titers of functional antibodies (OPA) are calculated per standard protocol.

In a first analysis, antibody levels are graphed as arbitrary units (a.u., for IgG) and titers (for functional antibodies) for comparison across all immunization groups. In another analysis, IgG levels measured in sera from each immunization group are compared pair-wise to a baseline. For each comparison, IgG levels against *S. pneumoniae* polysaccharides are expressed as geometric mean titer (GMT) ratio at 95% confidence interval, relative to a baseline represented as a dotted line at GMT ratio of 1. If the point estimate of the GMT ratio >1, then anti-polysaccharide antibody levels for a given immunization group are higher. If the point estimate of the GMT ratio <1, then anti-polysaccharide antibody levels for a given immunization group are lower.

Sequence Listing

SEQ ID NO: 1, Rhizavidin protein, full-length [aa 1-179]:
MIITSLYATFGTIADGRRTSGGKTMIRTNAVAALVFAVATSALAFDASNFKDFSSIASASS
SWQNQSGSTMIIQVDSFGNVSGQYVNRAQGTGCQNSPYPLTGRVNGTFIAFSVGWNNS
TENCNSATGWTGYAQVNGNNTEIVTSWNLAYEGGSGPAIEQGQDTFQYVPTTENKSLL
KD SEQ ID NO: 2, truncated rhizavidin protein [aa 45-179], denoted Rhavi:
FDASNFKDFSSIASASSSWQNQSGSTMIIQVDSFGNVSGQYVNRAQGTGCQNSPYPLTGR
VNGTFIAFSVGWNNSTENCNSATGWTGYAQVNGNNTEIVTSWNLAYEGGSGPAIEQGQ
DTFQYVPTTENKSLLKD SEQ ID NO: 3, *Streptococcus pneumoniae* Pneumolysin protein:
MANKAVNDFILAMNYDKKKLLTHQGESIENRFIKEGNQLPDEFVVIERKKRSLSTNTSDI
SVTATNDSRLYPGALLVVDETLLENNPTLLAVDRAPMTYSIDLPGLASSDSFLQVEDPSN
SSVRGAVNDLLAKWHQDYGQVNNVPARMQYEKITAHSMEQLKVKFGSDFEKTGNSLD
IDFNSVHSGEKQIQIVNFKQIYYTVSVDAVKNPGDVFQDTVTVEDLKQRGISAERPLVYI
SSVAYGRQVYLKLETTSKSDEVEAAFEALIKGVKVAPQTEWKQILDNTEVKAVILGGDP
SSGARVVTGKVDMVEDLIQEGSRFTADHPGLPISYTTSFLRDNVVATFQNSTDYVETKV
TAYRNGDLLLDHSGAYVAQYYITWDELSYDHQGKEVLTPKAWDRNGQDLTAHFTTSIP
LKGNVRNLSVKIRECTGLAWEWWRTVYEKTDLPLVRKRTISIWGTTLYPQVEDKVEND SEQ ID NO: 4, *Streptococcus pneumoniae* Pneumolysin protein with mutations D385N, C428G, and W433F, denoted PdT:
MANKAVNDFILAMNYDKKKLLTHQGESIENRFIKEGNQLPDEFVVIERKKRSLSTNTSDI
SVTATNDSRLYPGALLVVDETLLENNPTLLAVDRAPMTYSIDLPGLASSDSFLQVEDPSN
SSVRGAVNDLLAKWHQDYGQVNNVPARMQYEKITAHSMEQLKVKFGSDFEKTGNSLD
IDFNSVHSGEKQIQIVNFKQIYYTVSVDAVKNPGDVFQDTVTVEDLKQRGISAERPLVYI
SSVAYGRQVYLKLETTSKSDEVEAAFEALIKGVKVAPQTEWKQILDNTEVKAVILGGDP
SSGARVVTGKVDMVEDLIQEGSRFTADHPGLPISYTTSFLRDNVVATFQNSTDYVETKV
TAYRNGDLLLDHSGAYVAQYYITWDELSYNHQGKEVLTPKAWDRNGQDLTAHFTTSIP
LKGNVRNLSVKIREGTGLAFEWWRTVYEKTDLPLVRKRTISIWGTTLYPQVEDKVEND SEQ ID NO: 5, *Streptococcus pneumoniae* Pneumolysin protein with mutations G294P, D385N, C428G, and W433F, denoted PdT(G294P):
MANKAVNDFILAMNYDKKKLLTHQGESIENRFIKEGNQLPDEFVVIERKKRSLSTNTSDI
SVTATNDSRLYPGALLVVDETLLENNPTLLAVDRAPMTYSIDLPGLASSDSFLQVEDPSN
SSVRGAVNDLLAKWHQDYGQVNNVPARMQYEKITAHSMEQLKVKFGSDFEKTGNSLD
IDFNSVHSGEKQIQIVNFKQIYYTVSVDAVKNPGDVFQDTVTVEDLKQRGISAERPLVYI
SSVAYGRQVYLKLETTSKSDEVEAAFEALIKGVKVAPQTEWKQILDNTEVKAVILGPDP
SSGARVVTGKVDMVEDLIQEGSRFTADHPGLPISYTTSFLRDNVVATFQNSTDYVETKV
TAYRNGDLLLDHSGAYVAQYYITWDELSYNHQGKEVLTPKAWDRNGQDLTAHFTTSIP
LKGNVRNLSVKIREGTGLAFEWWRTVYEKTDLPLVRKRTISIWGTTLYPQVEDKVEND SEQ ID NO: 6, *Streptococcus pneumoniae* Pneumolysin PdT(G294P) [aa 2-470] protein:
ANKAVNDFILAMNYDKKKLLTHQGESIENRFIKEGNQLPDEFVVIERKKRSLSTNTSDIS
VTATNDSRLYPGALLVVDETLLENNPTLLAVDRAPMTYSIDLPGLASSDSFLQVEDPSNS
SVRGAVNDLLAKWHQDYGQVNNVPARMQYEKITAHSMEQLKVKFGSDFEKTGNSLDI
DFNSVHSGEKQIQIVNFKQIYYTVSVDAVKNPGDVFQDTVTVEDLKQRGISAERPLVYIS
SVAYGRQVYLKLETTSKSDEVEAAFEALIKGVKVAPQTEWKQILDNTEVKAVILGPDPS
SGARVVTGKVDMVEDLIQEGSRFTADHPGLPISYTTSFLRDNVVATFQNSTDYVETKVT
AYRNGDLLLDHSGAYVAQYYITWDELSYNHQGKEVLTPKAWDRNGQDLTAHFTTSIPL
KGNVRNLSVKIREGTGLAFEWWRTVYEKTDLPLVRKRTISIWGTTLYPQVEDKVEND -continued Sequence Listing SEQ ID NO: 7, *Streptococcus pneumoniae* SP0435 protein, full length, TIGR4 strain (GenBank: ABJ54475.1):
MIEASKLKAGMTFETADGKLIRVLEASHHKPGKGNTIMRMKLRDVRTGSTFDTSYRPEE
KFEQAIIETVPAQYLYKMDDTAYFMNTETYDQYEIPVVNVENELLYILENSDVKIQFYGT
EVIGVTVPTTVELTVAETQPSIKGATVTGSGKPATMETGLVVNVPDFIEAGQKLVINTAE
GTYVSRA SEQ ID NO: 8, *Streptococcus pneumoniae* SP0435 [aa 62-185] protein, TIGR4 strain:
EQAIIETVPAQYLYKMDDTAYFMNTETYDQYEIPVVNVENELLYILENSDVKIQFYGTEV
IGVTVPTTVELTVAETQPSIKGATVTGSGKPATMETGLVVNVPDFIEAGQKLVINTAEGT
YVSR SEQ ID NO: 9, SP0785 protein, full-length [aa 1-399], TIGR4 strain: (Note: One T394A mismatch with SP0785 NCBI Sequences ABJ54007.1 and YP816180)
MKKKNGKAKKWQLYAAIGAASVVVLGAGGILLFRQPSQTALKDEPTHLVVAKEGSVA
SSVLLSGTVTAKNEQYVYFDASKGDLDEILVSVGDKVSEGQALVKYSSSEAQAAYDSA
SRAVARADRHINELNQARNEAASAPAPQLPAPVGGEDATVQSPTPVAGNSVASIDAQLG
DARDARADAAAQLSKAQSQLDATTVLSTLEGTVVEVNSNVSKSPTGASQVMVHIVSNE
NLQVKGELSEYNLANLSVGQEVSFTSKVYPDKKWTGKLSYISDYPKNNGEAASPAAGN
NTGSKYPYTIDVTGEVGDLKQGFSVNIEVKSKTKAILVPVSSLVMDDSKNYVWIVDEQQ
KAKKVEVSLGNADAENQEITSGLTNGAKVISNPTSSLEEGKEVKADEATN SEQ ID NO: 10, SP0785 protein lacking signal sequence [aa 33-399]: (Note: One T394A mismatch with SP0785 NCBI Sequences ABJ54007.1 and YP816180)
FRQPSQTALKDEPTHLVVAKEGSVASSVLLSGTVTAKNEQYVYFDASKGDLDEILVSVG
DKVSEGQALVKYSSSEAQAAYDSASRAVARADRHINELNQARNEAASAPAPQLPAPVG
GEDATVQSPTPVAGNSVASIDAQLGDARDARADAAAQLSKAQSQLDATTVLSTLEGTV
VEVNSNVSKSPTGASQVMVHIVSNENLQVKGELSEYNLANLSVGQEVSFTSKVYPDKK
WTGKLSYISDYPKNNGEAASPAAGNNTGSKYPYTIDVTGEVGDLKQGFSVNIEVKSKTK
AILVPVSSLVMDDSKNYVWIVDEQQKAKKVEVSLGNADAENQEITSGLTNGAKVISNPT
SSLEEGKEVKADEATN SEQ ID NO: 11, SP1500 protein, full-length [aa 1-278], TIGR4 strain:
MKKWMLVLVSLMTALFLVACGKNSSETSGDNWSKYQSNKSITIGFDSTFVPMGFAQKD
GSYAGFDIDLATAVFEKYGITVNWQPIDWDLKEAELTKGTIDLIWNGYSATDERREKVA
FSNSYMKNEQVLVTKKSSGITTAKDMTGKTLGAQAGSSGYADFEANPEILKNIVANKEA
NQYQTFNEALIDLKNDRIDGLLIDRVYANYYLEAEGVLNDYNVFTVGLETEAFAVGAR
KEDTNLVKKINEAFSSLYKDGKFQEISQKWFGEDVATKEVKEGQ SEQ ID NO: 12, SP1500 [aa 27-278]:
TSGDNWSKYQSNKSITIGFDSTFVPMGFAQKDGSYAGFDIDLATAVFEKYGITVNWQPI
DWDLKEAELTKGTIDLIWNGYSATDERREKVAFSNSYMKNEQVLVTKKSSGITTAKDM
TGKTLGAQAGSSGYADFEANPEILKNIVANKEANQYQTFNEALIDLKNDRIDGLLIDRVY
ANYYLEAEGVLNDYNVFTVGLETEAFAVGARKEDTNLVKKINEAFSSLYKDGKFQEISQ
KWFGEDVATKEVKEGQ SEQ ID NO: 13, Ply gene encoding Ply protein, full-length [aa 1-470]
ATGGCAAATAAAGCAGTAAATGACTTTATACTAGCTATGAATTACGATAAAAAGAA
ACTCTTGACCCATCAGGGAGAAAGTATTGAAAATCGTTTCATCAAAGAGGGTAATC
AGCTACCCGATGAGTTTGTTGTTATCGAAAGAAAGAAGCGGAGCTTGTCGACAAAT
ACAAGTGATATTTCTGTAACAGCTACCAACGACAGTCGCCTCTATCCTGGAGCACTT
CTCGTAGTGGATGAGACCTTGTTAGAGAATAATCCCACTCTTCTTGCGGTCGATCGT
GCTCCGATGACTTATAGTATTGATTTGCCTGGTTTGGCAAGTAGCGATAGCTTTCTCC
AAGTGGAAGACCCCAGCAATTCAAGTGTTCGCGGAGCGGTAAACGATTTGTTGGCT
AAGTGGCATCAAGATTATGGTCAGGTCAATAATGTCCCAGCTAGAATGCAGCATGA
AAAAATCACGGCTCACAGCATGGAACAACTCAAGGTCAAGTTTGGTTCTGACTTTGA
AAAGATAGGGAATTCTCTTGATATTGATTTTAACTCTGTCCATTCAGGCGAAAAGCA
GATTCAGATTGTTAATTTTAAGCAGATTTATTATACAGTCAGCGTAGATGCTGTTAA
AAATCCAGGAGATGTGTTTCAAGATACTGTAACGGTAGAGGATTTAAGGCAGAGAG
GAATTTCTGCAGAGCGTCCTTTGGTCTATATTTCGAGTGTTGCTTATGGGCGCCAAGT
CTATCTCAAGTTGGAAACCACGAGTAAGAGTGATGAAGTAGAGGCTGCTTTTGAATC
TTTGATAAAAGGAGTAGCTCCTCAGACAGAGTGGAAGCAGATTTTGGACAATACAG
AAGTGAAGGCGGTTATTTTAGGGGGCGACCCAAGTTCGGGTGCCCGAGTTGTAACA
GGCAAGGTGGATATGGTAGAGGACTTGATTCAAGAAGGCAGTCGCTTTACAGCCGA
TCATCCAGGCTTGCCGATTTCCTATACAACTTCTTTTTTACGTGACAATGTAGTTGCG
ACCTTTCAAAACAGTACAGACTATGTTGAGACTAAGGTTACAGCTTACAGAAACGG
AGATTTACTGCTGGATCATAGTGGTGCCTATGTTGCTCAATATTATATTACTTGGGAT
GAATTATCCTATGATCATCAAGGCAAGGAAGTCTTGACTCCTAAGGCTTGGGACAGA
AATGGGCAGGATTTGACGGCTCACTTTACCACTAGTATTCCTTTAAAAGGGAATGTT Sequence Listing CGCAATCTCTCTGTCAAAATTAGAGAGTGTACCGGGCTTGCCTGGGAATGGTGGCGT
ACGGTTTATGAAAAAACCGATTTGCCACTAGTGCGTAAGCGGACGATTTCTATTTGG
GGAACAACTCTCTATCCTCAGGTAGAGGATAAGGTAGAAAATGATTAG SEQ ID NO: 14, codon-optimized nucleotide sequence encoding PdT(G294P) [aa 1-470]:
ATGGCGAACAAGGCGGTGAACGATTTTATCCTGGCGATGAACTATGACAAGAAGAA
ACTGCTGACCCACCAAGGCGAGAGCATTGAGAACCGTTTCATTAAAGAAGGCAACC
AGCTGCCGGACGAGTTTGTGGTTATCGAGCGTAAGAAACGTAGCCTGAGCACCAAC
ACCAGCGACATTAGCGTGACCGCGACCAACGATAGCCGTCTGTACCCGGGTGCGCT
GCTGGTTGTGGATGAAACCCTGCTGGAAAACAACCCGACCCTGCTGGCGGTGGACC
GTGCGCCGATGACCTATAGCATCGATCTGCCGGGTCTGGCGAGCAGCGACAGCTTCC
TGCAAGTTGAGGATCCGAGCAACAGCAGCGTGCGTGGTGCGGTTAACGACCTGCTG
GCGAAGTGGCACCAGGATTACGGCCAAGTGAACAACGTTCCGGCGCGTATGCAGTA
TGAAAAAATCACCGCGCACAGCATGGAGCAACTGAAGGTTAAATTCGGTAGCGACT
TTGAAAAGACCGGCAACAGCCTGGACATTGATTTCAACAGCGTGCACAGCGGCGAG
AAGCAGATCCAAATCGTTAACTTCAAGCAGATCTACTACACCGTGAGCGTTGACGCG
GTGAAGAACCCGGGTGACGTTTTCCAGGATACCGTGACCGTTGAAGATCTGAAACA
ACGTGGCATTAGCGCGGAGCGTCCGCTGGTGTACATCAGCAGCGTTGCGTACGGTCG
TCAAGTGTATCTGAAGCTGGAAACCACCAGCAAAAGCGATGAGGTTGAAGCGGCGT
TTGAGGCGCTGATTAAGGGCGTGAAAGTTGCGCCGCAGACCGAATGGAAGCAAATT
CTGGACAACACCGAGGTGAAAGCGGTTATTCTGGGCCCGGATCCGAGCAGCGGCGC
GCGTGTGGTTACCGGTAAAGTGGACATGGTTGAGGATCTGATTCAGGAAGGTAGCC
GTTTTACCGCGGACCACCCGGGCCTGCCGATCAGCTACACCACCAGCTTCCTGCGTG
ACAACGTGGTTGCGACCTTTCAAAACAGCACCGATTACGTGGAAACCAAGGTTACC
GCGTATCGTAACGGTGACCTGCTGCTGGACCACAGCGGTGCGTACGTGGCGCAGTA
CTATATCACCTGGGATGAACTGAGCTATAACCACCAGGGTAAAGAGGTGCTGACCC
CGAAAGCGTGGGACCGTAACGGCCAGGATCTGACCGCGCACTTCACCACCAGCATT
CCGCTGAAGGGCAACGTGCGTAACCTGAGCGTTAAAATCCGTGAGGGTACCGGCCT
GGCGTTTGAATGGTGGCGTACCGTGTACGAGAAGACCGACCTGCCGCTGGTTCGTAA
ACGTACCATCAGCATTTGGGGTACCACCCTGTATCCGCAGGTGGAGGACAAAGTTG
AAAATGAT SEQ ID NO: 15, codon-optimized nucleotide sequence encoding PdT(G294P) [aa 2-470]:
GCGAACAAGGCGGTGAACGATTTTATCCTGGCGATGAACTATGACAAGAAGAAACT
GCTGACCCACCAAGGCGAGAGCATTGAGAACCGTTTCATTAAAGAAGGCAACCAGC
TGCCGGACGAGTTTGTGGTTATCGAGCGTAAGAAACGTAGCCTGAGCACCAACACC
AGCGACATTAGCGTGACCGCGACCAACGATAGCCGTCTGTACCCGGGTGCGCTGCT
GGTTGTGGATGAAACCCTGCTGGAAAACAACCCGACCCTGCTGGCGGTGGACCGTG
CGCCGATGACCTATAGCATCGATCTGCCGGGTCTGGCGAGCAGCGACAGCTTCCTGC
AAGTTGAGGATCCGAGCAACAGCAGCGTGCGTGGTGCGGTTAACGACCTGCTGGCG
AAGTGGCACCAGGATTACGGCCAAGTGAACAACGTTCCGGCGCGTATGCAGTATGA
AAAAATCACCGCGCACAGCATGGAGCAACTGAAGGTTAAATTCGGTAGCGACTTTG
AAAAGACCGGCAACAGCCTGGACATTGATTTCAACAGCGTGCACAGCGGCGAGAAG
CAGATCCAAATCGTTAACTTCAAGCAGATCTACTACACCGTGAGCGTTGACGCGGTG
AAGAACCCGGGTGACGTTTTCCAGGATACCGTGACCGTTGAAGATCTGAAACAACG
TGGCATTAGCGCGGAGCGTCCGCTGGTGTACATCAGCAGCGTTGCGTACGGTCGTCA
AGTGTATCTGAAGCTGGAAACCACCAGCAAAAGCGATGAGGTTGAAGCGGCGTTTG
AGGCGCTGATTAAGGGCGTGAAAGTTGCGCCGCAGACCGAATGGAAGCAAATTCTG
GACAACACCGAGGTGAAAGCGGTTATTCTGGGCCCGGATCCGAGCAGCGGCGCGCG
TGTGGTTACCGGTAAAGTGGACATGGTTGAGGATCTGATTCAGGAAGGTAGCCGTTT
TACCGCGGACCACCCGGGCCTGCCGATCAGCTACACCACCAGCTTCCTGCGTGACAA
CGTGGTTGCGACCTTTCAAAACAGCACCGATTACGTGGAAACCAAGGTTACCGCGTA
TCGTAACGGTGACCTGCTGCTGGACCACAGCGGTGCGTACGTGGCGCAGTACTATAT
CACCTGGGATGAACTGAGCTATAACCACCAGGGTAAAGAGGTGCTGACCCCGAAAG
CGTGGGACCGTAACGGCCAGGATCTGACCGCGCACTTCACCACCAGCATTCCGCTG
AAGGGCAACGTGCGTAACCTGAGCGTTAAAATCCGTGAGGGTACCGGCCTGGCGTT
TGAATGGTGGCGTACCGTGTACGAGAAGACCGACCTGCCGCTGGTTCGTAAACGTA
CCATCAGCATTTGGGGTACCACCCTGTATCCGCAGGTGGAGGACAAAGTTGAAAAT
GAT SEQ ID NO: 16, SP0435 gene encoding SP0435 protein, full-length [aa 1-186], TIGR4 strain:
ATGATTGAAGCAAGTAAATTAAAAGCTGGTATGACCTTTGAAACAGCTGACGGCAA
ATTGATTCGCGTTTTGGAAGCTAGTCACCACAAACCAGGTAAAGGAAACACGATCA
TGCGTATGAAATTGCGTGATGTCCGTACTGGTTCTACATTTGACACAAGCTACCGTC
CAGAGGAAAAATTTGAACAAGCTATTATCGAGACTGTCCCAGCTCAATACTTGTACA
AAATGGATGACACAGCATACTTCATGAATACAGAAACTTATGACCAATACGAAATC
CCTGTAGTCAATGTTGAAAACGAATTGCTTTACATCCTTGAAAACTCTGATGTGAAA
ATCCAATTCTACGGAACTGAAGTGATCGGTGTCACCGTTCCTACTACTGTTGAGTTG
ACAGTTGCTGAAACTCAACCATCTATCAAAGGTGCTACTGTTACAGGTTCTGGTAAA
CCAGCAACGATGGAAACTGGACTTGTCGTAAACGTTCCAGACTTCATCGAAGCAGG
ACAAAAACTCGTTATCAACACTGCAGAAGGAACTTACGTTTCTCGTGCC -continued Sequence Listing SEQ ID NO: 17, SP0785 gene encoding SP0785 protein,
full-length [aa 1-399], TIGR4 strain:
ATGAAGAAAAAGAATGGTAAAGCTAAAAAGTGGCAACTGTATGCAGCAATCGGTGC
TGCGAGTGTAGTTGTATTGGGTGCTGGGGGGATTTTACTCTTTAGACAACCTTCTCA
GACTGCTCTAAAAGATGAGCCTACTCATCTTGTTGTTGCCAAGGAAGGAAGCGTGGC
CTCCTCTGTTTTATTGTCAGGGACAGTAACAGCAAAAAATGAACAATATGTTTATTT
TGATGCTAGTAAGGGTGATTTAGATGAAATCCTTGTTTCTGTGGGCGATAAGGTCAG
CGAAGGGCAGGCTTTAGTCAAGTACAGTAGTTCAGAAGCGCAGGCGGCCTATGATT
CAGCTAGTCGAGCAGTAGCTAGGGCAGATCGTCATATCAATGAACTCAATCAAGCA
CGAAATGAAGCCGCTTCAGCTCCGGCTCCACAGTTACCAGCGCCAGTAGGAGGAGA
AGATGCAACGGTGCAAAGCCCAACTCCAGTGGCTGGAAATTCTGTTGCTTCTATTGA
CGCTCAATTGGGTGATGCCCGTGATGCGCGTGCAGATGCTGCGGCGCAATTAAGCA
AGGCTCAAAGTCAATTGGATGCAACAACTGTTCTCAGTACCCTAGAGGGAACTGTG
GTCGAAGTCAATAGCAATGTTTCTAAATCTCCAACAGGGGCGAGTCAAGTTATGGTT
CATATTGTCAGCAATGAAAATTTACAAGTCAAGGGAGAATTGTCTGAGTACAATCTA
GCCAACCTTTCTGTAGGTCAAGAAGTAAGCTTTACTTCTAAAGTGTATCCTGATAAA
AAATGGACTGGGAAATTAAGCTATATTTCTGACTATCCTAAAAACAATGGTGAAGC
AGCTAGTCCAGCAGCCGGGAATAATACAGGTTCTAAATACCCTTATACTATTGATGT
GACAGGCGAGGTTGGTGATTTGAAACAAGGTTTTTCTGTCAACATTGAGGTTAAAAG
CAAAACTAAGGCTATTCTTGTTCCTGTTAGCAGTCTAGTAATGGATGATAGTAAAAA
TTATGTCTGGATTGTGGATGAACAACAAAAGGCTAAAAAAGTTGAGGTTTCATTGGG
AAATGCTGACGCAGAAAATCAAGAAATCACTTCTGGTTTAACGAACGGTGCTAAGG
TCATCAGTAATCCAACATCTTCCTTGGAAGAAGGAAAAGAGGTGAAGGCTGATGAA
GCAACTAAT SEQ ID NO: 18, SP1500 gene encoding SP1500 protein,
full-length [aa 1-278], TIGR4 strain:
ATGAAAAAAATGGATGCTTGTATTAGTCAGTCTGATGACTGCTTTGTTCTTAGTAGCTT
GTGGGAAAAAATTCTAGCGAAACTAGTGGAGATAATTGGTCAAAGTACCAGTCTAAC
AAGTCTATTACTATTGGATTTGATAGTACTTTTGTTCCAATGGGATTTGCTCAGAAAG
ATGGTTCTTATGCAGGATTTGATATTGATTTAGCTACAGCTGTTTTTGAAAAATACGG
AATCACGGTAAATTGGCAACCGATTGATTGGGATTTGAAAGAAGCTGAATTGACAA
AAGGAACGATTGATCTGATTTGGAATGGCTATTCCGCTACAGACGAACGCCGTGAA
AAGGTGGCTTTCAGTAACTCATATATGAAGAATGAGCAGGTATTGGTTACGAAGAA
ATCATCTGGTATCACGACTGCAAAGGATATGACTGGAAAGACATTAGGAGCTCAAG
CTGGTTCATCTGGTTATGCGGACTTTGAAGCAAATCCAGAAATTTTGAAGAATATTG
TCGCTAATAAGGAAGCGAATCAATACCAAACCTTTAATGAAGCCTTGATTGATTTGA
AAAACGATCGAATTGATGGTCTATTGATTGACCGTGTCTATGCAAACTATTATTTAG
AAGCAGAAGGTGTTTTAAACGATTATAATGTCTTTACAGTTGGACTAGAAACAGAA
GCTTTTGCGGTTGGAGCCCGTAAGGAAGATACAAACTTGGTTAAGAAGATAAATGA
AGCTTTTTCTAGTCTTTACAAGGACGGCAAGTTCCAAGAAATCAGCCAAAAATGGTT
TGGAGAAGATGTAGCAACCAAAGAAGTAAAAGAAGGACAG SEQ ID NO: 19, Rhavi-linker-PdT(G294P)-linker-SP0435
[aa 62-185] fusion protein, denoted SPP2:
FDASNFKDFSSIASASSSWQNQSGSTMIIQVDSFGNVSGQYVNRAQGTGCQNSPYPLTGR
VNGTFIAFSVGWNNSTENCNSATGWTGYAQVNGNNTEIVTSWNLAYEGGSGPAIEQGQ
DTFQYVPTTENKSLLKDGGGGSSSANKAVNDFILAMNYDKKKLLTHQGESIENRFIKEG
NQLPDEFVVIERKKRSLSTNTSDISVTATNDSRLYPGALLVVDETLLENNPTLLAVDRAP
MTYSIDLPGLASSDSFLQVEDPSNSSVRGAVNDLLAKWHQDYGQVNNVPARMQYEKIT
AHSMEQLKVKFGSDFEKTGNSLDIDFNSVHSGEKQIQIVNFKQIYYTVSVDAVKNPGDV
FQDTVTVEDLKQRGISAERPLVYISSVAYGRQVYLKLETTSKSDEVEAAFEALIKGVKVA
PQTEWKQILDNTEVKAVILGPDPSSGARVVTGKVDMVEDLIQEGSRFTADHPGLPISYTT
SFLRDNVVATFQNSTDYVETKVTAYRNGDLLLDHSGAYVAQYYITWDELSYNHQGKE
VLTPKAWDRNGQDLTAHFTTSIPLKGNVRNLSVKIREGTGLAFEWWRTVYEKTDLPLV
RKRTISIWGTTLYPQVEDKVENDGGGGSSSEQAIIETVPAQYLYKMDDTAYFMNTETYD
QYEIPVVNVENELLYILENSDVKIQFYGTEVIGVTVPTTVELTVAETQPSIKGATVTGSGK
PATMETGLVVNVPDFIEAGQKLVINTAEGTYVSR SEQ ID NO: 20, Rhavi-linker-PdT(G294P)-linker-SP0435
[aa 62-185]-Hisx6 fusion protein, denoted SPP2-H:
FDASNFKDFSSIASASSSWQNQSGSTMIIQVDSFGNVSGQYVNRAQGTGCQNSPYPLTGR
VNGTFIAFSVGWNNSTENCNSATGWTGYAQVNGNNTEIVTSWNLAYEGGSGPAIEQGQ
DTFQYVPTTENKSLLKDGGGGSSSANKAVNDFILAMNYDKKKLLTHQGESIENRFIKEG
NQLPDEFVVIERKKRSLSTNTSDISVTATNDSRLYPGALLVVDETLLENNPTLLAVDRAP
MTYSIDLPGLASSDSFLQVEDPSNSSVRGAVNDLLAKWHQDYGQVNNVPARMQYEKIT
AHSMEQLKVKFGSDFEKTGNSLDIDFNSVHSGEKQIQIVNFKQIYYTVSVDAVKNPGDV
FQDTVTVEDLKQRGISAERPLVYISSVAYGRQVYLKLETTSKSDEVEAAFEALIKGVKVA
PQTEWKQILDNTEVKAVILGPDPSSGARVVTGKVDMVEDLIQEGSRFTADHPGLPISYTT
SFLRDNVVATFQNSTDYVETKVTAYRNGDLLLDHSGAYVAQYYITWDELSYNHQGKE
VLTPKAWDRNGQDLTAHFTTSIPLKGNVRNLSVKIREGTGLAFEWWRTVYEKTDLPLV
RKRTISIWGTTLYPQVEDKVENDGGGGSSSEQAIIETVPAQYLYKMDDTAYFMNTETYD
QYEIPVVNVENELLYILENSDVKIQFYGTEVIGVTVPTTVELTVAETQPSIKGATVTGSGK
PATMETGLVVNVPDFIEAGQKLVINTAEGTYVSRHHHHHH -continued

| Sequence Listing |
|---|

SEQ ID NO: 21, Rhavi-linker-SP0435 [aa 62-185]-linker-PdT (G294P)fusion protein:
FDASNFKDFSSIASASSSWQNQSGSTMIIQVDSFGNVSGQYVNRAQGTGCQNSPYPLTGR
VNGTFIAFSVGWNNSTENCNSATGWTGYAQVNGNNTEIVTSWNLAYEGGSGPAIEQGQ
DTFQYVPTTENKSLLKDGGGGSSSEQAIIETVPAQYLYKMDDTAYFMNTETYDQYEIPV
VNVENELLYILENSDVKIQFYGTEVIGVTVPTTVELTVAETQPSIKGATVTGSGKPATME
TGLVVNVPDFIEAGQKLVINTAEGTYVSRGGGGSSSANKAVNDFILAMNYDKKKLLTH
QGESIENRFIKEGNQLPDEFVVIERKKRSLSTNTSDISVTATNDSRLYPGALLVVDETLLE
NNPTLLAVDRAPMTYSIDLPGLASSDSFLQVEDPSNSSVRGAVNDLLAKWHQDYGQVN
NVPARMQYEKITAHSMEQLKVKFGSDFEKTGNSLDIDFNSVHSGEKQIQIVNFKQIYYT
VSVDAVKNPGDVFQDTVTVEDLKQRGISAERPLVYISSVAYGRQVYLKLETTSKSDEVE
AAFEALIKGVKVAPQTEWKQILDNTEVKAVILGPDPSSGARVVTGKVDMVEDLIQEGSR
FTADHPGLPISYTTSFLRDNVVATFQNSTDYVETKVTAYRNGDLLLDHSGAYVAQYYIT
WDELSYNHQGKEVLTPKAWDRNGQDLTAHFTTSIPLKGNVRNLSVKIREGTGLAFEWW
RTVYEKTDLPLVRKRTISIWGTTLYPQVEDKVEND SEQ ID NO: 22, PdT(G294P)-linker-SP0435 [aa 62-185]-linker-Rhavi fusion protein:
ANKAVNDFILAMNYDKKKLLTHQGESIENRFIKEGNQLPDEFVVIERKKRSLSTNTSDIS
VTATNDSRLYPGALLVVDETLLENNPTLLAVDRAPMTYSIDLPGLASSDSFLQVEDPSNS
SVRGAVNDLLAKWHQDYGQVNNVPARMQYEKITAHSMEQLKVKFGSDFEKTGNSLDI
DFNSVHSGEKQIQIVNFKQIYYTVSVDAVKNPGDVFQDTVTVEDLKQRGISAERPLVYIS
SVAYGRQVYLKLETTSKSDEVEAAFEALIKGVKVAPQTEWKQILDNTEVKAVILGPDPS
SGARVVTGKVDMVEDLIQEGSRFTADHPGLPISYTTSFLRDNVVATFQNSTDYVETKVT
AYRNGDLLLDHSGAYVAQYYITWDELSYNHQGKEVLTPKAWDRNGQDLTAHFTTSIPL
KGNVRNLSVKIREGTGLAFEWWRTVYEKTDLPLVRKRTISIWGTTLYPQVEDKVENDG
GGGSSSEQAIIETVPAQYLYKMDDTAYFMNTETYDQYEIPVVNVENELLYILENSDVKI
QFYGTEVIGVTVPTTVELTVAETQPSIKGATVTGSGKPATMETGLVVNVPDFIEAGQKLV
INTAEGTYVSRGGGGSSSFDASNFKDFSSIASASSSWQNQSGSTMIIQVDSFGNVSGQYV
NRAQGTGCQNSPYPLTGRVNGTFIAFSVGWNNSTENCNSATGWTGYAQVNGNNTEIVT
SWNLAYEGGSGPAIEQGQDTFQYVPTTENKSLLKD SEQ ID NO: 23, SP0435 [aa 62-185]-linker-PdT(G294P)-linker-Rhavi fusion protein:
EQAIIETVPAQYLYKMDDTAYFMNTETYDQYEIPVVNVENELLYILENSDVKIQFYGTEV
IGVTVPTTVELTVAETQPSIKGATVTGSGKPATMETGLVVNVPDFIEAGQKLVINTAEGT
YVSRGGGGSSSANKAVNDFILAMNYDKKKLLTHQGESIENRFIKEGNQLPDEFVVIERK
KRSLSTNTSDISVTATNDSRLYPGALLVVDETLLENNPTLLAVDRAPMTYSIDLPGLASS
DSFLQVEDPSNSSVRGAVNDLLAKWHQDYGQVNNVPARMQYEKITAHSMEQLKVKFG
SDFEKTGNSLDIDFNSVHSGEKQIQIVNFKQIYYTVSVDAVKNPGDVFQDTVTVEDLKQ
RGISAERPLVYISSVAYGRQVYLKLETTSKSDEVEAAFEALIKGVKVAPQTEWKQILDNT
EVKAVILGPDPSSGARVVTGKVDMVEDLIQEGSRFTADHPGLPISYTTSFLRDNVVATFQ
NSTDYVETKVTAYRNGDLLLDHSGAYVAQYYITWDELSYNHQGKEVLTPKAWDRNGQ
DLTAHFTTSIPLKGNVRNLSVKIREGTGLAFEWWRTVYEKTDLPLVRKRTISIWGTTLYP
QVEDKVENDGGGGSSSFDASNFKDFSSIASASSSWQNQSGSTMIIQVDSFGNVSGQYVN
RAQGTGCQNSPYPLTGRVNGTFIAFSVGWNNSTENCNSATGWTGYAQVNGNNTEIVTS
WNLAYEGGSGPAIEQGQDTFQYVPTTENKSLLKD SEQ ID NO: 24, PdT(G294P)-linker-Rhavi-linker-SP0435 [aa 62-185] fusion protein:
ANKAVNDFILAMNYDKKKLLTHQGESIENRFIKEGNQLPDEFVVIERKKRSLSTNTSDIS
VTATNDSRLYPGALLVVDETLLENNPTLLAVDRAPMTYSIDLPGLASSDSFLQVEDPSNS
SVRGAVNDLLAKWHQDYGQVNNVPARMQYEKITAHSMEQLKVKFGSDFEKTGNSLDI
DFNSVHSGEKQIQIVNFKQIYYTVSVDAVKNPGDVFQDTVTVEDLKQRGISAERPLVYIS
SVAYGRQVYLKLETTSKSDEVEAAFEALIKGVKVAPQTEWKQILDNTEVKAVILGPDPS
SGARVVTGKVDMVEDLIQEGSRFTADHPGLPISYTTSFLRDNVVATFQNSTDYVETKVT
AYRNGDLLLDHSGAYVAQYYITWDELSYNHQGKEVLTPKAWDRNGQDLTAHFTTSIPL
KGNVRNLSVKIREGTGLAFEWWRTVYEKTDLPLVRKRTISIWGTTLYPQVEDKVENDG
GGGSSSFDASNFKDFSSIASASSSWQNQSGSTMIIQVDSFGNVSGQYVNRAQGTGCQNS
PYPLTGRVNGTFIAFSVGWNNSTENCNSATGWTGYAQVNGNNTEIVTSWNLAYEGGSG
PAIEQGQDTFQYVPTTENKSLLKDGGGGSSSEQAIIETVPAQYLYKMDDTAYFMNTETY
DQYEIPVVNVENELLYILENSDVKIQFYGTEVIGVTVPTTVELTVAETQPSIKGATVTGSG
KPATMETGLVVNVPDFIEAGQKLVINTAEGTYVSR SEQ ID NO: 25, SP0435 [aa 62-185]-linker-Rhavi-linker-PdT (G294P) fusion protein:
EQAIIETVPAQYLYKMDDTAYFMNTETYDQYEIPVVNVENELLYILENSDVKIQFYGTEV
IGVTVPTTVELTVAETQPSIKGATVTGSGKPATMETGLVVNVPDFIEAGQKLVINTAEGT
YVSRGGGGSSSFDASNFKDFSSIASASSSWQNQSGSTMIIQVDSFGNVSGQYVNRAQGT
GCQNSPYPLTGRVNGTFIAFSVGWNNSTENCNSATGWTGYAQVNGNNTEIVTSWNLAY
EGGSGPAIEQGQDTFQYVPTTENKSLLKDGGGGSSSANKAVNDFILAMNYDKKKLLTH
QGESIENRFIKEGNQLPDEFVVIERKKRSLSTNTSDISVTATNDSRLYPGALLVVDETLLE
NNPTLLAVDRAPMTYSIDLPGLASSDSFLQVEDPSNSSVRGAVNDLLAKWHQDYGQVN
NVPARMQYEKITAHSMEQLKVKFGSDFEKTGNSLDIDFNSVHSGEKQIQIVNFKQIYYT
VSVDAVKNPGDVFQDTVTVEDLKQRGISAERPLVYISSVAYGRQVYLKLETTSKSDEVE
AAFEALIKGVKVAPQTEWKQILDNTEVKAVILGPDPSSGARVVTGKVDMVEDLIQEGSR -continued

| Sequence Listing |
| --- |

FTADHPGLPISYTTSFLRDNVVATFQNSTDYVETKVTAYRNGDLLLDHSGAYVAQYYIT
WDELSYNHQGKEVLTPKAWDRNGQDLTAHFTTSIPLKGNVRNLSVKIREGTGLAFEWW
RTVYEKTDLPLVRKRTISIWGTTLYPQVEDKVEND

SEQ ID NO: 26, Rhavi-linker-SP1500 [aa 27-278]-linker-SP0785 [aa 33-399] fusion protein, denoted CP1:
FDASNFKDFSSIASASSSWQNQSGSTMIIQVDSFGNVSGQYVNRAQGTGCQNSPYPLTGR
VNGTFIAFSVGWNNSTENCNSATGWTGYAQVNGNNTEIVTSWNLAYEGGSGPAIEQGQ
DTFQYVPTTENKSLLKDGGGGSSSTSGDNWSKYQSNKSITIGFDSTFVPMGFAQKDGSY
AGFDIDLATAVFEKYGITVNWQPIDWDLKEAELTKGTIDLIWNGYSATDERREKVAFSN
SYMKNEQVLVTKKSSGITTAKDMTGKTLGAQAGSSGYADFEANPEILKNIVANKEANQ
YQTFNEALIDLKNDRIDGLLIDRVYANYYLEAEGVLNDYNVFTVGLETEAFAVGARKED
TNLVKKINEAFSSLYKDGKFQEISQKWFGEDVATKEVKEGQAAAFRQPSQTALKDEPTH
LWAKEGSVASSVLLSGTVTAKNEQYVYFDASKGDLDEILVSVGDKVSEGQALVKYSS
SEAQAAYDSASRAVARADRHINELNQARNEAASAPAPQLPAPVGGEDATVQSPTPVAG
NSVASIDAQLGDARDARADAAAQLSKAQSQLDATTVLSTLEGTVVEVNSNVSKSPTGA
SQVMVHIVSNENLQVKGELSEYNLANLSVGQEVSFTSKVYPDKKWTGKLSYISDYPKN
NGEAASPAAGNNTGSKYPYTIDVTGEVGDLKQGFSVNIEVKSKTKAILVPVSSLVMDDS
KNYVWIVDEQQKAKKVEVSLGNADAENQEITSGLTNGAKVISNPTSSLEEGKEVKADE
ATN SEQ ID NO: 27, codon-optimized nucleotide sequence encoding Rhavi-linker-PdT(G294P)-linker-SP0435 [aa 62-185], denoted SPP2:
TTCGACGCATCCAACTTTAAAGACTTTAGCAGCATCGCGTCCGCAAGCTCTAGCTGG
CAGAATCAATCTGGTAGCACCATGATTATCCAAGTGGACAGCTTTGGTAACGTCAGC
GGTCAATATGTTAATCGTGCACAGGGTACGGGTTGTCAGAATTCTCCGTACCCGCTG
ACCGGTCGTGTTAACGGCACGTTCATCGCTTTCAGCGTCGGTTGGAACAATTCTACT
GAAAATTGCAACAGCGCGACCGGTTGGACGGGCTATGCACAAGTGAATGGCAATAA
CACCGAAATCGTCACGTCCTGGAATCTGGCGTATGAGGGTGGCAGCGGTCCGGCTAT
TGAACAGGGCCAGGATACCTTCCAATACGTCCCTACGACCGAGAATAAGTCCCTTCT
GAAAGACGGCGGTGGCGGTTCGAGCTCGGCGAACAAGGCGGTGAACGATTTTATCC
TGGCGATGAACTATGACAAGAAGAAACTGCTGACCCACCAAGGCGAGAGCATTGAG
AACCGTTTCATTAAAGAAGGCAACCAGCTGCCGGACGAGTTTGTGGTTATCGAGCGT
AAGAAACGTAGCCTGAGCACCAACACCAGCGACATTAGCGTGACCGCGACCAACGA
TAGCCGTCTGTACCCGGGTGCGCTGCTGGTTGTGGATGAAACCCTGCTGGAAAACAA
CCCGACCCTGCTGGCGGTGGACCGTGCGCCGATGACCTATAGCATCGATCTGCCGGG
TCTGGCGAGCAGCGACAGCTTCCTGCAAGTTGAGGATCCGAGCAACAGCAGCGTGC
GTGGTGCGGTTAACGACCTGCTGGCGAAGTGGCACCAGGATTACGGCCAAGTGAAC
AACGTTCCGGCGCGTATGCAGTATGAAAAAATCACCGCGCACAGCATGGAGCAACT
GAAGGTTAAATTCGGTAGCGACTTTGAAAAGACCGGCAACAGCCTGGACATTGATT
TCAACAGCGTGCACAGCGGCGAGAAGCAGATCCAAATCGTTAACTTCAAGCAGATC
TACTACACCGTGAGCGTTGACGCGGTGAAGAACCCGGGTGACGTTTTCCAGGATACC
GTGACCGTTGAAGATCTGAAACAACGTGGCATTAGCGCGGAGCGTCCGCTGGTGTA
CATCAGCAGCGTTGCGTACGGTCGTCAAGTGTATCTGAAGCTGGAAACCACCAGCA
AAAGCGATGAGGTTGAAGCGGCGTTTGAGGCGCTGATTAAGGGCGTGAAAGTTGCG
CCGCAGACCGAATGGAAGCAAATTCTGGACAACACCGAGGTGAAAGCGGTTATTCT
GGGCCCGGATCCGAGCAGCGGCGCGCGTGTGGTTACCGGTAAAGTGGACATGGTTG
AGGATCTGATTCAGGAAGGTAGCCGTTTTACCGCGGACCACCCGGGCCTGCCGATC
AGCTACACCACCAGCTTCCTGCGTGACAACGTGGTTGCGACCTTTCAAAACAGCACC
GATTACGTGGAAACCAAGGTTACCGCGTATCGTAACGGTGACCTGCTGCTGGACCAC
AGCGGTGCGTACGTGGCGCAGTACTATATCACCTGGGATGAACTGAGCTATAACCA
CCAGGGTAAAGAGGTGCTGACCCCGAAAGCGTGGGACCGTAACGGCCAGGATCTGA
CCGCGCACTTCACCACCAGCATTCCGCTGAAGGGCAACGTGCGTAACCTGAGCGTTA
AAATCCGTGAGGGTACCGGCCTGGCGTTTGAATGGTGGCGTACCGTGTACGAGAAG
ACCGACCTGCCGCTGGTTCGTAAACGTACCATCAGCATTTGGGGTACCACCCTGTAT
CCGCAGGTGGAGGACAAAGTTGAAAATGATGGTGGTGGTGGTAGCAGCAGCGAGCA
GGCGATCATTGAAACCGTGCCGGCGCAATACCTGTATAAGATGGACGATACCGCGT
ACTTCATGAACACCGAAACCTACGACCAATATGAAATTCCGGTGGTTAACGTTGAGA
ACGAACTGCTGTACATCCTGGAAAACAGCGATGTGAAAATTCAGTTTTATGGTACCG
AGGTTATCGGCGTGACCGTTCCGACCACCGTGGAGCTGACCGTTGCGGAAACCCAA
CCGAGCATCAAGGGTGCGACCGTGACCGGTAGCGGTAAACCGGCGACCATGGAAAC
CGGTCTGGTGGTTAACGTGCCGGACTTCATTGAGGCGGGCCAGAAGCTGGTTATCAA
TACCGCGGAGGGTACCTATGTTAGCCGTTAATGA SEQ ID NO: 28, codon-optimized nucleotide sequence encoding Rhavi-linker-SP0435 [aa 62-185]-linker-PdT(G294P):
TTCGACGCATCCAACTTTAAAGACTTTAGCAGCATCGCGTCCGCAAGCTCTAGCTGG
CAGAATCAATCTGGTAGCACCATGATTATCCAAGTGGACAGCTTTGGTAACGTCAGC
GGTCAATATGTTAATCGTGCACAGGGTACGGGTTGTCAGAATTCTCCGTACCCGCTG
ACCGGTCGTGTTAACGGCACGTTCATCGCTTTCAGCGTCGGTTGGAACAATTCTACT
GAAAATTGCAACAGCGCGACCGGTTGGACGGGCTATGCACAAGTGAATGGCAATAA
CACCGAAATCGTCACGTCCTGGAATCTGGCGTATGAGGGTGGCAGCGGTCCGGCTAT
TGAACAGGGCCAGGATACCTTCCAATACGTCCCTACGACCGAGAATAAGTCCCTTCT
GAAAGACGGCGGTGGCGGTTCGAGCTCGGAGCAGGCGATCATTGAAACCGTGCCGG
CGCAATACCTGTATAAGATGGACGATACCGCGTACTTCATGAACACCGAAACCTAC
GACCAATATGAAATTCCGGTGGTTAACGTTGAGAACGAACTGCTGTACATCCTGGAA -continued

| Sequence Listing |
|---|

AACAGCGATGTGAAAATTCAGTTTTATGGTACCGAGGTTATCGGCGTGACCGTTCCG
ACCACCGTGGAGCTGACCGTTGCGGAAACCCAACCGAGCATCAAGGGTGCGACCGT
GACCGGTAGCGGTAAACCGGCGACCATGGAAACCGGTCTGGTGGTTAACGTGCCGG
ACTTCATTGAGGCGGGCCAGAAGCTGGTTATCAATACCGCGGAGGGTACCTATGTTA
GCCGTTAATGAGGTGGTGGTGGTAGCAGCAGCGCGAACAAGGCGGTGAACGATTTT
ATCCTGGCGATGAACTATGACAAGAAGAAACTGCTGACCCACCAAGGCGAGAGCAT
TGAGAACCGTTTCATTAAAGAAGGCAACCAGCTGCCGGACGAGTTTGTGGTTATCGA
GCGTAAGAAACGTAGCCTGAGCACCAACACCAGCGACATTAGCGTGACCGCGACCA
ACGATAGCCGTCTGTACCCGGGTGCGCTGCTGGTTGTGGATGAAACCCTGCTGGAAA
ACAACCCGACCCTGCTGGCGGTGGACCGTGCGCCGATGACCTATAGCATCGATCTGC
CGGGTCTGGCGAGCAGCGACAGCTTCCTGCAAGTTGAGGATCCGAGCAACAGCAGC
GTGCGTGGTGCGGTTAACGACCTGCTGGCGAAGTGGCACCAGGATTACGGCCAAGT
GAACAACGTTCCGGCGCGTATGCAGTATGAAAAAATCACCGCGCACAGCATGGAGC
AACTGAAGGTTAAATTCGGTAGCGACTTTGAAAAGACCGGCAACAGCCTGGACATT
GATTTCAACAGCGTGCACAGCGGCGAGAAGCAGATCCAAATCGTTAACTTCAAGCA
GATCTACTACACCGTGAGCGTTGACGCGGTGAAGAACCCGGGTGACGTTTTCCAGG
ATACCGTGACCGTTGAAGATCTGAAACAACGTGGCATTAGCGCGGAGCGTCCGCTG
GTGTACATCAGCAGCGTTGCGTACGGTCGTCAAGTGTATCTGAAGCTGGAAACCACC
AGCAAAAGCGATGAGGTTGAAGCGGCGTTTGAGGCGCTGATTAAGGGCGTGAAAGT
TGCGCCGCAGACCGAATGGAAGCAAATTCTGGACAACACCGAGGTGAAAGCGGTTA
TTCTGGGCCCGGATCCGAGCAGCGGCGCGCGTGTGGTTACCGGTAAAGTGGACATG
GTTGAGGATCTGATTCAGGAAGGTAGCCGTTTTACCGCGGACCACCCGGGCCTGCCG
ATCAGCTACACCACCAGCTTCCTGCGTGACAACGTGGTTGCGACCTTTCAAAACAGC
ACCGATTACGTGGAAACCAAGGTTACCGCGTATCGTAACGGTGACCTGCTGCTGGAC
CACAGCGGTGCGTACGTGGCGCAGTACTATATCACCTGGGATGAACTGAGCTATAA
CCACCAGGGTAAAGAGGTGCTGACCCCGAAAGCGTGGGACCGTAACGGCCAGGATC
TGACCGCGCACTTCACCACCAGCATTCCGCTGAAGGGCAACGTGCGTAACCTGAGC
GTTAAAATCCGTGAGGGTACCGGCCTGGCGTTTGAATGGTGGCGTACCGTGTACGAG
AAGACCGACCTGCCGCTGGTTCGTAAACGTACCATCAGCATTTGGGGTACCACCCTG
TATCCGCAGGTGGAGGACAAAGTTGAAAATGAT

SEQ ID NO: 29, codon-optimized nucleic acid sequence encoding
Rhavi-linker-SP1500 [aa 27-278]-linker-SP0785 [aa 33-399]
fusion protein, denoted CP1:
TTCGACGCATCCAACTTTAAAGACTTTAGCAGCATCGCGTCCGCAAGCTCTAGCTGG
CAGAATCAATCTGGTAGCACCATGATTATCCAAGTGGACAGCTTTGGTAACGTCAGC
GGTCAATATGTTAATCGTGCACAGGGTACGGGTTGTCAGAATTCTCCGTACCCGCTG
ACCGGTCGTGTTAACGGCACGTTCATCGCTTTCAGCGTCGGTTGGAACAATTCTACT
GAAAATTGCAACAGCGCGACCGGTTGGACGGGCTATGCACAAGTGAATGGCAATAA
CACCGAAATCGTCACGTCCTGGAATCTGGCGTATGAGGGTGGCAGCGGTCCGGCTAT
TGAACAGGGCCAGGATACCTTCCAATACGTCCCTACGACCGAGAATAAGTCCCTTCT
GAAAGACGGCGGTGGCGGTTCGAGCTCGACCAGCGGCGACAATTGGTCCAAATACC
AGAGCAACAAGAGCATCACGATCGGCTTCGACAGCACTTTTGTGCCGATGGGTTTCG
CGCAAAAAGACGGTAGCTACGCGGGTTTCGATATTGACCTGGCGACCGCTGTCTTTG
AGAAATACGGCATTACGGTTAATTGGCAGCCGATTGATTGGGACCTGAAAGAGGCC
GAACTCACCAAAGGCACCATCGACCTGATCTGGAATGGTTACTCCGCAACCGATGA
GCGTCGCGAAAAAGTTGCCTTCAGCAACAGCTATATGAAGAATGAACAAGTGTTGG
TAACCAAGAAATCTAGCGGCATTACGACCGCGAAAGACATGACCGGTAAGACGCTG
GGTGCGCAGGCCGGTAGCTCTGGCTATGCGGATTTCGAGGCGAATCCTGAGATTCTG
AAAAACATCGTTGCGAATAAAGAGGCGAACCAGTACCAGACCTTTAACGAAGCACT
GATCGACCTGAAAAACGATCGCATTGACGGTCTGCTGATCGATCGTGTGTACGCGAA
CTATTATCTGGAAGCCGAGGGCGTTCTGAACGATTATAATGTTTTTACCGTGGGTCT
GGAGACTGAGGCATTCGCGGTTGGTGCGCGCAAGGAAGATACCAACCTGGTTAAAA
AGATTAATGAGGCATTTAGCTCACTGTACAAGGACGGCAAGTTCCAAGAAATTAGC
CAGAAGTGGTTCGGTGAAGATGTTGCGACGAAAGAGGTTAAAGAGGGCCAAGCGGC
CGCATTTCGCCAACCGAGCCAGACTGCGTTGAAAGATGAGCCGACCCATCTGGTTGT
TGCGAAAGAGGGCAGCGTGGCATCGAGCGTGCTGCTGAGCGGTACGGTTACTGCCA
AAAACGAACAATACGTGTACTTCGATGCTAGCAAGGGTGATCTGGATGAAATTCTG
GTGAGCGTGGGTGACAAAGTTAGCGAAGGCCAGGCACTGGTGAAGTATTCATCCTC
CGAGGCACAGGCAGCGTACGACAGCGCAAGCCGCGCAGTGGCGCGTGCCGACCGTC
ACATTAACGAATTGAACCAAGCGCGTAACGAGGCCGCAAGCGCGCCAGCACCGCAG
CTGCCGGCTCCGGTGGGTGGCGAAGATGCGACGGTGCAGAGCCCGACCCCGGTTGC
GGGTAATTCGGTCGCCAGCATCGATGCGCAGCTGGGTGACGCGCGTGATGCCCGTG
CGGATGCGGCTGCTCAACTGAGCAAGGCTCAGAGCCAACTGGACGCGACGACGGTG
CTGAGCACCTTGGAGGGTACCGTTGTCGAAGTCAACAGCAATGTGAGCAAGAGCCC
AACGGGTGCGAGCCAGGTTATGGTCCACATTGTGAGCAATGAAAACTTACAGGTCA
AGGGTGAGCTGAGCGAGTATAACCTGGCGAATCTGAGCGTTGGTCAAGAGGTCAGC
TTTACCAGCAAGGTCTACCCGGATAAGAAATGGACCGGCAAGTTGAGCTACATCAG
CGACTACCCGAAGAACAATGGCGAGGCAGCCTCCCCGGCAGCCGGCAACAATACCG
GCTCTAAGTATCCGTACACCATCGACGTAACCGGTGAGGTCGGCGACCTGAAACAG
GGTTTTAGCGTGAATATCGAAGTGAAGTCCAAGACCAAGGCAATTTTGGTTCCGGTT
AGCTCCCTGGTGATGGACGATAGCAAGAATTATGTGTGGATTGTCGACGAGCAACA
GAAAGCGAAAAAAGTTGAAGTGAGCCTGGGCAATGCTGATGCCGAGAACCAAGAA
ATCACGTCTGGTCTGACCAACGGTGCGAAAGTTATTAGCAACCCGACCAGCAGCCT
GGAAGAGGGTAAAGAGGTCAAAGCCGACGAAGCTACGAAC -continued Sequence Listing SEQ ID NO: 30, linker sequence [7 amino acids]:
GGGGSSS linker sequence [3 amino acids]:
AAA SEQ ID NO: 32, linker sequence [5 amino acid repeats]:
$(GGGGS)_n$ SEQ ID NO: 33, linker sequence [6 amino acids]:
GGGGGG SEQ ID NO: 34, linker sequence [15 amino acids]:
GGGGSGGGGSGGGGS SEQ ID NO: 35, linker sequence [30 amino acids]:
GGGGSGGGGSGGGGSGGGGSGGGGSGGGGS SEQ ID NO: 36, linker sequence [18 amino acids]:
KESGSVSSEQLAQFRSLD SEQ ID NO: 37, linker sequence [14 amino acids]:
EGKSSGSGSESKST SEQ ID NO: 38, linker sequence:
$(Gly)_n$ SEQ ID NO: 39, linker sequence [8 amino acids]:
GGGGGGGG SEQ ID NO: 40, linker sequence [12 amino acids]:
GSAGSAAGSGEF SEQ ID NO: 41, linker sequence [5 amino acid repeats]:
$(EAAAK)_n$ SEQ ID NO: 42, linker sequence:
$A(EAAAK)_nA$ SEQ ID NO: 43, linker sequence:
$A(EAAAK)_4ALEA(EAAAK)_4A$ SEQ ID NO: 44, linker sequence:
$[A(EAAAK)_nA]_m$ SEQ ID NO: 45, linker sequence [12 amino acids]:
AEAAAKEAAAKA SEQ ID NO: 46, linker sequence [2 amino acid repeats]:
$(XP)_n$ SEQ ID NO: 47, linker sequence [2 amino acid repeats]:
$(AP)_n$ SEQ ID NO: 48, linker sequence [2 amino acid repeats]:
$(KP)_n$ SEQ ID NO: 49, linker sequence [2 amino acid repeats]:
$(QP)_n$ SEQ ID NO: 50, linker sequence [14 amino acids]:
APAPAPAPAPAPAP SEQ ID NO: 51, GAG linker sequence [21 amino acids]:
GAPGGGGGAAAAAGGGGGGAP SEQ ID NO: 52, GAG2 linker sequence [39 amino acids]:
GAPGGGGGAAAAAGGGGGGAPGGGGGAAAAAGGGGGGAP SEQ ID NO: 53, GAG3 linker sequence [57 amino acids]:
GAPGGGGGAAAAAGGGGGGAPGGGGGAAAAAGGGGGGAPGGGGGAAAAAGGGGG
GAP SEQ ID NO: 54, linker sequence [4 amino acids]:
GGGG -continued

| Sequence Listing |
|---|

SEQ ID NO: 55, His tag 1:
HHHHHH

SEQ ID NO: 56, His tag 2:
MSYYHHHHHH

SEQ ID NO: 57, truncated rhizavidin protein [aa 45-179], denoted Rhavi, includes leading methionine:
MFDASNFKDFSSIASASSSWQNQSGSTMIIQVDSFGNVSGQYVNRAQGTGCQNSPYPLT
GRVNGTFIAFSVGWNNSTENCNSATGWTGYAQVNGNNTEIVTSWNLAYEGGSGPAIEQ
GQDTFQYVPTTENKSLLKD SEQ ID NO: 58, Rhavi-linker-PdT(G294P)-linker-SP0435 [aa 62-185] fusion protein, denoted SPP2, includes leading methionine:
MFDASNFKDFSSIASASSSWQNQSGSTMIIQVDSFGNVSGQYVNRAQGTGCQNSPYPLT
GRVNGTFIAFSVGWNNSTENCNSATGWTGYAQVNGNNTEIVTSWNLAYEGGSGPAIEQ
GQDTFQYVPTTENKSLLKDGGGGSSSANKAVNDFILAMNYDKKKLLTHQGESIENRFIK
EGNQLPDEFVVIERKKRSLSTNTSDISVTATNDSRLYPGALLVVDETLLENNPTLLAVDR
APMTYSIDLPGLASSDSFLQVEDPSNSSVRGAVNDLLAKWHQDYGQVNNVPARMQYE
KITAHSMEQLKVKFGSDFEKTGNSLDIDFNSVHSGEKQIQIVNFKQIYYTVSVDAVKNPG
DVFQDTVTVEDLKQRGISAERPLVYISSVAYGRQVYLKLETTSKSDEVEAAFEALIKGVK
VAPQTEWKQILDNTEVKAVILGPDPSSGARVVTGKVDMVEDLIQEGSRFTADHPGLPIS
YTTSFLRDNVVATFQNSTDYVETKVTAYRNGDLLLDHSGAYVAQYYITWDELSYNHQ
GKEVLTPKAWDRNGQDLTAHFTTSIPLKGNVRNLSVKIREGTGLAFEWWRTVYEKTDL
PLVRKRTISIWGTTLYPQVEDKVENDGGGGSSSEQAIIETVPAQYLYKMDDTAYFMNTE
TYDQYEIPVVNVENELLYILENSDVKIQFYGTEVIGVTVPTTVELTVAETQPSIKGATVTG
SGKPATMETGLVVNVPDFIEAGQKLVINTAEGTYVSR SEQ ID NO: 59, Rhavi-linker-PdT(G294P)-linker-SP0435 [aa 62-185]-Hisx6
fusion protein, denoted SPP2-H, includes leading methionine:
MFDASNFKDFSSIASASSSWQNQSGSTMIIQVDSFGNVSGQYVNRAQGTGCQNSPYPLT
GRVNGTFIAFSVGWNNSTENCNSATGWTGYAQVNGNNTEIVTSWNLAYEGGSGPAIEQ
GQDTFQYVPTTENKSLLKDGGGGSSSANKAVNDFILAMNYDKKKLLTHQGESIENRFIK
EGNQLPDEFVVIERKKRSLSTNTSDISVTATNDSRLYPGALLVVDETLLENNPTLLAVDR
APMTYSIDLPGLASSDSFLQVEDPSNSSVRGAVNDLLAKWHQDYGQVNNVPARMQYE
KITAHSMEQLKVKFGSDFEKTGNSLDIDFNSVHSGEKQIQIVNFKQIYYTVSVDAVKNPG
DVFQDTVTVEDLKQRGISAERPLVYISSVAYGRQVYLKLETTSKSDEVEAAFEALIKGVK
VAPQTEWKQILDNTEVKAVILGPDPSSGARVVTGKVDMVEDLIQEGSRFTADHPGLPIS
YTTSFLRDNVVATFQNSTDYVETKVTAYRNGDLLLDHSGAYVAQYYITWDELSYNHQ
GKEVLTPKAWDRNGQDLTAHFTTSIPLKGNVRNLSVKIREGTGLAFEWWRTVYEKTDL
PLVRKRTISIWGTTLYPQVEDKVENDGGGGSSSEQAIIETVPAQYLYKMDDTAYFMNTE
TYDQYEIPVVNVENELLYILENSDVKIQFYGTEVIGVTVPTTVELTVAETQPSIKGATVTG
SGKPATMETGLVVNVPDFIEAGQKLVINTAEGTYVSRHHHHHH SEQ ID NO: 60, Rhavi-linker-SP0435 [aa 62-185]-linker-PdT (G294P)fusion protein, includes leading methionine:
MFDASNFKDFSSIASASSSWQNQSGSTMIIQVDSFGNVSGQYVNRAQGTGCQNSPYPLT
GRVNGTFIAFSVGWNNSTENCNSATGWTGYAQVNGNNTEIVTSWNLAYEGGSGPAIEQ
GQDTFQYVPTTENKSLLKDGGGGSSSEQAIIETVPAQYLYKMDDTAYFMNTETYDQYEI
PVVNVENELLYILENSDVKIQFYGTEVIGVTVPTTVELTVAETQPSIKGATVTGSGKPAT
METGLVVNVPDFIEAGQKLVINTAEGTYVSRGGGGSSSANKAVNDFILAMNYDKKKLL
THQGESIENRFIKEGNQLPDEFVVIERKKRSLSTNTSDISVTATNDSRLYPGALLVVDETL
LENNPTLLAVDRAPMTYSIDLPGLASSDSFLQVEDPSNSSVRGAVNDLLAKWHQDYGQ
VNNVPARMQYEKITAHSMEQLKVKFGSDFEKTGNSLDIDFNSVHSGEKQIQIVNFKQIY
YTVSVDAVKNPGDVFQDTVTVEDLKQRGISAERPLVYISSVAYGRQVYLKLETTSKSDE
VEAAFEALIKGVKVAPQTEWKQILDNTEVKAVILGPDPSSGARVVTGKVDMVEDLIQEG
SRFTADHPGLPISYTTSFLRDNVVATFQNSTDYVETKVTAYRNGDLLLDHSGAYVAQYY
ITWDELSYNHQGKEVLTPKAWDRNGQDLTAHFTTSIPLKGNVRNLSVKIREGTGLAFEW
WRTVYEKTDLPLVRKRTISIWGTTLYPQVEDKVEND SEQ ID NO: 61, Rhavi-linker-SP1500 [aa 27-278]-linker-SP0785 [aa 33-399]
fusion protein, denoted CP1, includes leading methionine:
MFDASNFKDFSSIASASSSWQNQSGSTMIIQVDSFGNVSGQYVNRAQGTGCQNSPYPLT
GRVNGTFIAFSVGWNNSTENCNSATGWTGYAQVNGNNTEIVTSWNLAYEGGSGPAIEQ
GQDTFQYVPTTENKSLLKDGGGGSSSTSGDNWSKYQSNKSITIGFDSTFVPMGFAQKDG
SYAGFDIDLATAVFEKYGITVNWQPIDWDLKEAELTKGTIDLIWNGYSATDERREKVAF
SNSYMKNEQVLTKKSSGITTAKDMTGKTLGAQAGSSGYADFEANPEILKNIVANKEA
NQYQTFNEALIDLKNDRIDGLLIDRVYANYYLEAEGVLNDYNVFTVGLETEAFAVGAR
KEDTNLVKKINEAFSSLYKDGKFQEISQKWFGEDVATKEVKEGQAAAFRQPSQTALKD
EPTHLVVAKEGSVASSVLLSGTVTAKNEQYVYFDASKGDLDEILVSVGDKVSEGQALV
KYSSSEAQAAYDSASRAVARADRHINELNQARNEAASAPAPQLPAPVGGEDATVQSPTP
VAGNSVASIDAQLGDARDARADAAAQLSKAQSQLDATTVLSTLEGTVVEVNSNVSKSP
TGASQVMVHIVSNENLQVKGELSEYNLANLSVGQEVSFTSKVYPDKKWTGKLSYISDY -continued Sequence Listing PKNNGEAASPAAGNNTGSKYPYTIDVTGEVGDLKQGFSVNIEVKSKTKAILVPVSSLVM
DDSKNYVWIVDEQQKAKKVEVSLGNADAENQEITSGLTNGAKVISNPTSSLEEGKEVK
ADEATN SEQ ID NO: 62, codon-optimized nucleotide sequence encoding Rhavi-linker-PdT(G294P)-linker-SP0435 [aa 62-185], denoted SPP2, includes leading ATG sequence:
ATGTTCGACGCATCCAACTTTAAAGACTTTAGCAGCATCGCGTCCGCAAGCTCTAGC
TGGCAGAATCAATCTGGTAGCACCATGATTATCCAAGTGGACAGCTTTGGTAACGTC
AGCGGTCAATATGTTAATCGTGCACAGGGTACGGGTTGTCAGAATTCTCCGTACCCG
CTGACCGGTCGTGTTAACGGCACGTTCATCGCTTTCAGCGTCGGTTGGAACAATTCT
ACTGAAAATTGCAACAGCGCGACCGGTTGGACGGGCTATGCACAAGTGAATGGCAA
TAACACCGAAATCGTCACGTCCTGGAATCTGGCGTATGAGGGTGGCAGCGGTCCGG
CTATTGAACAGGGCCAGGATACCTTCCAATACGTCCCTACGACCGAGAATAAGTCCC
TTCTGAAAGACGGCGGTGGCGGTTCGAGCTCGGCGAACAAGGCGGTGAACGATTTT
ATCCTGGCGATGAACTATGACAAGAAGAAACTGCTGACCCACCAAGGCGAGAGCAT
TGAGAACCGTTTCATTAAAGAAGGCAACCAGCTGCCGGACGAGTTTGTGGTTATCGA
GCGTAAGAAACGTAGCCTGAGCACCAACACCAGCGACATTAGCGTGACCGCGACCA
ACGATAGCCGTCTGTACCCGGGTGCGCTGCTGGTTGTGGATGAAACCCTGCTGGAAA
ACAACCCGACCCTGCTGGCGGTGGACCGTGCGCCGATGACCTATAGCATCGATCTGC
CGGGTCTGGCGAGCAGCGACAGCTTCCTGCAAGTTGAGGATCCGAGCAACAGCAGC
GTGCGTGGTGCGGTTAACGACCTGCTGGCGAAGTGGCACCAGGATTACGGCCAAGT
GAACAACGTTCCGGCGCGTATGCAGTATGAAAAAATCACCGCGCACAGCATGGAGC
AACTGAAGGTTAAATTCGGTAGCGACTTTGAAAAGACCGGCAACAGCCTGGACATT
GATTTCAACAGCGTGCACAGCGGCGAGAAGCAGATCCAAATCGTTAACTTCAAGCA
GATCTACTACACCGTGAGCGTTGACGCGGTGAAGAACCCGGGTGACGTTTTCCAGG
ATACCGTGACCGTTGAAGATCTGAAACAACGTGGCATTAGCGCGGAGCGTCCGCTG
GTGTACATCAGCAGCGTTGCGTACGGTCGTCAAGTGTATCTGAAGCTGGAAACCACC
AGCAAAAGCGATGAGGTTGAAGCGGCGTTTGAGGCGCTGATTAAGGGCGTGAAAGT
TGCGCCGCAGACCGAATGGAAGCAAATTCTGGACAACACCGAGGTGAAAGCGGTTA
TTCTGGGCCCGGATCCGAGCAGCGGCGCGCGTGTGGTTACCGGTAAAGTGGACATG
GTTGAGGATCTGATTCAGGAAGGTAGCCGTTTTACCGCGGACCACCCGGGCCTGCCG
ATCAGCTACACCACCAGCTTCCTGCGTGACAACGTGGTTGCGACCTTTCAAAACAGC
ACCGATTACGTGGAAACCAAGGTTACCGCGTATCGTAACGGTGACCTGCTGCTGGAC
CACAGCGGTGCGTACGTGGCGCAGTACTATATCACCTGGGATGAACTGAGCTATAA
CCACCAGGGTAAAGAGGTGCTGACCCCGAAAGCGTGGGACCGTAACGGCCAGGATC
TGACCGCGCACTTCACCACCAGCATTCCGCTGAAGGGCAACGTGCGTAACCTGAGC
GTTAAAATCCGTGAGGGTACCGGCCTGGCGTTTGAATGGTGGCGTACCGTGTACGAG
AAGACCGACCTGCCGCTGGTTCGTAAACGTACCATCAGCATTTGGGGTACCACCCTG
TATCCGCAGGTGGAGGACAAAGTTGAAAATGATGGTGGTGGTGGTAGCAGCAGCGA
GCAGGCGATCATTGAAACCGTGCCGGCGCAATACCTGTATAAGATGGACGATACCG
CGTACTTCATGAACACCGAAACCTACGACCAATATGAAATTCCGGTGGTTAACGTTG
AGAACGAACTGCTGTACATCCTGGAAAACAGCGATGTGAAAATTCAGTTTTATGGTA
CCGAGGTTATCGGCGTGACCGTTCCGACCACCGTGGAGCTGACCGTTGCGGAAACC
CAACCGAGCATCAAGGGTGCGACCGTGACCGGTAGCGGTAAACCGGCGACCATGGA
AACCGGTCTGGTGGTTAACGTGCCGGACTTCATTGAGGCGGGCCAGAAGCTGGTTAT
CAATACCGCGGAGGGTACCTATGTTAGCCGTTAATGA SEQ ID NO: 63, codon-optimized nucleotide sequence encoding Rhavi-linker-SP0435 [aa 62-185]-linker-PdT(G294P), includes leading ATG sequence:
ATGTTCGACGCATCCAACTTTAAAGACTTTAGCAGCATCGCGTCCGCAAGCTCTAGC
TGGCAGAATCAATCTGGTAGCACCATGATTATCCAAGTGGACAGCTTTGGTAACGTC
AGCGGTCAATATGTTAATCGTGCACAGGGTACGGGTTGTCAGAATTCTCCGTACCCG
CTGACCGGTCGTGTTAACGGCACGTTCATCGCTTTCAGCGTCGGTTGGAACAATTCT
ACTGAAAATTGCAACAGCGCGACCGGTTGGACGGGCTATGCACAAGTGAATGGCAA
TAACACCGAAATCGTCACGTCCTGGAATCTGGCGTATGAGGGTGGCAGCGGTCCGG
CTATTGAACAGGGCCAGGATACCTTCCAATACGTCCCTACGACCGAGAATAAGTCCC
TTCTGAAAGACGGCGGTGGCGGTTCGAGCTCGGAGCAGGCGATCATTGAAACCGTG
CCGGCGCAATACCTGTATAAGATGGACGATACCGCGTACTTCATGAACACCGAAAC
CTACGACCAATATGAAATTCCGGTGGTTAACGTTGAGAACGAACTGCTGTACATCCT
GGAAAACAGCGATGTGAAAATTCAGTTTTATGGTACCGAGGTTATCGGCGTGACCGT
TCCGACCACCGTGGAGCTGACCGTTGCGGAAACCCAACCGAGCATCAAGGGTGCGA
CCGTGACCGGTAGCGGTAAACCGGCGACCATGGAAACCGGTCTGGTGGTTAACGTG
CCGGACTTCATTGAGGCGGGCCAGAAGCTGGTTATCAATACCGCGGAGGGTACCTA
TGTTAGCCGTTAATGAGGTGGTGGTGGTAGCAGCAGCGCGAACAAGGCGGTGAACG
ATTTTATCCTGGCGATGAACTATGACAAGAAGAAACTGCTGACCCACCAAGGCGAG
AGCATTGAGAACCGTTTCATTAAAGAAGGCAACCAGCTGCCGGACGAGTTTGTGGTT
ATCGAGCGTAAGAAACGTAGCCTGAGCACCAACACCAGCGACATTAGCGTGACCGC
GACCAACGATAGCCGTCTGTACCCGGGTGCGCTGCTGGTTGTGGATGAAACCCTGCT
GGAAAACAACCCGACCCTGCTGGCGGTGGACCGTGCGCCGATGACCTATAGCATCG
ATCTGCCGGGTCTGGCGAGCAGCGACAGCTTCCTGCAAGTTGAGGATCCGAGCAAC
AGCAGCGTGCGTGGTGCGGTTAACGACCTGCTGGCGAAGTGGCACCAGGATTACGG
CCAAGTGAACAACGTTCCGGCGCGTATGCAGTATGAAAAAATCACCGCGCACAGCA
TGGAGCAACTGAAGGTTAAATTCGGTAGCGACTTTGAAAAGACCGGCAACAGCCTG
GACATTGATTTCAACAGCGTGCACAGCGGCGAGAAGCAGATCCAAATCGTTAACTT
CAAGCAGATCTACTACACCGTGAGCGTTGACGCGGTGAAGAACCCGGGTGACGTTT -continued Sequence Listing

```
TCCAGGATACCGTGACCGTTGAAGATCTGAAACAACGTGGCATTAGCGCGGAGCGT
CCGCTGGTGTACATCAGCAGCGTTGCGTACGGTCGTCAAGTGTATCTGAAGCTGGAA
ACCACCAGCAAAAGCGATGAGGTTGAAGCGGCGTTTGAGGCGCTGATTAAGGGCGT
GAAAGTTGCGCCGCAGACCGAATGGAAGCAAATTCTGGACAACACCGAGGTGAAAG
CGGTTATTCTGGGCCCGGATCCGAGCAGCGGCGCGCGTGTGGTTACCGGTAAAGTG
GACATGGTTGAGGATCTGATTCAGGAAGGTAGCCGTTTTACCGCGGACCACCCGGG
CCTGCCGATCAGCTACACCACCAGCTTCCTGCGTGACAACGTGGTTGCGACCTTTCA
AAACAGCACCGATTACGTGGAAACCAAGGTTACCGCGTATCGTAACGGTGACCTGC
TGCTGGACCACAGCGGTGCGTACGTGGCGCAGTACTATATCACCTGGGATGAACTG
AGCTATAACCACCAGGGTAAAGAGGTGCTGACCCCGAAAGCGTGGGACCGTAACGG
CCAGGATCTGACCGCGCACTTCACCACCAGCATTCCGCTGAAGGGCAACGTGCGTA
ACCTGAGCGTTAAAATCCGTGAGGGTACCGGCCTGGCGTTTGAATGGTGGCGTACCG
TGTACGAGAAGACCGACCTGCCGCTGGTTCGTAAACGTACCATCAGCATTTGGGGTA
CCACCCTGTATCCGCAGGTGGAGGACAAAGTTGAAAATGAT

SEQ ID NO: 64, codon-optimized nucleic acid sequence encoding
Rhavi-linker-SP1500 [aa 27-278]-linker-SP0785 [aa 33-399]
fusion protein, denoted CP1, includes leading ATG sequence:
ATGTTCGACGCATCCAACTTTAAAGACTTTAGCAGCATCGCGTCCGCAAGCTCTAGC
TGGCAGAATCAATCTGGTAGCACCATGATTATCCAAGTGGACAGCTTTGGTAACGTC
AGCGGTCAATATGTTAATCGTGCACAGGGTACGGGTTGTCAGAATTCTCCGTACCCG
CTGACCGGTCGTGTTAACGGCACGTTCATCGCTTTCAGCGTCGGTTGGAACAATTCT
ACTGAAAATTGCAACAGCGCGACCGGTTGGACGGGCTATGCACAAGTGAATGGCAA
TAACACCGAAATCGTCACGTCCTGGAATCTGGCGTATGAGGGTGGCAGCGGTCCGG
CTATTGAACAGGGCCAGGATACCTTCCAATACGTCCCTACGACCGAGAATAAGTCCC
TTCTGAAAGACGGCGGTGGCGGTTCGAGCTCGACCAGCGGCGACAATTGGTCCAAA
TACCAGAGCAACAAGAGCATCACGATCGGCTTCGACAGCACTTTTGTGCCGATGGGT
TTCGCGCAAAAAGACGGTAGCTACGCGGGTTTCGATATTGACCTGGCGACCGCTGTC
TTTGAGAAATACGGCATTACGGTTAATTGGCAGCCGATTGATTGGGACCTGAAAGA
GGCCGAACTCACCAAAGGCACCATCGACCTGATCTGGAATGGTTACTCCGCAACCG
ATGAGCGTCGCGAAAAAGTTGCCTTCAGCAACAGCTATATGAAGAATGAACAAGTG
TTGGTAACCAAGAAATCTAGCGGCATTACGACCGCGAAAGACATGACCGGTAAGAC
GCTGGGTGCGCAGGCCGGTAGCTCTGGCTATGCGGATTTCGAGGCGAATCCTGAGAT
TCTGAAAAACATCGTTGCGAATAAAGAGGCGAACCAGTACCAGACCTTTAACGAAG
CACTGATCGACCTGAAAAACGATCGCATTGACGGTCTGCTGATCGATCGTGTGTACG
CGAACTATTATCTGGAAGCCGAGGGCGTTCTGAACGATTATAATGTTTTTACCGTGG
GTCTGGAGACTGAGGCATTCGCGGTTGGTGCGCGCAAGGAAGATACCAACCTGGTT
AAAAAGATTAATGAGGCATTTAGCTCACTGTACAAGGACGGCAAGTTCCAAGAAAT
TAGCCAGAAGTGGTTCGGTGAAGATGTTGCGACGAAAGAGGTTAAAGAGGGCCAAG
CGGCCGCATTTCGCCAACCGAGCCAGACTGCGTTGAAAGATGAGCCGACCCATCTG
GTTGTTGCGAAAGAGGGCAGCGTGGCATCGAGCGTGCTGCTGAGCGGTACGGTTAC
TGCCAAAAACGAACAATACGTGTACTTCGATGCTAGCAAGGGTGATCTGGATGAAA
TTCTGGTGAGCGTGGGTGACAAAGTTAGCGAAGGCCAGGCACTGGTGAAGTATTCA
TCCTCCGAGGCACAGGCAGCGTACGACAGCGCAAGCCGCGCAGTGGCGCGTGCCGA
CCGTCACATTAACGAATTGAACCAAGCGCGTAACGAGGCCGCAAGCGCGCCAGCAC
CGCAGCTGCCGGCTCCGGTGGGTGGCGAAGATGCGACGGTGCAGAGCCCGACCCCG
GTTGCGGGTAATTCGGTCGCCAGCATCGATGCGCAGCTGGGTGACGCGCGTGATGCC
CGTGCGGATGCGGCTGCTCAACTGAGCAAGGCTCAGAGCCAACTGGACGCGACGAC
GGTGCTGAGCACCTTGGAGGGTACCGTTGTCGAAGTCAACAGCAATGTGAGCAAGA
GCCCAACGGGTGCGAGCCAGGTTATGGTCCACATTGTGAGCAATGAAAACTTACAG
GTCAAGGGTGAGCTGAGCGAGTATAACCTGGCGAATCTGAGCGTTGGTCAAGAGGT
CAGCTTTACCAGCAAGGTCTACCCGGATAAGAAATGGACCGGCAAGTTGAGCTACA
TCAGCGACTACCCGAAGAACAATGGCGAGGCAGCCTCCCCGGCAGCCGGCAACAAT
ACCGGCTCTAAGTATCCGTACACCATCGACGTAACCGGTGAGGTCGGCGACCTGAA
ACAGGGTTTTAGCGTGAATATCGAAGTGAAGTCCAAGACCAAGGCAATTTTGGTTCC
GGTTAGCTCCCTGGTGATGGACGATAGCAAGAATTATGTGTGGATTGTCGACGAGCA
ACAGAAAGCGAAAAAAGTTGAAGTGAGCCTGGGCAATGCTGATGCCGAGAACCAA
GAAATCACGTCTGGTCTGACCAACGGTGCGAAAGTTATTAGCAACCCGACCAGCAG
CCTGGAAGAGGGTAAAGAGGTCAAAGCCGACGAAGCTACGAAC
```

REFERENCES

Anttila M, Eskola J, Ahman H, Käyhty H. Avidity of IgG for *Streptococcus pneumoniae* type 6B and 23F polysaccharides in infants primed with pneumococcal conjugates and boosted with polysaccharide or conjugate vaccines. J Infect Dis. 1998 June; 177 (6): 1614-21.

Berry A M, Alexander J E, Mitchel T J, Andrew P W, Hansman D, Paton J C. Effect of defined point mutations in the pneumolysin gene on the virulence of *Streptococcus pneumoniae*. Infect Immun. 1995; 63 (5): 1969-74.

Buller H R, Halperin J, Hankey G J, Pillion G, Prins M H, Raskob G E. Comparison of idrabiotaparinux with vitamin K antagonists for prevention of thromboembolism in patients with atrial fibrillation: the Borsealis-Atrial Fibrillation study. J Throb Haemost. 2014; 12:824-30.

[CDC] Centers for Disease Control and Prevention. Preventing pneumococcal disease among infants and young children. Morbidity and Mortality Weekly Report. 2000; 49:1-55.

[CDC] Centers for Disease Control and Prevention. Prevention of pneumococcal disease among infants and children—use of 13-valent pneumococcal conjugate vaccine and 23-valent pneumococcal polysaccharide vaccine. Morbidity and Mortality Weekly Report. 2010; 59:1-24.

Chase (1967). Perinatal and infant mortality in the United States and six West European countries. Am J Public Health Nations Health. 1967 October; 57 (10): 1735-48.

Concepcion N F, Frasch C E. Pneumococcal type 22f polysaccharide absorption improves the specificity of a pneumococcal-polysaccharide enzyme-linked immunosorbent assay. Clin Diagn Lab Immunol. 2001 March; 8 (2): 266-72.

Douce et al. Mutants of *Escherichia coli* heat-labile toxin lacking ADP-ribosyltransferase activity act as non-toxic, mucosal adjuvants. PNAS Vol. 92, pp. 1644-1648 February 1995.

Douce et al. Genetically detoxified mutants of heat-labile toxin from *Escherichia coli* are able to act as oral adjuvants" Infect Immun. 1999 September; 67 (9): 4400-6)

Evans J T et al. Enhancement of antigen-specific immunity via the TLR-4 ligands MPL adjuvant and Ribi.529. Expert Rev Vaccines 2003 April; 2 (2): 219-29.

Geno K A, Gilbert G L, Song J Y, Skovsted I C, Klugman K P, Jones C et al. Pneumococcal Capsules and their types: past, present, and future. Clin Microbiol Rev 2015 July; 28 (3): 871-899.

Giuliani M M et al. Mucosal adjuvanticity and immunogenicity of LTR72, a novel mutant of *Escherichia coli* heat-labile enterotoxin with partial knockout of ADP-ribosyltransferase activity. J Exp Med. 1998 Apr. 6; 187 (7): 1123-32.

Gruber M F, Pratt D, Haase M. Licensing of pneumococcal conjugate vaccines for children and adults: Regulatory perspective from the European Medicines Agency and the U.S. Food and Drug Administration. In: Siber G R, Klugman K P, Mäkelä P H, eds. Pneumococcal Vaccines: The Impact of Conjugate Vaccine. Washington, D C: ASM Press; 2008; 183-96.

Helppolainen S H, Nurminen K P, Määttä J A, Halling K K, Slotte J P, Huhtala T, et al. Rhizavidin from *Rhizobium etli*: the first natural dimer in the avidin protein family. Biochem J. 2007; 405:397-405.

Holliger P, Prospero T, Winter G. "Diabodies": small bivalent and bispecific antibody fragments. Proc Natl Acad Sci USA. 1993 Jul. 15; 90 (14): 6444-8.

Ishizaka S T et al. "E6020: a synthetic Toll-like receptor 4 agonist as a vaccine adjuvant." Expert Rev. Vaccines. 2007 October; 6 (5): 773-84.

Kaufmann F, Lund E, Eddy B. Proposal for a change in the nomenclature of Diplococcus *pneumoniae* and a comparison of the Danish and American type designations. Intl Bulletin of Bacterial Nomenclature and Taxonomy 1960 January; 10 (1): 31-40.

Kim K H, Yu J, Nahm M H. Efficiency of a pneumococcal opsonophagocytic killing assay improved by multiplexing and by coloring colonies. Clin Diagn Lab Immunol. 2003 July; 10 (4): 616-21.

Lazzeri E, Pauwels E K, Erba P A, Volterrani D, Manca M, Bodei L, et al. Clinical feasibility of two-step streptavidin/111 In-biotin scintigraphy in patients with suspected vertebral osteomyelitis. Eur J Nucl Med Mol Imaging. 2004; 31:1505-11.

Kojima K, Ishizaka A, Oshika E, Taguchi Y, Tomizawa K, et al. Quantitation of IgG subclass antibodies to pneumococcal capsular polysaccharides by ELISA, using Pneumovax-specific antibodies as a reference. Tohoku J Exp Med. 1990 July; 161 (3): 209-15.

Koskela M, Leinonen M. Comparison of ELISA and RIA for measurement of pneumococcal antibodies before and after vaccination with 14-valent pneumococcal capsular polysaccharide vaccine. J Clin Pathol. 1981 January; 34 (1): 93-8.

Martin, E W, Ed. Remington's Pharmaceutical Sciences. 15th ed. Easton, P A: Mack Publishing Company, 1975.

Martinez J E, Romero-Steiner S, Pilishvili T, Barnard S, Schinsky J, et al. A flow cytometric opsonophagocytic assay for measurement of functional antibodies elicited after vaccination with the 23-valent pneumococcal polysaccharide vaccine. Clin Diagn Lab Immunol. 1999 July; 6 (4): 581-6.

Meyers and Miller. CABIOS, 1989, 4:11-17.

Munro C S, Stanley P J, Cole P J. Assessment of biological activity of immunoglobulin preparations by using opsonized micro-organisms to stimulate neutrophil chemiluminescence. Clin Exp Immunol. 1985 July; 61 (1): 183-8.

Ojo-Amaize E A, Church J A, Barka N E, Agopian M S, Peter J B. A rapid and sensitive chemiluminescence assay for evaluation of functional opsonic activity of *Haemophilus influenzae* type b-specific antibodies. Clin Diagn Lab Immunol. 1995 May; 2 (3): 286-90

Paty I, Trellu M, Destors J M, Cortez P, Boelle E, Sanderink G. Reversibility of the anti-FXa activity of idrabiotaparinux (biotinylated idraparinux) by intravenous avidin infusion. J Thromb Haemost. 2010; 8:722-9.

Oloo E O, Yethon J A, Ochs M M, Carpick B, Oomen R. Structure-guided antigen engineering yields pneumolysin mutants suitable for vaccination against pneumococcal disease. 2011; 286 (14): 12133-40.

PNEUMOVAX® 23 (prescribing information). Whitehouse Station, N J: Merck & Co.; May 2015.

PREVNAR 13® (prescribing information). New York, N Y: Pfizer; August 2017.

Poljak R J. Production and structure of diabodies. Structure. 1994 Dec. 15; 2 (12): 1121-3. Powell M F and Newman M J, Eds. Vaccine Design: The Subunit and Adjuvant Approach. New York, N Y: Plenum Press, 1995.

Richter S S, Diekema D J, Heilmann K P, Dohrn C L, Riahi F, Doern G V. Changes in pneumococcal serotypes and antimicrobial resistance after introduction of the 13 valent conjugate vaccine in the United States. Antimicrob Agents Chemother. 2014; 58:6484-9.

Romero-Steiner S, Libutti D, Pais L B, Dykes J, Anderson P, et al. Standardization of an opsonophagocytic assay for the measurement of functional antibody activity against *Streptococcus pneumoniae* using differentiated HL-60 cells. Clin Diagn Lab Immunol. 1997 July; 4 (4): 415-22.

Romero-Steiner S, Holder P F, Gomez de Leon P, Spear W, Hennessy T W, et al. Avidity determinations for *Haemophilus influenzae* Type b anti-polyribosylribitol phosphate antibodies. Clin Diagn Lab Immunol. 2005 Sep.; 12 (9): 1029-35.

Saeland E, Vidarsson G, Jonsdottir I. Pneumococcal pneumonia and bacteremia model in mice for the analysis of protective antibodies. Microb Pathog. 2000 August; 29 (2): 81-91.

Singh et al. Curr. HIV Res. 1:309-20, 2003.

Stack A M, Malley R, Thompson C M, Kobzik L, Siber G R, et al. Minimum protective serum concentrations of pneumococcal anti-capsular antibodies in infant rats. J Infect Dis. 1998 April; 177 (4): 986-90.

Williams et al., Innate imprinting by the modified heat-labile toxin of *Escherichia coli* (LTK63) provides generic protection against lung infectious disease. The Journal of Immunology, 2004 173:7435-7443.

Wu W, Huang J, Duan B, Traficante D C, Hong H, et al. $T_H17$-stimulating protein vaccines confer protection against *Pseudomonas aeruginosa* pneumonia. Am J Respir Crit Care Med. 2012 Sep. 1; 186 (5): 420-7.

Zhang F, Lu Y J, Malley R. Multiple antigen-presenting system (MAPS) to induce comprehensive B- and T-cell immunity. Proc Natl Acad Sci USA. 2013; 110:13564-9.

EQUIVALENTS

Those skilled in the art will recognize, or be able to ascertain using no more than routine experimentation, many equivalents to the specific embodiments of the invention described herein. The scope of the present disclosure is not intended to be limited to the above Description, but rather is as set forth in the following claims:

We claim:

1. A method of immunizing a subject against *Streptococcus pneumoniae* infection and/or colonization comprising administering to the subject an immunologically effective amount of a vaccine, wherein the vaccine comprises an immunogenic complex that comprises:

(a) a biotinylated polysaccharide; and (b) a fusion protein comprising an amino acid sequence at least 90% identical to SEQ ID NO: 19, SEQ ID NO: 20, SEQ ID NO: 58, or SEQ ID NO: 59, wherein the fusion protein comprises:

(i) a biotin-binding moiety;

(ii) a non-hemolytic pneumolysin (Ply) polypeptide comprising mutations at amino acid residues corresponding to amino acid residues 294, 385, 428, and 433 of wild-type *Streptococcus pneumoniae* pneumolysin (SEQ ID NO: 3) or antigenic fragment thereof; and (iii) an SP0435 polypeptide or antigenic fragment thereof;

wherein the biotinylated polysaccharide antigen is non-covalently associated with the biotin-binding moiety of the fusion protein to form the immunogenic complex.

2. The method of claim 1, wherein the biotinylated polysaccharide antigen comprises a polysaccharide of *Streptococcus pneumoniae.*

3. The method of claim 1, wherein the biotinylated polysaccharide antigen comprises a polysaccharide of *Streptococcus pneumoniae* having a serotype selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

4. The method of claim 1, wherein the biotinylated polysaccharide antigen comprises a polysaccharide of *Streptococcus pneumoniae* having a serotype selected from 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20B, 22F, 23A, 23B, 23F, 24F, 31, 33F, 35B, and 38.

5. The method of claim 1, wherein the biotinylated polysaccharide antigen comprises a polysaccharide of *Streptococcus pneumoniae* having a serotype selected from 6C, 7C, 15A, 16F, 23A, 23B, 24F, 31, 35B, and 38.

6. The method of claim 1, wherein the vaccine comprises:

a plurality of different species of immunogenic complexes comprising:

(a) a plurality of first biotinylated polysaccharide antigens, wherein the plurality comprises polysaccharide antigens of one or more of *Streptococcus pneumoniae* serotypes 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48; and (b) a plurality of first fusion proteins, wherein each first fusion protein comprises an amino acid sequence at least 90% identical to SEQ ID NO: 19, SEQ ID NO: 20, SEQ ID NO: 58, or SEQ ID NO: 59, and wherein each first fusion protein comprises:

(i) a biotin-binding moiety;

(ii) a non-hemolytic pneumolysin (Ply) polypeptide comprising mutations at amino acid residues corresponding to amino acid residues 294, 385, 428, and 433 of wild-type *Streptococcus pneumoniae* pneumolysin (SEQ ID NO: 3) or antigenic fragment thereof, wherein the non-hemolytic pneumolysin (Ply) polypeptide comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 6 or an antigenic fragment thereof; and (iii) an SP0435 polypeptide or antigenic fragment thereof, wherein the SP0435 polypeptide or antigenic fragment thereof comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 8 or an antigenic fragment thereof;

wherein each of the plurality of first biotinylated polysaccharide antigens is non-covalently associated with the biotin-binding moiety of one or more of the plurality of first fusion proteins to form one of the immunogenic complexes.

7. The method of claim 6, wherein the plurality of different species of immunogenic complexes further comprises:

(a) a plurality of second biotinylated polysaccharide antigens, wherein the plurality comprises polysaccharide antigens of one or more of *Streptococcus pneumoniae* serotypes 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48; and (b) a plurality of second fusion proteins, wherein each second fusion protein comprises:

(i) a biotin-binding moiety;

(ii) a first polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 12 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 10 or an antigenic fragment thereof;

wherein each of the plurality of second biotinylated polysaccharide antigens is non-covalently associated with the biotin-binding moiety of one or more of the plurality of second fusion proteins to form one of the immunogenic complexes.

8. The method of claim 7, wherein each of the plurality of second fusion proteins is or comprises an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 26 or SEQ ID NO: 61.

9. The method of claim 7, wherein the plurality of different species of immunogenic complexes comprises:

a biotinylated polysaccharide antigen of *Streptococcus pneumoniae* serotype 6C non-covalently complexed with the biotin-binding moiety of one or more of the plurality of first fusion proteins;

a biotinylated polysaccharide antigen of *Streptococcus pneumoniae* serotype 7C non-covalently complexed with the biotin-binding moiety of one or more of the plurality of first fusion proteins;

a biotinylated polysaccharide antigen of *Streptococcus pneumoniae* serotype 15A non-covalently complexed with the biotin-binding moiety of one or more of the plurality of first fusion proteins;

a biotinylated polysaccharide antigen of *Streptococcus pneumoniae* serotype 16F non-covalently complexed with the biotin-binding moiety of one or more of the plurality of first fusion proteins;

a biotinylated polysaccharide antigen of *Streptococcus pneumoniae* serotype 23A non-covalently complexed with the biotin-binding moiety of one or more of the plurality of first fusion proteins;

a biotinylated polysaccharide antigen of *Streptococcus pneumoniae* serotype 23B non-covalently complexed with the biotin-binding moiety of one or more of the plurality of first fusion proteins;

a biotinylated polysaccharide antigen of *Streptococcus pneumoniae* serotype 24F non-covalently complexed with the biotin-binding moiety of one or more of the plurality of first fusion proteins;

a biotinylated polysaccharide antigen of *Streptococcus pneumoniae* serotype 31 non-covalently complexed with the biotin-binding moiety of one or more of the plurality of first fusion proteins;

a biotinylated polysaccharide antigen of *Streptococcus pneumoniae* serotype 35B non-covalently complexed with the biotin-binding moiety of one or more of the plurality of first fusion proteins; and a biotinylated polysaccharide antigen of *Streptococcus pneumoniae* serotype 38 non-covalently complexed with the biotin-binding moiety of one or more of the plurality of first fusion proteins;

a biotinylated polysaccharide antigen of *Streptococcus pneumoniae* serotype 1 non-covalently complexed with the biotin-binding moiety of one or more of the plurality of second fusion proteins;

a biotinylated polysaccharide antigen of *Streptococcus pneumoniae* serotype 2 non-covalently complexed with the biotin-binding moiety of one or more of the plurality of second fusion proteins;

a biotinylated polysaccharide antigen of *Streptococcus pneumoniae* serotype 3 non-covalently complexed with the biotin-binding moiety of one or more of the plurality of second fusion proteins;

a biotinylated polysaccharide antigen of *Streptococcus pneumoniae* serotype 4 non-covalently complexed with the biotin-binding moiety of one or more of the plurality of second fusion proteins;

a biotinylated polysaccharide antigen of *Streptococcus pneumoniae* serotype 5 non-covalently complexed with the biotin-binding moiety of one or more of the plurality of second fusion proteins;

a biotinylated polysaccharide antigen of *Streptococcus pneumoniae* serotype 6A non-covalently complexed with the biotin-binding moiety of one or more of the plurality of second fusion proteins;

a biotinylated polysaccharide antigen of *Streptococcus pneumoniae* serotype 6B non-covalently complexed with the biotin-binding moiety of one or more of the plurality of second fusion proteins;

a biotinylated polysaccharide antigen of *Streptococcus pneumoniae* serotype 7F non-covalently complexed with the biotin-binding moiety of one or more of the plurality of second fusion proteins;

a biotinylated polysaccharide antigen of *Streptococcus pneumoniae* serotype 8 non-covalently complexed with the biotin-binding moiety of one or more of the plurality of second fusion proteins;

a biotinylated polysaccharide antigen of *Streptococcus pneumoniae* serotype 9N non-covalently complexed with the biotin-binding moiety of one or more of the plurality of second fusion proteins;

a biotinylated polysaccharide antigen of *Streptococcus pneumoniae* serotype 9V non-covalently complexed with the biotin-binding moiety of one or more of the plurality of second fusion proteins;

a biotinylated polysaccharide antigen of *Streptococcus pneumoniae* serotype 10A non-covalently complexed with the biotin-binding moiety of one or more of the plurality of second fusion proteins;

a biotinylated polysaccharide antigen of *Streptococcus pneumoniae* serotype 11A non-covalently complexed with the biotin-binding moiety of one or more of the plurality of second fusion proteins;

a biotinylated polysaccharide antigen of *Streptococcus pneumoniae* serotype 12F non-covalently complexed with the biotin-binding moiety of one or more of the plurality of second fusion proteins;

a biotinylated polysaccharide antigen of *Streptococcus pneumoniae* serotype 14 non-covalently complexed with the biotin-binding moiety of one or more of the plurality of second fusion proteins;

a biotinylated polysaccharide antigen of *Streptococcus pneumoniae* serotype 15B non-covalently complexed with the biotin-binding moiety of one or more of the plurality of second fusion proteins;

a biotinylated polysaccharide antigen of *Streptococcus pneumoniae* serotype 17F non-covalently complexed with the biotin-binding moiety of one or more of the plurality of second fusion proteins;

a biotinylated polysaccharide antigen of *Streptococcus pneumoniae* serotype 18C non-covalently complexed with the biotin-binding moiety of one or more of the plurality of second fusion proteins;

a biotinylated polysaccharide antigen of *Streptococcus pneumoniae* serotype 19A non-covalently complexed with the biotin-binding moiety of one or more of the plurality of second fusion proteins;

a biotinylated polysaccharide antigen of *Streptococcus pneumoniae* serotype 19F non-covalently complexed with the biotin-binding moiety of one or more of the plurality of second fusion proteins;

a biotinylated polysaccharide antigen of *Streptococcus pneumoniae* serotype 20B non-covalently complexed with the biotin-binding moiety of one or more of the plurality of second fusion proteins;

a biotinylated polysaccharide antigen of *Streptococcus pneumoniae* serotype 22F non-covalently complexed with the biotin-binding moiety of one or more of the plurality of second fusion proteins;

a biotinylated polysaccharide antigen of *Streptococcus pneumoniae* serotype 23F non-covalently complexed with the biotin-binding moiety of one or more of the plurality of second fusion proteins; and a biotinylated polysaccharide antigen of *Streptococcus pneumoniae* serotype 33F non-covalently complexed with the biotin-binding moiety of one or more of the plurality of second fusion proteins.

10. The method of claim 7, wherein the plurality of different species of immunogenic complexes comprises:

a biotinylated polysaccharide antigen of *Streptococcus pneumoniae* serotype 1 non-covalently complexed with the biotin-binding moiety of one or more of the plurality of first fusion proteins;

a biotinylated polysaccharide antigen of *Streptococcus pneumoniae* serotype 4 non-covalently complexed with the biotin-binding moiety of one or more of the plurality of first fusion proteins;

a biotinylated polysaccharide antigen of *Streptococcus pneumoniae* serotype 6A non-covalently complexed with the biotin-binding moiety of one or more of the plurality of first fusion proteins;

a biotinylated polysaccharide antigen of *Streptococcus pneumoniae* serotype 6B non-covalently complexed with the biotin-binding moiety of one or more of the plurality of first fusion proteins;

a biotinylated polysaccharide antigen of *Streptococcus pneumoniae* serotype 9V non-covalently complexed with the biotin-binding moiety of one or more of the plurality of first fusion proteins;

a biotinylated polysaccharide antigen of *Streptococcus pneumoniae* serotype 15B non-covalently complexed with the biotin-binding moiety of one or more of the plurality of first fusion proteins;

a biotinylated polysaccharide antigen of *Streptococcus pneumoniae* serotype 18C non-covalently complexed with the biotin-binding moiety of one or more of the plurality of first fusion proteins;

a biotinylated polysaccharide antigen of *Streptococcus pneumoniae* serotype 19A non-covalently complexed with the biotin-binding moiety of one or more of the plurality of first fusion proteins;

a biotinylated polysaccharide antigen of *Streptococcus pneumoniae* serotype 23F non-covalently complexed with the biotin-binding moiety of one or more of the plurality of first fusion proteins; and a biotinylated polysaccharide antigen of *Streptococcus pneumoniae* serotype 33F non-covalently complexed with the biotin-binding moiety of one or more of the plurality of first fusion proteins;

a biotinylated polysaccharide antigen of *Streptococcus pneumoniae* serotype 2 non-covalently complexed with the biotin-binding moiety of one or more of the plurality of second fusion proteins;

a biotinylated polysaccharide antigen of *Streptococcus pneumoniae* serotype 3 non-covalently complexed with the biotin-binding moiety of one or more of the plurality of second fusion proteins;

a biotinylated polysaccharide antigen of *Streptococcus pneumoniae* serotype 5 non-covalently complexed with the biotin-binding moiety of one or more of the plurality of second fusion proteins;

a biotinylated polysaccharide antigen of *Streptococcus pneumoniae* serotype 6C non-covalently complexed with the biotin-binding moiety of one or more of the plurality of second fusion proteins;

a biotinylated polysaccharide antigen of *Streptococcus pneumoniae* serotype 7C non-covalently complexed with the biotin-binding moiety of one or more of the plurality of second fusion proteins;

a biotinylated polysaccharide antigen of *Streptococcus pneumoniae* serotype 7F non-covalently complexed with the biotin-binding moiety of one or more of the plurality of second fusion proteins;

a biotinylated polysaccharide antigen of *Streptococcus pneumoniae* serotype 8 non-covalently complexed with the biotin-binding moiety of one or more of the plurality of second fusion proteins;

a biotinylated polysaccharide antigen of *Streptococcus pneumoniae* serotype 9N non-covalently complexed with the biotin-binding moiety of one or more of the plurality of second fusion proteins;

a biotinylated polysaccharide antigen of *Streptococcus pneumoniae* serotype 10A non-covalently complexed with the biotin-binding moiety of one or more of the plurality of second fusion proteins;

a biotinylated polysaccharide antigen of *Streptococcus pneumoniae* serotype 11A non-covalently complexed with the biotin-binding moiety of one or more of the plurality of second fusion proteins;

a biotinylated polysaccharide antigen of *Streptococcus pneumoniae* serotype 12F non-covalently complexed with the biotin-binding moiety of one or more of the plurality of second fusion proteins;

a biotinylated polysaccharide antigen of *Streptococcus pneumoniae* serotype 14 non-covalently complexed with the biotin-binding moiety of one or more of the plurality of second fusion proteins;

a biotinylated polysaccharide antigen of *Streptococcus pneumoniae* serotype 15A non-covalently complexed with the biotin-binding moiety of one or more of the plurality of second fusion proteins;

a biotinylated polysaccharide antigen of *Streptococcus pneumoniae* serotype 16F non-covalently complexed with the biotin-binding moiety of one or more of the plurality of second fusion proteins;

a biotinylated polysaccharide antigen of *Streptococcus pneumoniae* serotype 17F non-covalently complexed with the biotin-binding moiety of one or more of the plurality of second fusion proteins;

a biotinylated polysaccharide antigen of *Streptococcus pneumoniae* serotype 19F non-covalently complexed with the biotin-binding moiety of one or more of the plurality of second fusion proteins;

a biotinylated polysaccharide antigen of *Streptococcus pneumoniae* serotype 20B non-covalently complexed with the biotin-binding moiety of one or more of the plurality of second fusion proteins;

a biotinylated polysaccharide antigen of *Streptococcus pneumoniae* serotype 22F non-covalently complexed with the biotin-binding moiety of one or more of the plurality of second fusion proteins;

a biotinylated polysaccharide antigen of *Streptococcus pneumoniae* serotype 23A non-covalently complexed with the biotin-binding moiety of one or more of the plurality of second fusion proteins;

a biotinylated polysaccharide antigen of *Streptococcus pneumoniae* serotype 23B non-covalently complexed with the biotin-binding moiety of one or more of the plurality of second fusion proteins;

a biotinylated polysaccharide antigen of *Streptococcus pneumoniae* serotype 24F non-covalently complexed with the biotin-binding moiety of one or more of the plurality of second fusion proteins;

a biotinylated polysaccharide antigen of *Streptococcus pneumoniae* serotype 31 non-covalently complexed with the biotin-binding moiety of one or more of the plurality of second fusion proteins;

a biotinylated polysaccharide antigen of *Streptococcus pneumoniae* serotype 35B non-covalently complexed with the biotin-binding moiety of one or more of the plurality of second fusion proteins; and a biotinylated polysaccharide antigen of *Streptococcus pneumoniae* serotype 38 non-covalently complexed with the biotin-binding moiety of one or more of the plurality of second fusion proteins.

11. The method of claim 7, wherein the plurality of different species of immunogenic complexes comprise:

a biotinylated polysaccharide antigen of *Streptococcus pneumoniae* serotype 1 non-covalently complexed with the biotin-binding moiety of one or more of the plurality of first fusion proteins;

a biotinylated polysaccharide antigen of *Streptococcus pneumoniae* serotype 4 non-covalently complexed with the biotin-binding moiety of one or more of the plurality of first fusion proteins;

a biotinylated polysaccharide antigen of *Streptococcus pneumoniae* serotype 6A non-covalently complexed with the biotin-binding moiety of one or more of the plurality of first fusion proteins;

a biotinylated polysaccharide antigen of *Streptococcus pneumoniae* serotype 6B non-covalently complexed with the biotin-binding moiety of one or more of the plurality of first fusion proteins;

a biotinylated polysaccharide antigen of *Streptococcus pneumoniae* serotype 9V non-covalently complexed with the biotin-binding moiety of one or more of the plurality of first fusion proteins;

a biotinylated polysaccharide antigen of *Streptococcus pneumoniae* serotype 15B non-covalently complexed with the biotin-binding moiety of one or more of the plurality of first fusion proteins;

a biotinylated polysaccharide antigen of *Streptococcus pneumoniae* serotype 18C non-covalently complexed with the biotin-binding moiety of one or more of the plurality of first fusion proteins;

a biotinylated polysaccharide antigen of *Streptococcus pneumoniae* serotype 19A non-covalently complexed with the biotin-binding moiety of one or more of the plurality of first fusion proteins;

a biotinylated polysaccharide antigen of *Streptococcus pneumoniae* serotype 23F non-covalently complexed with the biotin-binding moiety of one or more of the plurality of first fusion proteins; and a biotinylated polysaccharide antigen of *Streptococcus pneumoniae* serotype 33F non-covalently complexed with the biotin-binding moiety of one or more of the plurality of first fusion proteins;

a biotinylated polysaccharide antigen of *Streptococcus pneumoniae* serotype 2 non-covalently complexed with the biotin-binding moiety of one or more of the plurality of second fusion proteins;

a biotinylated polysaccharide antigen of *Streptococcus pneumoniae* serotype 3 non-covalently complexed with the biotin-binding moiety of one or more of the plurality of second fusion proteins;

a biotinylated polysaccharide antigen of *Streptococcus pneumoniae* serotype 5 non-covalently complexed with the biotin-binding moiety of one or more of the plurality of second fusion proteins;

a biotinylated polysaccharide antigen of *Streptococcus pneumoniae* serotype 6C non-covalently complexed with the biotin-binding moiety of one or more of the plurality of second fusion proteins;

a biotinylated polysaccharide antigen of *Streptococcus pneumoniae* serotype 7C non-covalently complexed with the biotin-binding moiety of one or more of the plurality of second fusion proteins;

a biotinylated polysaccharide antigen of *Streptococcus pneumoniae* serotype 7F non-covalently complexed with the biotin-binding moiety of one or more of the plurality of second fusion proteins;

a biotinylated polysaccharide antigen of *Streptococcus pneumoniae* serotype 8 non-covalently complexed with the biotin-binding moiety of one or more of the plurality of second fusion proteins;

a biotinylated polysaccharide antigen of *Streptococcus pneumoniae* serotype 9N non-covalently complexed with the biotin-binding moiety of one or more of the plurality of second fusion proteins;

a biotinylated polysaccharide antigen of *Streptococcus pneumoniae* serotype 10A non-covalently complexed with the biotin-binding moiety of one or more of the plurality of second fusion proteins;

a biotinylated polysaccharide antigen of *Streptococcus pneumoniae* serotype 11A non-covalently complexed with the biotin-binding moiety of one or more of the plurality of second fusion proteins;

a biotinylated polysaccharide antigen of *Streptococcus pneumoniae* serotype 12F non-covalently complexed with the biotin-binding moiety of one or more of the plurality of second fusion proteins;

a biotinylated polysaccharide antigen of *Streptococcus pneumoniae* serotype 14 non-covalently complexed with the biotin-binding moiety of one or more of the plurality of second fusion proteins;

a biotinylated polysaccharide antigen of *Streptococcus pneumoniae* serotype 15A non-covalently complexed with the biotin-binding moiety of one or more of the plurality of second fusion proteins;

a biotinylated polysaccharide antigen of *Streptococcus pneumoniae* serotype 17F non-covalently complexed with the biotin-binding moiety of one or more of the plurality of second fusion proteins;

a biotinylated polysaccharide antigen of *Streptococcus pneumoniae* serotype 19F non-covalently complexed with the biotin-binding moiety of one or more of the plurality of second fusion proteins;

a biotinylated polysaccharide antigen of *Streptococcus pneumoniae* serotype 20B non-covalently complexed with the biotin-binding moiety of one or more of the plurality of second fusion proteins;

a biotinylated polysaccharide antigen of *Streptococcus pneumoniae* serotype 22F non-covalently complexed with the biotin-binding moiety of one or more of the plurality of second fusion proteins;

a biotinylated polysaccharide antigen of *Streptococcus pneumoniae* serotype 23A non-covalently complexed with the biotin-binding moiety of one or more of the plurality of second fusion proteins;

a biotinylated polysaccharide antigen of *Streptococcus pneumoniae* serotype 23B non-covalently complexed with the biotin-binding moiety of one or more of the plurality of second fusion proteins;

a biotinylated polysaccharide antigen of *Streptococcus pneumoniae* serotype 24F non-covalently complexed with the biotin-binding moiety of one or more of the plurality of second fusion proteins;

a biotinylated polysaccharide antigen of *Streptococcus pneumoniae* serotype 31 non-covalently complexed with the biotin-binding moiety of one or more of the plurality of second fusion proteins;

a biotinylated polysaccharide antigen of *Streptococcus pneumoniae* serotype 35B non-covalently complexed with the biotin-binding moiety of one or more of the plurality of second fusion proteins; and a biotinylated polysaccharide antigen of *Streptococcus pneumoniae* serotype 38 non-covalently complexed with the biotin-binding moiety of one or more of the plurality of second fusion proteins.

12. The method of claim 7, wherein the plurality of different species of immunogenic complexes comprise:

a biotinylated polysaccharide antigen of *Streptococcus pneumoniae* serotype 1 non-covalently complexed with the biotin-binding moiety of one or more of the plurality of first fusion proteins;

a biotinylated polysaccharide antigen of *Streptococcus pneumoniae* serotype 4 non-covalently complexed with the biotin-binding moiety of one or more of the plurality of first fusion proteins;

a biotinylated polysaccharide antigen of *Streptococcus pneumoniae* serotype 6A non-covalently complexed with the biotin-binding moiety of one or more of the plurality of first fusion proteins;

a biotinylated polysaccharide antigen of *Streptococcus pneumoniae* serotype 6B non-covalently complexed with the biotin-binding moiety of one or more of the plurality of first fusion proteins;

a biotinylated polysaccharide antigen of *Streptococcus pneumoniae* serotype 9V non-covalently complexed with the biotin-binding moiety of one or more of the plurality of first fusion proteins;

a biotinylated polysaccharide antigen of *Streptococcus pneumoniae* serotype 15B non-covalently complexed with the biotin-binding moiety of one or more of the plurality of first fusion proteins;

a biotinylated polysaccharide antigen of *Streptococcus pneumoniae* serotype 18C non-covalently complexed with the biotin-binding moiety of one or more of the plurality of first fusion proteins;

a biotinylated polysaccharide antigen of *Streptococcus pneumoniae* serotype 19A non-covalently complexed with the biotin-binding moiety of one or more of the plurality of first fusion proteins;

a biotinylated polysaccharide antigen of *Streptococcus pneumoniae* serotype 23F non-covalently complexed with the biotin-binding moiety of one or more of the plurality of first fusion proteins; and a biotinylated polysaccharide antigen of *Streptococcus pneumoniae* serotype 33F non-covalently complexed with the biotin-binding moiety of one or more of the plurality of first fusion proteins;

a biotinylated polysaccharide antigen of *Streptococcus pneumoniae* serotype 2 non-covalently complexed with the biotin-binding moiety of one or more of the plurality of second fusion proteins;

a biotinylated polysaccharide antigen of *Streptococcus pneumoniae* serotype 5 non-covalently complexed with the biotin-binding moiety of one or more of the plurality of second fusion proteins;

a biotinylated polysaccharide antigen of *Streptococcus pneumoniae* serotype 6C non-covalently complexed with the biotin-binding moiety of one or more of the plurality of second fusion proteins;

a biotinylated polysaccharide antigen of *Streptococcus pneumoniae* serotype 7C non-covalently complexed with the biotin-binding moiety of one or more of the plurality of second fusion proteins;

a biotinylated polysaccharide antigen of *Streptococcus pneumoniae* serotype 7F non-covalently complexed with the biotin-binding moiety of one or more of the plurality of second fusion proteins;

a biotinylated polysaccharide antigen of *Streptococcus pneumoniae* serotype 8 non-covalently complexed with the biotin-binding moiety of one or more of the plurality of second fusion proteins;

a biotinylated polysaccharide antigen of *Streptococcus pneumoniae* serotype 9N non-covalently complexed with the biotin-binding moiety of one or more of the plurality of second fusion proteins;

a biotinylated polysaccharide antigen of *Streptococcus pneumoniae* serotype 10A non-covalently complexed with the biotin-binding moiety of one or more of the plurality of second fusion proteins;

a biotinylated polysaccharide antigen of *Streptococcus pneumoniae* serotype 11A non-covalently complexed with the biotin-binding moiety of one or more of the plurality of second fusion proteins;

a biotinylated polysaccharide antigen of *Streptococcus pneumoniae* serotype 12F non-covalently complexed with the biotin-binding moiety of one or more of the plurality of second fusion proteins;

a biotinylated polysaccharide antigen of *Streptococcus pneumoniae* serotype 14 non-covalently complexed with the biotin-binding moiety of one or more of the plurality of second fusion proteins;

a biotinylated polysaccharide antigen of *Streptococcus pneumoniae* serotype 15A non-covalently complexed with the biotin-binding moiety of one or more of the plurality of second fusion proteins;

a biotinylated polysaccharide antigen of *Streptococcus pneumoniae* serotype 16F non-covalently complexed with the biotin-binding moiety of one or more of the plurality of second fusion proteins;

a biotinylated polysaccharide antigen of *Streptococcus pneumoniae* serotype 17F non-covalently complexed with the biotin-binding moiety of one or more of the plurality of second fusion proteins;

a biotinylated polysaccharide antigen of *Streptococcus pneumoniae* serotype 19F non-covalently complexed with the biotin-binding moiety of one or more of the plurality of second fusion proteins;

a biotinylated polysaccharide antigen of *Streptococcus pneumoniae* serotype 20B non-covalently complexed with the biotin-binding moiety of one or more of the plurality of second fusion proteins;

a biotinylated polysaccharide antigen of *Streptococcus pneumoniae* serotype 22F non-covalently complexed with the biotin-binding moiety of one or more of the plurality of second fusion proteins;

a biotinylated polysaccharide antigen of *Streptococcus pneumoniae* serotype 23A non-covalently complexed with the biotin-binding moiety of one or more of the plurality of second fusion proteins;

a biotinylated polysaccharide antigen of *Streptococcus pneumoniae* serotype 23B non-covalently complexed with the biotin-binding moiety of one or more of the plurality of second fusion proteins;

a biotinylated polysaccharide antigen of *Streptococcus pneumoniae* serotype 24F non-covalently complexed with the biotin-binding moiety of one or more of the plurality of second fusion proteins;

a biotinylated polysaccharide antigen of *Streptococcus pneumoniae* serotype 31 non-covalently complexed with the biotin-binding moiety of one or more of the plurality of second fusion proteins;

a biotinylated polysaccharide antigen of *Streptococcus pneumoniae* serotype 35B non-covalently complexed with the biotin-binding moiety of one or more of the plurality of second fusion proteins; and a biotinylated polysaccharide antigen of *Streptococcus pneumoniae* serotype 38 non-covalently complexed with the biotin-binding moiety of one or more of the plurality of second fusion proteins.

13. The method of claim 1, wherein the biotin-binding moiety is (i) a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 1 or a biotin-binding fragment thereof; or (ii) a polypeptide comprising an amino acid sequence at least 90%, at least 91%, at least 92%, at least 93%, at least 94%, at least 95%, at least 96%, at least 97%, at least 98%, at least 99%, at least 99.5%, or 100% identical to SEQ ID NO: 2 or SEQ ID NO: 57, or a biotin-binding fragment thereof.

14. The method of claim 1, wherein the fusion protein comprises an amino acid sequence at least 91%, at least 92%, at least 93%, at least 94%, at least 95%, at least 96%, at least 97%, at least 98%, at least 99%, at least 99.5%, or 100% identical to SEQ ID NO: 19, SEQ ID NO: 20, SEQ ID NO: 58, or SEQ ID NO: 59.

15. The method of claim 1, wherein the fusion protein comprises an amino acid sequence at least 95% identical to SEQ ID NO: 19, SEQ ID NO: 20, SEQ ID NO: 58, or SEQ ID NO: 59.

16. The method of claim 1, wherein the fusion protein comprises an amino acid sequence at least 98% identical to SEQ ID NO: 19, SEQ ID NO: 20, SEQ ID NO: 58, or SEQ ID NO: 59.

17. The method of claim 1, wherein the fusion protein comprises the amino acid sequence of SEQ ID NO: 19, SEQ ID NO: 20, SEQ ID NO: 58, or SEQ ID NO: 59.

18. The method of claim 6, wherein each first fusion protein comprises an amino acid sequence at least 91%, at least 92%, at least 93%, at least 94%, at least 95%, at least 96%, at least 97%, at least 98%, at least 99%, at least 99.5%, or 100% identical to SEQ ID NO: 19, SEQ ID NO: 20, SEQ ID NO: 58, or SEQ ID NO: 59.

19. The method of claim 6, wherein each first fusion protein comprises an amino acid sequence at least 95% identical to SEQ ID NO: 19, SEQ ID NO: 20, SEQ ID NO: 58, or SEQ ID NO: 59.

20. The method of claim 6, wherein each first fusion protein comprises an amino acid sequence at least 98% identical to SEQ ID NO: 19, SEQ ID NO: 20, SEQ ID NO: 58, or SEQ ID NO: 59.

21. The method of claim 6, wherein each first fusion protein comprises the amino acid sequence of SEQ ID NO: 19, SEQ ID NO: 20, SEQ ID NO: 58, or SEQ ID NO: 59.

* * * * *

SEQUENCE LISTING

```
Sequence total quantity: 69
SEQ ID NO: 1            moltype = AA  length = 179
FEATURE                 Location/Qualifiers
source                  1..179
                        mol_type = protein
                        organism = Rhizobium sp.
SEQUENCE: 1
MIITSLYATF GTIADGRRTS GGKTMIRTNA VAALVFAVAT SALAFDASNF KDFSSIASAS  60
SSWQNQSGST MIIQVDSFGN VSGQYVNRAQ GTGCQNSPYP LTGRVNGTFI AFSVGWNNST  120
ENCNSATGWT GYAQVNGNNT EIVTSWNLAY EGGSGPAIEQ GQDTFQYVPT TENKSLLKD   179

SEQ ID NO: 2            moltype = AA  length = 135
FEATURE                 Location/Qualifiers
source                  1..135
                        mol_type = protein
                        organism = Rhizobium sp.
SEQUENCE: 2
FDASNFKDFS SIASASSSWQ NQSGSTMIIQ VDSFGNVSGQ YVNRAQGTGC QNSPYPLTGR  60
VNGTFIAFSV GWNNSTENCN SATGWTGYAQ VNGNNTEIVT SWNLAYEGGS GPAIEQGQDT  120
FQYVPTTENK SLLKD                                                   135

SEQ ID NO: 3            moltype = AA  length = 471
FEATURE                 Location/Qualifiers
source                  1..471
                        mol_type = protein
                        organism = Streptococcus pneumoniae
SEQUENCE: 3
MANKAVNDFI LAMNYDKKKL LTHQGESIEN RFIKEGNQLP DEFVVIERKK RSLSTNTSDI  60
SVTATNDSRL YPGALLVVDE TLLENNPTLL AVDRAPMTYS IDLPGLASSD SFLQVEDPSN  120
SSVRGAVNDL LAKWHQDYGQ VNNVPARMQY EKITAHSMEQ LKVKFGSDFE KTGNSLDIDF  180
NSVHSGEKQI QIVNFKQIYY TVSVDAVKNP GDVFQDTVTV EDLKQRGISA ERPLVYISSV  240
AYGRQVYLKL ETTSKSDEVE AAFEALIKGV KVAPQTEWKQ ILDNTEVKAV ILGGDPSSGA  300
RVVTGKVDMV EDLIQEGSRF TADHPGLPIS YTTSFLRDNV VATFQNSTDY VETKVTAYRN  360
GDLLLDHSGA YVAQYYITWD ELSYDHQGKE VLTPKAWDRN GQDLTAHFTT SIPLKGNVRN  420
LSVKIRECTG LAWEWWRTVY EKTDLPLVRK RTISIWGTTL YPQVEDKVEN D           471

SEQ ID NO: 4            moltype = AA  length = 471
FEATURE                 Location/Qualifiers
source                  1..471
                        mol_type = protein
                        organism = Streptococcus pneumoniae
SEQUENCE: 4
MANKAVNDFI LAMNYDKKKL LTHQGESIEN RFIKEGNQLP DEFVVIERKK RSLSTNTSDI  60
SVTATNDSRL YPGALLVVDE TLLENNPTLL AVDRAPMTYS IDLPGLASSD SFLQVEDPSN  120
SSVRGAVNDL LAKWHQDYGQ VNNVPARMQY EKITAHSMEQ LKVKFGSDFE KTGNSLDIDF  180
NSVHSGEKQI QIVNFKQIYY TVSVDAVKNP GDVFQDTVTV EDLKQRGISA ERPLVYISSV  240
AYGRQVYLKL ETTSKSDEVE AAFEALIKGV KVAPQTEWKQ ILDNTEVKAV ILGGDPSSGA  300
RVVTGKVDMV EDLIQEGSRF TADHPGLPIS YTTSFLRDNV VATFQNSTDY VETKVTAYRN  360
GDLLLDHSGA YVAQYYITWD ELSYNHQGKE VLTPKAWDRN GQDLTAHFTT SIPLKGNVRN  420
LSVKIREGTG LAFEWWRTVY EKTDLPLVRK RTISIWGTTL YPQVEDKVEN D           471

SEQ ID NO: 5            moltype = AA  length = 471
FEATURE                 Location/Qualifiers
source                  1..471
                        mol_type = protein
                        organism = Streptococcus pneumoniae
SEQUENCE: 5
MANKAVNDFI LAMNYDKKKL LTHQGESIEN RFIKEGNQLP DEFVVIERKK RSLSTNTSDI  60
SVTATNDSRL YPGALLVVDE TLLENNPTLL AVDRAPMTYS IDLPGLASSD SFLQVEDPSN  120
SSVRGAVNDL LAKWHQDYGQ VNNVPARMQY EKITAHSMEQ LKVKFGSDFE KTGNSLDIDF  180
NSVHSGEKQI QIVNFKQIYY TVSVDAVKNP GDVFQDTVTV EDLKQRGISA ERPLVYISSV  240
AYGRQVYLKL ETTSKSDEVE AAFEALIKGV KVAPQTEWKQ ILDNTEVKAV ILGPDPSSGA  300
RVVTGKVDMV EDLIQEGSRF TADHPGLPIS YTTSFLRDNV VATFQNSTDY VETKVTAYRN  360
GDLLLDHSGA YVAQYYITWD ELSYNHQGKE VLTPKAWDRN GQDLTAHFTT SIPLKGNVRN  420
LSVKIREGTG LAFEWWRTVY EKTDLPLVRK RTISIWGTTL YPQVEDKVEN D           471

SEQ ID NO: 6            moltype = AA  length = 470
FEATURE                 Location/Qualifiers
source                  1..470
                        mol_type = protein
                        organism = Streptococcus pneumoniae
SEQUENCE: 6
ANKAVNDFIL AMNYDKKKLL THQGESIENR FIKEGNQLPD EFVVIERKKR SLSTNTSDIS  60
VTATNDSRLY PGALLVVDET LLENNPTLLA VDRAPMTYSI DLPGLASSDS FLQVEDPSNS  120
SVRGAVNDLL AKWHQDYGQV NNVPARMQYE KITAHSMEQL KVKFGSDFEK TGNSLDIDFN  180
SVHSGEKQIQ IVNFKQIYYT VSVDAVKNPG DVFQDTVTVE DLKQRGISAE RPLVYISSVA  240
YGRQVYLKLE TTSKSDEVEA AFEALIKGVK VAPQTEWKQI LDNTEVKAVI LGPDPSSGAR  300
VVTGKVDMVE DLIQEGSRFT ADHPGLPISY TTSFLRDNVV ATFQNSTDYV ETKVTAYRNG  360
```

-continued

```
DLLLDHSGAY VAQYYITWDE LSYNHQGKEV LTPKAWDRNG QDLTAHFTTS IPLKGNVRNL  420
SVKIREGTGL AFEWWRTVYE KTDLPLVRKR TISIWGTTLY PQVEDKVEND             470

SEQ ID NO: 7           moltype = AA  length = 186
FEATURE                Location/Qualifiers
source                 1..186
                       mol_type = protein
                       organism = Streptococcus pneumoniae
SEQUENCE: 7
MIEASKLKAG MTFETADGKL IRVLEASHHK PGKGNTIMRM KLRDVRTGST FDTSYRPEEK  60
FEQAIIETVP AQYLYKMDDT AYFMNTETYD QYEIPVVNVE NELLYILENS DVKIQFYGTE  120
VIGVTVPTTV ELTVAETQPS IKGATVTGSG KPATMETGLV VNVPDFIEAG QKLVINTAEG  180
TYVSRA                                                             186

SEQ ID NO: 8           moltype = AA  length = 124
FEATURE                Location/Qualifiers
source                 1..124
                       mol_type = protein
                       organism = Streptococcus pneumoniae
SEQUENCE: 8
EQAIIETVPA QYLYKMDDTA YFMNTETYDQ YEIPVVNVEN ELLYILENSD VKIQFYGTEV  60
IGVTVPTTVE LTVAETQPSI KGATVTGSGK PATMETGLVV NVPDFIEAGQ KLVINTAEGT  120
YVSR                                                               124

SEQ ID NO: 9           moltype = AA  length = 399
FEATURE                Location/Qualifiers
source                 1..399
                       mol_type = protein
                       organism = Streptococcus pneumoniae
SEQUENCE: 9
MKKKNGKAKK WQLYAAIGAA SVVVLGAGGI LLFRQPSQTA LKDEPTHLVV AKEGSVASSV  60
LLSGTVTAKN EQYVYFDASK GDLDEILVSV GDKVSEGQAL VKYSSSEAQA AYDSASRAVA  120
RADRHINELN QARNEAASAP APQLPAPVGG EDATVQSPTP VAGNSVASID AQLGDARDAR  180
ADAAAQLSKA QSQLDATTVL STLEGTVVEV NSNVSKSPTG ASQVMVHIVS NENLQVKGEL  240
SEYNLANLSV GQEVSFTSKV YPDKKWTGKL SYISDYPKNN GEAASPAAGN NTGSKYPYTI  300
DVTGEVGDLK QGFSVNIEVK SKTKAILVPV SSLVMDDSKN YVWIVDEQQK AKKVEVSLGN  360
ADAENQEITS GLTNGAKVIS NPTSSLEEGK EVKADEATN                         399

SEQ ID NO: 10          moltype = AA  length = 367
FEATURE                Location/Qualifiers
source                 1..367
                       mol_type = protein
                       organism = Streptococcus pneumoniae
SEQUENCE: 10
FRQPSQTALK DEPTHLVVAK EGSVASSVLL SGTVTAKNEQ YVYFDASKGD LDEILVSVGD  60
KVSEGQALVK YSSSEAQAAY DSASRAVARA DRHINELNQA RNEAASAPAP QLPAPVGGED  120
ATVQSPTPVA GNSVASIDAQ LGDARDARAD AAAQLSKAQS QLDATTVLST LEGTVVEVNS  180
NVSKSPTGAS QVMVHIVSNE NLQVKGELSE YNLANLSVGQ EVSFTSKVYP DKKWTGKLSY  240
ISDYPKNNGE AASPAAGNNT GSKYPYTIDV TGEVGDLKQG FSVNIEVKSK TKAILVPVSS  300
LVMDDSKNYV WIVDEQQKAK KVEVSLGNAD AENQEITSGL TNGAKVISNP TSSLEEGKEV  360
KADEATN                                                            367

SEQ ID NO: 11          moltype = AA  length = 278
FEATURE                Location/Qualifiers
source                 1..278
                       mol_type = protein
                       organism = Streptococcus pneumoniae
SEQUENCE: 11
MKKWMLVLVS LMTALFLVAC GKNSSETSGD NWSKYQSNKS ITIGFDSTFV PMGFAQKDGS  60
YAGFDIDLAT AVFEKYGITV NWQPIDWDLK EAELTKGTID LIWNGYSATD ERREKVAFSN  120
SYMKNEQVLV TKKSSGITTA KDMTGKTLGA QAGSSGYADF EANPEILKNI VANKEANQYQ  180
TFNEALIDLK NDRIDGLLID RVYANYYLEA EGVLNDYNVF TVGLETEAFA VGARKEDTNL  240
VKKINEAFSS LYKDGKFQEI SQKWFGEDVA TKEVKEGQ                          278

SEQ ID NO: 12          moltype = AA  length = 252
FEATURE                Location/Qualifiers
source                 1..252
                       mol_type = protein
                       organism = Streptococcus pneumoniae
SEQUENCE: 12
TSGDNWSKYQ SNKSITIGFD STFVPMGFAQ KDGSYAGFDI DLATAVFEKY GITVNWQPID  60
WDLKEAELTK GTIDLIWNGY SATDERREKV AFSNSYMKNE QVLVTKKSSG ITTAKDMTGK  120
TLGAQAGSSG YADFEANPEI LKNIVANKEA NQYQTFNEAL IDLKNDRIDG LLIDRVYANY  180
YLEAEGVLND YNVFTVGLET EAFAVGARKE DTNLVKKINE AFSSLYKDGK FQEISQKWFG  240
EDVATKEVKE GQ                                                      252

SEQ ID NO: 13          moltype = DNA  length = 1410
FEATURE                Location/Qualifiers
source                 1..1410
```

```
                        mol_type = genomic DNA
                        organism = Streptococcus pneumoniae
SEQUENCE: 13
atggcaaata aagcagtaaa tgactttata ctagctatga attacgataa aaagaaactc  60
ttgacccatc agggagaaag tattgaaaat cgtttcatca aagagggtaa tcagctaccc  120
gatgagtttg ttgttatcga aagaaagaag cggagcttgt cgacaaatac aagtgatatt  180
tctgtaacag ctaccaacga cagtcgcctc tatcctggag cacttctcgt agtggatgag  240
accttgttag agaataatcc cactcttctt gcggtcgatc gtgctccgat gacttatagt  300
attgatttgc ctggtttggc aagtagcgat agctttctcc aagtggaaga ccccagcaat  360
tcaagtgttc gcggagcggt aaacgatttg ttggctaagt ggcatcaaga ttatggtcag  420
gtcaataatg tcccagctag aatgcagcat gaaaaaatca cggctcacag catggaacaa  480
ctcaaggtca agtttggttc tgactttgaa aagataggga attctcttga tattgatttt  540
aactctgtcc attcaggcga aaagcagatt cagattgtta attttaagca gatttattat  600
acagtcagcg tagatgctgt taaaaatcca ggagatgtgt ttcaagatac tgtaacggta  660
gaggatttaa ggcagagagg aatttctgca gagcgtcctt tggtctatat ttcgagtgtt  720
gcttatgggc gccaagtcta tctcaagttg gaaaccacga gtaagagtga tgaagtagag  780
gctgcttttg aatctttgat aaaaggagta gctcctcaga cagagtggaa gcagattttg  840
gacaatacag aagtgaaggc ggttatttta gggggcgacc caagttcggg tgcccgagtt  900
gtaacaggca aggtggatat ggtagaggac ttgattcaag aaggcagtcg ctttacagcc  960
gatcatccag gcttgccgat ttcctataca acttcttttt tacgtgacaa tgtagttgcg  1020
acctttcaaa acagtacaga ctatgttgag actaaggtta cagcttacag aaacggagat  1080
ttactgctgg atcatagtgg tgcctatgtt gctcaatatt atattacttg ggatgaatta  1140
tcctatgatc atcaaggcaa ggaagtcttg actcctaagg cttgggacag aaatgggcag  1200
gatttgacgg ctcactttac cactagtatt cctttaaaag ggaatgttcg caatctctct  1260
gtcaaaatta gagagtgtac cggcttgcc tgggaatggt ggcgtacggt ttatgaaaaa  1320
accgatttgc cactagtgcg taagcggacg atttctattt ggggaacaac tctctatcct  1380
caggtagagg ataaggtaga aaatgattag                                  1410

SEQ ID NO: 14           moltype = DNA  length = 1413
FEATURE                 Location/Qualifiers
source                  1..1413
                        mol_type = other DNA
                        organism = synthetic construct
SEQUENCE: 14
atggcgaaca aggcggtgaa cgattttatc ctggcgatga actatgacaa gaagaaactg  60
ctgacccacc aaggcgagag cattgagaac cgtttcatta aagaaggcaa ccagctgccg  120
gacgagtttg tggttatcga gcgtaagaaa cgtagcctga gcaccaacac cagcgacatt  180
agcgtgaccg cgaccaacga tagccgtctg tacccgggtg cgctgctggt tgtggatgaa  240
accctgctgg aaaacaaccc gaccctgctg gcggtggacc gtgcgccgat gacctatagc  300
atcgatctgc cgggtctggc gagcagcgac agcttcctgc aagttgagga tccgagcaac  360
agcagcgtgc gtggtgcggt taacgacctg ctggcgaagt ggcaccagga ttacggccaa  420
gtgaacaacg ttccggcgcg tatgcagtat gaaaaaatca ccgcgcacag catggagcaa  480
ctgaaggtta aattcggtag cgactttgaa aagaccggca acagcctgga cattgatttc  540
aacagcgtgc acagcggcga gaagcagatc caaatcgtta acttcaagca gatctactac  600
accgtgagcg ttgacgcggt gaagaacccg ggtgacgttt tccaggatac cgtgaccgtt  660
gaagatctga aacaacgtgg cattagcgcg gagcgtccgc tggtgtacat cagcagcgtt  720
gcgtacggtc gtcaagtgta tctgaagctg gaaaccacca gcaaaagcga tgaggttgaa  780
gcggcgtttg aggcgctgat taagggcgtg aaagttgcgc cgcagaccga atggaagcaa  840
attctggaca acaccgaggt gaaagcggtt attctgggcc cggatccgag cagcggcgcg  900
cgtgtggtta ccggtaaagt ggacatggtt gaggatctga ttcaggaagg tagccgtttt  960
accgcggacc acccgggcct gccgatcagc tacaccacca gcttcctgcg tgacaacgtg  1020
gttgcgacct ttcaaaacag caccgattac gtggaaacca aggttaccgc gtatcgtaac  1080
ggtgacctgc tgctggacca cagcggtgcg tacgtggcgc agtactatat cacctgggat  1140
gaactgagct ataaccacca gggtaaagag gtgctgaccc cgaaagcgtg ggaccgtaac  1200
ggccaggatc tgaccgcgca cttcaccacc agcattccgc tgaagggcaa cgtgcgtaac  1260
ctgagcgtta aaatccgtga gggtaccggc ctggcgtttg aatggtggcg taccgtgtac  1320
gagaagaccg acctgccgct ggttcgtaaa cgtaccatca gcatttgggg taccaccctg  1380
tatccgcagg tggaggacaa agttgaaaat gat                             1413

SEQ ID NO: 15           moltype = DNA  length = 1410
FEATURE                 Location/Qualifiers
source                  1..1410
                        mol_type = other DNA
                        organism = synthetic construct
SEQUENCE: 15
gcgaacaagg cggtgaacga ttttatcctg gcgatgaact atgacaagaa gaaactgctg  60
acccaccaag gcgagagcat tgagaaccgt ttcattaaag aaggcaacca gctgccggac  120
gagtttgtgg ttatcgagcg taagaaacgt agcctgagca ccaacaccag cgacattagc  180
gtgaccgcga ccaacgatag ccgtctgtac ccgggtgcgc tgctggttgt ggatgaaacc  240
ctgctggaaa acaacccgac cctgctggcg gtggaccgtg cgccgatgac ctatagcatc  300
gatctgccgg gtctggcgag cagcgacagc ttcctgcaag ttgaggatcc gagcaacagc  360
agcgtgcgtg gtgcggttaa cgacctgctg gcgaagtggc accaggatta cggccaagtg  420
aacaacgttc cggcgcgtat gcagtatgaa aaaatcaccg cgcacagcat ggagcaactg  480
aaggttaaat tcggtagcga ctttgaaaag accggcaaca gcctggacat tgatttcaac  540
agcgtgcaca gcggcgagaa gcagatccaa atcgttaact tcaagcagat ctactacacc  600
gtgagcgttg acgcggtgaa gaacccgggt gacgttttcc aggataccgt gaccgttgaa  660
gatctgaaac aacgtggcat tagcgcggag cgtccgctgg tgtacatcag cagcgttgcg  720
tacggtcgtc aagtgtatct gaagctggaa accaccagca aaagcgatga ggttgaagcg  780
gcgtttgagg cgctgattaa gggcgtgaaa gttgcgccgc agaccgaatg gaagcaaatt  840
```

```
ctggacaaca ccgaggtgaa agcggttatt ctgggcccgg atccgagcag cggcgcgcgt  900
gtggttaccg gtaaagtgga catggttgag gatctgattc aggaaggtag ccgttttacc  960
gcggaccacc cgggcctgcc gatcagctac accaccagct tcctgcgtga caacgtggtt  1020
gcgacctttc aaaacagcac cgattacgtg gaaaccaagg ttaccgcgta tcgtaacggt  1080
gacctgctgc tggaccacag cggtgcgtac gtggcgcagt actatatcac ctgggatgaa  1140
ctgagctata accaccaggg taaagaggtg ctgaccccga aagcgtggga ccgtaacggc  1200
caggatctga ccgcgcactt caccaccagc attccgctga agggcaacgt gcgtaacctg  1260
agcgttaaaa tccgtgaggg taccggcctg gcgtttgaat ggtggcgtac cgtgtacgag  1320
aagaccgacc tgccgctggt tcgtaaacgt accatcagca tttggggtac caccctgtat  1380
ccgcaggtgg aggacaaagt tgaaaatgat                                  1410

SEQ ID NO: 16          moltype = DNA  length = 558
FEATURE                Location/Qualifiers
source                 1..558
                       mol_type = genomic DNA
                       organism = Streptococcus pneumoniae
SEQUENCE: 16
atgattgaag caagtaaatt aaaagctggt atgacctttg aaacagctga cggcaaattg  60
attcgcgttt tggaagctag tcaccacaaa ccaggtaaag gaaacacgat catgcgtatg  120
aaattgcgtg atgtccgtac tggttctaca tttgacacaa gctaccgtcc agaggaaaaa  180
tttgaacaag ctattatcga gactgtccca gctcaatact tgtacaaaat ggatgacaca  240
gcatacttca tgaatacaga aacttatgac caatacgaaa tccctgtagt caatgttgaa  300
aacgaattgc tttacatcct tgaaaactct gatgtgaaaa tccaattcta cggaactgaa  360
gtgatcggtg tcaccgttcc tactactgtt gagttgacag ttgctgaaac tcaaccatct  420
atcaaaggtg ctactgttac aggttctggt aaaccagcaa cgatggaaac tggacttgtc  480
gtaaacgttc cagacttcat cgaagcagga caaaaactcg ttatcaacac tgcagaagga  540
acttacgttt ctcgtgcc                                               558

SEQ ID NO: 17          moltype = DNA  length = 1197
FEATURE                Location/Qualifiers
source                 1..1197
                       mol_type = genomic DNA
                       organism = Streptococcus pneumoniae
SEQUENCE: 17
atgaagaaaa agaatggtaa agctaaaaag tggcaactgt atgcagcaat cggtgctgcg  60
agtgtagttg tattgggtgc tggggggatt ttactcttta gacaaccttc tcagactgct  120
ctaaaagatg agcctactca tcttgttgtt gccaaggaag gaagcgtggc ctcctctgtt  180
ttattgtcag ggacagtaac agcaaaaaat gaacaatatg tttattttga tgctagtaag  240
ggtgatttag atgaaatcct tgtttctgtg ggcgataagg tcagcgaagg gcaggcttta  300
gtcaagtaca gtagttcaga agcgcaggcg gcctatgatt cagctagtcg agcagtagct  360
agggcagatc gtcatatcaa tgaactcaat caagcacgaa atgaagccgc ttcagctccg  420
gctccacagt taccagcgcc agtaggagga gaagatgcaa cggtgcaaag cccaactcca  480
gtggctggaa attctgttgc ttctattgac gctcaattgg gtgatgcccg tgatgcgcgt  540
gcagatgctg cggcgcaatt aagcaaggct caaagtcaat tggatgcaac aactgttctc  600
agtaccctag agggaactgt ggtcgaagtc aatagcaatg tttctaaatc tccaacaggg  660
gcgagtcaag ttatggttca tattgtcagc aatgaaaatt tacaagtcaa gggagaattg  720
tctgagtaca atctagccaa cctttctgta ggtcaagaag taagctttac ttctaaagtg  780
tatcctgata aaaaatggac tgggaaatta agctatattt ctgactatcc taaaaacaat  840
ggtgaagcag ctagtccagc agccgggaat aatacaggtt ctaaataccc ttatactatt  900
gatgtgacag gcgaggttgg tgatttgaaa caaggttttt ctgtcaacat tgaggttaaa  960
agcaaaacta aggctattct tgttcctgtt agcagtctag taatggatga tagtaaaaat  1020
tatgtctgga ttgtggatga acaacaaaag gctaaaaaag ttgaggtttc attgggaaat  1080
gctgacgcag aaaatcaaga aatcacttct ggtttaacga acggtgctaa ggtcatcagt  1140
aatccaacat cttccttgga agaaggaaaa gaggtgaagg ctgatgaagc aactaat     1197

SEQ ID NO: 18          moltype = DNA  length = 834
FEATURE                Location/Qualifiers
source                 1..834
                       mol_type = genomic DNA
                       organism = Streptococcus pneumoniae
SEQUENCE: 18
atgaaaaaat ggatgcttgt attagtcagt ctgatgactg ctttgttctt agtagcttgt  60
gggaaaaatt ctagcgaaac tagtggagat aattggtcaa agtaccagtc taacaagtct  120
attactattg gatttgatag tacttttgtt ccaatgggat ttgctcagaa agatggttct  180
tatgcaggat ttgatattga tttagctaca gctgtttttg aaaaatacgg aatcacggta  240
aattggcaac cgattgattg ggatttgaaa gaagctgaat tgacaaaagg aacgattgat  300
ctgatttgga atggctattc cgctacagac gaacgccgtg aaaaggtggc tttcagtaac  360
tcatatatga agaatgagca ggtattggtt acgaagaaat catctggtat cacgactgca  420
aaggatatga ctggaaagac attaggagct caagctggtt catctggtta tgcggacttt  480
gaagcaaatc cagaaatttt gaagaatatt gtcgctaata aggaagcgaa tcaataccaa  540
acctttaatg aagccttgat tgatttgaaa aacgatcgaa ttgatggtct attgattgac  600
cgtgtctatg caaactatta tttagaagca gaaggtgttt taaacgatta taatgtcttt  660
acagttggac tagaaacaga agcttttgcg gttggagccc gtaaggaaga tacaaacttg  720
gttaagaaga taaatgaagc tttttctagt ctttacaagg acggcaagtt ccaagaaatc  780
agccaaaaat ggtttggaga agatgtagca accaaagaag taaaagaagg acag        834

SEQ ID NO: 19          moltype = AA  length = 743
FEATURE                Location/Qualifiers
source                 1..743
```

```
                        mol_type = protein
                        organism = synthetic construct
SEQUENCE: 19
FDASNFKDFS SIASASSSWQ NQSGSTMIIQ VDSFGNVSGQ YVNRAQGTGC QNSPYPLTGR  60
VNGTFIAFSV GWNNSTENCN SATGWTGYAQ VNGNNTEIVT SWNLAYEGGS GPAIEQGQDT  120
FQYVPTTENK SLLKDGGGGS SSANKAVNDF ILAMNYDKKK LLTHQGESIE NRFIKEGNQL  180
PDEFVVIERK KRSLSTNTSD ISVTATNDSR LYPGALLVVD ETLLENNPTL LAVDRAPMTY  240
SIDLPGLASS DSFLQVEDPS NSSVRGAVND LLAKWHQDYG QVNNVPARMQ YEKITAHSME  300
QLKVKFGSDF EKTGNSLDID FNSVHSGEKQ IQIVNFKQIY YTVSVDAVKN PGDVFQDTVT  360
VEDLKQRGIS AERPLVYISS VAYGRQVYLK LETTSKSDEV EAAFEALIKG VKVAPQTEWK  420
QILDNTEVKA VILGPDPSSG ARVVTGKVDM VEDLIQEGSR FTADHPGLPI SYTTSFLRDN  480
VVATFQNSTD YVETKVTAYR NGDLLLDHSG AYVAQYYITW DELSYNHQGK EVLTPKAWDR  540
NGQDLTAHFT TSIPLKGNVR NLSVKIREGT GLAFEWWRTV YEKTDLPLVR KRTISIWGTT  600
LYPQVEDKVE NDGGGGSSSE QAIIETVPAQ YLYKMDDTAY FMNTETYDQY EIPVVNVENE  660
LLYILENSDV KIQFYGTEVI GVTVPTTVEL TVAETQPSIK GATVTGSGKP ATMETGLVVN  720
VPDFIEAGQK LVINTAEGTY VSR                                          743

SEQ ID NO: 20           moltype = AA  length = 749
FEATURE                 Location/Qualifiers
source                  1..749
                        mol_type = protein
                        organism = synthetic construct
SEQUENCE: 20
FDASNFKDFS SIASASSSWQ NQSGSTMIIQ VDSFGNVSGQ YVNRAQGTGC QNSPYPLTGR  60
VNGTFIAFSV GWNNSTENCN SATGWTGYAQ VNGNNTEIVT SWNLAYEGGS GPAIEQGQDT  120
FQYVPTTENK SLLKDGGGGS SSANKAVNDF ILAMNYDKKK LLTHQGESIE NRFIKEGNQL  180
PDEFVVIERK KRSLSTNTSD ISVTATNDSR LYPGALLVVD ETLLENNPTL LAVDRAPMTY  240
SIDLPGLASS DSFLQVEDPS NSSVRGAVND LLAKWHQDYG QVNNVPARMQ YEKITAHSME  300
QLKVKFGSDF EKTGNSLDID FNSVHSGEKQ IQIVNFKQIY YTVSVDAVKN PGDVFQDTVT  360
VEDLKQRGIS AERPLVYISS VAYGRQVYLK LETTSKSDEV EAAFEALIKG VKVAPQTEWK  420
QILDNTEVKA VILGPDPSSG ARVVTGKVDM VEDLIQEGSR FTADHPGLPI SYTTSFLRDN  480
VVATFQNSTD YVETKVTAYR NGDLLLDHSG AYVAQYYITW DELSYNHQGK EVLTPKAWDR  540
NGQDLTAHFT TSIPLKGNVR NLSVKIREGT GLAFEWWRTV YEKTDLPLVR KRTISIWGTT  600
LYPQVEDKVE NDGGGGSSSE QAIIETVPAQ YLYKMDDTAY FMNTETYDQY EIPVVNVENE  660
LLYILENSDV KIQFYGTEVI GVTVPTTVEL TVAETQPSIK GATVTGSGKP ATMETGLVVN  720
VPDFIEAGQK LVINTAEGTY VSRHHHHHH                                    749

SEQ ID NO: 21           moltype = AA  length = 743
FEATURE                 Location/Qualifiers
source                  1..743
                        mol_type = protein
                        organism = synthetic construct
SEQUENCE: 21
FDASNFKDFS SIASASSSWQ NQSGSTMIIQ VDSFGNVSGQ YVNRAQGTGC QNSPYPLTGR  60
VNGTFIAFSV GWNNSTENCN SATGWTGYAQ VNGNNTEIVT SWNLAYEGGS GPAIEQGQDT  120
FQYVPTTENK SLLKDGGGGS SSEQAIIETV PAQYLYKMDD TAYFMNTETY DQYEIPVVNV  180
ENELLYILEN SDVKIQFYGT EVIGVTVPTT VELTVAETQP SIKGATVTGS GKPATMETGL  240
VVNVPDFIEA GQKLVINTAE GTYVSRGGGG SSSANKAVND FILAMNYDKK KLLTHQGESI  300
ENRFIKEGNQ LPDEFVVIER KKRSLSTNTS DISVTATNDS RLYPGALLVV DETLLENNPT  360
LLAVDRAPMT YSIDLPGLAS SDSFLQVEDP SNSSVRGAVN DLLAKWHQDY GQVNNVPARM  420
QYEKITAHSM EQLKVKFGSD FEKTGNSLDI DFNSVHSGEK QIQIVNFKQI YYTVSVDAVK  480
NPGDVFQDTV TVEDLKQRGI SAERPLVYIS SVAYGRQVYL KLETTSKSDE VEAAFEALIK  540
GVKVAPQTEW KQILDNTEVK AVILGPDPSS GARVVTGKVD MVEDLIQEGS RFTADHPGLP  600
ISYTTSFLRD NVVATFQNST DYVETKVTAY RNGDLLLDHS GAYVAQYYIT WDELSYNHQG  660
KEVLTPKAWD RNGQDLTAHF TTSIPLKGNV RNLSVKIREG TGLAFEWWRT VYEKTDLPLV  720
RKRTISIWGT TLYPQVEDKV END                                          743

SEQ ID NO: 22           moltype = AA  length = 743
FEATURE                 Location/Qualifiers
source                  1..743
                        mol_type = protein
                        organism = synthetic construct
SEQUENCE: 22
ANKAVNDFIL AMNYDKKKLL THQGESIENR FIKEGNQLPD EFVVIERKKR SLSTNTSDIS  60
VTATNDSRLY PGALLVVDET LLENNPTLLA VDRAPMTYSI DLPGLASSDS FLQVEDPSNS  120
SVRGAVNDLL AKWHQDYGQV NNVPARMQYE KITAHSMEQL KVKFGSDFEK TGNSLDIDFN  180
SVHSGEKQIQ IVNFKQIYYT VSVDAVKNPG DVFQDTVTVE DLKQRGISAE RPLVYISSVA  240
YGRQVYLKLE TTSKSDEVEA AFEALIKGVK VAPQTEWKQI LDNTEVKAVI LGPDPSSGAR  300
VVTGKVDMVE DLIQEGSRFT ADHPGLPISY TTSFLRDNVV ATFQNSTDYV ETKVTAYRNG  360
DLLLDHSGAY VAQYYITWDE LSYNHQGKEV LTPKAWDRNG QDLTAHFTTS IPLKGNVRNL  420
SVKIREGTGL AFEWWRTVYE KTDLPLVRKR TISIWGTTLY PQVEDKVEND GGGGSSSEQA  480
IIETVPAQYL YKMDDTAYFM NTETYDQYEI PVVNVENELL YILENSDVKI QFYGTEVIGV  540
TVPTTVELTV AETQPSIKGA TVTGSGKPAT METGLVVNVP DFIEAGQKLV INTAEGTYVS  600
RGGGGSSSFD ASNFKDFSSI ASASSSWQNQ SGSTMIIQVD SFGNVSGQYV NRAQGTGCQN  660
SPYPLTGRVN GTFIAFSVGW NNSTENCNSA TGWTGYAQVN GNNTEIVTSW NLAYEGGSGP  720
AIEQGQDTFQ YVPTTENKSL LKD                                          743

SEQ ID NO: 23           moltype = AA  length = 743
FEATURE                 Location/Qualifiers
```

-continued

```
source                1..743
                      mol_type = protein
                      organism = synthetic construct
SEQUENCE: 23
EQAIIETVPA QYLYKMDDTA YFMNTETYDQ YEIPVVNVEN ELLYILENSD VKIQFYGTEV  60
IGVTVPTTVE LTVAETQPSI KGATVTGSGK PATMETGLVV NVPDFIEAGQ KLVINTAEGT 120
YVSRGGGGSS SANKAVNDFI LAMNYDKKKL LTHQGESIEN RFIKEGNQLP DEFVVIERKK 180
RSLSTNTSDI SVTATNDSRL YPGALLVVDE TLLENNPTLL AVDRAPMTYS IDLPGLASSD 240
SFLQVEDPSN SSVRGAVNDL LAKWHQDYGQ VNNVPARMQY EKITAHSMEQ LKVKFGSDFE 300
KTGNSLDIDF NSVHSGEKQI QIVNFKQIYY TVSVDAVKNP GDVFQDTVTV EDLKQRGISA 360
ERPLVYISSV AYGRQVYLKL ETTSKSDEVE AAFEALIKGV KVAPQTEWKQ ILDNTEVKAV 420
ILGPDPSSGA RVVTGKVDMV EDLIQEGSRF TADHPGLPIS YTTSFLRDNV VATFQNSTDY 480
VETKVTAYRN GDLLLDHSGA YVAQYYITWD ELSYNHQGKE VLTPKAWDRN GQDLTAHFTT 540
SIPLKGNVRN LSVKIREGTG LAFEWWRTVY EKTDLPLVRK RTISIWGTTL YPQVEDKVEN 600
DGGGGSSSFD ASNFKDFSSI ASASSSWQNQ SGSTMIIQVD SFGNVSGQYV NRAQGTGCQN 660
SPYPLTGRVN GTFIAFSVGW NNSTENCNSA TGWTGYAQVN GNNTEIVTSW NLAYEGGSGP 720
AIEQGQDTFQ YVPTTENKSL LKD                                        743

SEQ ID NO: 24         moltype = AA  length = 743
FEATURE               Location/Qualifiers
source                1..743
                      mol_type = protein
                      organism = synthetic construct
SEQUENCE: 24
ANKAVNDFIL AMNYDKKKLL THQGESIENR FIKEGNQLPD EFVVIERKKR SLSTNTSDIS  60
VTATNDSRLY PGALLVVDET LLENNPTLLA VDRAPMTYSI DLPGLASSDS FLQVEDPSNS 120
SVRGAVNDLL AKWHQDYGQV NNVPARMQYE KITAHSMEQL KVKFGSDFEK TGNSLDIDFN 180
SVHSGEKQIQ IVNFKQIYYT VSVDAVKNPG DVFQDTVTVE DLKQRGISAE RPLVYISSVA 240
YGRQVYLKLE TTSKSDEVEA AFEALIKGVK VAPQTEWKQI LDNTEVKAVI LGPDPSSGAR 300
VVTGKVDMVE DLIQEGSRFT ADHPGLPISY TTSFLRDNVV ATFQNSTDYV ETKVTAYRNG 360
DLLLDHSGAY VAQYYITWDE LSYNHQGKEV LTPKAWDRNG QDLTAHFTTS IPLKGNVRNL 420
SVKIREGTGL AFEWWRTVYE KTDLPLVRKR TISIWGTTLY PQVEDKVEND GGGGSSSFDA 480
SNFKDFSSIA SASSSWQNQS GSTMIIQVDS FGNVSGQYVN RAQGTGCQNS PYPLTGRVNG 540
TFIAFSVGWN NSTENCNSAT GWTGYAQVNG NNTEIVTSWN LAYEGGSGPA IEQGQDTFQY 600
VPTTENKSLL KDGGGGSSSE QAIIETVPAQ YLYKMDDTAY FMNTETYDQY EIPVVNVENE 660
LLYILENSDV KIQFYGTEVI GVTVPTTVEL TVAETQPSIK GATVTGSGKP ATMETGLVVN 720
VPDFIEAGQK LVINTAEGTY VSR                                        743

SEQ ID NO: 25         moltype = AA  length = 743
FEATURE               Location/Qualifiers
source                1..743
                      mol_type = protein
                      organism = synthetic construct
SEQUENCE: 25
EQAIIETVPA QYLYKMDDTA YFMNTETYDQ YEIPVVNVEN ELLYILENSD VKIQFYGTEV  60
IGVTVPTTVE LTVAETQPSI KGATVTGSGK PATMETGLVV NVPDFIEAGQ KLVINTAEGT 120
YVSRGGGGSS SFDASNFKDF SSIASASSSW QNQSGSTMII QVDSFGNVSG QYVNRAQGTG 180
CQNSPYPLTG RVNGTFIAFS VGWNNSTENC NSATGWTGYA QVNGNNTEIV TSWNLAYEGG 240
SGPAIEQGQD TFQYVPTTEN KSLLKDGGGG SSSANKAVND FILAMNYDKK KLLTHQGESI 300
ENRFIKEGNQ LPDEFVVIER KKRSLSTNTS DISVTATNDS RLYPGALLVV DETLLENNPT 360
LLAVDRAPMT YSIDLPGLAS SDSFLQVEDP SNSSVRGAVN DLLAKWHQDY GQVNNVPARM 420
QYEKITAHSM EQLKVKFGSD FEKTGNSLDI DFNSVHSGEK QIQIVNFKQI YYTVSVDAVK 480
NPGDVFQDTV TVEDLKQRGI SAERPLVYIS SVAYGRQVYL KLETTSKSDE VEAAFEALIK 540
GVKVAPQTEW KQILDNTEVK AVILGPDPSS GARVVTGKVD MVEDLIQEGS RFTADHPGLP 600
ISYTTSFLRD NVVATFQNST DYVETKVTAY RNGDLLLDHS GAYVAQYYIT WDELSYNHQG 660
KEVLTPKAWD RNGQDLTAHF TTSIPLKGNV RNLSVKIREG TGLAFEWWRT VYEKTDLPLV 720
RKRTISIWGT TLYPQVEDKV END                                        743

SEQ ID NO: 26         moltype = AA  length = 764
FEATURE               Location/Qualifiers
source                1..764
                      mol_type = protein
                      organism = synthetic construct
SEQUENCE: 26
FDASNFKDFS SIASASSSWQ NQSGSTMIIQ VDSFGNVSGQ YVNRAQGTGC QNSPYPLTGR  60
VNGTFIAFSV GWNNSTENCN SATGWTGYAQ VNGNNTEIVT SWNLAYEGGS GPAIEQGQDT 120
FQYVPTTENK SLLKDGGGGS SSTSGDNWSK YQSNKSITIG FDSTFVPMGF AQKDGSYAGF 180
DIDLATAVFE KYGITVNWQP IDWDLKEAEL TKGTIDLIWN GYSATDERRE KVAFSNSYMK 240
NEQVLVTKKS SGITTAKDMT GKTLGAQAGS SGYADFEANP EILKNIVANK EANQYQTFNE 300
ALIDLKNDRI DGLLIDRVYA NYYLEAEGVL NDYNVFTVGL ETEAFAVGAR KEDTNLVKKI 360
NEAFSSLYKD GKFQEISQKW FGEDVATKEV KEGQAAAFRQ PSQTALKDEP THLVVAKEGS 420
VASSVLLSGT VTAKNEQYVY FDASKGDLDE ILVSVGDKVS EGQALVKYSS SEAQAAYDSA 480
SRAVARADRH INELNQARNE AASAPAPQLP APVGGEDATV QSPTPVAGNS VASIDAQLGD 540
ARDARADAAA QLSKAQSQLD ATTVLSTLEG TVVEVNSNVS KSPTGASQVM VHIVSNENLQ 600
VKGELSEYNL ANLSVGQEVS FTSKVYPDKK WTGKLSYISD YPKNNGEAAS PAAGNNTGSK 660
YPYTIDVTGE VGDLKQGFSV NIEVKSKTKA ILVPVSSLVM DDSKNYVWIV DEQQKAKKVE 720
VSLGNADAEN QEITSGLTNG AKVISNPTSS LEEGKEVKAD EATN                 764

SEQ ID NO: 27         moltype = DNA  length = 2235
```

```
FEATURE                 Location/Qualifiers
source                  1..2235
                        mol_type = other DNA
                        organism = synthetic construct
SEQUENCE: 27
ttcgacgcat ccaactttaa agactttagc agcatcgcgt ccgcaagctc tagctggcag  60
aatcaatctg gtagcaccat gattatccaa gtggacagct ttggtaacgt cagcggtcaa  120
tatgttaatc gtgcacaggg tacgggttgt cagaattctc cgtacccgct gaccggtcgt  180
gttaacggca cgttcatcgc tttcagcgtc ggttggaaca attctactga aaattgcaac  240
agcgcgaccg gttggacggg ctatgcacaa gtgaatggca ataacaccga aatcgtcacg  300
tcctggaatc tggcgtatga gggtggcagc ggtccggcta ttgaacaggg ccaggatacc  360
ttccaatacg tccctacgac cgagaataag tcccttctga aagacggcgg tggcggttcg  420
agctcggcga acaaggcggt gaacgatttt atcctggcga tgaactatga caagaagaaa  480
ctgctgaccc accaaggcga gagcattgag aaccgtttca ttaaagaagg caaccagctg  540
ccggacgagt ttgtggttat cgagcgtaag aaacgtagcc tgagcaccaa caccagcgac  600
attagcgtga ccgcgaccaa cgatagccgt ctgtacccgg gtgcgctgct ggttgtggat  660
gaaaccctgc tggaaaacaa cccgaccctg ctggcggtgg accgtgcgcc gatgacctat  720
agcatcgatc tgccgggtct ggcgagcagc gacagcttcc tgcaagttga ggatccgagc  780
aacagcagcg tgcgtggtgc ggttaacgac ctgctggcga agtggcacca ggattacggc  840
caagtgaaca acgttccggc gcgtatgcag tatgaaaaaa tcaccgcgca cagcatggag  900
caactgaagg ttaaattcgg tagcgacttt gaaaagaccg gcaacagcct ggacattgat  960
ttcaacagcg tgcacagcgg cgagaagcag atccaaatcg ttaacttcaa gcagatctac  1020
tacaccgtga gcgttgacgc ggtgaagaac ccgggtgacg ttttccagga taccgtgacc  1080
gttgaagatc tgaaacaacg tggcattagc gcggagcgtc cgctggtgta catcagcagc  1140
gttgcgtacg gtcgtcaagt gtatctgaag ctggaaacca ccagcaaaag cgatgaggtt  1200
gaagcggcgt ttgaggcgct gattaagggc gtgaaagttg cgccgcagac cgaatggaag  1260
caaattctgg acaacaccga ggtgaaagcg gttattctgg gcccggatcc gagcagcggc  1320
gcgcgtgtgg ttaccggtaa agtggacatg gttgaggatc tgattcagga aggtagccgt  1380
tttaccgcgg accacccggg cctgccgatc agctacacca ccagcttcct gcgtgacaac  1440
gtggttgcga cctttcaaaa cagcaccgat tacgtggaaa ccaaggttac cgcgtatcgt  1500
aacggtgacc tgctgctgga ccacagcggt gcgtacgtgg cgcagtacta tatcacctgg  1560
gatgaactga gctataacca ccagggtaaa gaggtgctga ccccgaaagc gtgggaccgt  1620
aacggccagg atctgaccgc gcacttcacc accagcattc cgctgaaggg caacgtgcgt  1680
aacctgagcg ttaaaatccg tgagggtacc ggcctggcgt ttgaatggtg gcgtaccgtg  1740
tacgagaaga ccgacctgcc gctggttcgt aaacgtacca tcagcatttg gggtaccacc  1800
ctgtatccgc aggtggagga caaagttgaa aatgatggtg gtggtggtag cagcagcgag  1860
caggcgatca ttgaaaccgt gccggcgcaa tacctgtata agatggacga taccgcgtac  1920
ttcatgaaca ccgaaaccta cgaccaatat gaaattccgg tggttaacgt tgagaacgaa  1980
ctgctgtaca tcctggaaaa cagcgatgtg aaaattcagt tttatggtac cgaggttatc  2040
ggcgtgaccg ttccgaccac cgtggagctg accgttgcgg aaacccaacc gagcatcaag  2100
ggtgcgaccg tgaccggtag cggtaaaccg gcgaccatgg aaaccggtct ggtggttaac  2160
gtgccggact tcattgaggc gggccagaag ctggttatca ataccgcgga gggtacctat  2220
gttagccgtt aatga                                                   2235

SEQ ID NO: 28           moltype = DNA  length = 2235
FEATURE                 Location/Qualifiers
source                  1..2235
                        mol_type = other DNA
                        organism = synthetic construct
SEQUENCE: 28
ttcgacgcat ccaactttaa agactttagc agcatcgcgt ccgcaagctc tagctggcag  60
aatcaatctg gtagcaccat gattatccaa gtggacagct ttggtaacgt cagcggtcaa  120
tatgttaatc gtgcacaggg tacgggttgt cagaattctc cgtacccgct gaccggtcgt  180
gttaacggca cgttcatcgc tttcagcgtc ggttggaaca attctactga aaattgcaac  240
agcgcgaccg gttggacggg ctatgcacaa gtgaatggca ataacaccga aatcgtcacg  300
tcctggaatc tggcgtatga gggtggcagc ggtccggcta ttgaacaggg ccaggatacc  360
ttccaatacg tccctacgac cgagaataag tcccttctga aagacggcgg tggcggttcg  420
agctcggagc aggcgatcat tgaaaccgtg ccggcgcaat acctgtataa gatggacgat  480
accgcgtact tcatgaacac cgaaacctac gaccaatatg aaattccggt ggttaacgtt  540
gagaacgaac tgctgtacat cctggaaaac agcgatgtga aaattcagtt ttatggtacc  600
gaggttatcg gcgtgaccgt tccgaccacc gtggagctga ccgttgcgga aacccaaccg  660
agcatcaagg gtgcgaccgt gaccggtagc ggtaaaccgg cgaccatgga aaccggtctg  720
gtggttaacg tgccggactt cattgaggcg ggccagaagc tggttatcaa taccgcggag  780
ggtacctatg ttagccgtta atgaggtggt ggtggtagca gcagcgcgaa caaggcggtg  840
aacgatttta tcctggcgat gaactatgac aagaagaaac tgctgaccca ccaaggcgag  900
agcattgaga accgtttcat taaagaaggc aaccagctgc cggacgagtt tgtggttatc  960
gagcgtaaga aacgtagcct gagcaccaac accagcgaca ttagcgtgac cgcgaccaac  1020
gatagccgtc tgtacccggg tgcgctgctg gttgtggatg aaaccctgct ggaaaacaac  1080
ccgaccctgc tggcggtgga ccgtgcgccg atgacctata gcatcgatct gccgggtctg  1140
gcgagcagcg acagcttcct gcaagttgag gatccgagca acagcagcgt gcgtggtgcg  1200
gttaacgacc tgctggcgaa gtggcaccag gattacggcc aagtgaacaa cgttccggcg  1260
cgtatgcagt atgaaaaaat caccgcgcac agcatggagc aactgaaggt taaattcggt  1320
agcgactttg aaaagaccgg caacagcctg gacattgatt tcaacagcgt gcacagcggc  1380
gagaagcaga tccaaatcgt taacttcaag cagatctact acaccgtgag cgttgacgcg  1440
gtgaagaacc cgggtgacgt tttccaggat accgtgaccg ttgaagatct gaaacaacgt  1500
ggcattagcg cggagcgtcc gctggtgtac atcagcagcg ttgcgtacgg tcgtcaagtg  1560
tatctgaagc tggaaaccac cagcaaaagc gatgaggttg aagcggcgtt tgaggcgctg  1620
attaagggcg tgaaagttgc gccgcagacc gaatggaagc aaattctgga caacaccgag  1680
gtgaaagcgg ttattctggg cccggatccg agcagcggcg cgcgtgtggt taccggtaaa  1740
```

```
gtggacatgg ttgaggatct gattcaggaa ggtagccgtt ttaccgcgga ccacccgggc  1800
ctgccgatca gctacaccac cagcttcctg cgtgacaacg tggttgcgac ctttcaaaac  1860
agcaccgatt acgtggaaac caaggttacc gcgtatcgta acggtgacct gctgctggac  1920
cacagcggtg cgtacgtggc gcagtactat atcacctggg atgaactgag ctataaccac  1980
cagggtaaag aggtgctgac cccgaaagcg tgggaccgta acggccagga tctgaccgcg  2040
cacttcacca ccagcattcc gctgaagggc aacgtgcgta acctgagcgt taaaatccgt  2100
gagggtaccg gcctggcgtt tgaatggtgg cgtaccgtgt acgagaagac cgacctgccg  2160
ctggttcgta aacgtaccat cagcatttgg ggtaccaccc tgtatccgca ggtggaggac  2220
aaagttgaaa atgat                                                   2235

SEQ ID NO: 29           moltype = DNA  length = 2292
FEATURE                 Location/Qualifiers
source                  1..2292
                        mol_type = other DNA
                        organism = synthetic construct
SEQUENCE: 29
ttcgacgcat ccaactttaa agactttagc agcatcgcgt ccgcaagctc tagctggcag  60
aatcaatctg gtagcaccat gattatccaa gtggacagct ttggtaacgt cagcggtcaa  120
tatgttaatc gtgcacaggg tacgggttgt cagaattctc cgtacccgct gaccggtcgt  180
gttaacggca cgttcatcgc tttcagcgtc ggttggaaca attctactga aaattgcaac  240
agcgcgaccg gttggacggg ctatgcacaa gtgaatggca ataacaccga aatcgtcacg  300
tcctggaatc tggcgtatga gggtggcagc ggtccggcta ttgaacaggg ccaggatacc  360
ttccaatacg tccctacgac cgagaataag tcccttctga aagacggcgg tggcggttcg  420
agctcgacca gcggcgacaa ttggtccaaa taccagagca acaagagcat cacgatcggc  480
ttcgacagca cttttgtgcc gatgggtttc gcgcaaaaag acggtagcta cgcgggtttc  540
gatattgacc tggcgaccgc tgtctttgag aaatacggca ttacggttaa ttggcagccg  600
attgattggg acctgaaaga ggccgaactc accaaaggca ccatcgacct gatctggaat  660
ggttactccg caaccgatga gcgtcgcgaa aaagttgcct tcagcaacag ctatatgaag  720
aatgaacaag tgttggtaac caagaaatct agcggcatta cgaccgcgaa agacatgacc  780
ggtaagacgc tgggtgcgca ggccggtagc tctggctatg cggatttcga ggcgaatcct  840
gagattctga aaaacatcgt tgcgaataaa gaggcgaacc agtaccagac ctttaacgaa  900
gcactgatcg acctgaaaaa cgatcgcatt gacggtctgc tgatcgatcg tgtgtacgcg  960
aactattatc tggaagccga gggcgttctg aacgattata atgtttttac cgtgggtctg  1020
gagactgagg cattcgcggt tggtgcgcgc aaggaagata ccaacctggt taaaaagatt  1080
aatgaggcat ttagctcact gtacaaggac ggcaagttcc aagaaattag ccagaagtgg  1140
ttcggtgaag atgttgcgac gaaagaggtt aaagagggcc aagcggccgc atttcgccaa  1200
ccgagccaga ctgcgttgaa agatgagccg acccatctgg ttgttgcgaa agagggcagc  1260
gtggcatcga gcgtgctgct gagcggtacg gttactgcca aaaacgaaca atacgtgtac  1320
ttcgatgcta gcaagggtga tctggatgaa attctggtga gcgtgggtga caaagttagc  1380
gaaggccagg cactggtgaa gtattcatcc tccgaggcac aggcagcgta cgacagcgca  1440
agccgcgcag tggcgcgtgc cgaccgtcac attaacgaat tgaaccaagc gcgtaacgag  1500
gccgcaagcg cgccagcacc gcagctgccg gctccggtgg gtggcgaaga tgcgacggtg  1560
cagagcccga ccccggttgc gggtaattcg gtcgccagca tcgatgcgca gctgggtgac  1620
gcgcgtgatg cccgtgcgga tgcggctgct caactgagca aggctcagag ccaactggac  1680
gcgacgacgg tgctgagcac cttggagggt accgttgtcg aagtcaacag caatgtgagc  1740
aagagcccaa cgggtgcgag ccaggttatg gtccacattg tgagcaatga aaacttacag  1800
gtcaagggtg agctgagcga gtataacctg gcgaatctga gcgttggtca agaggtcagc  1860
tttaccagca aggtctaccc ggataagaaa tggaccggca agttgagcta catcagcgac  1920
tacccgaaga acaatggcga ggcagcctcc ccggcagccg gcaacaatac cggctctaag  1980
tatccgtaca ccatcgacgt aaccggtgag gtcggcgacc tgaaacaggg ttttagcgtg  2040
aatatcgaag tgaagtccaa gaccaaggca attttggttc cggttagctc cctggtgatg  2100
gacgatagca agaattatgt gtggattgtc gacgagcaac agaaagcgaa aaaagttgaa  2160
gtgagcctgg gcaatgctga tgccgagaac caagaaatca cgtctggtct gaccaacggt  2220
gcgaaagtta ttagcaaccc gaccagcagc ctggaagagg gtaaagaggt caaagccgac  2280
gaagctacga ac                                                      2292

SEQ ID NO: 30           moltype = AA  length = 7
FEATURE                 Location/Qualifiers
source                  1..7
                        mol_type = protein
                        organism = synthetic construct
SEQUENCE: 30
GGGGSSS                                                            7

SEQ ID NO: 31           moltype =   length =
SEQUENCE: 31
000

SEQ ID NO: 32           moltype = AA  length = 150
FEATURE                 Location/Qualifiers
source                  1..150
                        mol_type = protein
                        organism = synthetic construct
VARIANT                 1..150
                        note = This sequence may encompass 1-20, 25, or 30 GGGGS
                         repeating units
SEQUENCE: 32
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGSGGGGS GGGGSGGGGS GGGGSGGGGS  120
```

```
GGGGSGGGGS GGGGSGGGGS GGGGSGGGGS                                  150

SEQ ID NO: 33           moltype = AA  length = 6
FEATURE                 Location/Qualifiers
source                  1..6
                        mol_type = protein
                        organism = synthetic construct
SEQUENCE: 33
GGGGGG                                                            6

SEQ ID NO: 34           moltype = AA  length = 15
FEATURE                 Location/Qualifiers
source                  1..15
                        mol_type = protein
                        organism = synthetic construct
SEQUENCE: 34
GGGGSGGGGS GGGGS                                                  15

SEQ ID NO: 35           moltype = AA  length = 30
FEATURE                 Location/Qualifiers
source                  1..30
                        mol_type = protein
                        organism = synthetic construct
SEQUENCE: 35
GGGGSGGGGS GGGGSGGGGS GGGGSGGGGS                                  30

SEQ ID NO: 36           moltype = AA  length = 18
FEATURE                 Location/Qualifiers
source                  1..18
                        mol_type = protein
                        organism = synthetic construct
SEQUENCE: 36
KESGSVSSEQ LAQFRSLD                                               18

SEQ ID NO: 37           moltype = AA  length = 14
FEATURE                 Location/Qualifiers
source                  1..14
                        mol_type = protein
                        organism = synthetic construct
SEQUENCE: 37
EGKSSGSGSE SKST                                                   14

SEQ ID NO: 38           moltype = AA  length = 30
FEATURE                 Location/Qualifiers
source                  1..30
                        mol_type = protein
                        organism = synthetic construct
VARIANT                 1..30
                        note = This sequence may encompass 1-20, 25, or 30 residues
SEQUENCE: 38
GGGGGGGGGG GGGGGGGGGG GGGGGGGGGG                                  30

SEQ ID NO: 39           moltype = AA  length = 8
FEATURE                 Location/Qualifiers
source                  1..8
                        mol_type = protein
                        organism = synthetic construct
SEQUENCE: 39
GGGGGGGG                                                          8

SEQ ID NO: 40           moltype = AA  length = 12
FEATURE                 Location/Qualifiers
source                  1..12
                        mol_type = protein
                        organism = synthetic construct
SEQUENCE: 40
GSAGSAAGSG EF                                                     12

SEQ ID NO: 41           moltype = AA  length = 150
FEATURE                 Location/Qualifiers
source                  1..150
                        mol_type = protein
                        organism = synthetic construct
VARIANT                 1..150
                        note = This sequence may encompass 1-20, 25, or 30 EAAAK
                         repeating units
SEQUENCE: 41
EAAAKEAAAK EAAAKEAAAK EAAAKEAAAK EAAAKEAAAK EAAAKEAAAK EAAAKEAAAK  60
EAAAKEAAAK EAAAKEAAAK EAAAKEAAAK EAAAKEAAAK EAAAKEAAAK EAAAKEAAAK  120
```

```
EAAAKEAAAK EAAAKEAAAK EAAAKEAAAK                                 150

SEQ ID NO: 42           moltype = AA  length = 152
FEATURE                 Location/Qualifiers
source                  1..152
                        mol_type = protein
                        organism = synthetic construct
VARIANT                 2..151
                        note = This region may encompass 1-20, 25, or 30 EAAAK
                         repeating units
SEQUENCE: 42
AEAAAKEAAA KEAAAKEAAA KEAAAKEAAA KEAAAKEAAA KEAAAKEAAA KEAAAKEAAA  60
KEAAAKEAAA KEAAAKEAAA KEAAAKEAAA KEAAAKEAAA KEAAAKEAAA KEAAAKEAAA  120
KEAAAKEAAA KEAAAKEAAA KEAAAKEAAA KA                                152

SEQ ID NO: 43           moltype = AA  length = 46
FEATURE                 Location/Qualifiers
source                  1..46
                        mol_type = protein
                        organism = synthetic construct
SEQUENCE: 43
AEAAAKEAAA KEAAAKEAAA KALEAEAAAK EAAAKEAAAK EAAAKA                 46

SEQ ID NO: 44           moltype = AA  length = 44
FEATURE                 Location/Qualifiers
source                  1..44
                        mol_type = protein
                        organism = synthetic construct
VARIANT                 1..22
                        note = This region may encompass 2, 3, or 4 EAAAK repeating
                         units
VARIANT                 23..44
                        note = This region may encompass 2, 3, or 4 EAAAK repeating
                         units
VARIANT                 1..44
                        note = This sequence may encompass 1 or 2 A(EAAAK)nA
                         repeating units, wherein n is 2, 3, or 4
SEQUENCE: 44
AEAAAKEAAA KEAAAKEAAA KAAEAAAKEA AAKEAAAKEA AAKA                   44

SEQ ID NO: 45           moltype = AA  length = 12
FEATURE                 Location/Qualifiers
source                  1..12
                        mol_type = protein
                        organism = synthetic construct
SEQUENCE: 45
AEAAAKEAAA KA                                                      12

SEQ ID NO: 46           moltype = AA  length = 60
FEATURE                 Location/Qualifiers
source                  1..60
                        mol_type = protein
                        organism = synthetic construct
VARIANT                 1
                        note = Any amino acid
VARIANT                 3
                        note = Any amino acid
VARIANT                 5
                        note = Any amino acid
VARIANT                 7
                        note = Any amino acid
VARIANT                 9
                        note = Any amino acid
VARIANT                 11
                        note = Any amino acid
VARIANT                 13
                        note = Any amino acid
VARIANT                 15
                        note = Any amino acid
VARIANT                 17
                        note = Any amino acid
VARIANT                 19
                        note = Any amino acid
VARIANT                 21
                        note = Any amino acid
VARIANT                 23
                        note = Any amino acid
VARIANT                 25
                        note = Any amino acid
```

```
VARIANT                 27
                        note = Any amino acid
VARIANT                 29
                        note = Any amino acid
VARIANT                 31
                        note = Any amino acid
VARIANT                 33
                        note = Any amino acid
VARIANT                 35
                        note = Any amino acid
VARIANT                 37
                        note = Any amino acid
VARIANT                 39
                        note = Any amino acid
VARIANT                 41
                        note = Any amino acid
VARIANT                 43
                        note = Any amino acid
VARIANT                 45
                        note = Any amino acid
VARIANT                 47
                        note = Any amino acid
VARIANT                 49
                        note = Any amino acid
VARIANT                 51
                        note = Any amino acid
VARIANT                 53
                        note = Any amino acid
VARIANT                 55
                        note = Any amino acid
VARIANT                 57
                        note = Any amino acid
VARIANT                 59
                        note = Any amino acid
VARIANT                 1..60
                        note = This sequence may encompass 1-20, 25, or 30 XP
                         repeating units
SEQUENCE: 46
XPXPXPXPXP XPXPXPXPXP XPXPXPXPXP XPXPXPXPXP XPXPXPXPXP XPXPXPXPXP  60

SEQ ID NO: 47           moltype = AA  length = 60
FEATURE                 Location/Qualifiers
source                  1..60
                        mol_type = protein
                        organism = synthetic construct
VARIANT                 1..60
                        note = This sequence may encompass 1-20, 25, or 30 AP
                         repeating units
SEQUENCE: 47
APAPAPAPAP APAPAPAPAP APAPAPAPAP APAPAPAPAP APAPAPAPAP APAPAPAPAP  60

SEQ ID NO: 48           moltype = AA  length = 60
FEATURE                 Location/Qualifiers
source                  1..60
                        mol_type = protein
                        organism = synthetic construct
VARIANT                 1..60
                        note = This sequence may encompass 1-20, 25, or 30 KP
                         repeating units
SEQUENCE: 48
KPKPKPKPKP KPKPKPKPKP KPKPKPKPKP KPKPKPKPKP KPKPKPKPKP KPKPKPKPKP  60

SEQ ID NO: 49           moltype = AA  length = 60
FEATURE                 Location/Qualifiers
source                  1..60
                        mol_type = protein
                        organism = synthetic construct
VARIANT                 1..60
                        note = This sequence may encompass 1-20, 25, or 30 QP
                         repeating units
SEQUENCE: 49
QPQPQPQPQP QPQPQPQPQP QPQPQPQPQP QPQPQPQPQP QPQPQPQPQP QPQPQPQPQP  60

SEQ ID NO: 50           moltype = AA  length = 14
FEATURE                 Location/Qualifiers
source                  1..14
                        mol_type = protein
                        organism = synthetic construct
SEQUENCE: 50
```

-continued

```
APAPAPAPAP APAP                                                     14

SEQ ID NO: 51          moltype = AA  length = 21
FEATURE                Location/Qualifiers
source                 1..21
                       mol_type = protein
                       organism = synthetic construct
SEQUENCE: 51
GAPGGGGGAA AAAGGGGGGA P                                             21

SEQ ID NO: 52          moltype = AA  length = 39
FEATURE                Location/Qualifiers
source                 1..39
                       mol_type = protein
                       organism = synthetic construct
SEQUENCE: 52
GAPGGGGGAA AAAGGGGGGA PGGGGGAAAA AGGGGGGAP                          39

SEQ ID NO: 53          moltype = AA  length = 57
FEATURE                Location/Qualifiers
source                 1..57
                       mol_type = protein
                       organism = synthetic construct
SEQUENCE: 53
GAPGGGGGAA AAAGGGGGGA PGGGGGAAAA AGGGGGGAPG GGGGAAAAAG GGGGGAP      57

SEQ ID NO: 54          moltype = AA  length = 4
FEATURE                Location/Qualifiers
source                 1..4
                       mol_type = protein
                       organism = synthetic construct
SEQUENCE: 54
GGGG                                                                4

SEQ ID NO: 55          moltype = AA  length = 6
FEATURE                Location/Qualifiers
source                 1..6
                       mol_type = protein
                       organism = synthetic construct
SEQUENCE: 55
HHHHHH                                                              6

SEQ ID NO: 56          moltype = AA  length = 10
FEATURE                Location/Qualifiers
source                 1..10
                       mol_type = protein
                       organism = synthetic construct
SEQUENCE: 56
MSYYHHHHHH                                                          10

SEQ ID NO: 57          moltype = AA  length = 136
FEATURE                Location/Qualifiers
source                 1..136
                       mol_type = protein
                       organism = synthetic construct
SEQUENCE: 57
MFDASNFKDF SSIASASSSW QNQSGSTMII QVDSFGNVSG QYVNRAQGTG CQNSPYPLTG   60
RVNGTFIAFS VGWNNSTENC NSATGWTGYA QVNGNNTEIV TSWNLAYEGG SGPAIEQGQD   120
TFQYVPTTEN KSLLKD                                                   136

SEQ ID NO: 58          moltype = AA  length = 744
FEATURE                Location/Qualifiers
source                 1..744
                       mol_type = protein
                       organism = synthetic construct
SEQUENCE: 58
MFDASNFKDF SSIASASSSW QNQSGSTMII QVDSFGNVSG QYVNRAQGTG CQNSPYPLTG   60
RVNGTFIAFS VGWNNSTENC NSATGWTGYA QVNGNNTEIV TSWNLAYEGG SGPAIEQGQD   120
TFQYVPTTEN KSLLKDGGGG SSSANKAVND FILAMNYDKK KLLTHQGESI ENRFIKEGNQ   180
LPDEFVVIER KKRSLSTNTS DISVTATNDS RLYPGALLVV DETLLENNPT LLAVDRAPMT   240
YSIDLPGLAS SDSFLQVEDP SNSSVRGAVN DLLAKWHQDY GQVNNVPARM QYEKITAHSM   300
EQLKVKFGSD FEKTGNSLDI DFNSVHSGEK QIQIVNFKQI YYTVSVDAVK NPGDVFQDTV   360
TVEDLKQRGI SAERPLVYIS SVAYGRQVYL KLETTSKSDE VEAAFEALIK GVKVAPQTEW   420
KQILDNTEVK AVILGPDPSS GARVVTGKVD MVEDLIQEGS RFTADHPGLP ISYTTSFLRD   480
NVVATFQNST DYVETKVTAY RNGDLLLDHS GAYVAQYYIT WDELSYNHQG KEVLTPKAWD   540
RNGQDLTAHF TTSIPLKGNV RNLSVKIREG TGLAFEWWRT VYEKTDLPLV RKRTISIWGT   600
TLYPQVEDKV ENDGGGGSSS EQAIIETVPA QYLYKMDDTA YFMNTETYDQ YEIPVVNVEN   660
ELLYILENSD VKIQFYGTEV IGVTVPTTVE LTVAETQPSI KGATVTGSGK PATMETGLVV   720
NVPDFIEAGQ KLVINTAEGT YVSR                                          744
```

```
SEQ ID NO: 59          moltype = AA  length = 750
FEATURE                Location/Qualifiers
source                 1..750
                       mol_type = protein
                       organism = synthetic construct
SEQUENCE: 59
MFDASNFKDF SSIASASSSW QNQSGSTMII QVDSFGNVSG QYVNRAQGTG CQNSPYPLTG  60
RVNGTFIAFS VGWNNSTENC NSATGWTGYA QVNGNNTEIV TSWNLAYEGG SGPAIEQGQD  120
TFQYVPTTEN KSLLKDGGGG SSSANKAVND FILAMNYDKK KLLTHQGESI ENRFIKEGNQ  180
LPDEFVVIER KKRSLSTNTS DISVTATNDS RLYPGALLVV DETLLENNPT LLAVDRAPMT  240
YSIDLPGLAS SDSFLQVEDP SNSSVRGAVN DLLAKWHQDY GQVNNVPARM QYEKITAHSM  300
EQLKVKFGSD FEKTGNSLDI DFNSVHSGEK QIQIVNFKQI YYTVSVDAVK NPGDVFQDTV  360
TVEDLKQRGI SAERPLVYIS SVAYGRQVYL KLETTSKSDE VEAAFEALIK GVKVAPQTEW  420
KQILDNTEVK AVILGPDPSS GARVVTGKVD MVEDLIQEGS RFTADHPGLP ISYTTSFLRD  480
NVVATFQNST DYVETKVTAY RNGDLLLDHS GAYVAQYYIT WDELSYNHQG KEVLTPKAWD  540
RNGQDLTAHF TTSIPLKGNV RNLSVKIREG TGLAFEWWRT VYEKTDLPLV RKRTISIWGT  600
TLYPQVEDKV ENDGGGGSSS EQAIIETVPA QYLYKMDDTA YFMNTETYDQ YEIPVVNVEN  660
ELLYILENSD VKIQFYGTEV IGVTVPTTVE LTVAETQPSI KGATVTGSGK PATMETGLVV  720
NVPDFIEAGQ KLVINTAEGT YVSRHHHHHH                                   750

SEQ ID NO: 60          moltype = AA  length = 744
FEATURE                Location/Qualifiers
source                 1..744
                       mol_type = protein
                       organism = synthetic construct
SEQUENCE: 60
MFDASNFKDF SSIASASSSW QNQSGSTMII QVDSFGNVSG QYVNRAQGTG CQNSPYPLTG  60
RVNGTFIAFS VGWNNSTENC NSATGWTGYA QVNGNNTEIV TSWNLAYEGG SGPAIEQGQD  120
TFQYVPTTEN KSLLKDGGGG SSSEQAIIET VPAQYLYKMD DTAYFMNTET YDQYEIPVVN  180
VENELLYILE NSDVKIQFYG TEVIGVTVPT TVELTVAETQ PSIKGATVTG SGKPATMETG  240
LVVNVPDFIE AGQKLVINTA EGTYVSRGGG GSSSANKAVN DFILAMNYDK KKLLTHQGES  300
IENRFIKEGN QLPDEFVVIE RKKRSLSTNT SDISVTATND SRLYPGALLV VDETLLENNP  360
TLLAVDRAPM TYSIDLPGLA SSDSFLQVED PSNSSVRGAV NDLLAKWHQD YGQVNNVPAR  420
MQYEKITAHS MEQLKVKFGS DFEKTGNSLD IDFNSVHSGE KQIQIVNFKQ IYYTVSVDAV  480
KNPGDVFQDT VTVEDLKQRG ISAERPLVYI SSVAYGRQVY LKLETTSKSD EVEAAFEALI  540
KGVKVAPQTE WKQILDNTEV KAVILGPDPS SGARVVTGKV DMVEDLIQEG SRFTADHPGL  600
PISYTTSFLR DNVVATFQNS TDYVETKVTA YRNGDLLLDH SGAYVAQYYI TWDELSYNHQ  660
GKEVLTPKAW DRNGQDLTAH FTTSIPLKGN VRNLSVKIRE GTGLAFEWWR TVYEKTDLPL  720
VRKRTISIWG TTLYPQVEDK VEND                                         744

SEQ ID NO: 61          moltype = AA  length = 765
FEATURE                Location/Qualifiers
source                 1..765
                       mol_type = protein
                       organism = synthetic construct
SEQUENCE: 61
MFDASNFKDF SSIASASSSW QNQSGSTMII QVDSFGNVSG QYVNRAQGTG CQNSPYPLTG  60
RVNGTFIAFS VGWNNSTENC NSATGWTGYA QVNGNNTEIV TSWNLAYEGG SGPAIEQGQD  120
TFQYVPTTEN KSLLKDGGGG SSSTSGDNWS KYQSNKSITI GFDSTFVPMG FAQKDGSYAG  180
FDIDLATAVF EKYGITVNWQ PIDWDLKEAE LTKGTIDLIW NGYSATDERR EKVAFSNSYM  240
KNEQVLVTKK SSGITTAKDM TGKTLGAQAG SSGYADFEAN PEILKNIVAN KEANQYQTFN  300
EALIDLKNDR IDGLLIDRVY ANYYLEAEGV LNDYNVFTVG LETEAFAVGA RKEDTNLVKK  360
INEAFSSLYK DGKFQEISQK WFGEDVATKE VKEGQAAAFR QPSQTALKDE PTHLVVAKEG  420
SVASSVLLSG TVTAKNEQYV YFDASKGDLD EILVSVGDKV SEGQALVKYS SSEAQAAYDS  480
ASRAVARADR HINELNQARN EAASAPAPQL PAPVGGEDAT VQSPTPVAGN SVASIDAQLG  540
DARDARADAA AQLSKAQSQL DATTVLSTLE GTVVEVNSNV SKSPTGASQV MVHIVSNENL  600
QVKGELSEYN LANLSVGQEV SFTSKVYPDK KWTGKLSYIS DYPKNNGEAA SPAAGNNTGS  660
KYPYTIDVTG EVGDLKQGFS VNIEVKSKTK AILVPVSSLV MDDSKNYVWI VDEQQKAKKV  720
EVSLGNADAE NQEITSGLTN GAKVISNPTS SLEEGKEVKA DEATN                  765

SEQ ID NO: 62          moltype = DNA  length = 2238
FEATURE                Location/Qualifiers
source                 1..2238
                       mol_type = other DNA
                       organism = synthetic construct
SEQUENCE: 62
atgttcgacg catccaactt taaagacttt agcagcatcg cgtccgcaag ctctagctgg  60
cagaatcaat ctggtagcac catgattatc caagtggaca gctttggtaa cgtcagcggt  120
caatatgtta atcgtgcaca gggtacgggt tgtcagaatt ctccgtaccc gctgaccggt  180
cgtgttaacg gcacgttcat cgctttcagc gtcggttgga acaattctac tgaaaattgc  240
aacagcgcga ccggttggac gggctatgca caagtgaatg gcaataacac cgaaatcgtc  300
acgtcctgga atctggcgta tgagggtggc agcggtccgg ctattgaaca gggccaggat  360
accttccaat acgtccctac gaccgagaat aagtcccttc tgaaagacgg cggtggcggt  420
tcgagctcgg cgaacaaggc ggtgaacgat tttatcctgg cgatgaacta tgacaagaag  480
aaactgctga cccaccaagg cgagagcatt gagaaccgtt tcattaaaga aggcaaccag  540
ctgccggacg agtttgtggt tatcgagcgt aagaaacgta gcctgagcac caacaccagc  600
gacattagcg tgaccgcgac caacgatagc cgtctgtacc cgggtgcgct gctggttgtg  660
gatgaaaccc tgctggaaaa caacccgacc ctgctggcgg tggaccgtgc gccgatgacc  720
```

```
tatagcatcg atctgccggg tctggcgagc agcgacagct tcctgcaagt tgaggatccg  780
agcaacagca gcgtgcgtgg tgcggttaac gacctgctgg cgaagtggca ccaggattac  840
ggccaagtga acaacgttcc ggcgcgtatg cagtatgaaa aaatcaccgc gcacagcatg  900
gagcaactga aggttaaatt cggtagcgac tttgaaaaga ccggcaacag cctggacatt  960
gatttcaaca gcgtgcacag cggcgagaag cagatccaaa tcgttaactt caagcagatc  1020
tactacaccg tgagcgttga cgcggtgaag aacccgggtg acgttttcca ggataccgtg  1080
accgttgaag atctgaaaca acgtggcatt agcgcggagc gtccgctggt gtacatcagc  1140
agcgttgcgt acggtcgtca agtgtatctg aagctggaaa ccaccagcaa aagcgatgag  1200
gttgaagcgg cgtttgaggc gctgattaag ggcgtgaaag ttgcgccgca gaccgaatgg  1260
aagcaaattc tggacaacac cgaggtgaaa gcggttattc tgggcccgga tccgagcagc  1320
ggcgcgcgtg tggttaccgg taaagtggac atggttgagg atctgattca ggaaggtagc  1380
cgttttaccg cggaccaccc gggcctgccg atcagctaca ccaccagctt cctgcgtgac  1440
aacgtggttg cgacctttca aaacagcacc gattacgtgg aaaccaaggt taccgcgtat  1500
cgtaacggtg acctgctgct ggaccacagc ggtgcgtacg tggcgcagta ctatatcacc  1560
tgggatgaac tgagctataa ccaccagggt aaagaggtgc tgaccccgaa agcgtgggac  1620
cgtaacggcc aggatctgac cgcgcacttc accaccagca ttccgctgaa gggcaacgtg  1680
cgtaacctga gcgttaaaat ccgtgagggt accggcctgg cgtttgaatg gtggcgtacc  1740
gtgtacgaga agaccgacct gccgctggtt cgtaaacgta ccatcagcat ttggggtacc  1800
accctgtatc cgcaggtgga ggacaaagtt gaaaatgatg gtggtggtgg tagcagcagc  1860
gagcaggcga tcattgaaac cgtgccggcg caatacctgt ataagatgga cgataccgcg  1920
tacttcatga acaccgaaac ctacgaccaa tatgaaattc cggtggttaa cgttgagaac  1980
gaactgctgt acatcctgga aaacagcgat gtgaaaattc agttttatgg taccgaggtt  2040
atcggcgtga ccgttccgac caccgtggag ctgaccgttg cggaaaccca accgagcatc  2100
aagggtgcga ccgtgaccgg tagcggtaaa ccggcgacca tggaaaccgg tctggtggtt  2160
aacgtgccgg acttcattga ggcgggccag aagctggtta tcaataccgc ggagggtacc  2220
tatgttagcc gttaatga                                                2238

SEQ ID NO: 63          moltype = DNA  length = 2238
FEATURE                Location/Qualifiers
source                 1..2238
                       mol_type = other DNA
                       organism = synthetic construct
SEQUENCE: 63
atgttcgacg catccaactt taaagacttt agcagcatcg cgtccgcaag ctctagctgg  60
cagaatcaat ctggtagcac catgattatc caagtggaca gctttggtaa cgtcagcggt  120
caatatgtta atcgtgcaca gggtacgggt tgtcagaatt ctccgtaccc gctgaccggt  180
cgtgttaacg gcacgttcat cgctttcagc gtcggttgga acaattctac tgaaaattgc  240
aacagcgcga ccggttggac gggctatgca caagtgaatg gcaataacac cgaaatcgtc  300
acgtcctgga atctggcgta tgagggtggc agcggtccgg ctattgaaca gggccaggat  360
accttccaat acgtccctac gaccgagaat aagtcccttc tgaaagacgg cggtggcggt  420
tcgagctcgg agcaggcgat cattgaaacc gtgccggcgc aatacctgta taagatggac  480
gataccgcgt acttcatgaa caccgaaacc tacgaccaat atgaaattcc ggtggttaac  540
gttgagaacg aactgctgta catcctggaa aacagcgatg tgaaaattca gttttatggt  600
accgaggtta tcggcgtgac cgttccgacc accgtggagc tgaccgttgc ggaaacccaa  660
ccgagcatca agggtgcgac cgtgaccggt agcggtaaac cggcgaccat ggaaaccggt  720
ctggtggtta acgtgccgga cttcattgag gcgggccaga agctggttat caataccgcg  780
gagggtacct atgttagccg ttaatgaggt ggtggtggta gcagcagcgc gaacaaggcg  840
gtgaacgatt ttatcctggc gatgaactat gacaagaaga aactgctgac ccaccaaggc  900
gagagcattg agaaccgttt cattaaagaa ggcaaccagc tgccggacga gtttgtggtt  960
atcgagcgta agaaacgtag cctgagcacc aacaccagcg acattagcgt gaccgcgacc  1020
aacgatagcc gtctgtaccc gggtgcgctg ctggttgtgg atgaaaccct gctggaaaac  1080
aacccgaccc tgctggcggt ggaccgtgcg ccgatgacct atagcatcga tctgccgggt  1140
ctggcgagca gcgacagctt cctgcaagtt gaggatccga gcaacagcag cgtgcgtggt  1200
gcggttaacg acctgctggc gaagtggcac caggattacg gccaagtgaa caacgttccg  1260
gcgcgtatgc agtatgaaaa aatcaccgcg cacagcatgg agcaactgaa ggttaaattc  1320
ggtagcgact ttgaaaagac cggcaacagc ctggacattg atttcaacag cgtgcacagc  1380
ggcgagaagc agatccaaat cgttaacttc aagcagatct actacaccgt gagcgttgac  1440
gcggtgaaga acccgggtga cgttttccag gataccgtga ccgttgaaga tctgaaacaa  1500
cgtggcatta gcgcggagcg tccgctggtg tacatcagca gcgttgcgta cggtcgtcaa  1560
gtgtatctga agctggaaac caccagcaaa agcgatgagg ttgaagcggc gtttgaggcg  1620
ctgattaagg gcgtgaaagt tgcgccgcag accgaatgga agcaaattct ggacaacacc  1680
gaggtgaaag cggttattct gggcccggat ccgagcagcg gcgcgcgtgt ggttaccggt  1740
aaagtggaca tggttgagga tctgattcag gaaggtagcc gttttaccgc ggaccacccg  1800
ggcctgccga tcagctacac caccagcttc ctgcgtgaca acgtggttgc gacctttcaa  1860
aacagcaccg attacgtgga aaccaaggtt accgcgtatc gtaacggtga cctgctgctg  1920
gaccacagcg gtgcgtacgt ggcgcagtac tatatcacct gggatgaact gagctataac  1980
caccagggta aagaggtgct gaccccgaaa gcgtgggacc gtaacggcca ggatctgacc  2040
gcgcacttca ccaccagcat tccgctgaag ggcaacgtgc gtaacctgag cgttaaaatc  2100
cgtgagggta ccggcctggc gtttgaatgg tggcgtaccg tgtacgagaa gaccgacctg  2160
ccgctggttc gtaaacgtac catcagcatt tggggtacca ccctgtatcc gcaggtggag  2220
gacaaagttg aaaatgat                                                2238

SEQ ID NO: 64          moltype = DNA  length = 2295
FEATURE                Location/Qualifiers
source                 1..2295
                       mol_type = other DNA
                       organism = synthetic construct
SEQUENCE: 64
atgttcgacg catccaactt taaagacttt agcagcatcg cgtccgcaag ctctagctgg  60
```

```
cagaatcaat ctggtagcac catgattatc caagtggaca gctttggtaa cgtcagcggt  120
caatatgtta atcgtgcaca gggtacgggt tgtcagaatt ctccgtaccc gctgaccggt  180
cgtgttaacg gcacgttcat cgctttcagc gtcggttgga acaattctac tgaaaattgc  240
aacagcgcga ccggttggac gggctatgca caagtgaatg gcaataacac cgaaatcgtc  300
acgtcctgga atctggcgta tgagggtggc agcggtccgg ctattgaaca gggccaggat  360
accttccaat acgtccctac gaccgagaat aagtcccttc tgaaagacgg cggtggcggt  420
tcgagctcga ccagcggcga caattggtcc aaataccaga gcaacaagag catcacgatc  480
ggcttcgaca gcacttttgt gccgatgggt ttcgcgcaaa aagacggtag ctacgcgggt  540
ttcgatattg acctggcgac cgctgtcttt gagaaatacg gcattacggt taattggcag  600
ccgattgatt gggacctgaa agaggccgaa ctcaccaaag gcaccatcga cctgatctgg  660
aatggttact ccgcaaccga tgagcgtcgc gaaaaagttg ccttcagcaa cagctatatg  720
aagaatgaac aagtgttggt aaccaagaaa tctagcggca ttacgaccgc gaaagacatg  780
accggtaaga cgctgggtgc gcaggccggt agctctggct atgcggattt cgaggcgaat  840
cctgagattc tgaaaaacat cgttgcgaat aaagaggcga accagtacca gacctttaac  900
gaagcactga tcgacctgaa aaacgatcgc attgacggtc tgctgatcga tcgtgtgtac  960
gcgaactatt atctggaagc cgagggcgtt ctgaacgatt ataatgtttt taccgtgggt  1020
ctggagactg aggcattcgc ggttggtgcg cgcaaggaag ataccaacct ggttaaaaag  1080
attaatgagg catttagctc actgtacaag gacggcaagt tccaagaaat tagccagaag  1140
tggttcggtg aagatgttgc gacgaaagag gttaaagagg gccaagcggc cgcatttcgc  1200
caaccgagcc agactgcgtt gaaagatgag ccgacccatc tggttgttgc gaaagagggc  1260
agcgtggcat cgagcgtgct gctgagcggt acggttactg ccaaaaacga acaatacgtg  1320
tacttcgatg ctagcaaggg tgatctggat gaaattctgg tgagcgtggg tgacaaagtt  1380
agcgaaggcc aggcactggt gaagtattca tcctccgagg cacaggcagc gtacgacagc  1440
gcaagccgcg cagtggcgcg tgccgaccgt cacattaacg aattgaacca agcgcgtaac  1500
gaggccgcaa gcgcgccagc accgcagctg ccggctccgg tgggtggcga agatgcgacg  1560
gtgcagagcc cgaccccggt tgcgggtaat tcggtcgcca gcatcgatgc gcagctgggt  1620
gacgcgcgtg atgcccgtgc ggatgcggct gctcaactga gcaaggctca gagccaactg  1680
gacgcgacga cggtgctgag caccttggag ggtaccgttg tcgaagtcaa cagcaatgtg  1740
agcaagagcc caacgggtgc gagccaggtt atggtccaca ttgtgagcaa tgaaaactta  1800
caggtcaagg gtgagctgag cgagtataac ctggcgaatc tgagcgttgg tcaagaggtc  1860
agctttacca gcaaggtcta cccggataag aaatggaccg gcaagttgag ctacatcagc  1920
gactacccga agaacaatgg cgaggcagcc tccccggcag ccggcaacaa taccggctct  1980
aagtatccgt acaccatcga cgtaaccggt gaggtcggcg acctgaaaca gggttttagc  2040
gtgaatatcg aagtgaagtc caagaccaag gcaattttgg ttccggttag ctccctggtg  2100
atggacgata gcaagaatta tgtgtggatt gtcgacgagc aacagaaagc gaaaaaagtt  2160
gaagtgagcc tgggcaatgc tgatgccgag aaccaagaaa tcacgtctgg tctgaccaac  2220
ggtgcgaaag ttattagcaa cccgaccagc agcctggaag agggtaaaga ggtcaaagcc  2280
gacgaagcta cgaac                                                  2295

SEQ ID NO: 65          moltype = AA  length = 5
FEATURE                Location/Qualifiers
source                 1..5
                       mol_type = protein
                       organism = synthetic construct
SEQUENCE: 65
GGGGS                                                             5

SEQ ID NO: 66          moltype = AA  length = 5
FEATURE                Location/Qualifiers
source                 1..5
                       mol_type = protein
                       organism = synthetic construct
SEQUENCE: 66
EAAAK                                                             5

SEQ ID NO: 67          moltype = AA  length = 10
FEATURE                Location/Qualifiers
source                 1..10
                       mol_type = protein
                       organism = synthetic construct
VARIANT                1..10
                       note = This sequence may encompass 2-10 residues
SEQUENCE: 67
HHHHHHHHHH                                                        10

SEQ ID NO: 68          moltype = AA  length = 27
FEATURE                Location/Qualifiers
source                 1..27
                       mol_type = protein
                       organism = synthetic construct
VARIANT                2..26
                       note = This region may encompass 2-5 EAAAK repeating units
SEQUENCE: 68
AEAAAKEAAA KEAAAKEAAA KEAAAKA                                     27

SEQ ID NO: 69          moltype = AA  length = 34
FEATURE                Location/Qualifiers
source                 1..34
                       mol_type = protein
```

-continued

```
                          organism = synthetic construct
VARIANT                   1..34
                          note = This sequence may encompass 5-17 AP repeating units
SEQUENCE: 69
APAPAPAPAP APAPAPAPAP APAPAPAPAP APAP                          34
```